US012799485B2

(12) United States Patent
Smith et al.

(10) Patent No.: US 12,799,485 B2
(45) Date of Patent: Nov. 17, 2026

(54) RNA MOLECULES COMPRISING NON-CANONICAL BASE PAIRS

(71) Applicant: Commonwealth Scientific and Industrial Research Organisation, Acton (AU)

(72) Inventors: Neil Andrew Smith, Cook (AU); Ming Bo Wang, McKellar (AU); Daai Zhang, Hohhot City (CN); Timothy James Doran, Ocean Grove (AU); Mark Tizard, Highton (AU); Annapurna Devi Allu, Mangalam (IN); Ian Kevin Greaves, Richardson (AU); Lingling Gao, Floreat WA (AU); Jonathan Paul Anderson, Floreat WA (AU); Robert De Feyter, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 619 days.

(21) Appl. No.: 17/265,713

(22) PCT Filed: Aug. 2, 2019

(86) PCT No.: PCT/AU2019/050814

§ 371 (c)(1),
(2) Date: Feb. 3, 2021

(87) PCT Pub. No.: WO2020/024019

PCT Pub. Date: Feb. 6, 2020

(65) Prior Publication Data

US 2021/0269800 A1 Sep. 2, 2021

(30) Foreign Application Priority Data

| | | |
|---|---|---|
| Aug. 3, 2018 | (AU) | 2018902840 |
| Aug. 8, 2018 | (AU) | 2018902896 |
| Sep. 17, 2018 | (WO) | PCT/AU2018/051015 |
| Mar. 20, 2019 | (AU) | 2019900941 |

(51) Int. Cl.

| | |
|---|---|
| ***C12N 15/113*** | (2010.01) |
| ***A01N 63/60*** | (2020.01) |
| ***C12N 15/82*** | (2006.01) |

(52) U.S. Cl.

CPC ............ *C12N 15/113* (2013.01); *A01N 63/60* (2020.01); *C12N 15/8218* (2013.01); *C12N 2310/11* (2013.01); *C12N 2310/14* (2013.01); *C12N 2310/531* (2013.01)

(58) Field of Classification Search

CPC .............. C12N 15/113; C12N 15/8218; C12N 2310/11; C12N 2310/14; C12N 2310/531; C12N 2310/113; C12N 2310/33; C12N 2310/532; C12N 15/111; C12N 15/8279; C12N 2310/533; C12N 15/80; A01N 63/60

See application file for complete search history.

(56) References Cited

U.S. PATENT DOCUMENTS

| | | | |
|---|---|---|---|
| 4,766,072 | A | 8/1988 | Jendrisak |
| 5,264,221 | A | 11/1993 | Tagawa |
| 5,354,854 | A | 10/1994 | Bourque |
| 5,413,906 | A | 5/1995 | Eberle |
| 5,583,198 | A | 12/1996 | Whittaker |
| 5,602,242 | A | 2/1997 | Ahlquist |
| 5,665,710 | A | 9/1997 | Rahman |
| 5,719,054 | A | 2/1998 | Boursnell |
| 5,780,269 | A | 7/1998 | Inouye |
| 5,795,715 | A | 8/1998 | Livache |
| 5,854,224 | A | 12/1998 | Lockett |
| 5,869,606 | A | 2/1999 | Whittaker |
| 5,906,922 | A | 5/1999 | Whittaker |
| 5,989,864 | A | 11/1999 | Burnham |
| 6,135,942 | A | 10/2000 | Leptin |
| 6,146,886 | A | 11/2000 | Thompson |
| 6,171,612 | B1 | 1/2001 | Byk |
| 6,172,048 | B1 | 1/2001 | Behr |
| 6,423,885 | B1 | 7/2002 | Waterhouse |
| 6,451,603 | B1 | 9/2002 | Atkins |
| 6,506,559 | B1 | 1/2003 | Fire |
| 6,573,099 | B2 | 6/2003 | Graham |
| 6,919,466 | B2 | 7/2005 | Lightner |
| 6,933,146 | B2 | 8/2005 | Helliwell |
| 7,138,565 | B2 | 11/2006 | Waterhouse |
| 7,754,697 | B2 | 7/2010 | Graham |
| 8,048,670 | B2 | 11/2011 | Graham |

(Continued)

FOREIGN PATENT DOCUMENTS

| | | |
|---|---|---|
| EP | 0 532 380 A2 | 3/1993 |
| EP | 0 387 775 B1 | 7/1996 |

(Continued)

OTHER PUBLICATIONS

Weiss, B., Davidkova, G. & Zhou, LW. Antisense RNA gene therapy for studying and modulating biological processes. CMLS, Cell. Mol. Life Sci. 55, 334-358 (1999). https://doi.org/10.1007/s000180050296 (Year: 1998).*
Varani (EMBO reports 1.1 (2000): 18-23) (Year: 2000).*
Okamura (Genes & development 27.7 (2013): 778-792) (Year: 2013).*
Xie (Biologia plantarum 58.3 (2014): 575-581) (Year: 2014).*
Montgomery (Cell 133.1 (2008): 128-141) (Year: 2008).*

(Continued)

*Primary Examiner* — Neil P Hammell
*Assistant Examiner* — Kyle T Rega
(74) *Attorney, Agent, or Firm* — Gary J. Gershik

(57) ABSTRACT

The present invention relates to new double stranded RNA (dsRNA) structures and their use in gene silencing.

34 Claims, 45 Drawing Sheets

Figure 1:
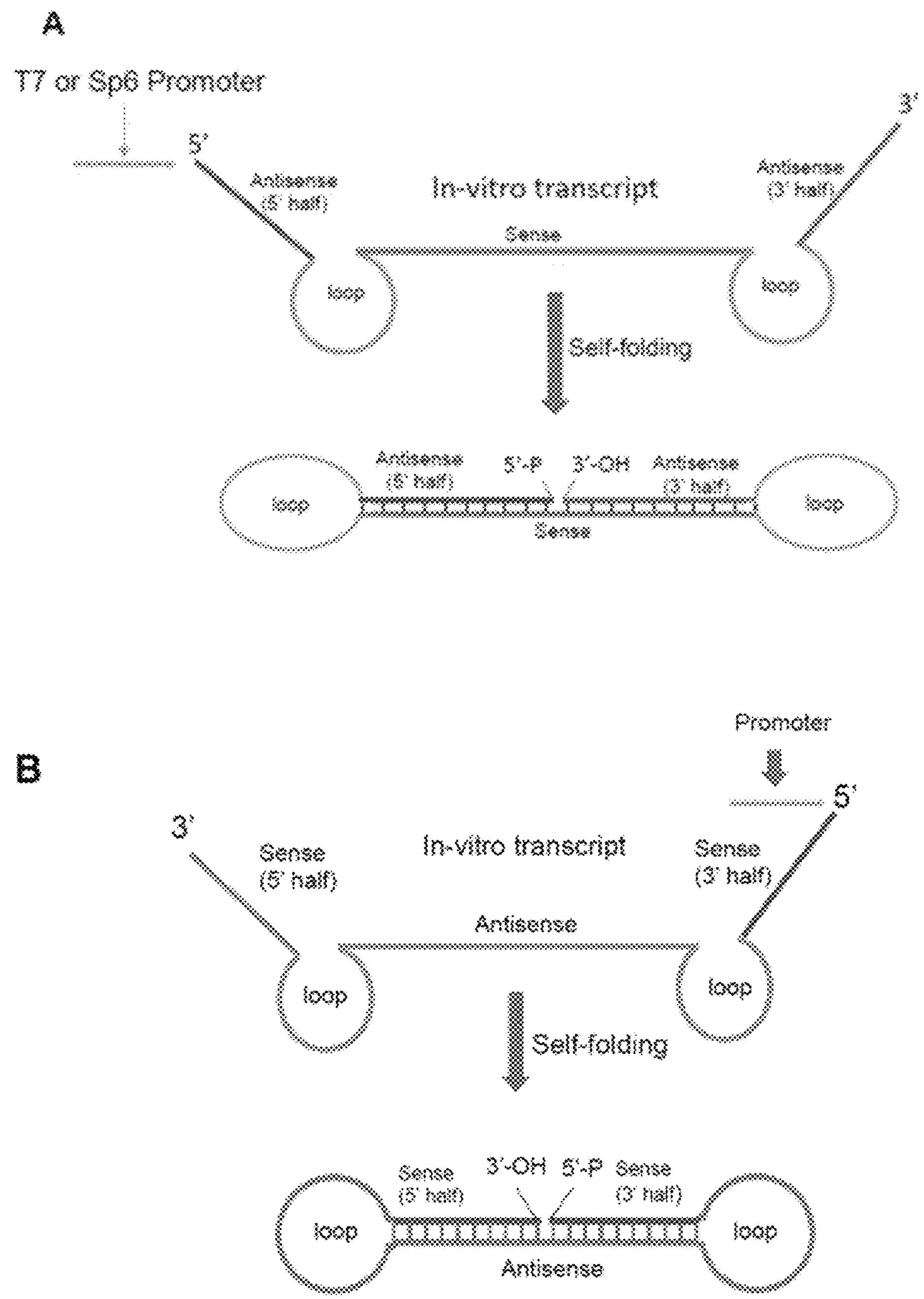

Specification includes a Sequence Listing.

(56) References Cited

U.S. PATENT DOCUMENTS

| | | | |
|---|---|---|---|
| 8,053,419 | B2 | 11/2011 | Graham |
| 8,067,383 | B2 | 11/2011 | Graham |
| 8,101,343 | B2 | 1/2012 | Whyard |
| 8,168,774 | B2 | 5/2012 | Graham |
| 8,183,217 | B2 | 5/2012 | Waterhouse |
| 8,263,573 | B2 | 9/2012 | Whyard |
| 8,293,974 | B2 | 10/2012 | Arbuthnot |
| 8,334,374 | B2 | 12/2012 | Graham |
| 8,415,320 | B2 | 4/2013 | Whyard |
| 8,431,547 | B2 | 4/2013 | Graham |
| 8,877,727 | B2 | 11/2014 | Whyard |
| 9,085,770 | B2 | 7/2015 | Whyard |
| 10,323,245 | B2 | 6/2019 | Whyard |
| 2003/0180945 | A1 | 9/2003 | Wang |
| 2004/0053875 | A1 | 3/2004 | Kreutzer |
| 2004/0053876 | A1 | 3/2004 | Turner |
| 2004/0138166 | A1 | 7/2004 | Damha |
| 2005/0037988 | A1 | 2/2005 | Zamore |
| 2008/0280848 | A1 | 11/2008 | Patzel |
| 2010/0137407 | A1 | 6/2010 | Abe |
| 2010/0305191 | A1 | 12/2010 | McSwiggen |
| 2011/0020816 | A1 | 1/2011 | Chen |
| 2012/0076823 | A1 | 3/2012 | Nair |
| 2012/0277285 | A1 | 11/2012 | Graham |
| 2013/0298264 | A1 | 11/2013 | Graham |
| 2013/0303589 | A1 | 11/2013 | Rossi |
| 2014/0193856 | A1 | 7/2014 | Graham |
| 2015/0259682 | A1 | 9/2015 | Wang |
| 2016/0108400 | A1 | 4/2016 | Ohgi |

FOREIGN PATENT DOCUMENTS

| | | | | |
|---|---|---|---|---|
| EP | 0 784 094 | A1 | 6/2001 | |
| EP | 0 779 365 | B1 | 9/2008 | |
| EP | 2 395 089 | A1 | 12/2011 | |
| EP | 2 431 466 | | 3/2012 | |
| WO | WO 1994/03607 | A1 | 2/1994 | |
| WO | WO 1994/07367 | A1 | 4/1994 | |
| WO | WO 1995/08350 | A1 | 3/1995 | |
| WO | WO 1996/05218 | A1 | 2/1996 | |
| WO | WO 1996/40062 | A1 | 12/1996 | |
| WO | WO 1997/04787 | A1 | 2/1997 | |
| WO | WO 1997/49814 | A1 | 12/1997 | |
| WO | WO 1998/50408 | A1 | 11/1998 | |
| WO | WO 1999/32619 | A1 | 7/1999 | |
| WO | WO 1999/49029 | A1 | 9/1999 | |
| WO | WO 1999/53050 | A1 | 10/1999 | |
| WO | WO 2000/32779 | A1 | 6/2000 | |
| WO | WO 2000/55178 | A1 | 9/2000 | |
| WO | WO 2000/55376 | A1 | 9/2000 | |
| WO | WO 2000/63397 | A2 | 10/2000 | |
| WO | WO 2000/76308 | A1 | 12/2000 | |
| WO | WO 2001/12824 | A1 | 2/2001 | |
| WO | WO 2001/19857 | A2 | 3/2001 | |
| WO | WO 2001/34815 | A1 | 5/2001 | |
| WO | WO 2001/37654 | A2 | 5/2001 | |
| WO | WO 2001/38359 | A2 | 5/2001 | |
| WO | WO 2001/49844 | A1 | 7/2001 | |
| WO | WO 2002/059294 | A1 | 8/2002 | |
| WO | WO 2003/004644 | A1 | 1/2003 | |
| WO | WO 2003/04644 | A1 | 1/2003 | |
| WO | WO 2003/076619 | A1 | 9/2003 | |
| WO | WO 2003/076620 | A1 | 9/2003 | |
| WO | WO 2003/95647 | A2 | 11/2003 | |
| WO | WO 2005/026356 | A1 | 3/2005 | |
| WO | WO 2005/049841 | A1 | 6/2005 | |
| WO | WO 2006/55727 | A2 | 5/2006 | |
| WO | WO 2006/055727 | A2 | 5/2006 | |
| WO | WO 2007/128052 | A1 | 11/2007 | |
| WO | WO 2008/93283 | A2 | 8/2008 | |
| WO | WO 2009/021288 | A1 | 2/2009 | |
| WO | WO 2010/089437 | A1 | 8/2010 | |
| WO | WO 2011/109380 | A1 | 9/2011 | |
| WO | WO 2012/051152 | A2 | 4/2012 | |
| WO | WO 2014/107763 | A1 | 7/2014 | |
| WO | WO-2016100333 | A1 * | 6/2016 | .......... C12N 15/113 |

OTHER PUBLICATIONS

Saayman (RNA Therapeutics: Function, Design, and Delivery. Totowa, NJ: Humana Press, 2010. 157-172) (Year: 2010).*

Holen (Nucleic acids research 33.15 (2005): 4704-4710) (Year: 2005).*

Eamens (Rna 15.12 (2009): 2219-2235) (Year: 2009).*

Horsch (science 227.4691 (1985): 1229-1231) (Year: 1985).*

Liu (Frontiers in microbiology 8 (2017): 256154) (Year: 2017).*

Padmanabhan (PLoS pathogens 9.3 (2013): e1003235) (Year: 2013).*

Abhary (Advances in plant breeding strategies: breeding, biotechnology and molecular tools (2015): 397-427) (Year: 2015).*

Wesley (The Plant Journal 27.6 (2001): 581-590) (Year: 2001).*

Oct. 10, 2003 International Preliminary Examination Report for PCT International Application No. PCT/AU02/00897.

Aug. 12, 2002 International Search Report for PCT International Application No. PCT/AU02/00897.

Jun. 14, 2022 Second Office Action for Russian Application No. 2020113448.

Feb. 9, 2023 Third Office Action for Russian Application No. 2020113448.

Mar. 21, 2023 First Office Action for Canadian Application No. 3075746.

Jan. 30, 2023 First Office Action for Indonesian Application No. P00202002784.

Aug. 29, 2022 First Office Action for Japanese Application No. JP2020-515126.

Feb. 28, 2023 First Office Action for Chinese Application No. 201880072998.2.

Apr. 24, 2023 Second Office Action for Japanese Application No. JP2020-515126.

Feb. 7, 2023 First Office Action for Australian Application No. 2019313162.

Mar. 20, 2023 First Office Action for Canadian Application No. 3108536.

Oct. 27, 2022 First Office Action for Indonesian Application No. P00202101536.

Jun. 23, 2020 International Preliminary Examination Report for PCT International Application No. PCT/AU2019/050814.

Oct. 16, 2019 International Search Report for PCT International Application No. PCT/AU2019/050814.

Apr. 22, 2021 Extended European Search Report for European Application No. 19844044.8.

Oct. 25, 2022 Response filed to first Office Action for Australian Application No. 2018333285.

Allen, Danny, et al. "Development of strategies for conditional RNA interference." The Journal of Gene Medicine: A cross-disciplinary journal for research on the science of gene transfer and its clinical applications 9.4 (2007): 287-298.

Appel, H. M., and L. W. Maines. "The influence of host plant on gut conditions of gypsy moth (*Lymantria dispar*) caterpillars." Journal of Insect Physiology 41.3 (1995): 241-246.

Baulcombe, David C. "Mechanisms of pathogen-derived resistance to viruses in transgenic plants." The plant cell 8.10 (1996): 1833.

Beck, Jürgen, and Michael Nassal. "Efficient hammerhead ribozyme-mediated cleavage of the structured heapatitis B virus encapsidation signal in vitro and in cell extracts, but not in intact cells." Nucleic Acids Research 23.24 (1995): 4954-4962.

Bosher, Julia M., and Michel Labouesse. "RNA interference: genetic wand and genetic watchdog." Nature Cell Biology 2.2 (2000).

Bourque, June E., and William R. Folk. "Suppression of gene expression in plant cells utilizing antisense sequences transcribed by RNA polymerase III." Plant molecular biology 19 (1992): 641-647.

Brown, Susan J., et al. "Using RNAi to investigate orthologous homeotic gene function during development of distantly related insects." Evolution & development 1.1 (1999): 11-15.

Caplen, Natasha J., et al. "dsRNA-mediated gene silencing in cultured *Drosophila* cells: a tissue culture model for the analysis of RNA interference." Gene 252.1-2 (2000): 95-105.

(56) References Cited

OTHER PUBLICATIONS

Carthew, Richard W. "Gene silencing by double-stranded RNA." Current opinion in cell biology 13.2 (2001): 244-248.
De Angelis, Fernanda Gabriella, et al. "Chimeric snRNA molecules carrying antisense sequences against the splice junctions of exon 51 of the dystrophin pre-mRNA induce exon skipping and restoration of a dystrophin synthesis in Δ48-50 DMD cells." Proceedings of the National Academy of Sciences 99.14 (2002): 9456-9461.
Dougherty, William G., and T. Dawn Parks. "Transgene and gene suppression: telling us something new ?." Current opinion in cell biology 7.3 (1995): 399-405.
Dorer, Douglas R., and Steven Henikoff "Expansions of transgene repeats cause heterochromatin formation and gene silencing in *Drosophila*." Cell 77.7 (1994): 993-1002.
Ebhardt, H. Alexander, et al. "Extensive 3' modification of plant small RNAs is modulated by helper component-proteinase expression." Proceedings of the National Academy of Sciences 102.38 (2005): 13398-13403.
Ecker, Joseph R., and Ronald W. Davis. "Inhibition of gene expression in plant cells by expression of antisense RNA." Proceedings of the National Academy of Sciences 83.15 (1986): 5372-5376.
Elbashir, Sayda M., Winfried Lendeckel, and Thomas Tuschl. "RNA interference is mediated by 21-and 22-nucleotide RNAs." Genes & development 15.2 (2001): 188-200.
Elbashir, S. M., et al. "Duplexes of 21—nucleotide RNAs mediate RNA interference in cultured mammalian cells." Nature 411: 6836.
Goto, Akira, et al. "*Drosophila* mitochondrial transcription factor A (d-TFAM) is dispensable for the transcription of mitochondrial DNA in Kc167 cells." Biochemical Journal 354.2 (2001): 243-248.
Gura, Trisha "A Silence that Speaks Volume: A biological gagging order, used in the fight against viruses, could revolutionize our understanding of genetics and development. Trisha Gura listens in on the world of gene silencing." Nature 404 (2000): 804-808.
Furusawa, Toshiharu, et al. "Double-stranded ribonuclease activity in the digestive juice and midgut of the silkworm, *Bombyx mori*." Comparative Biochemistry and Physiology Part B: Comparative Biochemistry 104.4 (1993): 795-801.
Izant, Jonathan G., and Harold Weintraub. "Inhibition of thymidine kinase gene expression by anti-sense RNA: a molecular approach to genetic analysis." Cell 36.4 (1984): 1007-1015.
Kennerdell, Jason R., and Richard W. Carthew. "Use of dsRNA-mediated genetic interference to demonstrate that frizzled and frizzled 2 act in the wingless pathway." Cell 95.7 (1998): 1017-1026.
Kennerdell, Jason R., and Richard W. Carthew. "Heritable gene silencing in *Drosophila* using double-stranded RNA." Nature biotechnology 18.8 (2000): 896-898.
Kim, Hangil, Hanako Shimura, and Chikara Masuta. "Advancing toward commercial application of RNA silencing-based strategies to protect plants from viral diseases." Journal of general plant pathology 85 (2019): 321-328.
Misquitta, Leonie, and Bruce M. Paterson. "Targeted disruption of gene function in Drosophila by RNA interference (RNA-i): a role for nautilus in embryonic somatic muscle formation." Proceedings of the National Academy of Sciences 96.4 (1999): 1451-1456.
Maeda, Ikuma, et al. "Large-scale analysis of gene function in Caenorhabditis elegans by high-throughput RNAi." Current Biology 11.3 (2001): 171-176.
Martinek, Sebastian, and Michael W. Young. "Specific genetic interference with behavioral rhythms in *Drosophila* by expression of inverted repeats." Genetics 156.4 (2000): 1717-1725.
Miller, Sherry C, Susan J. Brown, and Yoshinori Tomoyasu. "Larval RNAi in *Drosophila* ?." Development genes and evolution 218 (2008): 505-510.
Mishra, Krishna K., and Avtar K. Handa. "Post-transcriptional silencing of pectin methylesterase gene in transgenic tomato fruits results from impaired pre-mRNA processing." The Plant Journal 14.5 (1998): 583-592.
Murfett, Jane, June E. Bourque, and Bruce A. McClure. "Antisense suppression of S-RNase expression in Nicotiana using RNA polymerase II-and III-transcribed gene constructs." Plant molecular biology 29 (1995): 201-212.
Patankar, Aparna G., et al. "Complexity in specificities and expression of Helicoverpa armigera gut proteinases explains polyphagous nature of the insect pest." Insect biochemistry and molecular biology 31.4-5 (2001): 453-464.
Piccin, Alberto, et al. "Efficient and heritable functional knock-out of an adult phenotype in *Drosophila* using a GAL4-driven hairpin RNA incorporating a heterologous spacer." Nucleic acids research 29.12 (2001): e55-e55.
Rajagopal, R., et al. "Silencing of Midgut Aminopeptidase N of Spodoptera litura by Double-stranded RNA Establishes Its Role asBacillus thuringiensis Toxin Receptor." Journal of Biological Chemistry 277.49 (2002): 46849-46851.
Suter, Daniel, et al. "Double-target antisense U7 snRNAs promote efficient skipping of an aberrant exon in three human β-thalassemic mutations." Human molecular genetics 8.13 (1999): 2415-2423.
Tabara, Hiroaki, Alla Grishok, and Craig C. Mello. "RNAi in C. elegans: soaking in the genome sequence." Science 282.5388 (1998): 430-431.
Tieman, Denise M., et al. "An antisense pectin methylesterase gene alters pectin chemistry and soluble solids in tomato fruit." The Plant Cell 4.6 (1992): 667-679.
Timmons, Lisa, and Andrew Fire. "Specific interference by ingested dsRNA." Nature 395.6705 (1998): 854-854.
Vance, Vicki, and Hervé Vaucheret. "RNA silencing in plants—defense and counterdefense." science 292.5525 (2001): 2277-2280.
Waterhouse, Peter M., Michael W. Graham, and Ming-Bo Wang. "Virus resistance and gene silencing in plants can be induced by simultaneous expression of sense and antisense RNA." Proceedings of the National Academy of Sciences 95.23 (1998): 13959-13964.
Waterhouse, Peter M., Ming-Bo Wang, and Tony Lough. "Gene silencing as an adaptive defence against viruses." Nature 411.6839 (2001): 834-842.
Weiher, Birgit, and Hans Komnick. "Digestion of phosphatidylcholines, absorption, and esterification of lipolytic products by Aeshna cyanea larvae as studied in vivo and in vitro." Archives of Insect Biochemistry and Physiology: Published in Collaboration with the Entomological Society of America 36.4 (1997): 273-293.
Wesley, S. Varsha, et al. "Construct design for efficient, effective and high-throughput gene silencing in plants." The Plant Journal 27.6 (2001): 581-590.
Yang, Dun, Hong Lu, and James W. Erickson. "Evidence that processed small dsRNAs may mediate sequence-specific mRNA degradation during RNAi in *Drosophila* embryos." Current Biology 10.19 (2000): 1191-1200.
Zamore, Phillip D. "RNA interference: listening to the sound of silence." Nature structural biology 8.9 (2001): 746-750.
Zamore, Phillip D., et al. "RNAi: double-stranded RNA directs the ATP-dependent cleavage of mRNA at 21 to 23 nucleotide intervals." cell 101.1 (2000): 25-33.
NCBI Reference Sequence: AAS58481; ZCCT1 [Triticum monococcum], published Mar. 19, 2004.
NCBI Reference Sequence: AF143940; *Arabidopsis thaliana* SWI2/SNF2-like protein (DDM1) gene, complete cds; and tRNA-Glu gene, complete sequence, published May 11, 1999.
NCBI Reference Sequence: AF361932; Triticum aestivum seven transmembrane-spanning protein (Mlo2) mRNA, complete cds, published Feb. 10, 2003.
NCBI Reference Sequence: AF361933; Triticum aestivum seven transmembrane-spanning protein (Mlo1) mRNA, partial cds, published Jul. 23, 2016.
NCBI Reference Sequence: AF384145; Triticum aestivum MLo1 protein mRNA, complete cds, published Jan. 20, 2006.
NCBI Reference Sequence: AX063294; Sequence 3 from Patent WO0078799, published Jan. 24, 2001.
NCBI Reference Sequence: AX063296; Sequence 5 from Patent WO0078799, published Jan. 24, 2001.
NCBI Reference Sequence: AX063298; Sequence 7 from Patent WO0078799, published Jan. 24, 2001.

(56) References Cited

OTHER PUBLICATIONS

NCBI Reference Sequence: AB051865; Glycine max gene for beta-conglycinin alpha subunit, complete cds, published Jan. 8, 2003.
NCBI Reference Sequence: AF044293; *Zea mays* subsp. parviglumis strain P331786 alcohol dehydrogenase 1 (adh1) gene, exons 4 through 10 and partial cds, published Jul. 24, 2016.
NCBI Reference Sequence: X04333; Pea rbcS-3A gene for ribulose 1.5-bisphosphate carboxylase (RBC) small subunit, published PLN Nov. 14, 2006.
NCBI Reference Sequence: LT601589; Hordeum vulgare ALS gene for acetolactate synthase, cultivar Golden Promise, published Dec. 22, 2016.
NCBI Reference Sequence: NM_001333162; Arabidopsis thaliana DEAD/DEAH box RNA helicase family protein (FANCM), mRNA, published Oct. 20, 2022.
NCBI Reference Sequence: TaMlo-A1; Sequence 43 from Patent WO2017013409, published Jul. 12, 2017.
NCBI Reference Sequence: TaMlo-B1; Sequence 44 from Patent WO2017013409, published Jul. 12, 2017.
NCBI Reference Sequence: TaMlo-D1; Sequence 45 from Patent WO2017013409, published Jul. 12, 2017.
NCBI Reference Sequence: U75355; Lucilia cuprina ecdysteroid receptor (EcR) mRNA, complete cds, published Oct. 17, 2005.
NCBI Reference Sequence: XM_018659358; Predicted: *Brassica rapa* DEAD-box ATP-dependent RNA helicase FANCM (LOC103868821), mRNA, published Dec. 7, 2020.
NCBI Reference Sequence: XM_022308286; Predicted: Myzus persicae uncharacterized LOC111029319 (LOC111029319), mRNA, published Aug. 11, 2017.
NCBI Reference Sequence: XM_022312248; Predicted: Myzus persicae V-type proton ATPase subunit E (LOC111032063), mRNA, published Aug. 11, 2017.
NCBI Reference Sequence: XM_022313196; Predicted: Myzus persicae bombyxin C-2-like (LOC111032749), mRNA, published Aug. 11, 2017.
NCBI Reference Sequence: XM_022313819; Predicted: Myzus persicae protein hunchback (LOC111033178), mRNA, published Aug. 11, 2017.
NCBI Reference Sequence: XM_022314068; Predicted: Myzus persicae short neuropeptide F (LOC111033374), mRNA, published Aug. 11, 2017.
NCBI Reference Sequence: XM_022321900; Predicted: Myzus persicae tubulin-specific chaperone D (LOC111038691), mRNA, published Aug. 11, 2017.
NCBI Reference Sequence: XM_022323100; Predicted: Myzus persicae uncharacterized LOC111039542 (LOC111039542), mRNA, published Aug. 11, 2017.
NCBI Reference Sequence: XM_023443547; Predicted: Lucilia cuprina V-type proton ATPase catalytic subunit A (LOC111681663), transcript variant X2, mRNA, published Mar. 3, 2022.
NCBI Reference Sequence: XM_023448015; Predicted: Lucilia cuprina uncharacterized LOC111685735 (LOC111685735), mRNA, published Mar. 3, 2022.
NCBI Reference Sequence: XM_023449557; Predicted: Lucilia cuprina uncharacterized LOC111687139 (LOC111687139), mRNA, published Jan. 5, 2018.
NCBI Reference Sequence: XM_023449717; Predicted: Lucilia cuprina tubulin gamma-1 chain (LOC111687287), mRNA, published Mar. 3, 2022.
May 19, 2006 Office Action in connection with U.S. Appl. No. 10/482,888.
Oct. 23, 2006 Amendment in Response to May 19, 2006 Office Action in connection with U.S. Appl. No. 10/482,888.
Jan. 8, 2007 Restriction Requirement in connection with U.S. Appl. No. 10/482,888.
Feb. 12, 2007 Amendment in Response to Jan. 8, 2007 Restriction Requirement in connection with U.S. Appl. No. 10/482,888.
May 1, 2007 Final Office Action in connection with U.S. Appl. No. 10/482,888.
May 15, 2007 Amendment t in Response to May 1, 2007 Final Office Action in connection with U.S. Appl. No. 10/482,888.
Jun. 1, 2007 Advisory Action in connection with U.S. Appl. No. 10/482,888.
Jul. 11, 2007 Advisory Action in connection with U.S. Appl. No. 10/482,888.
Aug. 28, 2007 Amendment in Response to May 1, 2007 Final Office Action in connection with U.S. Appl. No. 10/482,888.
Nov. 14, 2007 Office Action in connection with U.S. Appl. No. 10/482,888.
May 14, 2008 Response to Nov. 14, 2007 Office Action in connection with U.S. Appl. No. 10/482,888.
Aug. 13, 2008 Final Office Action in connection with U.S. Appl. No. 10/482,888.
Aug. 17, 2009 Amendment in connection with U.S. Appl. No. 10/482,888.
Sep. 9, 2009 Supplemental Response to Aug. 17, 2009 122 Amendment in connection with U.S. Appl. No. 10/482,888.
Sep. 25, 2009 Second Supplemental Response to Aug. 17, 2009 Amendment in connection with U.S. Appl. No. 10/482,888.
Dec. 30, 2009 Office Action in connection with U.S. Appl. No. 10/482,888.
Jun. 30, 2010 Communication in Response to Dec. 30, 2009 Office Action in connection with U.S. Appl. No. 10/482,888.
Sep. 22, 2010 Final Office Action in connection with U.S. Appl. No. 10/482,888.
Feb. 22, 2011 Amendment in Response to Sep. 22, 2010 Final Office Action in connection with U.S. Appl. No. 10/482,888.
Apr. 18, 2011 Office Action in connection with U.S. Appl. No. 10/482,888.
Sep. 19, 2011 Response to Apr. 18, 2011 Office Action in connection with U.S. Appl. No. 10/482,888.
Oct. 27, 2011 Notice of Allowance issued in connection with U.S. Appl. No. 10/482,888.
Mar. 1, 2012 Office Action, issued in connection with U.S. Appl. No. 13/243,413.
Apr. 2, 2012 Response to Office Action, filed in connection with U.S. Appl. No. 13/243,413.
May 24, 2012 Notice of Allowance, issued in connection with U.S. Appl. No. 13/243,413.
Nov. 23, 2012 Notice of Allowance, issued in connection with U.S. Appl. No. 13/545,604.
Jul. 8, 2013 Office Action, issued in connection with U.S. Appl. No. 13/857,844.
Aug. 8, 2013 Response, filed in connection with U.S. Appl. No. 13/857,844.
Sep. 17, 2013 Office Action, issued in connection with U.S. Appl. No. 13/857,844.
Mar. 17, 2014 Response, filed in connection with U.S. Appl. No. 13/857,844.
Apr. 28, 2014 Office Action, issued in connection with U.S. Appl. No. 13/857,844.
May 19, 2014 Response, filed in connection with U.S. Appl. No. 13/857,844.
Jun. 4, 2014 Notice of Allowance, issued in connection with U.S. Appl. No. 13/857,844.
Bourhill, T., et al. (2016). Successful disabling of the 5' UTR of HCV using adeno-associated viral vectors to deliver modular multimeric primary microRNA mimics. Journal of virological methods, 235, 26-33.
Du, X., et al. (2018). Multi-target inhibition by four tandem shRNAs embedded in homo-or hetero-miRNA backbones. Molecular Medicine Reports, 17(1), 307-314.
Fahim, M., et al. (2012). Resistance to Wheat streak mosaic virus generated by expression of an artificial polycistronic microRNA in wheat. Plant biotechnology journal, 10(2), 150-163.
Fowler, D. K., et al. (2016). Improved knockdown from artificial microRNAs in an enhanced miR-155 backbone: a designer's guide to potent multi-target RNAi. Nucleic acids research, 44(5), e48-e48.
Higuchi, M., et al. (2009). Simple construction of plant RNAi vectors using long oligonucleotides. Journal of plant research, 122, 477-482.

(56) References Cited

OTHER PUBLICATIONS

Huang, M., et al. (2016). A novel multi-target RNAi adenovirus inhibits hepatoma cell proliferation, migration, and induction of angiogenesis. Oncotarget, 7(36), 57705.
Israsena, N., et al. (2009). Inhibition of rabies virus replication by multiple artificial microRNAs. Antiviral Research, 84(1), 76-83.
Liu, Y. P., et al. (2008). Inhibition of HIV-1 by multiple siRNAs expressed from a single microRNA polycistron. Nucleic acids research, 36(9), 2811-2824.
Liu, Y. P., et al. (2009). Combinatorial RNAi against HIV-1 using extended short hairpin RNAs. Molecular Therapy, 17(10), 1712-1723.
Qiu, X., et al. (2011). Creating a flexible multiple microRNA expression vector by linking precursor microRNAs. Biochemical and biophysical research communications, 411(2), 276-280.
Saayman, S., et al. (2008). The efficacy of generating three independent anti-HIV-1 siRNAs from a single U6 RNA Pol III-expressed long hairpin RNA. PLoS One, 3(7), e2602.
Seyhan, A. A. (2016). A multiplexed miRNA and transgene expression platform for simultaneous repression and expression of protein coding sequences. Molecular BioSystems, 12(1), 295-312.
Shan, Z. X., et al. (2009). A quick and efficient approach for gene silencing by using triple putative microRNA-based short hairpin RNAs. Molecular and cellular biochemistry, 323, 81-89.
Soifer, H. S., et al. (2008). A role for the Dicer helicase domain in the processing of thermodynamically unstable hairpin RNAs. Nucleic acids research, 36(20), 6511-6522.
Van Den Berg, F. T., et al. (2016). Design of effective primary microRNA mimics with different basal stem conformations. Molecular Therapy-Nucleic Acids, 5.
Wang, T., et al. (2016). Construction and characterization of a synthetic MicroRNA cluster for multiplex RNA interference in mammalian cells. ACS Synthetic Biology, 5(11), 1193-1200.
Weinberg, M. S., et al. (2007). Specific inhibition of HBV replication in vitro and in vivo with expressed long hairpin RNA. Molecular Therapy, 15(3), 534-541.
Zhu, X., et al. (2007). A versatile approach to multiple gene RNA interference using microRNA-based short hairpin RNAs. BMC molecular biology, 8, 1-11.
Feb. 7, 2023 First Examination Report issued in connection with Australian patent application No. 2019313162.
Oct. 23, 2023 Office Action issued in connection with Israeli Patent Application No. 273245.
Nov. 1, 2023 Office Action issued in connection with Thai Patent Application No. 2101000623 and English language translation thereof.
Nov. 7, 2023 Office Action issued in connection with Malaysian Patent Application No. PI 2020001363.
Nov. 11, 2023 Extended European Search Report issued in connection with European Patent Application No. 19844044.8.
Feb. 2, 2024 Response to Feb. 7, 2023 First Examination Report filed in connection with Australian patent application No. 2019313162.
Feb. 5, 2024 Second Examination Report issued in connection with Australian patent application No. 2019313162.
Feb. 6, 2024 Office Action issued in connection with Philippine Patent Application No. 1-2020-500527.
Feb. 6, 2024 Response to Feb. 5, 2024 Second Examination Report filed in connection with Australian patent application No. 2019313162.
Feb. 7, 2024 issued in connection with Thai Patent Application 2001001482 including English language translation thereof.
Feb. 7, 2024 Response to Nov. 7, 2023 Office Action filed in connection with Malaysian Patent Application No. PI 2020001363.
Feb. 21, 2024 Response to Office Action filed in connection with Israeli Patent Application 273245.
Mar. 25, 2024 Office Action issued in connection with Malaysian Patent Application No. PI 2021000568.
Apr. 8, 2024 Response to Feb. 6, 2024 Office Action filed in connection with Philippine Patent Application No. 1-2020-500527.
May 16, 2024 Office Action issued in connection with Philippine Patent Application No. 1-2021-5000009.
May 27, 2024 Notice of Final Rejection issued in connection with South Korean Patent Application No. 10-2020-7010839 and English language translation thereof.
Jun. 25, 2024 Response to Mar. 25, 2024 Office Action filed in connection with Malaysian patent application No. PI 2021000568.
Jun. 26, 2024 Third Examination Report issued in connection with Chinese Patent Application No. 201880072998.2 and English language translation thereof.
Sep. 16, 2024 First Examination Report issued in connection with Australian Patent Application No. 2023200995 (Divisional of AU 2018333285).
Sep. 16, 2024 Response to May 16, 2024 Office Action filed in connection with Philippine Patent Application No. 1-2021-5000009.
Dec. 28, 2024 Pre-Appeal Report issued in conneciton with Japanese patent application 2020-515126 and English translation thereof.
Feb. 26, 2025 Decision of Rejection issued in connection with Japanese Patent Application No. 2021-529494 and English language translation thereof.
Jan. 17, 2024 First Office Action for Chinese Application No. 201980065254.2 and English translation thereof.
Sano, Masayuki, et al. "Expression of long anti-HIV-1 hairpin RNAs for the generation of multiple siRNAs: advantages and limitations." Molecular Therapy 16.1 (2008): 170-177.
Dong, et al. "DRD1-Pol V-dependent self-silencing of an exogenous silencer restricts the non-cell autonomous silencing of an endogenous target gene" The Plant Journal 68, 633-645 (e-pub Aug. 30, 2011).
Hsieh and Fire. "Recognition and silencing of Repeated DNA" Annu. Rev. Genet. 34: 187-204 (2000).
Jeddeloh, et al. "Maintenance of genomic methylation requires a SWI2/SNF2-like protein" Nature Genetics 22: 94-97 (May 1999).
Mutti, et al. "A protein from the salivary glands of the pea aphid, Acyrthosiphon pisum, is essential in feeding on a host plant" Proc. Nat'l. Acad. Sci. USA 105 (29): 9965-9969 (Jul. 22, 2008).
Pitino and Hogenhout. "Aphid Protein Effectors Promote Aphid Colonization in a Plant Species-Specific Manner" Molecular Plant-Microbe Interactions 26 (1): 130-139 (Jan. 2013).
Pitino, et al. "Silencing of Aphid Genes by dsRNA Feeding from Plants" PLoS ONE 6 (10): e25709 (Oct. 5, 2011).
Scott, et al. "Towards the elements of successful insect RNAi" Journal of Insect Physiology 59: 1212-1221 (e-pub Sep. 13, 2013).
Smith, et al. "Total silencing by intronspliced hairpin RNAs" Nature 407, 319-320 (Sep. 21, 2000).
Timmons, et al. "Ingestion of bacterially expressed dsRNAs can produce specific and potent genetic interference in Caenorhabditis elegans" Gene 263: 103-112 (2001).
Wang, et al. "Characterization and sequencing of eDNA clone encoding the phloem protein PP2 of Cucurbita pepo" Plant Molecular Biology 24: 159-170 (1994).
Wang, et al. "Improved vectors for Agrobacterium tumefaciens-mediated transformation of monocot plants" Acta Horticulturae 461: 401-407 (1998).
Wang, et al. "Hairpin RNAs derived from RNA polymerase II and polymerase III promoter-directed transgenes are processed differently in plants" RNA 14(5): 903-913 (2008).
Wang, et al. "A Minimal Nitrogen Fixation Gene Cluster from *Paenibacillus* sp. WLY78 Enables Expression of Active Nitrogenase in *Escherichia coli*" PLOS Genetics 9(10): e1003865 (Oct. 17, 2013).
Wang, et al. "The concordance between RNA-seq and microarray data depends on chemical treatment and transcript abundance" Nature Biotechnology 32: 926-932 (e-pub Aug. 24, 2014).
Yu, et al. "RNAi-mediated plant protection against aphids" Pest Management Science 72: 1090-1098 (2016).
Zhang, et al. "Dynamics and function of DNA methylation in plants" Nat. Rev. Mol. Cell Biol. 19: 489-506 (2018).
Abe et al., "Synthesis, Structure, and Biological Activity of Dumbbell-Shaped Nanocircular RNAs for RNA Interference", Bioconjugate Chemistry, 2011, vol. 22, No. 10, pp. 2082-2092 (Abstract Only).
Brennecke, J. et al., "Principles of MicroRNA-Target Recognition", PLOS Biology, 2005, vol. 3, p. E85.

(56) References Cited

OTHER PUBLICATIONS

Cao, W. et al. "Functional characterization of the bovine foamy virus miRNA expression cassette and its dumbbell-shaped pri-miRNA", Virus Genes, 2018, vol. 54, pp. 550-560.
Dennis, M., "Welfare Issues of Genetically Modified Animals", ILAR Journal, 2002 vol. 43, No. 2, pp. 100-109.
Guo, Q. et al., "RNA Silencing in Plants: Mechanisms, Technologies and Applications in Horticultural Crops", Current Genomics, 2016, vol. 17, pp. 476-489.
Helliwell C.A. and Waterhouse, P.M., "Constructs and Methods for Hairpin RNA-Mediated Gene Silencing in Plants", Methods in enzymology, 2005, vol. 392, pp. 24-35.
Herrera-Carrillo, E. et al., "Probing the shRNA characteristics that hinder Dicer recognition and consequently allow Ago-mediated processing and AgoshRNA activity", RNA, 2014, vol. 20, pp. 1410-1418.
Khan, S.A. et al., "Functional analysis of the ABCs of eye color in Helicoverpa armigera with CRISPR/Cas9-induced mutations", Scientific Reports, 2016, vol. 7, pp. 1-14.
Liu, C. et al., "Efficacy Analysis of Combinatorial siRNA against HIV Derived from One Double Hairpin RNA Precursor", Frontiers in Microbiology, 2017, vol. 8, article 1651.
Melamed-Bessudo, C. and Levy, A.A., "Deficiency in DNA methylation increases meiotic crossover rates in euchromatic but not in heterochromatic regions in *Arabidopsis*", PNAS, 2012, vol. 109, pp. E981-E988.
Mutti, N.M. et al., "RNAi knockdown of a salivary transcript leading to lethality in the pea aphid, *Acyrthosiphon pisum*", Journal of Insect Science, 2006, vol. 6, article 38.
Saayman, S. et al., "Deriving four functional anti-HIV siRNAs from a single Pol III-generated transcript comprising two adjacent long hairpin RNA precursors", Nucleic Acids Research, 2010, vol. 38, No. 19, pp. 6652-6663.
Smith, N.A. et al., "Total silencing by intronspliced hairpin RNAs", Nature, 2000, vol. 407, pp. 319-320.
Zhou, H. et al., "Developing tTA Transgenic Rats for Inducible and Reveraible Gene Expression", International Journal of Biological Sciences, 2009, vol. 5, No. 2, pp. 171-181.
European Search Report issued Apr. 22, 2021 in connection with European Application No. 18856496.7.
Nov. 5, 2021 First Examination Report issued in connection with Australian Patent Application No. 2018333285.
Feb. 23, 2022 Response to European Search Report issued in connection with European Application No. 18856496.7.
Feb. 10, 2022 Official Action issued in connection with Russian Patent Application No. 2020113448 (including English language translation).
International Preliminary Report on Patentability issued Mar. 17, 2020 in connection with PCT International Application No. PCT/AU2018/051015.
Written Opinion of the International Searching Authority issued Nov. 23, 2018 in connection with PCT International Application No. PCT/AU2018/051015.
Feb. 7, 2023 Office Action issued in connection with U.S. Appl. No. 16/647,241.
Apr. 7, 2023 Amendment in Response to Feb. 7, 2023 Office Action filed in connection with U.S. Appl. No. 16/647,241.
Feb. 1, 2024 Final Office Action issued in connection with U.S. Appl. No. 16/647,241.
Jul. 24, 2024 Amendment in Response to Jul. 21, 2023 Office Action filed in connection with U.S. Appl. No. 16/647,241.
Aug. 22, 2024 Advisory Action issued in connection with U.S. Appl. No. 16/647,241.
Oct. 1, 2024 Amendment in Response to the Feb. 1, 2024 Final Office Action and Aug. 22, 2024 Advisory Action issued in connection with U.S. Appl. No. 16/647,241.
Nov. 4, 2024 Office Action issued in connection with U.S. Appl. No. 16/647,241.
Aug. 10, 2023 Office Action issued in connection with South Korean Patent Application 10-2020-7010839 and English translation thereof.
Saayman, S., Arbuthnot, P., & Weinberg, M. S. (2010). Deriving four functional anti-HIV siRNAs from a single Pol III-generated transcript comprising two adjacent long hairpin RNA precursors. Nucleic acids research, 38(19), 6652-6663.
Oct. 24, 2024 Second Examination Report issued in connection with Chinese patent application 201980065254.2 including English language translation thereof.
Nov. 18, 2024 Pre-Appeal Examination Report issued in connection with Japanese Patent Application 2021-529494 including English language translation thereof.
Nov. 25, 2024 Office Action issued in connection with Philippine patent application 1-2021-5000009.
Jan. 22, 2025 Response to Nov. 25, 2024 Office Action filed in connection with Philippine patent application 1-2021-5000009.
Dec. 26, 2024 Office Action issued in connection with Israeli Patent Application 280562.
Oct. 29, 2024 Preliminary Examination Report issued in connection with Brazilian Patent Application No. 112020005103 9 and English language translation thereof.
Jan. 7, 2025 Office Action issued in connection with Philippine Patent Application No. 1-2020-500527.
Jan. 27, 2025 Formality Examination Report dated Jan. 27, 2025 issued in connection with Philippine Patent Application No. 1-2024-550882 (Divisional PH 1-2020-500527).
Jan. 21, 2025 Second Examination Report issued in connection with Canadian Patent Application No. 3075746.
Feb. 16, 2025 Office Action issued in connection with South Korean patent application 10-2021-7006457 including English language translation thereof.
May 30, 2024 Response to Communication under R.70(2) and R.70a(2) EPC filed in connection with European Patent Application No. 19844044.8.
Mar. 7, 2025 Response to Jan. 7, 2025 Office Action filed in connection with Philippine Patent Application No. 1-2020-500527.
Mar. 27, 2025 Response to Jan. 27, 2025 Formality Examination Report filed in connection with Philippine Patent Application No. 1-2024-550882 (Divisional of PH 1-2020-500527).
Mar. 31, 2025 Decision of Rejection issued in connection with Chinese Patent Application No. 201980065254.2 and English language translation thereof.

* cited by examiner

Alignment with WT GUS ORF

```
GUS         GAGTGTGATATCTACCCGCTTCGCGTCGGCATCCGGTCAGTGGCAGTGAAGGGCGAACAG 840
GUS-GU      --------------------TTGTGTTGGTATTTGGTTAGTGGTAGTGAAGGGTGAATAG 40
                                * * ** ** **  *** ***** ********* *** **

GUS         TTCCTGATTAACCACAAACCGTTCTACTTTACTGGCTTTGGTCGTCATGAAGATGCGGAC 900
GUS-GU      TTTTTGATTAATTATAAATTGTTTTATTTTATTGGTTTTGGTTGTTATGAAGATGTGGAT 100
            **  *******  * ***  *** ** **** *** ****** ** ********* ***

GUS         TTGCGTGGCAAAGGATTCGATAACGTGCTGATGGTGCACGACCACGCATTAATGGACTGG 960
GUS-GU      TTGTGTGGTAAAGGATTTGATAATGTGTTGATGGTGTATGATTATGTATTAATGGATTGG 160
            *** **** ******** ***** *** ******** * **  * * ********* ***

GUS         ATTGGGGCCAACTCCTACCGTACCTCGCATTACCCTTACGCTGAAGAGATGCTCGACTGG 1020
GUS-GU      ATTGGGGTTAATTTTTATTGTATTTTGTATTATTTTTATG-------------------- 200
            *******  ** *  **  ***  * * ****   *** *
```

FIGURE 7

```
GUS          GAGTGTGATATCTACCCGCTTCGCGTCGGCATCCGGTCAGTGGCAGTGAAGGGCGAACAG 840
GUS-4M       --------------------TCGGGTCCGCAACCGCTCACTGGGAGTCAAGCGCGTACAC 40
                                 *** *** ***:*** *** *** *** *** ***:***

GUS          TTCCTGATTAACCACAAACCGTTCTACTTTACTGGCTTTGGTCGTCATGAAGATGCGGAC 900
GUS-4M       TTCGTGAATAAGCACTAACGGTTGTACATTAGTGGGTTTCGTCCTCAAGAACATGGGGAG 100
             *** ***:*** ***:*** *** ***:*** *** *** *** ***:*** *** ***

GUS          TTGCGTGGCAAAGGATTCGATAACGTGCTGATGGTGCACGACCACGCATTAATGGACTGG 960
GUS-4M       TTGGGTGCCAATGGAATCGTTAAGGTGGTGAAGGTCCACCACCTCGCTTTATTGGTCTGC 160
             *** *** ***:***:***:*** *** ***:*** *** ***:***:***:***:***

GUS          ATTGGGGCCAACTCCTACCGTACCTCGCATTACCCTTACGCTGAAGAGATGCTCGACTGG 1020
GUS-4M       ATTCGGGGCAAGTCCAACCCTACGTCGGATTTCCCATACC-------------------- 200
             *** *** *** ***:*** *** *** ***:***:***
```

FIGURE 8

Alignment with WT GUS ORF

```
GUS        GAGTGTGATATCTACCCGCTTCGCGTCGGCATCCGGTCAGTGGCAGTGAAGGGCGAACAG 840
GUS-10M    --------------------TCGCGTCGGCATCCGGTCTCTGGCAGTGTTGGGCGAACTC 40
                               ********   ********: ********::********:

GUS        TTCCTGATTAACCACAAACCGTTCTACTTTACTGGCTTTGGTCGTCATGAAGATGCGGAC 900
GUS-10M    TTCCTGATATACCACAAAGGGTTCTACTAAACTGGCTTACGTCGTCATCTAGATGCGGTG 100
           ********::********   ********::********: ******** :********:

GUS        TTGCGTGGCAAAGGATTCGATAACGTGCTGATGGTGCACGACCACGCATTAATGGACTGG 960
GUS-10M    TTGCGTGGGTAAGGATTCCTTAACGTGCACATGGTGCAGCACCACGCAAAAATGGACTCC 160
           ******** :******** :********: ********   ********::********

GUS        ATTGGGGCCAACTCCTACCGTACCTCGCATTACCCTTACGCTGAAGAGATGCTCGACTGG 1020
GUS-10M    ATTGGGGCGTACTCCTACGCTACCTCGCTATACCCTTAGC-------------------- 200
           ******** :********   ********::********
```

FIGURE 9

```
EIN2-GU         -----------------------------------------------------GATTTTA
EIN2-cDNA       AGTAATTATATTATCAGATAGATTTAGGATGGAAGCTGAAATTGTGAATGTGAGACCTCA
                                                                     **  * *

EIN2-GU         GTTAGGGTTTATTTAGAGAATGGTTTTTGTTTTATTTTTTGTTTTTTTGGTTTTTGTTGG
EIN2-cDNA       GCTAGGGTTTATCCAGAGAATGGTTCCTGCTCTACTTCCTGTCCTTTTGGTTTCTGTCGG
                * **********  ***********  ** * ** **  ***  ********* *** **

EIN2-GU         ATATATTGATTTTGGGAAATGGGTTGTAAATATTGAAGGAGGTGTTTGTTTTGGGTATGA
EIN2-cDNA       ATATATTGATCCCGGGAAATGGGTTGCAAATATCGAAGGAGGTGCTCGTTTCGGGTATGA
                **********   ************* ****** ********** * **** ********

EIN2-GU         TTTGGTGGTAATTATTTTGTTTTTTAATTTTGTTGTTATTTTATGTTAATATGTTGTAGT
EIN2-cDNA       CTTGGTGGCAATTACTCTGCTTTTCAATTTTGCCGCCATCTTATGCCAATATGTTGCAGC
                 ******* ***** * ** **** *******  *  ** *****  ********* **

EIN2-GU         TTGTATAAGTGTT-----------------------------------------------
EIN2-cDNA       TCGCATAAGCGTTGTGACTGGTAAACACTTGGCTCAGATCTGCAATGAAGAATATGACAA
                * * ***** ***
```

FIGURE 22

```
CHS-GU          --------------------------------------------------GTTGTTTGTT
CHS-cDNA        TCCGTATCGCTAAGGATCTCGCCGAGAACAATCGTGGAGCACGTGTCCTCGTTGTCTGCT
                                                                  ***** ** *

CHS-GU          TTGAGATTATAGTTGTTATTTTTTGTGGTTTTTTTGATATTTATTTTGATTTTTTTGTTG
CHS-cDNA        CTGAGATCACAGCCGTTACCTTCCGTGGTCCCTCTGACACCCACCTTGACTCCCTCGTCG
                 ****** * **  ****  **  *****   * *** *   *  **** *   * ** *

CHS-GU          GTTAGGTTTTTTTTAGTGATGGTGTTGTTGTATTTATTGTGGGGTTGGATTTTGATATAT
CHS-cDNA        GTCAGGCTCTTTTCAGTGATGGCGCCGCCGCACTCATTGTGGGGTCGGACCCTGACACAT
                ** *** * **** ******** *  *  * * * ********** ***   *** * **

CHS-GU          TTGTTGGAGAGAAATTTATTTTTGAGATGGTGTTTGTTGTTTAGATTATTTTTTTAGATT
CHS-cDNA        CTGTCGGAGAGAAACCCATCTTTGAGATGGTGTCTGCCGCTCAGACCATCCTTCCAGACT
                 *** *********   ** ************* **  * * ***  **  **  *** *

CHS-GU          TTGATGGTGT--------------------------------------------------
CHS-cDNA        CTGATGGTGCCATAGACGGACATTTGAGGGAAGTTGGTCTCACCTTCCATCTCCTCAAGG
                 ********
```

FIGURE 23

Antisense EIN2-GU align with antisense EIN2 cDNA

```
As-EIN2-GU      ~~~~~~~~~~~~~~~~~~~~~~~~~~~~~~~~~~~~~~AATGTTTATGTGAGTTGTAATA
asEIN2-cDNA     TCTTCATTGCAGATCTGAGCCAAGTGTTTACCAGTCACAACGCTTATGCGAGCTGCAACA
                                                      ** * ***** *** ** ** *

As-EIN2-GU      TATTGGTATAAGATGGTGGTAAAATTGAAAAGTAGAGTAATTGTTATTAAGTTATATTTG
asEIN2-cDNA     TATTGGCATAAGATGGCGGCAAAATTGAAAAGCAGAGTAATTGCCACCAAGTCATACCCG
                ****** ********* ** ************ ********** *  **** ***    *

As-EIN2-GU      AAATGAGTATTTTTTTTTGATATTTGTAATTTATTTTTTTGGGATTAATATATTTGATAGAA
asEIN2-cDNA     AAACGAGCACCTCCTTCGATATTTGCAACCCATTTCCCGGGATCAATATATCCGACAGAA
                *** *** *  *  ** ********* **   ****   ***** *******  ** ****

As-EIN2-GU      ATTAAAAGGATAGGAAGTAGAGTAGGAATTATTTTTTGGATAAATTTTAGTTGAGGTT--
asEIN2-cDNA     ACCAAAAGGACAGGAAGTAGAGCAGGAACCATTCTCTGGATAAACCCTAGCTGAGGTCTC
                *  ******* *********** *****  *** * ********   *** ******
```

FIGURE 24

Antisense CHS-GU align with antisense CHS cDNA

```
As-CHS-GU      -----------------------------------------GTATTATTAGAGTTTGGAA
asCHS-cDNA     GATGGAAGGTGAGACCAACTTCCCTCAAATGTCCGTCTATGGCACCATCAGAGTCTGGAA
                                                        * *  ** ***** *****

As-CHS-GU      GGATGGTTTGAGTGGTAGATATTATTTTAAAGATGGGTTTTTTTTTGATAGATGTGTTAG
asCHS-cDNA     GGATGGTCTGAGCGGCAGACACCATCTCAAAGATGGGTTTCTCTCCGACAGATGTGTCAG
               ******* **** ** *** *  ** * ************ * *  ** ******** **

As-CHS-GU      GGTTTGATTTTATAATGAGTGTGGTGGTGTTATTATTGAAAAGAGTTTGATTGATGAGGG
asCHS-cDNA     GGTCCGACCCCACAATGAGTGCGGCGGCGCCATCACTGAAAAGAGCCTGACCGACGAGGG
               ***  **    * ******** ** ** *  ** * *********  ***  ** *****

As-CHS-GU      AGTTAAGGTGGGTGTTAGAGGGATTATGGAAGGTAATGGTTGTGATTTTAGAGTAGATAA
asCHS-cDNA     AGTCAAGGTGGGTGTCAGAGGGACCACGGAAGGTAACGGCTGTGATCTCAGAGCAGACAA
               *** *********** *******  * ********** * ****** * **** *** **
```

FIGURE 25

A
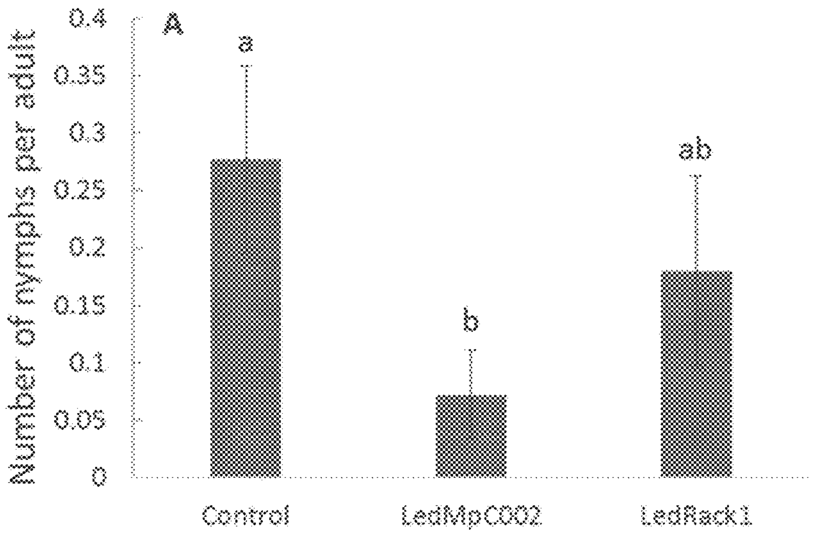
B
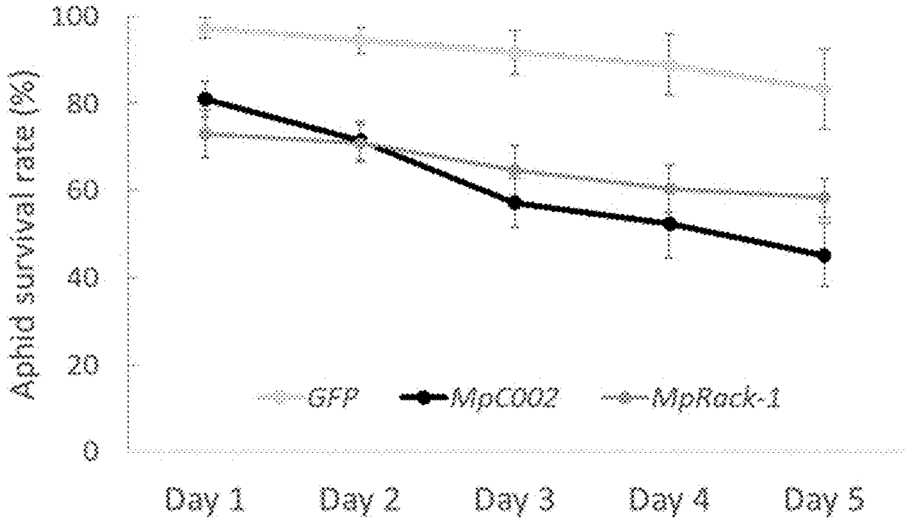
FIGURE 37

RNA MOLECULES COMPRISING NON-CANONICAL BASE PAIRS

CROSS-REFERENCE TO RELATED APPLICATIONS

This application is a § 371 national stage of PCT International Application No. PCT/AU2019/050814, filed Aug. 2, 2019, claiming benefit of PCT International Application No. PCT/AU2018/051015, filed Sep. 17, 2018, and claiming priority of Australian Patent Application Nos. AU 2019900941, filed Mar. 20, 2019, AU 2018902896, filed Aug. 8, 2018, and AU 2018902840, filed Aug. 3, 2018, the contents of each of which are hereby incorporated by reference into the application.

REFERENCE TO A SEQUENCE LISTING

This application incorporates-by-reference nucleotide and/or amino acid sequences which in the file are present named "210203_5938_91699_Sequence_Listing_SC.txt", which is 218,508 bytes in size, and which was created Feb. 3, 2021 in the IBM-PC machine format, having an operating system compatibility with MS-Windows, which is contained in the text file filed Feb. 3, 2021 as part of this application.

FIELD OF THE INVENTION

The present invention relates to new double stranded RNA (dsRNA) structures and their use in gene silencing.

BACKGROUND OF THE INVENTION

RNA silencing is an evolutionarily conserved gene silencing mechanism in eukaryotes that is induced by double-stranded RNA (dsRNA) which may be of a form designated hairpin structured RNA (hpRNA). In the basic RNA silencing pathway, dsRNA is processed by Dicer proteins into short, 20-25 nucleotide (nt) small RNA duplexes, of which one strand is bound to Argonaute (AGO) proteins to form an RNA-induced silencing complex (RISC). This silencing complex uses the small RNA as a guide to find and bind to complementary single-stranded RNA, where the AGO protein cleaves the RNA resulting in its degradation.

In plants, multiple RNA silencing pathways exist, including microRNA (miRNA), trans-acting small interfering RNA (tasiRNA), repeat-associated siRNA (rasiRNA) and exogenic (virus and transgene) siRNA (exosiRNA) pathways. miRNAs are 20-24 nt small RNAs processed in the nucleus by Dicer-like 1 (DCL1) from short stem-loop precursor RNAs that are transcribed by RNA polymerase II from MIR genes. tasiRNAs are phased siRNAs of primarily 21 nt in size derived from DCL4 processing of long dsRNA synthesized by RNA-dependent RNA polymerase 6 (RDR6) from miRNA-cleaved TAS RNA fragment. The 24-nt rasiRNAs are processed by DCL3, and the precursor dsRNA is generated by the combined function of plant-specific DNA-dependent RNA polymerase IV (PolIV) and RDR2 from repetitive DNA in the genome. The exosiRNA pathway overlaps with the tasiRNA and rasiRNA pathways and both DCL4 and DCL3 are involved in exosiRNA processing. In addition to DCL1, DCL3 and DCL4, the model plant *Arabidopsis thaliana* and other higher plants encodes DCL2 or equivalent, which generates 22-nt siRNAs including 22-nt exosiRNAs, and plays a key role in systemic and transitive gene silencing in plants. All of these plant small RNAs are methylated at the 2'-hydroxyl group of the 3' terminal nucleotide by HUA Enhancer 1 (HEN1), and this 3' terminal 2'-O-methylation is thought to stabilize the small RNAs in plant cells. miRNAs, tasiRNAs and exosiRNAs are functionally similar to small RNAs in animal cells which are involved in posttranscriptional gene silencing or sequence-specific degradation of RNA in animals. The rasiRNAs, however, are unique to plants and function to direct de novo cytosine methylation at the cognate DNA, a transcriptional gene silencing mechanism known as RNA-directed DNA methylation (RdDM).

RNA silencing induced by dsRNA has been extensively exploited to reduce gene activity in various eukaryotic systems, and a number of gene silencing technologies has been developed. Different organisms are often amenable to different gene silencing approaches. For instance, long dsRNA (at least 100 basepairs in length) is less suited to inducing RNA silencing in mammalian cells due to dsRNA-induced interferon responses, and so shorter dsRNAs (less than 30 basepairs) are generally used in mammalian cells, whereas in plants hairpin RNA (hpRNA) with a long dsRNA stem is highly effective. In plants, the different RNA silencing pathways have led to different gene silencing technologies, such as artificial miRNA, artificial tasiRNA and virus-induced gene silencing technologies. However, successful applications of RNA silencing in plants has so far been achieved primarily by using long hpRNA transgenes. A hpRNA transgene construct typically consists of an inverted repeat made up of fully complementary sense and antisense sequences of a target gene sequence (which when transcribed form the dsRNA stem of hpRNA) separated by a spacer sequence (forming the loop of hpRNA), which is inserted between a promoter and a transcription terminator for expression in plant cells. The spacer sequence functions to stabilize the inverted-repeat DNA in bacteria during construct preparation. The dsRNA stem of the resulting hpRNA transcript is processed by DCL proteins into siRNAs that direct target gene silencing. hpRNA transgenes have been widely used to knock down gene expression, modify metabolic pathways and enhance disease and pest resistance in plants for crop improvement, and many successful applications of the technology in crop improvement have now been reported (Guo et al., 2016; Kim et al., 2019).

Recent studies have suggested, however, that hpRNA transgenes are subject to self-induced transcriptional repression compromising the stability and efficacy of target gene silencing. While all transgenes are potentially subject to position or copy number-dependent transcriptional silencing, hpRNA transgenes are unique as they generate siRNAs that can direct DNA methylation to their own sequence via the RdDM pathway, and this has the potential to cause transcriptional self-silencing.

Whilst dsRNA induced gene silencing has proven to be a valuable tool in altering the phenotype of an organism, there is a need for alternate, preferably improved, dsRNA molecules which can be used for RNAi.

SUMMARY OF THE INVENTION

The inventors conceived of new designs of genetic constructs for producing RNA molecules which include one or more double-stranded RNA regions which comprise multiple non-canonically basepaired nucleotides or non-basepaired nucleotides, or both, including forms which have two or more loop sequences, herein called loop-ended dsRNA (ledRNA). These RNA molecules have one or more of the following features; they are easily synthesized, they accumulate to higher levels in cells upon transcription of the genetic constructs encoding them, they more readily form a dsRNA structure and induce efficient silencing of target RNA molecules in eukaryotic cells, and they may form circular RNA molecules upon processing in plant cells. The RNA molecules are also effective when topically applied to plants or fed to animals such as insects.

In a first aspect, the present invention provides a chimeric ribonucleic acid (RNA) molecule, comprising a double-stranded RNA (dsRNA) region which comprises a first sense ribonucleotide sequence of at least 20 contiguous nucleotides in length and a first antisense ribonucleotide sequence of at least 20 contiguous nucleotides in length, whereby the first sense ribonucleotide sequence and the first antisense ribonucleotide sequences are capable of hybridising to each other to form the dsRNA region, wherein i) the first sense ribonucleotide sequence consists of, covalently linked in 5' to 3' order, a first 5' ribonucleotide, a first RNA sequence and a first 3' ribonucleotide,
ii) the first antisense ribonucleotide sequence consists of, covalently linked in 5' to 3' order, a second 5' ribonucleotide, a second RNA sequence and a second 3' ribonucleotide,
iii) the first 5' ribonucleotide basepairs with the second 3' ribonucleotide to form a terminal basepair of the dsRNA region,
iv) the second 5' ribonucleotide basepairs with the first 3' ribonucleotide to form a terminal basepair of the dsRNA region,
v) between about 5% and about 40% of the ribonucleotides of the first sense ribonucleotide sequence and the first antisense ribonucleotide sequence, in total, are either basepaired in a non-canonical basepair or are not basepaired,
vi) the dsRNA region does not comprise 20 contiguous canonical basepairs,
vii) the RNA molecule is capable of being processed in a eukaryotic cell or in vitro whereby the first antisense ribonucleotide sequence is cleaved to produce short antisense RNA (asRNA) molecules of 20-24 ribonucleotides in length,
viii) the RNA molecule or at least some of the asRNA molecules, or both, are capable of reducing the expression or activity of a target RNA molecule in the eukaryotic cell, and
ix) the RNA molecule is capable of being made enzymatically by transcription in vitro or in a cell, or both.

In a preferred embodiment of the first aspect, the first sense ribonucleotide sequence is covalently linked to the first antisense ribonucleotide sequence by a first linking ribonucleotide sequence which comprises a loop sequence of at least 4 nucleotides, or between 4 and 1,000 ribonucleotides, or between 4 and 200 ribonucleotides, or between 4 and 50 ribonucleotides, or at least 10 nucleotides, or between 10 and 1,000 ribonucleotides, or between 10 and 200 ribonucleotides, or between 10 and 50 ribonucleotides, in length, whereby the first linking ribonucleotide sequence is covalently linked to either the first 3' ribonucleotide and the second 5' ribonucleotide or to the second 3' ribonucleotide and the first 5' ribonucleotide, so that the sequences are comprised in a single, contiguous strand of RNA. In another embodiment, the first linking ribonucleotide sequence is covalently linked to either the second 3' ribonucleotide and the first 5' ribonucleotide or, preferably, to the first 3' ribonucleotide and the second 5' ribonucleotide, so that the sequences are comprised in a single, contiguous strand of RNA.

In its simplest form, such an RNA molecule is referred to as a hairpin RNA (hpRNA). In a more preferred embodiment, between about 5% and about 40% of the ribonucleotides of the first sense ribonucleotide sequence and the first antisense ribonucleotide sequence of the dsRNA, in total, are basepaired in non-canonical basepairs, preferably G:U basepairs. That is, all of the ribonucleotides of the first sense ribonucleotide sequence are basepaired to ribonucleotides of the first antisense ribonucleotide sequence, either in canonical basepairs or non-canonical basepairs, whereby the dsRNA region comprises 20 contiguous basepairs including some non-canonical basepairs. The dsRNA region thereby does not comprise 20 contiguous canonical basepairs. In a more preferred embodiment of the hpRNA of the invention, the first antisense ribonucleotide sequence is fully complementary to a region of the target RNA. In this embodiment, the first sense ribonucleotide sequence is different in sequence to the region of the target RNA by the substitution of C nucleotides in the region of the target RNA with U nucleotides in the hpRNA. Such molecules are exemplified in the hairpin RNAs comprising G:U basepairs in Examples 6-11. In preferred embodiments, the length of the first antisense ribonucleotide sequence is 20 to about 1000 nucleotides, or 20 to about 500 nucleotides, or other lengths as described herein. More preferably, the hpRNA is produced in, or introduced into, a plant cell or a fungal cell. In these embodiments, the target RNA may be a transcript of an endogenous gene in the cell, or of a plant pathogen, or of a pest such as an insect pest.

In a more preferred embodiment, the RNA molecule comprises a second sense ribonucleotide sequence and the first sense ribonucleotide sequence and the first antisense ribonucleotide sequence are linked by a first linking ribonucleotide sequence comprising a loop sequence of at least 4 nucleotides in length, whereby the first linking ribonucleotide sequence is covalently linked to the first 3' ribonucleotide and the second 5' ribonucleotide, and the RNA molecule further comprises a second linking ribonucleotide sequence which comprises a loop sequence of at least 4 nucleotides in length and which is covalently linked to the second 3' ribonucleotide and the second sense ribonucleotide sequence, thereby forming an ledRNA structure. In an alternative preferred embodiment, the RNA molecule comprises a second antisense ribonucleotide sequence and the first sense ribonucleotide sequence and the first antisense ribonucleotide sequence are linked by a first linking ribonucleotide sequence comprising a loop sequence of at least 4 nucleotides in length, whereby the first linking ribonucleotide sequence is covalently linked to the second 3' ribonucleotide and the first 5' ribonucleotide, and the RNA molecule further comprises a second linking ribonucleotide sequence which comprises a loop sequence of at least 4 nucleotides in length and which is covalently linked to the second 3' ribonucleotide and the second antisense ribonucleotide sequence, thereby forming an ledRNA structure.

In another preferred embodiment, the RNA molecule comprises a second sense ribonucleotide sequence and a second antisense ribonucleotide sequence, wherein the second sense ribonucleotide sequence and the second antisense ribonucleotide sequences are capable of hybridising to each other to form a second dsRNA region, and the first sense ribonucleotide sequence and the first antisense ribonucleotide sequence are linked by a first linking ribonucleotide sequence comprising a loop sequence of at least 4 nucleotides in length, whereby the first linking ribonucleotide sequence is covalently linked to the first 3' ribonucleotide and the second 5' ribonucleotide, and the RNA molecule further, or optionally, comprises a second linking ribonucleotide sequence which comprises a loop sequence of at least 4 nucleotides in length and which is covalently linked to the second 3' ribonucleotide and the second sense ribonucleotide sequence or which covalently links the second sense ribonucleotide sequence and the second antisense ribonucleotide sequence, thereby forming an ledRNA structure. In a further preferred embodiment, the RNA molecule comprises a second sense ribonucleotide sequence and a second antisense ribonucleotide sequence and the first sense ribonucleotide sequence and the first antisense ribonucleotide sequence are linked by a first linking ribonucleotide sequence comprising a loop sequence of at least 4 nucleotides in length, whereby the first linking ribonucleotide sequence is covalently linked to the second 3' ribonucleotide and the first 5' ribonucleotide, and the RNA molecule further, or optionally, comprises a second linking ribonucleotide sequence which comprises a loop sequence of at least 4 nucleotides in length and which is covalently linked to the first 3' ribonucleotide and the second antisense ribonucleotide sequence or which covalently links the second sense ribonucleotide sequence and the second antisense ribonucleotide sequence, thereby forming an ledRNA structure. In more preferred embodiments, the second sense ribonucleotide sequence and the second antisense ribonucleotide sequence, if present in the RNA molecule, each comprise at least 20 contiguous nucleotides in length. In these embodiments, the first and second sense ribonucleotide sequences may be covalently linked by an intervening ribonucleotide sequence which is unrelated in sequence to a target RNA molecule or which is related in sequence to a target RNA molecule, or the first and second sense ribonucleotide sequences are covalently linked without an intervening ribonucleotide sequence. The first and second sense ribonucleotide sequences may form one contiguous sense ribonucleotide region having at least 50% identity in sequence to a target RNA molecule. In further embodiments, the first and second antisense ribonucleotide sequences may be covalently linked by an intervening ribonucleotide sequence which is unrelated in sequence to the complement of a target RNA molecule, or which is related in sequence to the complement of a RNA molecule, or the first and second antisense ribonucleotide sequences are covalently linked without an intervening ribonucleotide sequence. The first and second antisense sense ribonucleotide sequences may form one contiguous antisense ribonucleotide region having at least 50% identity in sequence to the complement of a target RNA molecule. In these embodiments, the RNA molecule comprises a second sense ribonucleotide sequence and a second antisense ribonucleotide sequence which hybridise by basepairing, preferably between 5% and 40% of the ribonucleotides of the second sense ribonucleotide sequence and the second antisense ribonucleotide sequence, in total, are either basepaired in a non-canonical basepair or are not basepaired, preferably basepaired in G:U basepairs, wherein the second dsRNA region does not comprise 20 contiguous canonical basepairs, and wherein the RNA molecule is capable of being processed in a eukaryotic cell or in vitro whereby the second antisense ribonucleotide sequence is cleaved to produce short antisense RNA (asRNA) molecules of 20-24 ribonucleotides in length.

In a most preferred embodiment, considering the RNA molecule as a whole and each dsRNA region within the RNA molecule, between 5% and 40% of the ribonucleotides of each sense ribonucleotide sequence and its corresponding antisense ribonucleotide sequence which hybridise by basepairing, in total, are either basepaired in a non-canonical basepair or are not basepaired, the RNA molecule as a whole does not comprise 20 contiguous canonical basepairs in any of its dsRNA regions, and the RNA molecule is capable of being processed in a eukaryotic cell or in vitro whereby each antisense ribonucleotide sequence is cleaved to produce short antisense RNA (asRNA) molecules of 20-24 ribonucleotides in length.

In preferred embodiments, each linking ribonucleotide sequence is independently between 4 and about 2000 nucleotides in length, preferably between 4 and about 1200 nucleotides in length, more preferably between 4 and about 200 nucleotides in length and most preferably between 4 and about 50 nucleotides in length. In an embodiment, the RNA molecule further comprises a 5' leader sequence or a 3' trailer sequence, or both.

In a second aspect, the present invention provides a chimeric ribonucleic acid (RNA) molecule, comprising a double-stranded RNA (dsRNA) region which comprises a sense ribonucleotide sequence and an antisense ribonucleotide sequence which are capable of hybridising to each other to form the dsRNA region, wherein i) the sense ribonucleotide sequence consists of, covalently linked in 5' to 3' order, a first 5' ribonucleotide, a first RNA sequence and a first 3' ribonucleotide,
ii) the antisense ribonucleotide sequence consists of, covalently linked in 5' to 3' order, a second 5' ribonucleotide, a second RNA sequence and a second 3' ribonucleotide,
iii) the first 5' ribonucleotide basepairs with the second 3' ribonucleotide to form a terminal basepair of the dsRNA region,
iv) the second 5' ribonucleotide basepairs with the first 3' ribonucleotide to form a terminal basepair of the dsRNA region,
v) between about 5% and about 40% of the ribonucleotides of the sense ribonucleotide sequence and the antisense ribonucleotide sequence, in total, are either basepaired in a non-canonical basepair or are not basepaired,
vi) the dsRNA region does not comprise 20 contiguous canonical basepairs,
vii) the RNA molecule is capable of being processed in a eukaryotic cell or in vitro whereby the antisense ribonucleotide sequence is cleaved to produce short antisense RNA (asRNA) molecules of 20-24 ribonucleotides in length,
viii) the RNA molecule or at least some of the asRNA molecules, or both, are capable of reducing the expression or activity of a target RNA molecule in the eukaryotic cell, and
ix) the RNA molecule is capable of being made enzymatically by transcription in vitro or in a cell, or both.

As the skilled person would be aware, each of the embodiments relating to the first aspect, other than where the length of a sense ribonucleotide sequence and an antisense ribonucleotide sequence are less than 20 contiguous nucleotides, apply to the second aspect.

In a third aspect, the present invention provides a ribonucleic acid (RNA) molecule comprising a first RNA component, a second RNA component which is covalently linked to the first RNA component and, optionally, one or more or all of (i) a linking ribonucleotide sequence which covalently links the first and second RNA components, (ii) a 5' leader sequence and (iii) a 3' trailer sequence, wherein the first RNA component consists of, in 5' to 3' order, a first 5' ribonucleotide, a first RNA sequence and a first 3' ribonucleotide, wherein the first 5' and 3' ribonucleotides basepair to each other in the RNA molecule, wherein the first RNA sequence comprises a first sense ribonucleotide sequence of at least 20 contiguous ribonucleotides, a first loop sequence of at least 4 ribonucleotides and a first antisense ribonucleotide sequence of at least 20 contiguous ribonucleotides, wherein the first antisense ribonucleotide sequence hybridises with the first sense ribonucleotide sequence in the RNA molecule, wherein the first antisense ribonucleotide sequence is capable of hybridising to a first region of a target RNA molecule, wherein the second RNA component is covalently linked, via the linking ribonucleotide sequence if present or directly if the linking ribonucleotide sequence is not present, to the first 5' ribonucleotide or the first 3' ribonucleotide, wherein the second RNA component consists of, in 5' to 3' order, a second 5' ribonucleotide, a second RNA sequence and a second 3' ribonucleotide, wherein the second 5' and 3' ribonucleotides basepair to each other in the RNA molecule, wherein the second RNA sequence comprises a second sense ribonucleotide sequence, a second loop sequence of at least 4 ribonucleotides and a second antisense ribonucleotide sequence, wherein the second sense ribonucleotide sequence hybridises with the second antisense ribonucleotide sequence in the RNA molecule, wherein the 5' leader sequence, if present, consists of a sequence of ribonucleotides which is covalently linked to the first 5' ribonucleotide if the second RNA component is linked to the first 3' ribonucleotide or to the second 5' ribonucleotide if the second RNA component is linked to the first 5' ribonucleotide, and wherein the 3' trailer sequence, if present, consists of a sequence of ribonucleotides which is covalently linked to the second 3' ribonucleotide if the second RNA component is linked to the first 3' ribonucleotide or to the first 3' ribonucleotide if the second RNA component is linked to the first 5' ribonucleotide.

In a fourth aspect, the present invention provides an RNA molecule comprising a first RNA component, a second RNA component which is covalently linked to the first RNA component and, optionally, one or more or all of (i) a linking ribonucleotide sequence which covalently links the first and second RNA components, (ii) a 5' leader sequence and (iii) a 3' trailer sequence, wherein the first RNA component consists of, in 5' to 3' order, a first 5' ribonucleotide, a first RNA sequence and a first 3' ribonucleotide, wherein the first 5' and 3' ribonucleotides basepair, wherein the first RNA sequence comprises a first sense ribonucleotide sequence, a first loop sequence of at least 4 ribonucleotides and a first antisense ribonucleotide sequence, wherein the first sense ribonucleotide sequence and first antisense ribonucleotide sequence each consist of at least 20 contiguous ribonucleotides whereby the at least 20 contiguous ribonucleotides of the first sense ribonucleotide sequence fully basepair with the at least 20 contiguous ribonucleotides of the first antisense ribonucleotide sequence, wherein the at least 20 contiguous ribonucleotides of the first sense ribonucleotide sequence or the at least 20 contiguous ribonucleotides of the first antisense ribonucleotide sequence are identical in sequence to a first region of a target RNA molecule or its complement, respectively, or both, wherein the second RNA component is covalently linked, via the linking ribonucleotide sequence if present, to the first 5' ribonucleotide or the first 3' ribonucleotide, wherein the second RNA component consists of, in 5' to 3' order, a second 5' ribonucleotide, a second RNA sequence and a second 3' ribonucleotide, wherein the second 5' and 3' ribonucleotides basepair, wherein the second RNA sequence comprises a second sense ribonucleotide sequence, a second loop sequence of at least 4 ribonucleotides and a second antisense ribonucleotide sequence, wherein the second sense ribonucleotide sequence basepairs with the second antisense ribonucleotide sequence, wherein the 5' leader sequence, if present, consists of a sequence of ribonucleotides which is covalently linked to the first 5' ribonucleotide if the second RNA component is linked to the first 3' ribonucleotide or to the second 5' ribonucleotide if the second RNA component is linked to the first 5' ribonucleotide, and wherein the 3' trailer sequence, if present, consists of a sequence of ribonucleotides which is covalently linked to the second 3' ribonucleotide if the second RNA component is linked to the first 3' ribonucleotide or to the first 3' ribonucleotide if the second RNA component is linked to the first 5' ribonucleotide.

In preferred embodiments of the above aspects, the RNA molecule of the invention is a chimeric RNA molecule.

In a fifth aspect, the present invention provides a chimeric RNA molecule comprising a first RNA component and a second RNA component which is covalently linked to the first RNA component, wherein the first RNA component comprises a first double-stranded RNA (dsRNA) region, which comprises a first sense ribonucleotide sequence and a first antisense ribonucleotide sequence which are capable of hybridising to each other to form the first dsRNA region, and a first intervening ribonucleotide sequence of at least 4 nucleotides which covalently links the first sense ribonucleotide sequence and the first antisense ribonucleotide sequence, wherein the second RNA component comprises a second sense ribonucleotide sequence, a second antisense ribonucleotide sequence and a second intervening ribonucleotide sequence of at least 4 ribonucleotides which covalently links the second sense ribonucleotide sequence and the second antisense ribonucleotide sequence, wherein the second sense ribonucleotide sequence hybridises with the second antisense ribonucleotide sequence in the RNA molecule, wherein in the first RNA component, i) the first sense ribonucleotide sequence consists of at least 20 contiguous ribonucleotides covalently linked, in 5' to 3' order, a first 5' ribonucleotide, a first RNA sequence and a first 3' ribonucleotide, ii) the first antisense ribonucleotide sequence consists of at least 20 contiguous ribonucleotides covalently linked, in 5' to 3' order, a second 5' ribonucleotide, a second RNA sequence and a second 3' ribonucleotide, iii) the first 5' ribonucleotide basepairs with the second 3' ribonucleotide, iv) the second 5' ribonucleotide basepairs with the first 3' ribonucleotide, v) between 5% and 40% of the ribonucleotides of the first sense ribonucleotide sequence and the first antisense ribonucleotide sequence, in total, are either basepaired in a non-canonical basepair or are not basepaired, and vi) the first dsRNA region does not comprise 20 contiguous canonical basepairs, wherein the chimeric RNA molecule is capable of being processed in a eukaryotic cell or in vitro whereby the first antisense ribonucleotide sequence is cleaved to produce short antisense RNA (asRNA) molecules of 20-24 ribonucleotides in length, and wherein (a) the chimeric RNA molecule or at least some of the asRNA molecules, or both, are capable of reducing the expression or activity of a target RNA molecule in the eukaryotic cell, or (b) the first antisense ribonucleotide sequence comprises a sequence of at least 20 contiguous ribonucleotides which is at least 50% identical in sequence, preferably at least 90% or 100% identical in sequence, to a region of the complement of the target RNA molecule, or (c) both (a) and (b).

In an embodiment where the RNA molecule has a first RNA component, the first 5' ribonucleotide and first 3' ribonucleotide of the first RNA component basepair to each other. That basepair is defined herein as the terminal basepair of the dsRNA region formed by self-hybridisation of the first RNA component. In the embodiment where the first sense ribonucleotide sequence is linked covalently to the first 5' ribonucleotide without any intervening nucleotides and the first antisense ribonucleotide sequence is linked covalently to the first 3' ribonucleotide without any intervening nucleotides, the first 5' ribonucleotide is directly linked to one of the sense sequence and antisense sequence and the first 3' ribonucleotide is directly linked to the other of the sense sequence and antisense sequence.

In a preferred embodiment, the at least 20 contiguous ribonucleotides of the first antisense ribonucleotide sequence are all capable of basepairing to nucleotides of the first region of the target RNA molecule. In this context, basepairing may be canonical or non-canonical, for example with at least some G:U basepairs. Independently for each G:U basepair, the G may be in the first region of the target RNA molecule or preferably in the first antisense ribonucleotide sequence. Alternatively, not all of the at least 20 contiguous ribonucleotides of the first antisense ribonucleotide sequence basepair to nucleotides of the first region of the target RNA molecule. For example, 1, 2, 3, 4 or 5 of the at least 20 contiguous ribonucleotides of the first antisense ribonucleotide sequence are not basepaired to the first region of the target RNA molecule. In an embodiment, the first sense ribonucleotide sequence is linked covalently to the first 5' ribonucleotide without any intervening nucleotides, or the first antisense ribonucleotide sequence is linked covalently to the first 3' ribonucleotide without any intervening nucleotides, or both.

In an embodiment of the above aspects, the RNA molecule comprises one or more linking ribonucleotide sequence, wherein the linking ribonucleotide sequence is related in sequence to the target RNA molecule, either identical at least in part to a region of the target RNA molecule or to its complement. In a preferred embodiment, the linking ribonucleotide sequence together with sense sequences in the first and second RNA components form part of one contiguous sense sequence, or together with antisense sequences in the first and second RNA components form part of one contiguous antisense sequence. In an embodiment, the RNA molecule comprises the linking ribonucleotide sequence, wherein the linking ribonucleotide sequence is less than 20 ribonucleotides. In an embodiment, the linking ribonucleotide sequence hybridizes to the target RNA molecule. In an embodiment, the linking ribonucleotide sequence is identical to a portion of the complement of the target RNA molecule. In an embodiment, the linking ribonucleotide sequence is between 1 and 10 ribonucleotides.

In embodiments of the above aspects, the RNA molecule comprises one or more or all of (i) a linking ribonucleotide sequence which covalently links the first and second RNA components, (ii) a 5' extension sequence and (iii) a 3' extension sequence, wherein the 5' extension sequence, if present, consists of a sequence of ribonucleotides which is covalently linked to the first RNA component or to the second RNA component, and wherein the 3' extension sequence, if present, consists of a sequence of ribonucleotides which is covalently linked to the second RNA component or to the first RNA component, respectively. In an embodiment, the first RNA component and the second RNA component are covalently linked via a linking ribonucleotide sequence. In an alternative embodiment, the first RNA component and the second RNA component are directly linked, without any linking ribonucleotide sequence present.

In embodiments of the first to fifth aspects, the RNA molecule comprises two or more sense ribonucleotide sequences which are each identical in sequence to a region of a target RNA molecule, and the RNA molecule comprises one or more antisense ribonucleotide sequences based paired to the sense ribonucleotide sequences, wherein the one or more antisense sequences are complementary, preferably fully complementary, to the regions of the target molecule. In an embodiment, the two or more sense ribonucleotide sequences are identical in sequence to different regions of the same target RNA molecule, which may or may not be contiguous in the target RNA molecule. In an embodiment, the two or more sense ribonucleotide sequences are identical in sequence to a region of different target RNA molecules. In an embodiment, the two or more sense ribonucleotide sequences have no intervening loop sequences, i.e. they are contiguous relative to the target RNA molecule.

In preferred embodiments of the first to fifth aspects, the RNA molecule comprises two or more antisense ribonucleotide sequences, and sense ribonucleotide sequences based paired thereto, which antisense sequences are each complementary, preferably fully complementary, to a region of a target RNA molecule. The regions of the target RNA molecule to which they are complementary may or may not be contiguous in the target RNA molecule. In an embodiment, the two or more antisense ribonucleotide sequences are complementary to different regions of the same target RNA molecule. In an embodiment, the second of the two or more antisense ribonucleotide sequences is complementary to a region of a different target RNA molecule than the first of the two or more antisense ribonucleotide sequences. In a preferred embodiment, the two or more antisense ribonucleotide sequences have no intervening loop sequences, i.e. they are contiguous relative to the complement of the target RNA molecule. In a preferred embodiment, one or both of the two or more antisense ribonucleotide sequences and sense ribonucleotide sequences basepair along their full length through canonical basepairs, or through some canonical and some non-canonical basepairs, preferably G:U basepairs.

In a preferred embodiment of the first to fifth aspects, the RNA molecule is a single strand of ribonucleotides. In the simplest form, the RNA molecule comprises a hairpin RNA (hpRNA) structure having a 5' end, a sense ribonucleotide sequence which is at least 21 nucleotides in length, an antisense ribonucleotide sequence which is fully base paired with the sense ribonucleotide sequence over at least 21 contiguous nucleotides, an intervening loop sequence and a 3' end. The RNA molecule may comprise a 5'-leader sequence and/or a 3'-trailer sequence. In another form, the RNA molecule comprises a single strand of ribonucleotides having a 5' end, at least one sense ribonucleotide sequence which is at least 21 nucleotides in length, an antisense ribonucleotide sequence which is fully base paired with each sense ribonucleotide sequence over at least 21 contiguous nucleotides, at least two loop sequences and a 3' end. The order 5' to 3' may be the sense ribonucleotide sequence and then the antisense ribonucleotide sequence, or vice versa. In an embodiment, the ribonucleotide at the 5' end and the ribonucleotide at the 3' end are adjacent, each base paired and are not directly covalently bonded, see for example FIG. 1.

In another embodiment of the first to fifth aspects, the RNA molecule comprises a first antisense ribonucleotide sequence which hybridizes to a first region of a target RNA, a second antisense ribonucleotide sequence which hybridizes to a second region of a target RNA, the second region of the target RNA being different to the first region of the target RNA, and the RNA molecule comprising only one sense ribonucleotide sequence which has at least 50% sequence identity to the target RNA, wherein the two antisense sequences are not contiguous in the RNA molecule. In an embodiment, the first and second regions of the target RNA are contiguous in the target RNA. Alternatively, they are not contiguous.

In another embodiment of the first to fifth aspects, the RNA molecule comprises a first sense ribonucleotide sequence which is at least 60% identical to a first region of a target RNA, a second sense ribonucleotide sequence which is at least 60% identical to a second region of a target RNA, the second region of the target RNA being different to the first region of the target RNA, and the RNA molecule comprising only one antisense ribonucleotide sequence which hybridizes to the target RNA, wherein the two sense sequences are not contiguous in the RNA molecule. In an embodiment, the first and second regions of the target RNA are contiguous in the target RNA molecule. Alternatively, they are not contiguous. In preferred embodiments, the first and second sense ribonucleotide sequences are each, independently, at least 70%, at least 80%, at least 90%, at least 95%, or at least 99% identical to the respective region of target RNA i.e. the first sense sequence may be at least 70% identical to its target region and the second sequence at least 80% identical to its target sequence, etc.

In a preferred embodiment of the first to fourth aspects, the RNA molecule is a single strand of ribonucleotides having a 5' end, at least one sense ribonucleotide sequence which is at least 21 nucleotides in length, an antisense ribonucleotide sequence which is fully base paired with each sense ribonucleotide sequence over at least 21 contiguous nucleotides, at least two loop sequences and a 3' end. In a more preferred embodiment, the basepairing in the RNA molecule is comprised in a double-stranded region which is at least 21 contiguous basepairs in length which includes some non-canonical basepairs, most preferably some G:U basepairs, the double-stranded region comprising the at least one sense ribonucleotide sequence which is at least 21 nucleotides in length.

In preferred embodiments of the third and fourth aspects, the second RNA component is characterised in that:

i) the second sense ribonucleotide sequence consists of at least 20 contiguous ribonucleotides covalently linked, in 5' to 3' order, the second 5' ribonucleotide, a third RNA sequence and a third 3' ribonucleotide,
ii) the second antisense ribonucleotide sequence consists of at least 20 contiguous ribonucleotides covalently linked, in 5' to 3' order, a third 5' ribonucleotide, a fourth RNA sequence and the second 3' ribonucleotide,
iii) the second 5' ribonucleotide basepairs with the second 3' ribonucleotide,
iv) the third 3' ribonucleotide basepairs with the third 5' ribonucleotide, wherein the chimeric RNA molecule is capable of being processed in a eukaryotic cell or in vitro whereby the second antisense ribonucleotide sequence is cleaved to produce short antisense RNA (asRNA) molecules of 20-24 ribonucleotides in length. Most preferably, the asRNA molecules produced from the second antisense sequence are capable of reducing expression of the target RNA, either without or in combination with a sRNAs produced from the first antisense sequence of the first RNA component.

In a preferred embodiment of the fifth aspect, the second RNA component is characterised in that:

i) the second sense ribonucleotide sequence consists of at least 20 contiguous ribonucleotides covalently linked, in 5' to 3' order, a third 5' ribonucleotide, a third RNA sequence and a third 3' ribonucleotide,
ii) the second antisense ribonucleotide sequence consists of at least 20 contiguous ribonucleotides covalently linked, in 5' to 3' order, a fourth 5' ribonucleotide, a fourth RNA sequence and the fourth 3' ribonucleotide,
iii) the third 5' ribonucleotide basepairs with the fourth 3' ribonucleotide,
iv) the third 3' ribonucleotide basepairs with the third 5' ribonucleotide, wherein the chimeric RNA molecule is capable of being processed in a eukaryotic cell or in vitro whereby the second antisense ribonucleotide sequence is cleaved to produce short antisense RNA (asRNA) molecules of 20-24 ribonucleotides in length.

In each of the above preferred embodiments, it is more preferred that between 5% and 40% of the ribonucleotides of the first sense ribonucleotide sequence and the first antisense ribonucleotide sequence, and/or the second sense ribonucleotide sequence and the second antisense ribonucleotide sequence, and/or every sense ribonucleotide sequence and its corresponding antisense ribonucleotide sequence which hybridise, in total, are either basepaired in a non-canonical basepair or are not basepaired, and/or the dsRNA region formed between the complementary sense and antisense sequences does not comprise 20 contiguous canonical basepairs. More preferably, about 12%, about 15%, about 18%, about 21%, about 24%, about 27%, about 30%, between 10% and 30%, or between 15% and 30%, or even more preferably between 16% and 25%, of the ribonucleotides of a sense ribonucleotide sequence and its corresponding antisense ribonucleotide sequence, preferably for every dsRNA region in the RNA molecule, in total, are either basepaired in a non-canonical basepair or are not basepaired. Even more preferably, about 12%, about 15%, about 18%, about 21%, about 24%, about 27%, about 30%, between 10% and 30%, or between 15% and 30%, or even more preferably between 16% and 25%, of the ribonucleotides of the dsRNA region(s) in the RNA molecule, in total, are basepaired in non-canonical basepairs and all of the other ribonucleotides of the dsRNA region(s) in the RNA molecule are basepaired in canonical basepairs. In preferred embodiments, at least 50%, at least 60%, at least 70%, at least 80%, at least 90%, at least 95%, at least 97%, or 100% of the non-canonical basepairs in the first or second dsRNA region, or all dsRNA regions in total, are G:U basepairs. Most preferably, in these embodiments, (a) the chimeric RNA molecule or at least some of the asRNA molecules, or both, are capable of reducing the expression or activity of a target RNA molecule in an eukaryotic cell, or (b) the first and second antisense ribonucleotide sequences, preferably every antisense ribonucleotide sequence in the RNA molecule, comprises a sequence of at least 20 contiguous ribonucleotides which is at least 50% identical in sequence to a region of the complement of the target RNA molecule, preferably at least 60% identical, more preferably at least 70% identical, even more preferably at least 80% identical, most preferably at least 90% identical or 100% identical to the region of the complement of the target RNA molecule, or both (a) and (b).

In an embodiment of the first to fifth aspects, the RNA molecule comprises a 5' leader sequence or 5' extension sequence. In an embodiment, the RNA molecule comprises a 3' trailer sequence or 3' extension sequence. In a preferred embodiment, the RNA molecule comprises both the 5' leader/extension sequence and the 3' trailer/extension sequence.

In an embodiment of the first to fifth aspects, each ribonucleotide of the RNA molecule is covalently linked to two other nucleotides, i.e. it is a covalently closed circle. Alternatively, the RNA molecule may be represented as a dumbbell shape (FIG. 1) but have a gap or nick in one part of the double-stranded structure.

In an embodiment of the first to fifth aspects, at least one or all of the loop sequences of the RNA molecule are longer than 20 nucleotides. In a preferred embodiment, at least one of the loops of the RNA molecule is between 4 and 1,200 ribonucleotides in length, or between 4 and 1000 ribonucleotides in length. In a more preferred embodiment, all of the loops are between 4 and 1,000 ribonucleotides in length. In a more preferred embodiment, at least one of the loops of the RNA molecule is between 4 and 200 ribonucleotides in length. In an even more preferred embodiment, all of the loops are between 4 and 200 ribonucleotides in length. In an even more preferred embodiment, at least one of the loops of the RNA molecule is between 4 and 50 ribonucleotides in length. In a most preferred embodiment, all of the loops are between 4 and 50 ribonucleotides in length. In embodiments, the minimum length of the loop is 20 nucleotides, 30 nucleotides, 40 nucleotides, or 50 nucleotides. In an embodiment, the eukaryotic cell is a vertebrate animal cell or a plant cell, and each loop of the RNA molecule is independently between 20 and 50 ribonucleotides, or between 20 and 40 ribonucleotides or between 20 and 30 ribonucleotides in length.

In a preferred embodiment, at least one loop sequence in the RNA molecule comprises one or more binding sequences which are complementary to an RNA molecule which is endogenous to the eukaryotic cell, such as, for example, an miRNA or other regulatory RNA in the eukaryotic cell. As would readily be understood, this feature may be in combination with any of the loop length features, non-canonical basepairing and any of the other features described above for the RNA molecule. In an embodiment, at least one loop sequence comprises multiple binding sequences for a miRNA, or binding sequences for multiple miRNAs, or both. In an embodiment, at least one loop sequence in the RNA molecule comprises an open reading frame which encodes a polypeptide or a functional polynucleotide. The open reading frame is preferably operably linked to a translation initiation sequence, whereby the open reading frame is capable of being translated in a eukaryotic cell of interest. For example, the translation initiation sequence comprises, or is comprised in, an internal ribosome entry site (IRES). The IRES is preferably a eukaryotic IRES. The translated polypeptide is preferably 50-400 amino acid residues in length, or 50-300 or 50-250, or 50-150 amino acid residues in length. Such RNA molecules, when produced in a plant cell, are capable of being processed to form circular RNA molecules comprising most or all of the loop sequence and which are capable of being translated to provide high levels of the polypeptide.

In embodiments of the first to fifth aspects, the RNA molecule has none, or one, or two or more bulges in a double-stranded region. In this context, a bulge is a nucleotide, or two or more contiguous nucleotides, in the sense or antisense ribonucleotide sequence which is not basepaired in the dsRNA region and which does not have a mismatched nucleotide at the corresponding position in the complementary sequence in the dsRNA region. The dsRNA region of the RNA molecule may comprise a sequence of more than 2 or 3 nucleotides within the sense or antisense sequence, or both, which loops out from the dsRNA region when the dsRNA structure forms. The sequence which loops out may itself form some internal basepairing, for example it may itself form a stem-loop structure.

In embodiments of the first to fifth aspects, the RNA molecule has none, or one, or two or more bulges in a double-stranded region. In this context, a bulge is a nucleotide, or two or more contiguous nucleotides, in the sense or antisense ribonucleotide sequence which is not basepaired in the dsRNA region and which does not have a mismatched nucleotide at the corresponding position in the complementary sequence in the dsRNA region. The dsRNA region of the RNA molecule may comprise a sequence of more than 2 or 3 nucleotides within the sense or antisense sequence, or both, which loops out from the dsRNA region when the dsRNA structure forms. The sequence which loops out may itself form some internal basepairing, for example it may itself form a stem-loop structure.

In an embodiment, the RNA molecule has three, four or more loops. In a preferred embodiment, the RNA molecule has only two loops. In an embodiment, the first double-stranded region, or the first and second dsRNA region, or every dsRNA region, of the RNA molecule comprises one, or two, or more nucleotides which are not basepaired in the double-stranded region, or independently up to 2%, 3%, 4%, 5%, 6%, 7%, 8%, 9% or 10% of the nucleotides in the double-stranded region which are not basepaired.

In preferred embodiments of the first to fifth aspects, the target RNA molecule or the RNA molecule of the invention, or both, is in a eukaryotic cell. For example, the eukaryotic cell may be a plant cell, animal cell or fungal cell. In an embodiment, the eukaryotic cell is a fungal cell such as, for example, a cell of a fungal pathogen of one or more plant species, for example a *Fusarium* species, a *Verticillium* species or a fungus which causes powdery mildew. In an embodiment, the eukaryotic cell is an arthropod cell such as, for example, an insect cell. A preferred insect is a sap sucking insect such as an aphid. For example, the insect may be a Lepidopteran insect, a Coleopteran insect or a Dipteran insect. In an embodiment, the RNA molecule of the invention is produced in a cell, such as for example a bacterial cell or other microbial cell, which is different to the cell comprising the target RNA. In a preferred embodiment, the microbial cell is a cell in which the RNA molecule is produced by transcription from a genetic construct encoding the RNA molecule, wherein the RNA molecule is substantially, or preferably predominantly, not processed in the microbial cell by cleavage within one or more loop sequences, one or more dsRNA regions, or both. For example, the microbial cell is a yeast cell or another fungal cell which does not have a Dicer enzyme. A greatly preferred cell for production of the RNA molecule is a *Saccharomyces cerevisiae* cell. The microbial cell may be living, or may have been killed by some treatment such as heat treatment, or may be in the form of a dried powder. Similarly, in an embodiment the RNA molecule of the invention is produced in a eukaryotic cell which does not comprise the target RNA when the RNA molecule of the invention is produced, but the eukaryotic cell comprising the RNA molecule of the invention and/or its processed RNA products, may become a host for the target RNA, for example if the target RNA is a viral RNA or other introduced RNA. Such cells may be protected prophylactically against the viral or other introduced RNA.

In preferred embodiments of the first to fifth aspects, the RNA molecule is capable of being made enzymatically by transcription in vitro or in a cell, or both. In an embodiment, an RNA molecule of the present invention is expressed in a cell i.e. produced in the cell by transcription from one or more nucleic acids encoding the RNA molecule. The one or more nucleic acids encoding the RNA molecule is preferably a DNA molecule, which may be present on a vector in the cell or integrated into the genome of the cell, either the nuclear genome of the cell or in the plastid DNA of the cell. The one or more nucleic acids encoding the RNA molecule may also be an RNA molecule such as a viral vector.

Accordingly, in another aspect, the present invention provides a cell comprising an RNA molecule described herein. In a preferred embodiment, the present invention provides an RNA molecule described herein which was expressed in a cell and which has been isolated and/or purified from the cell. The present invention therefore provides a preparation of isolated RNA molecules according to one or more of the first to fifth aspects and any of the embodiments described in that context, which is suitable for administration to a cell comprising the target RNA or potentially comprising the target RNA.

In an embodiment, one or more of the target RNAs encodes a protein. Alternatively, one or more of the target RNAs do not encode a protein, such as a rRNA, tRNA, snoRNA or miRNA.

In embodiments of the first to fifth aspects, about 12%, about 15%, about 18%, about 21%, about 24%, or between about 15% and about 30%, or preferably between about 16% and about 25%, of the ribonucleotides of the sense ribonucleotide sequence and its corresponding antisense ribonucleotide sequence, in total, that form a dsRNA region are either basepaired in a non-canonical basepair or are not basepaired. In a preferred embodiment, at least 50%, at least 60%, at least 70%, at least 80%, at least 90%, at least 95%, at least 97%, or 100% of the non-canonical basepairs in a dsRNA region, or in all dsRNA regions in the RNA molecule, are G:U basepairs. The G nucleotide in each G:U basepair may independently be in the sense ribonucleotide sequence or preferably in the antisense ribonucleotide sequence. Regarding the G nucleotides in the G:U basepairs of a dsRNA region, preferably at least 50% are in the antisense ribonucleotide sequence, more preferably at least 60% or 70%, even more preferably at least 80% or 90%, and most preferably at least 95% of them are in the antisense ribonucleotide sequence in the dsRNA region. This feature may apply independently to one or more or all of the dsRNA regions in the RNA molecule. In an embodiment, less than 25%, less than 20%, less than 15%, less than 10%, preferably less than 5%, more preferably less than 1% or most preferably none, of the ribonucleotides in the dsRNA region, or in all of the dsRNA regions in the RNA molecule in total, are not basepaired. In a preferred embodiment, every one in four to every one in six ribonucleotides in the dsRNA region, or in the dsRNA regions in total, form a non-canonical basepair or are not basepaired within the RNA molecule. In a preferred embodiment, the dsRNA region, or in the dsRNA regions in total, do not comprise 10 or 9 or preferably 8 contiguous canonical basepairs. In an alternative embodiment, the dsRNA region comprises at least 8 contiguous canonical basepairs, for example 8 to 12 or 8 to 14 or 8 to 10 contiguous canonical basepairs. In a preferred embodiment, all of the ribonucleotides in the dsRNA region, or in all dsRNA regions in the RNA molecule, are base-paired with a canonical basepair or a non-canonical basepair. In an embodiment, one or more ribonucleotides of the sense ribonucleotide sequence or one or more ribonucleotides of the antisense ribonucleotide sequence, or both, are not basepaired. In an embodiment, one or more ribonucleotides of each sense ribonucleotide sequence and one or more ribonucleotides of each antisense ribonucleotide sequence are not basepaired in the RNA molecule of the invention.

In an embodiment, one or more or all of the antisense ribonucleotide sequences of the RNA molecule is less than 100% identical, or between about 80% and 99.9% identical, or between about 90% and 98% identical, or between about 95% and 98% identical, preferably between 98% and 99.9% identical, in sequence to the complement of a region of the target RNA molecule or to two such regions, which may or may not be contiguous in the target RNA molecule. In a preferred embodiment, one or more of the antisense RNA sequences is 100% identical in sequence to a region of the complement of the target RNA molecule, for example to a region comprising 21, 23, 25, 27, 30, or 32 contiguous nucleotides. In an embodiment, the sense or antisense ribonucleotide sequence, preferably both, is at least 40, at least 50, at least about 100, at least about 200, at least about 300, at least about 400, at least about 500, at least about 600, at least about 700, at least about 800, at least about 900, at least about 1,000, or about 100 to about 1,000, contiguous nucleotides in length. The lengths of at least 100 nucleotides are preferred when using the RNA molecule in plant cells or fungal cells, or for non-vertebrate animal cells. Lengths for the sense and antisense ribonucleotide sequence in the dsRNA of 50 nucleotides or less, for example 31 to 50 nucleotides, are preferred when using the RNA molecule in vertebrate animal cells. However, RNA molecules having more than 50 basepairs in a dsRNA region, for example up to 100 or even 200 basepairs, can be used in vertebrate animal cells provided the dsRNA regions have 10-30% of the nucleotides basepaired in G:U basepairs in the dsRNA region. In an embodiment, the number of ribonucleotides in the sense ribonucleotide sequence is between about 90% and about 110%, preferably between 95% and 105%, more preferably between 98% and 102%, even more preferably between 99% and 101%, of the number of ribonucleotides in the corresponding antisense ribonucleotide sequence to which it hybridises. In a most preferred embodiment, the number of ribonucleotides in the sense ribonucleotide sequence is the same as the number of ribonucleotides in the corresponding antisense ribonucleotide sequence. These features can be applied to each dsRNA region in the RNA molecule.

In embodiments of the first to fifth aspects, the first 3' ribonucleotide and the second 5' ribonucleotide in the RNA molecule are covalently joined by a loop sequence consisting of at least 4 ribonucleotides, or between 4 and 1,000 ribonucleotides, or preferably between 4 and 200 ribonucleotides, more preferably between 4 and 50 ribonucleotides. In an embodiment, the RNA molecule further comprises a 5' extension sequence which is covalently linked to the first 5' ribonucleotide or a 3' extension sequence which is covalently linked to the second 3' ribonucleotide, or both. In an embodiment, the chimeric RNA molecule further comprises a 5' extension sequence which is covalently linked to the second 5' ribonucleotide or a 3' extension sequence which is covalently linked to the first 3' ribonucleotide, or both. In this embodiment, the RNA molecule comprises two separate strands of RNA which hybridise to form the RNA molecule, although it may have been produced by transcription from a nucleic acid molecule as a single RNA transcript and subsequently been processed to comprise the two RNA strands.

The overall length of the RNA molecule of the invention, produced as a single strand of RNA, after splicing out of any introns but before any processing of the RNA molecule by Dicer enzymes or other RNAses, is typically between 50 and 2000 ribonucleotides, preferably between 60 or 70 and 2000 ribonucleotides, more preferably between 80 or 90 and 2000 ribonucleotides, even more preferably between 100 or 110 and 2000 ribonucleotides. In preferred embodiments, the minimum length of the RNA molecule is 120, 130, 140, 150, 160, 180, or 200 nucleotides, and the maximum length is 400, 500, 600, 700, 800, 900, 1000, 1200, 1400, 1500 or 2000 ribonucleotides. Each combination of these mentioned minimum and maximum lengths is contemplated. Production of RNA molecules of such lengths by transcription in vitro or in cells such as bacterial or other microbial cells, preferably *S. cerevisiae* cells, or in the eukaryotic cell where the target RNA molecule is to be down-regulated, is readily achieved.

In an embodiment of the first to fifth aspects, the chimeric RNA molecule comprises two or more dsRNA regions which are the same in sequence or preferably different.

In preferred embodiments of the first to fifth aspects, the RNA molecule is expressed in a eukaryotic cell i.e. produced by transcription in the cell. In these embodiments, a greater proportion of dsRNA molecules are formed by processing of the RNA molecule that are 22 and/or 20 ribonucleotides in length when compared to processing of an analogous RNA molecule which has a corresponding dsRNA region which is fully basepaired with canonical basepairs. That is, the RNA molecules of these embodiments are more readily processed to provide 22- and/or 20-ribonucleotide short antisense RNAs than the analogous RNA molecule whose dsRNA region is fully basepaired with canonical basepairs, as a proportion of the total number of 20-24 nucleotide a sRNAs produced from the RNA molecule. Expressed differently, a lesser proportion of dsRNA molecules are formed by processing of the RNA molecule that are 23 and/or 21 ribonucleotides in length when compared to processing of an analogous RNA molecule which has a corresponding dsRNA region which is fully basepaired with canonical basepairs. That is, the RNA molecules of these embodiments are less readily processed to provide 23- and/or 21-ribonucleotide short antisense RNAs than the analogous RNA molecule whose dsRNA region is fully basepaired with canonical basepairs, as a proportion of the total number of 20-24 nucleotide a sRNAs produced from the RNA molecule. Preferably, at least 50% of the RNA transcripts produced in the cell by transcription from the genetic construct are not processed by Dicer. In an embodiment, when the RNA molecule is expressed in a eukaryotic cell i.e. produced by transcription in the cell, a greater proportion of the short antisense RNA molecules that are formed by processing of the RNA molecule have more than one phosphate covalently attached at the 5' terminus when compared to processing of an analogous RNA molecule which has a corresponding dsRNA region which is fully basepaired with canonical basepairs. That is, a greater proportion of the short antisense RNA molecules have an altered charge which can be observed as a mobility shift of the molecules in gel electrophoresis experiments.

In an embodiment, the RNA molecule of the invention comprises a combination of two or more features of an RNA molecule described herein.

In another aspect, the present invention provides a polynucleotide encoding an RNA molecule described herein, preferably a chimeric RNA molecule described herein. In an embodiment, the polynucleotide is a DNA construct which may be integrated into a larger DNA molecule such as a chromosome. In an embodiment, the polynucleotide is operably linked to a promoter capable of directing expression of the RNA molecule in a host cell. The host cell may be a bacterial cell such as *E. coli*, a fungal cell such as a yeast cell, for example, *S. cerevisiae*, or a eukaryotic cell such as a plant cell or an animal cell. In an embodiment, the promoter is heterologous relative to the polynucleotide. The polynucleotide encoding the RNA molecule may be a chimeric or recombinant polynucleotide, or an isolated and/or exogenous polynucleotide. In an embodiment, the promoter can function in vitro, for example a bacteriophage promoter such as a T7 RNA polymerase promoter or SP6 RNA polymerase promoter. In an embodiment, the promoter is an RNA polymerase III promoter such as a U6 promoter or an H1 promoter. In an embodiment, the promoter is an RNA polymerase II promoter, which may be a constitutive promoter, a tissue-specific promoter, a developmentally regulated promoter or an inducible promoter. In an embodiment, the polynucleotide encodes an RNA precursor molecule comprising an intron in at least one loop sequence which is capable of being spliced out during or after transcription of the polynucleotide in a host cell. In an embodiment, the present invention provides a vector comprising a polynucleotide described herein. In an embodiment, the vector is a viral vector. In an embodiment, the vector is a plasmid vector such as a binary vector suitable for use with *Agrobacterium tumefaciens.*

In an embodiment, the polynucleotide is a chimeric DNA which comprises in order, a promoter capable of initiating transcription of the RNA molecule in a host cell, operably linked to a DNA sequence which encodes the RNA molecule, preferably a hpRNA, and a transcription termination and/or polyadenylation region. In a preferred embodiment, the RNA molecule comprises a hairpin RNA structure which comprises a sense ribonucleotide sequence, a loop sequence and an antisense ribonucleotide sequence, more preferably wherein the sense and antisense ribonucleotide sequences basepair to form a dsRNA region wherein between about 5% and about 40% of the ribonucleotides in the dsRNA region are basepaired in non-canonical basepairs, preferably G:U basepairs. In preferred embodiments, the host cell is a plant cell or a fungal cell.

In an embodiment where the polynucleotide or vector of the invention is in a eukaryotic host cell, preferably in a plant or in a fungal cell, the promoter region of the polynucleotide or vector, which is operably linked to the region which encodes an RNA molecule of the invention, has a lower level of methylation when compared to the promoter of a corresponding polynucleotide or vector encoding an RNA molecule which has a corresponding dsRNA region which is fully basepaired with canonical basepairs. In an embodiment, the lower level of methylation is less than 50%, less than 40%, less than 30% or less than 20%, when compared to the promoter of the corresponding polynucleotide or vector. In an embodiment, the host cell comprises at least two copies of the polynucleotide or vector encoding an RNA molecule of the invention. In this embodiment:

i) the level of reduction in the expression and/or activity of the target RNA molecule in the eukaryotic cell is at least the same relative to a corresponding eukaryotic cell having a single copy of the polynucleotide or vector, and/or ii) the level of reduction in the expression and/or activity of the target RNA molecule in the eukaryotic cell is lower when compared to a corresponding cell comprising an RNA molecule which has a corresponding dsRNA region which is fully basepaired with canonical basepairs.

In another aspect, the present invention provides a host cell comprising an RNA molecule described herein, small RNA molecules (20-24 nt in length) produced by processing of the chimeric RNA molecule, a polynucleotide described herein or a vector comprising the same. In an embodiment, the host cell is a non-human cell such as bacterial cell, a fungal cell, for example yeast cell such as a *S. cerevisiae* cell, a plant cell or a non-human animal cell, preferably a plant cell. In an embodiment, the cell is a non-human cell or a human cell in cell culture. In an embodiment, the cell is a eukaryotic cell such as a cell other than an animal cell. In an embodiment, the cell is a microbial cell such as a prokaryotic cell. In an embodiment, the host cell is alive. In an alternative embodiment, the host cell is dead and/or incapable of reproduction. The host cell may be the cell in which the RNA molecule was produced by transcription and/or processing, or the cell may be a cell other than the cell in which the RNA molecule was produced by transcription and/or processing, such as a cell comprising the target RNA molecule.

In an embodiment, the host cell preferably a plant cell or a fungal cell, comprising the chimeric RNA molecule or small RNA molecules produced by processing of the chimeric RNA molecule, or both, wherein the chimeric RNA molecule comprises, in 5' to 3' order, the first sense ribonucleotide sequence, the first linking ribonucleotide sequence which comprises a loop sequence, and the first antisense ribonucleotide sequence.

In another embodiment, the host cell is a eukaryotic cell and which comprises at least two copies of the polynucleotide encoding a chimeric RNA molecule according to any one of claims 1 to 39, and wherein i) the level of reduction in the expression or activity of the target RNA molecule in the eukaryotic cell is about the same as, or greater than, the level of reduction in the expression or activity of the target RNA molecule if the cell had a single copy of the polynucleotide, and/or ii) the level of reduction in the expression or activity of the target RNA molecule in the eukaryotic cell is lower when compared to a corresponding cell comprising an RNA molecule which has a corresponding dsRNA region which is fully basepaired with canonical basepairs.

In another aspect, the present invention provides a non-human organism, preferably an animal or plant, comprising an RNA molecule of the invention, preferably a chimeric RNA molecule described herein or small RNA molecules (20-24 nt in length) produced by processing of the chimeric RNA molecule or a polynucleotide or vector of the invention comprising the same or a host cell comprising the same. In an embodiment, the non-human organism, preferably a plant or fungus, is transgenic insofar as it comprises a polynucleotide of the invention. In an embodiment, the polynucleotide is stably integrated into the genome of the non-human organism. The invention also includes animal and plant parts, and products obtained therefrom, comprising the RNA molecule or small RNA molecules (20-24 nt in length) produced by processing of the chimeric RNA molecule, or both, and/or the polynucleotide or vector of the invention, for example to seeds, crops, harvested products and post-harvest products produced therefrom.

In another aspect, the present invention provides a method of producing an RNA molecule of the invention, the method comprising expressing the polynucleotide of the invention in a host cell or cell-free expression system. Preferably the polynucleotide is a chimeric DNA molecule encoding the RNA molecule. In this embodiment, the method may further comprise at least partially purifying the RNA molecule, or not.

In another aspect, the present invention provides a method of producing a cell or non-human organism, preferably a plant cell, plant or fungus, the method comprising introducing a polynucleotide or vector or RNA molecule of the invention into a cell, preferably an animal cell, a plant cell or fungus, preferably so that the polynucleotide or vector or part thereof encoding the RNA molecule is stably integrated into the genome of the cell. In an embodiment, the cell is an animal cell, for example a human cell, which may be an animal cell in culture. In an embodiment, the non-human organism is generated from the cell or a progeny cell, for example by regenerating a transgenic plant and optionally producing progeny plants therefrom. In an embodiment, the non-human organism is generated by introducing the cell or one or more progeny cells into a non-human organism. Alternatively to the stable integration of the polynucleotide or vector into the genome of the cell, the polynucleotide or vector may be introduced into the cell without integration of the polynucleotide or vector into the genome, for example to produce the RNA molecule transiently in the cell or organism. In an embodiment, the non-human organism, e.g. an animal or a plant, is resistant to a pest or pathogen, e.g. an animal pest or pathogen, a plant pest or pathogen, preferably an insect pest or fungal pathogen. In an embodiment, the method comprises a step of testing one or more non-human organisms, preferably plants, comprising the polynucleotide or vector or RNA molecule of the invention for resistance to the pest or pathogen. The non-human organisms, e.g. plants that are tested may be progeny from the non-human organism, preferably the plant, into which the polynucleotide or vector or RNA molecule of the invention was first introduced, and therefore the method may comprise a step of obtaining such progeny. The method may further comprise a step of identifying and/or selecting the non-human organism, e.g. an animal or a plant, which is resistant to a pest or pathogen. For example, multiple non-human organisms, e.g. animals or plants, which each comprise the polynucleotide or vector or RNA molecule of the invention may be tested to identify which is resistant to the pest or pathogen, and progeny obtained from the identified non-human organism, animal or plant.

In another aspect, the present invention provides an extract of a host cell or organism or part thereof of the invention, wherein the extract comprises an RNA molecule of the invention, small RNA molecules (20-24 nt in length) produced by processing of the chimeric RNA molecule, or both, and/or the polynucleotide or vector of the invention. In an embodiment, the present invention provides a composition comprising one or more of an RNA molecule of the invention, small RNA molecules (20-24 nt in length) produced by processing of the chimeric RNA molecule, or both, a polynucleotide of the invention, a vector of the invention, a host cell of the invention, or an extract produced by a method of the invention, and one or more suitable carriers. In an embodiment, the composition is a pharmaceutical composition, such as a composition suitable for administration to a human or other animal. The pharmaceutical composition may be suitable for prophylaxis or treatment of a disease, or for topical application such as a cosmetic application. In an embodiment, the composition is suitable for application to a plant, preferably a plant or population of plants in a field, e.g. as topical spray, or to an insect or population of insects. In an embodiment, the composition is suitable for application to a crop, for example by spraying on crop plants in a field.

In an embodiment, the extract or a composition comprising the RNA molecule of the invention or small RNA molecules (20-24 nt in length) produced by processing of the chimeric RNA molecule, or both, further comprises at least one compound which enhances the stability of the RNA molecule, or the polynucleotide and/or vector, whereby the at least one compound assists in the RNA molecule, polynucleotide or vector being taken up by a cell, such as for example a cell of an organism. In an embodiment, the compound is a transfection promoting agent, for example a lipid-containing compound.

In another aspect, the present invention provides a method for reducing or down-regulating the level and/or activity of a target RNA molecule in a cell or an organism, for example in a part thereof, the method comprising delivering to the cell or organism one or more RNA molecule(s) of the invention or small RNA molecules (20-24 nt in length) produced by processing of the chimeric RNA molecule, or both, a polynucleotide of the invention, a vector of the invention, or a composition of the invention. In this context, delivering may be via feeding, contacting, exposing, transforming or otherwise introducing the RNA molecule or small RNA molecules, or a mixture thereof, or the polynucleotide or vector of the invention to the cell or organism. The introduction may be enhanced by use of an agent that increases the uptake of the RNA molecules, polynucleotides or vectors of the invention, for example with the aid of transfection promoting agents, DNA- or RNA-binding polypeptides, or may be done without adding such agents, for example by planting seed which is transgenic for a polynucleotide or vector of the invention and allowing the seed to grow into a transgenic plant which expresses the RNA molecules of the invention. In an embodiment, the target RNA molecule encodes a protein. In an embodiment, the method reduces the level and/or activity of more than one target RNA molecule, the target RNA molecules being different, for example two or more target RNAs are reduced in level and/or activity which are related in sequence such as from a gene family. Thus, in an embodiment, the chimeric RNA molecule or small RNA molecules produced by processing of the chimeric RNA molecule, or both, are contacted with the cell or organism, preferably a plant cell, plant, fungus or insect, by topical application to the cell or organism, or provided in a feed for the organism.

In another aspect, the present invention provides a method of controlling a non-human organism, for example an animal pest or pathogen or a plant pest or pathogen, the method comprising delivering to the non-human organism one or more RNA molecule(s) of the invention or small RNA molecules (20-24 nt in length) produced by processing of the chimeric RNA molecule, or both, or a polynucleotide or vector of the invention, a host cell of the invention, an extract produced by a method of the invention, or a composition of the invention, wherein the RNA molecule and/or small RNA molecules have a deleterious effect on the non-human organism. In an embodiment, the non-human organism is an arthropod, such as for example an insect, or a plant such as for example a weed. In an embodiment, the non-human organism is a plant, and the insect eats the plant or a portion thereof, whereby the insect is controlled. The control may comprise reduced survival of the pest or pathogen, or reduced fitness or reproduction of the pest or pathogen, or both. The control may encompass reduced survival and/or reproduction of progeny of the pest or pathogen into which the RNA molecules were first introduced.

Another aspect of the invention relates to a method of reducing damage caused by a pest or pathogen to a non-human organism, e.g. an animal or plant, comprising delivering to the pest or pathogen, or contacting the pest or pathogen with, one or more RNA molecule(s) of the invention or small RNA molecules (20-24 nt in length) produced by processing of the chimeric RNA molecule, or both, a polynucleotide or vector of the invention, a host cell of the invention, an extract produced by a method of the invention, or a composition of the invention. In an embodiment, the method comprises sowing seed which is transgenic for a polynucleotide of the invention, whereby the resultant plants express the transgene to produce RNA molecules of the invention, thereby reducing damage caused by a pest or pathogen. The invention thereby provides a farmer with a means to control a pest or pathogen of animals or plants. The invention extends to the cells and organisms, e.g. animals or plants, or parts thereof, which comprise the RNA molecule, polynucleotide or vector of the invention which were provided to the cell or organism, and to the pest or pathogen which comprises the RNA molecule or small RNA molecules (20-24 nt in length) produced by processing of the chimeric RNA molecule, or both, or the polynucleotide or vector of the invention. The pest or pathogen may be alive or dead. The present invention also relates to progeny cells or organisms comprising the RNA molecule or small RNA molecules or both.

In an embodiment, the present invention provides a method of preventing or treating a disease in a subject, the method comprising administering to the subject one or more RNA molecule(s) of the invention or small RNA molecules (20-24 nt in length) produced by processing of the chimeric RNA molecule, or both, a polynucleotide or vector of the invention, a host cell of the invention, an extract produced by a method of the invention, or a composition of the invention, wherein the RNA molecule or small RNA molecules or both has a beneficial effect on at least one symptom of the disease. In an embodiment, the RNA molecule or small RNA molecules, polynucleotide, vector or composition are administered topically, orally or injected. In an embodiment, the subject is a vertebrate animal. In an embodiment, the vertebrate animal is a mammal such as a human, a livestock animal such as cattle or sheep, or birds such as chickens and other poultry.

In another aspect, the present invention provides an RNA molecule of the invention, a polynucleotide or vector of the invention, a host cell of the invention, an extract produced by a method of the invention, or a composition of the invention for use in preventing or treating a disease in a subject, wherein the RNA molecule or small RNA molecules or both has a beneficial effect on at least one symptom of the disease. In an embodiment, the present invention provides a use of an RNA molecule of the invention or small RNA molecules produced therefrom, a polynucleotide or vector of the invention, a host cell of the invention, an extract produced by a method of the invention, or a composition of the invention for the manufacture of a medicament for preventing or treating a disease in a subject, wherein the RNA molecule or small RNA molecules produced therefrom or both have a beneficial effect on at least one symptom of the disease.

In another aspect, the present invention provides a kit comprising one or more of an RNA molecule(s) of the invention or small RNA molecules produced therefrom, a polynucleotide or vector of the invention, a host cell of the invention, an extract produced by a method of the invention, or a composition of the invention. The kit may further comprise instructions for use of the kit.

Whilst more widely used in transgenic expression systems, as discussed herein there are also applications of dsRNA technology which rely on the need for the large scale production of dsRNA molecules, such as spraying a crop to control disease and/or pests. The present inventors have identified *S. cerevisiae* as a suitable organism to use in large scale production processes because dsRNA molecules expressed therein are not cleaved. Thus, in a further aspect, the present invention provides a process for producing dsRNA molecules, the process comprising a) culturing *S. cerevisiae* expressing one or more polynucleotides encoding one or more dsRNA molecules, and b) harvesting the *S. cerevisiae* producing the dsRNA molecules, or the dsRNA molecules from the *S. cerevisiae,* wherein the *S. cerevisiae* are cultured in a volume of at least 1 litre.

The dsRNA can have any structure, such as an shRNA, a miRNA or a dsRNA of the invention.

In an embodiment, the *S. cerevisiae* are cultured in a volume of at least 10 litres, at least 100 litres, at least 1,000 litres, at least 10,000 litres or at least 100,000 litres.

In an embodiment, the process produces at least 0.1, at least 0.5 or at least 1 g/litre of an RNA molecule of the invention.

The *S. cerevisiae* produced using the process, or dsRNA molecules isolated therefrom (either in a purified or partially purified (such as an extract) state) can be used in methods described herein such as, but not limited to, a method for reducing or down-regulating the level and/or activity of a target RNA molecule in a cell or an organism, a method reducing damage caused by a pest or pathogen to a non-human organism, a method of controlling a non-human organism or a method of preventing or treating a disease in a subject.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Schematic designs of two ledRNA molecules. (A) This ledRNA molecule comprises a sense sequence which can be considered to be two adjacent sense sequences, covalently linked without an intervening spacer sequence and having identity to the target RNA, an antisense sequence which is complementary to the sense sequence and which is divided into two regions, a 5' region and a 3' region, and two loops that separate the sense from the antisense sequences. (B) This ledRNA molecule comprises an antisense sequence which can be considered to be two adjacent antisense sequences, covalently linked without an intervening spacer sequence and having identity to the complement of a target RNA, a sense sequence which is complementary to the antisense sequence and which is divided into two regions, and two loops that separate the sense from the antisense sequences. The RNA molecule produced by transcription, for example by in vitro transcription from a promoter such as a T7 or Sp6 promoter, self-anneals by basepairing between the complementary sense and antisense sequences to form a double-stranded region with a loop at each end and having a “nick” in either the antisense or sense sequence. Additional sequences may be linked to the 5' and/or 3' ends as 5'- or 3'-extensions.

Figure 2:
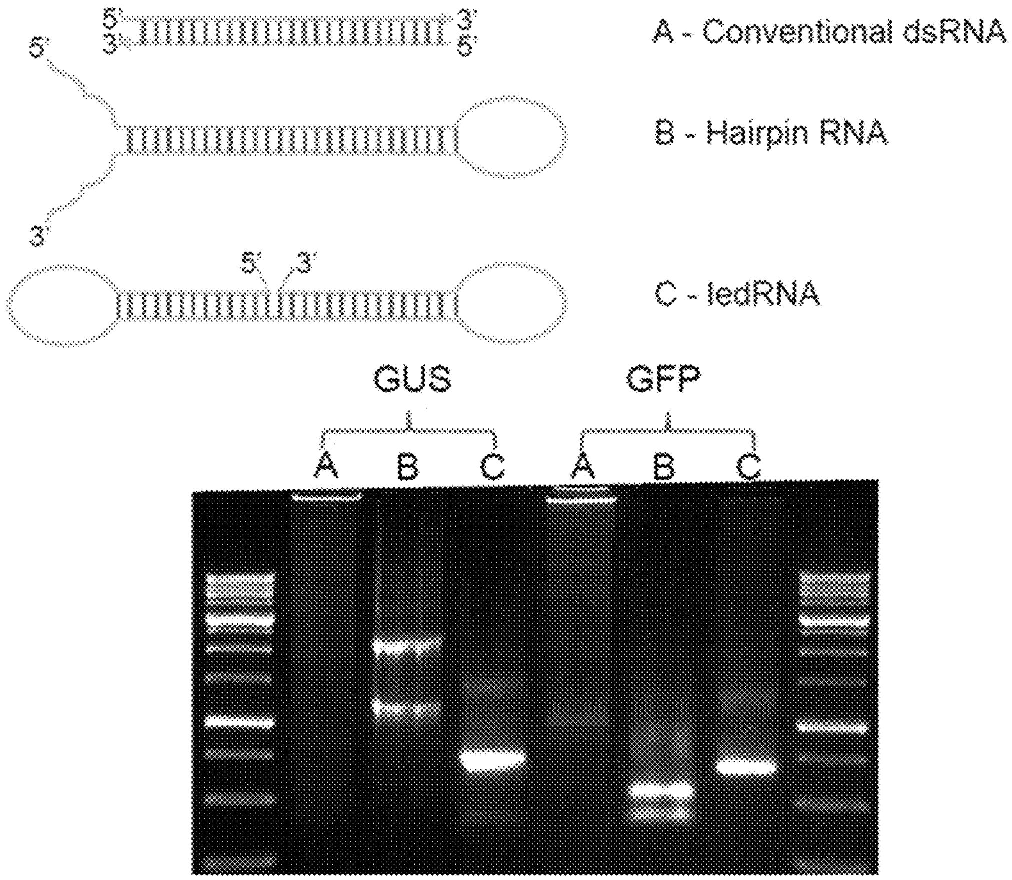

FIG. 2. ledRNA is more efficient in forming dsRNA than sense/antisense annealing or hairpin RNA. Schematic representations of three forms of double-stranded RNA molecules are shown: A, conventional dsRNA formed by annealing of two separate strands; B, a hairpin RNA having a 5'- and a 3'-extension; and C, ledRNA molecule. The lower panel shows a photograph after gel electrophoresis of the RNA transcripts for the three types of RNA molecules targeting either a GUS gene or a GFP gene.

Figure 3:
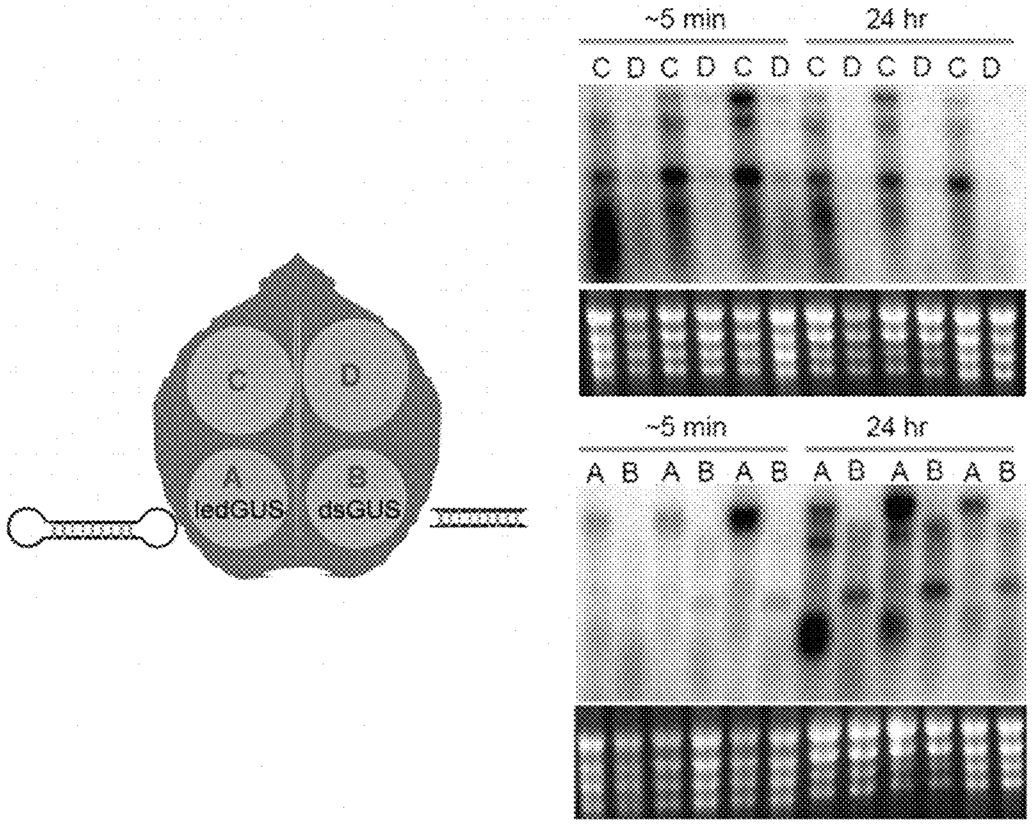

FIG. 3. Northern blot hybridization of treated (A and B) and untreated distal (C and D) tissues shows that ledRNA is more stable than dsRNA and spread through tobacco leaf tissue. In the distal tissues (C and D, top panel) the dsRNA signal could not be detected, in contrast to strong ledRNA signals.

Figure 4:
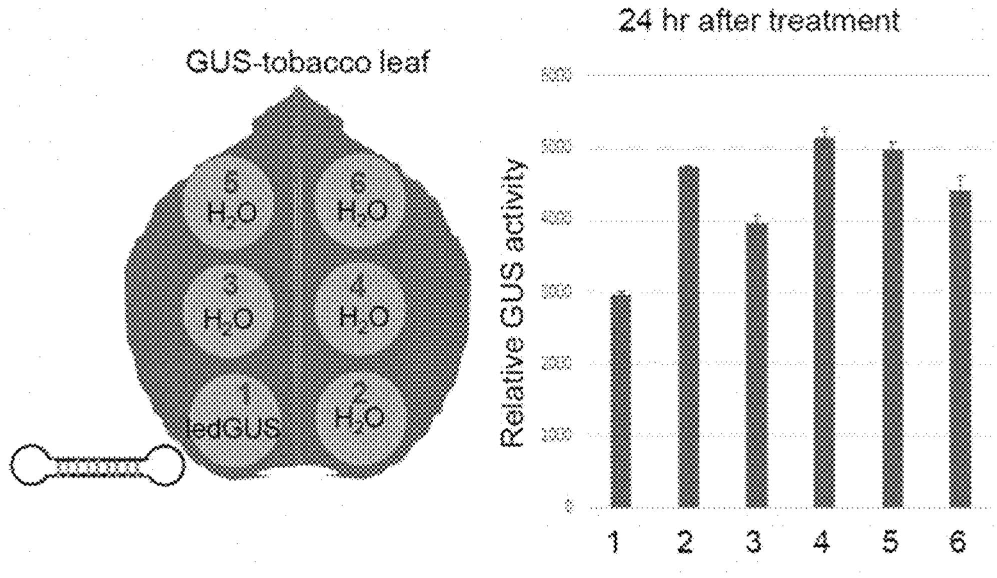

FIG. 4. ledRNA treatment induced downregulation of GUS in both the treated area (1) and the untreated area above (3).

Figure 5:
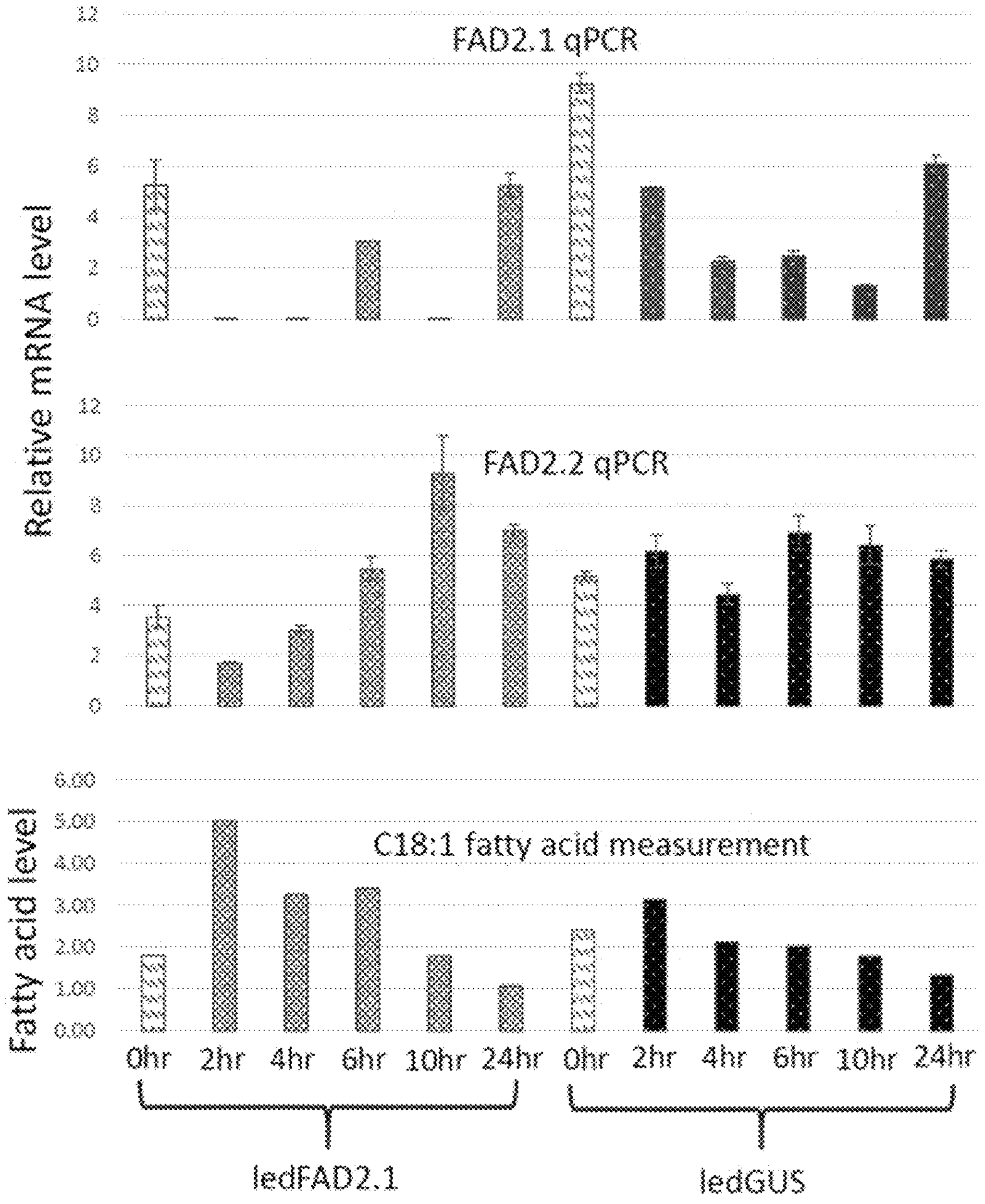

FIG. 5. ledRNA induces silencing of the FAD2.1 gene in *N. benthamiana* leaves.

Figure 6:
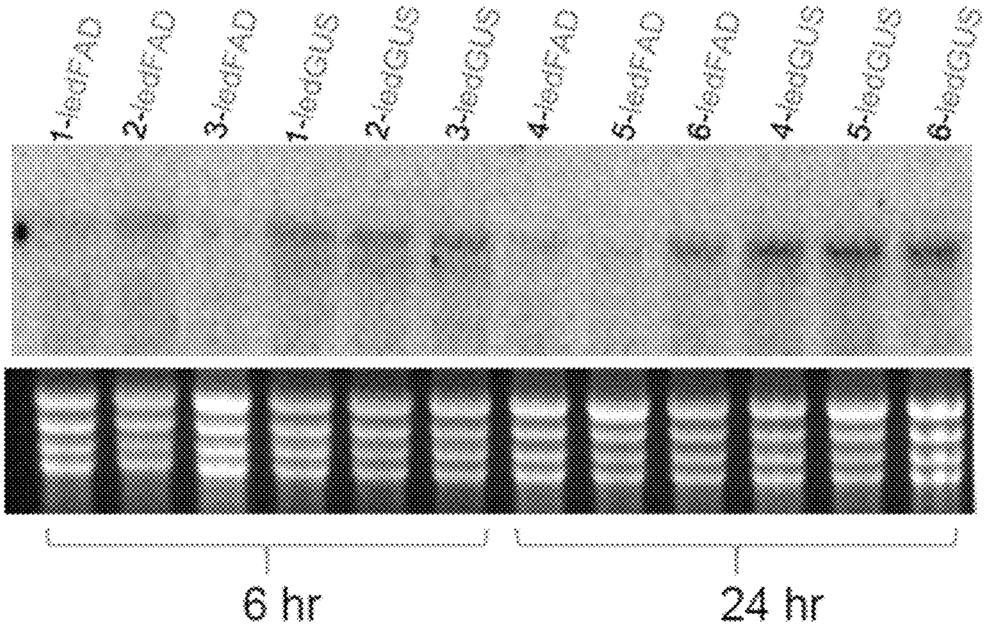

FIG. 6. Northern blot hybridization confirms strong downregulation of FAD2.1 mRNA by treatment with led FAD2.1 at 6 and 24 hours.

FIG. 7. Alignment of the nucleotide sequences of a region of the GUS target gene (SEQ ID NO:14) and the sense sequence of the hpGUS[G:U] construct (nucleotides 9 to 208 of SEQ ID NO:11). 52 cytidine (C) nucleotides were substituted with thymidine (T) nucleotides. Conserved nucleotides are asterisked, substituted C’s are not asterisked.

FIG. 8. Alignment of the nucleotide sequences of a region of the GUS target gene (SEQ ID NO:14) and the sense sequence of the hpGUS[1:4] construct (nucleotides 9 to 208 of SEQ ID NO:12). Every 4th nucleotide in hpGUS[1:4] was substituted relative to the corresponding wild-type sense sequence, whereby for every 4th nucleotide, C was changed to G, G was changed to C, A was changed to T, and T was changed to A. Conserved nucleotides are asterisked, substituted G's and C's are not asterisked, substituted A's and T's are shown with semi-colons.

FIG. 9. Alignment of the nucleotide sequences of a region of the GUS target gene (SEQ ID NO:14) and the sense sequence of the hpGUS[2:10] construct (nucleotides 9 to 208 of SEQ ID NO:13). Every 9th and 10th nucleotide in each block of 10 nucleotides in hpGUS[2:10] was substituted relative to the corresponding wild-type sense sequence, whereby for every 9th and 10th nucleotide, C was changed to G, G was changed to C, A was changed to T and T was changed to A. Conserved nucleotides are asterisked, substituted G's and C's are not asterisked, substituted A's and T's are shown with semi-colons.

Figure 10:
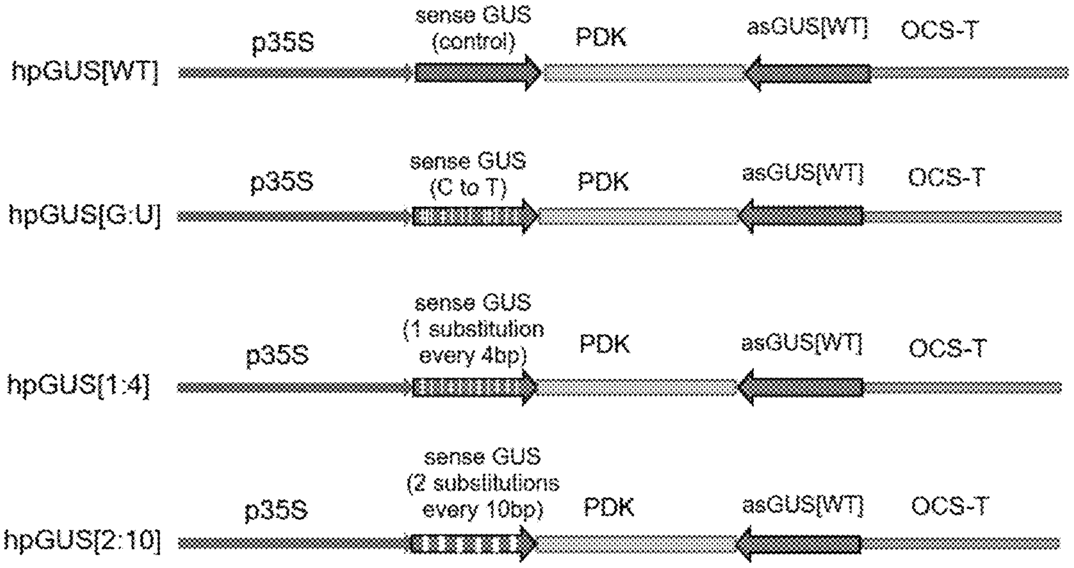

FIG. 10. Schematic diagram showing structures of the genetic constructs encoding modified hairpin RNAs targeting GUS mRNA.

Figure 11:
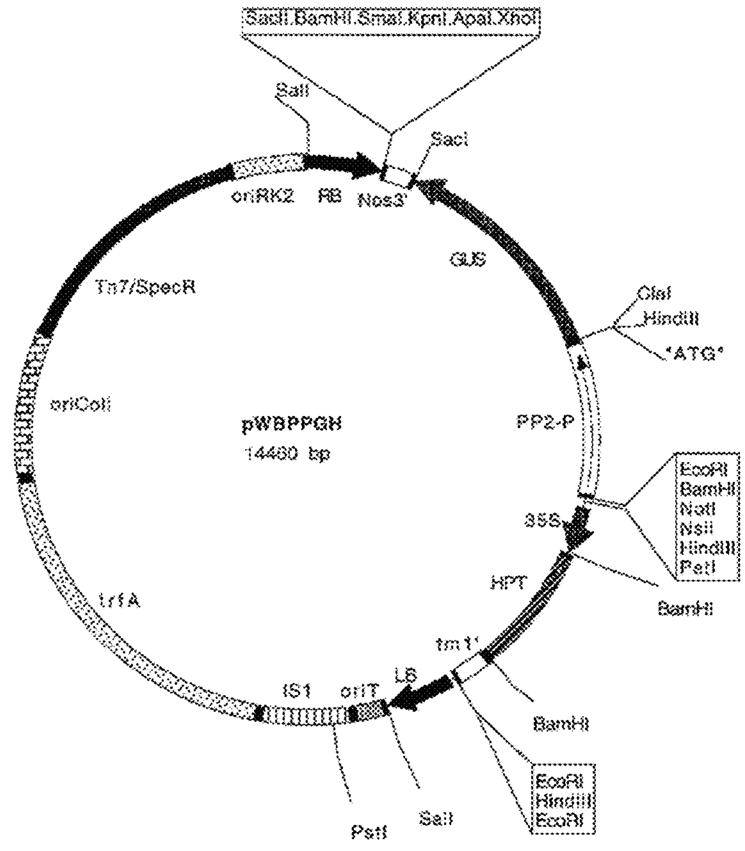

FIG. 11. Schematic diagram of vector pWBPPGH used to transform tobacco plants, providing a GUS target gene. The T-DNA extends from the right border (RB) to the left border (LB) of the vector. The selectable marker gene on the T-DNA is the 35S-HPT-tml' gene encoding hygromycin resistance.

Figure 12:
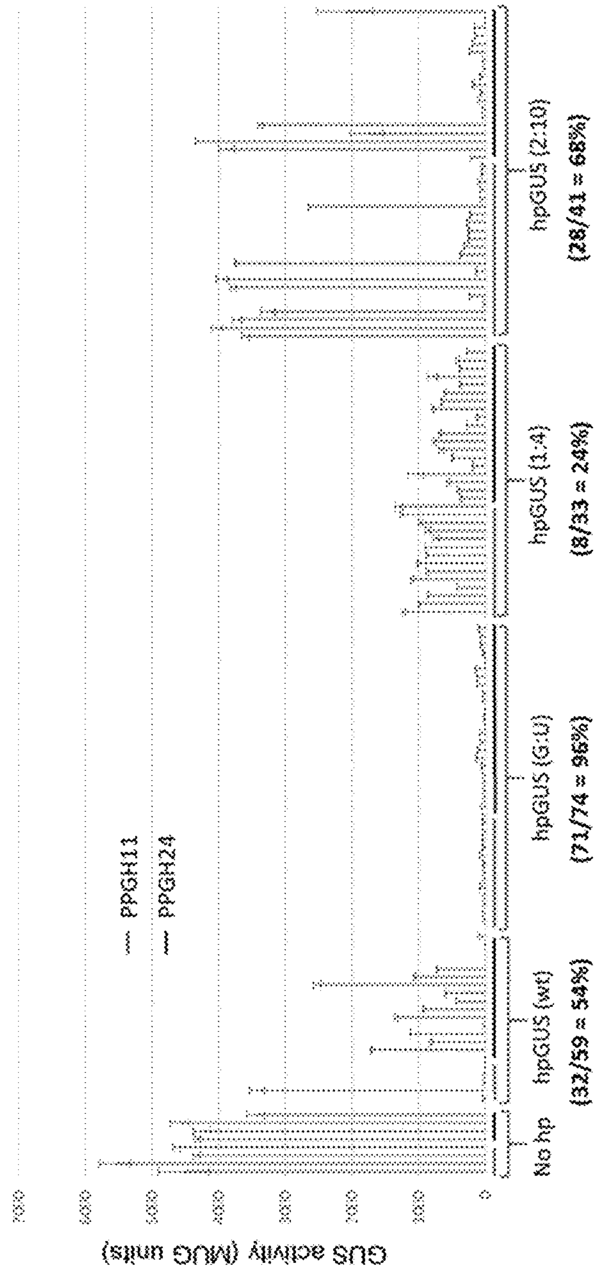

FIG. 12. GUS activity in plants transformed with constructs encoding modified hairpin RNAs for reducing expression of a GUS target gene. No hp: control PPGH11 and PPGH24 plants with no hpGUS constructs. The number of plants showing less than 10% GUS activity compared to the corresponding control PPGH11 or PPGH24 plants and the percentage of such plants relative to the number of plants tested are given in brackets.

Figure 13:
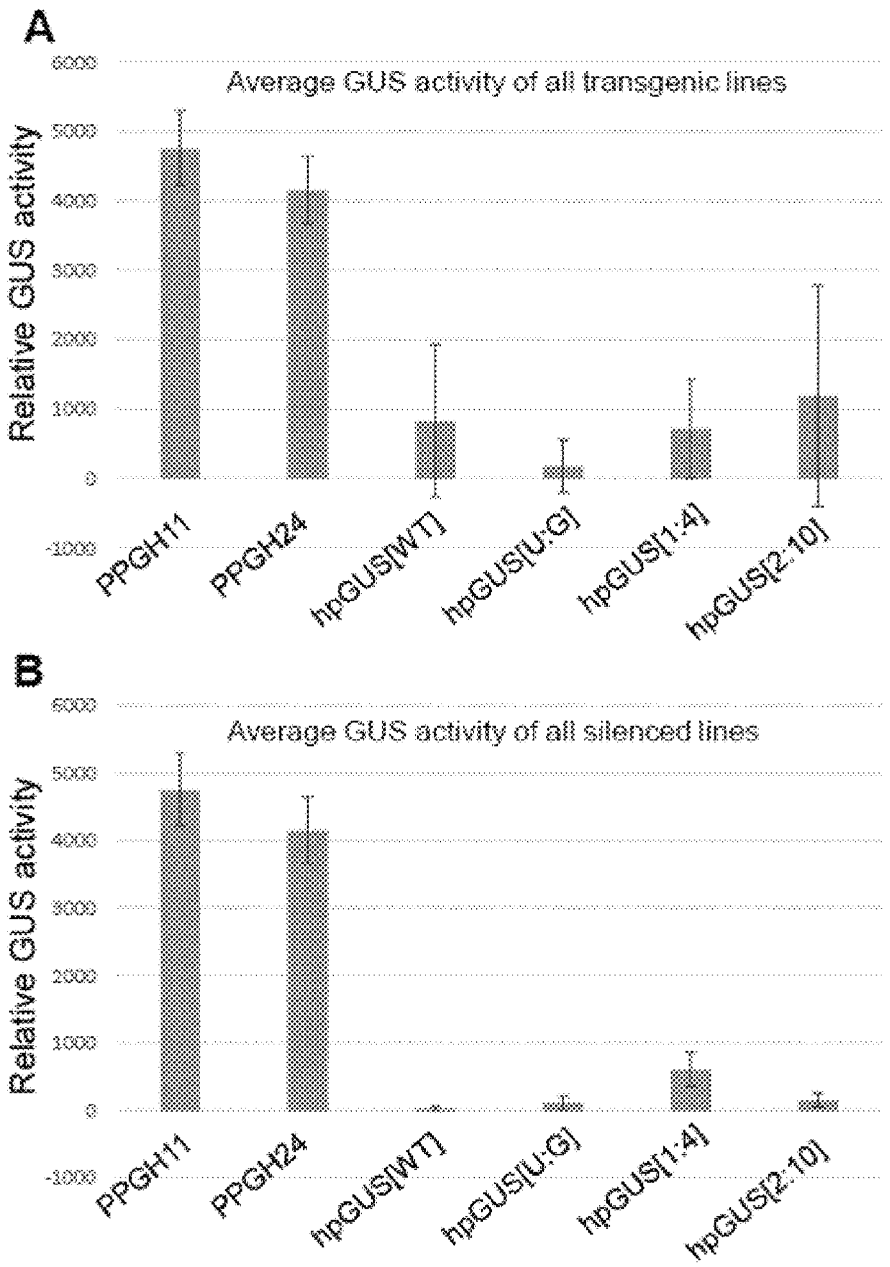

FIG. 13. (A) Average GUS activity of all transgenic plants: 59 plants for hpGUS[wt], 74 for hpGUS[G:U], 33 for hpGUS[1:4] and 41 for hpGUS[2:10]. (B) Average GUS activity of all silenced plants (32 for hpGUS[wt], 71 for hpGUS[G:U], 33 for hpGUS[1:4] and 28 for hpGUS[2:10].

Figure 14:
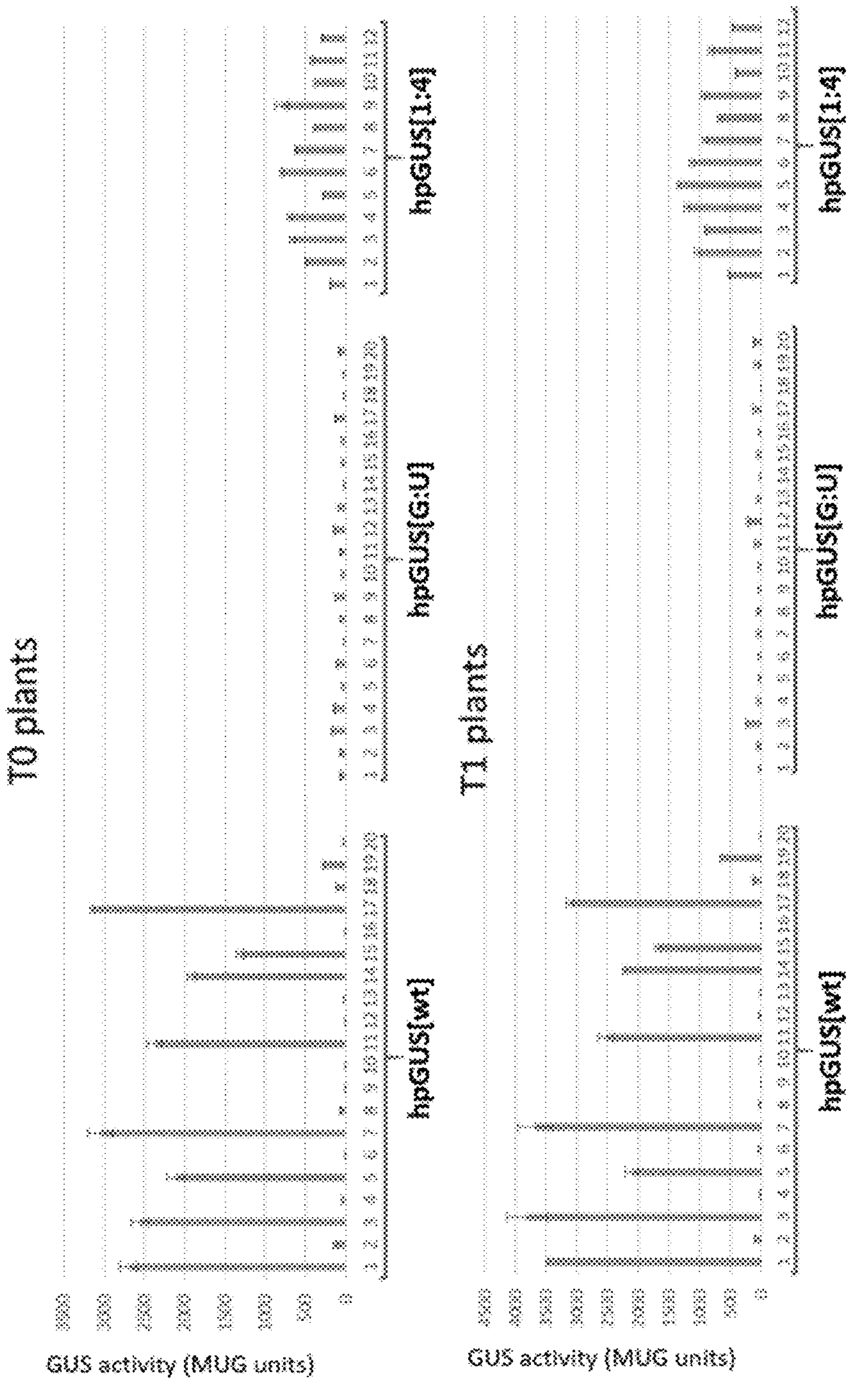

FIG. 14. GUS activity of transgenic progeny plants containing hpGUS[wt], hpGUS[G:U] or hpGUS[1:4].

Figure 15:
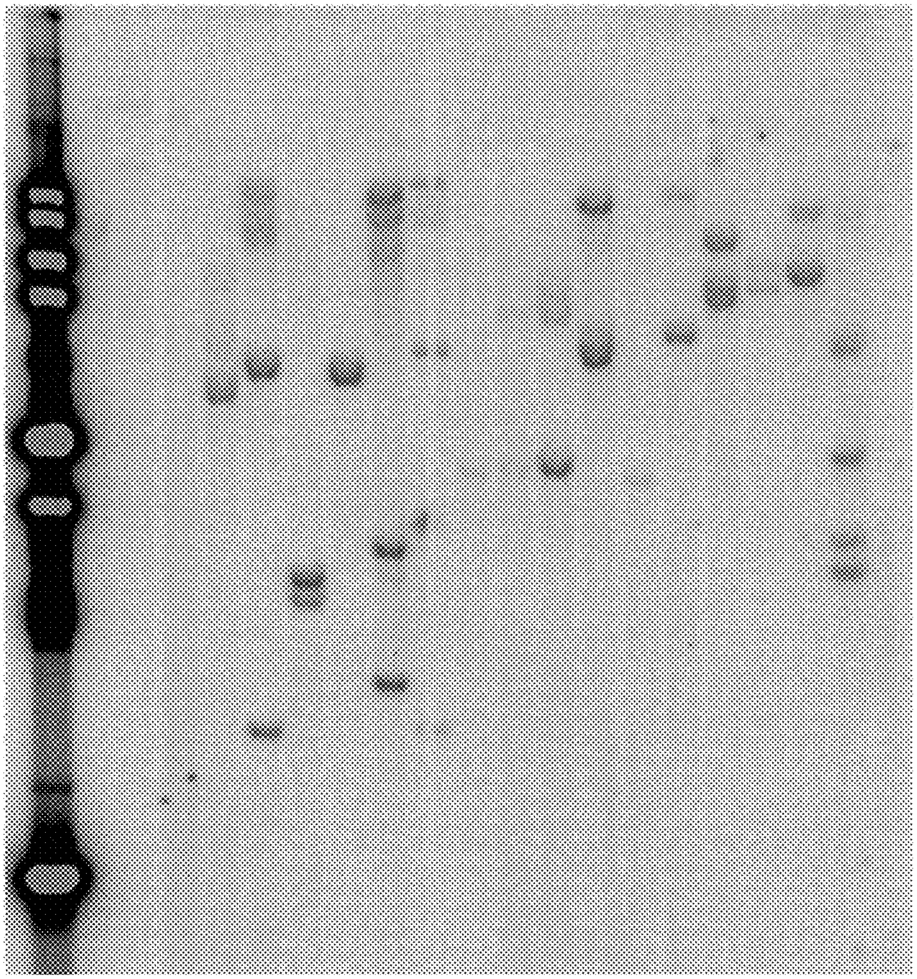

FIG. 15. Autoradiograph of a Southern blot of DNA from 16 plants transformed with the hpGUS[G:U] construct. DNAs were digested with HindIII prior to gel electrophoresis and probed with an OCS-T probe. Lane 1: size markers (HindIII-digested lambda DNA); Lanes 2 and 3, DNA from parental plants PPGH11 and PPGH24; Lanes 4-19: DNAs from 16 different transgenic plants.

Figure 16:
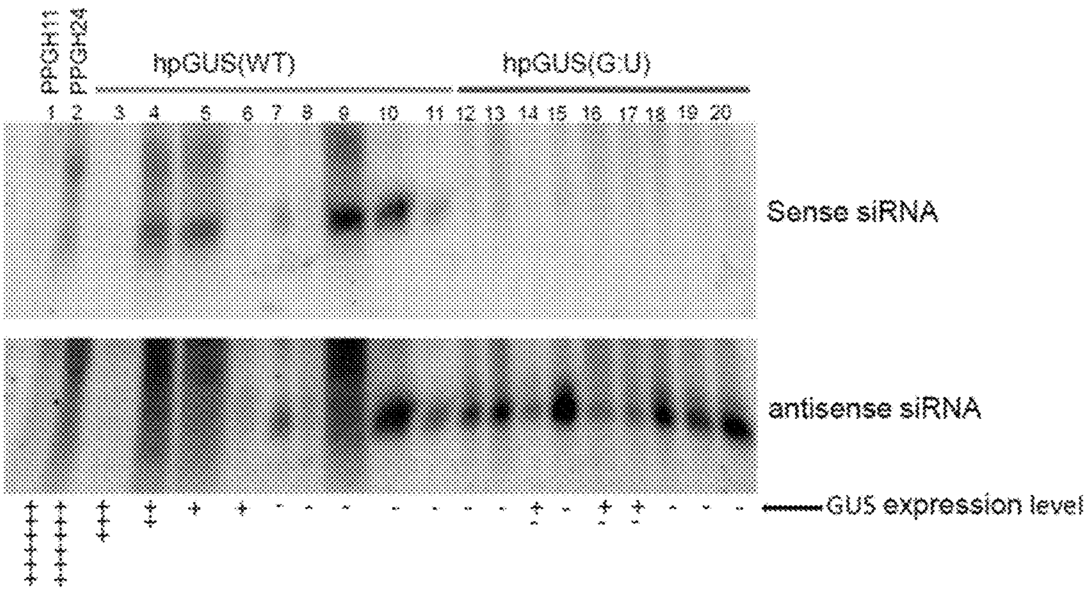

FIG. 16. Autoradiogram of a Northern blot hybridisation experiment to detect sense (upper panel) and antisense (lower panel) sRNAs derived from hairpin RNAs expressed in transgenic tobacco plants. Lanes 1 and 2 contained RNA obtained from the parental plants PPGH11 and PPGH24 lacking the hpGUS constructs. Lanes 3-11 contained RNA from hpGUS[wt] plants and lanes 12-20 contained RNA from hpGUS[G:U] plants.

Figure 17:
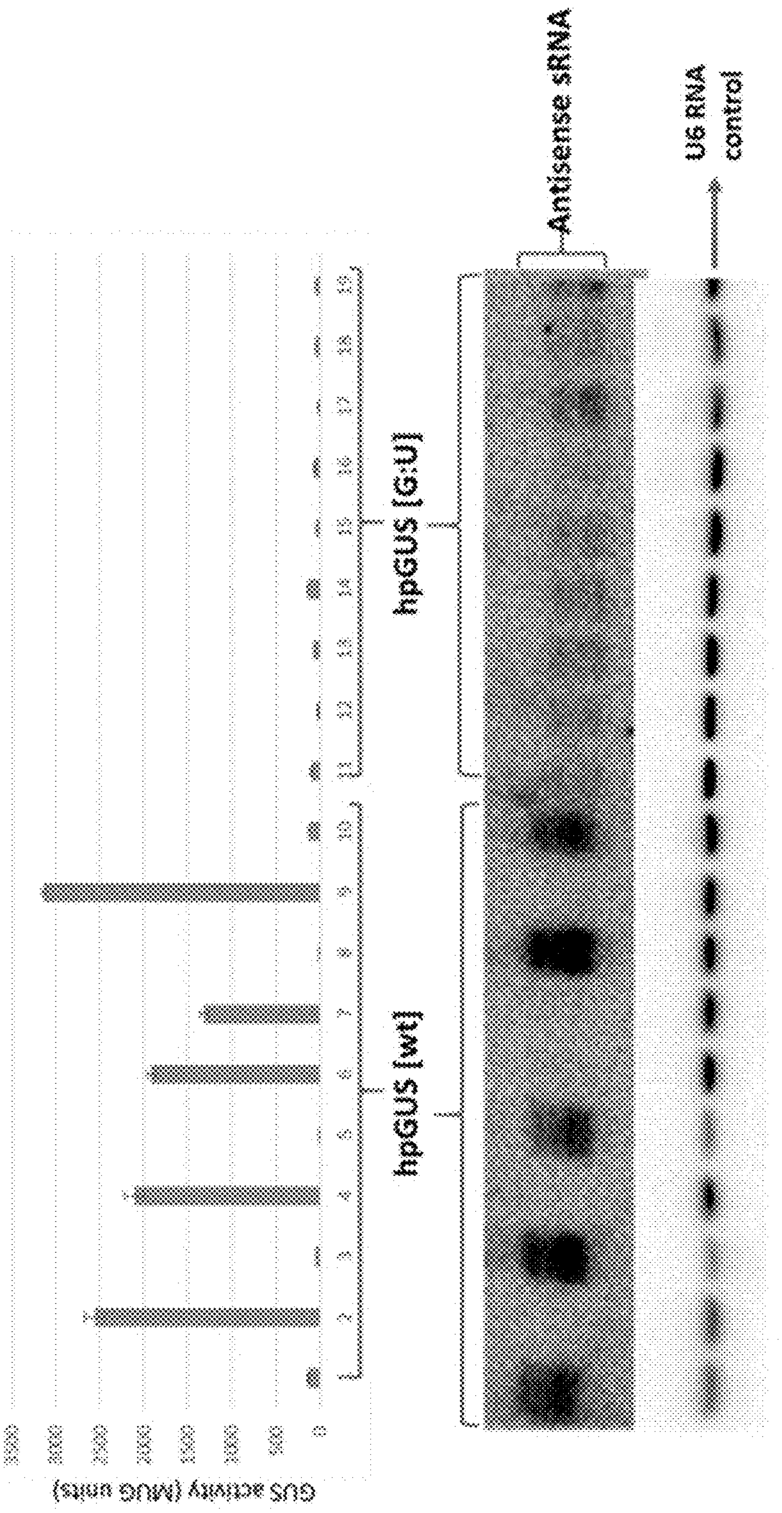

FIG. 17. Autoradiograph of a Northern blot hybridisation to detect antisense sRNAs from transgenic plants. Lanes 1-10 were from hpGUS[wt] plants, lanes 11-19 were from hpGUS[G:U] plants. The antisense sRNAs have mobility corresponding to 20-24 nt in length. The blot was reprobed with antisense to U6 RNA as a lane-loading control.

Figure 18:
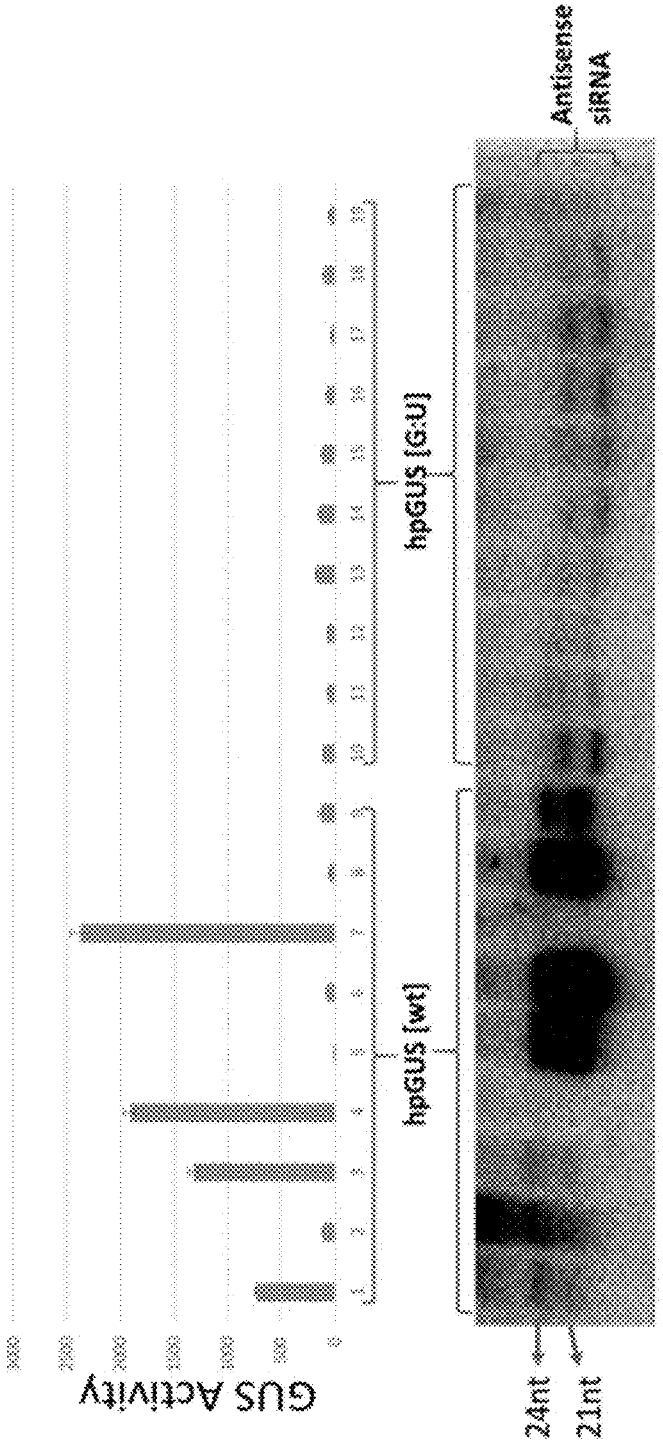

FIG. 18. Autoradiograph of a repeat Northern blot hybridisation to detect antisense sRNAs from transgenic plants FIG. 19. DNA methylation analysis of the junction region of the 35S promoter and sense GUS region in hpGUS constructs in transgenic plants. The junction fragments were PCR-amplified either with (+) or without (–) prior treatment of plant DNA with McrBC enzyme.

Figure 20:
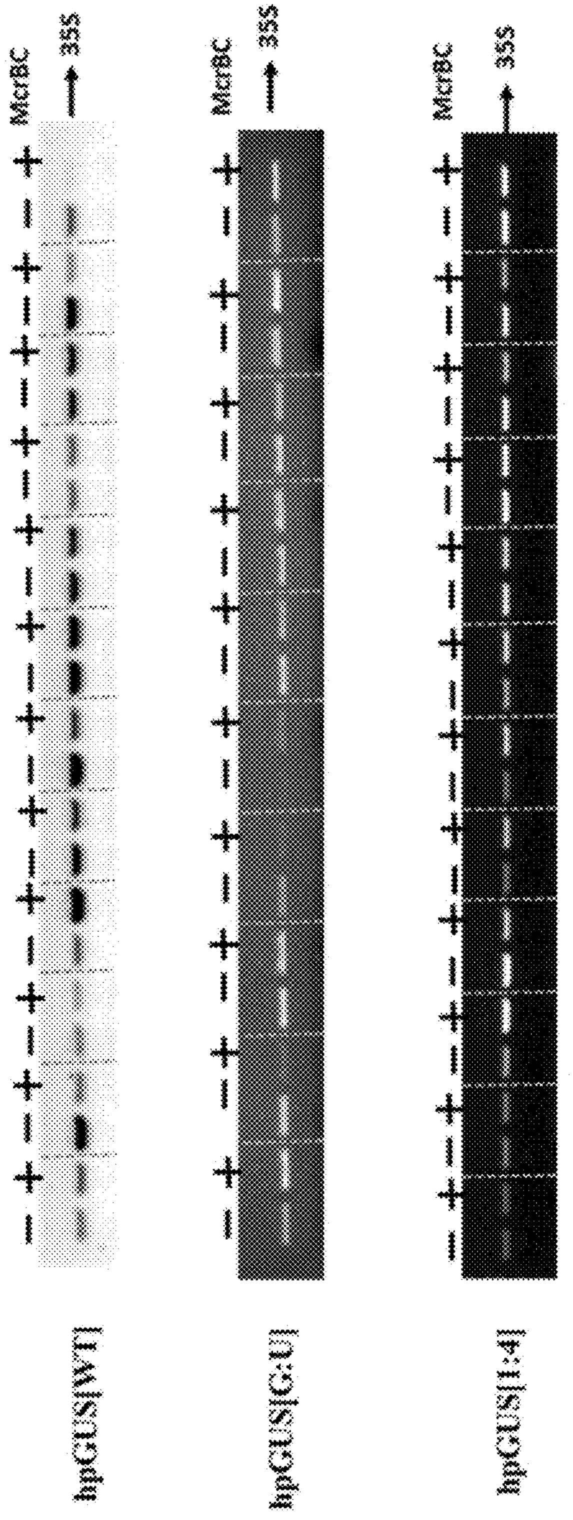

FIG. 20. DNA methylation analysis of the 35S promoter region in hpGUS constructs in transgenic plants. The 35S fragments were PCR-amplified either with (+) or without (–) prior treatment of plant DNA with McrBC enzyme.

Figure 21:
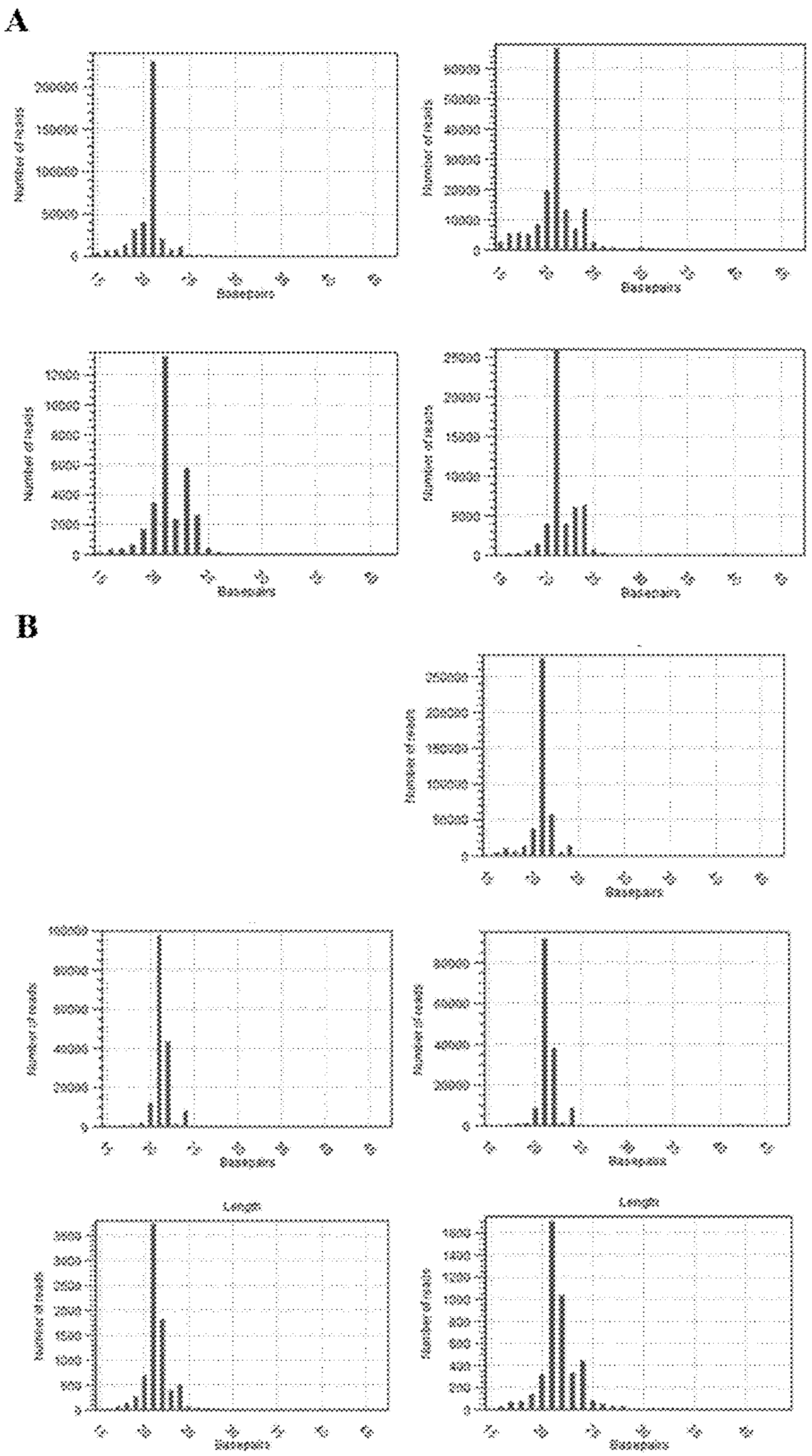

FIG. 21. Size distribution and abundance of processed RNA. (A) EIN2 constructs. (B) GUS constructs.

FIG. 22. Alignment of the sense sequence (upper sequence, nucleotides 17 to 216 of SEQ ID NO:22) of the hpEIN2[G:U] construct and the nucleotide sequence (lower sequence, SEQ ID NO:27) of a region of the cDNA corresponding to the *A. thaliana* EIN2 target gene. The sense sequence was made by replacing 43 cytidine (C) nucleotides in the wild-type sequence with thymidine (T) nucleotides. Conserved nucleotides are asterisked, substituted C's are not asterisked.

FIG. 23. Alignment of the sense sequence (upper sequence, nucleotides 13 to 212 of SEQ ID NO:24) of the hpCHS[G:U] construct with the nucleotide sequence of a region of the cDNA corresponding to the *A. thaliana* CHS target gene (SEQ ID NO:28, lower sequence). The sense sequence was made by replacing 65 cytidine (C) nucleotides in the wild-type sequence with thymidine (T) nucleotides. Conserved nucleotides are asterisked, substituted C's are not asterisked.

FIG. 24. Alignment of the antisense sequence (upper sequence, nucleotides 8 to 207 of SEQ ID NO:25) of the hpEIN2[G:U/U:G] construct and the nucleotide sequence (lower sequence, SEQ ID NO:29) of a region of the complement of the *A. thaliana* EIN2 target gene and the. The antisense sequence was made by replacing 49 cytidine (C) nucleotides in the wild-type sequence with thymidine (T) nucleotides. Conserved nucleotides are asterisked, substituted C's are not asterisked.

FIG. 25. Alignment of the antisense sequence (upper sequence, nucleotides 13 to 212 of SEQ ID NO:26) of the hpCHS[G:U/U:G] construct and the nucleotide sequence (lower sequence, SEQ ID NO:30) of a region of the complement of the *A. thaliana* CHS target gene. The antisense sequence was made by replacing 49 cytidine (C) nucleotides in the wild-type sequence with thymidine (T) nucleotides. Conserved nucleotides are asterisked, substituted C's are not asterisked.

Figure 26:
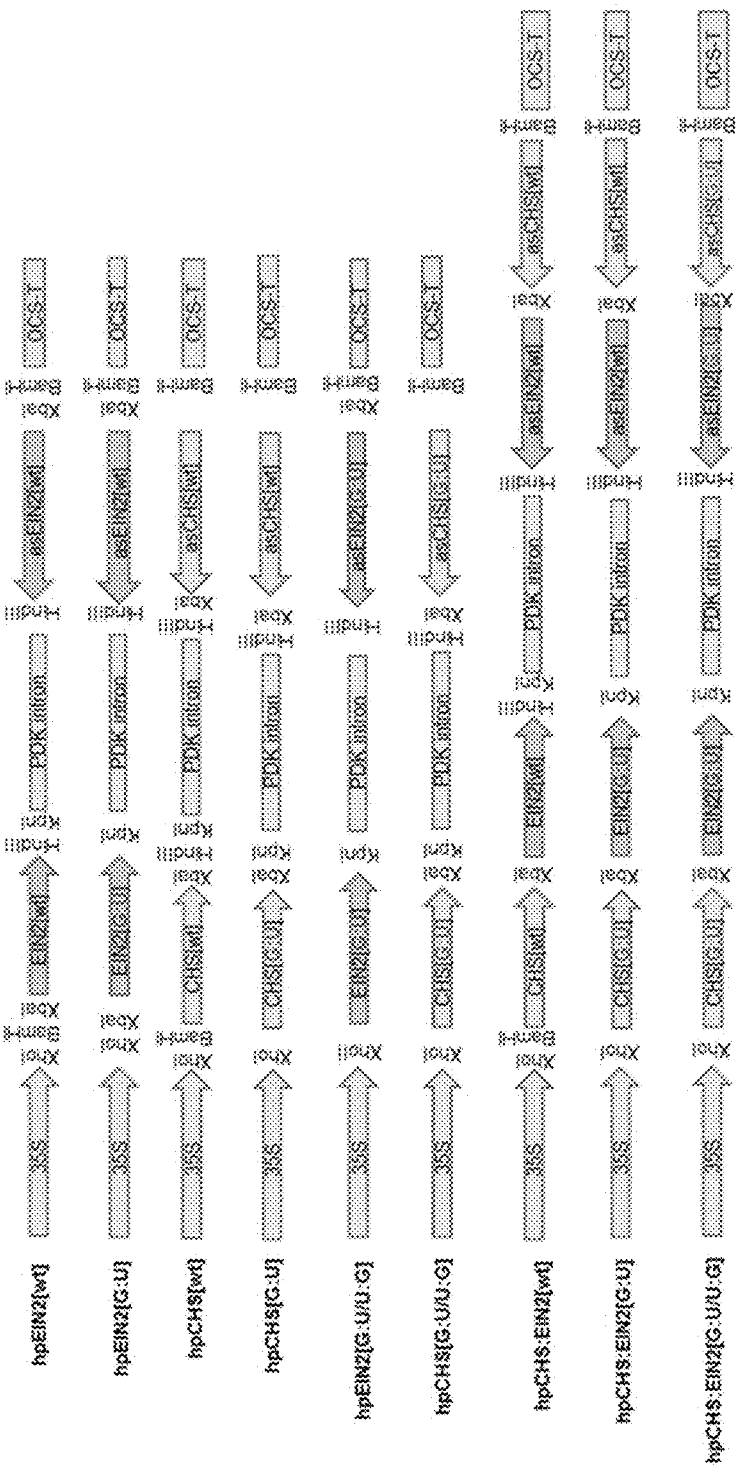

FIG. 26. Schematic diagrams of the ethylene insensitive 2 (EIN2) and chalcone synthase (CHS) hpRNA constructs. 35S: CaMV 35S promoter; EIN2 and CHS regions are show either as wild-type sequence (wt) or the G:U modified sequence (G:U). The arrows indicate the orientation of the DNA fragments—right to left arrows indicate the antisense sequences. Restriction enzyme sites are also shown.

Figure 27:
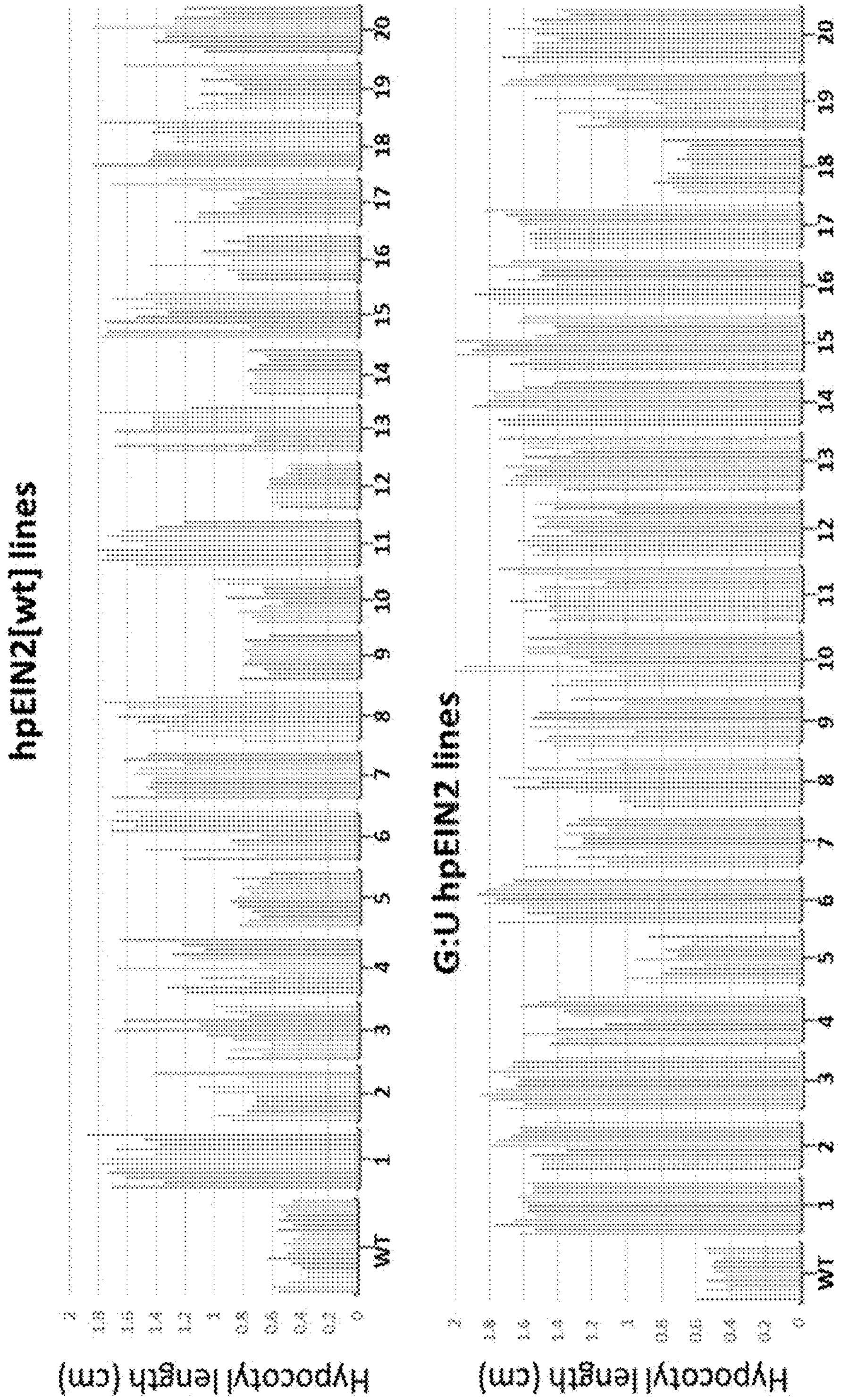

FIG. 27. Hypocotyl lengths of transgenic *A. thaliana* seedlings in the EIN2 assay, containing either the hpEIN2 [wt] or hpEIN2[G:U]

Figure 28:
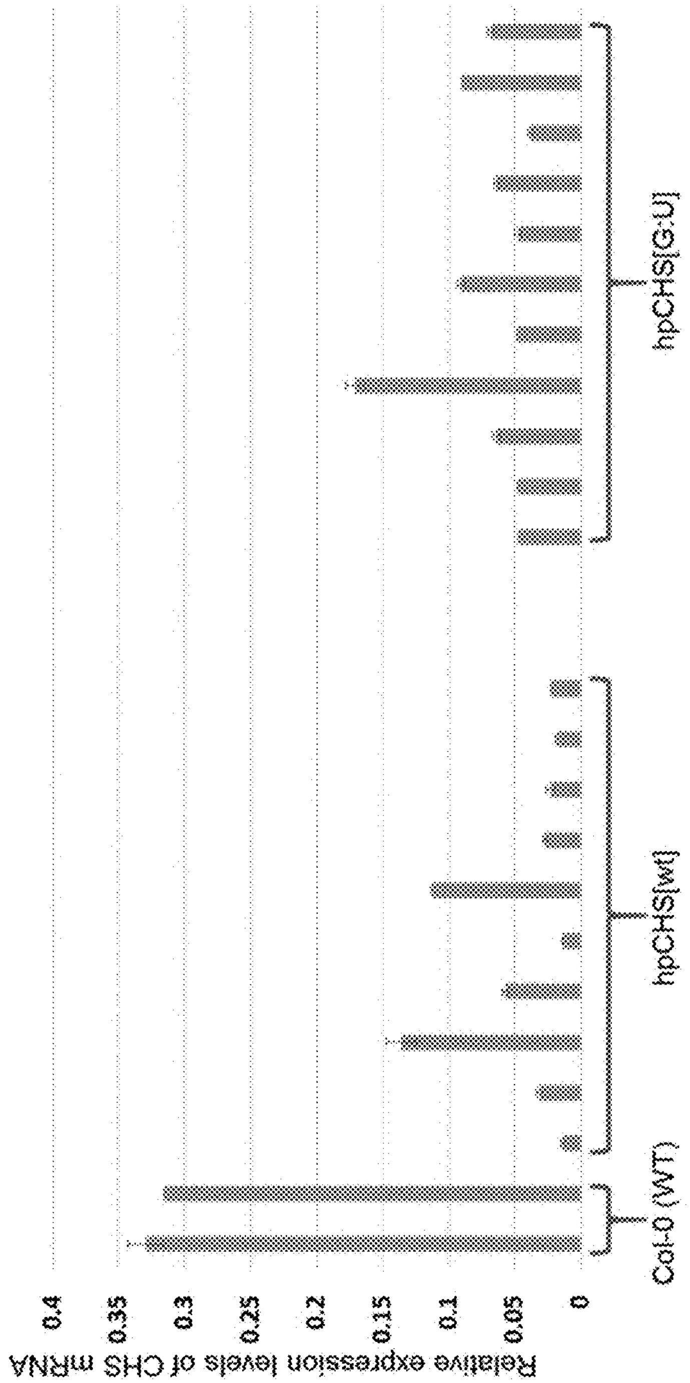

FIG. 28. qRT-PCR for CHS mRNA in transgenic *A. thaliana* transgenic for the hpCHS[wt] or hpCHS[G:U] constructs, normalised to the levels of Actin2 RNA. Col-0 is the wild-type (nontransgenic) *A. thaliana*.

Figure 29:
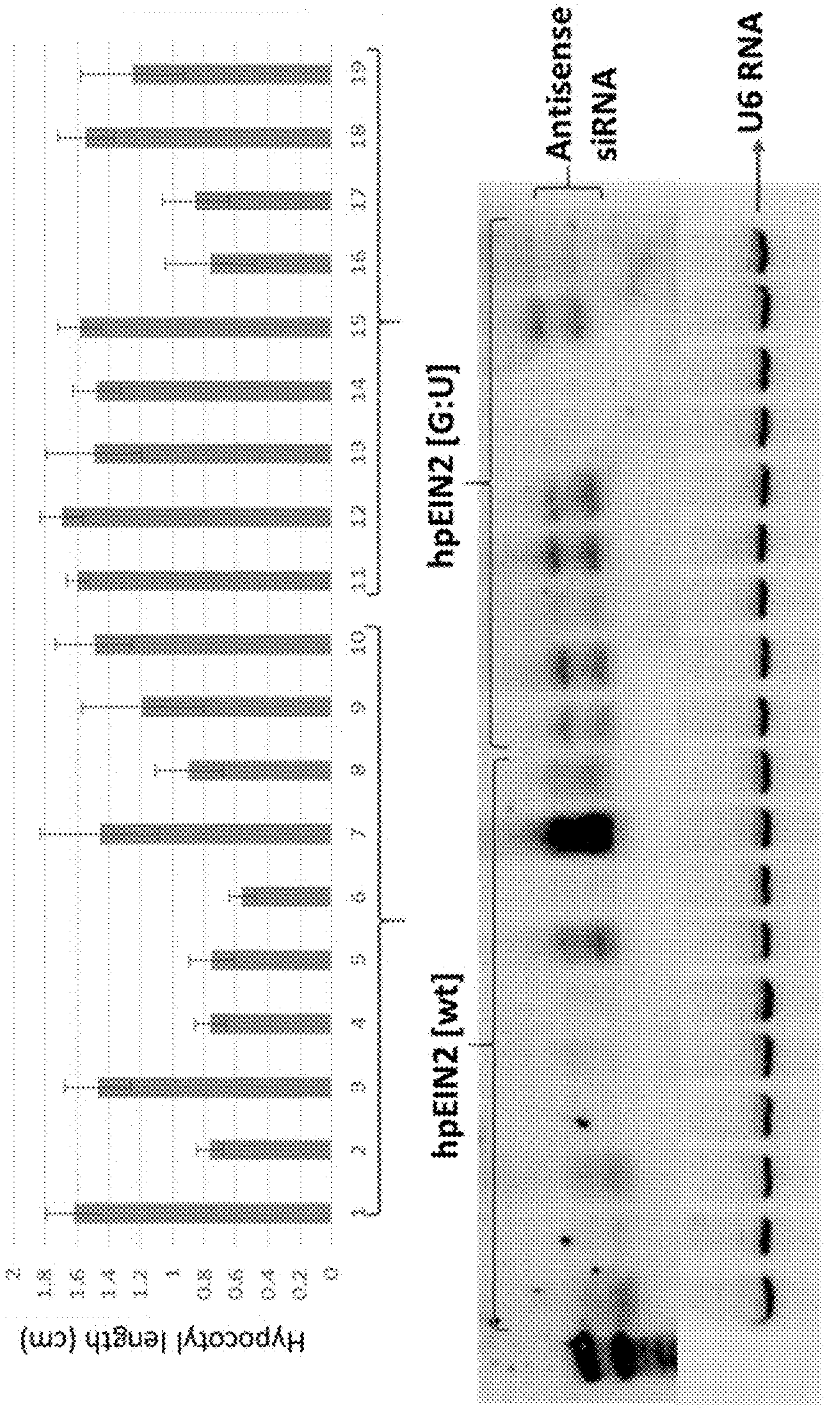

FIG. 29. Autoradiograph of Northern blot hybridisation of RNA from plants transformed with hpEIN2[wt] or hpEIN2 [G:U]. Upper panel shows the hypocotyl length for the lines. The autoradiograph shows Northern blot probed with an EIN2 sense probe to detect antisense sRNAs. The same blot was re-probed with a U6 RNA probe as a loading control (U6 RNA).

Figure 30:
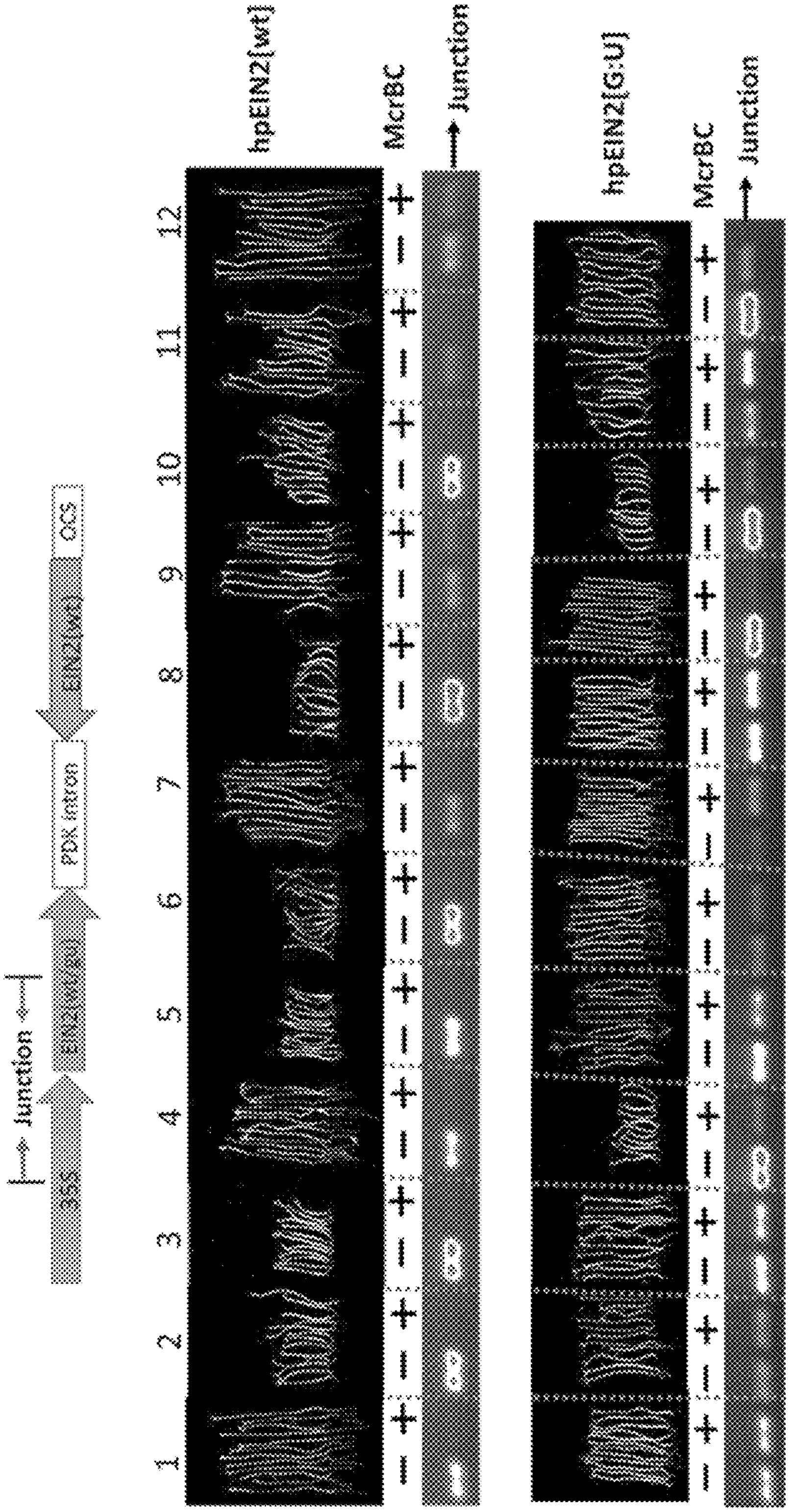

FIG. 30. DNA methylation analysis of 35S promoter and 35S-sense EIN2 sequences in genomic DNA of transgenic *A. thaliana* plants.

Figure 31:
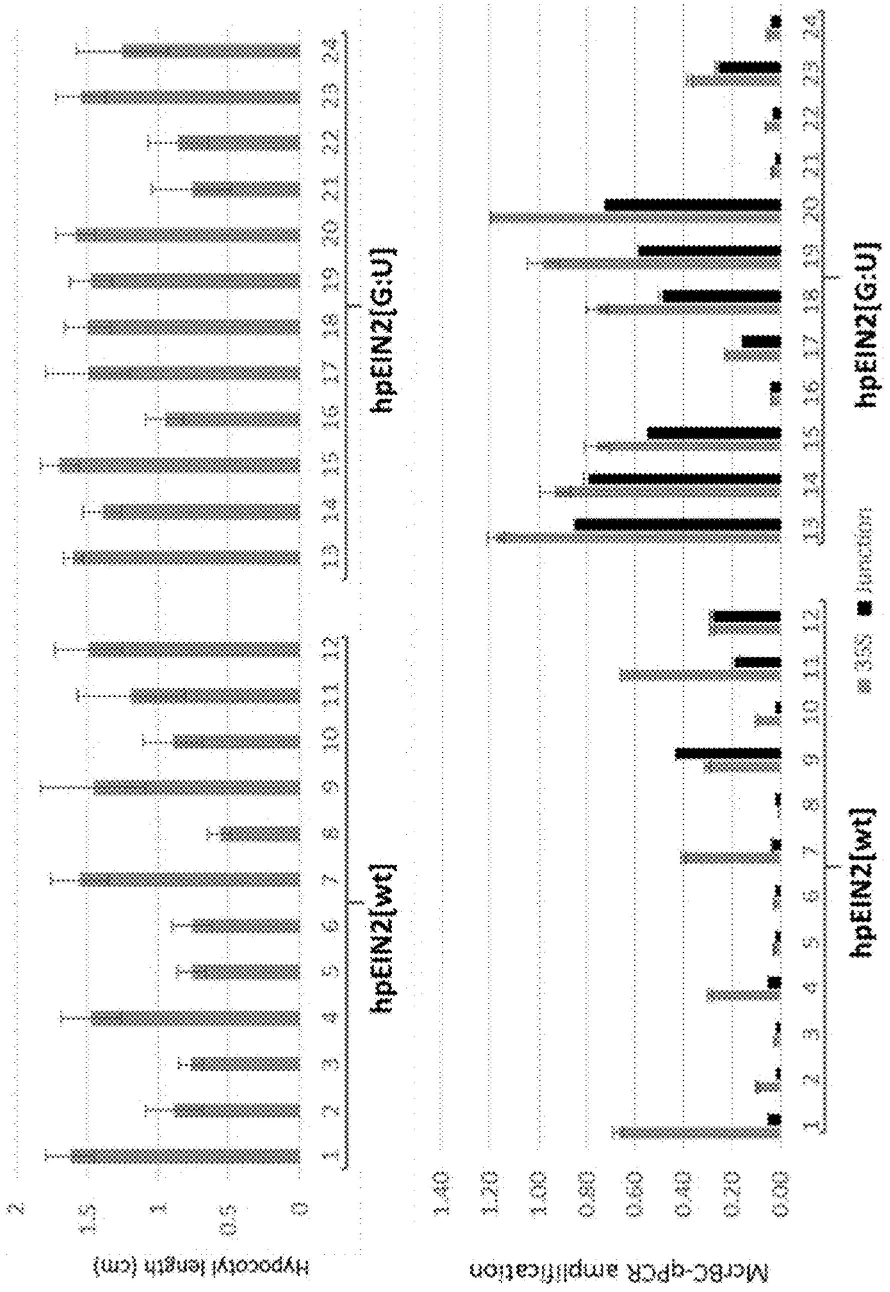

FIG. 31. Levels of DNA methylation in the promoter and 5' region of hairpin RNA constructs.

Figure 32:
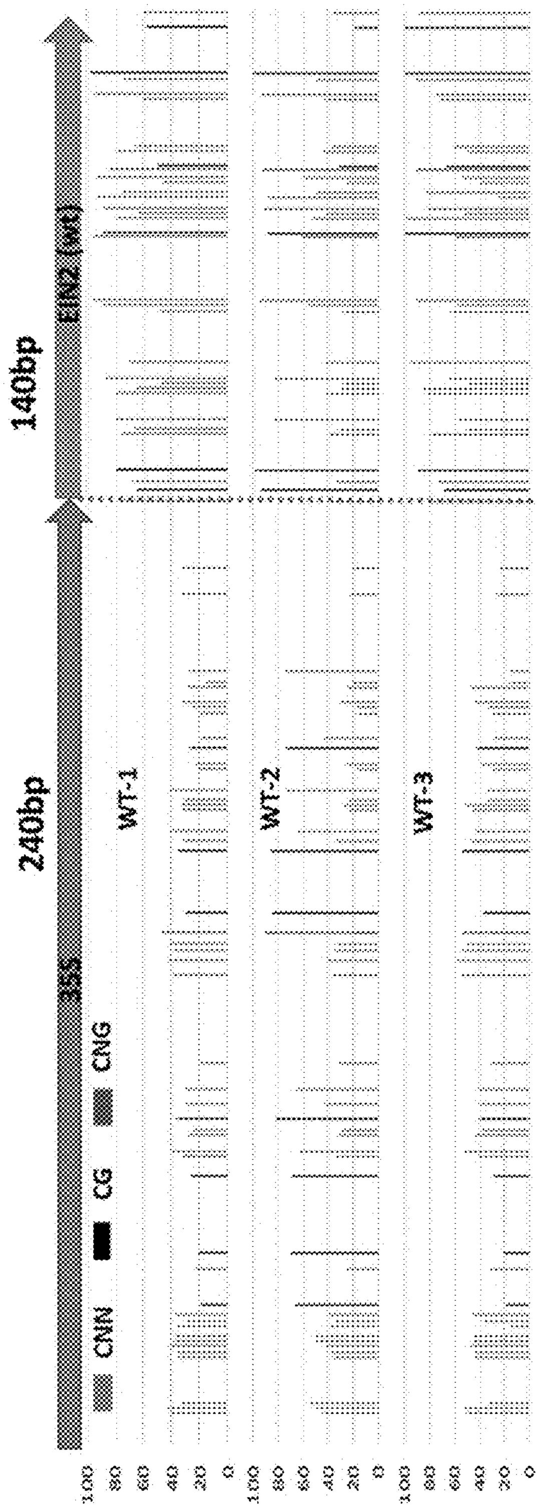

FIG. 32. 35S promoter in the least methylated lines of the hpEIN2[wt] population still shows significant methylation.

Figure 33:
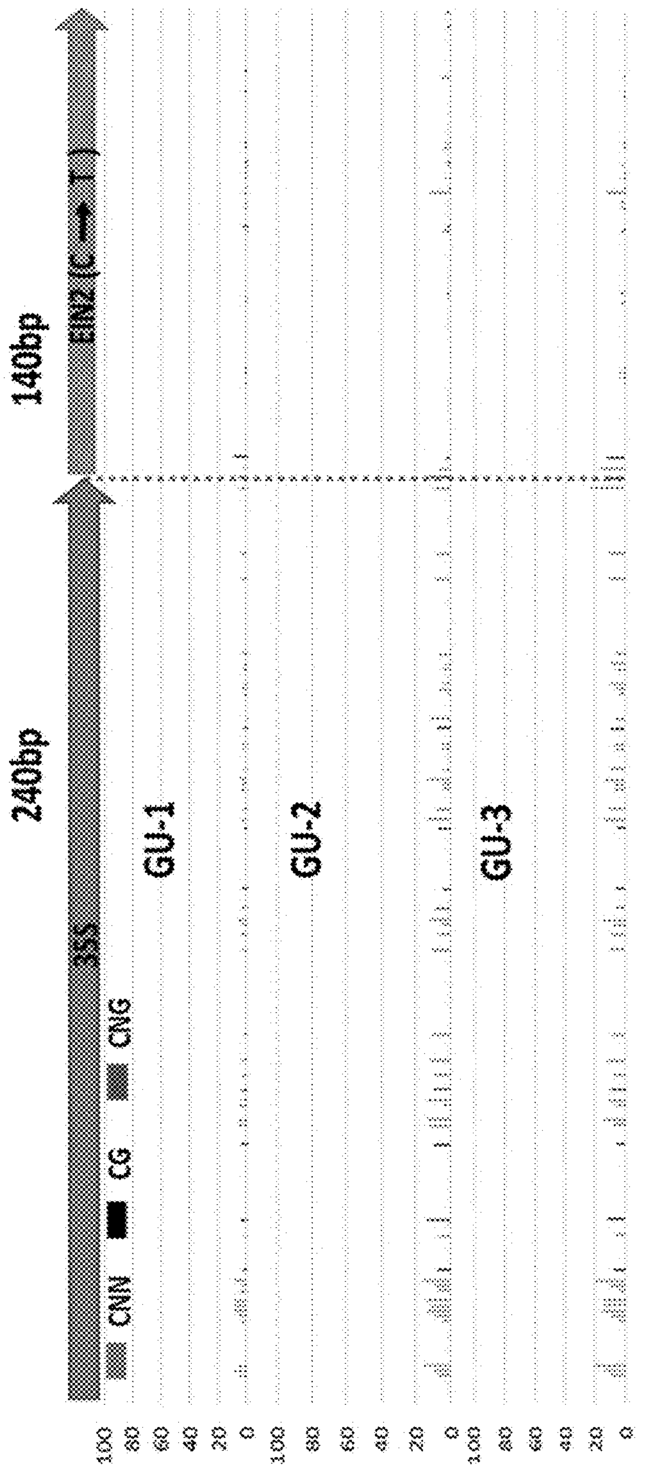

FIG. 33. 35S promoter in the G:U hpEIN2 lines shows only weak methylation (<10%).

Figure 34:
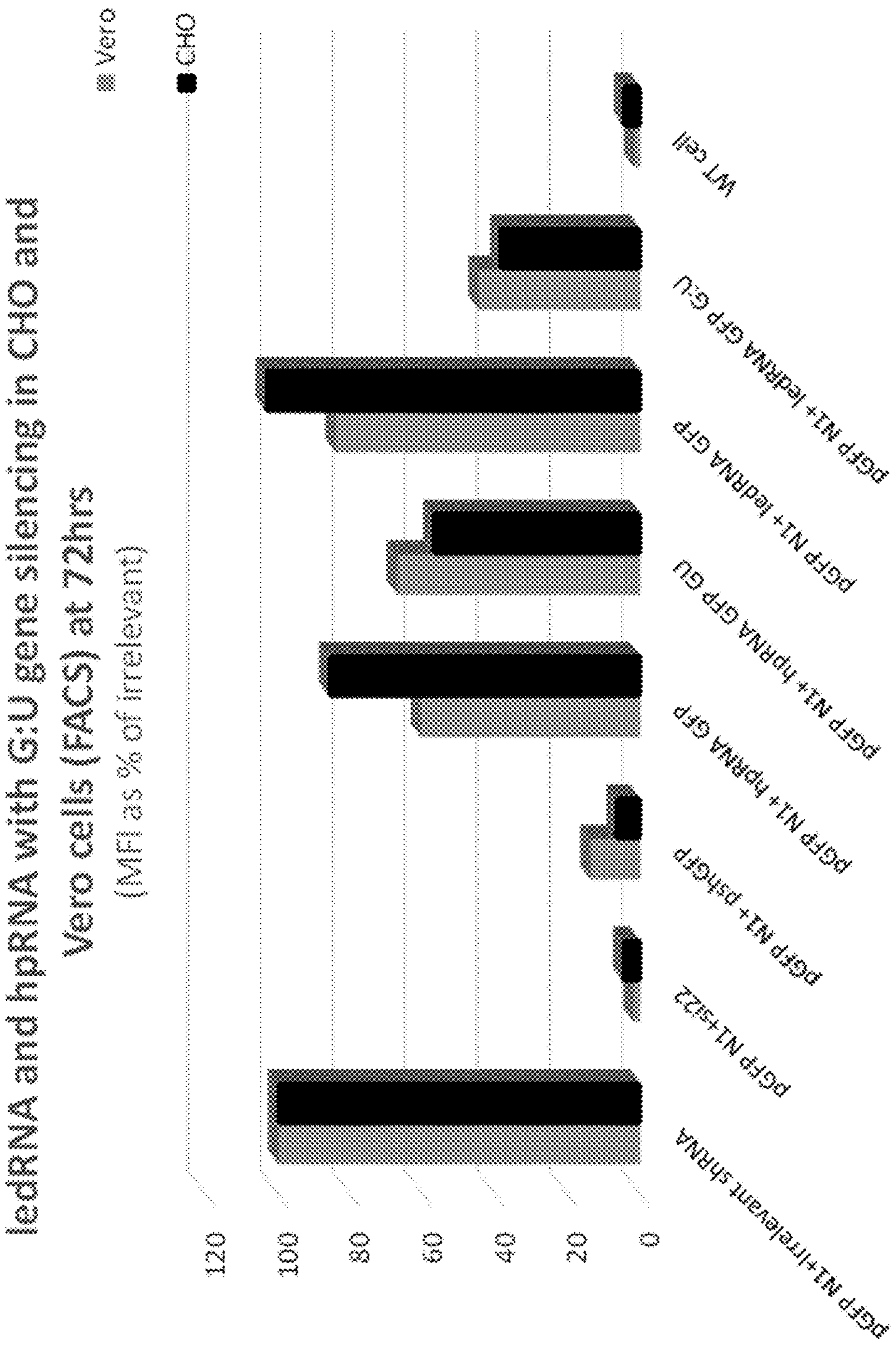

FIG. 34. ledRNA and hpRNA with G:U gene silencing in CHO and Vero cells at 72 hrs.

Figure 35:
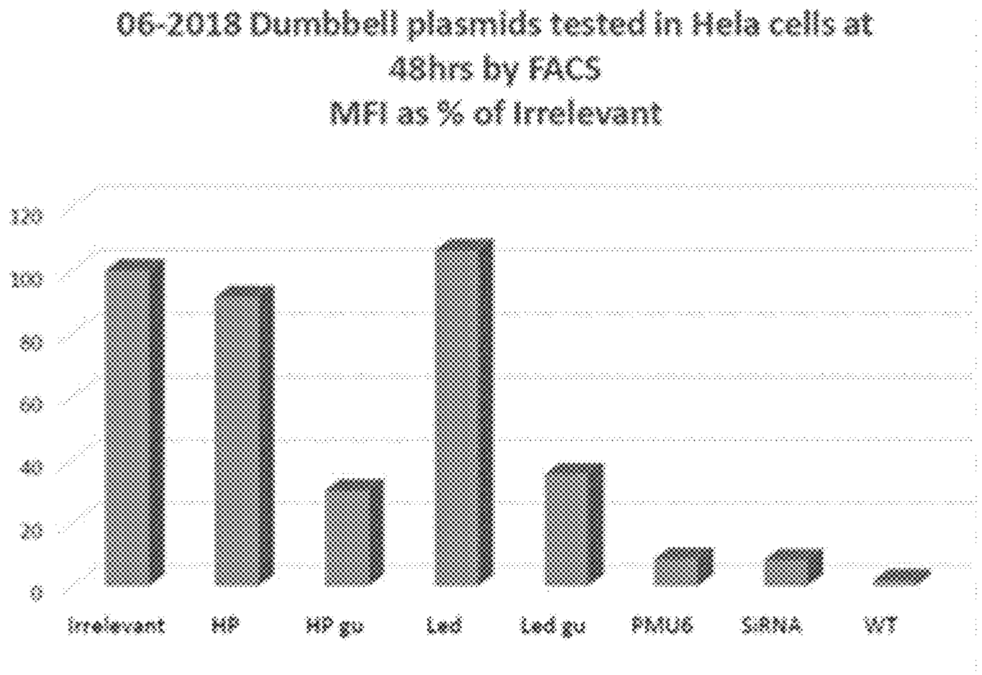

FIG. 35. Dumbbell plasmids tested in Hela cells at 48 hrs.

Figure 36:
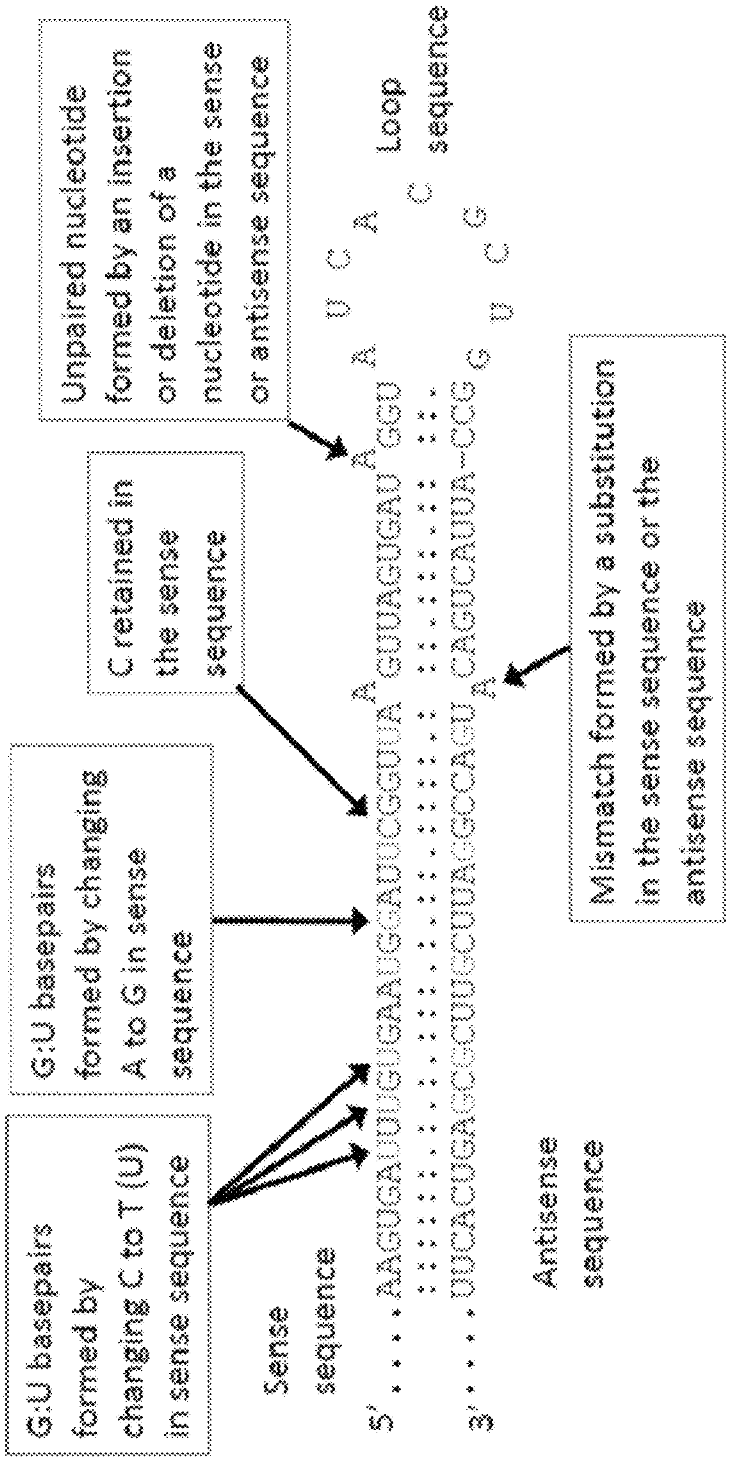

FIG. 36. Examples of possible modifications of dsRNA molecules.

FIG. 37. Reduced aphid performance following feeding from artificial diet supplemented with ledRNA for down-regulating expression of the MpC002 or MpRack-1 genes in green peach aphid. Upper panel (A): the average number of nymphs per adult aphid after a ten day period with 100 μl of 50 ng/μl ledRNA. Lower panel (B): percentage of aphids surviving over a five day time course after feeding on 100 μl containing 200 ng/μl ledRNA of MpC002, MpRack-1 or the control ledGFP.

Figure 38:
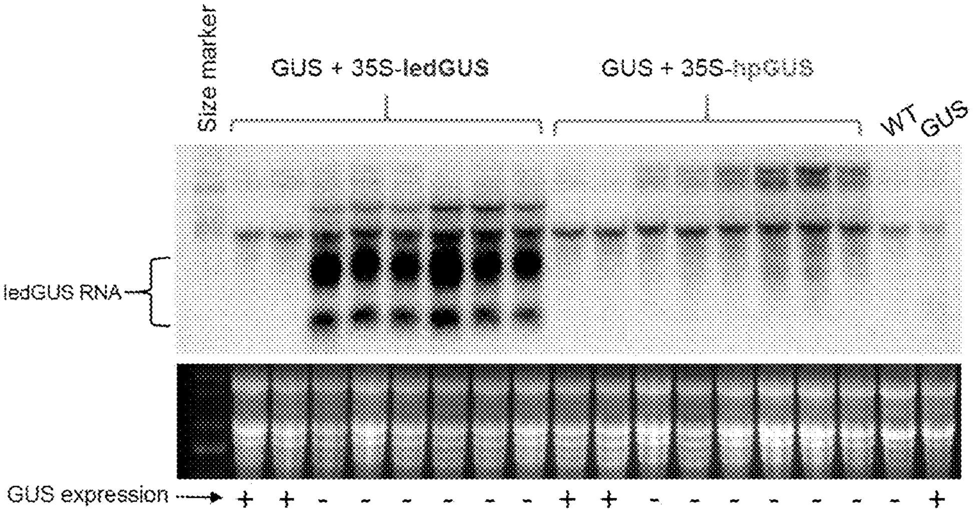

FIG. 38. Northern blot hybridization to detect ledGUS and hpGUS RNA using full-length sense GUS transcript as probe. "+" at the bottom indicates high GUS expression; "–" indicates low/no GUS expression i.e. strong GUS silencing.

Figure 39:
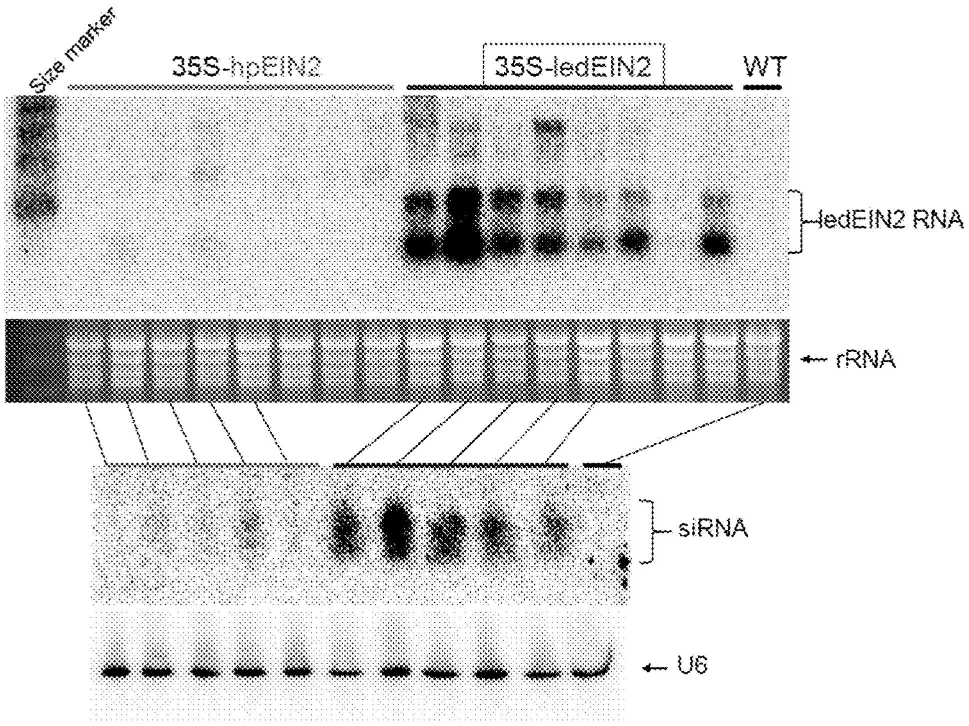

FIG. 39. Northern blot hybridization to detect long hpEIN2 and ledEIN2 RNA (upper panel) and siRNAs derived from the two constructs (lower panel).

Figure 40:
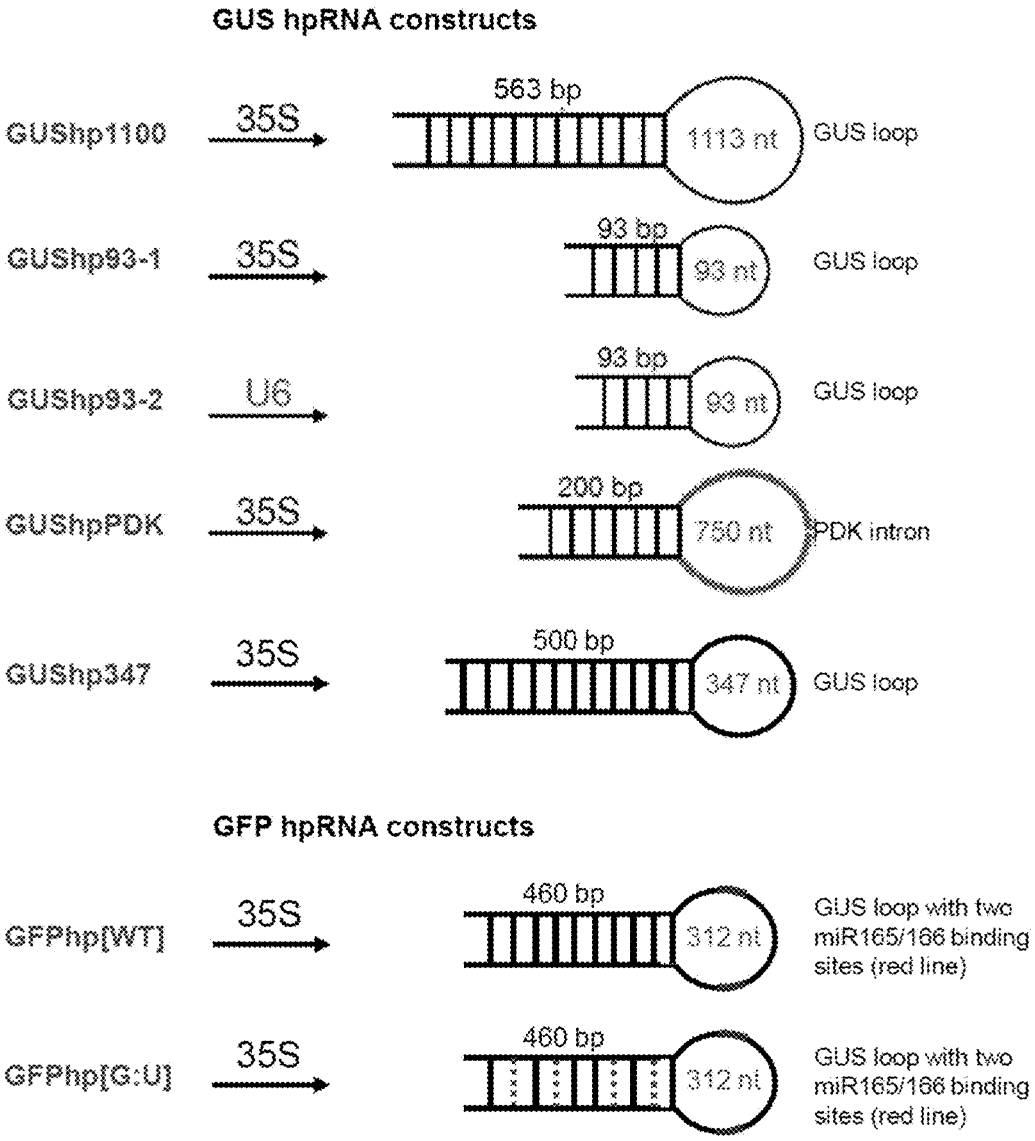

FIG. 40. Schematic representation of stem-loop structures of transcripts expressed from GUS hpRNA constructs. The transcripts have complementary sense and antisense sequences which basepair to form GUS sequence-specific dsRNA stems, with the indicated lengths in basepairs (bp) for the stems, and the number of nucleotides (nt) in the loops. The GFP hpRNA constructs encoded transcripts that formed a GFP-specific dsRNA stem with completely canonical basepairing (GFPhp[WT] or a dsRNA stem having about 25% of basepairs as G:U base-pairs (GFPhp[G:U], with a loop derived from a region of GUS coding sequence. The loop sequences for the GFPhp transcripts each comprised two sequences that were complementary to miR165/miR166 and therefore provide binding sites for these miRNAs.

Figure 41:
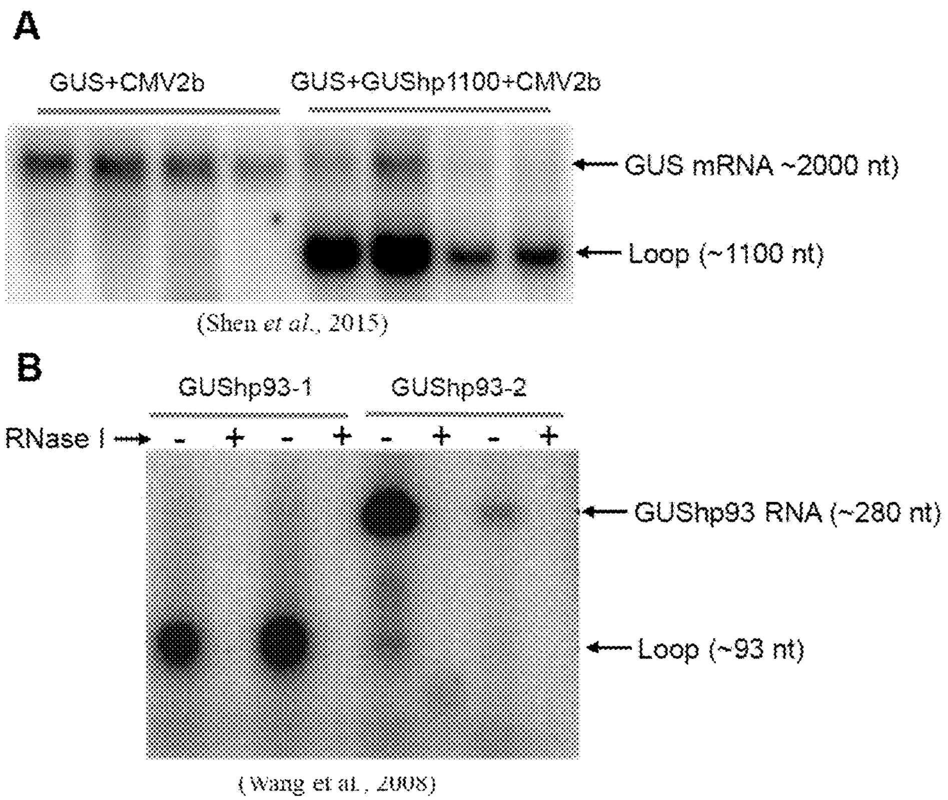

FIG. 41. Northern blot hybridisation analysis showing that transgenes encoding hpRNAs generate distinct fragments of the loop sequence when expressed in plant cells. (A) Expression of the GUS target gene (GUS) and the long hpRNA transgene GUShp1100 with a 1100 nt spacer/loop sequence. A construct encoding the cucumber mosaic virus 2b RNA silencing suppressor (CMV2b) was included to enhance transgene expression. (B) Northern blot analysis showing RNA from expression of the two short hpRNA transgenes GUShp93-1 and GUShp93-2 in stably transformed *A. thaliana* plants. RNA samples were either treated (+) or not treated (–) with RNAse I. Both RNA blots were hybridized with loop-specific antisense RNA probes.

Figure 42:
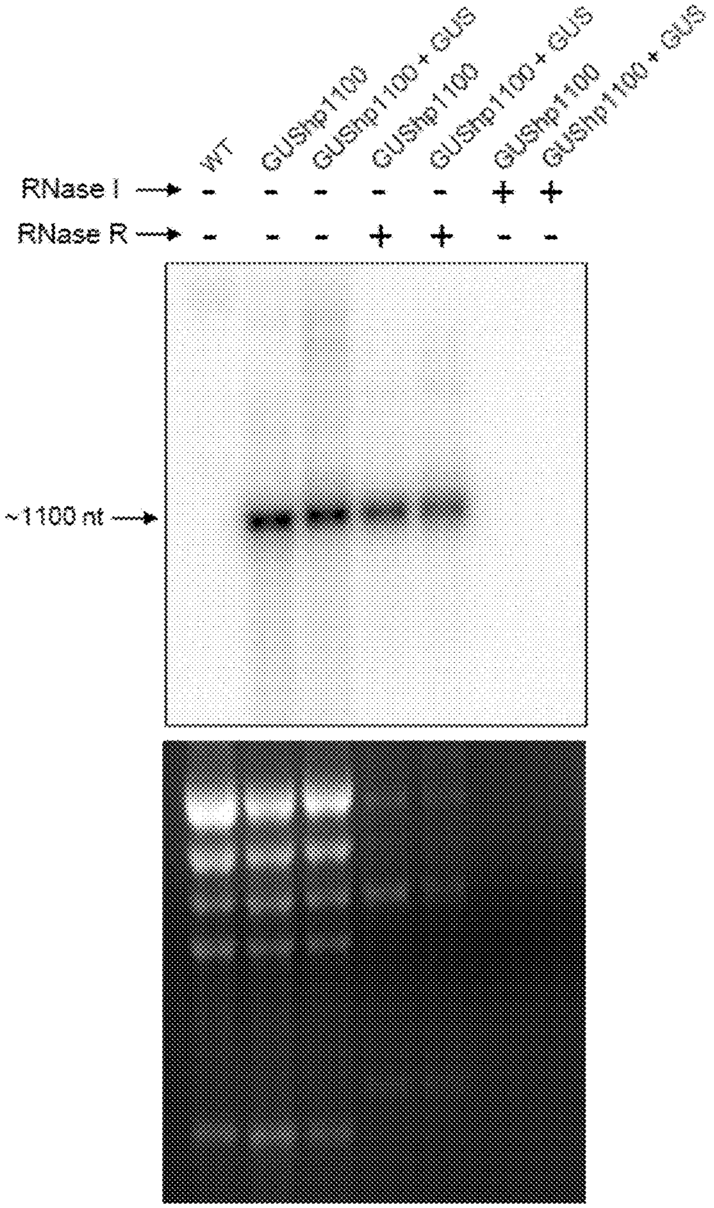

FIG. 42. The loop of GUShp1100 accumulated to high levels in *N. benthamiana* cells and was resistant to RNase R digestion.

Figure 43:
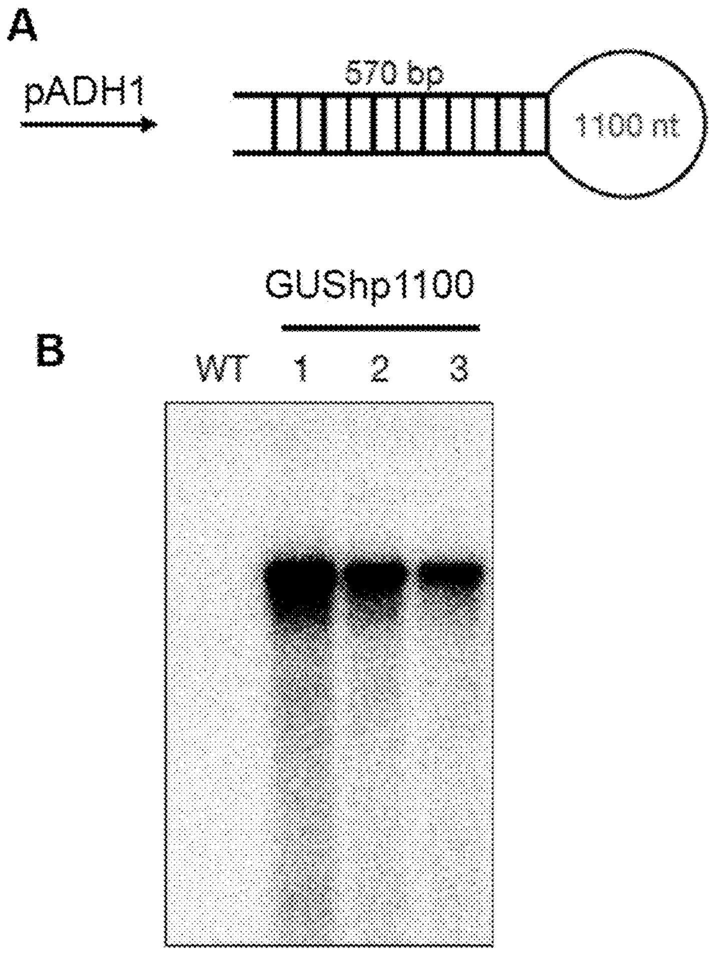

FIG. 43. Transgenic *S. cerevisiae* expressing a GUShp1100 construct showed a single RNA molecular species corresponding to the full length hairpin RNA transcript. The lower panel shows the Northern blot hybridisation of RNA samples from the transgenic *S. cerevisiae.*

Figure 44:
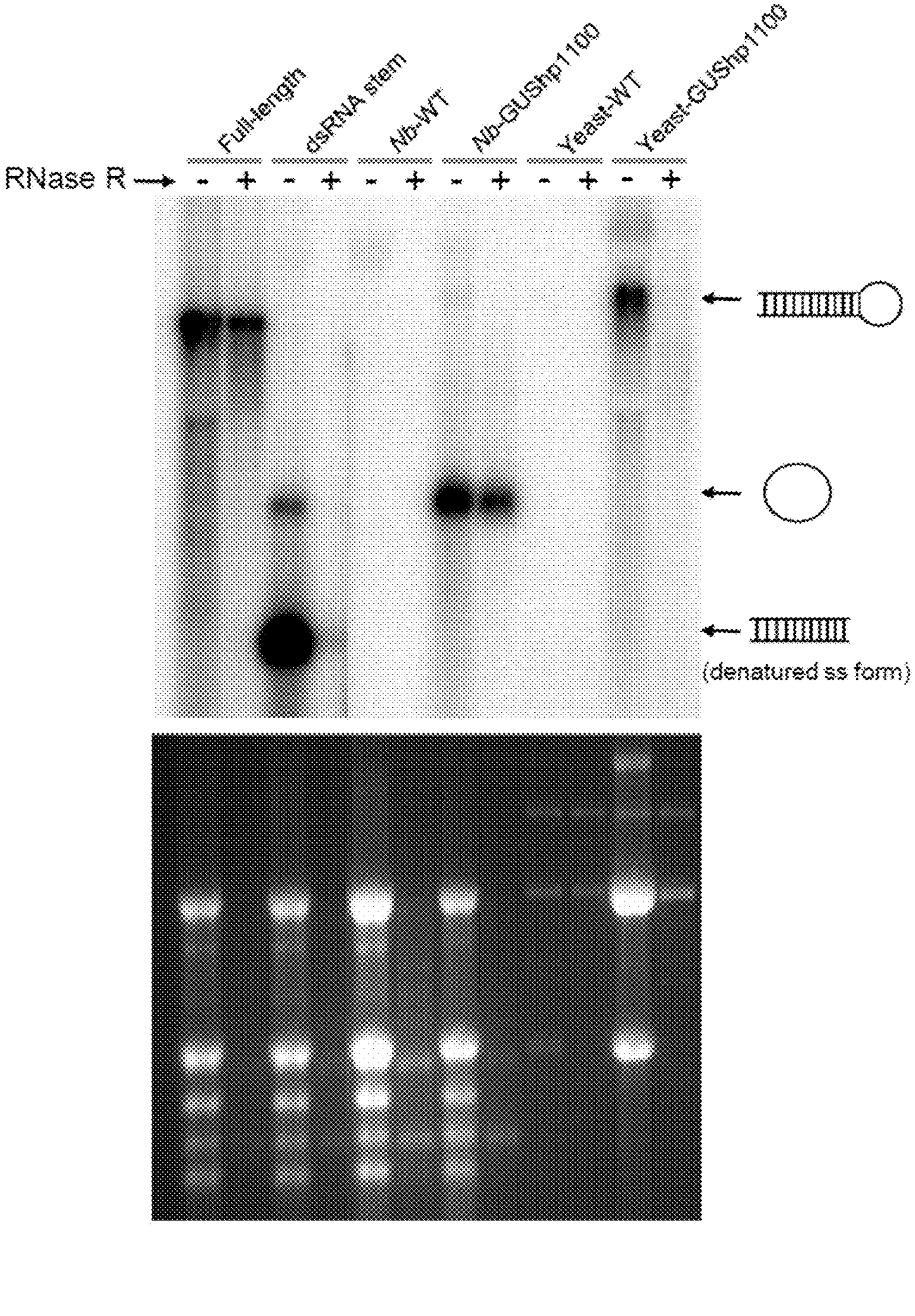

FIG. 44. GUShp1100 transcript expressed in *S. cerevisiae* remains full-length and does not form circular loop RNA. The first four lanes used in vitro transcripts of full-length or the dsRNA stem of GUShp1100, supplemented with total RNA isolated from wild-type *N. benthamiana* leaves.

Figure 45:
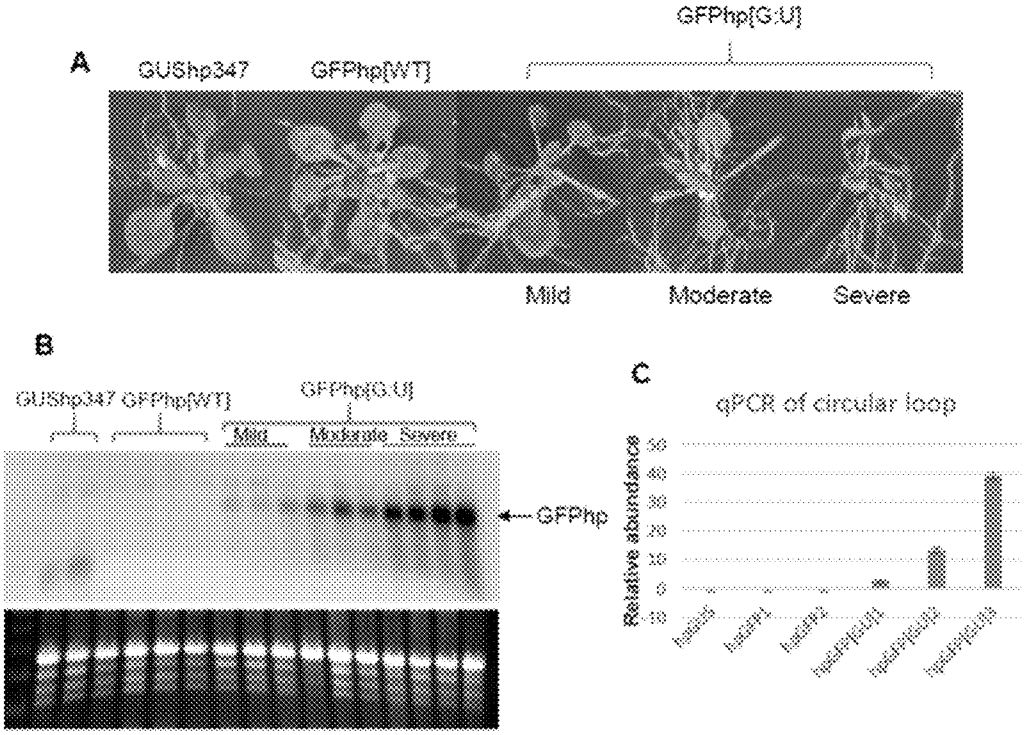

FIG. 45. hpRNA loops may be used as an effective sequence-specific repressor of miRNAs. (A) The GFPhp[G:U] construct induced strong miR165/166 suppression phenotypes in transgenic *Arabidopsis* plants. (B) Northern blot hybridization to determine the abundance of GFPhp transcript in RNA from transgenic *Arabidopsis* plants. (C) RT-qPCR analysis of circular RNA of the GFPhp loop.

KEY TO THE SEQUENCE LISTING

SEQ ID NO:1—Ribonucleotide sequence of GFP ledRNA.

SEQ ID NO:2—Ribonucleotide sequence of GUS ledRNA.

SEQ ID NO:3—Ribonucleotide sequence of *N. benthamiana* FAD2.1 ledRNA.

SEQ ID NO:4—Nucleotide sequence encoding GFP ledRNA.

SEQ ID NO:5—Nucleotide sequence encoding GUS ledRNA.

SEQ ID NO:6—Nucleotide sequence encoding *N. benthamiana* FAD2.1 ledRNA.

SEQ ID NO:7—Nucleotide sequence encoding GFP.

SEQ ID NO:8—Nucleotide sequence encoding GUS.

SEQ ID NO:9—Nucleotide sequence encoding *N. benthamiana* FAD2.1.

SEQ ID NO:10—Nucleotide sequence used to provide the GUS sense region for constructs encoding hairpin RNA molecules targeting the GUS mRNA.

SEQ ID NO:11—Nucleotide sequence used to provide the GUS sense region for the construct encoding the hairpin RNA molecule hpGUS[G:U].

SEQ ID NO:12—Nucleotide sequence used to provide the GUS sense region for constructs encoding the hairpin RNA molecule hpGUS[1:4].

SEQ ID NO:13—Nucleotide sequence used to provide the GUS sense region for constructs encoding the hairpin RNA molecule hpGUS[2:10].

SEQ ID NO:14—Nucleotide sequence of nucleotides 781-1020 of the protein coding region of the GUS gene.

SEQ ID NO:15—Ribonucleotide sequence of the hairpin structure (including its loop) of the hpGUS[wt] RNA.

SEQ ID NO:16—Ribonucleotide of the hairpin structure (including its loop) of the hpGUS[G:U] RNA.

SEQ ID NO:17—Ribonucleotide of the hairpin structure (including its loop) of the hpGUS[1:4] RNA.

SEQ ID NO:18—Ribonucleotide of the hairpin structure (including its loop) of the hpGUS[2:10] RNA.

SEQ ID NO:19—Nucleotide sequence of the cDNA corresponding to the *A. thaliana* EIN2 gene, Accession No. NM_120406.

SEQ ID NO:20—Nucleotide sequence of the cDNA corresponding to *A. thaliana* CHS gene, Accession No. NM_121396, 1703 nt.

SEQ ID NO:21—Nucleotide sequence of a DNA fragment comprising a 200 nt sense sequence from the cDNA corresponding to the *A. thaliana* EIN2 gene flanked by restriction enzyme sites.

SEQ ID NO:22—Nucleotide sequence of a DNA fragment comprising the 200 nt sense sequence of EIN2 as for SEQ ID NO:21 except that 43 C's were replaced with T's, used in constructing hpEIN2[G:U].

SEQ ID NO:23—Nucleotide sequence of a DNA fragment comprising a 200 nt sense sequence from the cDNA corresponding to *A. thaliana* CHS gene flanked by restriction enzyme sites.

SEQ ID NO:24—Nucleotide sequence of a DNA fragment comprising the 200 nt sense sequence of CHS as for SEQ ID NO:23 except that 65 C's were replaced with T's, used in constructing hpCHS[G:U].

SEQ ID NO:25—Nucleotide sequence of a DNA fragment comprising the 200 nt antisense sequence of EIN2 with 50 C's replaced with T's, used in constructing hpEIN2[G:U/U:G].

SEQ ID NO:26—Nucleotide sequence of a DNA fragment comprising the 200 nt antisense sequence of CHS with 49 C's replaced with T's, used in constructing hpCHS[G:U/U:G].

SEQ ID NO:27—Nucleotide sequence of nucleotides 601-900 of the cDNA corresponding to the EIN2 gene from *A. thaliana* (Accession No. NM_120406).

SEQ ID NO:28—Nucleotide sequence of nucleotides 813-1112 of the cDNA corresponding to the CHS gene from *A. thaliana* (Accession No. NM_121396).

SEQ ID NO:29—Nucleotide sequence of the complement of nucleotides 652-891 of the cDNA corresponding to the EIN2 gene from *A. thaliana* (Accession No. NM_120406).

SEQ ID NO:30—Nucleotide sequence of the complement of nucleotides 804-1103 of the cDNA corresponding to the CHS gene from *A. thaliana*.

SEQ ID NO:31—FANCM I protein coding region of the cDNA of *Arabidopsis thaliana*, Accession No NM_001333162. Target region nucleotides 675-1174 (500 nucleotides)

SEQ ID NO:32—FANCM I protein coding region of a cDNA of *Brassica napus*. Target region nucleotides 896-1395 (500 bp)

SEQ ID NO:33—Nucleotide sequence encoding hpFANCM-At[wt] targeting the FANCM I protein coding region of *A. thaliana*. FANCM sense sequence, nucleotides 38-537; loop sequence, nucleotides 538-1306; FANCM antisense sequence, nucleotides 1307-1806.

SEQ ID NO:34—Nucleotide sequence encoding hpFANCM-At[G:U] targeting the FANCM I protein coding region of *A. thaliana*. FANCM sense sequence, nucleotides 38-537; loop sequence, nucleotides 538-1306; FANCM antisense sequence, nucleotides 1307-1806.

SEQ ID NO:35—Nucleotide sequence encoding hpFANCM-Bn[wt] targeting the FANCM I protein coding region of *B. napus*. FANCM sense sequence, nucleotides 34-533; loop sequence, nucleotides 534-1300; FANCM antisense sequence, nucleotides 1301-1800.

SEQ ID NO:36—Nucleotide sequence encoding hpFANCM-Bn[G:U] targeting the FANCM I protein coding region of *B. napus*. FANCM sense sequence, nucleotides 34-533; loop sequence, nucleotides 534-1300; FANCM antisense sequence, nucleotides 1301-1800.

SEQ ID NO:37—Nucleotide sequence of the protein coding region of the cDNA corresponding to the *B. napus* DDM1 gene; Accession No. XR_001278527.

SEQ ID NO:38—Nucleotide sequence of DNA encoding hpDDM1-Bn[wt] targeting the DDM1 protein coding region of *B. napus*.

SEQ ID NO:39—Nucleotide sequence encoding hpDDM1-Bn[G:U] targeting the DDM1 protein coding region of *B. napus*. DDM1 sense sequence, nucleotides 35-536; loop sequence, nucleotides 537-1304; DDM1 antisense sequence, nucleotides 1305-1805.

SEQ ID NO:40—EGFP cDNA.

SEQ ID NO:41—Nucleotide sequence of the coding region of hpEGFP[wt], with the order antisense/loop/sense with respect to the promoter.

SEQ ID NO:42—Nucleotide sequence of the coding region of hpEGFP[G:U] which has 157 C to T substitutions in the EGFP sense sequence.

SEQ ID NO:43—Nucleotide sequence of the coding region of ledEGFP[wt] which has no C to T substitutions in the EGFP sense sequence.

SEQ ID NO:44—Nucleotide sequence of the coding region of ledEGFP[G:U] which has 162 C to T substitutions in the EGFP sense sequence.

SEQ ID NO:45—Nucleotide sequence used to provide the GUS sense region for the construct encoding the hairpin RNA molecule hpGUS[G:U] without flanking restriction enzyme sites.

SEQ ID NO:46—Nucleotide sequence used to provide the GUS sense region for constructs encoding the hairpin RNA molecule hpGUS[1:4] without flanking restriction enzyme sites.

SEQ ID NO:47—Nucleotide sequence used to provide the GUS sense region for constructs encoding the hairpin RNA molecule hpGUS[2:10] without flanking restriction enzyme sites.

SEQ ID NO:48—Nucleotide sequence of a DNA fragment comprising the 200 nt sense sequence of EIN2 as for SEQ ID NO:21 except that 43 C's were replaced with T's, used in constructing hpEIN2[G:U] without flanking sequences.

SEQ ID NO:49—Nucleotide sequence of a DNA fragment comprising the 200 nt sense sequence of CHS as for SEQ ID NO:23 except that 65 C's were replaced with T's, used in constructing hpCHS[G:U] without flanking sequences.

SEQ ID NO:50—Nucleotide sequence of a DNA fragment comprising the 200 nt antisense sequence of EIN2 with 50 C's replaced with T's, used in constructing hpEIN2[G:U/U:G] without flanking sequences SEQ ID NO:51—Nucleotide sequence of a DNA fragment comprising the 200 nt antisense sequence of CHS with 49 C's replaced with T's, used in constructing hpCHS[G:U/U:G] without flanking sequences.

SEQ ID NO:52—Oligonucleotide primer used for amplifying the 200 bp GUS sense sequence (GUS-WT-F)

SEQ ID NO:53—Oligonucleotide primer used for amplifying the 200 bp GUS sense sequence (GUS-WT-R)

SEQ ID NO:54—Oligonucleotide primer (forward) used for producing the hpGUS[G:U] fragment with every C replaced with T (GUS-GU-F)

SEQ ID NO:55—Oligonucleotide primer (reverse) used for producing the hpGUS[G:U] fragment with every C replaced with T (GUS-GU-R)

SEQ ID NO:56—Oligonucleotide primer (forward) used for producing the hpGUS[1:4] fragment with every 4th nucleotide substituted (GUS-4M-F)

SEQ ID NO:57—Oligonucleotide primer (reverse) used for producing the hpGUS[1:4] fragment with every 4th nucleotide substituted (GUS-4M-R)

SEQ ID NO:58—Oligonucleotide primer (forward) used for producing the hpGUS[2:10] fragment with every 9th and 10th nucleotide substituted (GUS-10M-F)

SEQ ID NO:59—Oligonucleotide primer (reverse) used for producing the hpGUS[2:10] fragment with every 9th and 10th nucleotide substituted (GUS-10M-R)

SEQ ID NO:60—Nucleotide sequence encoding forward primer (35S-F3)

SEQ ID NO:61—Nucleotide sequence encoding reverse primer (GUSwt-R2)

SEQ ID NO:62—Nucleotide sequence encoding forward primer (GUSgu-R2)

SEQ ID NO:63—Nucleotide sequence encoding reverse primer (GUS4m-R2)

SEQ ID NO:64—Nucleotide sequence encoding forward primer (35S-F2)

SEQ ID NO:65—Nucleotide sequence encoding reverse primer (35S-R1)

SEQ ID NO:66—Oligonucleotide primer used for amplifying the wild-type 200 bp EIN2 sense sequence (EIN2 wt-F)

SEQ ID NO:67—Oligonucleotide primer used for amplifying the wild-type 200 bp

EIN2 sense sequence (EIN2 wt-R)

SEQ ID NO:68—Oligonucleotide primer used for amplifying the wild-type 200 bp CHS sense sequence (CHSwt-F)

SEQ ID NO:69—Oligonucleotide primer used for amplifying the wild-type 200 bp CHS sense sequence (CHSwt-R)

SEQ ID NO:70—Oligonucleotide primer (forward) used for producing the hpEIN2[G:U] fragment, with every C replaced with T (EIN2gu-F)

SEQ ID NO:71—Oligonucleotide primer (reverse) used for producing the hpEIN2[G:U] fragment, with every C replaced with T (EIN2gu-R)

SEQ ID NO:72—Oligonucleotide primer (forward) used for producing the hpCHS[G:U] fragment, with every C replaced with T (CHSgu-F)

SEQ ID NO:73—Oligonucleotide primer (reverse) used for producing the hpCHS[G:U] fragment, with every C replaced with T (CHSgu-R)

SEQ ID NO:74—Oligonucleotide primer (forward) used for producing the hpEIN2[G:U/U:G] fragment, with every C replaced with T (asEIN2gu-F)

SEQ ID NO:75—Oligonucleotide primer (reverse) used for producing the hpEIN2[G:U/U:G] fragment with every C replaced with T (asEIN2gu-R)

SEQ ID NO:76—Oligonucleotide primer (forward) used for producing the hpCHS[G:U/U:G] fragment, with every C replaced with T (asCHSgu-F)

SEQ ID NO:77—Oligonucleotide primer (reverse) used for producing the hpCHS[G:U/U:G] fragment, with every C replaced with T (asCHSgu-R)

SEQ ID NO:78—Nucleotide sequence encoding forward primer (CHS-200-F2)

SEQ ID NO:79—Nucleotide sequence encoding reverse primer (CHS-200-R2)

SEQ ID NO:80—Nucleotide sequence encoding forward primer (Actin2-For)

SEQ ID NO:81—Nucleotide sequence encoding reverse primer (Actin2-Rev)

SEQ ID NO:82—Nucleotide sequence encoding forward primer (Top-35S-F2)

SEQ ID NO:83—Nucleotide sequence encoding reverse primer (Top-35S-R2)

SEQ ID NO:84—Nucleotide sequence encoding forward primer (Link-35S-F2)

SEQ ID NO:85—Nucleotide sequence encoding reverse primer (Link-EIN2-R2)

SEQ ID NO:86—Ribonucleotide sequence of sense si22

SEQ ID NO:87—Ribonucleotide sequence of antisense si22

SEQ ID NO:88—Ribonucleotide sequence of forward primer

SEQ ID NO:89—Ribonucleotide sequence of reverse primer

SEQ ID NO:90—Ribonucleotide sequence of forward primer

SEQ ID NO:91—Ribonucleotide sequence of reverse primer

SEQ ID NO:92-Possible modifications of dsRNA molecules

SEQ ID NO:93—Nucleotide sequence of a cDNA corresponding to the *Brassica napus* DDM1 gene (Accession No. XR_001278527).

SEQ ID NO:94—Nucleotide sequence of a chimeric DNA encoding a hairpin RNAi (hpRNA) construct targeting a DDM1 gene of *B. napus.*

SEQ ID NO:95—Nucleotide sequence of a chimeric DNA encoding a hairpin RNAi (hpRNA) construct with G:U basepairs, targeting a DDM1 gene of *B. napus.*

SEQ ID NO:96—Nucleotide sequence of a chimeric DNA encoding a ledRNA construct, targeting a DDM1 gene of *B. napus.*

SEQ ID NO:97—Nucleotide sequence of cDNA corresponding to *A. thaliana* FANCM gene (Accession No. NM_001333162).

SEQ ID NO:98—Nucleotide sequence of a chimeric DNA encoding a hairpin RNAi (hpRNA) construct targeting a FANCM gene of *A. thaliana.*

SEQ ID NO:99—Nucleotide sequence of a chimeric DNA encoding a hairpin RNAi (hpRNA) construct with G:U basepairs, targeting a FANCM gene of *A. thaliana.*

SEQ ID NO:100—Nucleotide sequence of a chimeric DNA encoding a ledRNA construct, targeting a FANCM gene of *A. thaliana.*

SEQ ID NO:101—Nucleotide sequence of cDNA corresponding to *B. napus* FANCM gene (Accession No. XM_022719486.1).

SEQ ID NO:102—Nucleotide sequence of a chimeric DNA encoding a hairpin RNAi (hpRNA) construct targeting a FANCM gene of *B. napus.*

SEQ ID NO:103—Nucleotide sequence of a chimeric DNA encoding a hairpin RNAi (hpRNA) construct with G:U basepairs, targeting a FANCM gene of *B. napus.*

SEQ ID NO:104—Nucleotide sequence of a chimeric DNA encoding a ledRNA construct, targeting a FANCM gene of *B. napus.*

SEQ ID NO:105—Nucleotide sequence of the protein coding region of the cDNA corresponding to the *Nicotiana benthamiana* TOR gene.

SEQ ID NO:106—Nucleotide sequence of a chimeric DNA encoding a ledRNA construct targeting a TOR gene of *N. benthamiana.*

SEQ ID NO:107—Nucleotide sequence of the protein coding region of the cDNA corresponding to the acetolactate synthase (ALS) gene of barley, *Hordeum vulgare* (Accession No. LT601589).

SEQ ID NO:108—Nucleotide sequence of a chimeric DNA encoding a ledRNA targeting the ALS gene of barley (*H. vulgare*).

SEQ ID NO:109—Nucleotide sequence of the protein coding region of the cDNA corresponding to the HvNCED1 gene of barley *Hordeum vulgare* (Accession No. AK361999).

SEQ ID NO:110—Nucleotide sequence the protein coding region of the cDNA corresponding to the HvNCED2 gene of barley *Hordeum vulgare* (Accession No. DQ145931).

SEQ ID NO:111—Nucleotide sequence of a chimeric DNA encoding a ledRNA construct targeting the NCED1 genes of barley *Hordeum vulgare* and wheat *Triticum aestivum.*

SEQ ID NO:112—Nucleotide sequence of a chimeric DNA encoding a ledRNA construct targeting the NCED2 genes of barley *Hordeum vulgare* and wheat *Triticum aestivum.*

SEQ ID NO:113—Nucleotide sequence of the protein coding region of a cDNA corresponding to the barley gene encoding ABA-OH-2 (Accession No. DQ145933).

SEQ ID NO:114—Nucleotide sequence of a chimeric DNA encoding a ledRNA construct targeting the ABA-OH-2 genes of barley *Hordeum vulgare* and wheat *Triticum aestivum.*

SEQ ID NO:115—Nucleotide sequence of the protein coding region of a cDNA corresponding to the *A. thaliana* gene encoding EIN2 (At5g03280).

SEQ ID NO:116—Nucleotide sequence of a chimeric DNA encoding a ledRNA construct targeting the EIN2 gene of *A. thaliana.*

SEQ ID NO:117—Nucleotide sequence of the protein coding region of a cDNA corresponding to the *A. thaliana* gene encoding CHS (Accession No. NM_121396).

SEQ ID NO:118—Nucleotide sequence of a chimeric DNA encoding a ledRNA construct targeting the CHS gene of *A. thaliana.*

SEQ ID NO:119—Nucleotide sequence of the protein coding region of a cDNA corresponding to the *L. angustifolius* N-like gene (Accession No. XM_019604347).

SEQ ID NO:120—Nucleotide sequence of a chimeric DNA encoding a ledRNA construct targeting the *L. angustifolius* N-like gene.

SEQ ID NO:121—Nucleotide sequence of the protein coding region of a cDNA corresponding to a *Vitis pseudoreticulata* MLO gene (Accession No. KR362912).

SEQ ID NO:122—Nucleotide sequence of a chimeric DNA encoding a first ledRNA construct targeting a *Vitis* MLO gene.

SEQ ID NO:123—Nucleotide sequence of the protein coding region of the cDNA corresponding to the MpC002 gene of *Myzus persicae.*

SEQ ID NO:124—Nucleotide sequence of the protein coding region of the cDNA corresponding to the MpRack-1 gene of *Myzus persicae.*

SEQ ID NO:125—Nucleotide sequence of the chimeric construct encoding the ledRNA targeting *M. persicae* C002 gene.

SEQ ID NO:126—Nucleotide sequence of the chimeric construct encoding the ledRNA targeting *M. persicae* Rack-1 gene.

SEQ ID NO:127—Nucleotide sequence of the cDNA corresponding to the *Helicoverpa armigera* ABCwhite gene.

SEQ ID NO:128—Nucleotide sequence of a chimeric DNA encoding a ledRNA construct targeting a ABC transporter white gene of *Helicoverpa armigera.*

SEQ ID NO:129—Nucleotide sequence of the cDNA corresponding to the *Linepithema humile* PBAN-type neuropeptides-like (XM_012368710).

SEQ ID NO:130—Nucleotide sequence of a chimeric DNA encoding a ledRNA construct targeting a PBAN gene in Argentine ants (Accession No. XM_012368710).

SEQ ID NO:131—Nucleotide sequence of a chimeric DNA encoding a ledRNA construct targeting a gene encoding V-type proton ATPase catalytic subunit A (Accession No. XM_023443547) of *L. cuprina.*

SEQ ID NO:132—Nucleotide sequence of a chimeric DNA encoding a ledRNA construct targeting a gene encoding RNAse 1/2 of *L. cuprina.*

SEQ ID NO:133—Nucleotide sequence of a chimeric DNA encoding a ledRNA construct targeting a gene encoding chitin synthase of *L. cuprina.*

SEQ ID NO:134—Nucleotide sequence of a chimeric DNA encoding a ledRNA construct targeting a gene encoding ecdysone receptor (EcR) of *L. cuprina.*

SEQ ID NO:135—Nucleotide sequence of a chimeric DNA encoding a ledRNA construct targeting a gene encoding gamma-tubulin 1/1-like of *L. cuprina.*

SEQ ID NO:136—TaMlo target gene (AF384144).

SEQ ID NO:137—Nucleotide sequence of a chimeric DNA encoding a ledRNA construct targeting a gene encoding TaMlo.

SEQ ID NO:138—Nucleotide sequence of the protein coding region of a cDNA corresponding to a *Vitis pseudoreticulata* MLO gene (Accession No. KR362912).

SEQ ID NO:139—Nucleotide sequence of a chimeric DNA encoding a first ledRNA construct targeting a *Vitis* MLO gene.

SEQ ID NO:140—Cyp51 homolog 1 (Accession No. KK764651.1, locus RSAG8_00934).

SEQ ID NO:141—Cyp51 homolog 2 (Accession No. KK764892.1, locus number RSAG8_12664).

SEQ ID NO:142—Nucleotide sequence of a chimeric DNA encoding a ledRNA construct targeting a gene encoding Cyp51.

SEQ ID NO:143—CesA3 target gene (Accession No. JN561774.1).

SEQ ID NO:144—Nucleotide sequence of a chimeric DNA encoding a ledRNA construct targeting a gene encoding CesA3.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, gene silencing, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "antisense regulatory element" or "antisense ribonucleic acid sequence" or "antisense RNA sequence" as used herein means an RNA sequence that is at least partially complementary to at least a part of a target RNA molecule to which it hybridizes. In certain embodiments, an antisense RNA sequence modulates (increases or decreases) the expression or amount of a target RNA molecule or its activity, for example through reducing translation of the target RNA molecule. In certain embodiments, an antisense RNA sequence alters splicing of a target pre-mRNA resulting in a different splice variant. Exemplary components of antisense sequences include, but are not limited to, oligonucleotides, oligonucleosides, oligonucleotide analogues, oligonucleotide mimetics, and chimeric combinations of these.

The term "antisense activity" is used in the context of the present disclosure to refer to any detectable and/or measurable activity attributable to the hybridization of an antisense RNA sequence to its target RNA molecule. Such detection and/or measuring may be direct or indirect. In an example, antisense activity is assessed by detecting and or measuring the amount of target RNA molecule transcript. Antisense activity may also be detected as a change in a phenotype associated with the target RNA molecule. As used herein, the term "target RNA molecule" refers to a gene transcript that is modulated by an antisense RNA sequence according to the present disclosure. Accordingly, "target RNA molecule" can be any RNA molecule the expression or activity of which is capable of being modulated by an antisense RNA sequence. Exemplary target RNA molecules include, but are not limited to, RNA (including, but not limited to pre-mRNA and mRNA or portions thereof) transcribed from DNA encoding a target protein, rRNA, tRNA, small nuclear RNA, and miRNA, including their precursor forms. The target RNA may be the genomic RNA of a pathogen or pest such as a virus, or an RNA molecule derived therefrom such as a replicative form of a viral pathogen, or transcript therefrom. For example, the target RNA molecule can be an RNA from an endogenous gene (or mRNA transcribed from the gene) or a gene which is introduced or may be introduced into the eukaryotic cell whose expression is associated with a particular phenotype, trait, disorder or disease state, or a nucleic acid molecule from an infectious agent. In an example, the target RNA molecule is in a eukaryotic cell. In another example, the target RNA molecule encodes a protein. In this context, antisense activity can be assessed by detecting and or measuring the amount of target protein, for example through its activity such as enzyme activity, or a function other than as an enzyme, or through a phenotype associated with its function. As used herein, the term "target protein" refers to a protein that is modulated by an antisense RNA sequence according to the present disclosure.

In certain embodiments, antisense activity is assessed by detecting and/or measuring the amount of target RNA molecules and/or cleaved target RNA molecules and/or alternatively spliced target RNA molecules.

Antisense activity can be detected or measured using various methods. For example, antisense activity can be detected or assessed by comparing activity in a particular sample and comparing the activity to that of a control sample.

The term "targeting" is used in the context of the present disclosure to refer to the association of an antisense RNA sequence to a particular target RNA molecule or a particular region of nucleotides within a target RNA molecule. In an example, an antisense RNA sequence according to the present disclosure shares complementarity with at least a region of a target RNA molecule. In this context, the term "complementarity" refers to a sequence of ribonucleotides that is capable of base pairing with a sequence of ribonucleotides on a target RNA molecule, through hydrogen bonding between bases on the ribonucleotides. For example, in RNA, adenine (A) is complementary to uracil (U) and guanine (G) to cytosine (C).

In certain embodiments, "complementary base" refers to a ribonucleotide of an antisense RNA sequence that is capable of base pairing with a ribonucleotide of a sense RNA sequence in an RNA molecule of the invention or of its target RNA molecule. For example, if a ribonucleotide at a certain position of an antisense RNA sequence is capable of hydrogen bonding with a ribonucleotide at a certain position of a target RNA molecule, then the position of hydrogen bonding between the antisense RNA sequence and the target RNA molecule is considered to be complementary at that ribonucleotide. In contrast, the term "non-complementary" refers to a pair of ribonucleotides that do not form hydrogen bonds with one another or otherwise support hybridization. The term "complementary" can also be used to refer to the capacity of an antisense RNA sequence to hybridize to another nucleic acid through complementarity. In certain embodiments, an RNA sequence and its target are complementary to each other when a sufficient number of corresponding positions in each molecule are occupied by ribonucleotides that can bond with each other to allow stable association between the antisense RNA sequence and a sense RNA sequence in the RNA molecule of the invention and/or the target RNA molecule. One skilled in the art recognizes that the inclusion of mismatches is possible without eliminating the ability of the antisense RNA sequence and target to remain in association. Therefore, described herein are antisense RNA sequence that may comprise up to about 20% nucleotides that are mismatched (i.e., are not complementary to the corresponding nucleotides of the target). Preferably the antisense compounds contain no more than about 15%, more preferably not more than about 10%, most preferably not more than 5% or no mismatches. The remaining ribonucleotides are complementary or otherwise do not disrupt hybridization (e.g., G:U or A:G pairs) between the antisense RNA sequence and the sense RNA sequence or the target RNA molecule. One of ordinary skill in the art would recognise the antisense RNA sequence s described herein are at least 80%, at least 85%, at least 90%, at least 95%, at least 96%, at least 97%, at least 98%, at least 99% or 100% (fully) complementary to at least a region of a target RNA molecule.

As used herein, "chimeric RNA molecule" refers to any RNA molecule that is not naturally found in nature. In an example, chimeric RNA molecules disclosed herein have been modified to create mismatches in region(s) of dsRNA. For example, chimeric RNA molecules may be modified to convert cytosines to uracils. In an example, chimeric RNA molecules have been modified via treatment with bisulfite for a time and under conditions sufficient to convert non-methylated cytosines to uracils.

One of skill in the art would appreciate that various ribonucleotide combinations can base pair. Both canonical and non-canonical base pairings are contemplated by the present disclosure. In an example, a base pairing can comprise A:T or G:C in a DNA molecule or U:A or G:C in an RNA molecule. In another example, a base pairing may comprise A:G or G:T or U:G.

The term "canonical base pairing" as used in the present disclosure means base pairing between two nucleotides which are A:T or G:C for deoxyribonucleotides or A:U or G:C for ribonucleotides.

The term "non-canonical base pairing" as used in the present disclosure means an interaction between the bases of two nucleotides other than canonical base pairings, in the context of two DNA or two RNA sequences. For example, non-canonical base pairing includes pairing between G and U (G:U) or between A and G (A:G). Examples of non-canonical base pairing include purine-purine or pyrimidine-pyrimidine. Most commonly in the context of this disclosure, the non-canonical base pairing is G:U. Other examples of non-canonical base pairs, less preferred, are A:C, G:T, G:G and A:A.

The present disclosure refers to RNA components that "hybridize" across a series of ribonucleotides. Those of skill in the art will appreciate that terms such as "hybridize" and "hybridizing" are used to describe molecules that anneal based on complementary nucleic acid sequences. Such molecules need not be 100% complementary in order to hybridize (i.e. they need not "fully base pair"). For example, there may be one or more mismatches in sequence complementarity. In an example, RNA components defined herein hybridise under stringent hybridization conditions. The term "stringent hybridization conditions" refers to parameters with which the art is familiar, including the variation of the hybridization temperature with length of an RNA molecule. Ribonucleotide hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2×SSC, 0.01% BSA at 50° C. Shorter RNA components such as RNA sequences of 20-24 nucleotides in length hybridise under lower stringency conditions. The term "low stringency hybridization conditions" refers to parameters with which the art is familiar, including the variation of the hybridization temperature with length of an RNA molecule. For example, low stringency hybridization conditions, as used herein, can refer to hybridization at 42° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2×SSC, 0.01% BSA at 30° C.

The present invention also encompasses RNA components that "fully base pair" across contiguous ribonucleotides. The term "fully base pair" is used in the context of the present disclosure to refer to a series of contiguous ribonucleotide base pairings. A fully base paired series of contiguous ribonucleotides does not comprise gaps or non-basepaired nucleotides within the series. The term "contiguous" is used to refer to a series of ribonucleotides. Ribonucleotides comprising a contiguous series will be joined by a continuous series of phosphodiester bonds, each ribonucleotide being directly bonded to the next.

RNA molecules of the present invention comprise a sense sequence and a corresponding antisense sequence. The relationship between these sequences is defined herein. The sequence relationship and activity of the antisense sequence in relation to a target RNA molecule is also defined herein.

The term "covalently linked" is used in the context of the present disclosure to refer to the link between the first and second RNA components or any RNA sequences or ribonucleotides. As one of skill in the art would appreciate, a covalent link or bond is a chemical bond that involves the sharing of electron pairs between atoms. In an example, the first and second RNA components or the sense RNA sequence and the antisense RNA sequence are covalently linked as part of a single RNA strand which may fold back on itself through self-complementarity. In this example, the components are covalently linked across one or more ribonucleotides by phosphodiester bonds.

In the context of the present disclosure, the term "hybridization" means the pairing of complementary polynucleotides through basepairing of complementary bases. While not limited to a particular mechanism, the most common mechanism of pairing involves hydrogen bonding, which may be Watson-Crick hydrogen bonding, between complementary ribonucleotides.

As used herein, the phrase "the RNA molecule has a deleterious effect on the non-human organism" or similar phrases means that the target RNA molecule of the molecule is present in the non-human organism and exposure of cells expressing the target RNA molecule to the target RNA molecule results in reduced levels and/or activity of the target RNA molecule when compared to the same cells lacking the RNA molecule. In an embodiment, the target RNA molecule encodes a protein important for growth, reproduction or survival. As an example, if the non-human organism is a crop pest or pathogen, or a pest or pathogen of an animal, the RNA molecule can have a deleterious effect on feeding by the pest or pathogen, cell apoptosis, cell differentiation and development, capacity or desire for sexual reproduction, muscle formation, muscle twitching, muscle contraction, juvenile hormone formation, juvenile hormone regulation, ion regulation and transport, maintenance of cell membrane potential, amino acid biosynthesis, amino acid degradation, sperm formation, pheromone synthesis, pheromone sensing, antennae formation, wing formation, leg formation, egg formation, larval maturation, digestive enzyme formation, haemolymph synthesis, haemolymph maintenance, neurotransmission, larval stage transition, pupation, emergence from pupation, cell division, energy metabolism, respiration, chitin metabolism, formation of cytoskeletal structure. In another example, the non-human organism is a weed and the RNA molecule has a deleterious effect on amino acid biosynthesis, photosynthesis, fatty acid synthesis, cell membrane integrity, pigment synthesis or growth.

As used herein, the phrase "the RNA molecule has a beneficial effect on at least one symptom of the disease" or similar phrases means that the target RNA of the molecule is present in the subject and exposure of cells expressing the target RNA to the RNA molecule results in reduced levels and/or activity of the target RNA when compared to the same cells lacking the RNA molecule. In an embodiment, the target RNA is encodes a protein which plays a role in the presence of the disease. In an embodiment, the disease is cancer or cancerous disease, an infectious disease, a cardiovascular disease, a neurological disease, a prion disease, an inflammatory disease, an autoimmune disease, a pulmonary disease, a renal disease, liver disease, mitochondrial disease, endocrine disease, reproduction related diseases and conditions, and any other indications that can respond to the level of an expressed gene product in a cell or organism.

RNA molecules according to the present disclosure and compositions comprising the same can be administered to a subject. Terms such as "subject", "patient" or "individual" are terms that can, in context, be used interchangeably in the present disclosure. In an example, the subject is a mammal. The mammal may be a companion animal such as a dog or cat, or a livestock animal such as a horse or cow. In one example, the subject is a human. For example, the subject can be an adult. In another example, the subject can be a child. In another example, the subject can be an adolescent. In another example, RNA molecules according to the present disclosure and compositions comprising the same can be administered to an insect. In another example, RNA molecules according to the present disclosure and compositions comprising the same can be administered to a plant. In another example, RNA molecules according to the present disclosure and compositions comprising the same can be administered to a fungal cell or population.

As used herein, "resistant" or variations thereof are relative terms in that the presence of the RNA molecule increases in resistance, e.g. a reduced reproduction of the pest or pathogen, or a reduced level of damage to the organism.

As used herein, the term "unrelated in sequence to a target" refers to molecules having less than 50% identity along the full-length of the intervening RNA sequence. On the other hand, the term "related in sequence to a target" refers to molecules having 50% or more identity along the full-length of the intervening RNA sequence.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Non-Canonical Basepairing

In an embodiment, RNA molecules of the present invention comprise a sense ribonucleotide sequence and an antisense ribonucleotide sequence which are capable of hybridising to each other to form a double stranded (ds)RNA region with some non-canonical basepairing i.e. with a combination of canonical and non-canonical basepairing. In an embodiment, RNA molecules of the present invention comprise two or more sense ribonucleotide sequences which are each capable of hybridising to regions of one (contiguous) antisense ribonucleotide sequence to form a dsRNA region with some non-canonical basepairing. See for example, FIG. 1B. In an embodiment, RNA molecules of the present invention comprise two or more antisense sense ribonucleotide sequences which are each capable of hybridising to regions of one (contiguous) sense ribonucleotide sequence to form a dsRNA region with some non-canonical basepairing. See for example, FIG. 1A. In an embodiment, RNA molecules of the present invention comprise two or more antisense sense ribonucleotide sequences and two or more sense ribonucleotide sequences wherein each antisense ribonucleotide sequence is capable of hybridising to an antisense ribonucleotide sequence to form two or more dsRNA regions, one or both comprising some non-canonical basepairing.

In the following embodiments, the full length of the dsRNA region (i.e. the whole dsRNA region) of the RNA molecule of the invention is considered as the context for the feature if there is only one (contiguous) dsRNA region, or for each of the dsRNA regions of the RNA molecule if there are two or more dsRNA regions in the RNA molecule. In an embodiment, at least 5% of the basepairs in a dsRNA region are non-canonical basepairs. In an embodiment, at least 6% of the basepairs in a dsRNA region are non-canonical basepairs. In an embodiment, at least 7% of the basepairs in a dsRNA region are non-canonical basepairs. In an embodiment, at least 8% of the basepairs in a dsRNA region are non-canonical basepairs. In an embodiment, at least 9% or 10% of the basepairs in a dsRNA region are non-canonical basepairs. In an embodiment, at least 11% or 12% of the basepairs in a dsRNA region are non-canonical basepairs. In an embodiment, at least 15% or about 15% of the basepairs in a dsRNA region are non-canonical basepairs. In an embodiment, at least 20% or about 20% of the basepairs in a dsRNA region are non-canonical basepairs. In an embodiment, at least 25% or about 25% of the basepairs in a dsRNA region are non-canonical basepairs. In an embodiment, at least 30% or about 30% of the basepairs in a dsRNA region are non-canonical basepairs. In each of these embodiments, it is preferred that a maximum of 40% of the basepairs in the dsRNA region are non-canonical basepairs, more preferably a maximum of 35% of the basepairs in the dsRNA region are non-canonical basepairs, still more preferably a maximum of 30% of the basepairs in the dsRNA region are non-canonical basepairs. In an embodiment, less preferred, about 35% of the basepairs in a dsRNA region are non-canonical basepairs. In an embodiment, even less preferred, about 40% of the basepairs in a dsRNA region are non-canonical basepairs. In each of the above embodiments, the dsRNA region may or may not comprise one or more non-basepaired ribonucleotides, in either the sense sequence or the antisense sequence, or both.

In an embodiment, between 10% and 40% of the basepairs in a dsRNA region of the RNA molecule of the invention are non-canonical basepairs. In an embodiment, between 10% and 35% of the basepairs in a dsRNA region are non-canonical basepairs. In an embodiment, between 10% and 30% of the basepairs in a dsRNA region are non-canonical basepairs. In an embodiment, between 10% and 25% of the basepairs in a dsRNA region are non-canonical basepairs. In an embodiment, between 10% and 20% of the basepairs in a dsRNA region are non-canonical basepairs. In an embodiment, between 10% and 15% of the basepairs in a dsRNA region are non-canonical basepairs. In an embodiment, between 15% and 30% of the basepairs in a dsRNA region are non-canonical basepairs. In an embodiment, between 15% and 25% of the basepairs in a dsRNA region are non-canonical basepairs. In an embodiment, between 15% and 20% of the basepairs in a dsRNA region are non-canonical basepairs. In an embodiment, between 5% and 30% of the basepairs in a dsRNA region are non-canonical basepairs. In an embodiment, between 5% and 25% of the basepairs in a dsRNA region are non-canonical basepairs. In an embodiment, between 5% and 20% of the basepairs in a dsRNA region are non-canonical basepairs. In an embodiment, between 5% and 15% of the basepairs in a dsRNA region are non-canonical basepairs. In an embodiment, between 5% and 10% of the basepairs in a dsRNA region are non-canonical basepairs. In each of the above embodiments, the dsRNA region may or may not comprise one or more non-basepaired ribonucleotides, in either the sense sequence or the antisense sequence, or both.

In an embodiment, the dsRNA region of the RNA molecule of the invention comprises 20 contiguous basepairs, wherein at least one basepair of the 20 contiguous basepairs is a non-canonical basepair. In an embodiment, the dsRNA region comprises 20 contiguous basepairs, wherein at least 2 basepairs of the 20 contiguous basepairs are non-canonical basepairs. In an embodiment, the dsRNA region comprises 20 contiguous basepairs, wherein at least 3 basepairs of the 20 contiguous basepairs are non-canonical basepairs. In an embodiment, the dsRNA region comprises 20 contiguous basepairs, wherein at least 4 basepairs of the 20 contiguous basepairs are non-canonical basepairs. In an embodiment, the dsRNA region comprises 20 contiguous basepairs, wherein at least 5 basepairs of the 20 contiguous basepairs are non-canonical basepairs. In an embodiment, the dsRNA region comprises 20 contiguous basepairs, wherein at least 6 basepairs of the 20 contiguous basepairs are non-canonical basepairs. In an embodiment, the dsRNA region comprises 20 contiguous basepairs, wherein at least 7 basepairs of the 20 contiguous basepairs are non-canonical basepairs. In an embodiment, the dsRNA region comprises 20 contiguous basepairs, wherein at least 8 basepairs of the 20 contiguous basepairs are non-canonical basepairs. In an embodiment, the dsRNA region comprises 20 contiguous basepairs, wherein at least 9 basepairs of the 20 contiguous basepairs are non-canonical basepairs. In each of these embodiments, it is preferred that a maximum of 10 of the 20 contiguous basepairs in the dsRNA region are non-canonical basepairs, more preferably a maximum of 9 of the basepairs in the dsRNA region are non-canonical basepairs, still more preferably a maximum of 8 of the basepairs in the dsRNA region are non-canonical basepairs, even still more preferably a maximum of 7 of the basepairs in the dsRNA region are non-canonical basepairs, and most preferably a maximum of 6 of the basepairs in the dsRNA region are non-canonical basepairs. Preferably, in the above embodiments, the non-canonical basepairs comprise at least one G:U basepair, more preferably all of the non-canonical basepairs are G:U basepairs. Preferably, the features of the above embodiments apply to each and every one of the 20 contiguous basepairs that are present in the RNA molecule of the invention.

In an embodiment, the dsRNA region of the RNA molecule of the invention comprises 21 contiguous basepairs, wherein at least one basepair of the 21 contiguous basepairs is a non-canonical basepair. In an embodiment, the dsRNA region comprises 21 contiguous basepairs, wherein at least 2 basepairs of the 21 contiguous basepairs are non-canonical basepairs. In an embodiment, the dsRNA region comprises 21 contiguous basepairs, wherein at least 3 basepairs of the 21 contiguous basepairs are non-canonical basepairs. In an embodiment, the dsRNA region comprises 21 contiguous basepairs, wherein at least 4 basepairs of the 21 contiguous basepairs are non-canonical basepairs. In an embodiment, the dsRNA region comprises 21 contiguous basepairs, wherein at least 5 basepairs of the 21 contiguous basepairs are non-canonical basepairs. In an embodiment, the dsRNA region comprises 21 contiguous basepairs, wherein at least 6 basepairs of the 21 contiguous basepairs are non-canonical basepairs. In an embodiment, the dsRNA region comprises 21 contiguous basepairs, wherein at least 7 basepairs of the 21 contiguous basepairs are non-canonical basepairs. In an embodiment, the dsRNA region comprises 21 contiguous basepairs, wherein at least 8 basepairs of the 21 contiguous basepairs are non-canonical basepairs. In an embodiment, the dsRNA region comprises 21 contiguous basepairs, wherein at least 9 basepairs of the 21 contiguous basepairs are non-canonical basepairs. In each of these embodiments, it is preferred that a maximum of 10 of the 21 contiguous basepairs in the dsRNA region are non-canonical basepairs, more preferably a maximum of 9 of the basepairs in the dsRNA region are non-canonical basepairs, still more preferably a maximum of 8 of the basepairs in the dsRNA region are non-canonical basepairs, even still more preferably a maximum of 7 of the basepairs in the dsRNA region are non-canonical basepairs, and most preferably a maximum of 6 of the basepairs in the dsRNA region are non-canonical basepairs. Preferably, in the above embodiments, the non-canonical basepairs comprise at least one G:U basepair, more preferably all of the non-canonical basepairs are G:U basepairs. Preferably, the features of the above embodiments apply to each and every one of the 21 contiguous basepairs that are present in the RNA molecule of the invention.

In an embodiment, the dsRNA region of the RNA molecule of the invention comprises 22 contiguous basepairs, wherein at least one basepair of the 22 contiguous basepairs is a non-canonical basepair. In an embodiment, the dsRNA region comprises 22 contiguous basepairs, wherein at least 2 basepairs of the 22 contiguous basepairs are non-canonical basepairs. In an embodiment, the dsRNA region comprises 22 contiguous basepairs, wherein at least 3 basepairs of the 22 contiguous basepairs are non-canonical basepairs. In an embodiment, the dsRNA region comprises 22 contiguous basepairs, wherein at least 4 basepairs of the 22 contiguous basepairs are non-canonical basepairs. In an embodiment, the dsRNA region comprises 22 contiguous basepairs, wherein at least 5 basepairs of the 22 contiguous basepairs are non-canonical basepairs. In an embodiment, the dsRNA region comprises 22 contiguous basepairs, wherein at least 6 basepairs of the 22 contiguous basepairs are non-canonical basepairs. In an embodiment, the dsRNA region comprises 22 contiguous basepairs, wherein at least 7 basepairs of the 22 contiguous basepairs are non-canonical basepairs. In an embodiment, the dsRNA region comprises 22 contiguous basepairs, wherein at least 8 basepairs of the 22 contiguous basepairs are non-canonical basepairs. In an embodiment, the dsRNA region comprises 22 contiguous basepairs, wherein at least 9 basepairs of the 22 contiguous basepairs are non-canonical basepairs. In each of these embodiments, it is preferred that a maximum of 10 of the 22 contiguous basepairs in the dsRNA region are non-canonical basepairs, more preferably a maximum of 9 of the basepairs in the dsRNA region are non-canonical basepairs, still more preferably a maximum of 8 of the basepairs in the dsRNA region are non-canonical basepairs, even still more preferably a maximum of 7 of the basepairs in the dsRNA region are non-canonical basepairs, and most preferably a maximum of 6 of the basepairs in the dsRNA region are non-canonical basepairs. Preferably, in the above embodiments, the non-canonical basepairs comprise at least one G:U basepair, more preferably all of the non-canonical basepairs are G:U basepairs. Preferably, the features of the above embodiments apply to each and every one of the 22 contiguous basepairs that are present in the RNA molecule of the invention.

In an embodiment, the dsRNA region of the RNA molecule of the invention comprises 23 contiguous basepairs, wherein at least one basepair of the 23 contiguous basepairs is a non-canonical basepair. In an embodiment, the dsRNA region comprises 23 contiguous basepairs, wherein at least 2 basepairs of the 23 contiguous basepairs are non-canonical basepairs. In an embodiment, the dsRNA region comprises 23 contiguous basepairs, wherein at least 3 basepairs of the 23 contiguous basepairs are non-canonical basepairs. In an embodiment, the dsRNA region comprises 23 contiguous basepairs, wherein at least 4 basepairs of the 23 contiguous basepairs are non-canonical basepairs. In an embodiment, the dsRNA region comprises 23 contiguous basepairs, wherein at least 5 basepairs of the 23 contiguous basepairs are non-canonical basepairs. In an embodiment, the dsRNA region comprises 23 contiguous basepairs, wherein at least 6 basepairs of the 23 contiguous basepairs are non-canonical basepairs. In an embodiment, the dsRNA region comprises 23 contiguous basepairs, wherein at least 7 basepairs of the 23 contiguous basepairs are non-canonical basepairs. In an embodiment, the dsRNA region comprises 23 contiguous basepairs, wherein at least 8 basepairs of the 23 contiguous basepairs are non-canonical basepairs. In an embodiment, the dsRNA region comprises 23 contiguous basepairs, wherein at least 9 basepairs of the 23 contiguous basepairs are non-canonical basepairs. In each of these embodiments, it is preferred that a maximum of 10 of the 23 contiguous basepairs in the dsRNA region are non-canonical basepairs, more preferably a maximum of 9 of the basepairs in the dsRNA region are non-canonical basepairs, still more preferably a maximum of 8 of the basepairs in the dsRNA region are non-canonical basepairs, even still more preferably a maximum of 7 of the basepairs in the dsRNA region are non-canonical basepairs, and most preferably a maximum of 6 of the basepairs in the dsRNA region are non-canonical basepairs. Preferably, in the above embodiments, the non-canonical basepairs comprise at least one G:U basepair, more preferably all of the non-canonical basepairs are G:U basepairs. Preferably, the features of the above embodiments apply to each and every one of the 23 contiguous basepairs that are present in the RNA molecule of the invention.

In an embodiment, the dsRNA region of the RNA molecule of the invention comprises 24 contiguous basepairs, wherein at least one basepair of the 24 contiguous basepairs is a non-canonical basepair. In an embodiment, the dsRNA region comprises 24 contiguous basepairs, wherein at least 2 basepairs of the 24 contiguous basepairs are non-canonical basepairs. In an embodiment, the dsRNA region comprises 24 contiguous basepairs, wherein at least 3 basepairs of the 24 contiguous basepairs are non-canonical basepairs. In an embodiment, the dsRNA region comprises 24 contiguous basepairs, wherein at least 4 basepairs of the 24 contiguous basepairs are non-canonical basepairs. In an embodiment, the dsRNA region comprises 24 contiguous basepairs, wherein at least 5 basepairs of the 24 contiguous basepairs are non-canonical basepairs. In an embodiment, the dsRNA region comprises 24 contiguous basepairs, wherein at least 6 basepairs of the 24 contiguous basepairs are non-canonical basepairs. In an embodiment, the dsRNA region comprises 24 contiguous basepairs, wherein at least 7 basepairs of the 24 contiguous basepairs are non-canonical basepairs. In an embodiment, the dsRNA region comprises 24 contiguous basepairs, wherein at least 8 basepairs of the 24 contiguous basepairs are non-canonical basepairs. In an embodiment, the dsRNA region comprises 24 contiguous basepairs, wherein at least 9 basepairs of the 24 contiguous basepairs are non-canonical basepairs. In each of these embodiments, it is preferred that a maximum of 10 of the 24 contiguous basepairs in the dsRNA region are non-canonical basepairs, more preferably a maximum of 9 of the basepairs in the dsRNA region are non-canonical basepairs, still more preferably a maximum of 8 of the basepairs in the dsRNA region are non-canonical basepairs, even still more preferably a maximum of 7 of the basepairs in the dsRNA region are non-canonical basepairs, and most preferably a maximum of 6 of the basepairs in the dsRNA region are non-canonical basepairs. Preferably, in the above embodiments, the non-canonical basepairs comprise at least one G:U basepair, more preferably all of the non-canonical basepairs are G:U basepairs. Preferably, the features of the above embodiments apply to each and every one of the 24 contiguous basepairs that are present in the RNA molecule of the invention.

In the following embodiments, the full length of the dsRNA region (i.e. the whole dsRNA region) of the RNA molecule of the invention is considered as the context for the feature if there is only one (contiguous) dsRNA region, or for each of the dsRNA regions of the RNA molecule if there are two or more dsRNA regions in the RNA molecule. In an embodiment, the dsRNA region does not comprise 20 contiguous canonical basepairs i.e. every subregion of 20 contiguous basepairs includes at least one non-canonical basepair, preferably at least one G:U basepair. In an embodiment, the dsRNA region does not comprise 19 contiguous canonical basepairs. In an embodiment, the dsRNA region does not comprise 18 contiguous canonical basepairs. In an embodiment, the dsRNA region does not comprise 17 contiguous canonical basepairs. In an embodiment, the dsRNA region does not comprise 16 contiguous canonical basepairs. In an embodiment, the dsRNA region does not comprise 15 contiguous canonical basepairs. In an embodiment, the dsRNA region does not comprise 14 contiguous canonical basepairs. In an embodiment, the dsRNA region does not comprise 13 contiguous canonical basepairs. In an embodiment, the dsRNA region does not comprise 12 contiguous canonical basepairs. In an embodiment, the dsRNA region does not comprise 11 contiguous canonical basepairs. In an embodiment, the dsRNA region does not comprise 10 contiguous canonical basepairs. In an embodiment, the dsRNA region does not comprise 9 contiguous canonical basepairs. In an embodiment, the dsRNA region does not comprise 8 contiguous canonical basepairs. In an embodiment, the dsRNA region does not comprise 7 contiguous canonical basepairs. In the above embodiments, it is preferred that the longest subregion of contiguous canonical basepairing in the dsRNA region of the RNA molecule, or each and every dsRNA region in the RNA molecule, is 5, 6 or 7 contiguous canonical basepairs i.e. towards the shorter lengths mentioned. Each of the features of the above embodiments is preferably combined in the RNA molecule with the following features. In an embodiment, the dsRNA region comprises between 10 and 19 or 20 contiguous basepairs. In a preferred embodiment, the dsRNA region comprises between 12 and 19 or 20 contiguous basepairs. In an embodiment, the dsRNA region comprises between 14 and 19 or 20 contiguous basepairs. In these embodiments, the dsRNA region comprises 15 contiguous basepairs. In an embodiment, the dsRNA region comprises 16, 17, 18 or 19 contiguous basepairs. In an embodiment, the dsRNA region comprises 20 contiguous basepairs. Preferably, in the above embodiments, the contiguous basepairs comprise at least one non-canonical basepair which comprises at least one G:U basepair, more preferably all of the non-canonical basepairs in the region of contiguous basepairs are G:U basepairs.

In an embodiment, the dsRNA region comprises a subregion of 4 canonical basepairs flanked by non-canonical basepairs, i.e. at least one, preferably one or two (not more than 2), non-canonical basepairs adjacent to each end of the 4 canonical basepairs. In an embodiment, the dsRNA region comprises 2 subregions each of 4 canonical basepairs flanked by non-canonical basepairs. In an embodiment, the dsRNA region comprises 3 subregions each of 4 canonical basepairs flanked by non-canonical basepairs. In an embodiment, the dsRNA region comprises 4 or 5 subregions each of 4 canonical basepairs flanked by non-canonical basepairs. In an embodiment, the dsRNA region comprises 6 or 7 subregions each of 4 canonical basepairs flanked by non-canonical basepairs. In an embodiment, the dsRNA region comprises 8 to 10 subregions each of 4 canonical basepairs flanked by non-canonical basepairs. In an embodiment, the dsRNA region comprises 11 to 15 subregions each of 4 canonical basepairs flanked by non-canonical basepairs. In an embodiment, the dsRNA region comprises between 2 and 50 subregions each of 4 canonical basepairs flanked by non-canonical basepairs. In an embodiment, the dsRNA region comprises between 2 and 40 subregions each of 4 canonical basepairs flanked by non-canonical basepairs. In an embodiment, the dsRNA region comprises between 2 and 30 subregions each of 4 canonical basepairs flanked by non-canonical basepairs. In an embodiment, the dsRNA region comprises between 2 and 20 subregions each of 4 canonical basepairs flanked by non-canonical basepairs. Preferably, in the above embodiments, the non-canonical basepairs comprise at least one G:U basepair, more preferably all of the non-canonical basepairs flanking the contiguous canonical basepairs in the subregions are G:U basepairs. In variations of the above embodiments, one or both of the flanking non-canonical basepairs are replaced with a non-basepaired ribonucleotide in the sense sequence, the antisense sequence or in both sequences, for some or all of the subregions. It is readily understood that, in the above embodiments, the maximum number of subregions is determined by the length of the dsRNA region in the RNA molecule.

In an embodiment, the dsRNA region comprises a subregion of 5 canonical basepairs flanked by non-canonical basepairs. In an embodiment, the dsRNA region comprises 2 subregions each of 5 canonical basepairs flanked by non-canonical basepairs. In an embodiment, the dsRNA region comprises 3 subregions each of 5 canonical basepairs flanked by non-canonical basepairs. In an embodiment, the dsRNA region comprises 4 or 5 subregions each of 5 canonical basepairs flanked by non-canonical basepairs. In an embodiment, the dsRNA region comprises 6 or 7 subregions each of 5 canonical basepairs flanked by non-canonical basepairs. In an embodiment, the dsRNA region comprises 8 to 10 subregions each of 5 canonical basepairs flanked by non-canonical basepairs. In an embodiment, the dsRNA region comprises 11 to 15 subregions each of 5 canonical basepairs flanked by non-canonical basepairs. In an embodiment, the dsRNA region comprises between 2 and 50 subregions each of 5 canonical basepairs flanked by non-canonical basepairs. In an embodiment, the dsRNA region comprises between 2 and 50 subregions each of 5 canonical basepairs flanked by non-canonical basepairs. In an embodiment, the dsRNA region comprises between 2 and 30 subregions each of 5 canonical basepairs flanked by non-canonical basepairs. In an embodiment, the dsRNA region comprises between 2 and 20 subregions each of 5 canonical basepairs flanked by non-canonical basepairs. Preferably, in the above embodiments, the non-canonical basepairs comprise at least one G:U basepair, more preferably all of the non-canonical basepairs flanking the contiguous canonical basepairs in the subregions are G:U basepairs. In variations of the above embodiments, one or both of the flanking non-canonical basepairs are replaced with a non-basepaired ribonucleotide in the sense sequence, the antisense sequence or in both sequences, for some or all of the subregions. It is readily understood that, in the above embodiments, the maximum number of subregions is determined by the length of the dsRNA region in the RNA molecule.

In an embodiment, the dsRNA region comprises a subregion of 6 canonical basepairs flanked by non-canonical basepairs. In an embodiment, the dsRNA region comprises 2 subregions each of 6 canonical basepairs flanked by non-canonical basepairs. In an embodiment, the dsRNA region comprises 3 subregions each of 6 canonical basepairs flanked by non-canonical basepairs. In an embodiment, the dsRNA region comprises 4 or 5 subregions each of 6 canonical basepairs flanked by non-canonical basepairs. In an embodiment, the dsRNA region comprises 6 or 7 subregions each of 6 canonical basepairs flanked by non-canonical basepairs. In an embodiment, the dsRNA region comprises 8 to 10 subregions each of 6 canonical basepairs flanked by non-canonical basepairs. In an embodiment, the dsRNA region comprises 11 to 16 subregions each of 6 canonical basepairs flanked by non-canonical basepairs. In an embodiment, the dsRNA region comprises between 2 and 60 subregions each of 6 canonical basepairs flanked by non-canonical basepairs. In an embodiment, the dsRNA region comprises between 2 and 60 subregions each of 6 canonical basepairs flanked by non-canonical basepairs. In an embodiment, the dsRNA region comprises between 2 and 30 subregions each of 6 canonical basepairs flanked by non-canonical basepairs. In an embodiment, the dsRNA region comprises between 2 and 20 subregions each of 6 canonical basepairs flanked by non-canonical basepairs. Preferably, in the above embodiments, the non-canonical basepairs comprise at least one G:U basepair, more preferably all of the non-canonical basepairs flanking the contiguous canonical basepairs in the subregions are G:U basepairs. In variations of the above embodiments, one or both of the flanking non-canonical basepairs are replaced with a non-basepaired ribonucleotide in the sense sequence, the antisense sequence or in both sequences, for some or all of the subregions. It is readily understood that, in the above embodiments, the maximum number of subregions is determined by the length of the dsRNA region in the RNA molecule.

In an embodiment, the dsRNA region comprises a subregion of 10 contiguous basepairs wherein 2-4 of the basepairs are non-canonical basepairs. In an embodiment, the dsRNA region comprises 2 subregions each of 10 contiguous basepairs wherein 2-4 of the 10 contiguous basepairs are non-canonical basepairs. In an embodiment, the dsRNA region comprises 3 subregions each of 10 contiguous basepairs wherein 2-4 of the 10 contiguous basepairs are non-canonical basepairs. In an embodiment, the dsRNA region comprises 4 subregions each of 10 contiguous basepairs wherein 2-4 of the 10 contiguous basepairs are non-canonical basepairs. In an embodiment, the dsRNA region comprises 5 subregions each of 10 contiguous basepairs wherein 2-4 of the 10 contiguous basepairs are non-canonical basepairs. In an embodiment, the dsRNA region comprises 10 subregions each of 10 contiguous basepairs wherein 2-4 of the 10 contiguous basepairs are non-canonical basepairs. In an embodiment, the dsRNA region comprises 4 subregions each of 15 contiguous basepairs wherein 2-6 of the 15 contiguous basepairs are non-canonical basepairs. In an embodiment, the dsRNA region comprises between 2 and 50 subregions each of 10 contiguous basepairs wherein 2-4 of the 10 contiguous basepairs are non-canonical basepairs. In an embodiment, the dsRNA region comprises between 2 and 40 subregions each of 10 contiguous basepairs wherein 2-4 of the 10 contiguous basepairs are non-canonical basepairs. In an embodiment, the dsRNA region comprises between 2 and 30 subregions each of 10 contiguous basepairs wherein 2-4 of the 10 contiguous basepairs are non-canonical basepairs. In an embodiment, the dsRNA region comprises between 2 and 20 subregions each of 10 contiguous basepairs wherein 2-4 of the 10 contiguous basepairs are non-canonical basepairs. In an embodiment, the non-canonical basepairs in one (contiguous) or more, or all dsRNA regions of the RNA molecule are not adjacent a non-base pair. In another embodiment, the non-canonical basepairs are at least 2 contiguous base pairs from a non-base pair. In another embodiment, the non-canonical basepairs are at least 3, 4, 5, 6, 7, 8, 9, 10 or more contiguous base pairs from a non-base pair. In an embodiment the non-canonical basepairs in one (contiguous) or more, or all dsRNA regions of the RNA molecule are not adjacent a loop sequence. In another embodiment, the non-canonical basepairs are at least 2 contiguous base pairs from a loop sequence. In another embodiment, the non-canonical basepairs are at least 3, 4, 5, 6, 7, 8, 9, 10 or more contiguous base pairs from a loop sequence. Preferably, in the above embodiments, the non-canonical basepairs comprise at least one G:U basepair, more preferably all of the non-canonical basepairs in the subregions are G:U basepairs. In variations of the above embodiments, one or more of the 2-4 or 2-6 non-canonical basepairs are replaced with a non-basepaired ribonucleotide in the sense sequence, the antisense sequence or in both sequences, for some or all of the subregions. It is readily understood that, in the above embodiments, the maximum number of subregions is determined by the length of the dsRNA region in the RNA molecule.

In an embodiment, the ratio of canonical to non-canonical basepairs in the dsRNA region is between 2.5:1 and 3.5:1, for example about 3:1. In an embodiment, the ratio of canonical to non-canonical basepairs in the dsRNA region is between 3.5:1 and 4.5:1, for example about 4:1. In an embodiment, the ratio of canonical to non-canonical basepairs in the dsRNA region is between 4.5:1 and 5.5:1, for example about 5:1. In an embodiment, the ratio of canonical to non-canonical basepairs in the dsRNA region is between 5.5:1 and 6.5:1, for example about 6:1. Different dsRNA regions in the RNA molecule may have different ratios.

In the above embodiments, the non-canonical basepairs in the dsRNA region(s) of the RNA molecule are preferably all G:U basepairs. In an embodiment, at least 99% of the non-canonical basepairs are G:U basepairs. In an embodiment, at least 98% of the non-canonical basepairs are G:U basepairs. In an embodiment, at least 97% of the non-canonical basepairs are G:U basepairs. In an embodiment, at least 95% of the non-canonical basepairs are G:U basepairs. In an embodiment, at least 90% of the non-canonical basepairs are G:U basepairs. In an embodiment, between 90 and 95% of the non-canonical basepairs are G:U basepairs. For example, if there are 10 non-canonical basepairs, at least 9 (90%) are G:U basepairs.

In another embodiment, between 3% and 50% of the non-canonical basepairs are G:U basepairs. In another embodiment, between 5% and 30% of the non-canonical basepairs are G:U basepairs. In another embodiment, between 10% and 30% of the non-canonical basepairs are G:U basepairs. In another embodiment, between 15% and 20% of the non-canonical basepairs are G:U basepairs.

In an example of the above embodiments, there are at least 3 G:U base pairings in one (contiguous) or more, or all dsRNA regions of the RNA molecule. In another example, there are at least 4, 5, 6, 7, 8, 9 or 10 G:U base pairings. In another example, there are at least between 3 and 10 G:U base pairings. In another example, there are at least between 5 and 10 G:U base pairings.

The dsRNA region comprising non-canonical basepairing(s) comprises an antisense sequence of 20 contiguous nucleotides which acts as an antisense regulatory element. In an embodiment, the antisense regulatory element is at least 80%, preferably at least 90%, more preferably at least 95% or most preferably 100% complementary to a target RNA molecule in a eukaryotic cell. In an embodiment, a dsRNA region comprises 2, 3, 4, or 5 antisense regulatory elements which either are complementary to the same target RNA molecule (i.e. to different regions of the same target RNA molecule) or are complementary to different target RNA molecules.

In an embodiment, one or more ribonucleotides of the sense ribonucleotide sequence or one or more ribonucleotides of the antisense ribonucleotide sequence, or both, are not basepaired in the dsRNA region when the sense and antisense sequences hybridize. In this embodiment, the dsRNA region does not include any loop sequence which covalently joins the sense and antisense sequences. One or more ribonucleotides of a dsRNA region or subregion may not be basepaired. Accordingly, in this embodiment, the sense strand of the dsRNA region does not fully basepair with its corresponding antisense strand.

In an embodiment, the chimeric RNA molecule does not comprise a non-canonical base pair at the base of a loop of the molecule. In another embodiment, one, two, three, four, five or more or all of the non-canonical base pairs are flanked by canonical base pairs.

In an embodiment, the chimeric RNA molecule comprises at least one plant DCL-1 cleavage site.

In an embodiment, the target RNA molecule is not a viral RNA molecule.

In an embodiment, the target RNA molecule is not a South African cassava mosaic virus RNA molecule.

In an embodiment, the chimeric RNA molecule comprises at least one non-basepair, or stretch of non-basepairs, flanked by canonical base pairs, non-canonical base pairs, or a canonical base pair and a non-canonical base pair. For example, this may be a bulge as described herein.

In an embodiment, the chimeric RNA molecule does not comprise a double stranded region with greater than 11 canonical base pairs.

Moreover, in an embodiment and optionally in combination with any of the features of the above embodiments, the total number of ribonucleotides in the sense sequence(s) and the total number of ribonucleotides in the antisense sequence(s) may not be identical, although preferably they are identical. In an embodiment, the total number of ribonucleotides in the sense ribonucleotide sequence(s) of the dsRNA region is between 90% and 110% of the total number of ribonucleotides in the antisense ribonucleotide sequence(s). In an embodiment, the total number of ribonucleotides in the sense ribonucleotide sequence(s) is between 95% and 105% of the total number of ribonucleotides in the antisense ribonucleotide sequence(s). In an embodiment, chimeric RNA molecules of the present disclosure can comprise one or more structural elements such as internal or terminal bulges or loops. Various embodiments of bulges and loops are discussed above. In an embodiment, dsRNA regions are separated by a structural element such as a bulge or loop. In an embodiment, dsRNA regions are separated by a intervening (spacer) sequence. Some of the ribonucleotides of the spacer sequence may be basepaired to other ribonucleotides in the RNA molecule, for example to other ribonucleotides within the spacer sequence, or they may not be basepaired in the RNA molecule, or some of each. In an embodiment, dsRNA regions are linked to a terminal loop. In an embodiment, dsRNA regions are flanked by terminal loops.

In an embodiment, where the dsRNA region of the RNA molecule of the invention has at least 3 non-canonical basepairs in any subregion of 5 contiguous basepairs, the non-canonical basepairs are not contiguous but are separated by one or more canonical basepairs i.e. the dsRNA region does not have 3 or more contiguous non-canonical basepairs. In an embodiment, the dsRNA region does not have 4 or more contiguous non-canonical basepairs. For example, in an embodiment, the dsRNA region comprises at least 3 non-canonical basepairs in a subregion of 10 basepairs, wherein each non-canonical basepair is separated by 4 canonical basepairs.

In an embodiment, an RNA molecule of the invention comprises more than one dsRNA region. For example, the RNA molecule comprises 2, 3, 4, 5, 6, 7, 8, 9, 10 or more dsRNA regions. In this example, one or more or all of the dsRNA regions can comprise above exemplified properties such as non-canonical basepairing and/or number of antisense regulatory elements.

Silencing Activity

RNA molecules of the present disclosure have antisense activity as they comprise a sense ribonucleotide sequence that is essentially complementary to a region of a target RNA molecule. For example, the ribonucleotide sequence is essentially complementary to a region of a target RNA molecule in a eukaryotic cell. In an example, the target RNA molecule can be in a bacterial cell, fungal cell, plant cell, insect cell or animal cell. Such components of the RNA molecules defined herein can be referred to as an "antisense regulatory element". "Essentially complementary" means that the sense ribonucleotide sequence may have insertions, deletions and individual point mutations in comparison with the complement of the target RNA molecule in the eukaryotic cell. Preferably, the homology is at least 80%, preferably at least 90%, preferably at least 95%, most preferably 100%, between the sense ribonucleotide sequence with antisense activity and the target RNA molecule. For example, the sense ribonucleotide sequence can comprise about 15, about 16, about 17, about 18, about 19 or more contiguous nucleotides that are identical in sequence to a first region of a target RNA molecule in a eukaryotic cell. In another example, the sense ribonucleotide sequence can comprise about 20 contiguous nucleotides that are identical in sequence to a first region of a target RNA molecule in a eukaryotic cell.

"Antisense activity" is used in the context of the present disclosure to refer to an antisense regulatory element from an RNA molecule defined herein that modulates (increase or decrease) expression of a target RNA molecule.

In various examples, antisense regulatory elements according to the present disclosure can comprise a plurality of monomeric subunits linked together by linking groups. Examples include primers, probes, antisense compounds, antisense oligonucleotides, external guide sequence (EGS) oligonucleotides, alternate splicers, gapmers, siRNAs and microRNAs. As such, RNA molecules according to the present disclosure can comprise antisense regulatory elements with single-stranded, double-stranded, circular, branched or hairpin structures. In an example, the antisense sequence can contain structural elements such as internal or terminal bulges or loops.

In an example, RNA molecules of the present disclosure comprise chimeric oligomeric components such as chimeric oligonucleotides. For example, an RNA molecule can comprise differently modified nucleotides, mixed-backbone antisense oligonucleotides or a combination thereof. In an example, chimeric oligomeric compounds can comprise at least one region modified so as to confer increased resistance to nuclease degradation, increased cellular uptake, and/or increased binding affinity for the target RNA molecule.

Antisense regulatory elements can have a variety of lengths. Across various examples, the present disclosure provides antisense regulatory elements consisting of X-Y linked bases, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 (provided that X<Y). For example, in certain embodiments, the present disclosure provides antisense regulatory elements comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked bases.

RNA molecules according to the present disclosure can comprise multiple antisense regulatory elements. For example, RNA molecules can comprise at least 2, at least 3, at least 4, at least 5, at least 6, at least 7, at least 8, at least 9, at least 10 antisense regulatory elements. In an example, the antisense regulatory elements are the same. In this example, the RNA molecule can comprise at least 2, at least 3, at least 4, at least 5, at least 6, at least 7, at least 8, at least 9, at least 10 copies of an antisense regulatory element. In another example, RNA molecules according to the present disclosure can comprise different antisense regulatory elements. For example, antisense regulatory elements may be provided to target multiple genes in a pathway such as lipid biosynthesis. In this example, the RNA molecule can comprise at least 2, at least 3, at least 4, at least 5, at least 6, at least 7, at least 8, at least 9, at least 10 different antisense regulatory elements.

Antisense regulatory elements according to the present disclosure can modulate (increase or decrease) expression or amount of various target RNA molecules. In an example, the target RNA molecule is a fatty acid biosynthesis gene. Examples of such genes include genes encoding acetyl transacylases, acyl transport proteins ("acyl carrier protein"), desaturases such as stearyl desaturases or microsomal D12-desaturases, in particular Fad2-1 genes, malonyl transacylase, -ketoacyl-ACP synthetases, 3-keto-ACP reductases, enoyl-ACP hydrases, thioesterases such as acyl-ACP thioesterases, enoyl-ACP reductases. In an example, the target RNA molecule is FAD2 gene (for example those described by Genbank Acc. No.: AF124360 (*Brassica carinata*), AF042841 (*Brassica rapa*), L26296 (*Arabidopsis thaliana*), A65102 (*Corylus avellana*)). For example, the target RNA molecule can be FAD2.1 gene. In another example, the target RNA molecule can be FAD2.2 gene. In another example, the target RNA molecule can be FAD2.1 and FAD2.2 genes. Examples of other genes involved in modifying lipid composition that can be a target RNA molecule are known in the art (see, for example, Shure et al., 1983; Preiss et al., 1987; Gupta et al., 1988; Olive et al., 1989; Bhattacharyya et al., 1990; Dunwell, 2000; Brar et al., 1996; Kishore and Somerville, 1993; U.S. Pat. No. 5,530,192 and WO 94/18337).

In another example, the target RNA molecule is an arthropod gene such as an insect gene transcript. Examples of such genes include chitin synthase genes, such as CHS1 and/or CHS2 or other genes that control insect activity, behaviour, reproduction, growth and/or development. Various essential genes of a variety of pathogens are known to the those of skill in the art (for example nematode resistance genes are summarised in WO 93/10251, WO 94/17194).

In another example, the target RNA molecule is associated with a disease. For example, the target RNA molecule can be an oncogene or tumour suppressor gene transcript. Exemplary oncogenes include ABL1, BCL1, BCL2, BCL6, CBFA2, CBL, CSFIR, ERBA, ERBB, EBRB2, FGR, FOS, FYN, HRAS, JUN, LCK, LYN, MYB, MYC, NRAS, RET or SRC. Exemplary tumour suppressor genes include BRCA1 or BRCA2; adhesion molecules; cyclin kinases and their inhibitors.

In another example, the target RNA molecule is associated with delay of fruit maturation. Delayed fruit maturation can be achieved for example by reducing the gene expression of genes selected from the group consisting of polygalacturonases, pectin esterases, β-(1-4) glucanases (cellulases), β-galactanases (β-galactosidases), or genes of ethylene biosynthesis, such as 1-aminocyclopropane-1-carboxylate synthase, genes of carotenoid biosynthesis such as, for example, genes of prephytoene or phytoene biosynthesis, for example phytoene desaturases.

In another example, the target RNA molecule is associated with delay of senescence symptoms. Suitable target RNA molecules include cinnamoyl-CoA:NADPH reductases or cinnamoyl alcohol dehydrogenases. Further target RNA molecules are described (in WO 1995/07993).

In another example, the target RNA molecule is associated with modification of the fibre content in foodstuffs, preferably in seeds. For example, the RNA molecule can reduce expression of coffeic acid O-methyltransferase or of cinnamoyl alcohol dehydrogenase.

ledRNA Molecule

In certain embodiments, RNA molecules of the present invention comprise a first RNA component which is covalently linked to a second RNA component. In preferred embodiments, the RNA molecule self-hybridizes or folds to form a “dumbbell” or ledRNA structure, for example see FIG. 1. In an embodiment, the molecule further comprises one or more of the following:

- a linking ribonucleotide sequence which covalently links the first and second RNA components;
- a 5' leader sequence; and,
- a 3' trailer sequence.

In an embodiment, the first RNA component consists of, in 5' to 3' order, a first 5' ribonucleotide, a first RNA sequence and a first 3' ribonucleotide, wherein the first 5' and 3' ribonucleotides basepair to each other in the RNA molecule, wherein the first RNA sequence comprises a first sense ribonucleotide sequence of at least 20 contiguous ribonucleotides, a first loop sequence of at least 4 ribonucleotides and a first antisense ribonucleotide sequence of at least 20 contiguous ribonucleotides, wherein the first antisense ribonucleotide sequence hybridises with the first sense ribonucleotide sequence in the RNA molecule, wherein the first antisense ribonucleotide sequence is capable of hybridising to a first region of a target RNA molecule.

In another embodiment, the first RNA component consists of, in 5' to 3' order, a first 5' ribonucleotide, a first RNA sequence and a first 3' ribonucleotide, wherein the first 5' and 3' ribonucleotides basepair to each other in the RNA molecule, wherein the first RNA sequence comprises a first sense ribonucleotide sequence of at least 20 contiguous ribonucleotides, a first loop sequence of at least 4 ribonucleotides and a first antisense ribonucleotide sequence of at least 20 contiguous ribonucleotides, wherein the first antisense ribonucleotide sequence fully basepairs with the first sense ribonucleotide sequence in the RNA molecule, wherein the first antisense ribonucleotide sequence is identical in sequence to the complement of a first region of a target RNA molecule. An example of this first RNA component of these two embodiments is shown schematically in the left-hand half of FIG. 1A or the right-hand half of FIG. 1B.

In another embodiment, the first RNA component consists of a first 5' ribonucleotide, a first RNA sequence and a first 3' ribonucleotide, wherein the first 5' and 3' ribonucleotides basepair with each other in the first RNA component, wherein the first RNA sequence comprises a first sense ribonucleotide sequence, a first loop sequence of at least 4 ribonucleotides and a first antisense ribonucleotide sequence, wherein the first sense ribonucleotide sequence and first antisense ribonucleotide sequence each of at least 20 contiguous ribonucleotides whereby the at least 20 contiguous ribonucleotides of the first sense ribonucleotide sequence fully basepair with the at least 20 contiguous ribonucleotides of the first antisense ribonucleotide sequence, wherein the at least 20 contiguous ribonucleotides of the first sense ribonucleotide sequence are substantially identical in sequence to a first region of a target RNA molecule.

In these embodiments, the basepair formed between the first 5' ribonucleotide and the first 3' ribonucleotide is considered to be the terminal basepair of the dsRNA region formed by self-hybridization of the first RNA component, i.e it defines the end of the dsRNA region.

In an embodiment, the first sense sequence has substantial sequence identity to a region of the target RNA, which identity may be to a sequence of less than 20 nucleotides in length. In an embodiment at least 15, at least 16, at least 17, at least 18, or at least 19 contiguous ribonucleotides, preferably at least 20 contiguous ribonucleotides, of the first sense ribonucleotide sequence and a first region of a target RNA molecule are at least 60%, at least 65%, at least 70%, at least 75%, at least 80%, at least 85%, at least 90%, at least 95%, at least 96%, at least 97%, at least 98%, or 99% identical in sequence. In another embodiment, the at least 15, at least 16, at least 17, at least 18, at least 19 contiguous ribonucleotides of the first sense ribonucleotide sequence and a first region of a target RNA molecule are 100% identical. In an embodiment, the first 3, first 4, first 5, first 6, or first 7 ribonucleotides from the 5' end of the first sense ribonucleotide sequence are 100% identical to the region of the target RNA molecule, with the remaining ribonucleotides being at least 60%, at least 65%, at least 70%, at least 75%, at least 80%, at least 85%, at least 90%, at least 95%, at least 96%, at least 97%, at least 98%, at least 99% identical to the target RNA molecule.

In an embodiment the at least 20 contiguous ribonucleotides of the first sense ribonucleotide sequence and a first region of a target RNA molecule are at least 60%, at least 65%, at least 70%, at least 75%, at least 80%, at least 85%, at least 90%, at least 95%, at least 96%, at least 97%, at least 98%, or at least 99% identical. Again, in this embodiment, the first 3, first 4, first 5, first 6, or first 7 ribonucleotides can be 100% identical to the region of the target RNA molecule, with the remaining ribonucleotides being at least 60%, at least 65%, at least 70%, at least 75%, at least 80%, at least 85%, at least 90%, at least 95%, at least 96%, at least 97%, at least 98%, or at least 99% identical to target RNA molecule. In another embodiment, the at least 20 contiguous ribonucleotides of the first sense ribonucleotide sequence and a first region of a target RNA molecule are 100% identical.

In an embodiment, the first antisense sequence has substantial sequence identity to the complement of a region of the target RNA, which identity may be to a sequence of less than 20 nucleotides in length of the complement. In an embodiment at least 15, at least 16, at least 17, at least 18, or at least 19 contiguous ribonucleotides, preferably at least 20 contiguous ribonucleotides, of the first antisense ribonucleotide sequence and the complement of a first region of a target RNA molecule are at least 60%, at least 65%, at least 70%, at least 75%, at least 80%, at least 85%, at least 90%, at least 95%, at least 96%, at least 97%, at least 98%, or 99% identical in sequence. In another embodiment, the at least 15, at least 16, at least 17, at least 18, at least 19 contiguous ribonucleotides of the first antisense ribonucleotide sequence and the complement of the first region of the target RNA molecule are 100% identical. In an embodiment, the first 3, first 4, first 5, first 6, or first 7 ribonucleotides from the 5' end of the first antisense ribonucleotide sequence are 100% identical to the complement of the region of the target RNA molecule, with the remaining ribonucleotides being at least 60%, at least 65%, at least 70%, at least 75%, at least 80%, at least 85%, at least 90%, at least 95%, at least 96%, at least 97%, at least 98%, at least 99% identical to the complement of the target RNA molecule.

In an embodiment the at least 20 contiguous ribonucleotides of the first antisense ribonucleotide sequence and the complement of a first region of the target RNA molecule are at least 60%, at least 65%, at least 70%, at least 75%, at least 80%, at least 85%, at least 90%, at least 95%, at least 96%, at least 97%, at least 98%, or at least 99% identical. Again, in this embodiment, the first 3, first 4, first 5, first 6, or first 7 ribonucleotides are 100% identical to the complement of the region of the target RNA molecule, with the remaining ribonucleotides being at least 60%, at least 65%, at least 70%, at least 75%, at least 80%, at least 85%, at least 90%, at least 95%, at least 96%, at least 97%, at least 98%, or at least 99% identical to the complement of the target RNA molecule. In another embodiment, the at least 20 contiguous ribonucleotides of the first antisense ribonucleotide sequence and a first region of a target RNA molecule are 100% identical.

In another embodiment, the second RNA component consists of, in 5' to 3' order, a second 5' ribonucleotide, a second RNA sequence and a second 3' ribonucleotide, wherein the second 5' and 3' ribonucleotides basepair, wherein the second RNA sequence comprises a second sense ribonucleotide sequence, a second loop sequence of at least 4 ribonucleotides and a second antisense ribonucleotide sequence, wherein the second sense ribonucleotide sequence basepairs with the second antisense ribonucleotide sequence. In this embodiment, the basepair formed between the second 5' ribonucleotide and the second 3' ribonucleotide is considered to be the terminal basepair of the dsRNA region formed by self-hybridization of the second RNA component.

In an embodiment, the RNA molecule comprises a 5' leader sequence, or 5' extension sequence, which may arise as a result of transcription from a promoter in the genetic construct, from the start site of transcription to the beginning of the polynucleotide encoding the remainder of the RNA molecule. It is preferred that this 5' leader sequence or 5' extension sequence is relatively short compared to the remainder of the molecule, and it may be removed from the RNA molecule post-transcriptionally, for embodiment by RNAse treatment. The 5' leader sequence or 5' extension sequence may be mostly non-basepaired, or it may contain one or more stem-loop structures. In this embodiment, the 5' leader sequence can consist of a sequence of ribonucleotides which is covalently linked to the first 5' ribonucleotide if the second RNA component is linked to the first 3' ribonucleotide or to the second 5' ribonucleotide if the second RNA component is linked to the first 5' ribonucleotide. In an embodiment, the 5' leader sequence is at least 10, at least 20, at least 30, at least 100, at least 200 ribonucleotides long, preferably to a maximum length of 250 ribonucleotides. In another embodiment, the 5' leader sequence is at least 50 ribonucleotides long. In an embodiment, the 5' leader sequence can act as an extension sequence for amplification of the RNA molecule via a suitable amplification reaction. For embodiment, the extension sequence may facilitate amplification via polymerase.

In another embodiment, the RNA molecule comprises a 3' trailer sequence or 3' extension sequence which may arise as a result of transcription continuing until a transcription termination or polyadenylation signal in the construct encoding the RNA molecule. The 3' trailer sequence or 3' extension sequence may comprise a polyA tail. It is preferred that this 3' trailer sequence or 3' extension sequence is relatively short compared to the remainder of the molecule, and it may be removed from the RNA molecule post-transcriptionally, for embodiment by RNAse treatment. The 3' trailer sequence or 3' extension sequence may be mostly non-basepaired, or it may contain one or more stem-loop structures. In this embodiment, the 3' trailer sequence can consist of a sequence of ribonucleotides which is covalently linked to the second 3' ribonucleotide if the second RNA component is linked to the first 3' ribonucleotide or to the first 3' ribonucleotide if the second RNA component is linked to the first 5' ribonucleotide. In an embodiment, the 3' leader sequence is at least 10, at least 20, at least 30, at least 100, at least 200 ribonucleotides long, preferably to a maximum length of 250 ribonucleotides. In another embodiment, the 3' leader sequence is at least 50 ribonucleotides long. In an embodiment, the 3' trailer sequence can act as an extension sequence for amplification of the RNA molecule via a suitable amplification reaction. For embodiment, the extension sequence may facilitate amplification via polymerase.

In an embodiment, all except for two of the ribonucleotides are covalently linked to two other nucleotides i.e. the RNA molecule consists of only one RNA strand which has self-complementary regions, and so has only one 5' terminal nucleotide and one 3' terminal nucleotide. In another embodiment, all except for four of the ribonucleotides are covalently linked to two other nucleotides i.e. the RNA molecule consists of two RNA strands which have complementary regions which hybridise, and so has only two 5' terminal nucleotides and two 3' terminal nucleotides. In another embodiment, each ribonucleotide is covalently linked to two other nucleotides i.e the RNA molecule is circular as well as having self-complementary regions, and so has no 5' terminal nucleotide and no 3' terminal nucleotide.

In an embodiment, the double-stranded region of the RNA molecule can comprise one or more bulges resulting from unpaired nucleotides in the sense RNA sequence or the antisense RNA sequence, or both. In an embodiment, the RNA molecule comprises a series of bulges. For embodiment, the double-stranded region of the RNA molecule may have 2, 3, 4, 5, 6, 7, 8, 9, 10 or more bulges. Each bulge may be, independently, one, two or more unpaired nucleotides, to as many as 10 nucleotides. Longer sequences may loop out of the sense or antisense sequences in the dsRNA region, which may basepair internally or remain unpaired. In another embodiment, the double-stranded region of the RNA molecule does not comprise a bulge i.e. is fully basepaired along the full length of the dsRNA region.

In another embodiment, the first sense ribonucleotide sequence is covalently linked to the first 5' ribonucleotide without any intervening nucleotides, or the first antisense ribonucleotide sequence is covalently linked to the first 3' ribonucleotide without any intervening nucleotides, or both. In another embodiment, there are at least one, at least two, at least three, at least four, at least five, at least six, at least seven, at least eight, at least nine, at least 10 intervening nucleotides. It is understood that such intervening nucleotides are unrelated in sequence to the target RNA molecule but may assist in stabilising the basepairing of adjacent sense and antisense sequences.

In another embodiment, the 20 consecutive nucleotides of the first sense ribonucleotide sequence are covalently linked to the first 5' ribonucleotide without any intervening nucleotides, and the 20 consecutive nucleotides of the first antisense ribonucleotide sequence are covalently linked to the first 3' ribonucleotide without any intervening nucleotides. In another embodiment, there are at least one, at least two, at least three, at least four, at least five, at least six, at least seven, at least eight, at least nine, at least 10 intervening nucleotides. The intervening nucleotides may be basepaired as part of the double-stranded region of the RNA molecule but are unrelated in sequence to the target RNA. They may assist in providing increased stability to the double-stranded region or to hold together two ends of the RNA molecule and not leave an unbasepaired 5' or 3' end, or both.

In an embodiment, the above referenced first and second RNA components comprise a linking ribonucleotide sequence. In an embodiment, the linking ribonucleotide sequence acts as a spacer between the first sense ribonucleotide sequence that is substantially identical in sequence to a first region of a target RNA molecule and the other components of the molecule. For example, the linking ribonucleotide sequence may act as a spacer between this region and a loop. In another embodiment, the RNA molecule comprises multiple sense ribonucleotide sequences that are substantially identical in sequence to a first region of a target RNA molecule and a linking ribonucleotide sequence which acts as a spacer between these sequences. In an embodiment, at least two, at least three, at least four, at least five, at least six, at least seven, at least eight, at least nine, at least 10 ribonucleotide sequences that are substantially identical in sequence to a first region of a target RNA molecule are provided in the RNA molecule, each being separated from the other(s) by a linking ribonucleotide sequence.

In an embodiment, the above referenced RNA molecules comprise a 5' leader sequence. In an embodiment, the 5' leader sequence consists of a sequence of ribonucleotides which is covalently linked to the first 5' ribonucleotide if the second RNA component is linked to the first 3' ribonucleotide or to the second 5' ribonucleotide if the second RNA component is linked to the first 5' ribonucleotide. In an embodiment, the RNA molecule has a modified 5' or 3' end, for embodiment by attachment of a lipid group such as cholesterol, or a vitamin such as biotin, or a polypeptide. Such modifications may assist in the uptake of the RNA molecule into the eukaryotic cell where the RNA is to function.

In an embodiment, the linking ribonucleotide sequence is less than 100 ribonucleotides in length. In an embodiment, the linking ribonucleotide sequence is less than 50 ribonucleotides in length. In an embodiment, the linking ribonucleotide sequence is less than 20 ribonucleotides in length. In an embodiment, the linking ribonucleotide sequence is less than 10 ribonucleotides in length. In an embodiment, the linking ribonucleotide sequence is less than 5 ribonucleotides in length. In an embodiment, the linking ribonucleotide sequence is between 1 and 100 ribonucleotides in length. In an embodiment, the linking ribonucleotide sequence is between 1 and 50 ribonucleotides in length. In an embodiment, the linking ribonucleotide sequence is between 1 and 20 ribonucleotides in length. In an embodiment, the linking ribonucleotide sequence is between 1 and 10 ribonucleotides in length. In an embodiment, the linking ribonucleotide sequence is between 1 and 5 ribonucleotides in length. In an embodiment, the ribonucleotides of the linking ribonucleotide sequence are not basepaired. In a preferred embodiment, the ribonucleotides of the linking ribonucleotide sequence are all basepaired, or all except for 1, 2 or 3 of the ribonucleotides are basepaired.

In an embodiment, the first or second RNA component comprises a hairpin structure. In a preferred embodiment, the first and second RNA components each comprise a hairpin structure. In these embodiments, the hairpin structure can be a stem-loop. Accordingly, in an embodiment, the RNA molecule can comprise first and second RNA components which each comprise a hairpin structure, wherein the hairpins are covalently bound by a linker sequence. See, for example, FIG. 1. In an embodiment, the linker sequence is one or more unpaired ribonucleic acid(s). In an embodiment, the linker sequence is between 1 and 10 unpaired ribonucleotides.

In an embodiment, the RNA molecule has a double hairpin structure i.e. an "ledRNA structure" or "dumbbell structure". In this embodiment, the first hairpin is the first RNA component and the second hairpin is the second RNA component. In these embodiments, either the first 3' ribonucleotide and the second 5' ribonucleotide, or the second 3' ribonucleotide and the first 5' ribonucleotide, but not both, are covalently joined. In this embodiment, the other 5'/3' ribonucleotides can be separated by a nick (i.e. a discontinuity in the dsRNA molecule where there is no phosphodiester bond between the 5'/3' ribonucleotides. An embodiment, of this type of arrangement is shown in FIG. 1B. In another embodiment, the respective 5'/3' ribonucleotides can be separated by a loop. The lengths of the 5' leader and 3' trailer sequences may be the same or different. For embodiment, the 5' leader may be around 5, 10, 15, 20, 25, 50, 100, 200, 500 ribonucleotides longer than the 3' trailer sequence or vice versa.

In embodiments where the RNA molecule has a double hairpin structure, the second hairpin (in addition to the first hairpin structure) comprises a sense RNA sequence and an antisense RNA sequence that are substantially identical in sequence to a region of a target RNA molecule or its complement, respectively. In an embodiment, each hairpin has a series of ribonucleotides that are substantially identical in sequence to a region of the same target RNA molecule. In an embodiment, each hairpin has a series of ribonucleotides that are substantially identical in sequence to different regions of the same target RNA molecule. In an embodiment, each hairpin has a series of ribonucleotides that are substantially identical in sequence to a region of different target RNA molecules i.e. the RNA molecule can be used to reduce the expression and/or activity of two target RNA molecules which may be unrelated in sequence.

In each hairpin of the double hairpin structure of the RNA molecule, the order of the sense and antisense RNA sequences in each hairpin, in 5' to 3' order, may independently be either sense then antisense, or antisense then sense. In preferred embodiments, the order of the sense and antisense sequences in the double hairpin structure of the RNA molecule is either antisense-sense-sense-antisense where the two sense sequences are contiguous (FIG. 1A), or sense-antisense-antisense-sense where the two antisense sequences are contiguous (FIG. 1B).

In an embodiment, the RNA molecule can comprise, in 5' to 3' order, a 5' leader sequence, a first loop, a sense RNA sequence, a second loop and a 3' trailer sequence, wherein the 5' and 3' leader sequences covalently bond to the sense strand to form a dsRNA sequence. In an embodiment, the 5' leader and 3' trailer sequences are not covalently bound to each other. In an embodiment, the 5' leader and 3' trailer sequences are separated by a nick. In an embodiment, the 5' leader and 3' trailer sequences are ligated together to provide a RNA molecule with a closed structure. In another embodiment, the 5' leader and 3' trailer sequences are separated by a loop.

The term "loop" is used in the context of the present disclosure to refer to a loop structure in an RNA molecule disclosed herein that is formed by a series of non-complementary ribonucleotides. Loops generally follow a series of base-pairs between the first and second RNA components or join a sense RNA sequence and an antisense RNA sequence in one or both of the first and second RNA components. In an embodiment, all of the loop ribonucleotides are non-complementary, generally for shorter loops of 4-10 ribonucleotides. In other embodiments, some ribonucleotides in one or more of the loops are complementary and capable of basepairing within the loop sequence, so long as these basepairings enable a loop structure to form. For example, at least 5%, at least 10%, or at least 15% of the loop ribonucleotides are complementary. Embodiments of loops include stem loops or hairpins, pseudoknots and tetraloops.

In an embodiment, the RNA molecule comprises only two loops, In another embodiment, the RNA molecule comprises at least two, at least three, at least 4, at least 5, at least 6, at least 7, at least 8, at least 9, or at least 10 loops, preferably to a maximum of 10 loops. For example, the RNA molecule can comprise 4 loops.

Loops of various sizes are contemplated by the present disclosure. For example, loops can comprise 4, 5, 6, 7, 8, 9, 10, 11 or 12 ribonucleotides. In other embodiments, loops comprise 15, 20, 25 or 30 nucleotides. In an embodiment, one or all of the loop sequences are longer than 20 nucleotides. In other embodiments, loops are larger, for example comprising 50, 100, 150, 200 or 300 ribonucleotides. In an embodiment, loops comprise 160 ribonucleotides. In another embodiment, less preferred, loops comprise 200, 500, 700 or 1,000 ribonucleotides provided that the loops do not interfere with the hybridisation of the sense and antisense RNA sequences. In an embodiment, each of the loops have the same number of ribonucleotides. For example, loops can have between 100 and 1,000 ribonucleotides in length. For example, loops can have between 600 and 1,000 ribonucleotides in length. For example, loops can have between 4 and 1,000 ribonucleotides. For example, loops preferably have between 4 and 50 ribonucleotides. In another embodiment, loops comprise differing numbers of ribonucleotides.

In another embodiment, one or more loops comprise an intron which can be spliced out of the RNA molecule. In an embodiment, the intron is from a plant gene. Exemplary introns include intron 3 of the maize alcohol dehydrogenase 1 (Adh1) (GenBank: AF044293), intron 4 of the soya beta-conglycinin alpha subunit (GenBank: AB051865); one of the introns of the pea rbcS-3A gene for the ribulose-1,5-bisphosphate carboxylase (RBC) small subunit (GenBank: X04333). Other embodiments of suitable introns are discussed in (Mccullough and Schuler, 1997; Smith et al., 2000).

In various embodiments, a loop may be at the end of at least 3, at least 4, at least 5, at least 6, at least 7, at least 8, at least 9, at least 10 consecutive basepairs, which may be canonical basepairs or may include one or more non-canonical basepairs. In other embodiments, less preferred, particularly for vertebrate animal cells, a loop may be at the end of at least 20, 30, 50, 100, 200, 500 or more consecutive basepairs.

In another embodiment, the RNA molecule comprises two or more sense ribonucleotide sequences, and an antisense ribonucleotide sequences fully based paired thereto, which are each identical in sequence to a region of a target RNA molecule. For example, the RNA molecule can comprise 2, 3, 4, 5, 6, 7, 8, 9, 10, 11, 12 or more sense ribonucleotide sequences, and antisense ribonucleotide sequences fully based paired thereto, which sense ribonucleotide sequences are each independently identical in sequence to a region of a target RNA molecule. In this embodiment, any one or more or all of the sequences can be separated by a linking ribonucleotide sequence(s). In this embodiment, any one or more or all of the sequences can be separated by a loop.

In an embodiment, the two or more sense ribonucleotide sequences are identical in sequence to different regions of the same target RNA molecule. For example, the sequences can be identical to at least 2, at least 3, at least 4, at least 5, at least 6 regions of the same target molecule. In another embodiment, the two or more sense ribonucleotide sequences are identical in sequence. In an embodiment, the two or more sense ribonucleotide sequences are identical in sequence to the same region of the same target RNA molecule. In another embodiment, the two or more sense ribonucleotide sequences are identical in sequence to different target RNA molecules. For embodiment, the sequences can be identical to at least 2, at least 3, at least 4, at least 5, at least 6 regions of different target molecules.

In another embodiment, the two or more sense ribonucleotide sequences have no intervening loop (spacer) sequences.

In an embodiment, the RNA molecule has a single strand of ribonucleotides having a 5' end, at least one sense ribonucleotide sequence which is at least 21 nucleotides in length, an antisense ribonucleotide sequence which is fully basepaired with each sense ribonucleotide sequence over at least 21 contiguous nucleotides, at least two loop sequences and a 3' end. In this embodiment, the ribonucleotide at the 5' end and the ribonucleotide at the 3' end are not directly covalently bonded but are rather positioned adjacent with each basepaired.

In another embodiment, consecutive basepairs of RNA components are interspaced by at least one gap. In an embodiment, the "gap" is provided by an unpaired ribonucleotide. In another embodiment, the "gap" is provided by un-ligated 5' leader sequence and/or 3' trailer sequence. In this embodiment, the gap can be referred to as an "unligated gap". Mismatches and unligated gap(s) can be located at various position(s) of the RNA molecule. For embodiment, an unligated gap can immediately follow an antisense sequence. In another embodiment, an unligated gap can be close to a loop of the RNA molecule. In another embodiment, an unligated gap is positioned about equidistant between at least two loops.

In an embodiment, the RNA molecule is produced from a single strand of RNA. In an embodiment, the single strand is not circularly closed, for example, comprising an unligated gap. In another embodiment, the RNA molecule is a circularly closed molecule. Closed molecules can be produced by ligating an above referenced RNA molecule comprising an unligated gap, for example with an RNA ligase.

In another embodiment, the RNA molecule comprises a 5'- or 3'-, or both, extension sequence. For example, the RNA molecule can comprise a 5' extension sequence which is covalently linked to the first 5' ribonucleotide. In another embodiment, the RNA molecule comprises a 3' extension sequence which is covalently linked to the second 3' ribonucleotide. In another embodiment, the RNA molecule comprises a 5' extension sequence which is covalently linked to the first 5' ribonucleotide and a 3' extension sequence which is covalently linked to the second 3' ribonucleotide.

In another embodiment, the RNA molecule comprises a 5' extension sequence which is covalently linked to the second 5' ribonucleotide. In another embodiment, the RNA molecule comprises a 3' extension sequence which is covalently linked to the first 3' ribonucleotide. In another embodiment, the RNA molecule comprises a 5' extension sequence which is covalently linked to the second 5' ribonucleotide and a 3' extension sequence which is covalently linked to the first 3' ribonucleotide.

In another embodiment, the RNA molecule can comprise one or more of the following:

- 5' extension sequence which is covalently linked to the first 5' ribonucleotide;
- 3' extension sequence which is covalently linked to the second 3' ribonucleotide;
- 5' extension sequence which is covalently linked to the first 5' ribonucleotide and a 3' extension sequence which is covalently linked to the second 3' ribonucleotide;
- 5' extension sequence which is covalently linked to the second 5' ribonucleotide;
- 3' extension sequence which is covalently linked to the first 3' ribonucleotide;
- a 5' extension sequence which is covalently linked to the second 5' ribonucleotide and a 3' extension sequence which is covalently linked to the first 3' ribonucleotide.

Nucleic Acids Encoding RNA Molecules

One of skill in the art will appreciate from the foregoing description that the present disclosure also provides an isolated nucleic acid encoding RNA molecules disclosed herein and the component parts thereof. For example, a nucleic acid comprising a sequence set forth in any one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. The nucleic acid may be partially purified after expression in a host cell. The term "partially purified" is used to refer to an RNA molecule that has generally been separated from the lipids, nucleic acids, other peptides, and other contaminating molecules with which it is associated in a host cell. Preferably, the partially purified polynucleotide is at least 60% free, more preferably at least 75% free, and more preferably at least 90% free from other components with which it is associated.

In another example, a polynucleotide according to the present disclosure is a heterologous polynucleotide. The term "heterologous polynucleotide" is well understood in the art and refers to a polynucleotide which is not endogenous to a cell, or is a native polynucleotide in which the native sequence has been altered, or a native polypeptide whose expression is quantitatively altered as a result of a manipulation of the cell by recombinant DNA techniques.

In another example, a polynucleotide according to the present disclosure is a synthetic polynucleotide. For example, the polynucleotide may be produced using techniques that do not require pre-existing nucleic acid sequences such as DNA printing and oligonucleotide synthesis. In another example, the polynucleotide is produced from xeno nucleic acids.

In an example, a polynucleotide disclosed herein which encodes an RNA precursor molecule comprising an intron, preferably in a 5' extension sequence or in at least one loop sequence, wherein the intron is capable of being spliced out during transcription of the polynucleotide in a host cell or in vitro. In another example, the loop sequence comprises two, three, four, five or more introns. The present disclosure also provides an expression construct such as a DNA construct comprising an isolated nucleic acid of the disclosure operably linked to a promoter. In an example, such isolated nucleic acids and/or expression constructs are provided in a cell or non-human organism. In an example isolated nucleic acids are stably integrated into the genome of the cell or non-human organism. Various examples of suitable expression constructs, promoters and cells comprising the same are discussed below.

Synthesis of RNA molecules according to the present disclosure can be achieved using various methods known in the art. The Examples section provides an example of in vitro synthesis. In this example, constructs comprising RNA molecules disclosed herein are restricted at the 3' end, precipitated, purified and quantified. RNA synthesis can be achieved in bacterial culture following transformation of HT115 electro competent cells and induction of RNA synthesis using the T7, IPTG system.

Recombinant Vectors

One embodiment of the present invention includes a recombinant vector, which comprises at least one RNA molecule defined herein and is capable of delivering the RNA molecule into a host cell. Recombinant vectors include expression vectors. Recombinant vectors contain heterologous polynucleotide sequences, that is, polynucleotide sequences that are not naturally found adjacent to an RNA molecule defined herein, that preferably, are derived from a different species. The vector can be either RNA or DNA, and typically is a viral vector, derived from a virus, or a plasmid.

Various viral vectors can be used to deliver and mediate expression of an RNA molecule according to the present disclosure. The choice of viral vector will generally depend on various parameters, such as the cell or tissue targeted for delivery, transduction efficiency of the vector and pathogenicity. In an example, the viral vector integrates into host cellular chromatin (e.g. lentiviruses). In another example, the viral vector persists in the cell nucleus predominantly as an extrachromosomal episome (e.g. adenoviruses). Examples of these types of viral vectors include oncoretroviruses, lentiviruses, adeno-associated virus, adenoviruses, herpes viruses and retroviruses.

Plasmid vectors typically include additional nucleic acid sequences that provide for easy selection, amplification, and transformation of the expression cassette in prokaryotic cells, e.g., pUC-derived vectors, pGEM-derived vectors or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

"Operably linked" as used herein, refers to a functional relationship between two or more nucleic acid (e.g., DNA) segments. Typically, it refers to the functional relationship of a transcriptional regulatory element (promoter) to a transcribed sequence. For example, a promoter is operably linked to a coding sequence of an RNA molecule defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers need not be physically contiguous or located in close proximity to the coding sequences whose transcription they enhance.

When there are multiple promoters present, each promoter may independently be the same or different.

To facilitate identification of transformants, the recombinant vector desirably comprises a selectable or screenable marker gene. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic). A screenable marker gene (or reporter gene) confers a trait that one can identify through observation or testing, that is, by "screening" (e.g., β-glucuronidase, luciferase, GFP or other enzyme activity not present in untransformed cells). Exemplary selectable markers for selection of plant transformants include, but are not limited to, a hyg gene which encodes hygromycin B resistance; a neomycin phosphotransferase (nptII) gene conferring resistance to kanamycin, paromomycin; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from *Streptomyces viridochromogenes* conferring resistance to the selective agent phosphinothricin as for example, described in EP 275957; a gene encoding a 5-enolshikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Expression Vector

As used herein, an "expression vector" is a DNA vector that is capable of transforming a host cell and of effecting expression of an RNA molecule defined herein. Expression vectors of the present invention contain regulatory sequences such as transcription control sequences, translation control sequences, origins of replication, and other regulatory sequences that are compatible with the host cell and that control the expression of RNA molecule according to the present disclosure. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. The choice of the regulatory sequences used depends on the target organism such as a plant and/or target organ or tissue of interest. Such regulatory sequences may be obtained from any eukaryotic organism such as plants or plant viruses, or may be chemically synthesized.

Exemplary vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, a transcription termination site, and/or a polyadenylation signal.

Vectors of the invention can also be used to produce RNA molecules defined herein in a cell-free expression system, such systems are well known in the art.

In an example, a polynucleotide encoding an RNA molecule according to the present disclosure is operably linked to a promoter capable of directing expressing of the RNA molecule in a host cell. In an example, the promoter functions in vitro. In an example, the promoter is an RNA polymerase promoter. For example, the promoter can be an RNA polymerase III promoter. In another example, the promoter can be an RNA polymerase II promoter. However, the choice of promoter can depend on the target organism such as a plant, insect and/or target organ or tissue of interest. Exemplary mammalian promoters include CMV, EF1a, SV40, PGK1, Ubc, human beta actin, CAG, TRE, UAS, CaMKIIa, CAL1, 10, TEF1, GDS, ADH1, CaMV35S, Ubi, H1 and U6. Exemplary insect promoters include Ac5 and polyhedron. A number of constitutive promoters that are active in plant cells have also been described. Suitable promoters for constitutive expression in plants include, but are not limited to, the cauliflower mosaic virus (CaMV) 35S promoter, the Figwort mosaic virus (FMV) 35S, the light-inducible promoter from the small subunit (SSU) of the ribulose-1,5-bisphosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab IR gene from rice, the pyruvate, orthophosphate dikinase (PPDK) promoter from *Zea mays*, the promoter for the tobacco Lhcb1*2 gene, the *Arabidopsis thaliana* Suc2 sucrose-$H^{30}$ symporter promoter, and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention such as the promoters for LhcB gene and PsbP gene from white mustard (*Sinapis alba*).

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

As used herein, the term "plant storage organ specific promoter" refers to a promoter that preferentially, when compared to other plant tissues, directs gene transcription in a storage organ of a plant. For the purpose of expression in sink tissues of the plant such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In a particularly preferred embodiment, the promoter directs expression in tissues and organs in which lipid biosynthesis take place. Such promoters may act in seed development at a suitable time for modifying lipid composition in seeds. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutinin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a fruit specific promoter. Examples include, but are not limited to, the tomato polygalacturonase, E8 and Pds promoters, as well as the apple ACC oxidase promoter (for review, see Potenza et al., 2004). In a preferred embodiment, the promoter preferentially directs expression in the edible parts of the fruit, for example the pith of the fruit, relative to the skin of the fruit or the seeds within the fruit.

In an embodiment, the inducible promoter is the *Aspergillus nidulans* alc system. Examples of inducible expression systems which can be used instead of the *Aspergillus nidulans* alc system are described in a review by Padidam (2003) and Corrado and Karali (2009). In another embodiment, the inducible promoter is a safener inducible promoter such as, for example, the maize In2-1 or In2-2 promoter (Hershey and Stoner, 1991), the safener inducible promoter is the maize GST-27 promoter (Jepson et al., 1994), or the soybean GH2/4 promoter (Ulmasov et al., 1995).

In another embodiment, the inducible promoter is a senescence inducible promoter such as, for example, senescence-inducible promoter SAG (senescence associated gene) 12 and SAG 13 from *Arabidopsis* (Gan, 1995; Gan and Amasino, 1995) and LSC54 from *Brassica napus* (Buchanan-Wollaston, 1994). Such promoters show increased expression at about the onset of senescence of plant tissues, in particular the leaves.

For expression in vegetative tissue leaf-specific promoters, such as the ribulose biphosphate carboxylase (RBCS) promoters, can be used. For example, the tomato RBCS1, RBCS2 and RBCS3A genes are expressed in leaves and light grown seedlings (Meier et al., 1997). A ribulose bisphosphate carboxylase promoters expressed almost exclusively in mesophyll cells in leaf blades and leaf sheaths at high levels, described by Matsuoka et al. (1994), can be used. Another leaf-specific promoter is the light harvesting chlorophyll a/b binding protein gene promoter (see, Shiina et al., 1997). The *Arabidopsis thaliana* myb-related gene promoter (Atmyb5) described by Li et al. (1996), is leaf-specific. The Atmyb5 promoter is expressed in developing leaf trichomes, stipules, and epidermal cells on the margins of young rosette and cauline leaves, and in immature seeds. A leaf promoter identified in maize by Busk et al. (1997), can also be used.

In some instances, for example when LEC2 or BBM is recombinantly expressed, it may be desirable that the transgene is not expressed at high levels. An example of a promoter which can be used in such circumstances is a truncated napin A promoter which retains the seed-specific expression pattern but with a reduced expression level (Tan et al., 2011).

The 5' non-translated leader sequence can be derived from the promoter selected to express the heterologous gene sequence of an RNA molecule of the present disclosure, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the expression vector to the RNA molecule of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Transfer Nucleic Acids

Transfer nucleic acids can be used to deliver an exogenous polynucleotide to a cell and comprise one, preferably two, border sequences and one or more RNA molecules of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell or, for transient expression experiments, merely of expression in the cell.

As used herein, the term "extrachromosomal transfer nucleic acid" refers to a nucleic acid molecule that is capable of being transferred from a bacterium such as *Agrobacterium* sp., to a eukaryotic cell such as a plant leaf cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. An RNA molecule of interest is typically positioned between the left border-like sequence and the right border-like sequence of a transfer nucleic acid. The RNA molecule contained within the transfer nucleic acid may be operably linked to a variety of different promoter and terminator regulatory elements that facilitate its expression, that is, transcription and/or translation of the RNA molecule. Transfer DNAs (T-DNAs) from *Agrobacterium* sp. such as *Agrobacterium tumefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to a T-DNA of an *Agrobacterium tumefaciens* Ti plasmid or from an *Agrobacterium rhizogenes* Ri plasmid, or variants thereof which function for transfer of DNA into plant cells. The T-DNA may comprise an entire T-DNA including both right and left border sequences, but need only comprise the minimal sequences required in cis for transfer, that is, the right T-DNA border sequence. The T-DNAs of the invention have inserted into them, anywhere between the right and left border sequences (if present), the RNA molecule of interest. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art. As used herein, "P-DNA" refers to a transfer nucleic acid isolated from a plant genome, or man made variants/mutants thereof, and comprises at each end, or at only one end, a T-DNA border-like sequence.

As used herein, a "border" sequence of a transfer nucleic acid can be isolated from a selected organism such as a plant or bacterium, or be a man made variant/mutant thereof. The border sequence promotes and facilitates the transfer of the RNA molecule to which it is linked and may facilitate its integration in the recipient cell genome. In an embodiment, a border-sequence is between 10-80 bp in length. Border sequences from T-DNA from *Agrobacterium* sp. are well known in the art and include those described in Lacroix et al. (2008).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mesorhizobium loti.*

Direct transfer of eukaryotic expression plasmids from bacteria to eukaryotic hosts was first achieved several decades ago by the fusion of mammalian cells and protoplasts of plasmid-carrying *Escherichia coli* (Schaffner, 1980). Since then, the number of bacteria capable of delivering genes into mammalian cells has steadily increased (Weiss, 2003), being discovered by four groups independently (Sizemore et al. 1995; Courvalin et al., 1995; Powell et al., 1996; Darji et al., 1997).

As used herein, the terms "transfection", "transformation" and variations thereof are generally used interchangeably. "Transfected" or "transformed" cells may have been manipulated to introduce the RNA molecule(s) of interest, or may be progeny cells derived therefrom.

Recombinant Cells

The invention also provides a recombinant cell, for example, a recombinant bacterial cell, fungal cell, plant cell, insect cell or animal cell, which is a host cell transformed with one or more RNA molecules or vectors defined herein, or combination thereof. Suitable cells of the invention include any cell that can be transformed with an RNA molecule or recombinant vector according to the present disclosure. In an example, the transformed host cell is dead.

The recombinant cell may be a cell in culture, a cell in vitro, or in an organism such as for example, a plant, or in an organ such as, for example, a seed or a leaf. Preferably, the cell is in a plant, more preferably in the seed of a plant. In one embodiment, the recombinant cell is a non-human cell. Accordingly, in an example, the present disclosure relates to a non-human organism comprising one or more or all of an RNA molecule disclosed herein.

In one example, the cells are insect cells. In one example, the insect cells are derived from *Trichoplusia.*

Another example of a suitable host cell is an electro competent HT115 cell.

Host cells into which the RNA molecules(s) are introduced can be either untransformed cells or cells that are already transformed with at least one nucleic acid. Such nucleic acids may be related to lipid synthesis, or unrelated. Host cells of the present invention either can be endogenously (i.e., naturally) capable of expressing RNA molecule(s) defined herein, in which case the recombinant cell derived therefrom has an enhanced capability of producing the RNA molecule(s), or can be capable of producing said RNA molecule(s) only after being transformed with at least one RNA molecule defined herein. In an example, the cell is a cell which is capable of being used for producing lipid. In an embodiment, a recombinant cell of the invention has an enhanced capacity to produce non-polar lipid such as TAG.

Host cells of the present disclosure can be any cell capable of expressing at least one RNA molecule described herein, and include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia, Agrobacterium*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells.

In a preferred embodiment, the plant cell is a seed cell, in particular, a cell in a cotyledon or endosperm of a seed. In one embodiment, the cell is an animal cell. The animal cell may be of any type of animal such as, for example, a non-human animal cell, a non-human vertebrate cell, a non-human mammalian cell, or cells of aquatic animals such as fish or crustacea, invertebrates, insects, etc. Examples of algal cells useful as host cells of the present invention include, for example, *Chlamydomonas* sp. (for example, *Chlamydomonas reinhardtii*), *Dunaliella* sp., *Haematococcus* sp., *Chlorella* sp., *Thraustochytrium* sp., *Schizochytrium* sp., and *Volvox* sp.

Transgenic Plants

The invention also provides a plant comprising one or more exogenous RNA molecules defined herein, a cell of according to the present disclosure, a vector according to the present disclosure, or a combination thereof. The term "plant" when used as a noun refers to whole plants, whilst the term "part thereof" refers to plant organs (e.g., leaves, stems, roots, flowers, fruit), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the terms "in a plant" and "in the plant" in the context of a modification to the plant means that the modification has occurred in at least one part of the plant, including where the modification has occurred throughout the plant, and does not exclude where the modification occurs in only one or more but not all parts of the plant. For example, a tissue-specific promoter is said to be expressed "in a plant", even though it might be expressed only in certain parts of the plant. Analogously, "a transcription factor polypeptide that increases the expression of one or more glycolytic and/or fatty acid biosynthetic genes in the plant" means that the increased expression occurs in at least a part of the plant.

As used herein, the term "plant" is used in it broadest sense, including any organism in the Kingdom Plantae. It also includes red and brown algae as well as green algae. It includes, but is not limited to, any species of flowering plant, grass, crop or cereal (e.g., oilseed, maize, soybean), fodder or forage, fruit or vegetable plant, herb plant, woody plant or tree. It is not meant to limit a plant to any particular structure. It also refers to a unicellular plant (e.g., microalga). The term "part thereof" in reference to a plant refers to a plant cell and progeny of same, a plurality of plant cells, a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

Different amounts of 18:3 and 16:3 fatty acids are found within the glycolipids of different plant species. This is used to distinguish between 18:3 plants whose fatty acids with 3 double bonds are generally always $C_{18}$ atoms long and the 16:3 plants that contain both $C_{16}$- and $C_{18}$-fatty acids. In 18:3 chloroplasts, enzymic activities catalyzing the conversion of phosphatidate to diacylglycerol and of diacylglycerol to monogalactosyl diacylglycerol (MGD) are significantly less active than in 16:3 chloroplasts. In leaves of 18:3 plants, chloroplasts synthesize stearoyl-ACP2 in the stroma, introduce the first double bond into the saturated hydrocarbon chain, and then hydrolyze the thioester. Released oleate is exported across chloroplast envelopes into membranes of the eucaryotic part of the cell, probably the endoplasmic reticulum, where it is incorporated into PC. PC-linked oleoyl groups are desaturated in these membranes and subsequently move back into the chloroplast. The MGD-linked acyl groups are substrates for the introduction of the third double bond to yield MGD with two linolenoyl residues. This galactolipid is characteristic of 18:3 plants such as Asteraceae and Fabaceae, for example. In photosynthetically active cells of 16:3 plants which are represented, for example, by members of Apiaceae and Brassicaceae, two pathways operate in parallel to provide thylakoids with MGD. The cooperative 'eucaryotic' sequence is supplemented to various extents by a 'procaryotic' pathway. Its reactions are confined to the chloroplast and result in a typical arrangement of acyl groups as well as their complete desaturation once they are esterified to MGD. Procaryotic DAG backbones carry C16:0 and its desaturation products at C-2 from which position C18: fatty acids are excluded. The C-1 position is occupied by C18 fatty acids and to a small extent by C16 groups. The similarity in DAG backbones of lipids from blue-green algae with those synthesized by the chloroplast-confirmed pathway in 16:3 plants suggests a phylogenetic relation and justifies the term procaryotic.

As used herein, the term "vegetative tissue" or "vegetative plant part" is any plant tissue, organ or part other than organs for sexual reproduction of plants. The organs for sexual reproduction of plants are specifically seed bearing organs, flowers, pollen, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem.

A "transgenic plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof. Transgenic plant parts has a corresponding meaning.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18%. In a preferred embodiment, the moisture content of the grain is at a level which is generally regarded as safe for storage, preferably between 5% and 15%, between 6% and 8%, between 8% and 10%, or between 10% and 15%. "Developing seed" as used herein refers to a seed prior to maturity, typically found in the reproductive structures of the plant after fertilisation or anthesis, but can also refer to such seeds prior to maturity which are isolated from a plant. Mature seed commonly has a moisture content of less than about 12%.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

As used herein, the term "phenotypically normal" refers to a genetically modified plant or part thereof, for example a transgenic plant, or a storage organ such as a seed, tuber or fruit of the invention not having a significantly reduced ability to grow and reproduce when compared to an unmodified plant or part thereof. Preferably, the biomass, growth rate, germination rate, storage organ size, seed size and/or the number of viable seeds produced is not less than 90% of that of a plant lacking said recombinant polynucleotide when grown under identical conditions. This term does not encompass features of the plant which may be different to the wild-type plant but which do not affect the usefulness of the plant for commercial purposes such as, for example, a ballerina phenotype of seedling leaves. In an embodiment, the genetically modified plant or part thereof which is phenotypically normal comprises a recombinant polynucleotide encoding a silencing suppressor operably linked to a plant storage organ specific promoter and has an ability to grow or reproduce which is essentially the same as a corresponding plant or part thereof not comprising said polynucleotide.

Plants provided by or contemplated for use in the practice of the present invention include both monocotyledons and dicotyledons. In preferred embodiments, the plants of the present invention are crop plants (for example, cereals and pulses, maize, wheat, potatoes, rice, sorghum, millet, cassava, barley) or legumes such as soybean, beans or peas. The plants may be grown for production of edible roots, tubers, leaves, stems, flowers or fruit. The plants may be vegetable plants whose vegetative parts are used as food. The plants of the invention may be: *Acrocomia aculeata* (macauba palm), *Arabidopsis thaliana, Aracinis hypogaea* (peanut), *Astrocaryum murumuru* (murumuru), *Astrocaryum vulgare* (tucumã), *Attalea geraensis* (Indaiá-rateiro), *Attalea humilis* (American oil palm), *Attalea oleifera* (andaiá), *Attalea phalerata* (uricuri), *Attalea speciosa* (babassu), *Avena sativa* (oats), *Beta vulgaris* (sugar beet), *Brassica* sp. such as *Brassica carinata, Brassica juncea, Brassica napobrassica, Brassica napus* (canola), *Camelina sativa* (false flax), *Cannabis sativa* (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis, Lemna disperma, Lemna ecuadoriensis, Lemna gibba* (swollen duckweed), *Lemna japonica, Lemna minor, Lemna minuta, Lemna obscura, Lemna paucicostata, Lemna perpusilla, Lemna tenera, Lemna trisulca, Lemna turionifera, Lemna valdiviana, Lemna yungensis, Licania rigida* (oiticica), *Linum usitatissimum* (flax), *Lupinus* angustifolius (lupin), *Mauritia flexuosa* (buriti palm), *Maximiliana maripa* (inaja palm), *Miscanthus* sp. such as *Miscanthus×giganteus* and *Miscanthus sinensis, Nicotiana* sp. (tabacco) such as *Nicotiana tabacum* or *Nicotiana benthamiana, Oenocarpus bacaba* (bacaba-do-azeite), *Oenocarpus bataua* (patauã), *Oenocarpus distichus* (bacaba-de-leque), *Oryza* sp. (rice) such as *Oryza sativa* and *Oryza glaberrima, Panicum virgatum* (switchgrass), *Paraqueiba paraensis* (mari), *Persea amencana* (avocado), *Pongamia pinnata* (Indian beech), *Populus trichocarpa, Ricinus communis* (castor), *Saccharum* sp. (sugarcane), *Sesamum indicum* (sesame), *Solanum tuberosum* (potato), *Sorghum* sp. such as *Sorghum bicolor, Sorghum vulgare, Theobroma grandiforum* (cupuassu), *Trifolium* sp., *Trithrinax brasiliensis* (Brazilian needle palm), *Triticum* sp. (wheat) such as *Triticum aestivum, Zea mays* (corn), alfalfa (*Medicago sativa*), rye (*Secale cerale*), sweet potato (*Lopmoea batatus*), cassava (*Manihot esculenta*), coffee (*Coffea* spp.), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), *papaya* (*Carica papaya*), cashew (*Anacardium occidentale*), macadamia (*Macadamia intergrifolia*) and almond (*Prunus amygdalus*). For example, plants of the disclosure may be *Nicotiana benthamiana.*

Other preferred plants include C4 grasses such as, in addition to those mentioned above, *Andropogon gerardi, Bouteloua curtipendula, B. gracilis, Buchloe dactyloides, Schizachyrium scoparium, Sorghastrum nutans, Sporobolus cryptandrus; C*3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa*. Other preferred plants include C3 grasses.

In a preferred embodiment, the plant is an angiosperm.

In an embodiment, the plant is an oilseed plant, preferably an oilseed crop plant. As used herein, an "oilseed plant" is a plant species used for the commercial production of lipid from the seeds of the plant. The oilseed plant may be, for example, oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, *Jatropha curcas* or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Transformation

RNA molecules disclosed herein may be stably introduced to above referenced host cells and/or non-human organisms such as plants. For the avoidance of doubt, an example of the present disclosure encompasses an above referenced plant stably transformed with an RNA molecule disclosed herein. As used herein, the terms "stably transforming", "stably transformed" and variations thereof refer to the integration of the RNA molecule or a nucleic acid encoding the same into the genome of the cell such that they are transferred to progeny cells during cell division without the need for positively selecting for their presence. Stable transformants, or progeny thereof, can be identified by any means known in the art such as Southern blots on chromosomal DNA, or in situ hybridization of genomic DNA, enabling their selection.

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

In an embodiment, plants may be transformed by topically applying an RNA molecule according to the present disclosure to the plant or a part thereof. For example, the RNA molecule may be provided as a formulation with a suitable carrier and sprayed, dusted or otherwise applied to the surface of a plant or part thereof. Accordingly, in an example, the methods of the present disclosure encompass introducing an RNA molecule disclosed herein to a plant, the method comprising topically applying a composition comprising the RNA molecule to the plant or a part thereof.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. For example, floral-dip (in planta) methods may be used. The use of *Agrobacterium*-mediated plant integrating vectors to introduce DNA into plant cells is well known in the art. The region of DNA to be transferred is defined by the border sequences, and the intervening DNA (T-DNA) is usually inserted into the plant genome. It is the method of choice because of the facile and defined nature of the gene transfer.

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells, for example of immature embryos, by a propelling force. Exemplary particles include those comprised of tungsten, gold, platinum, and the like.

In another method, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265). Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Northern blot hybridisation, Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics. Preferably, the vegetative plant parts are harvested at a time when the yield of non-polar lipids are at their highest. In one embodiment, the vegetative plant parts are harvested about at the time of flowering, or after flowering has initiated. Preferably, the plant parts are harvested at about the time senescence begins, usually indicated by yellowing and drying of leaves.

Transgenic plants formed using *Agrobacterium* or other transformation methods typically contain a single genetic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analysing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Similarly, a transgenic plant can be crossed with a second plant comprising a genetic modification such as a mutant gene and progeny containing both of the transgene and the genetic modification identified. Descriptions of other breeding methods that are commonly used for different traits and crops can be found in Fehr, In: Breeding Methods for Cultivar Development, Wilcox J. ed., American Society of Agronomy, Madison Wis. (1987).

Formulations

RNA molecules according to the present disclosure can be provided as various formulations. For example, RNA molecules may be in the form of a solid, ointment, gel, cream, powder, paste, suspension, colloid, foam or aerosol. Solid forms may include dusts, powders, granules, pellets, pills, pastilles, tablets, filled films (including seed coatings) and the like, which may be water-dispersible ("wettable"). In one example, the composition is in the form of a concentrate.

In an example, RNA molecules may be provided as a topical formulation. In an example, the formulation stabilises the RNA molecule in formulation and/or in-vivo. For example, RNA molecules may be provided in a lipid formulation. For example, RNA molecules may be provided in liposomes. In an example, the formulation comprises a transfection promoting agent.

The term "transfection promoting agent" as used herein refers to a composition added to the RNA molecule for enhancing the uptake into a cell including, but not limited to, a plant cell, an insect cell or a fungal cell. Any transfection promoting agent known in the art to be suitable for transfecting cells may be used. Examples include cationic lipid such as one or more of DOTMA (N-[1-(2.3-dioleoyloxy)-propyl]-N,N,N-trimethyl ammonium chloride), DOTAP (1,2-bis(oleoyloxy)-3-3-(trimethylammonium) propane), DMRIE (1,2-dimyristyloxypropyl-3-dimethyl-hydroxy ethyl ammonium bromide), DDAB (dimethyl dioctadecyl ammonium bromide). lipospermines, specifically DOSPA (2,3-dioleyloxy-N-[2 (sperminecarboxamido)ethyl]-N,N-dimethyl-1-propanamin-ium trifluoro-acetate) and DOSPER (1,3-dioleoyloxy-2-(6carboxy spermyl)-propyl-amid, and the di- and tetra-alkyl-tetra-methyl spermines, including but not limited to TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldioleyl spermine). Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. Non-limiting examples of suitable commercially available transfection reagents include Lipofectamine (Life Technologies) and Lipofectamine 2000 (Life Technologies).

In an example, RNA molecules can be incorporated into formulations suitable for application to a field. In an example, the field comprises plants. Suitable plants include crop plants (for example, cereals and pulses, maize, wheat, potatoes, tapioca, rice, sorghum, soybean millet, cassava, barley, or pea), or legumes. The plants may be grown for production of edible roots, tubers, leaves, stems, flowers or fruit. In an example, the crop plant is a cereal plant. Examples of cereal plants include, but are not limited to, wheat, barley, sorghum oats, and rye. In these examples, the RNA molecule may be formulated for administration to the plant, or to any part of the plant, in any suitable way. For example, the composition may be formulated for administration to the leaves, stem, roots, fruit vegetables, grains and/or pulses of the plant. In one example, the RNA molecule is formulated for administration to the leaves of the plant, and is sprayable onto the leaves of the plant.

Depending on the desired formulation, RNA molecules described herein may be formulated with a variety of other agents. Exemplary agents comprise one or more of suspension agents, agglomeration agents, bases, buffers, bittering agents, fragrances, preservatives, propellants, thixotropic agents, anti-freezing agents, and colouring agents.

In other examples, RNA molecule formulations can comprise an insecticide, a pesticide, a fungicide, an antibiotic, an insect repellent, an anti-parasitic agent, an anti-viral agent, or a nematicide.

In another example, RNA molecules can be incorporated into pharmaceutical compositions. Such compositions would typically include an RNA molecule described herein and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, inhalation, transdermal (topical), transmucosal, oral and rectal administration.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. For example, liposomal suspensions can also be used as pharmaceutically acceptable carriers. These can be prepared according to methods known to those skilled in the art, for example, as described in U.S. Pat. No. 4,522,811.

RNA molecules according to the present disclosure can be provided in a kit or pack. For example, RNA molecules disclosed herein may be packaged in a suitable container with written instructions for producing an above referenced cell or organism or treating a condition.

Methods of Controlling Non-Human Organisms

In an example, the RNA molecules according to the present disclosure can be used to control non-human organisms such as insects. Such uses involve administering RNA molecules according to the present disclosure using various methods. In an example, RNA molecules according to the present disclosure can be provided as an insect bait for ingestion by insects. In another example, RNA molecules can be sprayed onto insects as required. In another example, RNA molecules can be sprayed onto a plant or crop to protect said plant or crop from insects. Exemplary crops include cotton, maize, tomato, chickpea, pigeon pea, alfalfa, rice, sorghum and cowpea.

In an example, RNA molecules can be provided to modify insect behaviour. In another example, RNA molecules can be provided to kill insects. In another example, RNA molecules can be provided to reduce insect fertility. Exemplary insect targets include household insects. Other exemplary insect targets include sap sucking insects such as aphids (e.g. *Myzus persicae, Metopolophium dirhodum, Rhopalosiphum padi, Aphis glycines, Aphis fabae*). Further exemplary insect targets include, arachnids, mosquitoes, ecto-parasites, flies, spider mites, thrips, ticks, red poultry mite, ants, cockroaches, termites, crickets including house-crickets, silverfish, booklice, beetles, earwigs, mosquitos and fleas. Other exemplary insect targets include agricultural pests. Examples include sap feeders such as stink bugs and aphids, chewing insects such as caterpillars, beetles, worms, rasping insects such as thrips and slugs, moths, fly's such as fruit fly, grain pests such as grain borer, weevils, and grain moths.

In an embodiment the insect is a sap sucking insect. In this example, the RNA molecule can have antisense activity for MpC002 and/or MpRack-1. In an embodiment the sap sucking insect is an aphid. In another embodiment, the aphid is *Myzus persicae.*

In an embodiment the insect target is an ant (e.g. *Linepithema humile*), cotton bollworm or corn ear worm (*Helicoverpa armigera*) or blowfly (e.g. *Lucilia cuprina*). In an embodiment the target insect is *Helicoverpa armigera* and the RNA molecule has antisense activity for the ABC transporter white gene (ABC white). In another embodiment the target insect is *Linepithema humile* and the RNA molecule has antisense activity for pheromone biosynthesis activating neuropeptide (PBAN). In another embodiment the target insect is *Lucilia cuprina* and the RNA molecule has antisense activity for one or more genes encoding proteins selected from the group consisting of V-type proton ATPase catalytic subunit A, RNAse 1/2, chitin synthase, ecdysone receptor and gamma-tubulin 1/1-like.

In the above embodiment, compositions and RNA molecules disclosed herein may be provided in a dispenser. In an example, the dispenser is a trap or a lure. In an embodiment, the trap and/or lure comprises a bait comprising an RNA molecule(s) disclosed herein.

In an embodiment, the present disclosure encompasses methods of controlling insect behaviour, the method comprising spraying, dusting or otherwise applying RNA molecules disclosed herein to the insects. In this embodiment, RNA molecules can be sprayed, dusted or otherwise applied directly to the insects. In another embodiment, RNA molecules can be sprayed, dusted or otherwise applied to plants or crops prior to insect infestation.

In one embodiment of the invention, the insect or arachnid may belong to the following orders: Acari, Arachnida, Anoplura, Blattodea, Coleoptera, Collembola, Dermaptera, Dictyoptera, Diplura, Diptera, Embioptera, Ephemeroptera, Grylloblatodea, Hem iptera, Heteroptera, Homoptera, Hymenoptera, Isoptera, Lepidoptera, Mallophaga, Mecoptera, Neuroptera, Odonata, Orthoptera, Phasmida, Phithiraptera, Plecoptera, Protura, Psocoptera, Siphonaptera, Siphunculata, Thysanura, Sternorrhyncha, Strepsiptera, Thysanoptera, Trichoptera, Zoraptera and Zygentoma.

In preferred, but non-limiting, embodiments of the invention the insect or arachnid is chosen from the group consisting of: (1) Acari: mites including Ixodida (ticks) (2) Arachnida: Araneae (spiders) and Opiliones (harvestman), examples include: *Latrodectus mactans* (black widow) and *Loxosceles recluse* (Brown Recluse Spider) (3) Anoplura: lice, such as *Pediculus humanus* (human body louse) (4) Blattodea: cockroaches including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). A most preferred target is German cockroach (*Blatella germanica*). (5) Coleoptera: beetles, examples include: the family of Powderpost beetle (family of Bostrichoidea); *Dendroctonus* spp. (Black Turpentine Beetle, Southern Pine Beetle, IPS Engraver Beetle); Carpet Beetles (*Anthrenus* spp, *Attagenus* spp); Old House Borer (family of Cerambycidae: *Hylotrupes bajulus*); *Anobium punctatum; Tribolium* spp (flour beetle); *Trogoderma granarium* (Khapra Beetle); *Oryzaephilus sarinamensis* (Toothed Grain Beetle) etc. (Bookworm) (6) Dermaptera: family of earwigs (7) Diptera: mosquitoes (Culicidae) and flies (Brachycera), examples are: Anophelinae such as *Anopheles* spp, and Culicinae such as *Aedes fulvus*; Tabanidae such as *Tabanus punctifer* (Horse Fly), *Glossina morsitans morsitans* (tsetse fly), drain flies (Psychodidae) and Calyptratae such as *Musca domestica* (House fly), flesh flies (family of Sarcophagidae) etc. (8) Heteroptera: bugs, such as *Cimex lectularius* (bed bug) (9) Hymenoptera: wasps (Apocrita), including ants (Formicoidea), bees (Apoidea): *Solenopsis invicta* (Red Fire Ant), *Monomorium*

*pharaonis* (Pharaoh Ant), *Camponotus* spp (Carpenter Ants), *Iasius niger* (Small Black Ant), *Tetramorium caespitum* (Pavement Ant), *Myrmica rubra* (Red Ant), *Formica* spp (wood ants), *Crematogaster lineolata* (Acrobat Ant), *Iridomyrmex humilis* (Argentine Ant), *Pheidole* spp. (Big Headed Ants, *Dasymutilla occidentalis* (Velvet Ant) etc. (10) Isoptera: termites, examples include: *Amitermes floridensis* (Florida dark-winged subterranean termite), the eastern subterranean termite (*Reticulitermes flavipes*), the *R. hesperus* (Western Subterranean Termite), *Coptotermes formosanus* (Formosan Subterranean Termite), *Incisitermes minor* (Western Drywood Termite), *Neotermes connexus* (Forest Tree Termite) and Termitidae (11) Lepidoptera: moths, examples include: Tineidae & Oecophoridae such as *Tineola bisselliella* (Common Clothes Moth), and Pyralidae such as *Pyralis farinalis* (Meal Moth) etc (12) Psocoptera: booklice (Psocids) (13) Siphonaptera: fleas such as *Pulex irritans* (14) Sternorrhyncha: aphids (Aphididae) (15) Zygentoma: silverfish, examples are: *Thermobia domestica* and *Lepisma saccharina*

Other target insects or arachnids include household insects, ecto-parasites and insects and/or arachnids relevant for public health and hygiene such as, by way of example and not limitation, flies, spider mites, thrips, ticks, red poultry mite, ants (such as by targeting PBAN), cockroaches, termites, crickets including house-crickets, silverfish, booklice, beetles, earwigs, mosquitos and fleas. More preferred targets are cockroaches (Blattodea) such as but not limited to *Blatella* spp. (e.g. *Blatella germanica* (german cockroach)), *Periplaneta* spp. (e.g. *Periplaneta americana* (American cockroach) and *Periplaneta australiasiae* (Australian cockroach)), *Blatta* spp. (e.g. *Blatta orientalis* (Oriental cockroach)) and *Supella* spp. (e.g. *Supella longipalpa* (brown-banded cockroach); ants (Formicoidea), such as but not limited to *Solenopsis* spp. (e.g. *Solenopsis invicta* (Red Fire Ant)), *Monomorium* spp. (e.g. *Monomorium pharaonis* (Pharaoh Ant)), *Camponotus* spp. (e.g. *Camponotus* spp (Carpenter Ants)), *Lasius* spp. (e.g. *Lasius niger* (Small Black Ant)), *Tetramorium* spp. (e.g. *Tetramorium caespitum* (Pavement Ant)), *Myrmica* spp. (e.g. *Myrmica rubra* (Red Ant)), *Formica* spp (wood ants), *Crematogaster* spp. (e.g. *Crematogaster lineolata* (Acrobat Ant)), *Iridomyrmex* spp. (e.g. *Iridomyrmex humilis* (Argentine Ant)), *Pheidole* spp. (Big Headed Ants), and *Dasymutilla* spp. (e.g. *Dasymutilla occidentalis* (Velvet Ant)); termites (Isoptera and/or Termitidae) such as but not limited to *Amitermes* spp. (e.g. *Amitermes floridensis* (Florida dark-winged subterranean termite)), *Reticulitermes* spp. (e.g. *Reticulitermes flavipes* (the eastern subterranean termite), *Reticulitermes hesperus* (Western Subterranean Termite)), *Coptotermes* spp. (e.g. *Coptotermes formosanus* (Formosan Subterranean Termite)), *Incisitermes* spp. (e.g. *Incisitermes minor* (Western Drywood Termite)), *Neotermes* spp. (e.g. *Neotermes* connexus (Forest Tree Termite)).

In an embodiment, the target RNA encodes an insect acetolactate synthase.

The RNA molecules of the invention when delivered and/or expressed in a plant can have a wide range of desired properties which influence, for example, an agronomic trait, insect resistance (such as by targeting genes such as MpC002, MpRack-1 and an ABC transporter gene), disease resistance (such as by targeting genes such as LanR or MLO), herbicide resistance, sterility, grain characteristics, and the like. The target RNA molecule may be involved in metabolism of oil, starch, carbohydrates, nutrients, etc., or may be responsible for the synthesis of proteins, peptides, fatty acids, lipids, recombination frequency (by targeting genes such as DDM1 and FANCM), waxes, oils (by targeting genes such as TOR), starches, sugars, carbohydrates, flavors, odors, toxins, carotenoids, hormones (by targeting genes such as EIN2, NCED1 and NCED2), polymers, flavonoids (by targeting a gene such as chalcone synthase), storage proteins, phenolic acids, alkaloids, lignins, tannins, celluloses, glycoproteins, glycolipids, etc.

In a particular example, the plants produce increased levels of enzymes for oil production in plants such as Brassicas, for example oilseed rape or sunflower, safflower, flax, cotton, soybean or maize; enzymes involved in starch synthesis in plants such as potato, maize, and cereals such as wheat barley or rice; enzymes which synthesize, or proteins which are themselves, natural medicaments, such as pharmaceuticals or veterinary products.

In another embodiment, an RNA molecule of the present invention is directed to the prophylactic or therapeutic treatment of infection by a fungal pathogen selected from the group consisting of: *Alternaria* spp.; *Armillaria mellae; Arthrobotrys oligosporus; Blumeria graminis* (by targeting Mlo genes using an RNA molecule as described in Example 17), *Boletus granulatus; Botritis cinerea; Botrytis fabae; Candida albicans; Claviceps purpurea; Cronartium ribicola; Epicoccum purpurescens; Epidermophyton floccosum; Fomes annosus; Fusarium oxysporum; Gaeumannomyces graminis* var. *tritici; Glomerella cingulata; Gymnosporangium juniperi-virginianae; Microsporum canis; Monilinia fructicola; Physoderma alfalfae; Phytopthera infestans; Pityrosporum orbiculare* (*Malassezia furfur*); *Polyporus sulphureus; Puccinia* spp.; *Saccharomyces cerevisiae; Septoria apiicola; Trichophyton rubrum; T. mentagrophytes; Ustilago* spp.; *Venturia inaequalis*; and *Verticillium dahliae*.

Exemplary Conditions to be Treated

RNA molecules according to the present disclosure may be used in methods of various conditions. In some examples, the present disclosure relates to a method of treating cancer comprising administering an RNA molecule disclosed herein. The term "cancer" refers to or describes the physiological condition in mammals that is typically characterized by unregulated cell growth/proliferation. Examples of cancer include but are not limited to, carcinoma, lymphoma, blastoma, sarcoma, and leukemia or lymphoid malignancies. More particular examples of such cancers include, but are not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. Accordingly, in an example, the present disclosure relates to a method of treating breast, ovarian, colon, prostate, lung, brain, skin, liver, stomach, pancreatic or blood based cancer.

In other examples, a method described herein is used to treat cancers that are linked to mutations in BRCA1, BRCA2, PALB2, OR RAD51B, RAD51C, RAD51D or related genes. In other examples, a method described herein is used to treat cancers that are linked to mutations in genes associated with DNA mismatch repair, such as MSH2, MLH1, PMS2, and related genes. In other examples, a method described herein is used to treat cancers with silenced DNA repair genes, such as BRCA1, MLH1, OR RAD51B, RAD51C, OR RAD51D.

In other examples of the disclosure, a method described herein is used to kill cells with impaired DNA repair processes. For example, cells with impaired DNA repair may aberrantly express a gene involved in DNA repair, DNA synthesis, or homologous recombination. Exemplary genes include XRCC1, ADPRT (PARP-1), ADPRTL2, (PARP-2), POLYMERASE BETA, CTPS, MLH1, MSH2, FANCD2, PMS2, p53, p21, PTEN, RPA, RPA1, RPA2, RPA3, XPD, ERCC1, XPF, MMS19, RAD51, RAD51B, RAD51C, RAD51D, DMC1, XRCCR, XRCC3, BRCA1, BRCA2, PALB2, RAD52, RAD54, RAD50, MREU, NB51, WRN, BLM, KU70, KU80, ATM, ATR CPIK1, CHK2, FANCA, FANCB, FANCC, FANCD1, FANCD2, FANCE, FANCF, FANCG, FANCC, FANCD1, FANCD2, FANCE, FANCF, FANCG, RAD1, and RAD9. In an example, a method described herein is used to kill cells with a mutant tumour suppressor gene. For example, cells can have one or more mutations in BRCA1 or BRCA2.

In other examples of the disclosure, a method described herein is used to treat virally transformed cells. In other examples of the disclosure, a method described herein is used to kill cells transformed with a latent virus. Exemplary latent viruses include CMV, EBV, Herpes simplex virus (type 1 and 2), and Varicella zoster virus. In other examples of the disclosure, a method described herein is used to treat active viral infections due to viruses that give rise to cancer, immunodeficiency, hepatitis, encephalitis, pneumonitis or respiratory illness. Exemplary viruses include parvovirus, poxvirus, herpes virus.

In other examples of the disclosure, a method described herein is used to treat Zika Virus, Colorado Tick Fever (caused by Coltivirus, RNA virus), West Nile Fever (encephalitis, caused by a flavivirus that primarily occurs in the Middle East and Africa), Yellow Fever, Rabies (caused by a number of different strains of neurotropic viruses of the family Rhabdoviridae), viral hepatitis, gastroenteritis (viral)-acute viral gastroenteritis caused by Norwalk and Norwalk-like viruses, rotaviruses, caliciviruses, and astroviruses, poliomyelitis, influenza (flu), caused by orthomyxoviruses that can undergo frequent antigenic variation, measles (rubeola), paramyxoviridae, mumps, respiratory syndromes including viral pneumonia and acute respiratory syndromes including croup caused by a variety of viruses collectively referred to as acute respiratory viruses, and respiratory illness caused by the respiratory syncytial virus.

EXAMPLES

Example 1. Materials and Methods

Synthesis of Genetic Constructs

To design a typical ledRNA construct, a region of the target RNA of about 100-1000 nucleotides in length, typically 400-600 nucleotides, was identified. In one example, the 5' half of the sequence and approximately 130 nt of the flanking region and similarly the 3' half and 130 nt of flanking region were orientated in an antisense orientation relative to a promoter. These sequences were interrupted with the 400-600 nucleotide sense target sequence (FIG. 1A). The 5' end of the resultant construct was preceded with a promoter such as a T7 or SP6 RNA polymerase promoter and the 3' end engineered to include a restriction enzyme cleavage site to allow for termination of transcription in vitro.

For transcription in cells such as bacterial cells, promoter and terminator sequences were incorporated to facilitate expression as a transgene, for example using an inducible promoter. The double-stranded region and loop sequence lengths can be varied. The constructs were made using standard cloning methods or ordered from commercial service providers.

Synthesis of RNA

Following digestion with restriction enzyme to linearize the DNA at the 3' end, transcription using RNA polymerase resulted in the 5' and 3' arms of the ledRNAi transcript annealing to the central target sequence, the molecule comprising a central stem or double-stranded region with a single nick and terminal loops. The central sequence can be orientated in sense or antisense orientation relative to the promoter (FIG. 1A, 1B respectively).

For in vitro synthesis, DNA of the construct was digested at the 3' restriction site using the appropriate restriction enzyme, precipitated, purified and quantified. RNA synthesis was achieved using RNA polymerase according to the manufacturer's instructions. The ledRNA was resuspended in annealing buffer (25 mM Tris-HCL, pH 8.0, 10 mM $MgCl_2$) using DEPC-treated water to inactivate any traces of RNAse. The yield and integrity of the RNA produced by this method was determined by nano-drop analysis and gel electrophoresis (FIG. 2), respectively.

Synthesis of ledRNA was achieved in bacterial cells by introducing the constructs into *E. coli* strain HT115. Transformed cell cultures were induced with IPTG (0.4 mM) to express the T7 RNA polymerase, providing for transcription of the ledRNA constructs. RNA extraction from the bacterial cells and purification was performed essentially as described in Timmons et al. (2001).

For RNA transcription with Cy3 labelling, the ribonucleotide (rNTP) mix contained 10 mM each of ATP, GTP, CTP, 1.625 mM UTP and 8.74 mM Cy3-UTP. The transcription reactions were incubated at 37° C. for 2.5 hr. The transcription reactions (160 μl) were the transferred to Eppendorf tubes, 17.7 μl turbo DNase buffer and 1 μl turbo DNA added, and incubated at 37° C. for 10 minutes to digest the DNA. Then, 17.7 μl Turbo DNAse inactivation solution was added, mixed and incubated at room temperature for 5 min. The mixture was centrifuged for 2 min and the supernatant transferred to a new RNAse free Eppendorf tube. Samples of 1.5 μl of each transcription reaction were electrophoresed on gels to test the quality of the RNA product. Generally, one RNA band was observed of 500 bp to 1000 bp in size depending on the construct. The RNA was precipitated by adding to each tube: 88.5 μl 7.5M Ammonium acetate and 665 μl cold 100% ethanol. The tubes were cooled to −20° C. for several hours or overnight, then centrifuged at 4° C. for 30 min. The supernatant was removed carefully and the pellet of RNA washed with 1 ml 70% ethanol (made with nuclease free water) at −20° C. and centrifuged. The pellet was dried and the purified RNA resuspended in 50 μl 1×RNAi annealing buffer. The RNA concentration was measured using nanodrop method and stored at −80° C. until used.

Example 2. Design of ledRNA

As shown schematically in FIG. 1A, a typical ledRNA molecule comprises a sense sequence which can be considered to be two adjacent sense sequences, covalently linked and having identity to the target RNA, an antisense sequence which is complementary to the sense sequence and which is divided into two regions, and two loops that separate the sense from the antisense sequences. A DNA construct which encodes this form of ledRNA therefore comprises, in 5' to 3' order, a promoter for transcription of the ledRNA coding region, a first antisense region having complementarity with a region towards the 5' end of the target RNA, a first loop sequence, the sense sequence, a second loop sequence, then the second antisense region having complementarity with a region towards the 3' end of the target RNA, and finally a means to terminate transcription. In this arrangement, the two antisense sequences flanked the sense sequence and loop sequences. When transcribed, the two regions of antisense sequence anneal with the sense sequence, forming a dsRNA stem with two flanking loops.

In another but related form of ledRNA, the sense sequence is split into two regions whilst the two antisense regions remain as a single sequence (FIG. 1B). A DNA construct which encodes this second form of ledRNA therefore comprises, in 5' to 3' order, a promoter for transcription of the ledRNA coding region, a first sense region having identity with a region towards the 3' end of the target RNA, a first loop sequence, the antisense sequence, a second loop sequence, then the second sense region having identity towards the 5' end of the target RNA, and finally a means to terminate transcription. In this arrangement, the two sense sequences flanked the antisense sequence and loop sequences.

Without wishing to be limited by theory, because of the closed loops at each end, these ledRNA structures would be more resistant to exonucleases than an open-ended dsRNA formed between single-stranded sense and antisense RNAs and not having loops, and also compared to a hairpin RNA having only a single loop. In addition, the inventors conceived that a loop at both ends of the dsRNA stem would allow Dicer to access both ends efficiently, thereby enhancing processing of the dsRNA into sRNAs and silencing efficiency.

As a first example, a genetic construct was made for in vitro transcription using T7 or SP6 RNA polymerase to form ledRNAs targeting genes encoding GFP or GUS. The ledGFP construct comprised the following regions in order: the first half of antisense sequence corresponded to nucleotides 358 to 131 of the GFP coding sequence (CDS) (SEQ ID NO:7), the first antisense loop corresponded to nucleotides 130 to 1 of GFP CDS, the sense sequence corresponded of nucleotides 131 to 591 of GFP CDS, the second antisense loop corresponding to nucleotides 731 to 592 of GFP CDS, and the second half of the antisense sequence corresponded to nucleotides 591 to 359 of the GFP CDS.

The ledGUS construct comprised the following regions in order: the first half of antisense sequence corresponded to nucleotides 609 to 357 of GUS CDS (SEQ ID NO: 8); the first antisense loop corresponded to nucleotides 356 to 197 of GUS CDS, the sense sequence corresponded to nucleotides 357 to 860 of GUS CDS, the second antisense loop corresponding to nucleotides 1029 to 861 of GUS CDS; and the second half of antisense sequence corresponded to nucleotides 861 to 610 of GUS CDS.

For making the separate strand sense/antisense GUS dsRNA (conventional dsRNA), the same target sequence corresponding to nucleotides 357 to 860 of GUS CDS was ligated between the T7 and SP6 promoters in pGEM-T Easy vector. The sense and antisense strands were transcribed separately with T7 or SP6 polymerases, respectively, and annealed in annealing buffer after mixing the transcripts and heating the mixture to denature the RNA strands.

Example 3. Stability of ledRNAs

The ability of ledRNA to form dsRNA structures was compared with open-ended dsRNA (i.e no loops, formed by annealing of separate single-stranded sense and antisense RNA) and long hpRNA. ledRNA, long hpRNA, and the mixture of sense and antisense RNA, were denatured by boiling and allowed to anneal in annealing buffer (250 mM Tris-HCL, pH 8.0 and 100 mM $MgCl_2$), and then subjected to electrophoresis in a 1.0% agarose gel under non-denaturing conditions.

As shown in FIG. 2, both the GUS ledRNA and the GFP ledRNA gave a dominant RNA band of the mobility expected for a double-stranded molecule, indicating the formation of the predicted ledRNA structure. This was in contrast to the mixture of sense and antisense RNA, which showed only a weak band for a dsRNA, indicating that most of the sense and antisense RNAs were not readily annealed to each other to form dsRNA. The hairpin RNA samples gave two prominent bands, indicating that only part of the transcript formed the predicted hairpin RNA structure. Thus, ledRNA was the most efficient in forming the predicted dsRNA structure.

The ability of ledRNA to stay and spread on leaf surface was also compared with dsRNA. The GUS ledRNA (ledGUS), when applied to the lower part of tobacco leaf surface, could be readily detected in the untreated upper part of the leaf after 24 hrs (FIG. 3). However, the separate strand GUS dsRNA (dsGUS) could not be detected in the untreated upper part of the leaf (FIG. 3). This result indicates that the ledRNA is more resistant to degradation than dsRNA and therefore able to spread inside plant leaf tissues.

Example 4. Testing of ledRNAs by Topical Delivery

The ability of the ledRNAs to induce RNAi after topical delivery was tested in *Nicotiana benthamiana* and *Nicotiana tabacum* plants expressing a GFP or GUS reporter gene, respectively. The sequences of the GFP and GUS target sequences and of the ledRNA encoding constructs are shown in SEQ ID NOs: 7, 8, 4 and 5, respectively. The ribonucleotide sequence of the encoded RNA molecules are provided as SEQ ID NO's 1 (GFP ledRNA) and 2 (GUS ledRNA).

To facilitate reproducible and uniform application of ledRNA onto leaf surfaces, ledRNA at a concentration of 75-100 μg/ml, in 25 mM Tris-HCL, pH 8.0, 10 mM $MgCl_2$ and Silwet 77 (0.05%), was applied to the adaxial surface of leaves using a soft paint brush. At 6 hours and 3 days following ledRNA application, leaf samples were taken for the analysis of targeted gene silencing.

Application of ledRNA against GFP in *N. benthamiana* leaves and against GUS in *N. tabacum* leaves resulted in clear reductions of 20-40% and 40-50% of the respective target gene activity at the mRNA (GFP) or protein activity (GUS) level at 6 hours post treatment. However, in this experiment the reduction did not persist at 3 days post treatment. The inventors considered that the observation at 3 days was likely due to some nonspecific responses of transgenes to dsRNA treatment or dissipating amount of ledRNA. However, in a separate experiment, GUS silencing was detected in both the treated and distal untreated leaf areas at 24 hrs post ledRNA treatment (FIG. 4).

Example 5. LedRNA-Induced Silencing of an Endogenous Target Gene

In a further example, a ledRNA was designed to target an mRNA encoded by an endogenous gene, namely the FAD2.1 gene of *N. benthamiana*. The sequence of the target FAD2.1 mRNA and of the ledFAD2.1 encoding construct are shown in SEQ ID NOs: 9 and 6, respectively. The ribonucleotide sequence of the encoded RNA molecule is provided as SEQ ID NO: 3 (*N. benthamiana* FAD2.1 ledRNA).

The FAD2.1 ledRNA construct was comprised of the following: the first half of antisense sequence corresponding to nucleotides 678 to 379 of FAD2.1 CDS (Niben101Scf09417g01008.1); the first antisense loop corresponding to nt. 378 to 242 of FAD2.1 CDS; the sense sequence corresponding of nt. 379 to 979; the second antisense loop corresponding to nt 1115 to 980; and the second half of antisense sequence corresponding to nt 979 to nt 679 of FAD2.1 CDS.

The ledGUS RNA from the previous example was used in parallel as a negative control. In the first experiment, target gene silencing was assayed for both the level of FAD2.1 mRNA and the accumulation C18:1 fatty acid (FIG. 5). The level of activity of a related gene, FAD2.2, was also assayed. For each sample approximately 3 μg of total RNA was DNase treated and reverse transcribed at 50° C. for 50 minutes using oligo dT primers. The reactions were terminated at 85° C. for 5 minutes and diluted to 120 μl with water. Using a rotor gene PCR machine, 5 μl of each sample, in triplicate, were analysed for their relative expression of FAD 2.1 and FAD 2.2 mRNA using gene specific primers with reference to the house keeping gene actin. In a subsequent experiment, northern blot hybridization was also used to confirm the silencing of the FAD2.1 gene by topically applied ledFAD2.1 RNA (FIG. 6).

The FAD2.1 mRNA was reduced significantly, to a level which was barely detectable in leaf tissues treated with the ledRNA at the 2, 4 and 10 hour time points (FIG. 5). In this experiment, it was unclear why the level of FAD2.1 mRNA was not reduced as much at the 6 hour time point. In the repeated experiment shown in FIG. 6, strong FAD2.1 downregulation occurred at both 6 and 24 hrs, particularly at the 24 hr time point. The related FAD2.2 gene, with sequence homology to FAD2.1, also showed downregulation at the 2 and 4 hour time points by the ledRNA (FIG. 5).

Since FAD2.1 and FAD2.2 encode fatty acid Δ12 desaturases which desaturate oleic acid to linoleic acid, the levels of these fatty acids were assayed in leaf tissues treated with the ledRNAs. There was a clear increase in oleic acid (18:1) accumulation in ledRNA-treated leaf tissues at the 2, 4 and 6 hour time points, which indicated a reduced amount of the FAD2 enzyme (FIG. 5). Thus, both qRT-PCR and the fatty acid composition assay showed that the ledRNA induced silencing of the FAD2.1 gene.

Example 6. Design and Testing of Hairpin RNAs Comprising G:U Basepairs or Mismatched Nucleotides Modified Hairpin RNAs Targeting GUS RNA Reporter genes such as the gene encoding the enzyme β-glucuronidase (GUS) provide a simple and convenient assay system that can be used to measure gene silencing efficiency in a eukaryotic cell including in plant cells (Jefferson et al., 1987). The inventors therefore designed, produced and tested some modified hairpin RNAs for their ability to reduce the expression of a GUS gene as a target gene, using a gene-delivered approach to provide the hairpin RNAs to the cells, and compared the modified hairpins to a conventional hairpin RNA. The conventional hairpin RNA used as the control in the experiment had a double-stranded region of 200 contiguous basepairs in length in which all of the basepairs were canonical basepairs, i.e. G:C and A:U basepairs without any G:U basepairs, and without any non-basepaired nucleotides (mismatches) in the double-stranded region, targeting the same 200 nt region of the GUS mRNA molecule as the modified hairpin RNAs. The sense and antisense sequences that formed the double-stranded region were covalently linked by a spacer sequence included a PDK intron (Helliwell et al., 2005; Smith et al., 2000), providing for an RNA loop of 39 or 45 nucleotides in length (depending on the cloning strategy used) after splicing of the intron from the primary transcript. The DNA fragment used for the antisense sequence was flanked by XhoI-BamHI restriction sites at the 5' end and HindIII-KpnI restriction sites at the 3' end for easy cloning into an expression cassette, and each sense sequence was flanked by XhoI and KpnI restriction sites. The 200 bp dsRNA region of each hairpin RNA, both for the control hairpin and the modified hairpins, included an antisense sequence of 200 nucleotides which was fully complementary to a wild-type GUS sequence from within the protein coding region. This antisense sequence, corresponding to nucleotides 13-212 of SEQ ID NO:10, was the complement of nucleotides 804-1003 of the GUS open reading frame (ORF) (cDNA sequence provided as SEQ ID NO:8). The GUS target mRNA was therefore more than 1900 nt long. The length of 200 nucleotides for the sense and antisense sequences was chosen as small enough to be reasonably convenient for synthesis of the DNA fragments using synthetic oligonucleotides, but also long enough to provide multiple sRNA molecules upon processing by Dicer. Being part of an ORF, the sequence was unlikely to contain cryptic splice sites or transcription termination sites.

Preparation of Genetic Constructs

The 200 bp GUS ORF sequence was PCR-amplified using the oligonucleotide primer pair GUS-WT-F (SEQ ID NO:52) and GUS-WT-R (SEQ ID NO:53), containing XhoI and BamHI sites or HindIII and KpnI sites, respectively, to introduce these restriction enzyme sites 5' and 3' of the GUS sequence. The amplified fragment was inserted into the vector pGEM-T Easy and the correct nucleotide sequence confirmed by sequencing. The GUS fragment was excised by digestion with BamHI and HindIII and inserted into the BamHI/HindIII site of pKannibal (Helliwell and Waterhouse, 2005), which inserted the GUS sequence in the antisense orientation relative to the operably linked CaMV e35S promoter (Grave, 1992) and ocs gene polyadenylation/transcription terminator (Ocs-T). The resultant vector was designated pMBW606 and contained, in order 5' to 3', a 35S::PDK Intron::antisense GUS::Ocs-T expression cassette. This vector was the intermediate vector used as the base vector for assembling four hpRNA constructs.

Construct hpGUS[wt] Having Only Canonical Basepairs

To prepare the vector designated hpGUS[wt] encoding the hairpin RNA molecule used as a control in the experiment, having only canonical basepairs, the 200 bp GUS PCR fragment was excised from the pGEM-T Easy plasmid with XhoI and KpnI, and inserted into the XhoI/KpnI sites between the 35S promoter and the PDK intron in pMBW606. This produced the vector designated pMBW607, containing the 35S::Sense GUS [wt]::PDK Intron::antisense GUS::OCS-T expression cassette. This cassette was excised by digestion with NotI and inserted into the NotI site of pART27 (Gleave, 1992), resulting in the vector designated hpGUS[wt], encoding the canonically basepaired hairpin RNA targeting the GUS mRNA.

When self-annealed by hybridisation of the 200 nt sense and antisense sequences, this hairpin had a double-stranded region of 200 consecutive basepairs corresponding to GUS sequences. The sense and antisense sequences in the expression cassette were each flanked by BamHI and HindIII restrictions sites present at the 5' and 3' ends, respectively, relative to the GUS sense sequence. When transcribed, the nucleotides corresponding to these sites were also capable of hybridising, extending the double-stranded region by 6 bp at each end. After transcription of the expression cassette and splicing of the PDK intron from the primary transcript, the hairpin RNA structure prior to any processing by Dicer or other RNAses was predicted to have a loop structure of 39 nucleotides. The nucleotide sequence of the hairpin RNA structure including its loop is provided as SEQ ID NO:15, and its free energy of folding was predicted to be −471.73 kcal/mol. This was therefore an energetically stable hairpin structure. The free energy was calculated using "RNAfold" (http://rna.tbi.univie.ac.at/cgi-bin/RNAWebSuite/RNAfold.cgi) based on the nucleotide sequences after the splicing out of the PDK intron sequence.

When transcribed from the expression cassette having the 35S promoter and OCS-T terminator, the resultant hairpin RNAs were embedded in a larger RNA molecule with 8 nucleotides added to the 5' end and approximately 178 nucleotides added at the 3' end, without considering addition of any poly-A tail at the 3' end. Since the same promoter-terminator design was used for the modified hairpin RNAs, those molecules also had these extensions at the 5' and 3' ends. The length of the hairpin RNA molecules after splicing of the PDH intron was therefore approximately 630 nucleotides.

Construct hpGUS[G:U] Comprising G:U Basepairs

A DNA fragment comprising the same 200 nucleotide sense sequence, but in which all 52 cytidine nucleotides (C) of the corresponding wild-type GUS region were substituted with thymidine nucleotides (T), was assembled by annealing the overlapping oligonucleotides GUS-GU-F (SEQ ID NO:54) and GUS-GU-R (SEQ ID NO: 55) and PCR extension of the 3' ends using the high-fidelity LongAmp Taq polymerase (New England Biolabs, catalogue number M0323). The amplified DNA fragment was inserted into the pGEM-T Easy vector and the correct nucleotide sequence (SEQ ID NO:11) was confirmed by sequencing. A DNA fragment comprising the modified sequence was then excised by digestion with XhoI and KpnI and inserted into the XhoI/KpnI sites of the base vector pMBW606. This produced the construct designated pMBW608, containing the expression cassette 35S::sense GUS[G:U]::PDK Intron::antisense GUS::OCS-T. This expression cassette was excised with NotI digestion and inserted into the NotI site of pART27, resulting in the vector designated hpGUS[G:U], encoding the G:U basepaired hairpin RNA molecule.

This cassette encoded a hairpin RNA targeting the GUS mRNA and which, when self-annealed by hybridisation of the 200 nt sense and antisense sequences, had 52 G:U basepairs (instead of G:C basepairs in hpGUS[wt]) and 148 canonical basepairs, i.e. 26% of the nucleotides of the double-stranded region were involved in G:U basepairs. The 148 canonical basepairs in hpGUS[G:U] were the same as in the control hairpin RNA, in the corresponding positions, including 49 U:A basepairs, 45 A:U basepairs and 54 G:C basepairs. The longest stretches of contiguous canonical basepairing in the double-stranded region was 9 basepairs. The antisense nucleotide sequence of hpGUS[G:U] was thereby identical in length (200 nt) and sequence to the antisense sequence of the control hairpin RNA hpGUS[wt]. After transcription of the expression cassette and splicing of the PDK intron from the primary transcript, the hairpin RNA structure prior to any processing by Dicer or other RNAses was predicted to have a loop structure of 45 nucleotides. The nucleotide sequence of the hairpin structure including its loop is provided as SEQ ID NO:16, and its free energy of folding was predicted to be −331.73 kcal/mol. As for hpGUS [wt], this was therefore an energetically stable hairpin structure, despite the 52 G:U basepairs which individually are much weaker than the G:C basepairs in hpGUS[wt].

An alignment of the modified GUS sense sequence (nucleotides 9-208 of SEQ ID NO: 11) with the corresponding region of the GUS target gene (SEQ ID NO:14) is shown in FIG. 7.

Construct hpGUS[1:4] Comprising Mismatched Nucleotides Every Fourth Nucleotide

A DNA fragment comprising the same 200 bp sense sequence, but in which every fourth nucleotide of the corresponding wild-type GUS sequence was substituted, was designed and assembled. Every 4th nucleotide in each block of 4 nucleotides (nucleotides at positions 4, 8, 12, 16, 20 etc) was substituted by changing C's to G's, G's to C's, A's to T's and T's to A's, leaving the other nucleotides unchanged. These substitutions were all transversion substitutions, which were expected to have a greater destabilising effect on the resultant hairpin RNA structure than transition substitutions. The DNA fragment was assembled by annealing the overlapping oligonucleotides GUS-4M-F (SEQ ID NO:56) and GUS-4M-R (SEQ ID NO:57) and PCR extension of 3' ends using LongAmp Taq polymerase. The amplified DNA fragment was inserted into the pGEM-T Easy vector and the correct nucleotide sequence (SEQ ID NO:12) was confirmed by sequencing. A DNA fragment comprising the modified sequence was then excised by digestion with XhoI and KpnI and inserted into the XhoI/KpnI sites of the base vector pMBW606. This produced the construct designated pMBW609, containing the expression cassette 35S::sense GUS[1:4]::PDK Intron::antisense GUS::OCS-T. This expression cassette was excised with NotI digestion and inserted into the NotI site of pART27, resulting in the vector designated hpGUS[1:4], encoding the 1:4 mismatched hairpin RNA molecule.

This cassette encoded a hairpin RNA targeting the GUS mRNA and which, when self-annealed by hybridisation of the sense and antisense sequences, had mismatches for 50 nucleotides of the 200 nt antisense sequence, including the mismatch for the nucleotide at position 200. Excluding position 200, the double-stranded region of the hairpin RNA had 150 canonical basepairs and 49 mismatched nucleotide pairs over a length of 199 nt sense and antisense sequences, i.e. 24.6% of the nucleotides of the double-stranded region were predicted to be mismatched (not involved in basepairs). After transcription of the expression cassette and splicing of the PDK intron from the primary transcript, the hairpin RNA structure prior to any processing by Dicer or other RNAses was predicted to have a loop structure of 45 nucleotides. The nucleotide sequence of the hairpin structure including its loop is provided as SEQ ID NO: 17, and its free energy of folding was predicted to be −214.05 kcal/mol. As for hpGUS[wt], this was therefore an energetically stable hairpin structure, despite the mismatched nucleotides.

An alignment of the modified GUS sense sequence (nucleotides 9-208 of SEQ ID NO: 12) with the corresponding region of the GUS target gene (SEQ ID NO:14) is shown in FIG. 8.

Construct hpGUS[2:10] in which Nucleotides 9 and 10 of 10 Nucleotides was Mismatched A DNA fragment comprising the same 200 bp sense sequence, but in which every ninth and tenth nucleotide of the corresponding wild-type GUS sequence was substituted, was designed and assembled. Each 9th and $10^{th}$ nucleotide in each block of 10 nucleotides (nucleotides at positions 9, 10, 19, 20, 29, 30 etc) was substituted by changing C's to G's, G's to C's, A's to T's and T's to A's, leaving the other nucleotides unchanged. The DNA fragment was assembled by annealing the overlapping oligonucleotides GUS-10M-F (SEQ ID NO:58) and GUS-10M-R (SEQ ID NO: 59) and PCR extension of 3' ends using LongAmp Taq polymerase. The amplified DNA fragment was inserted into pGEM-T Easy and the correct nucleotide sequence (SEQ ID NO:13) was confirmed by sequencing. A DNA fragment comprising the modified sequence was then excised by digestion with XhoI and KpnI and inserted into the XhoI/KpnI sites of the base vector pMBW606. This produced the construct designated pMBW610, containing the expression cassette 35S:: sense GUS [2:10]::PDK Intron: antisense GUS::OCS-T. This expression cassette was excised with NotI digestion and inserted into the NotI site of pART27, resulting in the vector designated hpGUS[2:10], encoding the 2:10 mismatched hairpin RNA molecule.

This cassette encoded a hairpin RNA targeting the GUS mRNA which, when self-annealed by hybridisation of the sense and antisense sequences, had mismatches for 50 nucleotides of the 200 nt antisense sequence, including mismatches for the nucleotides at positions 199 and 200. Excluding positions 199 and 200, the double-stranded region of the hairpin RNA had 160 canonical basepairs and 19 di-nucleotide mismatches over a length of 198 nt sense and antisense sequences, i.e. 19.2% of the nucleotides of the double-stranded region were predicted to be mismatched (not involved in basepairs). The 160 basepairs in hpGUS[2:10] were the same as in the control hairpin RNA, in the corresponding positions, including 41 U:A basepairs, 34 A:U basepairs, 42 G:C and 43 C:G basepairs. After transcription of the expression cassette and splicing of the PDK intron from the primary transcript, the hairpin RNA structure prior to any processing by Dicer or other RNAses was predicted to have a loop structure of 45 nucleotides. The nucleotide sequence of the hairpin structure including its loop is provided as SEQ ID NO:18, and its free energy of folding was predicted to be −302.78 kcal/mol. As for hpGUS [wt], this was therefore an energetically stable hairpin structure, despite the mismatched nucleotides which were expected to bulge out of the stem of the hairpin structure.

An alignment of the modified GUS sense sequence (nucleotides 9-208 of SEQ ID NO: 13) with the corresponding region of the GUS target gene (SEQ ID NO:14) is shown in FIG. 9.

The four genetic constructs for expression of the control and modified hairpin RNAs are shown schematically in FIG. 10.

Example 7. Testing the Modified Hairpin RNAs in Transgenic Plants

Plants of the species *Nicotiana tabacum* (tobacco) transformed with a GUS target gene were used to test the efficacy of the four hairpin RNA constructs described Specifically, the target plants were from two homozygous, independent above. transgenic lines, PPGH11 and PPGH24, each containing a single-copy insertion of a GUS transgene from a vector pWBPPGH which is shown schematically in FIG. 11. The GUS gene in the T-DNA of pWBPPGH had a GUS coding region (nucleotides 7-1812 of SEQ ID NO:8) operably linked to a 1.3 kb long promoter of the phloem protein 2 (PP2) gene from *Cucurbita pepo* L. cv. Autumn Gold (Wang et al., 1994; Wang, 1994). The construct pWBPPGH was made by excising the PP2 promoter plus the 5' UTR and 54 nucleotides of the PP2 protein coding region, encoding the first 18 amino acids of PP2, from the lambda genomic clone CPP1.3 (Wang, 1994), and fusing this fragment with the GUS coding sequence starting with the nucleotides encoding the 3rd amino acid of GUS, generating an N-terminal fusion polypeptide having GUS activity. The pPP2::GUS:Nos-T cassette was inserted into pWBVec2a (Wang et al., 1998) to generate pWBPPGH, which was used to transform plants of *Nicotiana tabacum* cv. Wisconsin 38 using *Agrobacterium tumefaciens*-mediated leaf disk transformation (Ellis et al., 1987), selecting for resistance to hygromycin. GUS activities in homozygous progeny plants of two transgenic lines PPGH11 and PPGH24 were similar. GUS expression in both transgenic plants was not restricted to phloem but present in most tissues of the plants. GUS expression from the PP2 promoter in these plants therefore appeared to be constitutive. There were two reasons for choosing the PP2-GUS plants as the testing plants: i) they give constitutively high levels of GUS expression about the same as to a 35S-GUS plant; ii) the PP2 promoter is an endogenous PP2 gene promoter derived from *Cucurbita pepo* with a different sequence to the 35S promoter used to drive the expression of the hpRNA transgenes, which therefore would not be subject to transcriptional cosuppression by the incoming 35S promoter.

All four hairpin RNA constructs (Example 6) were used to transform PPGH11 and PPGH24 plants using the *Agrobacterium*-mediated leaf-disk method (Ellis et al., 1987), using 50 mg/L kanamycin as the selective agent. This selection system with kanamycin, a different agent to the previously used hygromycin used to introduce the T-DNA of pWBPPGH, was observed to yield only transformed plants, with no non-transformed plants being regenerated. Regenerated transgenic plants containing the T-DNAs from the hpGUS constructs were transferred to soil for growth in the greenhouse and maintained for about 4 weeks before assaying for GUS activity. When assayed, the transgenic plants were healthy and actively growing and in appearance were identical to non-transformed control plants and the parental PPGH11 and PPGH24 plants. In total, 59 transgenic plants were obtained that were transformed with the T-DNA encoding hpGUS[wt], 74 plants were obtained that were transformed with the T-DNA encoding hpGUS[G:U], 33 plants were obtained that were transformed with the T-DNA encoding hpGUS[1:4] and 41 plants were obtained that were transformed with the T-DNA encoding hpGUS[2:10].

GUS expression levels were measured using the fluorimetric 4-methylumbelliferyl β-D-glucuronide (MUG) assay (Jefferson et al., 1987) following the modified kinetic method described in Chen et al. (2005). Plants were assayed by taking leaf samples of about 1 cm diameter from three different leaves on each plant, choosing leaves which were well expanded, healthy and green. Care was taken that the test plants were at the same stage of growth and development as the control plants. Each assay used 5 μg protein extracted per leaf sample and measured the rate of cleavage of MUG as described in Chen et al. (2005).

Representative data are shown in FIG. 12, showing GUS activity (MUG units in the assay) for each independent transgenic plant. Since the data for the hpGUS[wt] construct showed that some plants exhibited strong silencing with a reduction in activity of at least 90% and others weaker silencing, 10% GUS activity relative to the control plants was chosen, in this context, as an activity level for classifying the plants into two categories and comparing the different constructs.

The genetic construct encoding the canonically base-paired hpGUS[wt] induced strong GUS silencing, using the 10% activity level as the benchmark for strong silencing, in 32 of the 59 transgenic plants tested (54.2%). The other 27 plants all showed reduced GUS activity but retained more than 10% of the enzyme activity relative to the control plants, and so were considered to exhibit weak silencing in this context. The transgenic plants with this construct showed a wide range in the extent of GUS gene silencing (FIG. 12), from less than 1% to about 80% activity remaining, which was typical for conventional hairpin designs (Smith et al., 2000).

In clear contrast, the hpGUS[G:U] construct induced consistent and uniform silencing across the independent transgenic lines, with 71 of the 74 plants (95.9%) that were tested showing strong GUS silencing. Different again, all of the 33 hpGUS[1:4] plants tested showed reduced levels of GUS activity, with only 8 (24%) yielding <10% of the GUS activity relative to the control plants, and the other 25 classified as having weaker silencing. These results indicated that this construct induced weaker but more uniform levels of GUS down-regulation across the transgenic lines. The hpGUS[2:10] construct performed more like the hpGUS[wt] construct, inducing good levels of silencing in some lines (28 of 41, or 68.3%) and gave little or no GUS silencing in the remaining 13 plants.

When only the silenced lines (<10% remaining activity) were used for comparison and average GUS activities calculated, the hpGUS[wt] plants showed the highest average extent of silencing, followed in order by the hpGUS[G:U] plants and the hpGUS[2:10] plants (FIG. 13). The hpGUS[1:4] plants showed the least average reduction in GUS activity. The extent of GUS silencing showed a good correlation with the thermodynamic stability of the predicted hpRNA structures derived from the four different hpRNA constructs (Example 6).

To test whether the differences would persist in progeny plants, representative transgenic plants containing both the target GUS gene, which was homozygous, and the hpGUS transgene (hemizygous) were self-fertilised. Kanamycin-resistant progeny plants from the hpGUS lines were selected, so discarding any null segregants lacking the hpGUS transgenes. This ensured that the hpGUS transgenes were present in all of the progeny, in either the homozygous or heterozygous state. The progeny plants were assayed for GUS activity and representative data are presented in FIG. 14. Progeny containing the hpGUS[wt] transgenes obviously fell into two categories, namely those that had strong GUS silencing and others that showed weak or no silencing. These classes correlated well with the phenotype of the previous generation, showing that the extent of target gene silencing was heritable. All of the plants in the hpGUS[G:U] lines tested consistently showed strong silencing, whilst the plants in the hpGUS[1:4] lines consistently showed weaker silencing. The inventors concluded that the phenotypes observed in the parental generation were generally maintained in the progeny plants.

Southern Blot Hybridisation Experiments on Transformed Plants

The uniformity of the strong gene silencing observed in the large number of independent transgenic plants generated with the hpGUS[G:U] construct was striking as well as surprising and unexpected. The inventors sought to establish whether any explanation other than an effect caused by the hpGUS[G:U] RNA was causing the uniformity of the silencing. To test whether the multiple transgenic plants arose from independent transformation events as intended, Southern blot hybridisation experiments were carried out on DNA isolated from 18 representative transgenic plants containing the hpGUS[G:U] construct. DNA was isolated from leaf tissues using the hot-phenol method described by Wang et al. (2008). For Southern blot hybridization, approximately 10 μg of DNA from each plant sample was digested with HindIII enzyme, separated by gel electrophoresis in 1% agarose gels in TBE buffer, and blotted onto Hybond-N+ membrane using the capillary method (Sambrook et al., 1989). The membrane was hybridized overnight at 42° C. with a $^{32}$P-labelled DNA fragment from the OCS-T terminator region. This probe was chosen as it hybridized to the hpGUS[G:U] transgene but not to the GUS target gene which did not have an OCS-T terminator sequence. The membrane was washed at high stringency and retained probe visualized with a PhosphoImager.

An autoradiograph of a hybridised blot is shown in FIG. 15. Each lane showed from one to five or six hybridising bands. No two lanes showed the same pattern i.e. the autoradiograph showed that the 16 representative hpGUS[G:U] plants each had different patterns of HindIII fragments that hybridized and therefore came from different transgene insertions. The inventors concluded that the uniform GUS silencing observed for hpGUS[G:U] lines was not due to similar transgene insertion patterns in the plants, and that the uniformity of silencing was caused by the structure of the hpGUS[G:U] RNA. The inventors also concluded that multiple copies of the hpGUS[G:U] transgene were not required in order to obtain strong gene silencing; a single copy of the transgene was sufficient.

Northern Blot Hybridisation Experiments on Transformed Plants

To determine whether the hpGUS[G:U] RNA was processed in the same manner as the control hairpin RNA in the transgenic plants, Northern blot hybridisation experiments were carried out on RNA isolated from leaves of the transgenic plants. The Northern blot experiments were carried out to detect the shorter RNAs (sRNA, approx 21-24 nucleotides in length) which resulted from Dicer-processing of the hairpin RNAs. The experiment was carried out on small RNA isolated from transgenic hpGUS[wt] and hpGUS[G:U] plants which also containing the GUS target gene which was expressed as a (sense) mRNA. Nine plants for each construct were selected for sRNA analysis. For the hpGUS[wt] transgenic population, plants showing weak GUS silencing were included as well as some exhibiting strong GUS silencing. The small RNA samples were isolated using the hot-phenol method (Wang et al., 2008), and Northern blot hybridization was performed according to Wang et al. (2008), with gel electrophoresis of the RNA samples carried out under denaturing conditions. The probes used were 32P-labelled RNAs corresponding to either the sense sequence or the antisense sequence corresponding to nucleotides 804-1003 of SEQ ID NO:8.

An autoradiograph of a Northern blot, hybridised with either the antisense probe (upper panel) to detect sense sRNA molecules derived from the hairpin RNAs, or hybridised with the sense probe to detect the antisense sRNAs (lower panel), is shown in FIG. 16. At the bottom, the Figure shows a qualitative score for the level of GUS expression relative to the control plants lacking the hpGUS constructs. Hybridisation to small RNAs of about 20-25 nucleotides was observed, based on the mobility of the sRNAs compared to RNAs of known length in other experiments. The hpGUS [wt] lines showed a range of variation in the amount of sRNA accumulation. This was observed for both the sense and antisense sRNAs, although the antisense sRNA bands were not as clear as the sense bands. Since the hpGUS[wt] plants contained both the hpGUS transgene, expressing both sense and antisense sequences corresponding to the 200 nt target region, and the GUS target gene expressing the full-length sense gene, the sense sRNAs could have been generated from either the hairpin RNA or the target mRNA. There appeared to be negative correlation between the level of sRNA and the degree of GUS silencing in the hpGUS[wt] plants. For example, the two plants represented in lanes 4 and 5 accumulated relatively more sRNA but showed only a moderate extent of GUS downregulation. In contrast, the two plants represented in lanes 7 and 8 had strong GUS silencing but accumulated relatively low levels of sRNA.

In contrast to the hpGUS[wt] plants and consistent with the relatively uniform extent of silencing by the hpGUS[G:U] construct, the hpGUS[G:U] plants accumulated uniform amounts of antisense sRNAs across the lines. Furthermore, the degree of GUS silencing appeared to show good correlation with the amount of antisense sRNA. Almost no sense sRNAs were detected in these plants. This was expected since the RNA probe used in the Northern blot hybridisation was transcribed from the wild-type GUS sequence and therefore had a lower level of complementarity to sense sRNAs from hpGUS[G:U] where all C nucleotides were replaced with U nucleotides, allowing only lower stringency hybridisation. However, this experiment did not exclude the possibility that the hpGUS[G:U] RNA was processed to produce less sense sRNAs or that they were degraded more quickly.

The Northern blot hybridisation experiment was repeated, this time using only a sense probe to detect antisense sRNAs; the autoradiograph is shown in FIG. 17. Once again, the production of antisense sRNAs from the hpGUS[wt] construct correlated negatively with the GUS activity (upper panel of FIG. 17). Plants which were strongly silenced yielded high levels of antisense sRNAs (lanes 1, 3, 5, 8 and 10) whereas plants that showed only weak or no silencing did not produce a hybridisation signal in this experiment (lanes 2, 4, 6, 7 and 9). In very clear contrast, the plants expressing hpGUS[G:U] produced a much lower, but consistent, amount of antisense sRNAs. The observation that the strongly silenced plants expressing hpGUS[G:U] accumulated much lower levels of sRNAs than the strongly silenced plants expressing hpGUS[wt] was intriguing and suggested to the inventors that the hpGUS[wt] was being processed by a different mechanism in the plants but was still about as effective as the hpGUS[wt] construct. A further observation in this experiment provided a clue in that the two, relatively faint antisense bands for the hpGUS[G:U] plants appeared to have the same mobility as the second and fourth bands observed for the antisense sRNA bands from hpGUS[wt]. This was confirmed in further experiments described below. The inventors postulated that the four bands for the sRNAs from hpGUS[wt] represent 24-, 22-, 21- and 20-mers, and that the hpGUS[G:U] RNA was processed primarily to produce 22- and 20-mers antisense sRNAs.

An important, definite conclusion from the data described above was that the hpGUS[G:U] RNA molecule was processed by one or more Dicer enzymes to produce sRNAs, in particular the production of antisense sRNAs which are thought to be mediators of RNA interference in the presence of various proteins such as Argonaute. The observed production of antisense sRNAs implied that the sense sRNAs were also produced, but the experiments did not distinguish between degradation/instability of the sense sRNAs or the lack of detection of sense sRNAs due to insufficient hybridisation with the probe that was used. From these experiments, the inventors also concluded that there were clear differences between the hpGUS[wt] and hpGUS[G:U] RNA molecules in their processing. This indicated that the molecules were recognised differently by one or more Dicers.

Example 8. Analysis of sRNAs from Transgenic Plants Expressing Modified Hairpin RNAs Another Northern blot hybridisation experiment was carried out to detect antisense sRNAs from hpGUS[G:U] plants and to compare their sizes to those produced from hpGUS [wt]. The autoradiograph is shown in FIG. 18. This time, the difference in size of the two antisense sRNA bands from hpGUS[G:U] compared to the main two bands from hpGUS [wt] was more distinct. This was best seen by comparing the mobility of the bands in adjacent lanes 9 and 10 of FIG. 18. This result confirmed that the two hairpin RNAs were processed differently by one or more Dicers in the plants.

To further investigate this, the small RNA populations from the hpGUS[wt] and hpGUS[G:U] were analysed by deep sequencing of the total, linker-amplifiable sRNAs isolated from the plants. The frequency of sRNAs which mapped to the double-stranded regions of the hairpin RNAs was determined. The length distribution of such sRNAs was also determined. The results showed that there was an increase in the frequency of 22-mer antisense RNAs from the hpGUS[G:U] construct relative to the hpGUS[wt] construct. The increase in the proportion of sRNAs of 22 nt in length indicated a shift in processing of the hpGUS[G:U] hairpin by Dicer-2 relative to hpGUS[wt].

Example 9. DNA methylation analysis of transgenes in plants

The observations on the variability in the extent of GUS silencing conferred by hpGUS[wt] and that antisense 24-mer sRNAs were detected in the hpGUS[wt] plants but apparently not in the hpGUS[G:U] plants led the inventors to question whether the two populations of plants differed in their level of DNA methylation of the target GUS gene. Sequence-specific 24-mer sRNAs are thought to be involved in promoting DNA methylation of inverted repeat structures in plants (Dong et al., 2011). The inventors therefore tested the levels of DNA methylation of the GUS transgene in the hpGUS plants, in particular of the 35S promoter region of the hairpin encoding gene (silencing gene).

To do this, the DNA-methylation dependent endonuclease McrBC was used. McrBC is a commercially available endonuclease which cleaves DNA containing methylcytosine ($^{m}$C) bases on one or both strands of double-stranded DNA (Stewart et al., 2000). McrBC recognises sites on the DNA which consist of two half-sites of the form 5' (G or A)$^{m}$C 3', preferably G$^{m}$C. These half-sites may be separated by several hundred basepairs, but the optimal separation is from 55 to about 100 bp. Double-stranded DNA having such linked G$^{m}$C dinucleotides on both strands serve as the best substrate. McrBC activity is dependent on either one or both of the GC dinucleotides being methylated. Since plant DNA can be methylated at the C in CG, CHG or CHH sequences where H stands for A, C or T (Zhang et al., 2018), digestion of DNA using McrBC with subsequent PCR amplification of gene-specific sequences can be used to detect the presence or absence of $^{m}$C in specific DNA sequences in plant genomes. In this assay, PCR amplification of McrBC-digested genomic DNA which is methylated yields reduced amounts of the amplification product compared to DNA which is not methylated, but will yield an equal amount of PCR product as untreated DNA if the DNA is not methylated.

Genomic DNA was isolated by standard methods from plants containing the hpGUS[wt], hpGUS[G:U] or hpGUS [1:4] construct in addition to the target GUS gene (Draper and Scott, 1988). Purified DNA samples were treated with McrBC (Catalog No. M0272; New England Biolabs, Massachusetts) according to the manufacturer's instructions, including the presence of $Mg^{2+}$ ion and GTP required for endonuclease activity. In summary, approximately 1 μg of genomic DNA was digested with McrBC overnight in a 30 μl reaction volume. The digested DNA samples were diluted to 100 μl and regions of interest were PCR-amplified as follows.

The treated DNA samples were used in PCR reactions using the following primers. For the 35S-GUS junction sequence for hpGUS[wt]: Forward primer (35S-F3), 5'-TGGCTCCTACAAATGCCATC-3' (SEQ ID NO:60); Reverse primer (GUSwt-R2), 5'-CARRAACTRTT-CRCCCTTCAC-3' (SEQ ID NO:61). For the 35S-GUS junction sequence for hpGUS[G:U]: Forward primer (GUSgu-R2), 5'-CAAAAACTATTCACCCTTCAC-3' (SEQ ID NO:62); reverse primer (GUS4m-R2), CACRAARTRTACRCRCTTRAC (SEQ ID NO:63). For the 35S promoter sequence for both constructs: Forward primer (35S-F2), 5'-GAGGATCTAACAGAACTCGC-3' (SEQ ID NO: 64); reverse primer (35S-R1), 5'-CTCTC-CAAATGAAATGAACTTCC-3' (SEQ ID NO:65). In each case, R=A or G, Y=C or T. PCR reactions were performed with the following cycling conditions: 94° C. for 1 min, 35 cycles of 94° C. for 30 sec, 55° C. annealing for 45 sec, 68° C. extension for 1 min, and final extension at 68° C. for 5 min. PCR amplification products were electrophoresed and the intensity of the bands quantitated.

Figure 19:
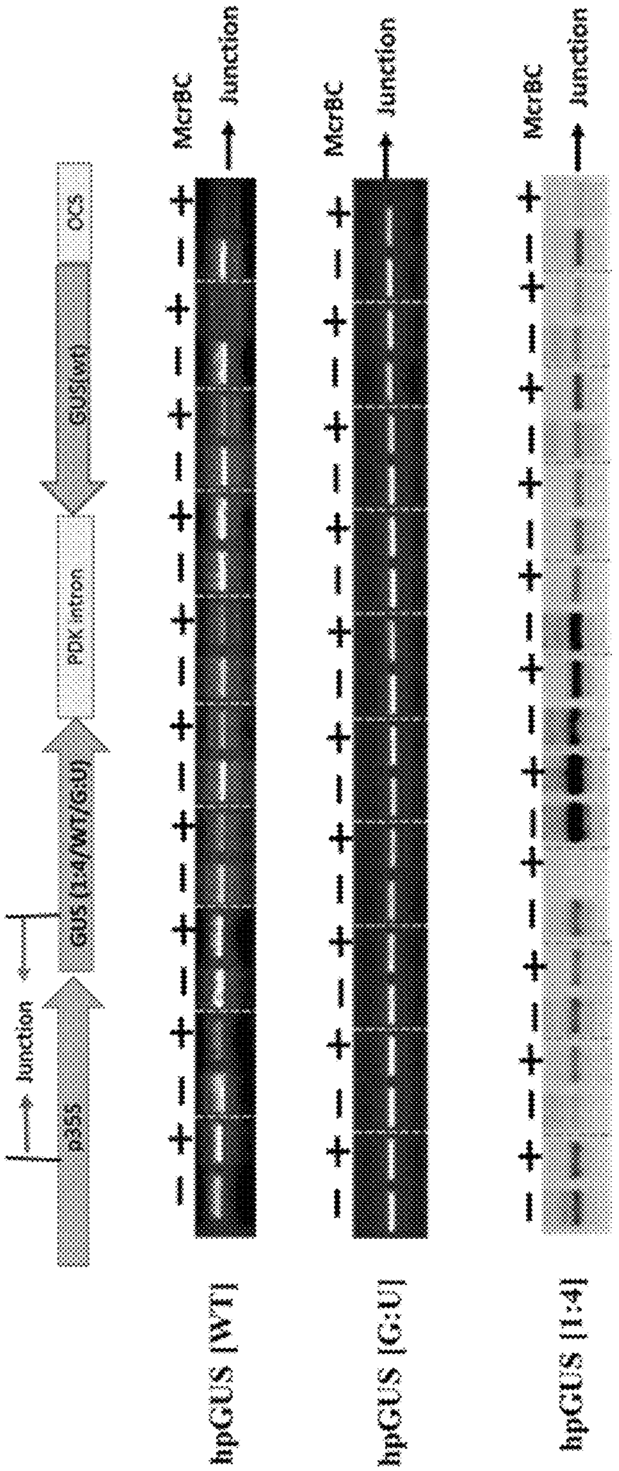

Representative results are shown in FIGS. 19 and 20. For the 35S-GUS junction region which included 200 bp of the 35S promoter sequence including the transcriptional start site, most of hpGUS[wt] plants showed significant levels of DNA methylation. Within the population of hpGUS[wt] plants, individual plants that retained higher levels of GUS activity i.e. less silencing, appeared to have more methylation of the promoter-GUS sense junction region. The results were similar for the 35S promoter region. In contrast, most of the hpGUS[G:U] and hpGUS[1:4] plants showed weaker DNA methylation at the 35S-GUS junction. The inventors considered that this proximal promoter sequence was important for expression of the transgene and methylation at this region would be likely to reduce expression of the silencing construct through transcriptional gene silencing (TGS) of the transgene. This is termed "self-silencing".

General Discussion in Relation to Examples 6 to 9

Disruption of Inverted Repeat DNA Structure in a Transgene Enhances its Stability Both of the populations of hpGUS[wt] and hpGUS[2:10] transgenic plants showed a wide range in the extent target gene silencing. In contrast, both of the populations containing hpGUS[G:U] and hpGUS[1:4] plants displayed relatively uniform GUS silencing in many independent lines, with strong silencing observed by the former construct and relatively weaker but still substantial reduction in gene activity by the latter construct. In the hairpin RNAs from the [G:U] and [1:4] constructs, about 25% of the nucleotides in the sense and antisense sequences were either involved in G:U basepairs or in a sequence mismatch that were evenly distributed across the 200 nucleotide sense/antisense sequences. Because of the sequence divergence between the sense and antisense sequences, the mismatches in the DNA constructs between the sense and antisense "arms" or the inverted request structure were considered to significantly disrupt that inverted-repeat DNA structure. Repetitive DNA structures may attract DNA methylation and silencing in various organisms (Hsieh and Fire, 2000). The hpGUS[2:10] construct also comprised mismatches between the sense and antisense region, but each of the 2 bp mismatches between the sense and antisense sequences were flanked by 8-bp consecutive matches, so the mismatches may not have disrupted the inverted repeat DNA structure as much as in the [G:U] and [1:4] transgenes. The uniformity of the GUS silencing induced by the hpGUS[G:U] and hpRNA [1:4] might therefore have been due, at least in part, to disruption of the inverted-repeat DNA structure that resulted in less methylation and therefore reduced the self-silencing of the two transgenes. Another benefit of the mismatches between the sense and antisense DNA regions was that cloning of the inverted repeat in *E. coli* was aided since the bacteria tend to delete or re-arrange perfect inverted repeats.

Thermodynamic Stability of hpRNA is Important for the Degree of Target Gene Silencing When only the strongly-silenced transgenic lines were compared, the hpGUS[wt] plants had the greatest extent of target gene downregulation, followed in order by hpGUS [G:U], hpGUS[2:10] and hpGUS[1:4]. RNAFold analysis predicted that the hpGUS[wt] hairpin RNA structure had the lowest free energy, i.e. the greatest stability, followed by hpGUS[G:U], hpGUS[2:10] and hpGUS[1:4] hairpins. The inventors considered that the more stable the hairpin RNA structure, the greater the extent of target gene silencing it could induce. This also favoured longer double-stranded RNA structures rather than shorter ones. Stable double-stranded RNA formation was thought to be required for efficient Dicer processing. The results of the experiments described here indicated another important advantage of the G:U basepaired construct over the constructs comprising mostly simple mismatched nucleotides such as hpGUS[1:4]: while both types of constructs had disrupted inverted repeat DNA structures which reduced self-silencing, at the RNA level the hpGUS[G:U] RNA was more stable due to the ability of G and U to form basepairs. A combination of the two types of modifications was also considered beneficial, including both G:U basepairs and some mismatched nucleotides in the double-stranded RNA structure but with relatively more nucleotides involved in G:U basepairs than in mismatches, by a factor of at least 2, 3, 4 or even 5.

The hpGUS[G:U] RNA was Efficiently Processed by Dicer

One important question that was answered in these experiments was whether the mismatched or G:U basepaired hpRNA could be processed by Dicer into small RNAs (sRNAs). The strong silencing in the hpGUS[G:U] plants and in the 1:4 and 2:10 mismatched hpRNA plants, implied that these hairpin RNA structures were processed by Dicer. This was confirmed for the [G:U] molecule by sRNA Northern blot hybridization, which readily detected antisense sRNAs. Furthermore, the degree of GUS silencing in the hpGUS[G:U] plants showed a good correlation with the amount of antisense sRNAs that accumulated. Small RNA deep sequencing analysis of two selected lines from each (only one for hpGUS[wt]) confirmed that hpGUS[G:U] plants, like the hpGUS[wt] plants, generated abundant sRNAs, whereas the hpGUS[1:4] plants also generated sRNAs but with a much lower abundance (FIG. 21). The lower level of sRNAs from the hpGUS[1:4] plants was consistent with the relatively low efficiency of GUS silencing and suggested that the low thermodynamic stability of the dsRNA stem in hpGUS[1:4] RNA reduced Dicer processing efficiency. It was noted that the extent of GUS silencing showed relatively poor correlation with the level of sRNA for the hpGUS[wt] construct, with some strongly silenced lines containing relatively low amounts of sRNA. This suggested that GUS silencing in some of the hpGUS [wt] lines was due at least in part to transcriptional silencing rather than sRNA-directed PTGS. The inventors recognised that the self-silencing of the hairpin-encoding gene, which involved methylation of the gene sequences such as the promoter region, was lessened by using the modified hairpin RNA constructs, particularly the G:U construct.

The G:U and 1:4 hpRNA Transgenes Showed Reduced DNA Methylation in the Proximal 35S Promoter Region McrBC digestion-PCR analysis showed that DNA methylation levels in the 240 bp 35S sequence near the transcription start site (TSS) was reduced in the hpGUS[G:U] and hpGUS[1:4] transgenic populations relative to the hpGUS [wt] population. This result indicated to the inventors that the disruption of the perfect inverted-repeat structure, due to the C to T modifications (in hpGUS[G:U]) or 25% nucleotide mismatches (in hpGUS[1:4]) in the sense sequence, minimized transcriptional self-silencing of the hpRNA transgenes. This was consistent with the uniformity of GUS gene silencing observed in the hpGUS[G:U] and hpGUS[1:4] populations relative to the hpGUS[wt] population. The inventors recognised that the hpGUS[G:U] construct was more ideal than the hpGUS[1:4] construct in reducing promoter methylation hence transcriptional self-silencing at least because it had a reduced number, or even lacked, cytosine nucleotides in the sense sequence and therefore did not attract DNA methylation that could spread to the promoter.

Example 10. Design and Testing of Hairpin RNAs Comprising G:U Basepairs Targeting Endogenous Genes Modified Hairpin RNAs Targeting EIN2 and CHS RNAs Since the G:U modified hairpin RNA appeared to induce more consistent and uniform silencing of the target gene compared to the conventional hairpin RNA as described above, the inventors wanted to test whether the improved design would also reduce expression of endogenous genes. The inventors therefore designed, produced and tested several [G:U]-modified hairpin RNA constructs targeting either the EIN2 or CHS genes, or both, which were endogenous genes in *Arabidopsis thaliana* chosen as exemplary target genes for attempted silencing. The EIN2 gene (SEQ ID NO:19) encodes ethylene-insensitive protein 2 (EIN2) which is a central factor in signalling pathways regulated by the plant signalling molecule ethylene, i.e. a regulatory protein, and the CHS gene (SEQ ID NO:20) encodes the enzyme chalcone synthase (CHS) which is involved in anthocyanin production in the seedcoat in *A. thaliana*. Another G:U modified construct was produced which simultaneously targeted both of the EIN2 and CHS genes, in which the EIN2 and CHS sequences were transcriptionally fused to produce a single hairpin RNA. Furthermore, three additional constructs were made targeting either EIN2, CHS or both EIN2 and CHS, in which cytidine bases in both the sense and antisense sequences were replaced with thymidine bases (herein designated a G:U/U:G construct), rather than in just the sense sequence as done for the modified hairpins targeting GUS. The modified hairpin RNA constructs were tested for their ability to reduce the expression of the endogenous EIN2 gene or the EIN2 and CHS genes using a gene-delivered approach to provide the hairpin RNAs to the cells. The conventional hairpin RNAs used as the controls in the experiment had a double-stranded RNA region of 200 basepairs in length for targeting the EIN2 or CHS mRNAs, singly, or a chimeric double-stranded RNA region comprising 200 basepairs from each of the EIN2 and CHS genes which were fused together as a single hairpin molecule. In the fused RNA, the EIN2 double-stranded portion was adjacent to the loop of the hairpin and the CHS region was distal to the loop. All of the basepairs in the double-stranded region of the control hairpin RNAs were canonical basepairs.

Construct Preparation

DNA fragments spanning the 200 bp regions of the wild-type EIN2 (SEQ ID NO: 19) and CHS cDNAs (SEQ ID NO:20) were PCR-amplified from *Arabidopsis thaliana* Col-0 cDNA using the oligonucleotide primer pairs EIN2 wt-F (SEQ ID NO: 66) and EIN2 wt-R (SEQ ID NO:67) or CHSwt-F (SEQ ID NO:68) and CHSwt-R (SEQ ID NO:69), respectively. The fragments were inserted into pGEMT-Easy as for the GUS hairpin constructs (Example 6). DNA fragments comprising the 200 bp modified sense EIN2[G:U] (SEQ ID NO:22) and CHS[G:U] (SEQ ID NO:24) fragments or the 200 bp modified antisense EIN2[G:U] (SEQ ID NO:25) and modified antisense CHS[G:U] (SEQ ID NO:26) fragments, each flanked by restriction enzyme sites, were assembled by annealing of the respective pairs of oligonucleotides, EIN2gu-F+EIN2gu-R, CHSgu-F+CHSgu-R, asEIN2gu-F+asEIN2gu-R, and asCHSgu-F+asCHSgu-R (SEQ ID NOs: 70-77), followed by PCR extension of 3' ends using LongAmp Taq polymerase. All the G:U-modified PCR fragments were cloned into pGEM-T Easy vector and the intended nucleotide sequences confirmed by sequencing. The CHS[wt]::EIN2[wt], CHS[G:U]:EIN2[G:U], and asCHS[G:U]::asEIN2[G:U] fusion fragments were prepared by ligating the appropriate CHS and EIN2 DNA fragments at the common XbaI site in the pGEM-T Easy plasmid.

The 35S::sense fragment::PDK intron::antisense fragment::OCS-T cassettes were prepared in an analogous manner as for the hpGUS constructs. Essentially, the antisense fragments were excised from the respective pGEM-T Easy plasmids by digestion with HindIII and BamHI, and inserted into pKannibal between the BamHI and HindIII sites so they would be in the antisense orientation relative to the 35S promoter. The sense fragments were then excised from the respective pGEM-T Easy plasmid using XhoI and KpnI and inserted into the same sites of the appropriate antisense-containing clone. All of the cassettes in the pGEM-T Easy plasmids were then excised with NotI and inserted into pART27 to form the final binary vectors for plant transformation.

The alignments of the modified sense[G:U] and antisense [G:U] nucleotide sequences with the corresponding wild-type sequences, showing the positions of the substituted nucleotides, are shown in FIGS. 22 to 25. The designs of the expression cassettes for the hairpin RNAs are shown schematically in FIG. 26.

The predicted free energy of formation of the hairpin RNAs was estimated by using the FOLD program. These were calculated as (kcal/mol): hpEIN2[wt], −453.5; hpEIN2 [G:U], −328.1; hpCHS[wt], −507.7; hpCHS[G:U] −328.5; hpEIN2[G:U/U:G], −173.5; hpCHS[G:Y/U:G], −186.0; hpCHS::EIN2[wt], −916.4; hpCHS::EIN2[G:U], −630.9; hpCHS::EIN2 [G:U/U:G), −333.8.

Plant Transformation

All of the EIN2, CHS and chimeric EIN2/CHS constructs were used to transform *Arabidopsis thaliana* race Col-0 plants using the floral dip method (Clough and Bent, 1998). To select for transgenic plants, seeds collected from the *Agrobacterium*-dipped flowers were sterilized with chlorine gas and plated on MS medium containing 50 mg/L kanamycin. Multiple transgenic lines were obtained for all nine constructs (Table 1). These primary transformants (T1 generation) were transferred to soil, self-fertilised and grown to maturity. Seed collected from these plants (T2 seed) was used to establish T2 plants and screened for lines that were homozygous for the transgene. These were used for analysing EIN2 and CHS silencing.

TABLE 1

Summary of transgenic plants obtained in Col-0 background

| Construct | Number of transgenic lines obtained |
|---|---|
| hpEIN2[wt] | 46 |
| hpCHS[wt] | 34 |
| hpEIN2[G:U] | 23 |
| hpCHS[G:U] | 32 |
| hpEIN2[G:U/U:G] | 52 |
| hpCHS[G:U/U:G] | 13 |
| hpCHS::EIN2[wt] | 28 |
| hpCHS::EIN2[G:U] | 26 |
| hpCHS::EIN2[G:U/U:G] | 20 |

Analysis of the Extent of EIN2 Silencing

EIN2 is a gene in *A. thaliana* that encodes a receptor protein involved in ethylene perception. The gene is expressed in seedlings soon after germination of seeds as well as later in plant growth and development. EIN2 mutant seedlings exhibit hypocotyl elongation relative to isogenic wild-type seedlings when germinated in the dark in the presence of 1-aminocyclopropane-1-carboxylic acid (ACC), an intermediate in the synthesis of ethylene in plants. EIN2 gene expression and the extent of silencing in the transgenic plants was therefore assayed by germinating seed on MS medium containing 50 μg/L of ACC in total darkness and measuring their hypocotyl length, compared to the wild-type seedlings. The hypocotyl length was an easy phenotype to measure and was a good indicator of the extent of reduction in EIN2 gene expression, indicating different levels of EIN2 silencing. Plants with silenced EIN2 gene expression were expected to have various degrees of hypocotyl elongation depending on the level of EIN2 silencing, somewhere in the range between wild-type seedlings (short hypocotyls) and null-mutant seedlings (long hypocotyls). Seeds from 20 randomly selected, independently transformed plants for each construct were assayed. Seeds from one plant of the 20 containing the hpCHS::EIN2[G:U] construct did not germinate. The data for hypocotyl length are shown in FIG. 27.

The hpEIN2[wt] lines showed a considerable range in the extent of EIN2 silencing, with 7 lines (plant lines 2, 5, 9, 10, 12, 14, 16 in FIG. 27) clearly showing low levels of silencing or the same hypocotyl length relative to the wild-type, and the other 13 lines having moderate to strong EIN2 silencing. Individual plants within each independent line tended to exhibit a range in the extent of EIN2 silencing, as indicated by differences in hypocotyl length. In contrast, only two lines (plant lines 5, 18 in FIG. 27) comprising the hpEIN2[G:U] construct showed weak EIN2 silencing, with the remaining 18 showing uniform, strong EIN2 silencing. In addition, individual plants within each of the 18 lines appeared to have relatively uniform EIN2 silencing compared to the plants transformed with the hpEIN2[wt] construct. The inventors concluded that the G:U modified hairpin RNA construct was able to confer more consistent, less variable gene silencing of an endogenous gene which was more uniform and more predictable than the conventional hairpin RNA targeting the same region of the endogenous RNA.

The transgenic hpEIN2[wt] and hpEIN2[G:U] populations also differed in the relationship between the extent of EIN2 silencing and the transgene copy number. The transgene copy number was indicated by the segregation ratios for the kanamycin resistance marker gene in progeny plants—a 3:1 ratio of resistant:susceptible seedlings indicating a single locus insertion, whereas a ratio that was much higher indicated multi-loci transgene insertions. Several multiple copy-number lines transformed with the hpEIN2 [wt] construct showed low levels of EIN2 silencing, but this was not the case for the hpEIN2[G:U] lines where both the single and multi-copy loci lines showed strong EIN2 silencing.

The EIN2 gene was also silencing in the seedlings transformed with the CHS::EIN2 fusion hairpin RNA. Similar to the plants containing the single hpEIN2[G:U] construct, the hpCHS::EIN2[G:U] seedlings clearly showed more uniform EIN2 silencing across the independent lines than the hpCHS::EIN2[wt] seedlings. The silencing among individual plants within an independent line also appeared to be more uniform for the hpCHS::EIN2[G:U] lines than the hpCHS::EIN2[wt] lines. At the same time, the extent of EIN2 silencing was slightly stronger for the highly silenced hpCHS::EIN2[wt] plants than for the hpCHS::EIN2[G:U] plants, similar to the comparison between plants transformed with hpGUS[wt] and hpGUS[G:U]. Comparison of the extent of silencing indicated that the fusion constructs did not induce stronger EIN2 silencing than the single hpEIN2[G:U] construct, indeed, the fusion G:U hairpin construct appeared to induce slightly weaker EIN2 silencing than the single gene-targeted hpEIN2[G:U] construct.

When the plants transformed with the G:U/U:G constructs were examined, where the cytidine (C) nucleotides of both the sense and antisense sequences were modified to thymidine (T) nucleotides, little to no increase in hypocotyl length was observed for all 20 independent lines analysed compared to wild-type plants. This was observed for both the hpEIN2[G:U/U:G] and hpCHS::EIN2[G:U/U:G] constructs. These results indicated to the inventors that the G:U/U:G basepaired hairpin RNA constructs having about 46% substitutions were not effective at inducing target gene silencing, perhaps because the basepairing of the hairpin RNAs had been destabilised too much. The inventors considered that two possible reasons might have contributed to the ineffectiveness. Firstly, the EIN2 double-stranded region of the hairpin RNAs had 92 G:U basepairs of the 200 potential basepairs between the sense and antisense sequences. Secondly, the alignment of the modified antisense sequence with the complement of the wild-type sense sequence showed that the 49 C to T replacements in the antisense sequence might have reduced the effectiveness of the antisense sequence to target the EIN2 mRNA. The inventors concluded from this experiment that, at least for the EIN2 target gene, there was an upper limit to the number of nucleotide substitutions that could be tolerated in the hairpin RNA and still maintain sufficient effectiveness for silencing. For instance, 92/200=46% substitutions was probably too high a percentage.

Analysis of the Extent of CHS Silencing

Transgenic plants were assayed for the level of CHS gene expression by quantitative reverse transcription PCR (qRT-PCR) on RNA extracted from the whole plants, grown in vitro on tissue culture medium. The primers used for the CHS mRNA were: forward primer (CHS-200-F2), 5'-GACATGCCTGGTGCTGACTA-3' (SEQ ID NO: 78); reverse primer (CHS-200-R2) 5'-CCTTAGCGATACGGAGGACA-3' (SEQ ID NO: 79). The primers used for the reference gene Actin2 used as a standard were: Forward primer (Actin2-For) 5'-TCCCTCAGCACATTCCAGCA-3' (SEQ ID NO:80) and reverse primer (Actin2-Rev) 5'-GATCCCATTCATAAAACCCCAG-3' (SEQ ID NO: 81).

The data showed that the level of CHS mRNA the accumulated in the plants relative to the reference mRNA for the Actin2 gene was decreased in the range of 50-96% (FIG. 28).

*A. thaliana* seed completely lacking CHS activity have a pale seed coat colour compared to the brown colour of wild-type seeds. Therefore, seed of the transgenic plants were examined visually for their seedcoat colour. An obvious reduction of seed coat colour was observed in seeds from several plants but not in other plants, despite the reduction in CHS mRNA in the leaves of those plants. It was considered, however, that the seed coat colour phenotype was exhibited only when CHS activity was almost completely abolished in the developing seed coat during growth of the plants. Moreover, the 35S promoter may not have been sufficiently active in the developing seed coat to provide the level of reduction in CHS activity to provide for the pale seed phenotype seen in null mutants. Improvement in the visual seed coat colour phenotype could be gained by using a promoter that is more active in the seed coat of the seed.

Reducing Expression of PDS Gene in *Arabidopsis thaliana*

Another *Arabidopsis* gene was selected as an exemplary target gene, namely the phytoene desaturase (PDS) gene which encodes the enzyme phytoene desaturase that catalyzes the desaturation of phytoene to zeta-carotene during carotenoid biosynthesis. Silencing of PDS was expected to result in photo-bleaching of *Arabidopsis* plants, which could easily be observed visually. A G:U-modified hpRNA construct was therefore made and tested in comparison to a traditional hpRNA constructs targeting a 450 nucleotide PDS mRNA sequence. The 450 nucleotide PDS sequence contained 82 cytosines (C) which were substituted with thymidines (T), resulting in 18.2% of the basepairs in the dsRNA region of the hpRNA hpPDS[G:U] being G:U base pairs. The genetic construct encoding hpPDS[G:U] and the control genetic construct encoding hpPDS[WT] were introduced into *Arabidopsis thaliana* Col-0 ecotype using *Agrobacterium*-mediated transformation.

For the hpPDS[WT] and hpPDS[G:U] constructs, 100 and 172 transgenic lines were identified, respectively. Strikingly, all these lines showed photo-bleaching in the cotyledons of young T1 seedlings that emerged on kanamycin-resistant selective medium, with no obvious difference between the two transgenic populations at this early stage of plant growth. These indicated that the two constructs were equally effective at inducing PDS silencing in cotyledons. However, some of the T1 plants developed true leaves that were no longer photo-bleached and looked green or pale green, indicating that PDS silencing was released or weakened in the true leaves. The proportion of transgenic lines showing green true leaves were much higher for the hpPDS[WT] population than for the hpPDS[G:U] population. The transgenic plants were grouped into three different categories based on strong PDS silencing (strong photo-bleaching in whole plant), moderate PDS silencing (pale green or mottled leaves) and weak PDS silencing (fully green or weakly mottled leaves). The proportion of plants with weak PDS silencing was 43% for the hpPDS[WT] lines, compared to 7% for the hpPDS[G:U] lines. In fact, all the hpPDS[G:U] lines of the weak silencing group still showed mild mottling on true leaves, in contrast to the weakly silenced hpPDS [WT] plants that mostly had fully green leaves. These results indicated that the G:U-modified hpRNA construct gave more uniform PDS silencing across the independent transgenic population than the conventional (fully canonically basepaired) hpPDS construct, which was consistent with the results from GUS and EIN2 silencing assays described above. More significantly, the PDS silencing results indicated a developmental variability of hpRNA transgene-induced gene silencing in plants that has not been noted before, and suggested that hpRNA transgene silencing was more efficient and stable in cotyledons than in true leaves. In accordance with the uniform gene silencing across independent lines, the PDS silencing result suggested that the G:U-modified hpRNA transgene was developmentally more stable than the conventional hpRNA construct, providing more stable and long-lasting silencing.

Example 11. Analysis of sRNAs from Hairpin RNA Constructs

Northern blot hybridisation was carried out on RNA samples to detect antisense sRNAs from hpEIN2[G:U] plants and to compare their amount and their sizes to sRNAs produced from hpEIN2[wt]. The probe was a 32P-labelled RNA probe corresponding to the 200 nucleotide sense sequence in the hpEIN2[wt] construct and hybridisation was carried out under low stringency conditions to allow for the detection of shorter (20-24 nucleotides) sequences. The autoradiograph from the probed Northern blot is shown in FIG. 29. This experiment showed that the hpEIN2[G:U] hairpin RNA was processed into sRNAs and the level of accumulation was relatively uniform across the 9 independently transformed hpEIN2[G:U] plants analysed compared to those of the hpEIN2[wt] lines. Similar to the analogous experiment for the GUS hairpin RNAs, a difference in mobility of the two antisense sRNA bands from hpEIN2[G:U] compared to the main two bands from hpEIN2[wt] was quite evident. This was best seen by comparing the mobility of the bands in adjacent lanes 10 and 11 of FIG. 28.

To further investigate this, the small RNA populations from the hpEIN2[wt] and hpEIN2[G:U] are analysed by deep sequencing of the total sRNA populations isolated from whole plants. The proportion of each population that mapped to the double-stranded regions of the hpEIN2[wt] and hpEIN2[G:U] was determined. From about 16 million reads in each population, about 50,000 sRNAs mapped to the hpEIN2[wt] double-stranded region, whereas only about 700 mapped to hpEIN2[G:U]. This indicated that many fewer sRNAs were generated from the [G:U] hairpin. An increase in the proportion of EIN2-specific 22-mers was also observed.

FIG. 29 showed that both the traditional (fully canonically basepaired) and the G:U-modified hpRNA lines accumulated two dominant size fractions of siRNAs. Consistent with previous reports, the dominant siRNAs from the traditional hpRNA lines migrated similarly to the 21 and 24-nt sRNA size markers. However, the two dominant siRNA bands from both of the G:U modified transgenes migrated slightly faster on the gel, suggesting that they either had a smaller size than, or different terminal chemical modifications to, those from the traditional hpRNA transgenes.

To investigate if the size profile of siRNAs might differ between the two different types of constructs, small RNAs were isolated from one hpGUS[WT] line and two lines each of hpGUS[G:U], hpEIN2[WT] and hpEIN2[G:U] and sequenced using the Illumina platform, resulting in approximately 16 million sRNA reads for each sample. Samples from two strongly silenced hpGUS[1:4] lines were also sequenced. The number of sRNAs which mapped to the double-stranded regions and the intron spacer region of the hairpin RNAs was determined. siRNAs were also mapped to the upstream and downstream regions in the target GUS mRNA and EIN2 mRNA to detect transitive siRNAs. The sequencing data confirmed that hpGUS[G:U] lines, like hpGUS[WT] lines, generated abundant siRNAs, whereas hpGUS[1:4] lines also generated siRNAs but with a much lower abundance. The lower levels of siRNAs from the hpGUS[1:4] lines were consistent with the relatively low efficiency of GUS silencing by hpGUS[1:4] and suggested that the low thermodynamic stability of the dsRNA stem in hpGUS[1:4] RNA reduced Dicer processing efficiency relative to the traditional hairpin. There was no clear difference in size distribution of siRNAs between the traditional and mismatched hpRNA lines despite the clear shift in mobility of antisense siRNAs shown on the Northern blot, with all samples showing the 21-nt sRNA as the dominant size class. There were some subtle differences in the proportional abundance of the 22 nt antisense siRNAs between the traditional and mismatched hpGUS lines: the hpGUS[G:U] and hpGUS[1:4] lines showed a higher proportion of the 22-nt size class than the hpGUS[WT] line. A distinct feature of the sequencing data for both the traditional and mismatched hpRNA lines was that the 24-nt siRNAs showed much lower abundance than the 21-nt siRNAs in all samples, namely about 3-21 fold less for the sense 24-nt siRNAs and about 4-35 fold less for the antisense 24-nt siRNAs. This differed markedly from the Northern blot result which showed relatively equal amounts of the two dominant size classes. It was also interesting to note that the hpEIN2[WT]-7 and hpEIN2[G:U]-14/15 samples showed similar abundance of antisense siRNAs on the Northern blot, but in the sequencing data the hpEIN2[G:U] lines gave much smaller numbers of total 20-24 nt antisense siRNA reads (17,290 and 29,211) than the hpEIN2[WT]-7 line (134, 112 reads).

For both the hpGUS[G:U] and hpEIN2[G:U] lines, almost all the sense siRNAs matched the G:U-modified sense sequence of the hpRNA, whereas most of the antisense siRNAs had the wild-type antisense sequence. This indicated that the great majority of these sense and antisense siRNAs were processed directly from the primary hpRNA [G:U] transcripts, but not due to RDR-mediated amplification from the hpRNA or target RNA transcripts, which would otherwise generate both sense and antisense siRNAs of the same template sequences. Consistent with this, only a small number of 20-24 nt sRNA reads (transitive siRNAs) were detected from the loop region (PDK intron) of the hpRNA transgenes or the untargeted downstream region of the GUS or EIN2 mRNA. However, the two hpGUS[1:4] lines showed a relatively high proportion of wild-type sense siRNAs, suggesting that the strong GUS silencing in these two lines, a relatively rare case for the hpGUS[1:4] population, may involve RDR amplification. Indeed, a higher amount of siRNAs were detected from the target gene sequence downstream of the hpRNA target region than from the dsRNA stem in the hpGUS[1:4] lines, indicating the presence of transitive silencing in these lines.

Taken together, the sRNA sequencing data indicated that siRNAs from the traditional and mismatched hpRNA lines had a similar size profile, with the exception of the 22-nt size class, suggesting that the differential migration detected by Northern blot was due to different 5' or 3' chemical modifications. The discrepancy in relative sRNA abundance (eg. the hpEIN2[WT] vs. hpEIN2[G:U]-derived siRNAs and the 21-nt vs. 24-nt) between the Northern blot result and the sequencing data implied that the different siRNA populations and size classes may have different cloning efficiencies during sRNA library preparation.

Plant sRNAs are known to have a 2'-O-methyl group at the 3' terminal nucleotide that is thought to stabilize the sRNAs. This 3' methylation was previously shown to inhibit, but not prevent, 3' adaptor ligation reducing sRNA cloning efficiency (Ebhardt et al 2005). Therefore, hpRNA[WT] and hpRNA[G:U]-derived siRNAs were with sodium periodate in B-elimination assays. The treatment did not cause a shift in gel mobility for both hpRNA[WT] and hpRNA[G:U]-derived siRNAs, indicating that both siRNA populations were methylated at the 3' terminus and there was no difference in 3' chemical modification between the hpRNA[WT] and hpRNA[G:U]-derived siRNAs.

The standard sRNA sequencing protocol is based on sRNAs having 5' monophosphate allowing 5' adaptor ligation (Lau et al., 2001). Dicer-processed sRNAs were assumed to have 5' monophosphate but in *C. elegans* many siRNAs are found to possess di- or tri-phosphate at the 5' terminus which changes gel mobility of sRNAs and prevents sRNA 5' adaptor ligation in the standard sRNA cloning procedure (Pak and Fire 2007). Whether plant sRNAs also have differential 5' phosphorylation was unknown. The 5' phosphorylation status of the hpRNA[WT] and hpRNA[G:U]-derived siRNAs was therefore examined by treating the total RNA with alkaline phosphatase followed by Northern blot hybridization. This treatment reduced the gel mobility for all hpRNA-derived sRNAs, indicating the presence of 5' phosphorylation. However, the hpRNA[G:U]-derived siRNAs showed greater mobility shift than the hpRNA[WT]-derived siRNAs after phosphatase treatment, resulting in the two groups of dephosphorylated siRNAs migrating at the same position on the gel. The 21 and 24-nt sRNA size markers were radio-actively labelled at the 5' end with 32P using polynucleotide kinase reaction, and so should have a monophosphorylated 5' terminus. This suggested that the hpRNA[WT]-derived siRNAs, migrating at the same positions as the size markers, were likely to be monophosphorylated siRNAs, whereas the hpRNA[G:U]-derived siRNAs, migrating faster, have more than one phosphate at the 5' terminus. Thus, it was concluded that the siRNAs produced from the traditional and G:U-modified hpRNA transgenes in plant cells were phosphorylated differently.

Example 12. DNA Methylation Analysis of EIN2 Silenced Plants

Both the GUS and the EIN2 silencing results indicated that the hpRNA constructs having unmodified sense sequences induced highly variable levels of target gene silencing compared to the constructs having modified sense sequences providing for G:U basepairs. As described above, the promoter region of the hpGUS[G:U] construct appeared to have less methylation compared to the hpGUS[wt] construct. To test for DNA methylation and compare the hpEIN2[wt] and hpEIN2[G:U] transgenic plants, 12 plants from each population were analysed for DNA methylation at the 35S promoter and the 35S-promoter-sense EIN2 junction region using the McrBC method. The primers used for the 35S promoter region: Forward primer (Top-35S-F2), 5'-AGAAAATYTTYGTYAAYATGGTGG-3' (SEQ ID NO:82), reverse primer (Top-35S-R2), 5'-TCARTRR-ARATRTCACATCAATCC-3' (SEQ ID NO:83). The primers used for the 35S promoter-sense EIN2 junction region: Forward primer (Link-35S-F2), 5'-YYATYATTGYGA-TAAAGGAAAGG-3' (SEQ ID NO:84) and reverse primer (Link-EIN2-R2), 5'-TAATTRCCACCAARTCATACCC-3' (SEQ ID NO:85). In each of these primer sequences, Y=C or T and R=A or G.

Quantitation of the extent of DNA methylation was determined by carrying out Real-Time PCR assays. For each plant, the quotient was calculated: rate of amplification of the DNA fragment after treatment of the genomic DNA with McrBC/rate of amplification of the DNA fragment without treatment of the genomic DNA with McrBC.

Almost every hpEIN2[wt] plant showed significant levels of DNA methylation at the 35S promoter, particularly at the 35S-EIN2 junction, but some more than others. As shown in FIGS. 30 and 31, the plant lines represented in lanes 1, 4, 7, 9, 11 and 12 all showed strong EIN2 silencing as shown by the longer hypocotyl lengths. In contrast, the other six lines represented in lanes 2, 3, 5, 6, 8, and 10 exhibited relatively weak EIN2 silencing, resulting in shorter hypocotyls. These weaker-silenced lines showed more DNA methylation at the promoter and junction sequences as indicated by much lower PCR band intensity when the genomic DNA was pre-digested with McrBC. The quantitative RealTime PCR (qPCR) assays confirmed these observations (FIG. 31). All 12 of the tested lines showed some extent of DNA methylation in both the 35S promoter region and in the 35S-sense junction region ("junction"). The greatest extent of methylation i.e. the lowest quotient in the qPCR assays, was for hpEIN2[wt] lines 2, 3, 5, 6, 8 and 10, correlating perfectly with the reduced extent of silencing as measured by hypocotyl length. These results confirmed that the reduced EIN2 silencing in some of the hpEIN2[wt] lines was associated with increased promoter methylation. Even in the hpEIN2 [wt] plant lines which were silenced for EIN2, there was still considerable levels of DNA methylation, particularly of the 35S-sense EIN2 junction fragment region. When promoters are methylated, this is thought to cause transcriptional silencing. In the case of silencing constructs, as here, this is a form of "self-silencing".

In contrast to the hpEIN2[wt] lines, the hpEIN2[G:U] lines showed less DNA methylation at both the 35S promoter and the 35S-EIN2 junction. Indeed, four of these 12 G:U lines, corresponding to lanes 1, 2, 3 and 7 in FIG. 30 (lanes 13, 14, 15 and 20 in FIG. 31), had no obvious DNA methylation as indicated by the equal strength of PCR bands between McrBC-treated and untreated samples. When these amplifications were quantitated by qPCR, six of the 12 lines showed little to no reduction in the fragment from the McrBC treatment and therefore little to no DNA methylation-see lower panel of FIG. 31, lines 13, 14, 15, 18, 19 and 20. These results indicated that the relatively uniform EIN2 silencing by the hpEIN2[G:U] construct, at least in some lines, was due to significantly less promoter methylation and therefore less transcriptional self-silencing compared to hpEIN2[wt].

These conclusions were further confirmed by analysis of the genomic DNA from the transgenic plant lines with bisulfite sequencing. This assay made use of the fact that treatment of DNA with bisulfite converted unmethylated cytosine bases in the DNA to uracil (U), but left 5-methylcytosine bases ($^{m}C$) unaffected. Following the bisulfite treatment, the defined segment of DNA of interest was amplified in PCR reactions in a way whereby only the sense strand of the treated DNA was amplified. The PCR product was then subjected to bulk sequencing, revealing the positions and extent of methylation of individual cytosine bases in the segment of DNA. Therefore, the assay yielded single-nucleotide resolution information about the methylation status of a segment of DNA.

The three plant lines showing the strongest levels of EIN2 silencing for each of hpEIN2[wt] and hpEIN2[G:U] were analysed by bisulfite sequencing, corresponding to hpEIN2 [wt] lines 1, 7 and 9 and hpEIN2[G:U] lines 13, 15 and 18 in FIG. 31. These plant lines showed the longest hypocotyl lengths and therefore were expected to have the lowest levels of DNA methylation out of the 20 lines for each construct. The results are presented in FIGS. 32 and 33 for hpEIN2[wt] and hpEIN2[G:U], respectively. When compared, it was clear that numerous cytosines in the 35S promoter region and the EIN2 sense region in the hpEIN2 [wt] plants were extensively methylated. In clear contrast, the three hpEIN2[G:U] plant lines showed much lower levels of cytosine methylation in the 35S promoter region.

Example 13. DNA Methylation Levels in Promoter of the hpGUS[1:4] Construct

When genomic DNA isolated from the hpGUS[1:4] plants was analysed for DNA methylation using the McrBC and bisulfite methods as described above, it was similarly observed that there was less methylation of cytosine bases in the 35S promoter and 35S promoter-GUS sense sequence regions relative to the hpGUS[wt] plants.

General Discussion Relating to Examples 10 to 13

Double-Stranded RNA Having G:U Basepairs Induce More Uniform Gene Silencing than Conventional dsRNA Like the GUS constructs, both hpEIN2[G:U] and hpCHS::EIN2[G:U] induced more consistent and uniform EIN2 silencing than the respective hpRNA[wt] constructs encoding a conventional hairpin RNA. The uniformity not only occurred across many independent transgenic lines, but also across sibling plants within a transgenic line each having the same transgenic insertion. In addition to the uniformity, the extent of EIN2 silencing induced by hpEIN2 [G:U] was close to that of strongly silenced hpEIN2[wt] lines. Analysis of CHS gene silencing indicated that the hpCHS[G:U] construct was effective at reducing CHS mRNA levels by 50-97% but few plants showed a clearly visible phenotype in reduced seed coat colour. The likely explanation for not seeing more visible phenotypes in seed coat colour was that even low levels of CHS activity might be sufficient for producing the flavonoid pigments. Other possible explanations were that the 35S promoter was not sufficiently active in the developing seedcoat to produce the phenotype, or that the hpCHS[G:U] construct sequence contained 65 cytosine substitutions (32.5%), compared to only 43 (21.5%) for the EIN2 sequence and 52 (26%) for the GUS sequence. Furthermore, many of these cytosine bases in the CHS sequence occurred in sets of two or three consecutive cytosines, so not all of those need be substituted. When all of the cytosines in the sense strand were substituted, this resulted in more G:U basepairs in the hpCHS[G:U] RNA than in the hpEIN2[G:U] and hpGUS [G:U] RNAs, perhaps more than optimal. To verify this, another set of CHS constructs are made using a sequence containing a range of cytosine substitutions, from about 5%, 10%, 15%, 20% or 25% cytosine bases substituted. These constructs are tested and an optimal level determined.

The hpEIN2[G:U] Lines Express More Uniform Levels of siRNAs

Consistent with the relatively uniform EIN2 gene silencing, the hpEIN2[G:U] lines accumulated sRNAs with a more uniform level across the independent lines. This confirmed the conclusion with the hpGUS constructs that [G:U] modified hpRNA was efficiently processed by Dicer and capable of inducing effective target gene silencing.

Fusion Constructs Also Provide for Gene Silencing

The purpose of including the CHS: EIN2 fusion constructs in the experiment was to test if two target genes could be silenced with a single hairpin-encoding construct. The GUS experiment suggested that the free energy and therefore stability of the hairpin RNA correlated positively with the extent of target gene silencing. The results showed that the CHS: EIN2 fusion construct did result in silencing of both genes—for CHS at least at the mRNA level.

The two hpRNA constructs, hpEIN2[G:U/U:G] and hpCHS::EIN2[G:U/U:G], in which both the sense and antisense sequences were modified from C to T so that 46% of basepairs were converted from canonical basepairs to G:U basepairs, induced only weak or no EIN2 silencing in most of the transgenic plants. Possible explanations include i) there were too many G:U basepairs which resulted in inefficient Dicer processing, and ii) sRNAs binding to target mRNA including too many G:U basepairs did not induce efficient mRNA cleavage, or a combination of factors.

Increased Uniformity in Target Gene Silencing by the G:U Basepaired Constructs is Associated with Reduced Promoter Methylation DNA methylation analysis using both McrBC-digestion PCR and bisulfite sequencing showed that all hpEIN2[wt] plant lines showed DNA methylation at the promoter region, and the degree of methylation correlated negatively to the level of EIN2 silencing. Even the three least methylated lines, as judged by McrBC-digestion PCR, showed around 40% DNA methylation levels in the 35S promoter, relative to all cytosines being methylated. The widespread promoter methylation was thought to be due to sRNA-directed DNA methylation at the EIN2 repeat sequence that spread to the adjacent promoter region. In contrast to the hpRNA[wt] plant lines, a number of the hpEIN2[G:U] lines showed little to no promoter methylation and most of the plants analysed showed less methylated cytosines. As discussed for the hpGUS lines, several factors may contribute to the reduced methylation: i) the inverted-repeat DNA structure was disrupted by changing C bases to T bases in the sense sequence, and ii) the sense EIN2 sequence lacked cytosines so could not be methylated by sRNA-directed DNA methylation, and iii) a reduced level of production of 24-mer RNAs due to the change in the structure of the dsRNA region with the G:U basepairs, resulting in changes in the recognition by some Dicers and so a decrease in Dicer 3 and/or Dicer 4 activity and relatively more Dicer 2 activity. Thus, the hpEIN2[G:U] transgene may behave like a normal, non-RNAi transgene (such as an over-expression transgene) and the promoter methylation observed in some of the lines was due to T-DNA insertion patterns rather than the inherent inverted-repeat DNA structure of a hpRNA transgene.

Example 14. Modified Hairpins for Reducing Expression of Another Endogenous Gene Genetic constructs for production of modified silencing RNAs, either for hairpin RNAs or ledRNAs, targeting other endogenous genes were designed and synthesized. These included the following.

The FANCM gene in *A. thaliana* and in *Brassica napus* encodes a Fanconi Anemia Complementation Group M (FANCM) protein, which is a DEAD/DEAH box RNA helicase protein, Accession Nos and NM_001333162 and XM_018659358. The nucleotide sequence of the protein coding region of the cDNA corresponding to the FANCM gene of *A. thaliana* is provided in SEQ ID NO:31, and for *B. napus* in SEQ ID NO: 32.

Genetic constructs were designed and made to express hairpin RNAs with or without C to T substitutions and an ledRNA targeting the FANCM gene in *A. thaliana* and in *Brassica napus*. A target region in the *A. thaliana* gene was selected: nucleotides 675-1174 (500 nucleotides) of SEQ ID NO:31. A target region in the *B. napus* gene was selected: nucleotides 896-1395 (500 bp) of SEQ ID NO:32. The constructs encoding the hairpin RNAs, using a wild-type sense sequence or a modified (G:U) sense sequence, were designed and assembled. Nucleotide sequences of the hpFANCM-At[wt], hpFANCM-At[G:U], hpFANCM-Bn [wt] and hpFANCM-Bn[G:U] constructs are provided in SEQ ID NOs: 33-36. To make the G:U constructs, all cytosine bases in the sense sequences were replaced with thymine bases-102/500 (providing 20.4% G:U basepairs) in the *A. thaliana* construct and 109/500 (21.8% G:U basepairs) in the *B. napus* construct. The longest stretch of contiguous canonical basepairing in the double-stranded region of the *B. napus* G:U modified hairpin was 17 basepairs, and the second longest 16 contiguous basepairs.

The DDM1 gene in *B. napus* encodes a methyltransferase which methylates cytosine bases in DNA (Zhang et al., 2018). The nucleotide sequence of the protein coding region of the cDNA corresponding to the DDM1 gene of *B. napus* in SEQ ID NO: 37.

Genetic constructs were designed and made to express hairpin RNAs with or without C to T substitutions and an ledRNA targeting the DDM1 gene in *Brassica napus*. Two non-contiguous target regions of the *B. napus* gene were selected: nucleotides 504-815 and 1885-2074 of SEQ ID NO:37, and were directly joined to make a chimeric sense sequence. The total length of the sense sequence was therefore 502 nucleotides. The constructs encoding the hairpin RNAs, using a wild-type sense sequence or a modified (G:U) sense sequence, were designed and assembled. Nucleotide sequences of the hpDDM1-Bn[wt] and hpDDM1-Bn[G:U] constructs are provided in SEQ ID NOs: 38-39. To make the G:U construct, cytosines in the sense sequences were replaced with thymines—106/502 (21.1% G:U basepairs) in the *B. napus* construct. The longest stretch of contiguous canonical basepairing in the double-stranded region of the G:U modified hairpin was 20 basepairs, and the second longest 15 contiguous basepairs.

For another construct targeting an endogenous gene, a genetic construct was designed to express a hairpin RNA with 95 C to T substitutions in the sense sequence, out of 104 C's in the sense sequence of 350 nucleotides, providing for 95/350=27.1% G:U basepairs in the double-stranded region of the hairpin RNA. That is, not all of the C's in the sense sequence were replaced with T's. In particular, where a run of 3, 4 or 5 contiguous C's occurred in the sense sequence, only 1 or 2 of the three C's, or only 2 or 3 of four C's, or only 2, 3 or 4 of 5 contiguous C's, were replaced with T's. This provided for a more even distribution of G:U basepairs in the double-stranded RNA region. The longest stretch of contiguous canonical basepairing in the double-stranded region was 15 basepairs, and the second longest 13 contiguous basepairs.

A further construct was designed where one or two basepairs in every block of 4, 5, 6 or 7 nucleotides was modified with C to T or A to G substitutions. Where the wild-type sense sequence had a stretch of 8 or more nucleotides consisting of T's or G's, one or more nucleotides were substituted either in the sense strand to create a mismatched nucleotide within that block or a C to T or A to G substitution was made in the antisense strand, so as to avoid a double-stranded stretch of 8 or more contiguous canonical basepairs in the double-stranded region of the resultant hairpin RNA transcribed from the construct.

Example 15. Modified Hairpins for Reducing Expression of Genes in Animal Cells

To test modified silencing RNAs in animal cells, of the G:U basepaired form, the ledRNA form or combining the two modifications, a gene encoding an enhanced green fluorescent protein (EGFP) was used in the following experiments as a model target gene. The nucleotide sequence of the coding region for EGFP is shown in SEQ ID NO: 40. A target region of 460 nucleotides was selected, corresponding to nucleotides 131-591 of SEQ ID NO:40.

A genetic construct designated hpEGFP[wt] was designed and made which expressed a hairpin RNA comprising, in order 5' to 3' with respect to the promoter for expression, an antisense EGFP sequence of 460 nucleotides which was fully complementary to the corresponding region (nucleotides 131-590) of the EGFP coding region, a loop sequence of 312 nucleotides derived in part from a GUS coding region (corresponding to nucleotides 802-1042 of the GUS ORF), and a sense EGFP sequence of 460 nucleotides which was identical in sequence to nucleotides 131-590 of the EGFP coding region. The sequence of the DNA encoding the hairpin RNA hpEGFP[wt] (SEQ ID NO: 41) included a NheI restriction enzyme site at the 5' end and a SalI site at the 3' end to provide for cloning into the vector pCI (Promega Corporation). This vector was suitable for mammalian cell transfection experiments and would provide for expression from the strong CMV promoter/enhancer. The construct also had a T7 promoter sequence inserted between the NheI site and the beginning of the antisense sequence to provide for in vitro transcription to produce the hairpin RNA using T7 RNA polymerase. The hairpin encoding cassette was inserted into the NheI to SalI site in the expression vector pCI whereby the RNA coding region was operably linked to the CMV promoter and the SV40-late polyadenylation/transcription termination region.

A corresponding hairpin construct which had 157 C to T substitutions in the sense sequence and no substitutions in the antisense sequence was designed and made, designated hpEGFP[G:U] (SEQ ID NO:42). The target region in the EGFP coding region was nucleotides 131-590. The percentage of C to T substitutions and therefore G:U basepairs in the stem of the hairpin RNA was 157/460=34.1%. The sense and antisense sequences were identical in length at 460 nucleotides. In the art of gene silencing, long double-stranded RNAs are generally avoided because of the potential for activating cellular response including interferon activation.

An ledRNA construct designated ledEGFP[wt] was designed and made to express an ledRNA comprising, in order 5' to 3' with respect to the promoter for expression, an antisense EGFP sequence of 228 nucleotides which was fully complementary to nucleotides 131-358 of the EGFP coding sequence, a loop sequence of 150 nucleotides, a sense EGFP sequence of 460 nucleotides which was identical in sequence to nucleotides 131-590 of the EGFP coding region (SEQ ID NO:40), a loop sequence of 144 nucleotides, and an antisense sequence of 232 nucleotides which was fully complementary to nucleotides 359-590 of the EGFP coding sequence, flanked by NheI and SalI restriction sites (SEQ ID NO:43). The encoded ledRNA was therefore of the type shown in FIG. 1A. The ledRNA structure, when self-annealed by basepairing between the one sense and two antisense sequences, had a double-stranded region of 460 basepairs corresponding to the EGFP target region, with the two antisense sequences not directly joined covalently to each other but having a "gap" or "nick" between the ends corresponding to nucleotides 358 and 359. The ledRNA structure was embedded in a larger RNA transcript including 5'- and 3'-regions coming from sequences in the CMV promoter and SV40-late polyadenylation/transcription termination regions.

A corresponding ledRNA construct which had 162 C to T substitutions in the sense sequence and no substitutions in the antisense sequence was also designed and made, designated ledEGFP[G:U] (SEQ ID NO:44). In each case, the target region in the EGFP coding region was nucleotides 131-590 relative to the protein coding region starting with the ATG start codon (SEQ ID NO:40). The percentage of C to T substitutions and therefore G:U basepairs in the stem of the ledRNA was 162/460=35.2%.

Plasmids encoding the hpEGFP[wt], hpEGFP[G:U], ledEGFP[wt] and ledEGFP[G:U] silencing RNAs were tested for gene silencing activity in CHO, HeLa and VERO cells by transfection of the vectors into the cells. The assays were conducted by co-transfection of the test plasmids with a GFP expressing plasmid. All assays were conducted in triplicate. CHO cells (Chinese Hamster Ovary cells) and VERO cells (African Green monkey kidney cells) were seeded into 24 well plates at a density of $1\times10^5$ cells per well. CHO cells were grown in MEMα modification (Sigma, USA), and HeLa and VERO cells were grown in DMEM (Invitrogen, USA). Both base media were supplemented with 10% foetal bovine serum, 2 mM glutamine, 10 mM Hepes, 1.5 g/L sodium bicarbonate, 0.01% penicillin and 0.01% streptomycin. Cells were grown at 37° C. with 5% $CO_2$. Cells were then transfected with 1 μg per well with plasmid DNA, or siRNA as a control for EGFP silencing, using Lipofectamine 2000. Briefly, the test siRNA or plasmid was combined with the GFP reporter plasmid (pGFP N1) and then mixed with 1 μl of Lipofectamine 2000, both diluted in 50 μl OPTI-MEM (Invitrogen, USA) and incubated at room temperature for 20 mins. The complex was then added to cells and incubated for 4 hr. Cell media was replaced and the cells incubated for 72 hr. Cells were next subjected to flow cytometry to measure GFP silencing. Briefly, cells to be analysed were trypsinized, washed in PBSA, resuspended in 200 μL of 0.01% sodium azide and 2% FCS in PBSA and analysed using a FACScalibur (Becton Dickinson) flow cytometer. Data analysis was performed using CELLQuest software (Becton Dickinson) and reported as mean fluorescence intensity (MFI) as a percentage of control cells with reporter and non-related (negative control) shRNA.

The anti-GFP siRNA referred to as si22 was obtained from Qiagen (USA). The anti-GFP siRNA sequence of si22 was sense 5'-GCAAGCUGACCCUGAAGUUCAU-3' (SEQ ID NO:86) and antisense 5'-GAACUUCAGGGUCAGCUUGCCG-3' (SEQ ID NO: 87). A positive control genetic construct designated as pshGFP was created via a one-step PCR reaction using the mouse U6 sequence as the template. Forward primer was 5'-TTTTAGTATATGTGCTGCCG-3' (SEQ ID NO:88) and reverse primer was 5'-CTCGAGTTCCAAAAAAGCTGACCCTGAAGTTCATCTCTCTTGAAGATGAAC TTCAGGGTCAGCCAAACAAGGCTTTTCTCCAA-3' (SEQ ID NO:89). An amplification product which included the full-length expression cassette was ligated into pGEM-T Easy. A non-related shRNA control plasmid was also constructed via the same PCR method. For that construction, the forward primer was 5'-TTTTAGTATATGTGCTGCCG-3' (SEQ ID NO:90) and the reverse primer was 5'-ctcgagttccaaaaaaataagtcgcagcagtacaatctcttgaattgtactgctgcgacttatgaataccgcttcctcctgag-3' (SEQ ID NO: 91).

The resultant data from one experiment are shown in FIG. 34. Clear reduction in EGFP activity (RNA silencing) was observed in both VERO and CHO cells for both si22 and pshGFP positive controls when compared to the irrelevant shRNA control. These positive controls were a well validated small dsRNA molecule (si22) or encoded a shRNA (pshGFP) that were known to have very strong silencing activity in mammalian cells. The control RNA molecules have double-stranded regions of 20 contiguous basepairs and 21 contiguous basepairs, respectively, using only canonical basepairs and without any mismatched nucleotides in the double-stranded regions, and within the range of 20-30 basepairs long generally used for mammalian cells. In contrast, the hpRNA and ledRNA constructs express molecules having long dsRNA regions. All fours constructs were observed to specifically silence EGFP expression to significant extents in both cell types (FIG. 34). The inclusion of the G:U substitutions gave a pronounced improvement in silencing for both constructs in CHO cells. In VERO cells, a pronounced improvement in silencing was only observed with the ledEGFP[G:U] construct relative to ledEGFP[wt].

In a second experiment using HeLa (human) cells and assaying EGFP activity at 48 hr post-transfection, similar results were obtained (FIG. 35).

It was significant to note that the gene silencing was observed in mammalian cells using the hpRNA and ledRNA effector molecules given that they had longer double-stranded regions than the conventional 20 to 30 bp size range. It was also clear that the modification to substitute nucleotides to create the G:U basepairs significantly enhanced the gene silencing effect of these longer dsRNA molecules. This effect may be due to these structures more closely resembling endogenous priRNAs, the precursors of miRNAs, observed in eukaryotic cells and thus improving the processing of the longer dsRNA for loading into the RNA induced silencing complex (RISC) effector proteins.

Example 16. RNA Constructs Targeting DDM1 and FANCM Genes in Plants

The inventors considered ways to increase the rate by which novel genetic profiles and diversity (genetic gain) could be generated and explored for desirable performance traits in plants. One way that was considered was to find a way to increase the rate of recombination that occurs during sexual reproduction of plants. Plant breeders rely on recombination events to create different genetic (allelic) combinations that they can search through for the desired genetic profile associated with performance gains. However, the number of recombination events in each breeding step is extremely low relative to the number of possible genetic profiles that could be explored. In addition, the elements that control where these events occur in the genome are not well understood. The inventors therefore considered whether ledRNA delivered either exogenously or endogenously through a transgenic approach could be used to modify recombination rates in plants to allow rapid increases in genetic diversity and make possible faster genetic gain within breeding populations.

The epigenome of plants is influenced by a range of different chemical modifications on the DNA and associated proteins that organize, package and stabilize the genome. These modifications also regulate where recombination takes place, with tight genome packaging being a strong inhibitor of recombination (Yelina et al, 2012; Melamed-Bessudo et al., 2012). DECREASED DNA METHYLATION 1 (DDM1) is an enzyme which regulates methylation of DNA and genome packaging. Mutation of this gene can alter the position of recombination events (Yelina et al, 2012; Melamed-Bessudo et al., 2012).

Recombination events during meiosis are tightly regulated with only 1-2 events occurring on each chromosome to ensure proper chromosome segregation at metaphase 1. Recombination events are initiated though double stranded breaks (DSB) of the DNA through the enzyme SPO11 (Wijnker et al, 2008). This results in hundreds of DSB along the chromosome. While a few of these DSB result in crossovers, the majority are repaired by DNA repair enzymes, before a recombination event can take place. Furthermore there are a number of negative regulators which inhibit DSB developing into crossovers. In an initial approach contemplated by the inventors, genetic constructs encoding ledRNA molecules or conventional hairpin RNA molecules as a comparison were to be introduced into *A. thaliana* plants, targeting a gene encoding a protein factor which could potentially impact recombination rates such as FANCONI ANEMIA COMPLEMENTATION GROUP M (FANCM).

The nucleotide sequence of the DDM1 gene of *A. thaliana* was provided by Accession No. AF143940 (Jeddeloh et al., 1999). Reduction of DDM1 gene expression has been shown to decrease DNA methylation and increase the number and position of cross over events in *A. thaliana* (Melamed-Bessudo and Levy, 2012).

*Brassica napus* is an allotetraploid species and has two DDM1 genes on each of the A and C subgenomes, on chromosomes A7, A9, C7 and C9, therefore having a total of four DDM1 genes. These genes are designated BnaA07g37430D-1, BnaC07g16550D-1, BnaA09g52610D-1 and BnaC09g07810D-1. The nucleotide sequence of the DDM1 gene BnaA07g37430D-1 of *B. napus* is provided by Accession No. XR 001278527 (SEQ ID NO:93). A hairpin RNA construct was designed and made targeting a 500 nucleotide region of the four genes, corresponding to nucleotides 650-959 and 2029-2218 of SEQ ID NO:93. The nucleotide region used to design the hpRNA and ledRNA constructs targeted all four of the DDM1 genes BnaA07g37430D-1, BnaC07g16550D-1, BnaA09g52610D-1 and BnaC09g07810D-1 present in *B. napus*, based on sequence conservation between the genes. The order of elements in the hpRNA construct was promoter-sense sequence-loop sequence comprising an intron from Hellsgate vector-antisense sequence-transcription terminator/polyadenylation region. The nucleotide sequence of the chimeric DNA encoding the hpRNA is provided as SEQ ID NO:94.

A second hairpin RNA construct was made encoding a hairpin RNA targeting the same 500 nucleotide region and having the same structure except that 97 cytosine nucleotides (C) of the sense sequence were replaced with thymidine nucleotides (T). When the chimeric DNA was transcribed and the G:U substituted hpRNA was self-annealed, this provided for 97/500=19.4% of the nucleotides in the dsRNA region being basepaired in a G:U basepair. The nucleotide sequence of the chimeric DNA encoding the G:U-modified hpRNA is provided as SEQ ID NO:95. Further, a chimeric DNA encoding a ledRNA targeting the same region of the DDM1 gene of *B. napus* was made. The nucleotide sequence of this chimeric DNA encoding the ledRNA is provided as SEQ ID NO:96.

For production of the RNAs by in vitro transcription, DNA preparations were cleaved with the restriction enzyme HincII which cleaved immediately after the coding region, transcribed in vitro with RNA polymerase T7, the RNA purified and then concentrated in an aqueous buffer solution. LedRNA was used to target endogenous DDM1 transcripts in *B. napus* (canola) cotyledons. Cotyledons from five-day-old seedlings grown aseptically on tissue culture medium were carefully excised and placed in a petri dish containing 2 ml MS liquid media, comprising 2% (w/v) sucrose, with 113 μg of ledRNA or 100 ul of aqueous buffer solution as a control. MS liquid media used for the treatments contained Silwett-77, a surfactant (0.5 μl in 60 ml). The petri dishes were incubated on a shaker with gentle shaking, so that the cotyledons soaked in the solution containing the ledRNA. Samples were harvested 5 hr and 7 hr after application of the ledRNA. In a parallel experiment, the upper surface of cotyledons was coated either with 10 μg of ledRNA or buffer solution and incubated on a wet tissue paper. Samples were collected 7 hr after ledRNA application.

Furthermore, in order to target the DDM1 endogenous transcripts in reproductive tissue of *B. napus*, canola floral buds were exposed to ledRNA either in the presence or absence of an aliquot of an *Agrobacterium tumefaciens* strain AGL1 cell suspension, i.e. living AGL1 cells. Aqueous buffer solution with or without the AGL1 cells served as respective controls. The AGL1 was grown in 10 ml of LB liquid media containing 25 mg/ml rifampicin for two days at 28° C. The cells were harvested by centrifugation at 3000 rpm for 5 minutes. The cell pellet was washed and the cells resuspended in 2 ml liquid MS media. Floral buds were incubated in a petri dish containing 2 ml of MS liquid media, including 0.5 μl of Silwett-77 in 50 ml of MS liquid media, with 62 μg of ledRNA or 62 μg+50 μl of AGL1 culture. As controls, 50 μl of buffer solution or 50 μl of buffer solution+50 μl of AGL1 culture was used. Samples were incubated on a shaker with gentle shaking for 7 hr. Three biological replicates were used for each of the treatments.

The treated and control cotyledons and floral buds were washed twice in sterile distilled water, the surface water removed using a tissue paper and flash frozen with liquid nitrogen. RNA was isolated from the treated and control tissues, treated with DNase to remove genomic DNA and quantified. First strand cDNA was synthesized using equal amounts of total RNA from ledRNA-treated samples and their respective controls. Expression of DDM1 was analysed using quantitative real-time PCR (qRT-PCR).

In the treated cotyledons that were soaked with the ledRNA, DDM1 transcript abundance was decreased by approximately 83-86% at 5 hr, which decreased further with a reduction of 91% at 7 hr compared to the controls. Similarly, a reduction of approximately 78-85% in the DDM1 mRNA level compared to the control was observed in cotyledons that were coated with ledRNA. No difference in DDM1 mRNA abundance was detected in the floral buds that were treated with ledRNA compared to control in the absence of *Agrobacterium* cells. However, a reduction of approximately 60-75% in DDM1 transcript levels was observed in floral buds that were treated with ledRNA in presence of *Agrobacterium* compared to its respective control. No significant difference in DDM1 transcript levels was detected when the control without *Agrobacterium* was compared with the control that had *Agrobacterium* showing that the *Agrobacterium* cells themselves were not causing the decrease in DDM1 transcript. Taken together, these results indicated that the ledRNA was able to reduce endogenous DDM1 transcript levels in both cotyledons and floral buds, while living *Agrobacterium* cells appeared to facilitate the ledRNA entry into the floral buds. Such accessibility of the ledRNA might also be achieved by physical means such as piercing the outer layers of the floral buds, centrifugation or vacuum infiltration, or a combination of such methods.

Certain *Arabidopsis thaliana* mutants such as zip4 mutants lack meiotic crossovers, causing mis-segregation of chromosome homologs and thus reduced fertility and leading to shorter siliques (fruit) that can be visually discriminated from that of the wild-type. The phenotype in zip4 mutants can be reversed by reducing FANCM gene expression.

The nucleotide sequence of the FANCM gene of *A. thaliana* was provided by Accession No. NM_001333162 (SEQ ID NO:97). A hairpin RNA construct was designed and made targeting a 500 nucleotide region of the gene, corresponding to nucleotides 853-1352 of SEQ ID NO:97. The order of elements in the construct was promoter-sense sequence-loop sequence comprising an intron from Hellsgate vector-antisense sequence-transcription terminator/polyadenylation region. The nucleotide sequence of the chimeric DNA encoding the hpRNA is provided as SEQ ID NO:98. A second hairpin RNA construct was made encoding a similar hairpin RNA targeting the same 500 nucleotide region except that 102 cytosine nucleotides (C) of the sense sequence were replaced with thymidine nucleotides (T). When the chimeric DNA was transcribed and the resultant G:U substituted hpRNA self-annealed, this provided for 102/500=20.4% of the nucleotides in the dsRNA region being basepaired in a G:U basepair. The nucleotide sequence of the chimeric DNA encoding the G:U-modified hpRNA is provided as SEQ ID NO:99. Further, a chimeric DNA encoding a ledRNA targeting the same region of the FANCM gene of *A. thaliana* was made. The nucleotide sequence of this chimeric DNA encoding the ledRNA is provided as SEQ ID NO:100.

*B. napus* has one FANCM gene on each of its A and C subgenomes, designated BnaA05g18180D-1 and BnaC05g27760D-1. The nucleotide sequence of one of the FANCM genes of *B. napus* is provided by Accession No. XM_022719486.1; SEQ ID NO: 101). A chimeric DNA encoding the hairpin RNA was designed and made targeting a 503 nucleotide region of the genes, corresponding to nucleotides 2847-3349 of SEQ ID NO:101. The order of elements in the construct was promoter-sense sequence-loop sequence comprising an intron from Hellsgate vector-antisense sequence-transcription terminator/polyadenylation region. The nucleotide sequence of the chimeric DNA encoding the hpRNA is provided as SEQ ID NO:102. A second hairpin RNA construct was made encoding a similar hairpin RNA targeting the same 503 nucleotide region except that 107 cytosine nucleotides (C) of the sense sequence were replaced with thymidine nucleotides (T). When the chimeric DNA was transcribed and the G:U substituted hpRNA self-annealed, this provided for 107/500=21.4% of the nucleotides in the dsRNA region being basepaired in a G:U basepair. The nucleotide sequence of the chimeric DNA encoding the G:U-modified hpRNA is provided as SEQ ID NO:103. Further, a chimeric DNA encoding a ledRNA targeting the same region of the FANCM gene of *B. napus* was made. The nucleotide sequence of this chimeric DNA encoding the ledRNA is provided as SEQ ID NO: 104.

For production of the RNAs by in vitro transcription, DNA preparations were cleaved with the restriction enzyme HincII which cleaved immediately after the coding region, transcribed in vitro with RNA polymerase T7, the RNA purified and then concentrated in an aqueous buffer solution. LedRNA was used together with *Agrobacterium tumefaciens* AGL1 to target FANCM transcripts in pre-meiotic buds of a zip4 mutant of *A. thaliana*. Siliques of the zip4 mutant were shorter, readily observed visually, relative to wild-type siliques due to attenuated crossover formation, thus causing reduced fertility. Repressing FANCM in the zip4 mutant has been shown to restore the fertility and restore silique length.

The *A. thaliana* zip4 inflorescences containing the pre-meiotic buds were contacted with ledRNA targeting FANCM together with AGL1 or buffer solution with AGL1 as control, in each case in the presence of a surfactant, in this case Silwett-77. Once the seed setting was complete, the siliques developed from pre-meiotic buds were excised to determine the seed numbers. Among the 15 siliques from ledRNA-treated samples, two siliques displayed 10 seeds, one silique had 9 seeds, while the number of seeds in control siliques ranged from 3 to 6. These results indicated that the observed increase in seed number was due to the repression of FANCM transcript levels by the ledRNA, thereby resulting in an increased number of meiotic crossovers and increased fertility.

Example 17. RNA Constructs for Resistance to Fungal Disease

LedRNA Targeting Mlo Genes of Barley and Wheat

The fungal disease of cereal plants, powdery mildew, is caused by the ascomycete *Blumeria graminis* f. sp. *hordei* in barley and the related *Blumeria graminis* f. sp. *tritici* in wheat. *B. graminis* is an obligate biotrophic fungal pathogen of the order Erysiphales (Glawe, 2008) which requires a plant host for reproduction, involving a close interaction between fungal and host cells in order for the fungus to acquire nutrient from the plant. The fungus initially infects the epidermal layer of leaves, leaf sheaths or ears after fungal ascospores or conidia contact the surface. Leaves remain green and active for some time following infection, then powdery, mycelial masses grow and the leaves gradually become chlorotic and die off. As the disease progresses, the fungal mycelium may become dotted with tiny black points which are the sexual fruiting bodies of the fungus. Powdery mildew disease has a worldwide distribution and is most damaging in cool, wet climates. The disease impacts grain yield mainly by reducing the number of heads as well as reducing kernel size and weight. Currently, disease control is by spraying crops with fungicide which needs to be applied frequently when conditions are cool and damp, and is expensive, or by growing resistant cultivars. Moreover, fungicide resistance has emerged for powdery mildew in wheat in Australia.

The Mlo genes of barley and wheat encode Mlo polypeptides which confer susceptibility to *B. graminis* by an unknown mechanism. There are multiple, closely related MLO proteins encoded by a Mlo gene family which are unique to plants. Each gene encodes a seven-transmembrane domain protein of unknown biochemical activity localized in the plasma membrane. Significantly, only specific Mlo genes within the family are capable of acting as powdery mildew susceptibility genes and these encode polypeptides with conserved motifs within the cytoplasmic C-terminal domain of the Mlo proteins. The mechanism by which Mlo polypeptides act as powdery mildew susceptibility factors is unknown. Occurrence of natural wheat mlo mutants has not been reported, presumably because of the polyploid nature of wheat. However, artificially generated mlo mutants show some resistance to the disease but often exhibit substantially reduced grain yield or premature leaf senescence (Wang et al., 2014; Acevedo-Garcia et al., 2017).

Hexaploid wheat has three homeologs of Mlo genes, designated as TaMlo-A1, TaMlo-B1 and TaMlo-D1 located on chromosomes 5AL, 4BL and 4DL respectively (Elliott et al., 2002). Nucleotide sequences of cDNAs corresponding to the genes are available as Accession Nos: TaMlo-A1, AF361933 and AX063298; TaMlo-B1, AF361932, AX063294 and AF384145; and TaMlo-D1, AX063296. The nucleotide sequences of the genes on the A, B and D genomes and the amino acid sequences of the encoded polypeptides are approximately 95-97% and 98% identical, respectively. All three genes are expressed in leaves of the plants with the expression levels increasing as the plants grow and mature. The inventors therefore designed and made a ledRNA construct which would be capable of reducing expression of all three genes, taking advantage of the degree of sequence identity between the genes and targeting a gene region with high degree of sequence conservation.

A chimeric DNA encoding a ledRNA construct targeting all three of the TaMlo-A1, TaMlo-B1 and TaMlo-D1 genes was made. The genetic construct was made using the design principles for ledRNAs described above, with the split sequence being the antisense sequence and the contiguous sequence being the sense sequence (FIG. 1A).

A 500 bp nucleotide sequence of a TaMlo target gene was selected, corresponding to nucleotides 916-1248 fused with 1403-1569 of SEQ ID NO: 136. The dsRNA region of each ledRNA was 500 bp in length; the sense sequence in the dsRNA region was an uninterrupted, contiguous sequence, for example corresponded to nucleotides 916-1248 fused with 1403-1569 of SEQ ID NO:136. The nucleotide sequence encoding the ledRNA is provided herein as SEQ ID NO: 137.

The ledRNA was prepared by in vitro transcription using T7 RNA polymerase, purified and resuspended in buffer. 10 μg of ledRNA per leaf was applied using a paint brush to a zone of leaves in wheat plants at the Zadoks 23 stage of growth. As controls, some leaves were mock-treated using buffer alone. Treated and control leaf samples were harvested and RNA extracted. QPCR assays on the extracted RNAs showed that TaMlo mRNA levels, being a combination of the three TaMlo mRNAs, were reduced by 95.7%. Plants at the Z73 stage of growth were also treated and assayed. They showed a 91% reduction in TaMlo gene expression by QPCR relative to the control leaf samples. The reduction in TaMlo gene expression observed in the treated leaf areas was specific to the treated zones—there was no reduction in TaMlo mRNA levels in distal, untreated parts of the leaves.

In barley mlo mutants, expression of a variety of disease defence-related genes was observed to be increased. Therefore, the ledRNA-treated wheat leaves were assayed by QPCR for the levels of defence related genes encoding PR4, PR10, ß-1,3-glucanase, chitinase, germin and ADP-ribosylation factor. None of these genes were altered significantly in expression level in the treated leaf areas relative to the control leaf areas.

To test for ability of the ledRNA to increase disease resistance by reducing Mlo gene expression, spores of the powdery mildew fungus were applied to the treated and untreated zones of the leaves. Leaves were detached from wheat plants, treated with the ledRNA as before and maintained on medium (50 mg Benzimidazole and 10 g agar per Litre of water) to prevent the leaves from senescencing, under light. Twenty-four hours later, the leaves were inoculated with powdery mildew spores and disease progression followed for 5 to 24 days. Treated leaves showed little to no fungal mycelium growth and no leaf chlorosis relative to control leaves, not having received the ledRNA, which showed extensive mycelial growth surrounded by chlorotic zones.

In further experiments, lower levels of the ledRNA were applied to identify the minimal level of the ledRNA that was effective. Application of RNA in concentrations as low as 200 ng/μl (2 μg per leaf total) showed significant suppression of powdery mildew lesions in the current formulations, suggesting the amount of inhibitory RNA could be substantially reduced while still providing suppression of fungal growth and development. Further, leaves were inoculated 1, 2, 4, 7 and 14 days after the ledRNA treatment to see how long the protective effect remained. Effective silencing of the endogenous gene was observed throughout the time course from the first time point at 24 hours after treatment until the last time point at 14 days after treatment when the endogenous genes still showed 91% reduction in expression. Whole plants will also be sprayed with ledRNA preparations and tested for disease resistance after being inoculated with the fungal disease agent.

LedRNA Targeting VvMLO Genes of *Vitis vinifera*

The MLO genes of *Vitis vinifera* and *Vitis pseudoreticulata* encode MLO polypeptides which confer susceptibility to the fungal disease powdery mildew, caused by the ascomycete fungus, *Erysiphe necator. E. necator* is an obligate biotrophic fungal pathogen which requires a plant host for reproduction, involving a close interaction between fungal and host cells in order for the fungus to acquire nutrient from the plant. There are multiple, closely related MLO proteins encoded by a gene family all of which are unique to plants and encode seven-transmembrane domain proteins of unknown biochemical activity localized in the plasma membrane. Significantly, only specific MLO genes within the family are capable of acting as powdery mildew susceptibility genes and these encode polypeptides with conserved motifs within the cytoplasmic C-terminal domain of the MLO proteins. The mechanism by which MLO polypeptides act as powdery mildew susceptibility factors is unknown.

LedRNA constructs targeting three different but related MLO genes of *Vitis* species, namely VvMLO3, VvMLO4 and VvMLO17 (nomenclature according to Feechan et al., Functional Plant Biology, 2008, 35:1255-1266) were designed and made as follows. For the first one, for example, a 860 nucleotide sequence of a VvMLO3 target gene was selected, corresponding to nucleotides 297-1156 of SEQ ID NO: 138. Chimeric DNAs encoding three ledRNA constructs targeting VvMLO3, VvMLO4 and VvMLO17 genes were made. The genetic constructs were made using the design principles for ledRNAs described above, with the split sequence being the antisense sequence and the contiguous sequence being the sense sequence (FIG. 1A). The dsRNA region of each ledRNA was 600 bp in length; the sense sequence in the dsRNA region was an uninterrupted, contiguous sequence, for example corresponded to nucleotides 427-1156 of SEQ ID NO:138. The nucleotide sequence encoding one of the ledRNAs is provided herein as SEQ ID NO: 139.

The ledRNAs are prepared by in vitro transcription and applied, separately or as a mixture of all three, to leaves of *Vitis vinifera* plants, variety Cabernet Sauvignon. Subsequently, spores of the powdery mildew fungus are applied to the treated and untreated zones of the leaves. Reduction in the levels of the target mRNAs was observed using quantitative RT-PCR. Disease progression is followed over time. Substantial down-regulation of VvMlo4 was observed from application of ledRNA solution at 1 μg/ml targeting VvMlo3, VvMlo4 or VvMlo11.

LedRNA Targeting Fungal Genes

LedRNA constructs were designed against the coding region of the Cyp51 gene of the fungal pathogen *Rhizoctonia solani*, a gene which is required for synthesis of ergosterol and survival and growth of the fungus. The genetic constructs were made using the design principles for ledRNAs described above, with the split sequence being the antisense sequence and the contiguous sequence being the sense sequence (FIG. 1A). A single ledRNA construct was designed to target two genes from *R. solani* with the dsRNA region of the ledRNA containing 350 bp from each gene; the sense sequence in the dsRNA region was an uninterrupted, contiguous sequence, for example corresponded to nucleotides 884-1233 of SEQ ID NO:140 and nucleotides 174-523 of SEQ ID NO:141. The nucleotide sequence encoding one of the ledRNAs is provided herein as SEQ ID NO:142. The ledRNAs were prepared by in vitro transcription and applied to culture medium at a concentration of 5 μg per 100 μl culture with an inoculum of *R. solani* mycelium. Growth of the fungus was measured at time zero and each day over the following week by reading the optical density of the culture at 600 nm. The growth of *R. solani* in cultures containing the ledRsCyp51 was significantly less than the control cultures containing either RNA buffer or the control ledGFP for which there is no corresponding target in *R. solani*.

A ledRNA-encoding construct was also designed and made against the coding region of the CesA3 cellulose synthase gene in *Phytophthora cinnamomi* isolate 94.48. The genetic constructs were made using the design principles for ledRNAs described above, with the split sequence being the antisense sequence and the contiguous sequence being the sense sequence (FIG. 1A). A ledRNA construct was designed to target the CesA3 gene of *Phytophthora cinnamomi* with the dsRNA region of the ledRNA containing 500 bp from the coding region of the gene; the sense sequence in the dsRNA region was an uninterrupted, contiguous sequence, for example corresponded to nucleotides 884-1233 of SEQ ID NO:143. The nucleotide sequence encoding one of the ledRNAs is provided herein as SEQ ID NO:144. The ledRNA was transcribed in vitro and applied to culture media at a rate of 3 μg per 100 μl culture. Substantial loss of directional mycelial growth was observed in cultures with the ledRNA targeting PcCesA3 compared to mock treated (RNA buffer only) or ledGFP treated cultures. The loss of directional growth and resulting amorphous, bulbous growth pattern was reminiscent of cells with disruption of cell wall biosynthesis and thus was consistent with silencing of the PcCesA3 gene.

Example 18. RNA Constructs Targeting Other Genes in Plants

LedRNAs Targeting Tor Genes of *A. Thaliana* and *N. benthamiana*

The Target of Rapamycin (TOR) gene encodes a serine-threonine protein kinase polypeptide that controls many cellular functions in eukaryotic cells, for example in response to various hormones, stress and nutrient availability. It is known as a master regulator that regulates the translational machinery to optimise cellular resources for growth (Abraham, 2002). At least in animals and yeast, TOR polypeptide is inactivated by the antifungal agent rapamycin, leading to its designation as Target of Rapamycin. In plants, TOR is essential for embryonic development in the developing seed, as shown by the lethality of homozygous mutants in TOR (Mahfouz et al., 2006), as well as being involved in the coupling of growth cues to cellular metabolism. Down-regulation of TOR gene expression was thought to result in an increase in fatty acid synthesis resulting in increased lipid content in plant tissues.

LedRNA constructs targeting a TOR gene of *Nicotiana benthamiana*, the nucleotide sequence of the cDNA protein coding region is provided as SEQ ID NO: 105, were designed and made using the design principles for ledRNAs with the split sequence being the sense sequence and the contiguous sequence being the antisense sequence (FIG. 1B). The target region was 603 nucleotides in length, corresponding to nucleotides 2595-3197 of SEQ ID NO: 105. The dsRNA region of the ledRNA was 603 bp in length; the antisense sequence in the dsRNA region was an uninterrupted, contiguous sequence corresponded to the complement of nucleotides 2595-3197 of SEQ ID NO:105. The nucleotide sequences encoding the ledRNA is provided herein as SEQ ID NO:106. DNA preparations of the genetic constructs encoding the ledRNA constructs were cleaved with the restriction enzyme MlyI which cleaved the DNA immediately after the coding region, transcribed in vitro with RNA polymerase SP6 and the RNA purified and then concentrated in an aqueous buffer solution. Samples of the ledRNA were applied to the upper surface of *N. benthamiana* leaves. After 2 days and 4 days, the treated leaf samples were harvested, dried, and the total fatty acid content measured by quantitative gas chromatography (GC). The leaf samples treated with the TOR ledRNAs showed an increase in total fatty acid (TFA) content from 2.5-3.0% (weight of TFA/dry weight) observed in the control (untreated) samples to between 3.5-4.0% for the ledRNA treated samples. That represented an increase of between 17% and 60% in the TFA content relative to the control, indicating that the TOR gene expression had been reduced in the ledRNA treated tissues.

LedRNA Targeting ALS Gene of *H. vulgare*

Acetolactate synthase (ALS) genes encode an enzyme (EC 2.2.1.6) found in plants and microorganisms which catalyse the first step in the synthesis of the branched chain amino acids leucine, valine and isoleucine. The ALS enzyme catalyses the conversion of pyruvate to acetolactate which is then further converted to the branched chain amino acids by other enzymes. Inhibitors of ALS are used as herbicides such as the sulfonylurea, imidazolinone, triazolopyrimidine, pyrimidinyl oxybenzoate and sulfonylamino carbonyl triazolinones classes of herbicides.

To test whether a ledRNA could reduce ALS gene expression by exogenous delivery of the RNA to plants, a genetic construct encoding a ledRNA was designed and made that targeted an ALS gene in barley, *Hordeum vulgare*. The *H. vulgare* ALS gene sequence is provided herein as SEQ ID NO:107 (Accession No. LT601589). The genetic construct was made using the design principles for ledRNAs, with the split sequence being the sense sequence and the contiguous sequence being the antisense sequence (FIG. 1B). The target region was 606 nucleotides in length, corresponding to nucleotides 1333-1938 of SEQ ID NO:107. The dsRNA region of the ledRNA was 606 bp in length; the antisense sequence in the dsRNA region was an uninterrupted, contiguous sequence corresponded to the complement of nucleotides 1333-1938 of SEQ ID NO:107. The nucleotide sequences encoding the ledRNA is provided herein as SEQ ID NO:108. The coding region was under the control of a SP6 RNA polymerase promoter for in vitro transcription.

The genetic construct encoding the ledRNA was digested with the restriction enzyme MlyI, which cleaved downstream of the ledRNA coding region, and transcribed in vitro with RNA polymerase SP6 according to the instructions with the transcription kit. The RNA was applied on the upper surface of leaves of barley plants. RNA was extracted from the treated leaf samples (after 24 hours). Quantitative reverse transcription-PCR (QPCR) assays were carried out on the RNA samples. The assays showed that the level of ALS mRNA was reduced in the ledRNA treated tissues. (Total RNA was extracted for treated and untreated plants, DNase treated, quantified and 2 μg reverse transcribed using primer CTTGCCAATCTCAGCTGGATC. The cDNA was used as template for quantitative PCR using the forward primer TAAGGCTGACCTGTTGCTTGC and reverse primer CTTGCCAATCTCAGCTGGATC. ALS mRNA expression was normalised against the *Hordeum chilense* isolate H1 lycopene-cyclase gene. ALS expression was reduced by 82% in LED treated plants.

LedRNAs Targeting NCED1 and NCED2 Genes of Wheat and Barley

In plants, the plant hormone abscisic acid (ABA) is synthesized from carotenoid precursors with the first committed step in the synthesis pathway being catalyzed by the enzyme 9-cis epoxy-carotenoid dioxygenase (NCED) which cleaves 9-cis xanthophylls to xanthoxin (Schwartz et al., 1997). The hormone ABA is known to promote dormancy in seeds (Millar et al., 2006) as well as being involved in other processes such as stress responses. Increased expression of an NCED gene was thought to increase ABA concentration and thereby promote dormancy. There are two NCED isoenzymes in cereals such as wheat and barley, designated NCED1 and NCED2, encoded by separate, homologous genes.

For breakdown of ABA, the enzyme ABA-8-hydroxylase (ABA8OH-2, also known as CYP707A2) hydroxylates ABA as a step in its catabolism, resulting in the breaking of dormancy and seed germination.

LedRNA constructs targeting genes encoding HvNCED1 (Accession No. AK361999, SEQ ID NO:109) or HvNCED2 (Accession No. AB239298; SEQ ID NO: 110) in barley *Hordeum vulgare* and the corresponding homologous genes in wheat were designed for transgenic expression in barley and wheat plants. These constructs used a highly conserved region of the wheat and barley NCED1 and NCED2 genes, the wheat and barley nucleotide sequences being about 97% identical in the conserved region. The genetic constructs were made using the design principles for ledRNAs described above, with the split sequence being the antisense sequence and the contiguous sequence being the sense sequence (FIG. 1A). The target region was 602 nucleotides in length, corresponding to nucleotides 435-1035 of SEQ ID NO:109. The dsRNA region of the ledRNA was 602 bp in length; the sense sequence in the dsRNA region was an uninterrupted, contiguous sequence corresponded to nucleotides 435-1035 of SEQ ID NO:110. The nucleotide sequences encoding the NCED1 and NCED2 ledRNAs are provided herein as SEQ ID NO:111 and 112.

In similar fashion, an ledRNA construct was made targeting an ABA-OH-2 gene of wheat *T. aestivum* and barley *H. vulgare* (Accession No. DQ145933, SEQ ID NO: 113). The target region was 600 nucleotides in length, corresponding to nucleotides 639-1238 of SEQ ID NO:113. The dsRNA region of the ledRNA was 600 bp in length; the sense sequence in the dsRNA region was an uninterrupted, contiguous sequence corresponded to nucleotides 639-1238 of SEQ ID NO:113. The nucleotide sequence of the chimeric DNA encoding the ledRNA is provided as SEQ ID NO:114.

The chimeric DNAs encoding the ledRNAs were inserted into an expression vector under the control of a Ubi gene promoter that is expressed constitutively in most tissues including in developing seed. The expression cassettes were excised and inserted into a binary vector. These were used to produce transformed wheat plants.

The transgenic wheat plants are grown to maturity, seed obtained from them and analysed for decreased expression of the NCED or ABA-OH-2 genes and for effects on grain dormancy corresponding to decreased gene expression. A range of phenotypes in the extent of altered dormancy is expected. To modulate the extent of the altered phenotypes, modified genetic constructs are produced for expression of ledRNAs having G:U basepairs in the double-stranded RNA regions, particularly for ledRNAs where between 15-25% of the nucleotides in the double-stranded region of the ledRNA are involved in a G:U basepair, as a percentage of the total number of nucleotides in the double-stranded region.

LedRNA Targeting EIN2 Gene of *A. Thaliana*

As described in Example 10, the EIN2 gene of *Arabidopsis thaliana* encodes a receptor protein involved in ethylene perception. EIN2 mutant seedlings exhibit hypocotyl elongation relative to wild-type seedlings when germinated on ACC. Since the gene is expressed in seedlings soon after germination of seeds, delivery of a ledRNA by transgenic means was considered the most suitable approach for tested the extent of down-regulation of EIN2, relative to exogenous delivery of preformed RNA.

An ledRNA construct targeting the EIN2 gene of *Arabidopsis thaliana* (SEQ ID NO: 115) was designed, targeting a 400 nucleotide region of the target gene mRNA. The construct is made by inserting a sequence (SEQ ID NO:116) encoding the ledRNA into a vector comprising a 35S promoter to express the ledRNA in *A. thaliana* plants. Transgenic *A. thaliana* plants are produced and tested for reduction of expression of the EIN2 gene by QPCR and for the hypocotyl length assay in the presence of ACC. Reduction in EIN2 expression levels and increased hypocotyl lengths are observed in plants of some transgenic lines.

LedRNA Targeting CHS Gene of *A. Thaliana*

The chalcone synthase (CHS) gene in plants encodes an enzyme that catalyzes the conversion of 4-coumaroyl-CoA and malonyl-CoA to naringenin chalcone which is the first committed enzyme in flavonoid biosynthesis. Flavonoids are a class of organic compounds found mainly in plants, involved in defense mechanisms and stress tolerance.

An ledRNA construct targeting the CHS gene of *Arabidopsis thaliana* (SEQ ID NO: 117) was designed, targeting a 338 nucleotide region of the target gene mRNA. The construct is made by inserting a DNA sequence (SEQ ID NO:118) encoding the ledRNA into a vector comprising a 35S promoter to express the ledRNA in *A. thaliana* plants. Transgenic *A. thaliana* plants are produced by transformation with the genetic construct in a binary vector and tested for reduction of expression of the CHS gene by QPCR and for the reduced flavonoid production. Reduction in CHS expression levels and reduced levels of flavonoids are observed in plants of some transgenic lines, for example in the seed coat of transgenic seeds.

LedRNA Targeting LanR Gene of *Lupinus* Angustifolius

The LanR gene of narrow-leafed lupin, *Lupinus angustifolius* L., encodes a polypeptide that is related in sequence to the tobacco N gene, which confers resistance to viral disease caused by tobacco mosaic virus (TMV).

A chimeric DNA for producing ledRNA molecules targeting the LanR gene of *L. angustifolius* (Accession No. XM_019604347, SEQ ID NO:119) was designed and made. The genetic construct was made using the design principles for ledRNAs described above, with the split sequence being the antisense sequence and the contiguous sequence being the sense sequence (FIG. 1A). The nucleotide sequence encoding the ledRNA is provided herein as SEQ ID NO:120. The ledRNA was produced by in vitro transcription, purified and concentrated, and aliquots of the RNA are applied to leaves of *L. angustifolius* plants which contain the LanR gene. Samples of virus are applied to treated and non-treated plants, and disease symptoms compared after several days.

LedRNAi Targeting the VRN2 Gene Conferring Vernalisation Responsiveness to Wheat The wheat VRN2A, VRN2B and VRN2D candidate genes as identified in TGACv1_scaffold_374416_5AL, TGACv1_scaffold_320642_4BL and TGACv1_scaffold_342601_4DL being homologs of the wheat ZCCT1 gene (Genbank Accession No. AAS58481.1) were identified as targets for design of a ledRNAi construct. A 309 bp region of the VRN2B gene was used for the dsRNA region of the ledRNAi construct designated LedTaVRN2. Led RNAi was produced by in vitro transcription using T7 RNA polymerase and diluted in water. The solution was used to imbibe wheat grains for germination at 4° C. for 3 days. Seeds of the vernalisation sensitive wheat variety CSIRO W7 were used. Treated seeds were planted in soil and the resultant plants observed over time for the transition from vegetative growth to floral development. The time of flowering, as indicated by emergence of the ear from the boot, and the number of leaves on the main stem at the time of flowering were recorded. Plants derived from seeds incubated with LedTaVRN2 flowered on average at least 17 days earlier than plants derived from seeds incubated with buffer only or non-specific dsRNA controls. Furthermore, plants derived from seeds incubated with LedTaVRN2 had on average 2.3 fewer leaves on the main stem at the time of flowering indicating fewer nodes were dedicated to leaf production and more nodes dedicated to flowers/grain.

Example 19. RNA Constructs Targeting an Insect Gene

Introduction

Aphids are sap-sucking insects that cause substantial and at times severe damage to plants directly through feeding of plant sap and, in some cases, indirectly through transmitting various viruses that cause disease in the plants. While Bt toxin has in some instances been effective in protecting crop plants from chewing insects, it generally hasn't been effective for sap-sucking insects. Use of plant cultivars that contain resistance genes can be an effective way to control aphids. However, most resistance genes are highly specific to certain aphid species or biotypes and resistance is frequently over-come due to rapid evolution of new biotypes through genetic or epigenetic changes. Moreover, resistance genes are not accessible in many crops or may not exist for certain generalist aphid species such as green peach aphid which infest a broad host species. Aphids are currently controlled primarily through frequent application of pesticides which has led to pesticide resistance in aphids. For example, only one pesticide mode of action group remains effective in Australia against the green peach aphid as it has managed to gain resistance to all the other registered insecticides.

RNAi-mediated gene silencing has been shown in a few studies to be useful as a research tool in a number of aphid species, for reviews see Scott et al., 2013; Yu et al., 2016, but has not been shown to effectively protect plants from aphid attack. In those studies, dsRNAs targeting key genes involved in aphid growth and development, infestation or feeding processes were delivered through direct injection to the aphids or by feeding the aphids on artificial diets containing the dsRNA.

To test the potential of modified RNAi molecules such as the ledRNA molecules described herein for the control of sap-sucking insects, the inventors selected green peach aphid (*Myzus persicae*) as a model sap-sucking insect, for several reasons. Firstly, green peach aphid is a polyphagous insect which infests a broad range of host plant species including major grain and horticultural crops worldwide. Secondly, green peach aphid is responsible for the transmission of some devastating viruses, such as Beet Western Yellows Virus which has been highly damaging in some canola growing areas. Two aphid genes were initially selected for this study as target genes for down-regulation, one encoding a key effector protein (C002) and the second encoding a receptor of activated protein kinase C (Rack-1). The C002 protein is an aphid salivary gland protein which is essential for aphid feeding on its host plant (Mutti et al., 2006; Mutti et al., 2008). Rack1 is an intracellular receptor that binds activated protein kinase C, an enzyme primarily involved in signal transduction cascades (McCahill et al., 2002; Seddas et al., 2004). MpC002 is predominantly expressed in the aphid salivary gland and MpRack1 is predominantly expressed in the gut. In previous studies, use of RNAi via direct injection or artificial diet feeding led to the death of several aphid species tested (Pitino et al., 2011; Pitino and Hogenhout, 2012; Yu et al., 2016).

Materials and Methods: Aphid Culture and Plant Materials

Green peach aphids (*Myzus persicae*) were collected in Western Australia. Before each experiment, aphids were reared on radish plants (*Raphanus sativus* L.) under ambient light in an insectary room. Aphids were transferred to experimental artificial diet cages with a fine paintbrush.

The components of the artificial diet for the aphid feeding were the same as described in Dadd and Mittler (1966). The apparatus used for the aphid artificial diet used a plastic tube with 1 cm diameter and 1 cm height. The artificial aphid diet, 100 μl with or without ledRNA, was enclosed between two layers of parafilm to create a diet sachet. On top of that sachet, there was a chamber for the aphids to move around and feed from the diet by piercing their stylets through the top layer of the stretched parafilm. Eight first- or second-instar nymphs were gently transferred to the aphid chamber using a fine paint brush. The experiment was carried out in a growth cabinet at 20° C.

The tobacco and radish leaves used in one experiment were collected from plants grown in soil under 16 hr light/8 hr dark cycle at 22° C. With the experiments involving excised radish leaves, a small radish leaf (2-4 $cm^2$) attached to a fragment of stem (~2 cm long) was excised. To keep the leaf fresh, the stem was inserted into medium comprising 1.5 g Bacto Agar and 1.16 g Aquasol per 100 ml water in a petri dish of 5 cm diameter. Aphids were transferred to the leaves with a fine painting brush. The petri dishes with the leaves and aphids were kept in a growth cabinet under 16 hr light/8 hr dark cycle at 20° C.

Double strand RNA (dsRNA) was prepared by in vitro RNA transcription of DNA templates comprising one or more T7 promotors and T7 RNA polymerase using standard methods.

MpC002 and MpRack-1 Genes and LedRNA Constructs

The green peach aphid MpC002 and MpRack-1 genes tested as target genes were the same as described by Pitino et al. (2011; 2012). The DNA sequences of both genes were obtained from the NCBI website, MpC002 (>MYZPE13164_0_v1.0 000024990.1|894 nt) and MpRack-1 (>MYZPE13164_0_v1.0_000198310.1|960 nt). The cDNA sequences of the two genes are provided herein as SEQ ID NOs: 123 and 124. LedRNA constructs were designed in the same manner as described in earlier Examples. The DNA sequences encoding the ledRNA molecules are provided herein as SEQ ID NOs: 125 and 126 were used as transcription templates to synthesize the ledRNA. The vector DNAs encoding the ledRNA molecules targeting the MpC002 and MpRack-1 genes were introduced into *E. coli* strain DH5α for preparing plasmid DNA for in vitro RNA transcription and into *E. coli* strain HT115 for in vivo (in bacteria) transcription.

Efficacy of ledRNA Molecules on the Reduction of Aphid Performance

To examine if the ledRNAs targeting the MpC002 or MpRack-1 genes affected aphid performance, each ledRNA was delivered to the aphids through the artificial diet means as described in Example 1. In each experiment, ten biological replicates were set up; each biological replicate had eight one- to two-instar nymphs of green peach aphid. The controls in each experiment used equivalent concentrations of an unrelated ledRNA, namely ledGFP.

At a lower concentration of 50 ng/μl of each ledRNA molecule, aphid survival after feeding from the artificial diet containing either MpC002 or MpRack-1 ledRNA was not significantly different from the control ledGFP. However, the ledRNA targeting the MpC002 gene significantly ($P<0.05$) reduced the reproduction rate of green peach aphids (FIG. 37A). The average number of nymphs produced per adult aphid was reduced by about 75% compared to the number of nymphs produced from adults maintained on the control diet having the control ledRNA. At a higher concentration of 200 ng/μl, the ledRNAs targeting either MpC002 or MpRack-1 increased adult aphid mortality (FIG.

37B). The reduction of aphid survival on the diets including the MpC002 or MpRack-1 ledRNAs was also observed after 24 hours and continued over the five-day period of the experiment. The results indicated that use of the ledRNAs targeting the essential aphid genes was able to cause the death of aphids and reduce aphid reproduction. The efficacy of each ledRNA was compared to double-stranded RNA molecules (dsRNAi) comprised of separate but annealed sense and antisense RNA strands targeting the same region of the target gene.

Uptake of ledRNA Molecules by Aphids

To track the uptake and distribution of the ledRNAs inside the aphids, the ledRNAs targeting the MpC002 or MpRack-1 genes were labelled with Cy3 (Cyanine-dye labelled nucleotide triphosphates) during the synthesis process as described in Example 1. The Cy3 labelling has been reported to have no effect on the biological function of conventional dsRNA molecules and so could be used as a label for detection by fluorescence. Aphids which had been fed the labelled ledRNAs were examined using confocal microscopy using a Leica EL 6000 microsystems instrument. The Cy3-labelled ledRNA targeting MpC002 or MpRack-1 was detectable in aphid guts within hours of feeding on the artificial diet and subsequently in the reproduction system and even in newborn nymphs which were the progeny of the adults that had been fed. The results indicated that aphid genes critical for digestive system function or reproduction could be effective targets for the ledRNA molecules through feeding.

LedRNA Stability

To examine the stability of ledRNA in the diet and as recovered from the fed aphids, RNA was recovered from the artificial diet and from aphid honeydew after feeding on the diets containing the labelled ledRNA molecules. The RNA samples were electrophoresed on gels and examined by fluorescence detection. The ledMpC002 RNA prior to feeding clearly displayed a single product of about 700 bp on the agarose gel. The RNA recovered from the artificial diet showed a smear of RNA from 100-700 bp in size, indicating some degradation after being exposed to the diet at room temperature for 25 days, but still largely intact. RNA recovered from the aphid honeydew showed fluorescence in the RNA range from 350 to 700 bp, so again was largely intact. Despite the degradation of some ledRNA, a large proportion of the ledRNA molecules was able to stay intact in the artificial diet and also in the aphid honeydew for a considerable period of time. This degree of stability of the ledRNA molecules should allow the ledRNA to be active and retain activity when applied exogenously.

Absorbance of Labelled ledRNA by Plant Leaves

The Cy3-labelled ledMpC002 RNA was painted on the upper surface of tobacco leaves in order to see if it was able to penetrate the leaf tissues. Ten microliters of Cy3-labelled ledMpC002 (1 μg/μl concentration) was painted in a circle of 2 cm diameter and the applied region marked with a black marker pen. Images of leaf fluorescence at an excitation of 525 nm were captured over a five hour period using a Leica EL 6000 microsystems instrument, comparing the painted tissues with those not painted. The Cy3 label was clearly detectable in mesophyll tissue within one hour after application, so had clearly penetrated through the waxy cuticle layer on the leaf surface. The level of fluorescence increased at 2 hours and was maintained to the 5 hr time point. It was not clear if the ledRNA molecules got into the cells or into the nuclei of the cells. However, as sap-sucking insects feed specifically from the phloem sieve elements of plant leaves and stems, RNA transmission into the plant cells was not required for the silencing of aphid genes. The experiment indicated that the ledRNA molecules were found in the plant tissues through topical application.

Uptake of Topical LedRNA by Aphids

The Cy3-labelled ledGFP RNA was painted on radish leaves in order to see if aphids were able to uptake topically applied ledRNA from plants. Ten microliters of each Cy3-labelled ledGFP (10 μg/μl concentration) was painted on a small excised radish leaf (~2 $cm^2$). The control leaf was painted with an equal amount of unlabelled ledGFP. The labelled and control radish leaves were each infested with eight aphids of various developmental stages. Images of leaf and aphid fluorescence were captured using the method described above for the tobacco leaves. While there was no detectable fluorescence in the control leaves and aphids, the leaf painted with Cy3 labelled ledGFP was highly fluorescent. Within 24 hours after feeding on the leaf with Cy3-labelled ledRNA, aphids showed strong fluorescence in the whole body but more pronounced in the guts and legs than other body parts. The experiment indicated that aphids were able to uptake the ledRNA molecules from plants through topical application.

Screening Additional Aphid RNAi Target Genes

In order to identify more aphid target genes, in total 16 aphid genes were evaluated for their suitability as RNAi targets. The candidate genes selected were involved in aphid development, reproduction, feeding or detoxification. Conventional dsRNA (dsRNAi) targeting each gene by comprising sense and antisense sequences corresponding to a region of target gene mRNA was supplemented to the aphid artificial diet at a concentration of 2 μg RNA per μl diet. Impact on aphid survival and reproduction rates was used to determine the suitability of the aphid RNAi target genes. Of the 16 genes investigated, nine genes showed the reduction of aphid survival and/or reproduction rates. In addition to MpC002 and MpRack-1, other suitable target genes were genes encoding the following polypeptides and the type of function they had in aphids: tubulin (Accession No. XM_022321900.1, cellular structure), Insulin-related peptide (XM_022313196.1, embryo development), V-type ATPase E subunit (XM_022312248.1, energy metabolism), gap hunchback (XM_022313819.1, growth and development), Ecdysis triggering hormone (XM_022323100.1, development—moulting), short neuropeptide F (XM_022314068.1, nervous system) and leucokinin (XM_022308286.1, water balance and food intake). For most genes, the impact of the RNAi appeared more robust and stronger on the aphid reproduction than on the survival, i.e. there was greater effects on reproduction.

Trans-Generation Effect of Exogenous RNAi on Aphids

To examine how long the RNAi effect could last, aphids at the two or three instars developmental stage were fed on an artificial diet supplemented with dsRNAi targeting MpC002, MpRack-1, MpGhb or with control dsGFP for 10 days. The aphids that survived were then transferred to excised radish leaves without RNA application. For all three genes, up to 6 days, the number of nymphs produced per survived aphid was significantly lower than the number for aphids fed on the control dsGFP RNA molecules or water. For the MpC002 and MpRack-1 dsRNAs, the lower reproduction rate on the radish leaves was maintained for at least 9 days. To investigate if the dsRNAi affected the following generations, the aphids which were born within three days on the radish leaves and which did not feed directly on RNA-containing diet were removed onto fresh excised radish leaves and their survival and production rate were monitored for 15 days. While there was no significant difference in the survival rate, the aphids which had been born from the mother aphids fed on the diet with MpC002, MpRack-1 or MpGh dsRNA, all produced a significantly lower number of aphids compared to the mother aphids fed on the diet with the control dsGFP or water. It was concluded that the effects caused by feeding dsRNA molecules to the parent aphid persisted in the progeny aphids.

Conclusions

The aims of this study were to test the application of exogenous RNAi using the ledRNA design for the control of aphids, a major group of sap-sucking insect pests that are a problem throughout the world, and to identify suitable target genes. Aphids are known to possess the RNAi machinery to process exogenous RNA (Scott et al., 2013; Yu et al., 2016). Here, oral delivery through an artificial diet containing ledRNA molecules targeting the MpC002 or MpRack-1 genes was able to cause aphid mortality and reduce the reproduction of the aphids. The molecules were tested against two different target genes, one encoding effector protein C002 and the other a receptor of activated protein kinase (Rack-1), which are essential for feeding and development of green peach aphid (*Myzus persicae*). When added to the artificial diet with a concentration as low as 50 ng/μl, the ledRNA molecules targeting these genes significantly reduced aphid reproduction. At a higher concentration of 200 ng/μl, the ledRNAs also increased aphid mortality. When ledRNA uptake was investigated using Cy3 labelling, ledRNA molecules were observed in aphid guts within hours of feeding on the artificial diet and subsequently in the reproduction system and even in newborn nymphs that were progeny of fed adults. The ledRNA effect on aphid reproduction could last for at least two generations as indicated in the results with the traditional dsRNA.

It was also shown that the ledRNA molecules stayed largely intact in the artificial diet for at least three and half weeks. Largely intact ledRNA molecules were also found in the aphid honeydew, an excretion product from the aphids. When labelled ledRNA was applied onto plant leaves, it could get into the phloem where the aphids feed and was detected in the aphids. Together these results indicated the strong potential for ledRNA to be used for the control of aphids and other sap-sucking insects, including by exogenous delivery through the diet, providing a practical approach for management of aphids and other sap-sucking insects. These RNA molecules can also be expressed in transgenic plants, using promoters that favour synthesis of the RNA in phloem tissues, to control aphids and other sap-sucking insects. Furthermore, use of ledRNA [G:U] or hairpin [G:U] RNA comprising 10-30% G:U basepairs in the dsRNA region of the molecules is expected to provide even better control, based on the increased levels of accumulation of these dsRNA molecules through reduced self-silencing of the transgenes encoding these molecules.

Example 20. RNA Constructs Targeting Other Insect Genes

LedRNA Targeting Genes of Insect Pests

*Helicoverpa armigera* is an insect pest in the order Lepidoptera, also known as the cotton bollworm or corn earworm. The larvae of *H. armigera* feed on a wide range of plants including many important cultivated crops and cause considerable crop damage worth billions of dollars per year. The larvae are polyphagous and cosmopolitan pests which can feed on a wide range of plant species including cotton, maize, tomato, chickpea, pigeon pea, alfalfa, rice, sorghum and cowpea.

The *H. armigera* ABC transporter white gene (ABCwhite) was selected as a target gene with a readily detected phenotype to test ledRNA and ledRNA (G:U) constructs in an insect larva. ABC transporters belong to the ATP Binding Cassette transporter superfamily—for example, 54 different ABC transporter genes were identified in the *Helicoverpa* genome. ABC transporters encode membrane-bound proteins that carry any one or more of a wide range of molecules across membranes. The proteins use energy released by ATP hydrolysis to transport the molecules across the membrane. Some ABC transporters were implicated in the degradation of plant secondary metabolites in the cotton bollworm, *H. armigera* (Khan et al., 2017). The ABCwhite protein transports monochrome and pteridine pathway precursors into pigment granules in the eye and knockout mutants exhibit white eyes.

The nucleotide sequence of the ABCwhite gene is provided as SEQ ID NO:127 (Accession No. KU754476). To test whether a ledRNA could reduce ABCwhite gene expression by exogenous delivery of the RNA in the larval diet, a genetic construct encoding a ledRNA was designed and made that targeted the gene. The genetic construct was made using the design principles for ledRNAs, with the split sequence being the sense sequence and the contiguous sequence being the antisense sequence (FIG. 1B). The target region was 603 nucleotides in length, corresponding to nucleotides 496-1097 of SEQ ID NO:127. The dsRNA region of the ledRNA was 603 bp in length; the antisense sequence in the dsRNA region was an uninterrupted, contiguous sequence corresponded to the complement of nucleotides 496-1097 of SEQ ID NO: 127. The nucleotide sequences encoding the ledRNA is provided herein as SEQ ID NO: 128. The coding region was under the control of a T7 RNA polymerase promoter for in vitro transcription.

The genetic construct encoding the ledRNA was digested with the restriction enzyme SnaBI, which cleaved downstream of the ledRNA coding region, and transcribed in vitro with RNA polymerase T7 according to the instructions with the transcription kit. The RNA is added to an artificial diet and provided to *H. armigera* larvae.

A corresponding ledRNA construct having G:U basepairs in the double-stranded stem is made and compared to the canonically basepaired ledRNA.

LedRNAs Targeting a Gene in Ants

*Linepithema humile*, commonly known as the Argentine ant, is an insect pest that has spread widely in several continents. The *L. humile* gene encoding pheromone biosynthesis activating neuropeptide (PBAN) neuropeptides-like (LOC105673224) was selected as a target gene, involved in communication between the insects by pheromones.

The nucleotide sequence of the PBAN gene is provided as SEQ ID NO:129 (Accession No. XM_012368710). To test whether a ledRNA could reduce PBAN gene expression by exogenous delivery of the RNA in the diet in the form of a bait, a genetic construct encoding a ledRNA was designed and made that targeted the gene. The genetic construct was made using the design principles for ledRNAs, with the split sequence being the sense sequence and the contiguous sequence being the antisense sequence (FIG. 1B). The target region was 540 nucleotides in length, corresponding to nucleotides 136-675 of SEQ ID NO:129. The dsRNA region of the ledRNA was 540 bp in length; the antisense sequence in the dsRNA region was an uninterrupted, contiguous sequence corresponded to the complement of nucleotides 136-675 of SEQ ID NO: 129. The nucleotide sequences encoding the ledRNA is provided herein as SEQ ID NO: 130. The coding region was under the control of a T7 RNA polymerase promoter for in vitro transcription.

The genetic construct encoding the ledRNA was digested with the restriction enzyme SnaBI, which cleaved downstream of the ledRNA coding region, and transcribed in vitro with RNA polymerase T7 according to the instructions with the transcription kit. The RNA is coated onto corn powder for oral delivery into *L. humile* ants.

LedRNA Targeting Genes of *L. cuprina*

*Lucilia cuprina* is an insect pest more commonly known as the Australian sheep blowfly. It belongs to the blowfly family, Calliphoridae, and is a member of the insect order Diptera. Five target genes were selected for testing with ledRNA constructs, namely genes encoding V-type proton ATPase catalytic subunit A (Accession No. XM_023443547), RNAse 1/2 (Accession No. XM_023448015), chitin synthase (Accession No. XM_023449557), ecdysone receptor (EcR; Accession No. U75355) and gamma-tubulin 1/1-like (Accession No. XM_023449717) of *L. cuprina*. Each of the genetic constructs was made using the design principles for ledRNAs, with the split sequence being the sense sequence and the contiguous sequence being the antisense sequence (FIG. 1B). In each case, the target region was about 600 nucleotides in length and the antisense sequence in the dsRNA region was an uninterrupted, contiguous sequence. The nucleotide sequence encoding the ledRNA targeting the ATPase-A gene is provided herein as SEQ ID NO:131. The nucleotide sequence encoding the ledRNA targeting the RNAse 1/2 gene is provided herein as SEQ ID NO: 132. The nucleotide sequence encoding the ledRNA targeting the chitin synthase gene is provided herein as SEQ ID NO:133. The nucleotide sequence encoding the ledRNA targeting the EcR gene is provided herein as SEQ ID NO:134. The nucleotide sequence encoding the ledRNA targeting the gamma-tubulin 1/1-like gene is provided herein as SEQ ID NO:135. In each construct, the coding region was under the control of a T7 RNA polymerase promoter for in vitro transcription.

Example 21. Transgene-Derived ledRNA Accumulates at High Levels in Stably Transformed Plants The DNA fragments encoding ledRNA sequences targeting the mRNAs from a GUS reporter gene or the *A. thaliana* EIN2 gene were synthesized and cloned into pART7 to form p35S:ledRNA:Ocs3' polyadenylation region/terminator expression cassettes for expression in plant cells. The fragments were then excised with NotI and inserted into the NotI site of pART27 to form the ledGUS and ledEIN2 vectors for plant transformation. The ledGUS construct and the existing hpGUS construct designed to generate a long hpRNA with a 563 bp dsRNA stem and 1113 nt loop were separately into the GUS-expressing *N. tabacum* line PPGH24 by *Agrobacterium*-mediated transformation methods. RNA samples from independent transformants which exhibited either strong GUS silencing or little or no apparent reduction in GUS activity were used in Northern blot hybridization assays to detect the transgene-encoded hpGUS or ledGUS RNA. As shown in FIG. 38, much more intense hybridizing signals were detected from the ledGUS-transformed plants than from the hpGUS-transformed plants that showed strong GUS silencing (indicated by "–" in FIG. 38). Indeed, most of the hybridizing signals for the hpGUS RNA samples were non-specific background signals that were also observed for RNA from the control, untransformed plants (WT). Several intense hybridizing bands were observed for the ledGUS lines, presumably due to some partial processing of the full-length ledRNA.

The nucleotide sequence of the genetic construct encoding ledGUS is shown in SEQ ID NO:5. Nucleotides 1-17 correspond to a T7 RNA polymerase promoter for in vitro RNA synthesis, nucleotides 18-270 correspond to the 5' half of GUS antisense sequence, nucleotides 271-430 correspond to loop 1 sequence, nucleotides 431-933 correspond to GUS sense sequence, nucleotides 934-1093 correspond to loop 2 sequence, and nucleotides 1094-1343 correspond to the 3' half of GUS antisense sequence.

In similar fashion, the ledEIN2 and hpEIN2 constructs were separately introduced into *A. thaliana* plants of the Col-0 ecotype by *Agrobacterium*-mediated transformation. The hpEIN2 construct, encoding the hpEIN2[wt] RNA, was as described previously and contained 200 bp sense and antisense EIN2 sequences in an inverted repeat configuration, separated by the PDK intron. The nucleotide sequence of the genetic construct encoding ledEIN2 is shown in SEQ ID NO:116. Nucleotides 37-225 correspond to the 5' half of EIN2 antisense sequence, nucleotides 226-373 correspond to loop 1 sequence, nucleotides 374-773 correspond to EIN2 sense sequence, nucleotides 774-893 correspond to loop 2 sequence, and nucleotides 894-1085 correspond to the 3' half of EIN2 antisense sequence. Nucleotides 37-225 (antisense) are complementary to nucleotides 374-573 (sense) and nucleotides 894-1085 (antisense) are complementary to nucleotides 574-773 (sense).

RNA samples from primary independent transformants were used for Northern blot hybridization analysis. As shown in FIG. 39, the ledEIN2 plants showed more intense hybridizing signals than the hpEIN2 plants for larger RNA molecules (FIG. 39, upper panel), indicating that ledEIN2-derived RNA accumulated at greater levels than hpEIN2-derived RNAs. For processed RNAs in the 20-25 nucleotide size range (siRNAs), siRNAs were detected in the ledEIN2 plants at greater abundance than in the hpEIN2 plants (FIG. 39, lower panel), and the amount of siRNAs correlated well with the abundance of the larger RNA molecules. These results indicated that transgene-derived ledRNA was processed to some extent, but not completely, by Dicer into siRNAs. It also indicated that the ledRNA transgenes generated more siRNAs than a corresponding hpRNA transgene.

These results indicated that the ledRNA constructs, when expressed in plant cells, resulted in greater levels of accumulated transcripts, unprocessed and processed, than the corresponding hpRNA constructs. It was thought this was an indication of increased stability of the ledRNA molecules.

Example 22. Hairpin RNA is an Efficient Precursor of Circular RNA in Plants

Circular RNAs (circRNAs) are covalently linked, closed circles with no free 5' and 3' termini or polyadenylated sequences as 3' regions. They are generally non-coding in that they lydo not encode polypeptides and so are not translated. circRNAs are relatively resistant to digestion by RNAses, in particular to exonucleases such as RNase R. circRNAs of viral or viroid origin or as satellite RNAs associated with viruses have long been observed in plants and animals. For instance, Potato Spindle Tuber Viroid, a subviral RNA pathogen in plants, has a circular RNA genome of around 360 nt in size. In plants, such satellite RNAs are often capable of being replicated in the presence of a helper virus. In contrast, viroids depend entirely on host functions including endogenous plant RNA polymerase for their replication.

Using RNA deep sequencing technologies in conjunction with specially designed bioinformatics tools, a large number of cirRNAs have now been identified from plant and animal genomes. Thousands of putative circRNAs have been identified in plants including *A. thaliana*, rice and soybean which tend to show tissue-specific or biotic and abiotic stress-responsive expression patterns, but the biological function(s) of circRNAs in plants have yet to be demonstrated. The tissue-specific or stress responsive expression patterns of many putative plant circRNAs suggest that they may have potential roles in plant development and defence responses, but this has yet to be demonstrated.

A consensus view on the biogenesis of circRNAs is that they are formed by intron back-splicing, namely the splicing machinery "back-splices" pre-mRNA and covalently joins the spliced exons together. Thus, the endogenous intron splicing machinery is essential for the current model of circRNA biogenesis. This biogenesis model is based primarily on studies in mammalian systems where the majority of exonic circRNAs are shown to contain canonical intron splicing signals including the consensus GT/AG intron border dinucleotides. In animals, the intron regions flanking exonic circRNAs often contain short inverted repeats of transposable element sequences, and this has led to the suggestion that complementary intron sequences facilitate circRNA formation. Indeed, vector systems for expressing circRNAs in animals have been developed based on the naturally occurring exon-intron sequences with spliceable introns containing complementary TE repeats. However, the role of complementary flanking sequences in circRNA formation remains unclear in plants, as the proportion of identified exonic circRNAs with such flanking intron sequences is very low, ranging from 0.3% in *Arabidopsis* to 6.2% in rice.

Long hairpin RNA (hpRNA) transgenes have been widely used to induce gene silencing or RNA interference in plants (Wesley et al., 2001). An hpRNA transgene construct is typically comprised of an inverted repeat having complementary sense and antisense sequences with reference to a promoter sequence, and with a spacer sequence in between to separate and link the sense and antisense sequences. The spacer also stabilizes the inverted repeat structure in a DNA plasmid in bacterial cells during vector construction. Consequently, the RNA transcript from a typical hpRNA transgene is expected to form a stem-loop structure with a double-stranded (ds) stem of base-paired sense and antisense sequences and a "loop" corresponding to the spacer sequence. Such RNA transcripts are also referred to as self-complementary RNAs because of the ability of the sense and antisense regions to anneal by base-pairing, forming the dsRNA region or stem region of the molecule.

Loop Fragments from Long hpRNA Accumulate in Plant Cells and are Resistant to RNase R A transgene was made which encoded a long hpRNA targeting the GUS mRNA, having 563 bp sense and antisense sequences and a 1113 bp spacer (FIG. 40, GUShp1100). A second transgene was also made which encoded a shorter hpRNA targeting the same GUS mRNA, having 93 bp sense and antisense sequences and a 93 bp spacer (GUShp93-1). Both constructs were introduced separately into *Nicotiana benthamiana* leaf cells for transient expression of the hairpin RNAs and were also used to transform *A. thaliana* plants for expression as stably integrated and heritable transgenes. As previously reported, both constructs generated distinct RNA fragments of the expected size for the loop sequences when introduced and expressed in plant cells (FIG. 41; Wang et al., 2008; Shen et al., 2015). In the present study, the inventors wanted to determine whether the loop sequences were converted to circular RNAs.

A third construct was made having an *Arabidopsis* U6 promoter rather than the 35S promoter for expression of the shorter hpRNA (GUShp93-2). A fourth GUS hpRNA construct was also made which included a PDK intron as spacer sequence (GUShpPDK in FIG. 40). That construct encoded a hairpin RNA where the intron was expected to be spliced out after transcription, leaving a much shorter loop sequence. These constructs were also introduced into *N. benthamiana* leaves to examine whether the loop sequences could be detected and whether they formed circular RNA. The dsRNA stem and the loop sequences in these constructs were all derived from the GUS coding sequence, and no known intron sequences were introduced. The constructs were separately introduced into *N. benthamiana* leaves using *Agrobacterium*-mediated infiltration, either in the presence or absence of a target GUS-expressing construct, together with a genetic construct encoding and expressing the cucumber mosaic virus 2b protein as a viral suppressor protein (VSP) to enhance transgene expression. The accumulation and size of the loop fragments was analysed using Northern blot hybridization assays. The autoradiograph of a representative Northern blot is shown in FIG. 42.

As shown in FIG. 42, the long loop fragment of GUShp1100 was readily detected in *Agrobacterium*-infiltrated samples, as previously reported (Shen et al., 2015). To test if this loop fragment was circular, the RNA samples were treated with RNase R and electrophoresed on polyacrylamide gels. The RNase R treatment used 10 μg of total RNA (or 50 ng of in vitro transcript) mixed with RNase R buffer and water in a total volume of 20 μl. The mixtures were heated in boiling water for 3 min, chilled quickly on ice, then 0.5 μl RNase R was added and the tube was incubated at 37° C. for 10 min. The enzyme was inactivated and the residual RNA recovered by precipitation with ethanol. The RNase R treatment degraded most of the RNA as indicated by the dramatic reduction in ethidium bromide stained material in the gels (FIG. 42, lower panel). With all of the RNase R treatment assays, several ribosomal RNA fragments remained visible in the gels, indicating partial resistance of some RNA species to RNase R. Despite the depletion of total RNA in the RNase R-treated samples, the approximately 1100 nt loop fragment remained abundant, with only about 24% reduction in amount compared to the untreated samples. This indicated that the loop fragment was relatively resistant to RNase R digestion and was therefore circular in structure. The 24% reduction in the amount of loop RNA relative to the untreated sample was attributed to either residual amounts of endonuclease activity in the commercially obtained RNase R enzyme or to reduced RNA recovery after RNase R digestion during the ethanol precipitation step.

The RNase R treatment assay was repeated with inclusion of 50 ng of in vitro transcribed RNA corresponding to the loop sequence as a linear RNA control. In addition, a sample of hpGUS1100-infiltrated *N. benthamiana* RNA was treated with two rounds of RNase R treatment, to more stringently test RNase R resistance. It was observed that 76% of the loop fragment from GUShp1100-infiltrated *N. benthamiana* leaves remained after one RNase R treatment, whereas only about 8.5% of the linear in-vitro transcript remained. The two-fold RNase R treatment further reduced the loop-derived material but did not eliminate it. It was also noted that the RNA band from *N. benthamiana* samples corresponding to the loop sequence appeared larger on the gel blot than the in-vitro transcript, consistent with circular RNA which has been reported to migrate more slowly in gel electrophoresis than linear RNA molecules having the same number of nucleotides. It was concluded from these experiments that the loop sequence of about 1100 nucleotides was circular.

Northern blot hybridization analysis of GUShp93-1 and GUShpPDK-infiltrated *N. benthamiana* RNA samples also detected RNA molecules of a size corresponding to the length of the loop sequences. For the GUShp93-1 and GUShp93-2 constructs, the U6 promoter-directed GUShp93-2 yielded more loop fragment than the 35S promoter driven GUShp93-1, indicating that the U6 promoter had stronger transcriptional activity than the 35S promoter in *N. benthamiana* leaf cells or that the molecules were somehow more stable.

The GUShpPDK construct had a spacer sequence that included a spliceable PDK intron of 0.76 kb in size, and primary transcripts from this construct therefore contained an approximately 0.8 kb loop. The Northern blots were treated to remove the GUS probe and re-probed with a full-length antisense probe against the PDK intron sequence. The PDK probe hybridized strongly to an unknown RNA species which was observed as an intense band across all lanes. RNase A treatment reduced but could not eliminate this non-specific band entirely. Nevertheless, a PDK intron-specific band of the expected size could be detected in the GUShpPDK-infiltrated RNA samples, although the abundance of the fragment looked relatively weak, possibly because the intron sequence was spliced out from the majority of the GUShpPDK primary transcripts. To examine if the PDK loop fragment was circular, RNA of GUShpPDK-infiltrated *N. benthamiana* leaves was treated with RNase R. The non-specific hybridizing band was almost completely removed by RNase R treatment. In contrast, the PDK intron band was readily detected after RNase R treatment, although the abundance could not be easily compared with the untreated sample due to the strong signal from the non-specific band. Taken together, these results indicated that hpRNA transcripts were an effective precursor for circular RNA formation, and suggested that the circular RNA corresponded to the whole loop sequence.

RNase R-Resistant Loop Fragment Also Accumulates in Stably Transformed *Arabidopsis* Plants The hpGUS347 and the two hpGFP constructs (FIG. 40) were used to transform *A. thaliana* plants of ecotype Col-0 and two plants expressing the transgene selected for each construct. The hpGUS347 construct was used in this experiment as a control for the hpGFP constructs which were designed to contain miR165/166 binding sites for testing miRNA sponge function (discussed in Example 24). Transgenic plants of the T2 generation were analysed for accumulation of RNA molecules produced from the hpGUS347 construct, in particular to detect loop sequences and whether they were circular. A band corresponding to the loop of hpGUS347 transcripts was detected in both the RNase R-treated and untreated RNA samples from two hpGUS347 lines. As for RNA samples from the *Agrobacterium*-infiltrated *N. benthamiana* tissues, there appeared to be a slight reduction in band intensity in the RNase R-treated samples compared to untreated ones, but most of the RNA signal was retained. RT-qPCR analysis, using primers designed to detect circRNA, confirmed the presence of circRNA in RNase R-treated hpGUS347 samples with a slight reduction in abundance compared to the untreated samples. These results indicated that stably integrated hpRNA transgenes which were expressed to produce hairpin RNAs also generated circRNAs from the loop sequences.

The Loops of hpRNA Transcripts were Excised at the dsRNA Stem-Loop Junction and Formed Circular RNA To further confirm the circular nature of the RNA molecules derived from the loop sequences and to characterise their junction sequences, loop sequences were amplified by RT-PCR from GUShp1100, GUShp93 and GUShpPDK-infiltrated samples using oligonucleotide primers that would amplify putative junction sequences. The RT-PCR products were then cloned into pGEM-T Easy vector and sequenced, confirming the nucleotide sequences at the junctions. The nucleotide positions of loop excision and joining in the circular RNAs were somewhat variable, with the 5' sites located within the 3' end of the dsRNA stem and the 3' sites near the 3' end of the loop, but the 5' sites showed a clear preference for the G nucleotide located 10 nucleotides from the 3' end of the dsRNA stem. It was noted that the excision and joining sites of the PDK intron circular RNA followed the same pattern as those from GUShp1100 and GUShp93 RNA, and were outside the canonical intron splicing sites. It was concluded that the formation of the circular RNA was determined by the stem-loop structure independently of intron splicing. It was also concluded that, at least in this example, the hairpin RNA was processed to release and circularise the loop sequence by a 5' cleavage within the 3' end of the dsRNA stem and a 3' cleavage near the 3' end of the loop sequence, with a covalent linkage formed between the 5' and 3' ends of the excised sequence.

Example 23. HpRNA Expressed in *Saccharomyces cerevisiae* was not Processed into Circular RNA The yeast species, *Saccharomyces cerevisiae*, is a eukaryotic organism and possesses intron splicing machinery as do all eukaryotes. As the current, consensus model for circular RNA formation is based on intron splicing, the inventors investigated whether hpRNA could form circular RNA in *S. cerevisiae* as it did in plant cells. To generate a construct to express a hpRNA, the inverted repeat region of GUShp1100 was excised from the plant expression vector and inserted into a yeast expression vector under the control of a yeast ADH1 promoter (FIG. 43), and the resultant genetic construct introduced into *S. cerevisiae* cells. As shown in FIG. 43, Northern blot hybridization analysis of RNA extracted from each of three independent transgenic yeast strains detected one, high molecular weight band corresponding to the GUShp1100 transcript. This indicated that the GUShp1100 transcript was not processed in *S. cerevisiae* but remained full-length. To confirm this, the *S. cerevisiae*-expressed and *N. benthamiana*-expressed GUShp1100 transcripts were compared for their response to RNase R treatment. As shown in FIG. 44, the *S. cerevisiae*-expressed RNA showed a high molecular weight band which was highly sensitive to RNase R treatment and therefore not circular. That is, the yeast RNA samples did not exhibit circular molecules derived from the loop sequence as was produced in the *N. benthamiana* cells. The results indicated that the GUShp1100 transcript expressed in *S. cerevisiae* was not processed and remained full-length. The size of the *S. cerevisiae* RNA band appeared larger by gel electrophoresis than the in vitro GUShp1100 transcript, presumably due to the 5' and 3' UTR and poly(A) sequences that were present in the *S. cerevisiae*-expressed RNA but not in the in vitro transcript. Thus, the presence of intron splicing machinery in *S. cerevisiae* was not sufficient to allow processing of the hpRNA loop and formation of circular RNA as occurred in the plant cells.

In a similar fashion, the genetic construct GUShp347 was introduced into *S. cerevisiae* and expressed. Northern blot hybridisation analysis again showed that the hpRNA appeared full-length and was apparently not processed, at least not with cleavage of the loop sequence or the dsRNA region.

The inventors concluded that the yeast *S. cerevisiae* and its related budding yeasts, which do not have Dicer enzymes (Drinnenberg et al., 2003), are advantageous as an organism for the production of full length hairpin and ledRNAs, including the modified RNA molecules described herein. Such full-length RNAs are useful where the unprocessed dsRNA is desired, for example for silencing gene activity by topical application to insects.

Example 24. HpRNA Loops can Function as an Effective "Sponge" to Suppress miRNA Function A few circular RNAs in animals have been found to contain multiple sequences which are complementary to specific miRNAs and thereby act as binding sites for those miRNAs, referred to as miRNA "sponges". The inventors tested whether circular RNA produced from long hpRNA constructs could function as a miRNA sponge in plant cells. Two GFP hpRNA constructs were designed (FIG. 40) which had the same GUS sequence-derived spacer except that one was modified in sequence to have two *Arabidopsis* miR165/166 binding sites. That construct, GFPhp[G:U], had an inverted repeat sequence which had the same antisense sequence as the second (control) construct GFPhp[WT] but with a modified sense sequence in which all cytosine nucleotides were replaced with thymines. The transcript from GFPhp[G:U] would therefore form a dsRNA region corresponding to the GFP sequence except that about 25% of the basepairs were G:U basepairs. The other construct, GFPhp [WT], encoded a hairpin RNA with a fully canonically basepaired dsRNA stem of the same length as the hairpin from GFPhp[G:U], and was used as a control (FIG. 40). The GUS hpRNA construct GUShp347, containing a spacer without miR165/166 binding sites, was included as second control.

The constructs were used to separately transform *A. thaliana* and transgenic plants were obtained for each of the three constructs. The transformed plants were examined visually for phenotypes related to reduction in miR165/166, which included a distinctive folding of leaves into "trumpets". As expected, the GUShp347 transformed plants showed no phenotypes associated with miR165/166 repression. Similarly, no clear phenotype was observed in GFPhp [WT]-transformed plants. In contrast, the majority of the GFPhp[G:U] plants showed various levels of phenotypes reminiscent of miR165/166 repression including the trumpet phenotype.

Northern blot hybridization was performed on RNA extracted from GFPhp[G:U] transformed plants with a range of mild, moderate and strong to severe phenotypes to examine the accumulation of hpRNA expression. The probe used was a full-length antisense RNA corresponding to GUS mRNA. The probe had a 822 bp continuous sequence complementarity with the sense and adjacent loop of the GUShp347 transcript. The probe had less sequence complementarity to the GFPhp transcripts which had a total of 228 bp of the loop region as GUS-derived sequence, in three non-contiguous regions of 49, 109 and 70 bp in length flanking the two miRNA binding sequences. As shown in FIG. 45B, highly abundant amounts of GFP hpRNA molecules were detected in the GFPhp[G:U] plants, and the amounts of RNA molecules detected in the Northern blots correlated positively with the severity of phenotypes. The GFPhp[WT] plants exhibited low levels of accumulation of hpRNA molecules which were only just detectable in the Northern blot analyses, consistent with relatively low transcription levels of conventional hpRNA transgenes compared to G:U modified hpRNA transgenes. That is, as shown in the Examples above, the hpRNA[G:U] transgenes were less subject to self-silencing compared to the corresponding hpRNA[WT] transgene.

RT-qPCR was used to quantitate the accumulation of the circular RNA molecules derived from the loop sequences. The results showed that high amounts of the circRNA were present in the GFPhp[G:U] transgenic plants that correlated with the levels of full-length hpRNA accumulation (FIG. 45C). Northern blot hybridization analyses to detect small RNAs in the 20-25 nt size range confirmed the down-regulation of miR165/166 in the GFPhp[G:U] plants. The extent of reduction correlated with the amount of hpRNA and circRNA and the severity of phenotypes. Expression analysis of the miR165/166 target gene using RT-qPCR showed that target gene repression by miR165/166 was released in the plants that showed strong miR165/166 down-regulation and severe phenotypes. Taken together, these results showed that hpRNA loops could be used as a specific miRNA sponge to repress miRNA function in plants.

The inventors also conceived of the use of the circular RNAs, produced at high levels in plant cells as stable molecules, to be translated as a means to produce high levels of polypeptides. For initiation of cap-independent translation, internal ribosome entry sites (IRES) are ideally used. Numerous IRES sequences have been identified.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2018902840 filed 3 Aug. 2018, AU 2018902896 filed 8 Aug. 2018, PCT/AU2018/051015 filed 17 Sep. 2018 and AU 2019900941 filed 20 Mar. 2019 the disclosures of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abraham (2002). Cell 111:9-12.

Acevedo-Garcia et al., (2017). Plant Biotechnology Journal 15:367-378.

Alvarez et al., (2000). Theor Appl Genet 100:319-327.

Baumlein et al., (1991). Mol. Gen. Genet. 225:459-467.

Baumlein et al., (1992). Plant J. 2:233-239.

Bhattacharyya et al., (1990) Cell 60:155-122.

Brar et al., (1996) Biotech Genet. Eng Rev 13:167-79.
Broothaerts et al., (2005). Nature 433:629-633.
Broun et al., (1998). Plant J. 13:201-210.
Buchanan-Wollaston, (1994) Plant physiology 105:839-846.
Busk et al., (1997). Plant J. 11:1285-1295.
Chen et al., (2005). Functional Plant Biology 32:671-681.
Chikwamba et al., (2003). Proc. Natl. Acad. Sci. U.S.A. 100:11127-11132.
Christou and Klee, (2004) Handbook of Plant Biotechnology, John Wiley and Sons.
Chung et al., (2006). BMC Genomics 7:120.
Clough and Bent (1998). Plant J. 16:735-743.
Corrado and Karali (2009). Biotechnol. Adv. 27:733-743.
Courvalin et al., (1995). Life Sci. 318:1209-1212.
Dadd and Mittler (1966). Experientia 22:832-833.
Darji et al., (1997). Cell 91:765-775.
Dong et al., (2011) Plant J. 68:633-45.
Draper and Scott (1988). In: J. Draper et al., (Eds.), Plant Genetic Transformation and
Gene Expression: A Laboratory Manual, Alden Press, Oxford, pp. 199-236.
Drinnenberg et al. (2009) Science 326:544-550.
Dunwell (2000). J Exp Botany 51Spec No: 487-496.
Ebhardt et al., (2005) Proc. Nat. Acad. Sci. USA 102:13398-13403.
Ellerstrom et al., (1996). Plant Mol. Biol. 32:1019-1027.
Elliott et al., (2002). Mol. Plant Microbe Interact. 15:1069-1077.
Ellis et al., (1987). EMBO J 6:11-16.
Feechan et al., Functional Plant Biology, 2008, 35:1255-1266.
Fehr, In: Breeding Methods for Cultivar Development, Wilcox J. ed., American Society of Agronomy, Madison Wis. (1987).
Gan (1995). Molecular characterization and genetic manipulation of plant senescence. PhD thesis. University of Wisconsin, Madison.
Gan and Amasino (1995). Science 270:1986-1988.
Glawe (2008). Ann. Rev. Phytopathol. 46:27-51.
Gleave (1992). Plant Mol Biol 20:1203-1207.
Guo et al., (2016) Curr. Genom. 17:476-489.
Gupta et al., (1988) Plant Mol. Biol. 10:215-224.
Helliwell and Waterhouse (2005). Methods in Enzymology 392:24-35.
Hershey and Stoner, (1991) Plant Molecular Biol. 17:679-690.
Hinchee et al., (1988). Biotechnology 6:915-922.
Horvath et al., (2000). Proc. Natl. Acad. Sci. U.S.A. 97:1914-1919.
Hsieh and Fire (2000) Annu Rev Genet 14:187-204.
Jeddeloh, et al., (1999). Nat. Genet. 22:94-97.
Jefferson et al., (1987). EMBO J 6:3901-3907.
Jepson et al., (1994). Plant Mol. Biol. 26:1855-1866.
Khan (2017). Sci Rep 7, 40025
Kim et al., (2019) J. Gen. Plant Path. https://doi.org/10.1007/s10327-019-00865-7
Kishore and Somerville (1993). Curr Opin Biotechnol. 4:152-158.
Koziel et al., (1996). Plant Mol. Biol. 32:393-405.
Lacroix et al., (2008). Proc. Natl. Acad. Sci. U.S.A. 105: 15429-15434.
Lau et al., (2001) Science 294:858-862.
Li et al., (1996). FEBS Lett. 379:117-121.
McCahill et al., (2002). Molecular Pharmacology 62:1261-1273.
Mccullough and Schuler (1997). Nucl Acids Res. 25:1071-1077.
Mahfouz et al., (2006). Plant Cell 18:477-490.
Matsuoka et al., (1994). Plant J. 6:311-319.
Meier et al., (1997). FEBS Lett. 415:91-95.
Melamed-Bessudo et al., (2012) Proc. Natl. Acad. Sci. USA 109 (16): e981-988.
Millar et al., (2006). Plant J. 45:942-954.
Mutti et al., (2006). J Insect Sci 6:38.
Mutti et al., (2008). Proceedings of the National Academy of Sciences 105:9965-9969.
Olive et al., (1989) Plant Mol Biol 12:525-538.
Padidam (2003). Transgenic Res. 12:101-109.
Perrin et al., (2000). Mol Breed 6:345-352.
Pitino et al., (2011). PLoS ONE 6, e25709.
Pitino and Hogenhout (2012). Molecular Plant-Microbe Interactions 26:130-139.
Potenza et al., (2004). In Vitro Cell Dev. Biol. Plant 40:1-22.
Powell et al., (1996). Vaccines 183, Abstract.
Preiss et al., (1987). In: Tailoring Genes for Crop Improvement (Bruening et al., eds.), Plenum Press, S. 133-152.
Sambrook et al., (1989). Molecular Cloning: A Laboratory Manual, Cold Spring Harbour Laboratory Press.
Schaffner (1980). Proc. Natl. Acad. Sci. U.S.A. 77:2163-2167.
Schwartz et al., (1997). Science 276:1872-1874.
Scott et al., (2013). Journal of Insect Physiology 59:1212-1221.
Seddas et al., (2004). Virology 325:399-412.
Shen et al., (2015) Frontiers in Plant Science 6:281.
Shiina et al., (1997). Plant Physiol. 115:477-483.
Shure et al., (1983). Cell 35:225-233.
Sizemore et al., (1995). Science 270:299-302.
Slater et al., Plant Biotechnology—The Genetic Manipulation of Plants, Oxford University Press (2003).
Smith et al., (2000). Nature 407:319-320.
Stalker et al., (1988). Science 242:419-423.
Stewart et al., (2000). J Mol Biol 298:611-622.
Tan et al., (2011). Plant Physiol. 156:1577-1588.
Thillet et al., (1988). J. Biol. Chem 263:12500-12508.
Timmons et al., (2001). Gen 263:103-112.
Ulmasov et al., (1995). Plant Physiol. 108:919-927.
Wang (1994) Isolation of phloem specific gene promoters for use in genetic engineering of insect resistance in rice. PhD thesis, University of Durham, UK.
Wang et al., (1994) Plant Molecular Biology 24:159-170.
Wang et al., (1998) Acta Horticulturae 461:401-407.
Wang et al., (2008) RNA 14:903-913. Wang et al., (2013). PLoS Genet 9, e1003865.
Wang et al., (2014). Nature Biotechnology 32:9.
Weiss (2003). Int. J. Med. Microbiol. 293:95:106.
Weissbach et al., (1988). In: Methods for Plant Molecular Biology, Academic Press, San Diego, Calif.
Wijnker et al., (2008). Trends in Plant Science 13:640-646.
Wesley et al. (2001) Plant J. 27:581-590.
Yang et al., (1994) Particle Bombardment Technology for Gene Transfer, Oxford Press, Oxford, England.
Yang et al., (2003). Planta 216:597-603.
Yelina et al., (2012). PLoS Genetics 8 (8): e1002844. doi: 10.1371/journal.pgen.1002844
Yu et al., (2016). Pest Management Science 72:1090-1098.
Zhang et al., (2018). Nat Rev Mol Cell Biol. 19:489-506.

The invention claimed is:

1. A chimeric ribonucleic acid (RNA) molecule, comprising a double-stranded RNA (dsRNA) region which comprises a first sense ribonucleotide sequence of at least 50 contiguous ribonucleotides in length and a first antisense ribonucleotide sequence of at least 50 contiguous ribonucleotides in length, the whereby first sense ribonucleotide sequence and the first antisense ribonucleotide sequences are capable of hybridising to each other to form the dsRNA region, wherein at least 50 contiguous ribonucleotides of the first antisense ribonucleotide sequence are capable of basepairing to nucleotides of a first region of a target RNA molecule in a plant, arthropod or fungal cell, wherein i) the first sense ribonucleotide sequence consists of, covalently linked in 5' to 3' order, a first 5' ribonucleotide, a first RNA sequence and a first 3' ribonucleotide, ii) the first antisense ribonucleotide sequence consists of, covalently linked in 5' to 3 order, a second 5' ribonucleotide, a second RNA sequence and a second 3' ribonucleotide, iii) the first 5' ribonucleotide basepairs with the second 3' ribonucleotide to form a terminal basepair of the dsRNA region, iv) the second 5' ribonucleotide basepairs with the first 3' ribonucleotide to form a terminal basepair of the dsRNA region, v) between 5% and 40% of the ribonucleotides of the at least 50 contiguous ribonucleotides of the first sense ribonucleotide sequence and the at least 50 contiguous ribonucleotides of the first antisense ribonucleotide sequence, in total, are basepaired in G:U basepairs in the dsRNA region, vi) the dsRNA region does not comprise 20 contiguous canonical basepairs, vii) the RNA molecule is capable of being processed in the plant, arthropod or fungal cell or in vitro whereby the first antisense ribonucleotide sequence is cleaved to produce short antisense RNA (asRNA) molecules of 20-24 ribonucleotides in length, viii) the RNA molecule or at least some of the asRNA molecules, or both, are capable of reducing the expression or activity of the target RNA molecule in the plant, arthropod or fungal cell, ix) the RNA molecule is capable of being made enzymatically by transcription in vitro or in a plant, arthropod or fungal cell, or both, and x) more than 90% of the ribonucleotides in the dsRNA region are basepaired.

2. The chimeric RNA molecule of claim 1, wherein the first sense ribonucleotide sequence is covalently linked to the first antisense ribonucleotide sequence by a first linking ribonucleotide sequence which comprises a loop sequence of between 4 and 1,000 ribonucleotides, whereby the first linking ribonucleotide sequence is covalently linked to either the second 3' ribonucleotide and the first 5' ribonucleotide or to the first 3' ribonucleotide and the second 5' ribonucleotide, so that the sequences are comprised in a single, contiguous strand of RNA.

3. The chimeric RNA molecule of claim 2, wherein the loop sequence in the RNA molecule comprises one or more binding sequences which are complementary to an RNA molecule which is endogenous to the plant, arthropod or fungal cell.

4. The chimeric RNA molecule of claim 2, wherein:

the chimeric RNA molecule comprises two or more antisense ribonucleotide sequences, and sense ribonucleotide sequences based paired thereto, which antisense sequences are each complementary to a region of a target RNA molecule, wherein the two or more antisense ribonucleotide sequences are complementary to different regions of the same target RNA molecule.

5. The chimeric RNA molecule of claim 2, wherein one or more ribonucleotides of the first antisense ribonucleotide sequence are not basepaired in the dsRNA region.

6. The chimeric RNA molecule of claim 2, wherein all of the ribonucleotides in the first sense ribonucleotide sequence are basepaired in the chimeric RNA molecule.

7. The chimeric RNA molecule of claim 2, wherein the loop sequence in the chimeric RNA molecule comprises an open reading frame which encodes a polypeptide or a functional polynucleotide.

8. The chimeric RNA molecule of claim 2, comprising a second sense ribonucleotide sequence and a second antisense ribonucleotide sequence which each comprise at t least 50 contiguous nucleotides in length and which hybridise to form a second double-stranded RNA region, wherein between 5% and 40% of the ribonucleotides of the second sense ribonucleotide sequence and the second antisense ribonucleotide sequence, in total, are basepaired in G:U basepairs, wherein the second dsRNA region does not comprise 20 contiguous canonical basepairs.

9. The chimeric RNA molecule of claim 2, wherein the chimeric RNA molecule comprises a second antisense ribonucleotide sequence and a second sense ribonucleotide sequence which each comprise at least 50 contiguous nucleotides in length and which hybridise to form a double-stranded RNA region, wherein the first and second antisense sequences are complementary to regions of different target RNA molecules.

10. The chimeric RNA molecule of claim 2, wherein between 10% and 30% of the at least 50 contiguous nucleotides ribonucleotides of the first sense ribonucleotide sequence and the at least 50 contiguous nucleotides ribonucleotides of the first antisense ribonucleotide sequence, in total, are basepaired in G:U basepairs in the dsRNA region.

11. The chimeric RNA molecule of claim 2, wherein one or more ribonucleotides of the first sense ribonucleotide sequence or one or more ribonucleotides of the first antisense ribonucleotide sequence, or both, are not basepaired in the dsRNA region.

12. The chimeric RNA molecule of claim 2, wherein one or more ribonucleotides of the first antisense ribonucleotide sequence are not basepaired in the dsRNA region.

13. An isolated and/or exogenous polynucleotide encoding the chimeric RNA molecule of claim 2, wherein the polynucleotide is operably linked to a promoter capable of directing expression of the chimeric RNA molecule in a plant, arthropod or fungal cell or in vitro.

14. The chimeric RNA molecule of claim 1, wherein between 15% and 30% of the at least 50 contiguous ribonucleotides of the first sense ribonucleotide sequence and the at least 50 contiguous ribonucleotides of the first antisense ribonucleotide sequence, in total, are basepaired in G:U basepairs in the dsRNA region.

15. The chimeric RNA molecule of claim 1, wherein the first antisense ribonucleotide sequence is fully complementary to a region of the target RNA.

16. The chimeric RNA molecule of claim 1, wherein either a) the chimeric RNA molecule comprises a second sense ribonucleotide sequence and a second antisense ribonucleotide sequence which each comprise at least 50 contiguous nucleotides in length and which hybridise to form a second double-stranded RNA region, wherein the first and second sense ribonucleotide sequences are covalently linked by an intervening ribonucleotide sequence which is related in sequence to the target RNA molecule, or the first and second sense ribonucleotide sequences are covalently linked without an intervening ribonucleotide sequence; or b) the chimeric RNA molecule comprises a second sense ribonucleotide sequence and antisense a second ribonucleotide sequence which each comprise at least 50 contiguous nucleotides in length and which hybridise to form a second double-stranded RNA region, wherein the first and second antisense ribonucleotide sequences are covalently linked by an intervening ribonucleotide sequence which is related in sequence to the complement of the target RNA molecule, or the first and second antisense ribonucleotide sequences are covalently linked without an intervening ribonucleotide sequence.

17. An isolated and/or exogenous polynucleotide encoding the chimeric RNA molecule of claim 1, wherein the polynucleotide is operably linked to a promoter capable of directing expression of the RNA molecule in a plant, arthropod or fungal cell or in vitro.

18. A host cell comprising one or both of: (i) the chimeric RNA molecule of claim 1, and (ii) a polynucleotide encoding the chimeric RNA molecule.

19. The host cell of claim 18 which is a plant cell.

20. The host cell of claim 18 which is a fungal cell or an arthropod cell.

21. The host cell of claim 20 which has been killed by some treatment or is in the form of a dried powder.

22. A plant comprising one or more or all of: (i) the chimeric RNA molecule of claim 1, (ii) asRNA molecules produced by processing of the chimeric RNA molecule, and (iii) a polynucleotide encoding the chimeric RNA molecule.

23. A method of producing the chimeric RNA molecule of claim 1, the method comprising expressing a polynucleotide encoding the chimeric RNA molecule in a host cell or cell-free expression system.

24. A composition comprising one or more suitable carriers, and the chimeric RNA molecule of claim 1.

25. The composition according to claim 24 which further comprises at least one compound which (i) enhances the stability of the chimeric RNA molecule, and/or (ii) assists in the chimeric RNA molecule being taken up by a cell of a plant, arthropod or fungus.

26. The chimeric RNA molecule of claim 1, wherein all of the ribonucleotides in the dsRNA region are basepaired.

27. The chimeric RNA molecule of claim 2, wherein all of the ribonucleotides in the dsRNA region are basepaired.

28. The chimeric RNA molecule of claim 1, wherein the dsRNA region does not comprise 8 contiguous canonical basepairs.

29. The chimeric RNA molecule of claim 1, wherein the first antisense ribonucleotide sequence is between 80% and 99.9% identical in sequence to the complement of the region of the target RNA molecule.

30. The chimeric RNA molecule of claim 1, wherein the first sense ribonucleotide sequence and the first antisense ribonucleotide sequence are both at least 100 ribonucleotides in length.

31. The chimeric RNA molecule of claim 1, wherein the first antisense ribonucleotide sequence is less than 100% identical in sequence to the complement of a region of the target RNA molecule.

32. The chimeric RNA molecule of claim 1, wherein a G ribonucleotide in at least one G:U basepair in the dsRNA region is in the first sense ribonucleotide sequence.

33. The chimeric RNA molecule of claim 1, which was produced in a cell-free expression system or in a cell which is different to the plant, arthropod or fungal cell comprising the target RNA molecule.

34. An arthropod or fungus comprising one or more or all of: (i) the chimeric RNA molecule of claim 2, (ii) asRNA molecules produced by processing of the chimeric RNA molecule, and (iii) a polynucleotide encoding the chimeric RNA molecule.

* * * * *

SEQUENCE LISTING

<160> NUMBER OF SEQ ID NOS: 144

<210> SEQ ID NO 1
<211> LENGTH: 1229
<212> TYPE: RNA
<213> ORGANISM: Artificial Sequence
<220> FEATURE:
<223> OTHER INFORMATION: GFP ledRNA

<400> SEQUENCE: 1
gggugucgcc cucgaacuuc accucggcgc gggucuugua guugccgucg uccuugaaga 60
agauggugcg cuccuggacg uagccuucgg gcauggcgga cuugaagaag ucgugcugcu 120
ucaugugguc gggguagcgg cugaagcacu gcacgccgua ggugaaggug gucacgaggg 180
ugggccaggg cacgggcagc uugccggugg ugcagaugaa cuucagggc agcuugccgu 240 agguggcauc gcccucgccc ucgccggaca cgcugaacuu guggccguuu acgucgccgu 300
ccagcucgac caggaugggc accaccccgg ugaacagcuc cucgcccuug cucacuaugg 360
aucaacuagg gaucccccug aaguucaucu gcaccaccgg caagcugccc gugcccuggc 420
ccacccucgu gaccaccuuc accuacggcg ugcagugcuu cagccgcuac cccgaccaca 480
ugaagcagca cgacuucuuc aaguccgcca ugcccgaagg cuacguccag gagcgcacca 540
ucuucuucaa ggacgacggc aacuacaaga cccgcgccga ggugaaguuc gagggcgaca 600
cccuggugaa ccgcaucgag cugaagggca ucgacuucaa ggaggacggc aacauccugg 660
ggcacaagcu ggaguacaac uacaacagcc acaacgucua uaucauggcc gacaagcaga 720
agaacggcau caaggugaac uucaagaucc gccacaacau cgaggacggc agcgugcagc 780
ucgccgacca cuaccagcag aacaccccca ucggcgacgg ccccgugcug cugccaagcu 840
uuaggugauc caagcuugau ccgggcuuua cuuguacagc ucguccaugc cgagagugau 900
cccggcggcg gucacgaacu ccagcaggac caugugaucg cgcuucucgu uggggucuuu 960
gcucagggcg gacugggugc ucagguagug guugucgggc agcagcacgg ggccgucgcc 1020 gauggggggug uucugcuggu aguggucggc gagcugcacg cugccguccu cgauguugug 1080
gcggaucuug aaguucaccu ugaugccguu cuucugcuug ucggccauga uauagacguu 1140
guggcuguug uaguuguacu ccagcuugug ccccaggaug uugccguccu ccuugaaguc 1200
gaugcccuuc agcucgaugc gguucacca 1229

<210> SEQ ID NO 2
<211> LENGTH: 1326
<212> TYPE: RNA
<213> ORGANISM: Artificial Sequence
<220> FEATURE:
<223> OTHER INFORMATION: GUS ledRNA

<400> SEQUENCE: 2
gggaacagac gcgugguuac agucuugcgc gacaugcguc accacgguga uaucguccac 60
ccagguguuc ggcguggugu agagcauuac gcugcgaugg auuccggcau aguuaaagaa 120
aucauggaag uaagacugcu uuuucuugcc guuuucgucg guaaucacca uucccggcgg 180
gauagucugc caguucaguu cguuguucac acaaacggug auacguacac uuuucccggc 240
aauaacauac ggcgugacau cggcuucaaa uggcguauag ccgcccugau gcuccaucac 300
uuccugauua uugacccaca cuuugccgua augagugacc gcaucgaaac gcagcacgau 360
acgcuggccu gcccaaccuu ucgguauaaa gacuucgcgc ugauaccaga cgugccguau 420
guuauugccg ggaaaagugu acguaucacc guuuguguga acaacgaacu gaacuggcag 480
acuaucccgc cgggaauggu gauuaccgac gaaaacggca agaaaaagca gucuuacuuc 540
caugauuucu uuaacuaugc cggaauccau cgcagcguaa ugcucuacac cacgccgaac 600
accugggugg acgauaucac cgugguggacg caugucgcgc aagacuguaa ccacgcgucu 660
guucccgacu ggcaggugu ggccaauggu gaugucagcg uugaacugcg ugaugcggau 720
caacaggugg uugcaacugg acaaggcacu agcgggacuu ugcaaguggu gaauccgcac 780
cucuggcaac cgggugaagg uuaucucuau gaacugugcg ucacagccaa aagccagaca 840
gagugugaua ucuacccgcu ucgcgucggc auccggucag uggcagugaa gggccaacag 900
uuccugauua accacaaacc guucuacuuu acuggcuuug gucgucauga agaugcggac 960
uuacguggca aaggauucga uaacgugcug auggugcacg accacgcauu aauggacugg 1020
auuggggcca acuccuaccg uaccucgcau uacccuuacg cugaagagau gcucgaugug 1080
guuaaucagg aacuguuggc ccuucacugc cacugaccgg augccgacgc gaagcgggua 1140
gauaucacac ucugucuggc uuuuggcugu gacgcacagu ucauagagau aaccuucacc 1200
cgguugccag aggugcggau ucaccacuug caaagucccg cuagugccuu guccaguugc 1260
aaccaccugu ugauccgcau cacgcaguuc aacgcugaca ucaccauugg ccaccaccug 1320
ccaguc 1326

<210> SEQ ID NO 3
<211> LENGTH: 1485
<212> TYPE: RNA
<213> ORGANISM: Artificial Sequence
<220> FEATURE:
<223> OTHER INFORMATION: FAD2.1 ledRNA

<400> SEQUENCE: 3
gaagaucugu agccucucgc ggucauugua gauugggccg uaagggucau agugacaugc 60
aaagcgauca uaaugucggc cagaaacauu gaaagccaag uacaaaggcc agccaagagu 120
aagggugauc guaagugaaa uaacccggcc ugguggauug uucaaguacu uggaauacca 180
uccgaguugu gauuucggcu uaggcacaaa aaccucaucg cgcucgagug agccagugu 240 ggaguggugg cgacgaugac uauauuucca agagaaguag ggcaccauca gagcagagug 300
gaggauaagc ccgacagugu caucaaccca cugguaguca cuaaaggcau gguggccaca 360
uucgugcgca auaacccaaa uaccagugca aacacaaccc ugacaaaucc aguaaauagg 420
ccaugcaagg uagcaauccu aggcacucug cucugauggu gcccuacuuc ucuuggaaau 480
auagucaucg ucgccaccac uccaacacug gcucacucga gcgcgaugag guuuuugugc 540
cuaagccgaa aucacaacuc ggaugguauu ccaaguacuu gaacaaucca ccaggccggg 600
uuauuucacu uacgaucacc cuuacucuug gcuggccuuu guacuuggcu uucaauguuu 660
cuggccgaca uuaugaucgc uuugcauguc acuaugaccc uuacggccca aucuacaaug 720
accgcgagag gcuacagauc uuccuuucug augcuggagu uauuggagcu gguuaucuac 780
uauaucguau ugccuuggua aaagggcuag cuuggcucgu guguauguau ggcguaccac 840
uccuaaucgu gaacggcuuc cuugucuuga ucacuuauuu gcagcacacu cacccgucau 900
ugccucacua cgauucaucc gaaugggauu ggcuaagggg agcuuuggca accgucgaca 960
gagacuaugg cauucuaaac aaggucuucc acaacaucac cgauacucac guaguccacc 1020
aucuguucuc gaccaugcca cacucuagag ugaugcuuca ucuuucucca cauagauaca 1080
cucuuuugcu ucccuccaca uugccuugaa aaccgggguu ccgucaaauu gguaguaguc 1140
uccgaguaau ggcuugacug cuuuuguugc cuccauugca uuguagugug gcauggucga 1200
gaacagaugg uggacuacgu gaguaucggu gauguugugg aagaccuugu uuagaaugcc 1260
auagucucug ucgacgguug ccaaagcucc ccuuagccaa ucccauucgg augaaucgua 1320
gugaggcaau gacgggugag ugugcugcaa auaagugauc aagacaagga agccguucac 1380
gauuaggagu gguacgccau acauacacac gagccaagcu agcccuuuua ccaaggcaau 1440
acgauauagu agauaaccag cuccaauaac uccagcauca gaaag 1485

<210> SEQ ID NO 4
<211> LENGTH: 1258
<212> TYPE: DNA
<213> ORGANISM: Artificial Sequence
<220> FEATURE:
<223> OTHER INFORMATION: DNA construct encoding GFP ledRNA

<400> SEQUENCE: 4
taatacgact cactataggg tgtcgccctc gaacttcacc tcggcgcggg tcttgtagtt 60
gccgtcgtcc ttgaagaaga tggtgcgctc ctggacgtag ccttcgggca tggcggactt 120
gaagaagtcg tgctgcttca tgtggtcggg gtagcggctg aagcactgca cgccgtaggt 180
gaaggtggtc acgagggtgg gccagggcac gggcagcttg ccggtggtgc agatgaactt 240
cagggtcagc ttgccgtagg tggcatcgcc ctcgccctcg ccggacacgc tgaacttgtg 300
gccgtttacg tcgccgtcca gctcgaccag gatgggcacc accccggtga acagctcctc 360
gcccttgctc actatggatc aactagggat cccccctgaag ttcatctgca ccaccggcaa 420
gctgcccgtg ccctggccca ccctcgtgac caccttcacc tacggcgtgc agtgcttcag 480
ccgctacccc gaccacatga agcagcacga cttcttcaag tccgccatgc ccgaaggcta 540
cgtccaggag cgcaccatct tcttcaagga cgacggcaac tacaagaccc gcgccgaggt 600
gaagttcgag ggcgacaccc tggtgaaccg catcgagctg aagggcatcg acttcaagga 660
ggacggcaac atcctggggc acaagctgga gtacaactac aacagccaca acgtctatat 720
catggccgac aagcagaaga acggcatcaa ggtgaacttc aagatccgcc acaacatcga 780
ggacggcagc gtgcagctcg ccgaccacta ccagcagaac acccccatcg gcgacggccc 840
cgtgctgctg ccaagcttta ggtgatccaa gcttgatccg ggctttactt gtacagctcg 900
tccatgccga gagtgatccc ggcggcggtc acgaactcca gcaggaccat gtgatcgcgc 960
ttctcgttgg ggtctttgct cagggcggac tgggtgctca ggtagtggtt gtcgggcagc 1020
agcacggggc cgtcgccgat gggggtgttc tgctggtagt ggtcggcgag ctgcacgctg 1080
ccgtcctcga tgttgtggcg gatcttgaag ttcaccttga tgccgttctt ctgcttgtcg 1140
gccatgatat agacgttgtg gctgttgtag ttgtactcca gcttgtgccc caggatgttg 1200
ccgtcctcct tgaagtcgat gcccttcagc tcgatgcggt tcaccattgt cgggatac 1258

<210> SEQ ID NO 5
<211> LENGTH: 1346
<212> TYPE: DNA
<213> ORGANISM: Artificial Sequence
<220> FEATURE:
<223> OTHER INFORMATION: DNA construct encoding Gus ledRNA

<400> SEQUENCE: 5
taatacgact cactataggg aacagacgcg tggttacagt cttgcgcgac atgcgtcacc 60
acggtgatat cgtccaccca ggtgttcggc gtggtgtaga gcattacgct gcgatggatt 120
ccggcatagt taaagaaatc atggaagtaa gactgctttt tcttgccgtt ttcgtcggta 180
atcaccattc ccggcgggat agtctgccag ttcagttcgt tgttcacaca aacggtgata 240
cgtacacttt tcccggcaat aacatacggc gtgacatcgg cttcaaatgg cgtatagccg 300
ccctgatgct ccatcacttc ctgattattg acccacactt tgccgtaatg agtgaccgca 360
tcgaaacgca gcacgatacg ctggcctgcc caacctttcg gtataaagac ttcgcgctga 420
taccagacgt gccgtatgtt attgccggga aaagtgtacg tatcaccgtt tgtgtgaaca 480
acgaactgaa ctggcagact atcccgccgg gaatggtgat taccgacgaa aacggcaaga 540
aaaagcagtc ttacttccat gatttcttta actatgccgg aatccatcgc agcgtaatgc 600
tctacaccac gccgaacacc tgggtggacg atatcaccgt ggtgacgcat gtcgcgcaag 660
actgtaacca cgcgtctgtt cccgactggc aggtggtggc caatggtgat gtcagcgttg 720
aactgcgtga tgcggatcaa caggtggttg caactggaca aggcactagc gggactttgc 780
aagtggtgaa tccgcacctc tggcaaccgg gtgaaggtta tctctatgaa ctgtgcgtca 840
cagccaaaag ccagacagag tgtgatatct acccgcttcg cgtcggcatc cggtcagtgg 900
cagtgaaggg ccaacagttc ctgattaacc acaaaccgtt ctactttact ggctttggtc 960
gtcatgaaga tgcggactta cgtggcaaag gattcgataa cgtgctgatg gtgcacgacc 1020
acgcattaat ggactggatt ggggccaact cctaccgtac ctcgcattac ccttacgctg 1080
aagagatgct cgatgtggtt aatcaggaac tgttggccct tcactgccac tgaccggatg 1140
ccgacgcgaa gcgggtagat atcacactct gtctggcttt tggctgtgac gcacagttca 1200
tagagataac cttcacccgg ttgccagagg tgcggattca ccacttgcaa agtcccgcta 1260
gtgccttgtc cagttgcaac cacctgttga tccgcatcac gcagttcaac gctgacatca 1320
ccattggcca ccacctgcca gtcaac 1346

<210> SEQ ID NO 6
<211> LENGTH: 1512
<212> TYPE: DNA
<213> ORGANISM: Artificial Sequence
<220> FEATURE:
<223> OTHER INFORMATION: DNA construct encoding FAD2.1 ledRNA

<400> SEQUENCE: 6
atttaggtga cactatagaa gatctgtagc ctctcgcggt cattgtagat tgggccgtaa 60
gggtcatagt gacatgcaaa gcgatcataa tgtcggccag aaacattgaa agccaagtac 120
aaaggccagc caagagtaag ggtgatcgta agtgaaataa cccggcctgg tggattgttc 180
aagtacttgg aataccatcc gagttgtgat ttcggcttag gcacaaaaac ctcatcgcgc 240
tcgagtgagc cagtgttgga gtggtggcga cgatgactat atttccaaga gaagtagggc 300
accatcagag cagagtggag gataagcccg acagtgtcat caacccactg gtagtcacta 360
aaggcatggt ggccacattc gtgcgcaata acccaaatac cagtgcaaac acaaccctga 420
caaatccagt aaataggcca tgcaaggtag caatcctagg cactctgctc tgatggtgcc 480
ctacttctct tggaaatata gtcatcgtcg ccaccactcc aacactggct cactcgagcg 540
cgatgaggtt tttgtgccta agccgaaatc acaactcgga tggtattcca agtacttgaa 600
caatccacca ggccgggtta tttcacttac gatcaccctt actcttggct ggcctttgta 660
cttggctttc aatgtttctg gccgacatta tgatcgcttt gcatgtcact atgaccctta 720
cggcccaatc tacaatgacc gcgagaggct acagatcttc ctttctgatg ctggagttat 780
tggagctggt tatctactat atcgtattgc cttggtaaaa gggctagctt ggctcgtgtg 840

```
tatgtatggc gtaccactcc taatcgtgaa cggcttcctt gtcttgatca cttatttgca    900

gcacactcac ccgtcattgc ctcactacga ttcatccgaa tgggattggc taaggggagc    960

tttggcaacc gtcgacagag actatggcat tctaaacaag gtcttccaca acatcaccga   1020

tactcacgta gtccaccatc tgttctcgac catgccacac tctagagtga tgcttcatct   1080

ttctccacat agatacactc ttttgcttcc ctccacattg ccttgaaaac cggggttccg   1140

tcaaattggt agtagtctcc gagtaatggc ttgactgctt ttgttgcctc cattgcattg   1200

tagtgtggca tggtcgagaa cagatggtgg actacgtgag tatcggtgat gttgtggaag   1260

accttgttta gaatgccata gtctctgtcg acggttgcca aagctcccct tagccaatcc   1320

cattcggatg aatcgtagtg aggcaatgac gggtgagtgt gctgcaaata agtgatcaag   1380

acaaggaagc cgttcacgat taggagtggt acgccataca tacacacgag ccaagctagc   1440

ccttttacca aggcaatacg atatagtaga taaccagctc caataactcc agcatcagaa   1500

agcccgggac tc                                                       1512
```

<210> SEQ ID NO 7
<211> LENGTH: 732
<212> TYPE: DNA
<213> ORGANISM: Aequorea victoria

<400> SEQUENCE: 7

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccttcaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720

agcccggatc tc                                                        732
```

<210> SEQ ID NO 8
<211> LENGTH: 1855
<212> TYPE: DNA
<213> ORGANISM: Escherichia coli

<400> SEQUENCE: 8

```
atggtccgtc ctgtagaaac cccaacccgt gaaatcaaaa aactcgacgg cctgtgggca     60

ttcagtctgg atcgcgaaaa ctgtggaatt gatcagcgtt ggtgggaaag cgcgttacaa    120

gaaagccggg caattgctgt gccaggcagt tttaacgatc agttcgccga tgcagatatt    180

cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtatc accgtttgtg tgaacaacga actgaactgg    420
```

```
cagactatcc cgccgggaat ggtgattacc gacgaaaacg gcaagaaaaa gcagtcttac    480
ttccatgatt tctttaacta tgccggaatc catcgcagcg taatgctcta caccacgccg    540
aacacctggg tggacgatat caccgtggtg acgcatgtcg cgcaagactg taaccacgcg    600
tctgttcccg actggcaggt ggtggccaat ggtgatgtca gcgttgaact gcgtgatgcg    660
gatcaacagg tggttgcaac tggacaaggc actagcggga ctttgcaagt ggtgaatccg    720
cacctctggc aaccgggtga aggttatctc tatgaactgt gcgtcacagc caaaagccag    780
acagagtgtg atatctaccc gcttcgcgtc ggcatccggt cagtggcagt gaagggccaa    840
cagttcctga ttaaccacaa accgttctac tttactggct ttggtcgtca tgaagatgcg    900
gacttacgtg gcaaaggatt cgataacgtg ctgatggtgc acgaccacgc attaatggac    960
tggattgggg ccaactccta ccgtacctcg cattaccctt acgctgaaga gatgctcgac   1020
tgggcagatg aacatggcat cgtggtgatt gatgaaactg ctgctgtcgg ctttaacctc   1080
tctttaggca ttggtttcga agcgggcaac aagccgaaag aactgtacag cgaagaggca   1140
gtcaacgggg aaactcagca agcgcactta caggcgatta aagagctgat agcgcgtgac   1200
aaaaaccacc caagcgtggt gatgtggagt attgccaacg aaccggatac ccgtccgcaa   1260
gtgcacggga atatttcgcc actggcggaa gcaacgcgta aactcgaccc gacgcgtccg   1320
atcacctgcg tcaatgtaat gttctgcgac gctcacaccg ataccatcag cgatctcttt   1380
gatgtgctgt gcctgaaccg ttattacgga tggtatgtcc aaagcggcga tttggaaacg   1440
gcagagaagg tactggaaaa agaacttctg gcctggcagg agaaactgca tcagccgatt   1500
atcatcaccg aatacggcgt ggatacgtta gccgggctgc actcaatgta caccgacatg   1560
tggagtgaag agtatcagtg tgcatggctg gatatgtatc accgcgtctt tgatcgcgtc   1620
agcgccgtcg tcggtgaaca ggtatggaat ttcgccgatt ttgcgacctc gcaaggcata   1680
ttgcgcgttg gcggtaacaa gaaagggatc ttcactcgcg accgcaaacc gaagtcggcg   1740
gcttttctgc tgcaaaaacg ctggactggc atgaacttcg gtgaaaaacc gcagcaggga   1800
ggcaaacaat gaatcaacaa ctctcctggc gcaccatcgt cggctacagc ctcgg        1855
```

```
<210> SEQ ID NO 9
<211> LENGTH: 1152
<212> TYPE: DNA
<213> ORGANISM: Nicotiana benthamiana

<400> SEQUENCE: 9

atgggagctg gtggtaatat gtctcttgta accagcaaga ctggcgaaaa gaagaatcct     60
cttgaaaagg taccaacctc aaagcctcct ttcacagttg gtgatatcaa gaaggccatc    120
ccacctcact gctttcagcg gtctctcgtt cgttcgttct cctatgttgt gtatgacctt    180
ttactggtgt ccgtcttcta ctacattgcc accacttact tccacctcct cccgtcccca    240
tattgctacc ttgcatggcc tatttactgg atttgtcagg gttgtgtttg cactggtatt    300
tgggttattg cgcacgaatg tggccaccat gcctttagtg actaccagtg ggttgatgac    360
actgtcgggc ttatcctcca ctctgctctg atggtgccct acttctcttg gaaatatagt    420
catcgtcgcc accactccaa cactggctca ctcgagcgcg atgaggtttt tgtgcctaag    480
ccgaaatcac aactcggatg gtattccaag tacttgaaca atccaccagg ccgggttatt    540
tcacttacga tcacccttac tcttggctgg cctttgtact tggctttcaa tgtttctggc    600
cgacattatg atcgctttgc atgtcactat gacccttacg gcccaatcta caatgaccgc    660
```

```
gagaggctac agatcttcct ttctgatgct ggagttattg gagctggtta tctactatat    720

cgtattgcct tggtaaaagg gctagcttgg ctcgtgtgta tgtatggcgt accactccta    780

atcgtgaacg gcttccttgt cttgatcact tatttgcagc acactcaccc gtcattgcct    840

cactacgatt catccgaatg ggattggcta aggggagctt tggcaaccgt cgacagagac    900

tatggcattc taaacaaggt cttccacaac atcaccgata ctcacgtagt ccaccatctg    960

ttctcgacca tgccacacta caatgcaatg gaggcaacaa aagcagtcaa gccattactc   1020

ggagactact accaatttga cggaaccccg gttttcaagg caatgtggag ggaagcaaaa   1080

gagtgtatct atgtggagaa agatgaagca tcacaaggca aaggtgtttt ctggtacaaa   1140

aacaaattct ga                                                       1152
```

<210> SEQ ID NO 10
<211> LENGTH: 225
<212> TYPE: DNA
<213> ORGANISM: Artificial Sequence
<220> FEATURE:
<223> OTHER INFORMATION: GUS sense region for constructs encoding hairpin RNA molecules targeting the GUS mRNA

<400> SEQUENCE: 10

```
cctcgaggat cctcgcgtcg gcatccggtc agtggcagtg aagggcgaac agttcctgat     60

taaccacaaa ccgttctact ttactggctt tggtcgtcat gaagatgcgg acttgcgtgg    120

caaaggattc gataacgtgc tgatggtgca cgaccacgca ttaatggact ggattggggc    180

caactcctac cgtacctcgc attaccctta cgaagcttgg taccc                   225
```

<210> SEQ ID NO 11
<211> LENGTH: 216
<212> TYPE: DNA
<213> ORGANISM: Artificial Sequence
<220> FEATURE:
<223> OTHER INFORMATION: GUS sense region for the construct encoding the hairpin RNA molecule hpGUS[G:U]

<400> SEQUENCE: 11

```
ccctcgagtt gtgttggtat ttggttagtg gtagtgaagg gtgaatagtt tttgattaat     60

tataaattgt tttattttat tggttttggt tgttatgaag atgtggattt gtgtggtaaa    120

ggatttgata atgtgttgat ggtgtatgat tatgtattaa tggattggat tggggttaat    180

ttttattgta ttttgtatta tttttatggg taccccc                             216
```

<210> SEQ ID NO 12
<211> LENGTH: 216
<212> TYPE: DNA
<213> ORGANISM: Artificial Sequence
<220> FEATURE:
<223> OTHER INFORMATION: GUS sense region for constructs encoding the hairpin RNA molecule hpGUS[1:4]

<400> SEQUENCE: 12

```
ccctcgagtc gggtccgcaa ccgctcactg ggagtcaagc gcgtacactt cgtgaataag     60

cactaacggt tgtacattag tgggtttcgt cctcaagaac atggggagtt gggtgccaat    120

ggaatcgtta aggtggtgaa ggtccaccac ctcgctttat tggtctgcat tcggggcaag    180

tccaacccta cgtcggattt cccataccgg taccccc                             216
```

<210> SEQ ID NO 13
<211> LENGTH: 216
<212> TYPE: DNA

<213> ORGANISM: Artificial Sequence
<220> FEATURE:
<223> OTHER INFORMATION: GUS sense region for constructs encoding the hairpin RNA molecule hpGUS[2:10]

<400> SEQUENCE: 13
ccctcgagtc gcgtcgcgat ccggtctctg gcagtgttgg gcgaactctt cctgatatac 60
cacaaagggt tctactaaac tggcttacgt cgtcatctag atgcggtgtt gcgtgggtaa 120
ggattcctta acgtgcacat ggtgcagcac cacgcaaaaa tggactccat tggggcgtac 180
tcctacgcta cctcgctata cccttagcgg taccccc 216

<210> SEQ ID NO 14
<211> LENGTH: 240
<212> TYPE: DNA
<213> ORGANISM: Artificial Sequence
<220> FEATURE:
<223> OTHER INFORMATION: DNA sequence of nucleotides 781-1020 of the protein coding region of the GUS gene

<400> SEQUENCE: 14
gagtgtgata tctacccgct tcgcgtcggc atccggtcag tggcagtgaa gggcgaacag 60
ttcctgatta accacaaacc gttctacttt actggctttg gtcgtcatga agatgcggac 120
ttgcgtggca aaggattcga taacgtgctg atggtgcacg accacgcatt aatggactgg 180
attggggcca actcctaccg tacctcgcat taccccttacg ctgaagagat gctcgactgg 240

<210> SEQ ID NO 15
<211> LENGTH: 463
<212> TYPE: RNA
<213> ORGANISM: Artificial Sequence
<220> FEATURE:
<223> OTHER INFORMATION: hairpin structure (including its loop) of the hpGUS[wt] RNA

<400> SEQUENCE: 15
ggauccucgc gucggcaucc ggucaguggc agugaagggc gaacaguucc ugauuaacca 60
caaaccguuc uacuuuacug gcuuuggucg ucaugaagau gcggacuugc guggcaaagg 120
auucgauaac gugcugaugg ugcacgacca cgcauuaaug gacuggauug gggccaacuc 180
cuaccguacc ucgcauuacc cuuacgaagc uugguacccc agcuuguugg gaagcugggu 240
ucgaaaucga uaagcuucgu aaggguaaug cgagguacgg uaggaguugg ccccaaucca 300
guccauuaau gcguggucgu gcaccaucag cacguuaucg aauccuuugc cacgcaaguc 360
cgcaucuuca ugacgaccaa agccaguaaa guagaacggu uugugguuaa ucaggaacug 420
uucgcccuuc acugccacug accggaugcc gacgcgagga ucc 463

<210> SEQ ID NO 16
<211> LENGTH: 457
<212> TYPE: RNA
<213> ORGANISM: Artificial Sequence
<220> FEATURE:
<223> OTHER INFORMATION: hairpin structure (including its loop) of the hpGUS[G:U] RNA

<400> SEQUENCE: 16
cucgaguugu guugguauuu gguuaguggu agugaagggu gaauaguuuu ugauuaauua 60
uaaauuguuu uauuuuauug guuuugguug uuaugaagau guggauuugu gugguaaagg 120
auuugauaau guguugaugg uguaugauua uguauuaaug gauuggauug ggguuaauuu 180
uuauuguauu uuguauuauu uuuaugggua ccccagcuug uugggaagcu ggguucgaaa 240
ucgauaagcu ucguaagggu aaugcgaggu acgguaggag uuggccccaa uccaguccau 300
uaaugcgugg ucgugcacca ucagcacguu aucgaauccu uugccacgca aguccgcauc 360
uucaugacga ccaaagccag uaaaguagaa cgguuugugg uuaaucagga acuguucgcc 420
cuucacugcc acugaccgga ugccgacgcg aggaucc 457

<210> SEQ ID NO 17
<211> LENGTH: 457
<212> TYPE: RNA
<213> ORGANISM: Artificial Sequence
<220> FEATURE:
<223> OTHER INFORMATION: hairpin structure (including its loop) of the hpGUS[1:4] RNA

<400> SEQUENCE: 17
cucgagucgg guccgcaacc gcucacuggg agucaagcgc guacacuucg ugaauaagca 60
cuaacgguug uacauuagug gguuucgucc ucaagaacau ggggaguugg gugccaaugg 120
aaucguuaag guggugaagg uccaccaccu cgcuuuauug gucugcauuc ggggcaaguc 180
caacccuacg ucggauuucc cauaccggua ccccagcuug uugggaagcu ggguucgaaa 240
ucgauaagcu ucguaagggu aaugcgaggu acgguaggag uuggccccaa uccaguccau 300
uaaugcgugg ucgugcacca ucagcacguu aucgaauccu uugccacgca aguccgcauc 360
uucaugacga ccaaagccag uaaaguagaa cgguuugugg uuaaucagga acuguucgcc 420
cuucacugcc acugaccgga ugccgacgcg aggaucc 457

<210> SEQ ID NO 18
<211> LENGTH: 457
<212> TYPE: RNA
<213> ORGANISM: Artificial Sequence
<220> FEATURE:
<223> OTHER INFORMATION: hairpin structure (including its loop) of the hpGUS[2:10] RNA

<400> SEQUENCE: 18
cucgagucgc gucgcgaucc ggucucuggc aguguugggc gaacucuucc ugauauacca 60
caaaggguuc uacuaaacug gcuuacgucg ucaucuagau gcgguguugc gugguaagg 120 auuccuuaac gugcacaugg ugcagcacca cgcaaaaaug gacuccauug gggcguacuc 180
cuacgcuacc ucgcuauacc cuuagcggua ccccagcuug uugggaagcu ggguucgaaa 240
ucgauaagcu ucguaagggu aaugcgaggu acgguaggag uuggccccaa uccaguccau 300
uaaugcgugg ucgugcacca ucagcacguu aucgaauccu uugccacgca aguccgcauc 360
uucaugacga ccaaagccag uaaaguagaa cgguuugugg uuaaucagga acuguucgcc 420
cuucacugcc acugaccgga ugccgacgcg aggaucc 457

<210> SEQ ID NO 19
<211> LENGTH: 4851
<212> TYPE: DNA
<213> ORGANISM: Arabidopsis thaliana

<400> SEQUENCE: 19
atctctctct ttcgatggaa ctgagctctt tctctctttc ctcttctttt ctctctctat 60
ctctatctct cgtagcttga taagagtttc tctcttttga agatccgttt ctctctctct 120
cactgagact attgttgtta ggtcaacttg cgatcatggc gatttcgaag gtctgaagct 180
gatttcgaat ggtttggaga tatccgtagt ggttaagcat atggaagtct atgttctgct 240

-continued

```
cttggttgct ctgttagggc ttcctccatt tggaccaact tagctgaatg ttgtatgatc    300
tctctccttg aagcagcaaa taagaagaag gtctggtcct taacttaaca tctggttact    360
agaggaaact tcagctatta ttaggtaaag aaagactgta cagagttgta taacaagtaa    420
gcgttagagt ggctttgttt gcctcggtga tagaagaacc gactgattcg ttgttgtgtg    480
ttagctttgg agggaatcag atttcgcgag ggaaggtgtt ttagatcaaa tctgtgaatt    540
ttactcaact gaggctttta gtgaaccacg actgtagagt tgaccttgaa tcctactctg    600
agtaattata ttatcagata gatttaggat ggaagctgaa attgtgaatg tgagacctca    660
gctagggttt atccagagaa tggttcctgc tctacttcct gtccttttgg tttctgtcgg    720
atatattgat cccgggaaat gggttgcaaa tatcgaagga ggtgctcgtt tcgggtatga    780
cttggtggca attactctgc ttttcaattt tgccgccatc ttatgccaat atgttgcagc    840
tcgcataagc gttgtgactg gtaaacactt ggctcagatc tgcaatgaag aatatgacaa    900
gtggacgtgc atgttcttgg gcattcaggc ggagttctca gcaattctgc tcgaccttac    960
catggttgtg ggagttgcgc atgcacttaa ccttttgttt ggggtggagt tatccactgg   1020
agtgtttttg gccgccatgg atgcgttttt atttcctgtt ttcgcctctt tccttgaaaa   1080
tggtatggca aatacagtat ccatttactc tgcaggcctg gtattacttc tctatgtatc   1140
tggcgtcttg ctgagtcagt ctgagatccc actctctatg aatggagtgt taactcggtt   1200
aaatggagag agcgcattcg cactgatggg tcttcttggc gcaagcatcg tccctcacaa   1260
tttttatatc cattcttatt ttgctgggga aagtacatct tcgtctgatg tcgacaagag   1320
cagcttgtgt caagaccatt tgttcgccat ctttggtgtc ttcagcggac tgtcacttgt   1380
aaattatgta ttgatgaatg cagcagctaa tgtgtttcac agtactggcc ttgtggtact   1440
gacttttcac gatgccttgt cactaatgga gcaggtattt atgagtccgc tcattccagt   1500
ggtctttttg atgctcttgt tcttctctag tcaaattacc gcactagctt gggctttcgg   1560
tggagaggtc gtcctgcatg acttcctgaa gatagaaata cccgcttggc ttcatcgtgc   1620
tacaatcaga attcttgcag ttgctcctgc gctttattgt gtatggacat ctggtgcaga   1680
cggaatatac cagttactta tattcaccca ggtcttggtg gcaatgatgc ttccttgctc   1740
ggtaataccg cttttccgca ttgcttcgtc gagacaaatc atgggtgtcc ataaaatccc   1800
tcaggttggc gagttcctcg cacttacaac gtttttggga tttctggggt tgaatgttgt   1860
tttgttgtt gagatggtat ttgggagcag tgactgggct ggtggtttga gatggaatac   1920
cgtgatgggc acctcgattc agtacaccac tctgcttgta tcgtcatgtg catccttatg   1980
cctgatactc tggctggcag ccacgccgct gaaatctgcg agtaacagag cggaagctca   2040
aatatggaac atggatgctc aaaatgcttt atcttatcca tctgttcaag aagaggaaat   2100
tgaaagaaca gaaacaagga ggaacgaaga cgaatcaata gtgcggttgg aaagcagggt   2160
aaaggatcag ttggatacta cgtctgttac tagctcggtc tatgatttgc cagagaacat   2220
tctaatgacg gatcaagaaa tccgttcgag ccctccagag gaaagagagt tggatgtaaa   2280
gtactctacc tctcaagtta gtagtcttaa ggaagactct gatgtaaagg aacagtctgt   2340
attgcagtca acagtggtta atgaggtcag tgataaggat ctgattgttg aaacaaagat   2400
ggcgaaaatt gaaccaatga gtcctgtgga gaagattgtt agcatggaga ataacagcaa   2460
gtttattgaa aaggatgttg aaggggtttc atgggaaaca gaagaagcta ccaaagctgc   2520
tcctacaagc aactttactg tcggatctga tggtcctcct tcattccgca gcttaagtgg   2580
ggaaggggga agtgggactg gaagcctttc acggttgcaa ggtttgggac gtgctgcccg   2640
```

```
gagacactta tctgcgatcc ttgatgaatt ttggggacat ttatatgatt ttcatgggca   2700
attggttgct gaagccaggg caaagaaact agatcagctg tttggcactg atcaaaagtc   2760
agcctcttct atgaaagcag attcgtttgg aaaagacatt agcagtggat attgcatgtc   2820
accaactgcg aagggaatgg attcacagat gacttcaagt ttatatgatt cactgaagca   2880
gcagaggaca ccgggaagta tcgattcgtt gtatggatta caaagaggtt cgtcaccgtc   2940
accgttggtc aaccgtatgc agatgttggg tgcatatggt aacaccacta ataataataa   3000
tgcttacgaa ttgagtgaga gaagatactc tagcctgcgt gctccatcat cttcagaggg   3060
ttgggaacac caacaaccag ctacagttca cggataccag atgaagtcat atgtagacaa   3120
tttggcaaaa gaaaggcttg aagccttaca atcccgtgga gagatcccga catcgagatc   3180
tatggcgctt ggtacattga gctatacaca gcaacttgct ttagccttga aacagaagtc   3240
ccagaatggt ctaacccctg gaccagctcc tgggtttgag aattttgctg ggtctagaag   3300
catatcgcga caatctgaaa gatcttatta cggtgttcca tcttctggca atactgatac   3360
tgttggcgca gcagtagcca atgagaaaaa atatagtagc atgccagata tctcaggatt   3420
gtctatgtcc gcaaggaaca tgcatttacc aaacaacaag agtggatact gggatccgtc   3480
aagtggagga ggagggtatg gtgcgtctta tggtcggtta agcaatgaat catcgttata   3540
ttctaatttg gggtcacggg tgggagtacc ctcgacttat gatgacattt ctcaatcaag   3600
aggaggctac agagatgcct acagtttgcc acagagtgca acaacaggga ccggatcgct   3660
ttggtccaga cagccctttg agcagtttgg tgtagcggag aggaatggtg ctgttggtga   3720
ggagctcagg aatagatcga atccgatcaa tatagacaac aacgcttctt ctaatgttga   3780
tgcagaggct aagcttcttc agtcgttcag gcactgtatt ctaaagctta ttaaacttga   3840
aggatccgag tggttgtttg gacaaagcga tggagttgat gaagaactga ttgaccgggt   3900
agctgcacga gagaagttta tctatgaagc tgaagctcga gaaataaacc aggtgggtca   3960
catgggggag ccactaattt catcggttcc taactgtgga gatggttgcg tttggagagc   4020
tgatttgatt gtgagctttg gagtttggtg cattcaccgt gtccttgact tgtctctcat   4080
ggagagtcgg cctgagcttt ggggaaagta cacttacgtt ctcaaccgcc tacagggagt   4140
gattgatccg gcgttctcaa agctgcggac accaatgaca ccgtgctttt gccttcagat   4200
tccagcgagc caccagagag cgagtccgac ttcagctaac ggaatgttac ctccggctgc   4260
aaaaccggct aaaggcaaat gcacaaccgc agtcacactt cttgatctaa tcaaagacgt   4320
tgaaatggca atctcttgta gaaaaggccg aaccggtaca gctgcaggtg atgtggcttt   4380
cccaaagggg aaagagaatt tggcttcggt tttgaagcgg tataaacgtc ggttatcgaa   4440
taaaccagta ggtatgaatc aggatggacc cggttcaaga aaaaacgtga ctgcgtacgg   4500
atcattgggt tgaagaagaa gaacattgtg agaaatctca tgatcaaagt gacgtcgaga   4560
gggaagccga agaatcaaaa ctctcgcttt tgattgctcc tctgcttcgt taattgtgta   4620
ttaagaaaag aagaaaaaaa atggattttt gttgcttcag aatttttcgc tcttttttc    4680
ttaatttggt tgtaatgtta tgtttatata catatatcat catcatagga ccatagctac   4740
aaaccgaatc cggtttgtgt aattctatgc ggaatcataa agaaatcgtc ggtttgaaat   4800
gttaaatctc ctaaaccgga tctctgcacg tagctgacac atcgacgcta g            4851
```

<210> SEQ ID NO 20
<211> LENGTH: 1703
<212> TYPE: DNA

<213> ORGANISM: Arabidopsis thaliana

<400> SEQUENCE: 20
gttgcaaata tataaatcaa tcaaaagatt taaaacccac cattcaatct tggtaagtaa 60
cgaaaaaaaa gggaagcaag aagaaccaca gaaaaggggg ctaacaacta gacacgtaga 120
tcttcatctg cccgtccatc taacctacca cactctcatc ttctttttcc cgtgtcagtt 180
tgttatataa gctctcactc tccggtatat ttccaaatac acctaacttg tttagtacac 240
aacagcaaca tcaaactcta ataaacccaa gttggtgtat actataatgg tgatggctgg 300
tgcttcttct ttggatgaga tcagacaggc tcagagagct gatggacctg caggcatctt 360
ggctattggc actgctaacc ctgagaacca tgtgcttcag gcggagtatc ctgactacta 420
cttccgcatc accaacagtg aacacatgac cgacctcaag gagaagttca agcgcatgtg 480
cgacaagtcg acaattcgga aacgtcacat gcatctgacg gaggaattcc tcaaggaaaa 540
cccacacatg tgtgcttaca tggctccttc tctggacacc agacaggaca tcgtggtggt 600
cgaagtccct aagctaggca aagaagcggc agtgaaggcc atcaaggagt ggggccagcc 660
caagtcaaag atcactcatg tcgtcttctg cactacctcc ggcgtcgaca tgcctggtgc 720
tgactaccag ctcaccaagc ttcttggtct ccgtccttcc gtcaagcgtc tcatgatgta 780
ccagcaaggt tgcttcgccg gcggtactgt cctccgtatc gctaaggatc tcgccgagaa 840
caatcgtgga gcacgtgtcc tcgttgtctg ctctgagatc acagccgtta ccttccgtgg 900
tccctctgac acccaccttg actccctcgt cggtcaggct cttttcagtg atggcgccgc 960
cgcactcatt gtggggtcgg accctgacac atctgtcgga gagaaaccca tctttgagat 1020
ggtgtctgcc gctcagacca tccttccaga ctctgatggt gccatagacg gacatttgag 1080
ggaagttggt ctcaccttcc atctcctcaa ggatgttccc ggcctcatct ccaagaacat 1140
tgtgaagagt ctagacgaag cgtttaaacc tttggggata agtgactgga actccctctt 1200
ctggatagcc caccctggag gtccagcgat cctagaccag gtggagataa agctaggact 1260
aaaggaagag aagatgaggg cgacacgtca cgtgttgagc gagtatggaa acatgtcgag 1320
cgcgtgcgtt ctcttcatac tagacgagat gaggaggaag tcagctaagg atggtgtggc 1380
cacgacagga gaagggttgg agtggggtgt cttgtttggt ttcggaccag gtctcactgt 1440
tgagacagtc gtcttgcaca gcgttcctct ctaaacagaa cgcttgcctt ctatctgcct 1500
acctacctac gcaaaacttt aatcctgtct tatgttttat ataatataat cattatatgt 1560
ttacgcaata attaaggaag aattcatttg atgtgatatg tgatatgtgc tggacaggtc 1620
tattcgactg tttttgtact ctctttttttg tgtcttttta caatattaaa tctatgggtc 1680
ttgaatgaca tcaaatcttt gtt 1703

<210> SEQ ID NO 21
<211> LENGTH: 229
<212> TYPE: DNA
<213> ORGANISM: Arabidopsis thaliana

<400> SEQUENCE: 21
cctcgaggat cctctagacc tcagctaggg tttatccaga gaatggttcc tgctctactt 60
cctgtccttt tggtttctgt cggatatatt gatcccggga aatgggttgc aaatatcgaa 120
ggaggtgctc gtttcgggta tgacttggtg gcaattactc tgcttttcaa ttttgccgcc 180
atcttatgcc aatatgttgc agctcgcata agcgttaagc ttggtaccc 229

<210> SEQ ID NO 22
<211> LENGTH: 218
<212> TYPE: DNA
<213> ORGANISM: Artificial Sequence
<220> FEATURE:
<223> OTHER INFORMATION: fragment comprising the 200nt sense sequence of EIN2

<400> SEQUENCE: 22
cctcgagtct agattttagt tagggtttat ttagagaatg gtttttgttt tattttttgt 60 tttttggtt tttgttggat atattgattt tgggaaatgg gttgtaaata ttgaaggagg 120
tgtttgtttt gggtatgatt tggtggtaat tattttgttt tttaattttg ttgttatttt 180
atgttaatat gttgtagttt gtataagtgt tggtaccc 218

<210> SEQ ID NO 23
<211> LENGTH: 230
<212> TYPE: DNA
<213> ORGANISM: Arabidopsis thaliana

<400> SEQUENCE: 23
cctcgaggat ccgttgtctg ctctgagatc acagccgtta ccttccgtgg tccctctgac 60
acccaccttg actccctcgt cggtcaggct cttttcagtg atggcgccgc cgcactcatt 120
gtggggtcgg accctgacac atctgtcgga gagaaaccca tctttgagat ggtgtctgcc 180
gctcagacca tccttccaga ctctgatggt gctctagaag cttggtaccc 230

<210> SEQ ID NO 24
<211> LENGTH: 219
<212> TYPE: DNA
<213> ORGANISM: Artificial Sequence
<220> FEATURE:
<223> OTHER INFORMATION: fragment comprising the 200nt sense sequence of CHS

<400> SEQUENCE: 24
cctcgaggtt gtttgttttg agattatagt tgttattttt tgtggttttt ttgatattta 60
ttttgatttt tttgttggtt aggtttttt tagtgatggt gttgttgtat ttattgtggg 120
gttggatttt gatatatttg ttggagagaa atttattttt gagatggtgt ttgttgttta 180
gattattttt ttagattttg atggtgtcta gaggtaccc 219

<210> SEQ ID NO 25
<211> LENGTH: 219
<212> TYPE: DNA
<213> ORGANISM: Artificial Sequence
<220> FEATURE:
<223> OTHER INFORMATION: fragment comprising the 200nt antisense sequence of EIN2

<400> SEQUENCE: 25
caagcttaat gtttatgtga gttgtaatat attggtataa gatggtggta aaattgaaaa 60
gtagagtaat tgttattaag ttatatttga aatgagtatt ttttttgata tttgtaattt 120
attttttggg attaatatat ttgatagaaa ttaaaaggat aggaagtaga gtaggaatta 180
ttttttggat aaattttagt tgaggttcta gaggatccc 219

<210> SEQ ID NO 26
<211> LENGTH: 219
<212> TYPE: DNA
<213> ORGANISM: Artificial Sequence
<220> FEATURE:
<223> OTHER INFORMATION: fragment comprising the 200nt antisense sequence of CHS

<400> SEQUENCE: 26

```
caagcttcta gagtattatt agagtttgga aggatggttt gagtggtaga tattatttta     60

aagatgggtt tttttttgat agatgtgtta gggtttgatt ttataatgag tgtggtggtg    120

ttattattga aaagagtttg attgatgagg gagttaaggt gggtgttaga gggattatgg    180

aaggtaatgg ttgtgatttt agagtagata atggatccc                           219
```

<210> SEQ ID NO 27
<211> LENGTH: 300
<212> TYPE: DNA
<213> ORGANISM: Arabidopsis thaliana

<400> SEQUENCE: 27

```
agtaattata ttatcagata gatttaggat ggaagctgaa attgtgaatg tgagacctca     60

gctagggttt atccagagaa tggttcctgc tctacttcct gtccttttgg tttctgtcgg    120

atatattgat cccgggaaat gggttgcaaa tatcgaagga ggtgctcgtt tcgggtatga    180

cttggtggca attactctgc ttttcaattt tgccgccatc ttatgccaat atgttgcagc    240

tcgcataagc gttgtgactg gtaaacactt ggctcagatc tgcaatgaag aatatgacaa    300
```

<210> SEQ ID NO 28
<211> LENGTH: 300
<212> TYPE: DNA
<213> ORGANISM: Arabidopsis thaliana

<400> SEQUENCE: 28

```
tccgtatcgc taaggatctc gccgagaaca atcgtggagc acgtgtcctc gttgtctgct     60

ctgagatcac agccgttacc ttccgtggtc cctctgacac ccaccttgac tccctcgtcg    120

gtcaggctct tttcagtgat ggcgccgccg cactcattgt ggggtcggac cctgacacat    180

ctgtcggaga gaaacccatc tttgagatgg tgtctgccgc tcagaccatc cttccagact    240

ctgatggtgc catagacgga catttgaggg aagttggtct caccttccat ctcctcaagg    300
```

<210> SEQ ID NO 29
<211> LENGTH: 240
<212> TYPE: DNA
<213> ORGANISM: Arabidopsis thaliana

<400> SEQUENCE: 29

```
tcttcattgc agatctgagc caagtgttta ccagtcacaa cgcttatgcg agctgcaaca     60

tattggcata agatggcggc aaaattgaaa agcagagtaa ttgccaccaa gtcatacccg    120

aaacgagcac ctccttcgat atttgcaacc catttcccgg gatcaatata tccgacagaa    180

accaaaagga caggaagtag agcaggaacc attctctgga taaaccctag ctgaggtctc    240
```

<210> SEQ ID NO 30
<211> LENGTH: 300
<212> TYPE: DNA
<213> ORGANISM: Arabidopsis thaliana

<400> SEQUENCE: 30

```
gatggaaggt gagaccaact tccctcaaat gtccgtctat ggcaccatca gagtctggaa     60

ggatggtctg agcggcagac accatctcaa agatgggttt ctctccgaca gatgtgtcag    120

ggtccgaccc cacaatgagt gcggcggcgc catcactgaa aagagcctga ccgacgaggg    180

agtcaaggtg ggtgtcagag ggaccacgga aggtaacggc tgtgatctca gagcagacaa    240
```

cgaggacacg tgctccacga ttgttctcgg cgagatcctt agcgatacgg aggacagtac 300

<210> SEQ ID NO 31
<211> LENGTH: 4035
<212> TYPE: DNA
<213> ORGANISM: Arabidopsis thaliana

<400> SEQUENCE: 31
atgggatcta gggttccaat agaaaccatc gaagaagacg gcgaattcga ttgggaagca 60
gcagtcaaag aaatcgactt ggcttgtctt aaaaccacaa acgcttcttc ttcttcgtca 120
tcccatttca ctcctttggc taatccacca attacggcaa atctcactaa gccacctgcg 180
aagagacaat ctactctcga taaattcatc ggcagaaccg aacataaacc ggagaatcat 240
caagttgttt ccgagtgtgg tgttaacgat aacgataata gtcctttagt tgggattgat 300
cctgaggcag ctaaaacttg gatttatcca gtgaatggga gtgttccttt aagagattat 360
cagtttgcta taacgaagac tgctttgttt tcgaatacat tggtggcttt gcctacggga 420
cttggtaaaa cgcttatagc tgcggttgtt atgtataatt acttcagatg gtttccacaa 480
ggtaaaatag tatttgcggc gccttctagg cctcttgtga tgcagcagat tgaggcgtgt 540
cataatattg ttggaatacc acaagaatgg acgattgact tgacgggtca gacatgtcct 600
tcgaaaagag ctttttgtg gaaaagcaaa cgggttttct ttgtcactcc acaagtgtta 660
gagaaggata tacagtcagg aacatgtctt actaactact tggtttgctt ggtgatcgac 720
gaggcacatc gagctttagg gaattattct tattgtgttg tagttcgtga gttgatggcg 780
gtaccgatac agctgagaat actggctctt actgcaactc ctggatcaaa gacacaggcc 840
atccagggta tcattgataa tttgcagata tccacacttg aatatcgaaa tgagagtgac 900
catgatgttt gcccttatgt ccacgacaga aaattagaag tcatcgaggt tcccttgggt 960
caagatgcag atgatgtatc gaaacgcctg tttcatgtta tacgtccata tgcagtcagg 1020
cttaaaaact ttggggttaa tctaaataga gatatacaaa ctttaagtcc acacgaagta 1080
cttatggcaa gggataagtt tcgtcaagca cctctaccag gccttcccca tgtaaatcac 1140
ggagatgtag aatcttgctt tgcagctctt atcactcttt atcatattcg taagctcctt 1200
tctagtcatg gaataagacc agcgtatgag atgctagaag agaaattgaa agaagggcca 1260
tttgctaggt tgatgagtaa gaatgaagat attaggatga cgaagctttt gatgcagcaa 1320
aggttgtcac atggagcacc aagcccaaaa ttgtcgaaga tgttagaaat actggttgat 1380
catttcaaag tgaaagatcc gaagacatca cgggtcatta ttttctcaaa tttcagagga 1440
agcgtaagag acataatgaa cgcattaagt aatattggag atatggtcaa agcaactgag 1500
tttattggtc aaagttcagg taagacattg aaaggccagt cgcaaaaaat tcagcaggct 1560
gttttggaga aatttagagc tggggggttc aatgttattg tcgcaacatc tattggtgaa 1620
gaaggcttgg atatcatgga agttgaccta gttatatgtt ttgatgctaa tgtatctcct 1680
ctgaggatga ttcaacggat gggaagaact ggaaggaaaa ataatggtcg agttgtagtt 1740
cttgcttgtg aaggatcaga aaagaacagc tatatgcgaa agcaagcaag tggacgggct 1800
attaaaaaac acatgcggaa tggaggaaca aatagtttta attttcatcc tagtccaagg 1860
atgattcccc atgtttataa gccagaagtt cagcatgttg agttttcaat caagcaattc 1920
gttccacgtg gaaagaaact acaagaggag tatgccactg agactccagc tttccagaaa 1980
aagcttacac ctgcagagac gcatatgctc gctaagtatt acaacaaccc cgatgaggaa 2040
aagttgagag tgtccttaat tgcgttccct cacttccaga cattgccatc caaggtgcac 2100
aaagtaatgc attcacgtca aacaggcatg ttaattgacg ctatgcagca cttgcaagag 2160
ccaacttttt cagaacagag taaaagcttc ttcactgagt ttcgagctcc tttgggtgaa 2220
agagaagagc ttgatacagg tctgagggtt actaatgatc caaaagatct acactctgtc 2280
cgtgatttgg aagtcaacac atcacagaga aaggcaaaac aagttgaatc tcccacaagc 2340
accttagaga caacagagaa ggattacgaa gaatcttcac ccacacaccg ttatcttttc 2400
agttcagaat gtgcatccgt tgatactctg gggaacgtct tcgtaatgcc agttcctctt 2460
ttattctttc ctaatgttct ggagtcagac aatacgcctc tgcctaaaac agaaaaacaa 2520
cattcttgcc ggaatacatc tcacattgac ttagttccag tagatacttc ggaaaaacat 2580
cggcaagata atatctcatg caagttaaag gaaagattct cgccagacgg tgccagcgag 2640
acactagaga ctcatagcct tgtgaaaagg aactccacca gagtaggtga agatgatgta 2700
gcgaattctg ttggagaaat tgtgttatca tcggatgaag atgactgtga gggattggag 2760
cttagtccac ggctcactaa cttcatcaag agcggcattg ttccagagtc acctgtctat 2820
gaccaagggg aagcgaacag agaagaagat cttgaatttc ctcagctttc ttcacccatg 2880
aggttcagta acgaattggc aggagagtct tctttccctg agagaaaggt tcagcataag 2940
tgcaacgatt ataacattgt gtctacaacc actgaattga gaactcctca gaaggaggta 3000
ggtttggcca acggaacaga atgcttggct gtttctccta ttcctgagga ttggagaact 3060
cccttggcga atctgacaaa cacaaacagc agcgctcgca aagattggcg ggtgagttct 3120
ggagaaaagt tagaaactct tcgacagcct cgcaagttga agagactacg tagacttgga 3180
gattgctcga gtgctgtaaa ggagaattat cctggtatta cagaggcaga ccatatcaga 3240
tctcgttctc gcggtaaaaa gcacattaga ggtaagaaga agatgatcat ggatgatgat 3300
gtccaagtct tcattgacga ggaagctgag gtctcttcgg gagcagagat gtcggctgat 3360
gagaacgaag atgtgactgg cgattcattt gaagatagtt tcatagatga cggaacaatg 3420
cctacagcaa atactcaagc cgagtctggt aaagttgaca tgatggctgt ttacaggcgt 3480
tctcttctca gccagtcacc attaccggcg agatttcgtg atttagccgc atcaagtctg 3540
agtccttatt ctgctggacc cttgacgaga ataaatgaga gcagaagcga ctcagataaa 3600
tcattgtctt ctcttcgaac accaaaaaca acaaactctg agtcaaacca agatgcaatg 3660
atgataggaa acctttcggt agtacaaatc tcgtcagata gccggaaaag gaaatttagc 3720
ttatgcaact cggcgaatgc ccccgtgatt aacttagaaa gcaagtttgc agctcatgca 3780
caagccacgg agaaggaaag ccatgaaggc gtgagaagca atgcaggtgc gttagagtac 3840
aatgatgatg atgatgatgc attctttgcg acactagact ttgatgcaat ggaagcacaa 3900
gccacattgt tattgtcgaa acagagatcc gaagcaaaag agaaagaaga cgcaacggtt 3960
atacctaatc caggcatgca gagaagtgat ggtatggaga aagatgcacc atcttttgat 4020
cttggtctgt ggtga 4035

<210> SEQ ID NO 32
<211> LENGTH: 2310
<212> TYPE: DNA
<213> ORGANISM: Brassica napus

<400> SEQUENCE: 32
atgtcaaatg aaaataaaaa tataaaaact aaatttcatc ctagttcaag gatgattccc 60
catgtttata agccagaagt tcagcatgtt aagttttcga tcgagcaatt cattccacgt 120

```
ggaaagaagc tacaagatga gcctgccact gagactccag ctttcaagaa aaagcttaca    180
ccggaagaga tggatatgct cgccaagtat ttcaaaccca acgaggaaaa gtggagagtt    240
tccttgattg ctttccctca cttccaaaca ttgccatcca aagtgcacaa agtaatgcat    300
tcacgccaaa caagcatatt aattgatgct atgcagcatc tgcaagagac aactttgaca    360
gagcaaagta aaagtttctt cattaagtat ggagctcctt tggctgaaag agatgagctt    420
gacgcaggtc tgagggttgg tgatgatccg aaagatttac cctcttccga tgatttggat    480
gtcaacacat cacagagaaa ggcaaaacaa attttagaat ctcccacaag cacattagag    540
actacagaga aggatttcga agcatcttca cccacacact gttatctttt cagttcagaa    600
tgtgcgtccg ttgatactct ggggaaggtc tttgtattgc cggttcctct ctcattctct    660
tctaatgtac cagggtcaga ctgcgtggga agagaaaaag aactttcttc cccgaataag    720
tcccacactg acgttgttcc gatagatagt tcctcaaaac atcggcaaga taatatttca    780
tgcaagttaa agcaaggatt cttgccagat tgtgccaacg agactttgga gtcccaaagc    840
cttttgaaaa ggcactccac cgatgtaggt aaaggagata tagagaattg tgctggagaa    900
attatgatat catcggatga agaagacgac tgtgaggatt tggagcttag tccaaggctc    960
actaacttca tcaagagtgg cgttgttcca gattcacctg tctatgacca agttgcatac   1020
gaagcaaaca gagaagaaga ccttgatctt ccacacacga gtttaactaa tgaattggca   1080
gaagagccat cgacacctga gaaaaaggtt cacattgctt ctacggccaa tgaattcaga   1140
actcctcaga aggaagaaga tttagccaac gaaacagaaa gcttcgctgt ttctccaatg   1200
cctgaggagt ggagaactcc cttggcgaat atcaccaacg caagcagcag cgctagcaaa   1260
gattggcgcg tgagttcggg agaaaagtca gaaactcttc gacagcctcg caagttgaag   1320
agacttcgta gacttggaga ttgctcgagt gctgtgaagg agaataatcc tggtattgca   1380
aagacagacc atatcagatc tcgttctcgc agtgtaaaga acataagagg taaaatgatt   1440
ctgtatttcc ttttgctctg tgttcaaggc aagaagaaga tacgcgcgga taataatgct   1500
agaatcttca ttgaagcgga agctgaggtg tcttcggaat cagaaatgtc ggttgatgag   1560
aacgtagatt tgaccagcga ttcatttgaa gatagcttca tagatgacgg tacaatgcct   1620
acagcaaata ctcaagccga gtgtgctaaa gttgacatga tggccgttta caggtatata   1680
tcgaatcaaa acaagtcttt cttctactat gatttactaa gaatcataag ctatggtttc   1740
cacagacgtt ctctactcag ccaatcacca ttaccggcaa gatttcgtga tgtagctgca   1800
tcaagtccga gtccttattc ttctggtctc ttgaagacaa taaatgagag cagaagcgac   1860
tcagataaat cattgtcttc tcttagaacc ccacaaacaa cgaacaacga gtcaaacaag   1920
gatgcaatgg ccacaggaga cctttcggta gcacaaatct caacagacag ccggaaaagg   1980
aaattcagct tatgcaactc agcgaatgtc ccagtgatta acttggaaaa caagtttgaa   2040
gctcatgcac aagccacgga gaaggaaagc catgaaggtc cgagaagcaa tgcaggtgca   2100
tcacagtaca aggatgagga tgaagatgat gatgcattct acgcgacact ggactttgat   2160
gccatggaag cgcatgcgac attgctattg tcgaaacaaa ggtcagaaac gaaaacaaaa   2220
gaagatgcat cggtgaaacc tcatttgggc aatcagagga atgatggttt gccgaaggat   2280
gggccatctt ttgatcttgg tttgtggtga                                    2310
```

<210> SEQ ID NO 33
<211> LENGTH: 1822
<212> TYPE: DNA

<213> ORGANISM: Artificial Sequence
<220> FEATURE:
<223> OTHER INFORMATION: hpFANCM-At[wt]

<400> SEQUENCE: 33

```
ggctcgagaa ccgaattcta atacgactca ctatagggtc aggaacatgt cttactaact     60
acttggtttg cttggtgatc gacgaggcac atcgagcttt agggaattat tcttattgtg    120
ttgtagttcg tgagttgatg gcggtaccga tacagctgag aatactggct cttactgcaa    180
ctcctggatc aaagacacag gccatccagg gtatcattga taatttgcag atatccacac    240
ttgaatatcg aaatgagagt gaccatgatg tttgccctta tgtccccgac agaaaattag    300
aagtcatcga ggttcccttg ggtcaagatg cagatgatgt atcgaaacgc ctgtttcatg    360
ttatacgtcc atatgcagtc aggcttaaaa actttggggt taatctaaat agagatatac    420
aaactttaag tccacacgaa gtacttatgg caagggataa gtttcgtcaa gcacctctac    480
caggccttcc ccatgtaaat cacggagatg tagaatcttg ctttgcagct cttatcaggt    540
aaggaaataa ttattttctt ttttcctttt agtataaaat agttaagtga tgttaattag    600
tatgattata ataatatagt tgttataatt gtgaaaaaat aatttataaa tatattgttt    660
acataaacaa catagtaatg taaaaaaata tgacaagtga tgtgtaagac gaagaagata    720
aaagttgaga gtaagtatat tatttttaat gaatttgatc gaacatgtaa gatgatatac    780
tagcattaat atttgtttta atcataatag taattctagc tggtttgatg aattaaatat    840
caatgataaa atactatagt aaaaataaga ataaataaat taaaataata ttttttttatg    900
attaatagtt tattatataa ttaaatatct ataccattac taaatatttt agtttaaaag    960
ttaataaata ttttgttaga aattccaatc tgcttgtaat ttatcaataa acaaaatatt   1020
aaataacaag ctaaagtaac aaataatatc aaactaatag aaacagtaat ctaatgtaac   1080
aaaacataat ctaatgctaa tataacaaag cgcaagatct atcattttat atagtattat   1140
tttcaatcaa cattcttatt aatttctaaa taatacttgt agttttatta acttctaaat   1200
ggattgacta ttaattaaat gaattagtcg aacatgaata aacaaggtaa catgatagat   1260
catgtcattg tgttatcatt gatcttacat ttggattgat tacagttgat aagagctgca   1320
aagcaagatt ctacatctcc gtgatttaca tggggaaggc ctggtagagg tgcttgacga   1380
aacttatccc ttgccataag tacttcgtgt ggacttaaag tttgtatatc tctatttaga   1440
ttaaccccaa agtttttaag cctgactgca tatggacgta taacatgaaa caggcgtttc   1500
gatacatcat ctgcatcttg acccaaggga acctcgatga cttctaattt tctgtcgggg   1560
acataagggc aaacatcatg gtcactctca tttcgatatt caagtgtgga tatctgcaaa   1620
ttatcaatga taccctggat ggcctgtgtc tttgatccag gagttgcagt aagagccagt   1680
attctcagct gtatcggtac cgccatcaac tcacgaacta caacacaata agaataattc   1740
cctaaagctc gatgtgcctc gtcgatcacc aagcaaacca agtagttagt aagacatgtt   1800
cctgaccccg ggatccaagc tt                                            1822
```

<210> SEQ ID NO 34
<211> LENGTH: 1822
<212> TYPE: DNA
<213> ORGANISM: Artificial Sequence
<220> FEATURE:
<223> OTHER INFORMATION: hpFANCM-At[G:U]

<400> SEQUENCE: 34

```
ggctcgagaa ccgaattcta atacgactca ctatagggtt aggaatatgt tttattaatt     60
```

```
atttggtttg tttggtgatt gatgaggtat attgagtttt agggaattat ttttattgtg    120

ttgtagtttg tgagttgatg gtggtattga tatagttgag aatattggtt tttattgtaa    180

tttttggatt aaagatatag gttatttagg gtattattga taatttgtag atatttatat    240

ttgaatattg aaatgagagt gattatgatg tttgttttta tgtttttgat agaaaattag    300

aagttattga ggttttttg ggttaagatg tagatgatgt attgaaatgt ttgttttatg    360

ttatatgttt atatgtagtt aggtttaaaa attttggggt taatttaaat agagatatat    420

aaattttaag tttatatgaa gtatttatgg taagggataa gttttgttaa gtatttttat    480

taggtttttt ttatgtaaat tatggagatg tagaattttg ttttgtagtt tttattaggt    540

aaggaaataa ttattttctt ttttcctttt agtataaaat agttaagtga tgttaattag    600

tatgattata ataatatagt tgttataatt gtgaaaaaat aatttataaa tatattgttt    660

acataaacaa catagtaatg taaaaaaata tgacaagtga tgtgtaagac gaagaagata    720

aaagttgaga gtaagtatat tatttttaat gaatttgatc gaacatgtaa gatgatatac    780

tagcattaat atttgtttta atcataatag taattctagc tggtttgatg aattaaatat    840

caatgataaa atactatagt aaaaataaga ataaataaat taaaataata ttttttatg    900

attaatagtt tattatataa ttaaatatct ataccattac taaatatttt agtttaaaag    960

ttaataaata ttttgttaga aattccaatc tgcttgtaat ttatcaataa acaaaatatt   1020

aaataacaag ctaaagtaac aaataatatc aaactaatag aaacagtaat ctaatgtaac   1080

aaaacataat ctaatgctaa tataacaaag cgcaagatct atcattttat atagtattat   1140

tttcaatcaa cattcttatt aatttctaaa taatacttgt agttttatta acttctaaat   1200

ggattgacta ttaattaaat gaattagtcg aacatgaata aacaaggtaa catgatagat   1260

catgtcattg tgttatcatt gatcttacat ttggattgat tacagttgat aagagctgca   1320

aagcaagatt ctacatctcc gtgatttaca tggggaaggc ctggtagagg tgcttgacga   1380

aacttatccc ttgccataag tacttcgtgt ggacttaaag tttgtatatc tctatttaga   1440

ttaaccccaa agtttttaag cctgactgca tatggacgta taacatgaaa caggcgtttc   1500

gatacatcat ctgcatcttg acccaaggga acctcgatga cttctaattt tctgtcgggg   1560

acataagggc aaacatcatg gtcactctca tttcgatatt caagtgtgga tatctgcaaa   1620

ttatcaatga taccctggat ggcctgtgtc tttgatccag gagttgcagt aagagccagt   1680

attctcagct gtatcggtac cgccatcaac tcacgaacta caacacaata agaataattc   1740

cctaaagctc gatgtgcctc gtcgatcacc aagcaaacca agtagttagt aagacatgtt   1800

cctgaccccg ggatccaagc tt                                            1822
```

<210> SEQ ID NO 35
<211> LENGTH: 1818
<212> TYPE: DNA
<213> ORGANISM: Artificial Sequence
<220> FEATURE:
<223> OTHER INFORMATION: hpFANCM-Bn[wt]

<400> SEQUENCE: 35

```
ggatccttgg tacctaatac gactcactat agggagaaat tatgatatca tcggatgaag     60

aagacgactg tgaggatttg gagcttagtc caaggctcac taacttcatc aagagtggcg    120

ttgttccaga ttcacctgtc tatgaccaag ttgcatacga agcaaacaga gaagaagacc    180

ttgatcttcc acacacgagt ttaactaatg aattggcaga agagccatcg acacctgaga    240
```

aaaaggttca cattgcttct acggccaatg aattcagaac cccaacgaag gaagaagatt 300
tagccaacga aacagaaagc ttcgctgttt ctccaatgcc tgaggagtgg agaactccct 360
tggcgaatat caccaacgca agcagcagcg ctagcaaaga ttggcgcgtg agttcgggag 420
aaaagtcaga aactcttcga cagcctcgca agttgaagag acttcgtaga cttggagatt 480
gctcgagtgc tgtgaaggag aataatcctg gtattgcaaa gacagaccat atcgtaagga 540
aataattatt ttcttttttc cttttagtat aaaatagtta agtgatgtta attagtatga 600
ttataataat atagttgtta taattgtgaa aaaataattt ataaatatat tgtttacata 660
aacaacatag taatgtaaaa aaatatgaca agtgatgtgt aagacgaaga agataaaagt 720
tgagagtaag tatattattt ttaatgaatt tgatcgaaca tgtaagatga tatactagca 780
ttaatatttg ttttaatcat aatagtaatt ctagctggtt tgatgaatta aatatcaatg 840
ataaaatact atagtaaaaa taagaataaa taaattaaaa taatattttt ttatgattaa 900
tagtttatta tataattaaa tatctatacc attactaaat attttagttt aaaagttaat 960
aaatattttg ttagaaattc caatctgctt gtaatttatc aataaacaaa atattaaata 1020
acaagctaaa gtaacaaata atatcaaact aatagaaaca gtaatctaat gtaacaaaac 1080
ataatctaat gctaatataa caaagcgcaa gatctatcat tttatatagt attattttca 1140
atcaacattc ttattaattt ctaaataata cttgtagttt tattaacttc taaatggatt 1200
gactattaat taaatgaatt agtcgaacat gaataaacaa ggtaacatga tagatcatgt 1260
cattgtgtta tcattgatct tacatttgga ttgattacag gatatggtct gtctttgcaa 1320
taccaggatt attctccttc acagcactcg agcaatctcc aagtctacga agtctcttca 1380
acttgcgagg ctgtcgaaga gtttctgact tttctcccga actcacgcgc caatctttgc 1440
tagcgctgct gcttgcgttg gtgatattcg ccaagggagt tctccactcc tcaggcattg 1500
gagaaacagc gaagctttct gtttcgttgg ctaaatcttc ttccttcgtt ggggttctga 1560
attcattggc cgtagaagca atgtgaacct tttctcagg tgtcgatggc tcttctgcca 1620
attcattagt taaactcgtg tgtggaagat caaggtcttc ttctctgttt gcttcgtatg 1680
caacttggtc atagacaggt gaatctggaa caacgccact cttgatgaag ttagtgagcc 1740
ttggactaag ctccaaatcc tcacagtcgt cttcttcatc cgatgatatc ataatttctc 1800
tctagaaagg atcccggg 1818

<210> SEQ ID NO 36
<211> LENGTH: 1818
<212> TYPE: DNA
<213> ORGANISM: Artificial Sequence
<220> FEATURE:
<223> OTHER INFORMATION: hpFANCM-Bn[G:U]

<400> SEQUENCE: 36
ggatccttgg tacctaatac gactcactat agggagaaat tatgatatta ttggatgaag 60
aagatgattg tgtggatttg gagtttagtt taaggtttat taattttatt aagagtggtg 120
ttgttttaga tttatttgtt tatgattaag ttgtatatga agtaaatagt gaagaagatt 180
ttgatttttt atatatgagt ttaattaatg aattggtaga agagttattg atatttgaga 240
aaaaggttta tattgttttt atggttaatg aatttagaat tttaatgaag gaagaagatt 300
tagttaatga aatagaaagt tttgttgttt ttttaatgtt tgaggagtgg agaatttttt 360
tggtgaatat tattaatgta agtagtagtg ttagtaaaga ttggtgtgtg agtttgggag 420
aaaagttaga aattttttga tagttttgta agttgaagag attttgtaga tttggagatt 480

```
gtttgagtgt tgtgaaggag aataattttg gtattgtaaa gatagattat attgtaagga    540
aataattatt ttcttttttc cttttagtat aaaatagtta agtgatgtta attagtatga    600
ttataataat atagttgtta taattgtgaa aaaataattt ataaatatat tgtttacata    660
aacaacatag taatgtaaaa aaatatgaca agtgatgtgt aagacgaaga agataaaagt    720
tgagagtaag tatattattt ttaatgaatt tgatcgaaca tgtaagatga tatactagca    780
ttaatatttg ttttaatcat aatagtaatt ctagctggtt tgatgaatta aatatcaatg    840
ataaaatact atagtaaaaa taagaataaa taaattaaaa taatattttt ttatgattaa    900
tagtttatta tataattaaa tatctatacc attactaaat attttagttt aaaagttaat    960
aaatattttg ttagaaattc caatctgctt gtaatttatc aataaacaaa atattaaata   1020
acaagctaaa gtaacaaata atatcaaact aatagaaaca gtaatctaat gtaacaaaac   1080
ataatctaat gctaatataa caaagcgcaa gatctatcat tttatatagt attattttca   1140
atcaacattc ttattaattt ctaaataata cttgtagttt tattaacttc taaatggatt   1200
gactattaat taaatgaatt agtcgaacat gaataaacaa ggtaacatga tagatcatgt   1260
cattgtgtta tcattgatct tacatttgga ttgattacag gatatggtct gtctttgcaa   1320
taccaggatt attctccttc acagcactcg agcaatctcc aagtctacga agtctcttca   1380
acttgcgagg ctgtcgaaga gtttctgact tttctcccga actcacgcgc caatctttgc   1440
tagcgctgct gcttgcgttg gtgatattcg ccaagggagt tctccactcc tcaggcattg   1500
gagaaacagc gaagctttct gtttcgttgg ctaaatcttc ttccttcgtt ggggttctga   1560
attcattggc cgtagaagca atgtgaacct tttctcaggt tgtcgatggc tcttctgcca   1620
attcattagt taaactcgtg tgtggaagat caaggtcttc ttctctgttt gcttcgtatg   1680
caacttggtc atagacaggt gaatctggaa caacgccact cttgatgaag ttagtgagcc   1740
ttggactaag ctccaaatcc tcacagtcgt cttcttcatc cgatgatatc ataatttctc   1800
tctagaaagg atcccggg                                                 1818
```

<210> SEQ ID NO 37
<211> LENGTH: 2274
<212> TYPE: DNA
<213> ORGANISM: Brassica napus

<400> SEQUENCE: 37

```
atggttagtc tgcgctccac agaaaacact ccggcttcgg aaatggccag cgacggcaaa     60
acggagaaag atggctccgg cgactcaccc acttctgttc tcagcgatga ggaaaactgt    120
gaagagaaaa ctgctactgt tgctgtagag gaagagatac ttctagccaa gaatggagat    180
tcgtctctta tctctgaggc catggctcag gaagaagagc agcttctcaa aatccgggaa    240
gatgaagaga ttgctaaacg tgctgctggc tctggtgaag ctcctgatct gaatgatact    300
cagtttacta aacttgatga gctcttgacc caaacccagc tctactctga gtttctcctt    360
gagaaaatgg aggatatcac caaaaatggg atagaaggtg agacccaaaa ggccgagcct    420
gagcctgagc ctgagcccga gaagaaaggc cgtggacgta aaagaaaggc tgctcctcag    480
ggcgacagta tgaaggctaa gaaagctgtt gctgctatga tttcaagatc caaagaaggc    540
cgtgaatctg ccgactcaga tctgacagag gaagaaagag tcatgaaaga gcagggtgaa    600
cttgttcctc ttctgactgg cggaaagtta aagtcttatc agctcaaagg tgtcaaatgg    660
ctgatatcat tgtggcaaaa tggtttgaat ggaattttag ctgatcaaat gggtcttgga    720
```

```
aagacaattc aaaccattgg tttcctatca cacctcaaag gaaatgggtt ggatggtcca    780
tatctagtca ttgccccact ctctactctt tcaaactgga tgaatgagat cgctaggttc    840
acgccttcca ttaatgcaat catttaccat ggagataaga aagaaaggga tgagctcagg    900
aagaggcaca tgcccagaac tgttggtccg aagttcccta tagtcataac ttcttatgag    960
gttgctatga atgatgctaa aaagaatctg cggcactatc catggaaata tgttgtgatt   1020
gatgagggtc acaggttgaa aaaccacaag tgtaaactgc tgagggagct aagatacttg   1080
aatatggaga acaaacttct gctgacagga acacctctgc aaaataattt gtctgagctt   1140
tggtcactgt tgaattttat tctgcctgac atctttgcat cacatgacga atttgaatca   1200
tggtttgatt tttctggaaa gaataataat gaagcaacta aggaagaagg agaagagaaa   1260
agaagagctc aagtggttgc gaaacttcat aatatactac gacctttcat cctccggaga   1320
atgaaatgtg atgttgagct ctcacttccc cggaaaaaag agattatcat ctatgctaca   1380
atgacggacc atcagaagaa gttccaggaa catcttgtga accacacctt ggaagcacac   1440
attagagatg atactgtccg aggtcatggc ttgaagggaa agcttaacaa tcttgctatt   1500
caacttcgaa agaactgcaa ccatcctgac cttcttgtgg ggcaactaga tggctcatat   1560
ctctacccac ctttggaaga cattgtggga cagtgcggta aattccgctt attggagaga   1620
ttgcttgttc ggttatttgc caaaaatcac agagtcctta tcttctccca gtggacaaaa   1680
atactggaca ttatggatta ctacttcagt gagaaggggt ttgaggtttg ccgaatcgac   1740
ggtagtgtga aactagaaga aaggagaaga cagatccaag aattcaatga tgagaagagc   1800
aactgcagga tatttcttct cagtaccaga gccggaggac tcggaattaa tcttactgct   1860
gcagatacat gcatcctcta cgatagcgat tggaaccctc aaatggactt gcaagccatg   1920
gacagatgcc acagaattgg tcagacaaaa cctgttcatg tttacaggct tgcgacggct   1980
cagtcaatag agggccgagt tctgaaacga gcatacagta agcttaagct ggaacatgtg   2040
gttattggca aggggcagtt tcatcaagaa cgtgccaagt cttcaacacc gttagaggaa   2100
gatgacatac tggcgttgct taaggacgac gaaaatgctg aagataaact gatacaaacc   2160
gacataagcg aggaggatct tgacagggtg cttgaccgta gtgatctgat gattacctta   2220
ccgggcgaga ctcaagcaca tgaagctttt ccagtgaagg gtccgggttg ggaa          2274
```

<210> SEQ ID NO 38
<211> LENGTH: 1824
<212> TYPE: DNA
<213> ORGANISM: Artificial Sequence
<220> FEATURE:
<223> OTHER INFORMATION: hpDDM1-Bn[wt]

<400> SEQUENCE: 38

```
ggatccttgg tacctaatac gactcactat agggagctgt tgctgctatg atttcaagat     60
ccaaagaagg ccgtgaatct gccgactcag atctgacaga ggaagaaaga gtcatgaatg    120
agcagggtga acttgttcct cttctgactg gcggaaagtt aaagtcttat cagctcaaag    180
gtgtcaaatg gctgatatca ttgtggcaaa atggtttgaa tggaatttta gctgatcaaa    240
tgggtcttgg aaagacaatt caaaccattg gtttcctatc accccaacaa ggaaatgggt    300
tggatggtcc atatctagtc attgccccac tctctactct ttcaaaagcg attggaaccc    360
tcaaatggac ttgcaagcca tggacagatg ccacagaatt ggtcagacaa aacctgttca    420
tgtttacagg cttgcgacgg ctcagtcaat agagggccga gttctgaaac gagcatacag    480
taagcttaag ctggaacatg tggttattgg caaggggcag tttcatcaag aacgtggtaa    540
```

```
ggaaataatt attttctttt ttccttttag tataaaatag ttaagtgatg ttaattagta    600

tgattataat aatatagttg ttataattgt gaaaaaataa tttataaata tattgtttac    660

ataaacaaca tagtaatgta aaaaaatatg acaagtgatg tgtaagacga agaagataaa    720

agttgagagt aagtatatta tttttaatga atttgatcga acatgtaaga tgatatacta    780

gcattaatat ttgttttaat cataatagta attctagctg gtttgatgaa ttaaatatca    840

atgataaaat actatagtaa aaataagaat aaataaatta aaataatatt tttttatgat    900

taatagttta ttatataatt aaatatctat accattacta aatattttag tttaaaagtt    960

aataaatatt ttgttagaaa ttccaatctg cttgtaattt atcaataaac aaaatattaa   1020

ataacaagct aaagtaacaa ataatatcaa actaatagaa acagtaatct aatgtaacaa   1080

aacataatct aatgctaata taacaaagcg caagatctat cattttatat agtattattt   1140

tcaatcaaca ttcttattaa tttctaaata atacttgtag ttttattaac ttctaaatgg   1200

attgactatt aattaaatga attagtcgaa catgaataaa caaggtaaca tgatagatca   1260

tgtcattgtg ttatcattga tcttacattt ggattgatta cagtcacgtt cttgatgaaa   1320

ctgccccttg ccaataacca catgttccag cttaagctta ctgtatgctc gtttcagaac   1380

tcggccctct attgactgag ccgtcgcaag cctgtaaaca tgaacaggtt ttgtctgacc   1440

aattctgtgg catctgtcca tggcttgcaa gtccatttga gggttccaat cgcttttgaa   1500

agagtagaga gtggggcaat gactagatat ggaccatcca acccatttcc ttgttggggt   1560

gataggaaac caatggtttg aattgtcttt ccaagaccca tttgatcagc taaaattcca   1620

ttcaaaccat tttgccacaa tgatatcagc catttgacac ctttgagctg ataagacttt   1680

aactttccgc cagtcagaag aggaacaagt tcaccctgct ctttcatgac tctttcttcc   1740

tctgtcagat ctgagtcggc agattcacgg ccttctttgg atcttgaaat catagcagca   1800

acagcttcta gaaaggatcc cggg                                          1824
```

<210> SEQ ID NO 39
<211> LENGTH: 1823
<212> TYPE: DNA
<213> ORGANISM: Artificial Sequence
<220> FEATURE:
<223> OTHER INFORMATION: hpDDM1-Bn[G:U]

<400> SEQUENCE: 39

```
ggatccttgg tacctaatac gactcactat agggttgttg ttgttatgat tttaagattt     60

aaagaaggtt gtgaatttgt tgatttagat ttgatagagg aagaaagagt tatgaatgag    120

tagggtgaat ttgttttttt tttgattggt ggaaagttaa agttttatta gtttaaaggt    180

gttaaatggt tgatattatt gtggtaaaat ggtttgaatg gaattttagt tgattaaatg    240

ggttttggaa agataattta aattattggt tttttattat attttaaagg aaatgggttg    300

gatggtttat atttagttat tgttttattt tttatttttt taaaagtgat tggaattttt    360

aaatggattt gtaagttatg gatagatgtt atagaattgg ttagataaaa tttgtttatg    420

tttataggtt tgtgatggtt tagttaatag agggttgagt tttgaaatga gtatatagta    480

agtttaagtt ggaatatgtg gttattggta aggggtagtt ttattaagaa tgtgtggtaa    540

ggaaataatt attttctttt ttccttttag tataaaatag ttaagtgatg ttaattagta    600

tgattataat aatatagttg ttataattgt gaaaaaataa tttataaata tattgtttac    660

ataaacaaca tagtaatgta aaaaaatatg acaagtgatg tgtaagacga agaagataaa    720
```

agttgagagt aagtatatta tttttaatga atttgatcga acatgtaaga tgatatacta 780
gcattaatat ttgttttaat cataatagta attctagctg gtttgatgaa ttaaatatca 840
atgataaaat actatagtaa aaataagaat aaataaatta aaataatatt tttttatgat 900
taatagttta ttatataatt aaatatctat accattacta aatattttag tttaaaagtt 960
aataaatatt ttgttagaaa ttccaatctg cttgtaattt atcaataaac aaaatattaa 1020
ataacaagct aaagtaacaa ataatatcaa actaatagaa acagtaatct aatgtaacaa 1080
aacataatct aatgctaata taacaaagcg caagatctat cattttatat agtattattt 1140
tcaatcaaca ttcttattaa tttctaaata atacttgtag ttttattaac ttctaaatgg 1200
attgactatt aattaaatga attagtcgaa catgaataaa caaggtaaca tgatagatca 1260
tgtcattgtg ttatcattga tcttacattt ggattgatta cagtcacgtt cttgatgaaa 1320
ctgccccttg ccaataacca catgttccag cttaagctta ctgtatgctc gtttcagaac 1380
tcggccctct attgactgag ccgtcgcaag cctgtaaaca tgaacaggtt ttgtctgacc 1440
aattctgtgg catctgtcca tggcttgcaa gtccatttga gggttccaat cgcttttgaa 1500
agagtagaga gtggggcaat gactagatat ggaccatcca acccatttcc ttgttggggt 1560
gataggaaac caatggtttg aattgtcttt ccaagaccca tttgatcagc taaaattcca 1620
ttcaaaccat tttgccacaa tgatatcagc catttgacac ctttgagctg ataagacttt 1680
aactttccgc cagtcagaag aggaacaagt tcaccctgct ctttcatgac tctttcttcc 1740
tctgtcagat ctgagtcggc agattcacgg ccttctttgg atcttgaaat catagcagca 1800
acagttctag aaaggatccc ggg 1823

<210> SEQ ID NO 40
<211> LENGTH: 720
<212> TYPE: DNA
<213> ORGANISM: Artificial Sequence
<220> FEATURE:
<223> OTHER INFORMATION: EGFP

<400> SEQUENCE: 40
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccttcaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 41
<211> LENGTH: 1262
<212> TYPE: DNA
<213> ORGANISM: Artificial Sequence
<220> FEATURE:
<223> OTHER INFORMATION: hpEGFP[wt]

<400> SEQUENCE: 41
gctagctaat acgactcact atagggcagc agcacggggc cgtcgccgat gggggtgttc 60
tgctggtagt ggtcggcgag ctgcacgctg ccgtcctcga tgttgtggcg gatcttgaag 120
ttcaccttga tgccgttctt ctgcttgtcg gccatgatgt atacgttgtg gctgttgaag 180
ttgtactcca gcttgtgccc caggatgttg ccgtcctcct tgaagtcgat gcccttcagc 240
tcgatgcggt tcaccagggt gtcgccctcg aacttcacct cggcgcgggt cttgtagttg 300
ccgtcgtcct tgaagaagat ggtgcgctcc tggacgtagc cttcgggcat ggcggacttg 360
aagaagtcgt gctgcttcat gtggtcgggg tagcggctga agcactgcac gccgtaagcg 420
aaggtggtca ctagtgtggg ccagggcacg ggcagcttgc cggtggtgca gatgaacttc 480
agggtctaga ccgcgtcggc atccggtcag tggcagtgaa gggcgaacag ttcctgatta 540
gggggatgaa gctacctggt ccgaaccaca aaccgttcta ctttactggc tttggtcgtc 600
atgaagatgc ggacttgcgt ggcaaaggat tcgataacgt gctgatggtg cacgaccacg 660
cattaatgga ctttaccttt taatggggaa tgaagctacc tggtccgaac tcctaccgta 720
cctcgcatta cccttacgct gaagagatgc tcgactgggc agatgaacat ggcatcgtat 780
ttaggtgaca ctatagccct gaagttcatc tgcaccaccg gcaagctgcc cgtgccctgg 840
cccacactag tgaccacctt cgcttacggc gtgcagtgct tcagccgcta ccccgaccac 900
atgaagcagc acgacttctt caagtccgcc atgcccgaag gctacgtcca ggagcgcacc 960
atcttcttca aggacgacgg caactacaag acccgcgccg aggtgaagtt cgagggcgac 1020
accctggtga accgcatcga gctgaagggc atcgacttca aggaggacgg caacatcctg 1080
gggcacaagc tggagtacaa cttcaacagc cacaacgtat acatcatggc cgacaagcag 1140
aagaacggca tcaaggtgaa cttcaagatc cgccacaaca tcgaggacgg cagcgtgcag 1200
ctcgccgacc actaccagca gaacaccccc atcggcgacg gccccgtgct gctgccgtcg 1260
ac 1262

<210> SEQ ID NO 42
<211> LENGTH: 1262
<212> TYPE: DNA
<213> ORGANISM: Artificial Sequence
<220> FEATURE:
<223> OTHER INFORMATION: hpEGFP[G:U]

<400> SEQUENCE: 42
gctagctaat acgactcact atagggcagc agcacggggc cgtcgccgat gggggtgttc 60
tgctggtagt ggtcggcgag ctgcacgctg ccgtcctcga tgttgtggcg gatcttgaag 120
ttcaccttga tgccgttctt ctgcttgtcg gccatgatgt atacgttgtg gctgttgaag 180
ttgtactcca gcttgtgccc caggatgttg ccgtcctcct tgaagtcgat gcccttcagc 240
tcgatgcggt tcaccagggt gtcgccctcg aacttcacct cggcgcgggt cttgtagttg 300
ccgtcgtcct tgaagaagat ggtgcgctcc tggacgtagc cttcgggcat ggcggacttg 360
aagaagtcgt gctgcttcat gtggtcgggg tagcggctga agcactgcac gccgtaagcg 420
aaggtggtca ctagtgtggg ccagggcacg ggcagcttgc cggtggtgca gatgaacttc 480
agggtctaga ccgcgtcggc atccggtcag tggcagtgaa gggcgaacag ttcctgatta 540
gggggatgaa gctacctggt ccgaaccaca aaccgttcta ctttactggc tttggtcgtc 600
atgaagatgc ggacttgcgt ggcaaaggat tcgataacgt gctgatggtg cacgaccacg 660
cattaatgga ctttaccttt taatggggaa tgaagctacc tggtccgaac tcctaccgta 720
cctcgcatta cccttacgct gaagagatgc tcgactgggc agatgaacat ggcatcgtat 780
ttaggtgaca ctatagcctt gaagtttatt tgtattattg gtaagttgtt tgtgttttgg 840
tttatattag tgattatttt tgtttatggt gtgtagtgtt ttagttgtta ttttgattat 900
atgaagtagt atgatttttt taagtttgtt atgtttgaag gttatgttta ggagtgtatt 960 attttttta aggatgatgg taattataag atttgtgttg aggtgaagtt tgagggtgat 1020
attttggtga attgtattga gttgaagggt attgatttta aggaggatgg taatattttg 1080
gggtataagt tggagtataa ttttaatagt tataatgtat atattatggt tgataagtag 1140
aagaatggta ttaaggtgaa ttttaagatt tgttataata ttgaggatgg tagtgtgtag 1200
tttgttgatt attattagta gaatattttt attggtgatg gttttgtgtt gttgttgtcg 1260
ac 1262

<210> SEQ ID NO 43
<211> LENGTH: 1259
<212> TYPE: DNA
<213> ORGANISM: Artificial Sequence
<220> FEATURE:
<223> OTHER INFORMATION: ledEGFP[wt]

<400> SEQUENCE: 43
gctagctaat acgactcact atagggtgtc gccctcgaac ttcacctcgg cgcgggtctt 60
gtagttgccg tcgtccttga agaagatggt gcgctcctgg acgtagcctt cgggcatggc 120
ggacttgaag aagtcgtgct gcttcatgtg gtcggggtag cggctgaagc actgcacgcc 180
gtaggtgaag gtggtcacga gggtgggcca gggcacgggc agcttgccgg tggtgcagat 240
gaacttcagg gtctagaccg cgtcggcatc cggtcagtgg cagtgaaggg cgaacagttc 300
ctgattaggg ggatgaagct acctggtccg aaccacaaac cgttctactt tactggcttt 360
ggtcgtcatg aagatgcgga cttgcgtggc aaaggattcg accctgaagt tcatctgcac 420
caccggcaag ctgcccgtgc cctggcccac cctcgtgacc accttcacct acggcgtgca 480
gtgcttcagc cgctaccccg accacatgaa gcagcacgac ttcttcaagt ccgccatgcc 540
cgaaggctac gtccaggagc gcaccatctt cttcaaggac gacggcaact acaagacccg 600
cgccgaggtg aagttcgagg gcgacaccct ggtgaaccgc atcgagctga agggcatcga 660
cttcaaggag gacggcaaca tcctggggca caagctggag tacaactaca acagccacaa 720
cgtctatatc atggccgaca agcagaagaa cggcatcaag gtgaacttca agatccgcca 780
caacatcgag gacggcagcg tgcagctcgc cgaccactac cagcagaaca cccccatcgg 840
cgacggcccc gtgctgctgc ctaacgtgct gatggtgcac gaccacgcat taatggactt 900 tacctttaa tggggaatga agctacctgg tccgaactcc taccgtacct cgcattaccc 960
ttacgctgaa gagatgctcg actgggcaga tgaacatggc atcgtggcag cagcacgggg 1020
ccgtcgccga tgggggtgtt ctgctggtag tggtcggcga gctgcacgct gccgtcctcg 1080
atgttgtggc ggatcttgaa gttcaccttg atgccgttct tctgcttgtc ggccatgata 1140
tagacgttgt ggctgttgta gttgtactcc agcttgtgcc ccaggatgtt gccgtcctcc 1200
ttgaagtcga tgcccttcag ctcgatgcgg ttcaccattg tcgggataca ctcgtcgac 1259

<210> SEQ ID NO 44
<211> LENGTH: 1259
<212> TYPE: DNA
<213> ORGANISM: Artificial Sequence
<220> FEATURE:
<223> OTHER INFORMATION: ledEGFP[G:U]

<400> SEQUENCE: 44

```
gctagctaat acgactcact atagggtgtc gccctcgaac ttcacctcgg cgcgggtctt     60
gtagttgccg tcgtccttga agaagatggt gcgctcctgg acgtagcctt cgggcatggc    120
ggacttgaag aagtcgtgct gcttcatgtg gtcggggtag cggctgaagc actgcacgcc    180
gtaggtgaag gtggtcacga gggtgggcca gggcacgggc agcttgccgg tggtgcagat    240
gaacttcagg gtctagaccg cgtcggcatc cggtcagtgg cagtgaaggg cgaacagttc    300
ctgattaggg ggatgaagct acctggtccg aaccacaaac cgttctactt tactggcttt    360
ggtcgtcatg aagatgcgga cttgcgtggc aaaggattcg attttgaagt ttatttgtat    420
tattggtaag ttgtttgtgt tttggtttat ttttgtgatt atttttattt atggtgtgta    480
gtgttttagt tgttattttg attatatgaa gtagtatgat ttttttaagt ttgttatgtt    540
tgaaggttat gtttaggagt gtattatttt ttttaaggat gatggtaatt ataagatttg    600
tgttgaggtg aagtttgagg gtgatatttt ggtgaattgt attgagttga agggtattga    660
ttttaaggag gatggtaata ttttggggta taagttggag tataattata atagttataa    720
tgtttatatt atggttgata agtagaagaa tggtattaag gtgaatttta agatttgtta    780
taatattgag gatggtagtg tgtagtttgt tgattattat tagtagaata tttttattgg    840
tgatggtttt gtgttgttgt ttaacgtgct gatggtgcac gaccacgcat taatggactt    900
taccttttaa tggggaatga agctacctgg tccgaactcc taccgtacct cgcattaccc    960
ttacgctgaa gagatgctcg actgggcaga tgaacatggc atcgtggcag cagcacgggg   1020
ccgtcgccga tgggggtgtt ctgctggtag tggtcggcga gctgcacgct gccgtcctcg   1080
atgttgtggc ggatcttgaa gttcaccttg atgccgttct tctgcttgtc ggccatgata   1140
tagacgttgt ggctgttgta gttgtactcc agcttgtgcc ccaggatgtt gccgtcctcc   1200
ttgaagtcga tgcccttcag ctcgatgcgg ttcaccattg tcgggataca ctcgtcgac    1259
```

<210> SEQ ID NO 45
<211> LENGTH: 200
<212> TYPE: DNA
<213> ORGANISM: Artificial Sequence
<220> FEATURE:
<223> OTHER INFORMATION: hpGUS[G:U]

<400> SEQUENCE: 45

```
ttgtgttggt atttggttag tggtagtgaa gggtgaatag tttttgatta attataaatt     60
gttttatttt attggttttg gttgttatga agatgtggat ttgtgtggta aaggatttga    120
taatgtgttg atggtgtatg attatgtatt aatggattgg attggggtta atttttattg    180
tattttgtat tatttttatg                                                200
```

<210> SEQ ID NO 46
<211> LENGTH: 200
<212> TYPE: DNA
<213> ORGANISM: Artificial Sequence
<220> FEATURE:
<223> OTHER INFORMATION: hpGUS[1:4]

<400> SEQUENCE: 46

```
tcgggtccgc aaccgctcac tgggagtcaa gcgcgtacac ttcgtgaata agcactaacg     60
gttgtacatt agtgggtttc gtcctcaaga acatggggag ttgggtgcca atggaatcgt    120
```

taaggtggtg aaggtccacc acctcgcttt attggtctgc attcggggca agtccaaccc 180
tacgtcggat ttcccatacc 200

<210> SEQ ID NO 47
<211> LENGTH: 200
<212> TYPE: DNA
<213> ORGANISM: Artificial Sequence
<220> FEATURE:
<223> OTHER INFORMATION: hpGUS[2:10]

<400> SEQUENCE: 47
tcgcgtcgcg atccggtctc tggcagtgtt gggcgaactc ttcctgatat accacaaagg 60
gttctactaa actggcttac gtcgtcatct agatgcggtg ttgcgtgggt aaggattcct 120
taacgtgcac atggtgcagc accacgcaaa aatggactcc attggggcgt actcctacgc 180
tacctcgcta tacccttagc 200

<210> SEQ ID NO 48
<211> LENGTH: 200
<212> TYPE: DNA
<213> ORGANISM: Artificial Sequence
<220> FEATURE:
<223> OTHER INFORMATION: hpEIN2[G:U]

<400> SEQUENCE: 48
gattttagtt agggtttatt tagagaatgg tttttgtttt attttttgtt tttttggttt 60
ttgttggata tattgatttt gggaaatggg ttgtaaatat tgaaggaggt gtttgttttg 120
ggtatgattt ggtggtaatt attttgtttt ttaattttgt tgttatttta tgttaatatg 180
ttgtagtttg tataagtgtt 200

<210> SEQ ID NO 49
<211> LENGTH: 200
<212> TYPE: DNA
<213> ORGANISM: Artificial Sequence
<220> FEATURE:
<223> OTHER INFORMATION: hpCHS[G:U]

<400> SEQUENCE: 49
gttgtttgtt ttgagattat agttgttatt ttttgtggtt tttttgatat ttattttgat 60
ttttttgttg gttaggtttt ttttagtgat ggtgttgttg tatttattgt ggggttggat 120
tttgatatat ttgttggaga gaaatttatt tttgagatgg tgtttgttgt ttagattatt 180
tttttagatt ttgatggtgt 200

<210> SEQ ID NO 50
<211> LENGTH: 200
<212> TYPE: DNA
<213> ORGANISM: Artificial Sequence
<220> FEATURE:
<223> OTHER INFORMATION: hpEIN2[G:U/U:G]

<400> SEQUENCE: 50
aatgtttatg tgagttgtaa tatattggta taagatggtg gtaaaattga aaagtagagt 60
aattgttatt aagttatatt tgaaatgagt atttttttg atatttgtaa tttattttttt 120 gggattaata tatttgatag aaattaaaag gataggaagt agagtaggaa ttatttttttg 180 gataaatttt agttgaggtt 200

<210> SEQ ID NO 51
<211> LENGTH: 199

<212> TYPE: DNA
<213> ORGANISM: Artificial Sequence
<220> FEATURE:
<223> OTHER INFORMATION: hpCHS[G:U/U:G]

<400> SEQUENCE: 51
gtattattag agtttggaag gatggtttga gtggtagata ttattttaaa gatgggtttt 60
tttttgatag atgtgttagg gtttgatttt ataatgagtg tggtggtgtt attattgaaa 120
agagtttgat tgatgaggga gttaaggtgg gtgttagagg gattatggaa ggtaatggtt 180
gtgattttag agtagataa 199

<210> SEQ ID NO 52
<211> LENGTH: 30
<212> TYPE: DNA
<213> ORGANISM: Artificial Sequence
<220> FEATURE:
<223> OTHER INFORMATION: GUS-WT-F

<400> SEQUENCE: 52
cctcgaggat cctcgcgtcg gcatccggtc 30

<210> SEQ ID NO 53
<211> LENGTH: 33
<212> TYPE: DNA
<213> ORGANISM: Artificial Sequence
<220> FEATURE:
<223> OTHER INFORMATION: GUS-WT-R

<400> SEQUENCE: 53
gggtaccaag cttcgtaagg gtaatgcgag gta 33

<210> SEQ ID NO 54
<211> LENGTH: 118
<212> TYPE: DNA
<213> ORGANISM: Artificial Sequence
<220> FEATURE:
<223> OTHER INFORMATION: GUS-GU-F

<400> SEQUENCE: 54
ccctcgagtt gtgttggtat ttggttagtg gtagtgaagg gtgaatagtt tttgattaat 60
tataaattgt tttattttat tggttttggt tgttatgaag atgtggattt gtgtggta 118

<210> SEQ ID NO 55
<211> LENGTH: 118
<212> TYPE: DNA
<213> ORGANISM: Artificial Sequence
<220> FEATURE:
<223> OTHER INFORMATION: GUS-GU-R

<400> SEQUENCE: 55
ggggtaccca taaaaataat acaaaataca ataaaaatta accccaatcc aatccattaa 60
tacataatca tacaccatca acacattatc aaatccttta ccacacaaat ccacatct 118

<210> SEQ ID NO 56
<211> LENGTH: 118
<212> TYPE: DNA
<213> ORGANISM: Artificial Sequence
<220> FEATURE:
<223> OTHER INFORMATION: GUS-4M-F

<400> SEQUENCE: 56
ccctcgagtc gggtccgcaa ccgctcactg ggagtcaagc gcgtacactt cgtgaataag 60
cactaacggt tgtacattag tgggtttcgt cctcaagaac atggggagtt gggtgcca 118

<210> SEQ ID NO 57
<211> LENGTH: 118
<212> TYPE: DNA
<213> ORGANISM: Artificial Sequence
<220> FEATURE:
<223> OTHER INFORMATION: GUS-4M-R

<400> SEQUENCE: 57
ggggtaccgg tatgggaaat ccgacgtagg gttggacttg ccccgaatgc agaccaataa 60
agcgaggtgg tggaccttca ccaccttaac gattccattg gcacccaact ccccatgt 118

<210> SEQ ID NO 58
<211> LENGTH: 118
<212> TYPE: DNA
<213> ORGANISM: Artificial Sequence
<220> FEATURE:
<223> OTHER INFORMATION: GUS-10M-F

<400> SEQUENCE: 58
ccctcgagtc gcgtcgcgat ccggtctctg gcagtgttgg gcgaactctt cctgatatac 60
cacaaagggt tctactaaac tggcttacgt cgtcatctag atgcggtgtt gcgtgggt 118

<210> SEQ ID NO 59
<211> LENGTH: 118
<212> TYPE: DNA
<213> ORGANISM: Artificial Sequence
<220> FEATURE:
<223> OTHER INFORMATION: GUS-10M-R

<400> SEQUENCE: 59
ggggtaccgc taagggtata gcgaggtagc gtaggagtac gccccaatgg agtccatttt 60
tgcgtggtgc tgcaccatgt gcacgttaag gaatccttac ccacgcaaca ccgcatct 118

<210> SEQ ID NO 60
<211> LENGTH: 20
<212> TYPE: DNA
<213> ORGANISM: Artificial Sequence
<220> FEATURE:
<223> OTHER INFORMATION: Forward primer (35S-F3)

<400> SEQUENCE: 60
tggctcctac aaatgccatc 20

<210> SEQ ID NO 61
<211> LENGTH: 21
<212> TYPE: DNA
<213> ORGANISM: Artificial Sequence
<220> FEATURE:
<223> OTHER INFORMATION: Reverse primer (GUSwt-R2)
<220> FEATURE:
<221> NAME/KEY: R
<222> LOCATION: (3)..(4)
<223> OTHER INFORMATION: A or G
<220> FEATURE:
<221> NAME/KEY: R
<222> LOCATION: (9)..(9)
<223> OTHER INFORMATION: A or G
<220> FEATURE:
<221> NAME/KEY: R
<222> LOCATION: (13)..(13)
<223> OTHER INFORMATION: A or G

<400> SEQUENCE: 61
carraactrt tcrcccttca c 21

<210> SEQ ID NO 62
<211> LENGTH: 21
<212> TYPE: DNA
<213> ORGANISM: Artificial Sequence
<220> FEATURE:
<223> OTHER INFORMATION: Forward primer (GUSgu-R2)

<400> SEQUENCE: 62
caaaaactat tcacccttca c 21

<210> SEQ ID NO 63
<211> LENGTH: 21
<212> TYPE: DNA
<213> ORGANISM: Artificial Sequence
<220> FEATURE:
<223> OTHER INFORMATION: reverse primer (GUS4m-R2)
<220> FEATURE:
<221> NAME/KEY: R
<222> LOCATION: (4)..(4)
<223> OTHER INFORMATION: A or G
<220> FEATURE:
<221> NAME/KEY: R
<222> LOCATION: (7)..(7)
<223> OTHER INFORMATION: A or G
<220> FEATURE:
<221> NAME/KEY: R
<222> LOCATION: (9)..(9)
<223> OTHER INFORMATION: A or G
<220> FEATURE:
<221> NAME/KEY: R
<222> LOCATION: (13)..(13)
<223> OTHER INFORMATION: A or G
<220> FEATURE:
<221> NAME/KEY: R
<222> LOCATION: (15)..(15)
<223> OTHER INFORMATION: A or G
<220> FEATURE:
<221> NAME/KEY: R
<222> LOCATION: (19)..(19)
<223> OTHER INFORMATION: A or G

<400> SEQUENCE: 63
cacraartrt acrcrcttra c 21

<210> SEQ ID NO 64
<211> LENGTH: 20
<212> TYPE: DNA
<213> ORGANISM: Artificial Sequence
<220> FEATURE:
<223> OTHER INFORMATION: Forward primer (35S-F2)

<400> SEQUENCE: 64
gaggatctaa cagaactcgc 20

<210> SEQ ID NO 65
<211> LENGTH: 23
<212> TYPE: DNA
<213> ORGANISM: Artificial Sequence
<220> FEATURE:
<223> OTHER INFORMATION: reverse primer (35S-R1)

<400> SEQUENCE: 65
ctctccaaat gaaatgaact tcc 23

<210> SEQ ID NO 66
<211> LENGTH: 36
<212> TYPE: DNA
<213> ORGANISM: Artificial Sequence
<220> FEATURE:

<223> OTHER INFORMATION: EIN2wt-F

<400> SEQUENCE: 66
cctcgaggat cctctagacc tcagctaggg tttatc 36

<210> SEQ ID NO 67
<211> LENGTH: 33
<212> TYPE: DNA
<213> ORGANISM: Artificial Sequence
<220> FEATURE:
<223> OTHER INFORMATION: EIN2wt-R

<400> SEQUENCE: 67
gggtaccaag cttaacgctt atgcgagctg caa 33

<210> SEQ ID NO 68
<211> LENGTH: 32
<212> TYPE: DNA
<213> ORGANISM: Artificial Sequence
<220> FEATURE:
<223> OTHER INFORMATION: CHSwt-F

<400> SEQUENCE: 68
cctcgaggat ccgttgtctg ctctgagatc ac 32

<210> SEQ ID NO 69
<211> LENGTH: 38
<212> TYPE: DNA
<213> ORGANISM: Artificial Sequence
<220> FEATURE:
<223> OTHER INFORMATION: CHSwt-R

<400> SEQUENCE: 69
gggtaccaag cttctagagc accatcagag tctggaag 38

<210> SEQ ID NO 70
<211> LENGTH: 119
<212> TYPE: DNA
<213> ORGANISM: Artificial Sequence
<220> FEATURE:
<223> OTHER INFORMATION: EIN2gu-F

<400> SEQUENCE: 70
cctcgagtct agattttagt tagggtttat ttagagaatg gtttttgttt tattttttgt 60 tttttggtt tttgttggat atattgattt tgggaaatgg gttgtaaata ttgaaggag 119

<210> SEQ ID NO 71
<211> LENGTH: 119
<212> TYPE: DNA
<213> ORGANISM: Artificial Sequence
<220> FEATURE:
<223> OTHER INFORMATION: EIN2gu-R

<400> SEQUENCE: 71
gggtaccaac acttatacaa actacaacat attaacataa aataacaaca aaattaaaaa 60
acaaaataat taccaccaaa tcatacccaa aacaaacacc tccttcaata tttacaacc 119

<210> SEQ ID NO 72
<211> LENGTH: 119
<212> TYPE: DNA
<213> ORGANISM: Artificial Sequence
<220> FEATURE:
<223> OTHER INFORMATION: CHSgu-F

<400> SEQUENCE: 72
cctcgaggtt gtttgttttg agattatagt tgttattttt tgtggttttt ttgatattta 60
ttttgatttt tttgttggtt aggttttttt tagtgatggt gttgttgtat ttattgtgg 119

<210> SEQ ID NO 73
<211> LENGTH: 119
<212> TYPE: DNA
<213> ORGANISM: Artificial Sequence
<220> FEATURE:
<223> OTHER INFORMATION: CHSgu-R

<400> SEQUENCE: 73
gggtacctct agacaccatc aaaatctaaa aaaataatct aaacaacaaa caccatctca 60
aaaataaatt tctctccaac aaatatatca aaatccaacc ccacaataaa tacaacaac 119

<210> SEQ ID NO 74
<211> LENGTH: 120
<212> TYPE: DNA
<213> ORGANISM: Artificial Sequence
<220> FEATURE:
<223> OTHER INFORMATION: asEIN2gu-F

<400> SEQUENCE: 74
caagcttaat gtttatgtga gttgtaatat attggtataa gatggtggta aaattgaaaa 60
gtagagtaat tgttattaag ttatatttga aatgagtatt ttttttgata tttgtaattt 120

<210> SEQ ID NO 75
<211> LENGTH: 120
<212> TYPE: DNA
<213> ORGANISM: Artificial Sequence
<220> FEATURE:
<223> OTHER INFORMATION: asEIN2gu-R

<400> SEQUENCE: 75
gggatcctct agaacctcaa ctaaaattta tccaaaaaat aattcctact ctacttccta 60
tccttttaat ttctatcaaa tatattaatc ccaaaaaata aattacaaat atcaaaaaaa 120

<210> SEQ ID NO 76
<211> LENGTH: 120
<212> TYPE: DNA
<213> ORGANISM: Artificial Sequence
<220> FEATURE:
<223> OTHER INFORMATION: asCHSgu-F

<400> SEQUENCE: 76
caagcttcta gagtattatt agagtttgga aggatggttt gagtggtaga tattatttta 60
aagatgggtt ttttttgat agatgtgtta gggtttgatt ttataatgag tgtggtggtg 120

<210> SEQ ID NO 77
<211> LENGTH: 120
<212> TYPE: DNA
<213> ORGANISM: Artificial Sequence
<220> FEATURE:
<223> OTHER INFORMATION: asCHSgu-R

<400> SEQUENCE: 77
gggatccatt atctactcta aaatcacaac cattaccttc cataatccct ctaacaccca 60
ccttaactcc ctcatcaatc aaactctttt caataataac accaccacac tcattataaa 120

<210> SEQ ID NO 78
<211> LENGTH: 20
<212> TYPE: DNA

<213> ORGANISM: Artificial Sequence
<220> FEATURE:
<223> OTHER INFORMATION: CHS-200-F2

<400> SEQUENCE: 78
gacatgcctg gtgctgacta 20

<210> SEQ ID NO 79
<211> LENGTH: 20
<212> TYPE: DNA
<213> ORGANISM: Artificial Sequence
<220> FEATURE:
<223> OTHER INFORMATION: CHS-200-R2

<400> SEQUENCE: 79
ccttagcgat acggaggaca 20

<210> SEQ ID NO 80
<211> LENGTH: 20
<212> TYPE: DNA
<213> ORGANISM: Artificial Sequence
<220> FEATURE:
<223> OTHER INFORMATION: Actin2-For

<400> SEQUENCE: 80
tccctcagca cattccagca 20

<210> SEQ ID NO 81
<211> LENGTH: 22
<212> TYPE: DNA
<213> ORGANISM: Artificial Sequence
<220> FEATURE:
<223> OTHER INFORMATION: Actin2-Rev

<400> SEQUENCE: 81
gatcccattc ataaaacccc ag 22

<210> SEQ ID NO 82
<211> LENGTH: 24
<212> TYPE: DNA
<213> ORGANISM: Artificial Sequence
<220> FEATURE:
<223> OTHER INFORMATION: Top-35S-F2
<220> FEATURE:
<221> NAME/KEY: Y
<222> LOCATION: (8)..(8)
<223> OTHER INFORMATION: C or T
<220> FEATURE:
<221> NAME/KEY: Y
<222> LOCATION: (11)..(11)
<223> OTHER INFORMATION: C or T
<220> FEATURE:
<221> NAME/KEY: Y
<222> LOCATION: (14)..(14)
<223> OTHER INFORMATION: C or T
<220> FEATURE:
<221> NAME/KEY: Y
<222> LOCATION: (17)..(17)
<223> OTHER INFORMATION: C or T

<400> SEQUENCE: 82
agaaaatytt ygtyaayatg gtgg 24

<210> SEQ ID NO 83
<211> LENGTH: 24
<212> TYPE: DNA
<213> ORGANISM: Artificial Sequence
<220> FEATURE:
<223> OTHER INFORMATION: Top-35S-R2

<220> FEATURE:
<221> NAME/KEY: R
<222> LOCATION: (4)..(4)
<223> OTHER INFORMATION: A or G
<220> FEATURE:
<221> NAME/KEY: R
<222> LOCATION: (6)..(7)
<223> OTHER INFORMATION: A or G
<220> FEATURE:
<221> NAME/KEY: R
<222> LOCATION: (9)..(9)
<223> OTHER INFORMATION: A or G
<220> FEATURE:
<221> NAME/KEY: R
<222> LOCATION: (12)..(12)
<223> OTHER INFORMATION: A or G

<400> SEQUENCE: 83
tcartrrara trtcacatca atcc 24

<210> SEQ ID NO 84
<211> LENGTH: 23
<212> TYPE: DNA
<213> ORGANISM: Artificial Sequence
<220> FEATURE:
<223> OTHER INFORMATION: Link-35S-F2
<220> FEATURE:
<221> NAME/KEY: Y
<222> LOCATION: (1)..(2)
<223> OTHER INFORMATION: C or T
<220> FEATURE:
<221> NAME/KEY: Y
<222> LOCATION: (5)..(5)
<223> OTHER INFORMATION: C or T
<220> FEATURE:
<221> NAME/KEY: Y
<222> LOCATION: (10)..(10)
<223> OTHER INFORMATION: C or T

<400> SEQUENCE: 84
yyatyattgy gataaaggaa agg 23

<210> SEQ ID NO 85
<211> LENGTH: 22
<212> TYPE: DNA
<213> ORGANISM: Artificial Sequence
<220> FEATURE:
<223> OTHER INFORMATION: Link-EIN2-R2
<220> FEATURE:
<221> NAME/KEY: R
<222> LOCATION: (6)..(6)
<223> OTHER INFORMATION: A or G
<220> FEATURE:
<221> NAME/KEY: R
<222> LOCATION: (14)..(14)
<223> OTHER INFORMATION: A or G

<400> SEQUENCE: 85
taattrccac caartcatac cc 22

<210> SEQ ID NO 86
<211> LENGTH: 22
<212> TYPE: RNA
<213> ORGANISM: Artificial Sequence
<220> FEATURE:
<223> OTHER INFORMATION: sense si22

<400> SEQUENCE: 86
gcaagcugac ccugaaguuc au 22

<210> SEQ ID NO 87

<211> LENGTH: 22
<212> TYPE: RNA
<213> ORGANISM: Artificial Sequence
<220> FEATURE:
<223> OTHER INFORMATION: antisense si22

<400> SEQUENCE: 87
gaacuucagg gucagcuugc cg 22

<210> SEQ ID NO 88
<211> LENGTH: 20
<212> TYPE: DNA
<213> ORGANISM: Artificial Sequence
<220> FEATURE:
<223> OTHER INFORMATION: Forward primer

<400> SEQUENCE: 88
ttttagtata tgtgctgccg 20

<210> SEQ ID NO 89
<211> LENGTH: 83
<212> TYPE: DNA
<213> ORGANISM: Artificial Sequence
<220> FEATURE:
<223> OTHER INFORMATION: reverse primer

<400> SEQUENCE: 89
ctcgagttcc aaaaaagctg accctgaagt tcatctctct tgaagatgaa cttcagggtc 60
agccaaacaa ggcttttctc caa 83

<210> SEQ ID NO 90
<211> LENGTH: 20
<212> TYPE: DNA
<213> ORGANISM: Artificial Sequence
<220> FEATURE:
<223> OTHER INFORMATION: forward primer

<400> SEQUENCE: 90
ttttagtata tgtgctgccg 20

<210> SEQ ID NO 91
<211> LENGTH: 83
<212> TYPE: DNA
<213> ORGANISM: Artificial Sequence
<220> FEATURE:
<223> OTHER INFORMATION: reverse primer

<400> SEQUENCE: 91
ctcgagttcc aaaaaaataa gtcgcagcag tacaatctct tgaattgtac tgctgcgact 60
tatgaatacc gcttcctcct gag 83

<210> SEQ ID NO 92
<211> LENGTH: 88
<212> TYPE: RNA
<213> ORGANISM: Artificial Sequence
<220> FEATURE:
<223> OTHER INFORMATION: dsRNA molecules

<400> SEQUENCE: 92
aagugauuug ugaauggauu cgguuaaguu agugauaggu aucacgcugg ccauuacuga 60
caugaccgga uucguucgcg agucacuu 88

<210> SEQ ID NO 93
<211> LENGTH: 2653

<212> TYPE: DNA
<213> ORGANISM: Brassica napus

<400> SEQUENCE: 93

```
agaaaaatcg aaaaatgtga cagtgcgtct tttcacttaa taccctcgtt ttgaatttgc     60
tctcggaaag cgtctgagag agtgttcggt gatttctccc gccgcttggg gtttttttccg   120
ttaccggaat atccttctcc tccgatggtt agtctgcgct ccacagaaaa cactccggct    180
tcggaaatgg ccagcgacgg caaaacggag aaagatggct ccggcgactc acccacttct    240
gttctcagcg atgaggaaaa ctgtgaagag aaaactgcta ctgttgctgt agaggaagag    300
atacttctag ccaagaatgg agattcgtct cttatctctg aggccatggc tcaggaagaa    360
gagcagcttc tcaaaatccg ggaagatgaa gagattgcta aacgtgctgc tggctctggt    420
gaagctcctg atctgaatga tactcagttt actaaacttg atgagctctt gacccaaacc    480
cagctctact ctgagtttct ccttgagaaa atggaggata tcaccaaaaa tgggatagaa    540
ggtgagaccc aaaaggccga gcctgagcct gagcctgagc ccgagaagaa aggccgtgga    600
cgtaaaagaa aggctgctcc tcagggcgac agtatgaagg ctaagaaagc tgttgctgct    660
atgatttcaa gatccaaaga aggccgtgaa tctgccgact cagatctgac agaggaagaa    720
agagtcatga aagagcaggg tgaacttgtt cctcttctga ctggcggaaa gttaaagtct    780
tatcagctca aggtgtcaa atggctgata tcattgtggc aaaatggttt gaatggaatt    840
ttagctgatc aaatgggtct tggaaagaca attcaaacca ttggtttcct atcacacctc    900
aaaggaaatg ggttggatgg tccatatcta gtcattgccc cactctctac tctttcaaac    960
tggatgaatg agatcgctag gttcacgcct tccattaatg caatcattta ccatggagat   1020
aagaaagaaa gggatgagct caggaagagg cacatgccca gaactgttgg tccgaagttc   1080
cctatagtca taacttctta tgaggttgct atgaatgatg ctaaaaagaa tctgcggcac   1140
tatccatgga aatatgttgt gattgatgag ggtcacaggt tgaaaaacca caagtgtaaa   1200
ctgctgaggg agctaagata cttgaatatg gagaacaaac ttctgctgcc aggaacacct   1260
ctgcaaaata atttgtctga gcttcggtca ctgttgaatt ttattctgcc tgacatcttt   1320
gcatcacatg acgaatttga atcatggttt gatttttctt gaaagaataa taatgaagca   1380
actaaggaag aaggagaaga gaaaagaaga gctcaagtgg ttgcgaaact tcataatata   1440
ctacgacctt tcatcctccg gagaatgaaa tgtgatgttg agctctcact tccccggaaa   1500
aaagagatta tcatctatgc tacaatgacg gaccatcaga agaagttcca ggaacatctt   1560
gtgaaccaca ccttggaagc acacattaga gatgatactg tccgaggtca tggcttgaag   1620
ggaaagctta acaatcttgc tattcaactt cgaaagaact gcaaccatcc tgaccttctt   1680
gtggggcaac tagatggctc atatctctac ccacctttgg aagacattgt gggacagtgc   1740
ggtaaattcc gcttattgga gagattgctt gttcggttat ttgccaaaaa tcacagagtc   1800
cttatcttct cccagtggac aaaaatactg gacattatgg attactactt cagtgagaag   1860
gggtttgagg tttgccgaat cgacggtagt gtgaaactag aagaaaggag aagacagatc   1920
caagaattca atgatgagaa gagcaactgc aggatatttc ttctcagtac cagagccgga   1980
ggactcggaa ttaatcttac tgctgcagat acatgcatcc tctacgatag cgattggaac   2040
cctcaaatgg acttgcaagc catggacaga tgccacagaa ttggtcagac aaaacctgtt   2100
catgtttaca ggcttgcgac ggctcagtca atagagggcc gagttctgaa acgagcatac   2160
agtaagctta agctggaaca tgtggttatt ggcaaggggc agtttcatca agaacgtgcc   2220
```

```
aagtcttcaa caccgttaga ggaagatgac atactggcgt tgcttaagga cgacgaaaat   2280

gctgaagata aactgataca aaccgacata agcgaggagg atcttgacag ggtgcttgac   2340

cgtagtgatc tgatgattac cttaccgggc gagactcaag cacatgaagc ttttccagtg   2400

aagggtccgg gttgggaagt ggtctcgtct agctcagctg gagggatgct gtcttccctc   2460

aacagttaga accactcttt gcaaaaccac ttcggtgtgt ttttttttcc ggaacataac   2520

cggttacttt tgcctgctac tcggaagttt taacttgaaa ccttggaaac atctgatgaa   2580

aacaattgcg gatattatgt tattagacta tttatttatg ccttttgaaa tttggcagta   2640

attttttagt taa                                                      2653
```

<210> SEQ ID NO 94
<211> LENGTH: 1773
<212> TYPE: DNA
<213> ORGANISM: Artificial Sequence
<220> FEATURE:
<223> OTHER INFORMATION: Chimeric DNA encoding a hairpin RNAi (hpRNA) construct targeting a DDM1 gene of B. napus

<400> SEQUENCE: 94

```
gggagctgtt gctgctatga tttcaagatc caaagaaggc cgtgaatctg ccgactcaga     60

tctgacagag gaagaaagag tcatgaatga gcagggtgaa cttgttcctc ttctgactgg    120

cggaaagtta aagtcttatc agctcaaagg tgtcaaatgg ctgatatcat tgtggcaaaa    180

tggtttgaat ggaattttag ctgatcaaat gggtcttgga aagacaattc aaaccattgg    240

tttcctatca ccccaacaag gaaatgggtt ggatggtcca tatctagtca ttgccccact    300

ctctactctt tcaaaagcga ttggaaccct caaatggact tgcaagccat ggacagatgc    360

cacagaattg gtcagacaaa acctgttcat gtttacaggc ttgcgacggc tcagtcaata    420

gagggccgag ttctgaaacg agcatacagt aagcttaagc tggaacatgt ggttattggc    480

aaggggcagt ttcatcaaga acgtggtaag gaaataatta ttttcttttt tccttttagt    540

ataaaatagt taagtgatgt taattagtat gattataata atatagttgt tataattgtg    600

aaaaaataat ttataaatat attgtttaca taaacaacat agtaatgtaa aaaaatatga    660

caagtgatgt gtaagacgaa gaagataaaa gttgagagta agtatattat ttttaatgaa    720

tttgatcgaa catgtaagat gatatactag cattaatatt tgttttaatc ataatagtaa    780

ttctagctgg tttgatgaat taaatatcaa tgataaaata ctatagtaaa aataagaata    840

aataaattaa aataatattt ttttatgatt aatagtttat tatataatta aatatctata    900

ccattactaa atattttagt ttaaaagtta ataaatattt tgttagaaat tccaatctgc    960

ttgtaattta tcaataaaca aaatattaaa taacaagcta aagtaacaaa taatatcaaa   1020

ctaatagaaa cagtaatcta atgtaacaaa acataatcta atgctaatat aacaaagcgc   1080

aagatctatc attttatata gtattatttt caatcaacat tcttattaat ttctaaataa   1140

tacttgtagt tttattaact tctaaatgga ttgactatta attaaatgaa ttagtcgaac   1200

atgaataaac aaggtaacat gatagatcat gtcattgtgt tatcattgat cttacatttg   1260

gattgattac agtcacgttc ttgatgaaac tgccccttgc caataaccac atgttccagc   1320

ttaagcttac tgtatgctcg tttcagaact cggccctcta ttgactgagc cgtcgcaagc   1380

ctgtaaacat gaacaggttt tgtctgacca attctgtggc atctgtccat ggcttgcaag   1440

tccatttgag ggttccaatc gcttttgaaa gagtagagag tggggcaatg actagatatg   1500

gaccatccaa cccatttcct tgttggggtg ataggaaacc aatggtttga attgtctttc   1560
```

caagacccat ttgatcagct aaaattccat tcaaaccatt ttgccacaat gatatcagcc 1620
atttgacacc tttgagctga taagacttta actttccgcc agtcagaaga ggaacaagtt 1680
caccctgctc tttcatgact ctttcttcct ctgtcagatc tgagtcggca gattcacggc 1740
cttctttgga tcttgaaatc atagcagcaa cag 1773

<210> SEQ ID NO 95
<211> LENGTH: 1773
<212> TYPE: DNA
<213> ORGANISM: Artificial Sequence
<220> FEATURE:
<223> OTHER INFORMATION: Chimeric DNA encoding a hairpin RNAi (hpRNA) construct with G:U basepairs, targeting a DDM1 gene of B. napus

<400> SEQUENCE: 95
gggttgttgt tgttatgatt ttaagattta aagaaggttg tgaatttgtt gatttagatt 60
tgatagagga agaaagagtt atgaatgagt agggtgaatt tgtttttttt ttgattggtg 120
gaaagttaaa gttttattag tttaaaggtg ttaaatggtt gatattattg tggtaaaatg 180
gtttgaatgg aattttagtt gattaaatgg gttttggaaa gataatttaa attattggtt 240
ttttattata ttttaaagga aatgggttgg atggtttata tttagttatt gttttatttt 300
ttattttttt aaaagtgatt ggaattttta aatggatttg taagttatgg atagatgtta 360
tagaattggt tagataaaat ttgtttatgt ttataggttt gtgatggttt agttaataga 420
gggttgagtt ttgaaatgag tatatagtaa gtttaagttg gaatatgtgg ttattggtaa 480
ggggtagttt tattaagaat gtgtggtaag gaaataatta ttttcttttt tcctttttagt 540 ataaaatagt taagtgatgt taattagtat gattataata atatagttgt tataattgtg 600
aaaaaataat ttataaatat attgtttaca taaacaacat agtaatgtaa aaaaatatga 660
caagtgatgt gtaagacgaa gaagataaaa gttgagagta agtatattat ttttaatgaa 720
tttgatcgaa catgtaagat gatatactag cattaatatt tgttttaatc ataatagtaa 780
ttctagctgg tttgatgaat taaatatcaa tgataaaata ctatagtaaa aataagaata 840
aataaattaa aataatattt ttttatgatt aatagtttat tatataatta aatatctata 900
ccattactaa atattttagt ttaaaagtta ataaatattt tgttagaaat tccaatctgc 960
ttgtaattta tcaataaaca aaatattaaa taacaagcta aagtaacaaa taatatcaaa 1020
ctaatagaaa cagtaatcta atgtaacaaa acataatcta atgctaatat aacaaagcgc 1080
aagatctatc attttatata gtattatttt caatcaacat tcttattaat ttctaaataa 1140
tacttgtagt tttattaact tctaaatgga ttgactatta attaaatgaa ttagtcgaac 1200
atgaataaac aaggtaacat gatagatcat gtcattgtgt tatcattgat cttacatttg 1260
gattgattac agtcacgttc ttgatgaaac tgccccttgc caataaccac atgttccagc 1320
ttaagcttac tgtatgctcg tttcagaact cggccctcta ttgactgagc cgtcgcaagc 1380
ctgtaaacat gaacaggttt tgtctgacca attctgtggc atctgtccat ggcttgcaag 1440
tccatttgag ggttccaatc gcttttgaaa gagtagagag tggggcaatg actagatatg 1500
gaccatccaa cccatttcct tgttggggtg ataggaaacc aatggtttga attgtctttc 1560
caagacccat ttgatcagct aaaattccat tcaaaccatt ttgccacaat gatatcagcc 1620
atttgacacc tttgagctga taagacttta actttccgcc agtcagaaga ggaacaagtt 1680
caccctgctc tttcatgact ctttcttcct ctgtcagatc tgagtcggca gattcacggc 1740
cttctttgga tcttgaaatc atagcagcaa cag 1773

<210> SEQ ID NO 96
<211> LENGTH: 1260
<212> TYPE: DNA
<213> ORGANISM: Artificial Sequence
<220> FEATURE:
<223> OTHER INFORMATION: Chimeric DNA encoding a ledRNA construct, targeting a DDM1 gene of B. napus

<400> SEQUENCE: 96

```
ggggtgatag gaaaccaatg gtttgaattg tctttccaag acccatttga tcagctaaaa     60

ttccattcaa accattttgc cacaatgata tcagccattt gacacctttg agctgataag    120

actttaactt tccgccagtc agaagaggaa caagttcacc ctgctctttc atgactcttt    180

cttcctctgt cagatctgag tcggcagatt cacggccttc tttggatctt gaaatcatag    240

cagcaacagc tttcttagcc ttcatactgt cgccctgagg agcagccttt cttttacgtc    300

cacggccttt cttctcgggc tcaggctcag gctcaggctc ggccttttgg gtctcacctt    360

ctatcccatt tttggtgata gctgttgctg ctatgatttc aagatccaaa gaaggccgtg    420

aatctgccga ctcagatctg acagaggaag aaagagtcat gaatgagcag ggtgaacttg    480

ttcctcttct gactggcgga aagttaaagt cttatcagct caaaggtgtc aaatggctga    540

tatcattgtg gcaaaatggt ttgaatggaa ttttagctga tcaaatgggt cttggaaaga    600

caattcaaac cattggtttc ctatcacccc aacaaggaaa tgggttggat ggtccatatc    660

tagtcattgc ccccactctct actctttcaa aagcgattgg aaccctcaaa tggacttgca    720

agccatggac agatgccaca gaattggtca gacaaaacct gttcatgttt acaggcttgc    780

gacggctcag tcaatagagg gccgagttct gaaacgagca tacagtaagc ttaagctgga    840

acatgtggtt attggcaagg ggcagtttca tcaagaacgt cactacggtc aagcaccctg    900

tcaagatcct cctcgcttat gtcggtttgt atcagtttat cttcagcatt ttcgtcgtcc    960

ttaagcaacg ccagtatgtc atcttcctct aacggtgttg aagacttggc acgttcttga   1020

tgaaactgcc ccttgccaat aaccacatgt tccagcttaa gcttactgta tgctcgtttc   1080

agaactcggc cctctattga ctgagccgtc gcaagcctgt aaacatgaac aggttttgtc   1140

tgaccaattc tgtggcatct gtccatggct tgcaagtcca tttgagggtt ccaatcgctt   1200

ttgaaagagt agagagtggg gcaatgacta gatatggacc atccaaccca tttccttgtt   1260
```

<210> SEQ ID NO 97
<211> LENGTH: 4421
<212> TYPE: DNA
<213> ORGANISM: Arabidopsis thaliana

<400> SEQUENCE: 97

```
tcttccaaaa tttgcccgcc attctctgtg tctcttcgtc taagggtttc ttccaaagaa     60

cgacgacaaa accactgaac ctaaaatccg aaatccaaaa gattcatgcg aaaaaatcgt    120

taaagagtac caatttcaga aagttacatt cttacagaga acaagtaatt ccccagaaat    180

gggatctagg gttccaatag aaaccatcga agaagacggc gaattcgatt gggaagcagc    240

agtcaaagaa atcgacttgg cttgtcttaa aaccacaaac gcttcttctt cttcgtcatc    300

ccatttcact cctttggcta atccaccaat tacggcaaat ctcactaagc cacctgcgaa    360

gagacaatct actctcgata aattcatcgg cagaaccgaa cataaaccgg agaatcatca    420

agttgtttcc gagtgtggtg ttaacgataa cgataatagt cctttagttg ggattgatcc    480

tgaggcagct aaaacttgga tttatccagt gaatgggagt gttcctttaa gagattatca    540
```

```
gtttgctata acgaagactg ctttgttttc gaatacattg gtggctttgc ctacgggact    600
tggtaaaacg cttatagctg cggttgttat gtataattac ttcagatggt ttccacaagg    660
taaaatagta tttgcggcgc cttctaggcc tcttgtgatg cagcagattg aggcgtgtca    720
taatattgtt ggaataccac aagaatggac gattgacttg acgggtcaga catgtccttc    780
gaaaagagct tttttgtgga aaagcaaacg ggttttcttt gtcactccac aagtgttaga    840
gaaggatata cagtcaggaa catgtcttac taactacttg gtttgcttgg tgatcgacga    900
ggcacatcga gctttaggga attattctta ttgtgttgta gttcgtgagt tgatggcggt    960
accgatacag ctgagaatac tggctcttac tgcaactcct ggatcaaaga cacaggccat   1020
ccagggtatc attgataatt tgcagatatc cacacttgaa tatcgaaatg agagtgacca   1080
tgatgtttgc ccttatgtcc acgacagaaa attagaagtc atcgaggttc ccttgggtca   1140
agatgcagat gatgtatcga aacgcctgtt tcatgttata cgtccatatg cagtcaggct   1200
taaaaacttt ggggttaatc taaatagaga tatacaaact ttaagtccac acgaagtact   1260
tatggcaagg gataagtttc gtcaagcacc tctaccaggc cttccccatg taaatcacgg   1320
agatgtagaa tcttgctttg cagctcttat cactctttat catattcgta agctcctttc   1380
tagtcatgga ataagaccag cgtatgagat gctagaagag aaattgaaag aagggccatt   1440
tgctaggttg atgagtaaga atgaagatat taggatgacg aagcttttga tgcagcaaag   1500
gttgtcacat ggagcaccaa gcccaaaatt gtcgaagatg ttagaaatac tggttgatca   1560
tttcaaagtg aaagatccga agacatcacg ggtcattatt ttctcaaatt tcagaggaag   1620
cgtaagagac ataatgaacg cattaagtaa tattggagat atggtcaaag caactgagtt   1680
tattggtcaa agttcaggta agacattgaa aggccagtcg caaaaaattc agcaggctgt   1740
tttggagaaa tttagagctg gggggttcaa tgttattgtc gcaacatcta ttggtgaaga   1800
aggcttggat atcatggaag ttgacctagt tatatgtttt gatgctaatg tatctcctct   1860
gaggatgatt caacggatgg gaagaactgg aaggaaaaat aatggtcgag ttgtagttct   1920
tgcttgtgaa ggatcagaaa agaacagcta tatgcgaaag caagcaagtg gacgggctat   1980
taaaaaacac atgcggaatg gaggaacaaa tagttttaat tttcatccta gtccaaggat   2040
gattccccat gtttataagc cagaagttca gcatgttgag ttttcaatca agcaattcgt   2100
tccacgtgga aagaaactac aagaggagta tgccactgag actccagctt tccagaaaaa   2160
gcttacacct gcagagacgc atatgctcgc taagtattac aacaaccccg atgaggaaaa   2220
gttgagagtg tccttaattg cgttccctca cttccagaca ttgccatcca aggtgcacaa   2280
agtaatgcat tcacgtcaaa caggcatgtt aattgacgct atgcagcact tgcaagagcc   2340
aactttttca gaacagagta aaagcttctt cactgagttt cgagctcctt tgggtgaaag   2400
agaagagctt gatacaggtc tgagggttac taatgatcca aaagatctac actctgtccg   2460
tgatttggaa gtcaacacat cacagagaaa ggcaaaacaa gttgaatctc ccacaagcac   2520
cttagagaca acagagaagg attacgaaga atcttcaccc acacaccgtt atcttttcag   2580
ttcagaatgt gcatccgttg atactctggg gaacgtcttc gtaatgccag ttcctctttt   2640
attctttcct aatgttctgg agtcagacaa tacgcctctg cctaaaacag aaaaacaaca   2700
ttcttgccgg aatacatctc acattgactt agttccagta gatacttcgg aaaaacatcg   2760
gcaagataat atctcatgca agttaaagga aagattctcg ccagacggtg ccagcgagac   2820
actagagact catagccttg tgaaaaggaa ctccaccaga gtaggtgaag atgatgtagc   2880
gaattctgtt ggagaaattg tgttatcatc ggatgaagat gactgtgagg gattggagct   2940
```

```
tagtccacgg ctcactaact tcatcaagag cggcattgtt ccagagtcac ctgtctatga   3000

ccaaggggaa gcgaacagag aagaagatct tgaatttcct cagctttctt cacccatgag   3060

gttcagtaac gaattggcag gagagtcttc tttccctgag agaaaggttc agcataagtg   3120

caacgattat aacattgtgt ctacaaccac tgaattgaga actcctcaga aggaggtagg   3180

tttggccaac ggaacagaat gcttggctgt ttctcctatt cctgaggatt ggagaactcc   3240

cttggcgaat ctgacaaaca caaacagcag cgctcgcaaa gattggcggg tgagttctgg   3300

agaaaagtta gaaactcttc gacagcctcg caagttgaag agactacgta gacttggaga   3360

ttgctcgagt gctgtaaagg agaattatcc tggtattaca gaggcagacc atatcagatc   3420

tcgttctcgc ggtaaaaagc acattagagg taagaagaag atgatcatgg atgatgatgt   3480

ccaagtcttc attgacgagg aagctgaggt ctcttcggga gcagagatgt cggctgatga   3540

gaacgaagat gtgactggcg attcatttga agatagtttc atagatgacg gaacaatgcc   3600

tacagcaaat actcaagccg agtctggtaa agttgacatg atggctgttt acaggcgttc   3660

tcttctcagc cagtcaccat taccggcgag atttcgtgat ttagccgcat caagtctgag   3720

tccttattct gctggaccct tgacgagaat aaatgagagc agaagcgact cagataaatc   3780

attgtcttct cttcgaacac caaaaacaac aaactctgag tcaaaccaag atgcaatgat   3840

gataggaaac ctttcggtag tacaaatctc gtcagatagc cggaaaagga aatttagctt   3900

atgcaactcg gcgaatgccc ccgtgattaa cttagaaagc aagtttgcag ctcatgcaca   3960

agccacggag aaggaaagcc atgaaggcgt gagaagcaat gcaggtgcgt tagagtacaa   4020

tgatgatgat gatgatgcat tctttgcgac actagacttt gatgcaatgg aagcacaagc   4080

cacattgtta ttgtcgaaac agagatccga agcaaaagag aaagaagacg caacggttat   4140

acctaatcca ggcatgcaga gaagtgatgg tatggagaaa gatgcaccat cttttgatct   4200

tggtctgtgg tgattcttct ttcatacgaa gatactaagt tatgtatata gattgacaaa   4260

ggagacagta gagcataggc atttggatgt atgttttgtg tattaagttt aggtatatcc   4320

tattgaagta cagtgcttaa ggcagtgcac atggttaaat caaggttaat gcctcaattc   4380

gttgaaccct ttaagtaatg acacaaatat gactacatcg g                       4421
```

<210> SEQ ID NO 98
<211> LENGTH: 1771
<212> TYPE: DNA
<213> ORGANISM: Artificial Sequence
<220> FEATURE:
<223> OTHER INFORMATION: Chimeric DNA encoding a hairpin RNAi (hpRNA) construct targeting a FANCM gene of A. thaliana

<400> SEQUENCE: 98

```
gggtcaggaa catgtcttac taactacttg gtttgcttgg tgatcgacga ggcacatcga     60

gctttaggga attattctta ttgtgttgta gttcgtgagt tgatggcggt accgatacag    120

ctgagaatac tggctcttac tgcaactcct ggatcaaaga cacaggccat ccagggtatc    180

attgataatt tgcagatatc cacacttgaa tatcgaaatg agagtgacca tgatgtttgc    240

ccttatgtcc ccgacagaaa attagaagtc atcgaggttc ccttgggtca agatgcagat    300

gatgtatcga aacgcctgtt tcatgttata cgtccatatg cagtcaggct taaaaacttt    360

ggggttaatc taaatagaga tatacaaact ttaagtccac acgaagtact tatggcaagg    420

gataagtttc gtcaagcacc tctaccaggc cttccccatg taaatcacgg agatgtagaa    480

tcttgctttg cagctcttat caggtaagga aataattatt ttcttttttc cttttagtat    540
```

```
aaaatagtta agtgatgtta attagtatga ttataataat atagttgtta taattgtgaa    600

aaaataattt ataaatatat tgtttacata aacaacatag taatgtaaaa aaatatgaca    660

agtgatgtgt aagacgaaga agataaaagt tgagagtaag tatattattt ttaatgaatt    720

tgatcgaaca tgtaagatga tatactagca ttaatatttg ttttaatcat aatagtaatt    780

ctagctggtt tgatgaatta aatatcaatg ataaaatact atagtaaaaa taagaataaa    840

taaattaaaa taatattttt ttatgattaa tagtttatta tataattaaa tatctatacc    900

attactaaat attttagttt aaaagttaat aaatattttg ttagaaattc caatctgctt    960

gtaatttatc aataaacaaa atattaaata acaagctaaa gtaacaaata atatcaaact   1020

aatagaaaca gtaatctaat gtaacaaaac ataatctaat gctaatataa caaagcgcaa   1080

gatctatcat tttatatagt attattttca atcaacattc ttattaattt ctaaataata   1140

cttgtagttt tattaacttc taaatggatt gactattaat taaatgaatt agtcgaacat   1200

gaataaacaa ggtaacatga tagatcatgt cattgtgtta tcattgatct tacatttgga   1260

ttgattacag ttgataagag ctgcaaagca agattctaca tctccgtgat ttacatgggg   1320

aaggcctggt agaggtgctt gacgaaactt atcccttgcc ataagtactt cgtgtggact   1380

taaagtttgt atatctctat ttagattaac cccaaagttt ttaagcctga ctgcatatgg   1440

acgtataaca tgaaacaggc gtttcgatac atcatctgca tcttgaccca agggaacctc   1500

gatgacttct aatttctgt cggggacata agggcaaaca tcatggtcac tctcatttcg   1560

atattcaagt gtggatatct gcaaattatc aatgataccc tggatggcct gtgtctttga   1620

tccaggagtt gcagtaagag ccagtattct cagctgtatc ggtaccgcca tcaactcacg   1680

aactacaaca caataagaat aattccctaa agctcgatgt gcctcgtcga tcaccaagca   1740

aaccaagtag ttagtaagac atgttcctga c                                  1771
```

<210> SEQ ID NO 99
<211> LENGTH: 1771
<212> TYPE: DNA
<213> ORGANISM: Artificial Sequence
<220> FEATURE:
<223> OTHER INFORMATION: Chimeric DNA encoding a hairpin RNAi (hpRNA) construct with G:U basepairs, targeting a FANCM gene of A. thaliana

<400> SEQUENCE: 99

```
gggttaggaa tatgttttat taattatttg gtttgtttgg tgattgatga ggtatattga     60

gttttaggga attattttta ttgtgttgta gtttgtgagt tgatggtggt attgatatag    120

ttgagaatat tggtttttat tgtaattttt ggattaaaga tataggttat ttagggtatt    180

attgataatt tgtagatatt tatatttgaa tattgaaatg agagtgatta tgatgtttgt    240

ttttatgttt ttgatagaaa attagaagtt attgaggttt ttttgggtta agatgtagat    300

gatgtattga aatgtttgtt ttatgttata tgtttatatg tagttaggtt taaaaatttt    360

ggggttaatt taaatagaga tatataaatt ttaagtttat atgaagtatt tatggtaagg    420

gataagtttt gttaagtatt tttattaggt ttttttttatg taaattatgg agatgtagaa    480

ttttgttttg tagtttttat taggtaagga aataattatt ttctttttttc cttttagtat    540

aaaatagtta agtgatgtta attagtatga ttataataat atagttgtta taattgtgaa    600

aaaataattt ataaatatat tgtttacata aacaacatag taatgtaaaa aaatatgaca    660

agtgatgtgt aagacgaaga agataaaagt tgagagtaag tatattattt ttaatgaatt    720
```

```
tgatcgaaca tgtaagatga tatactagca ttaatatttg ttttaatcat aatagtaatt    780

ctagctggtt tgatgaatta aatatcaatg ataaaatact atagtaaaaa taagaataaa    840

taaattaaaa taatattttt ttatgattaa tagtttatta tataattaaa tatctatacc    900

attactaaat attttagttt aaaagttaat aaatattttg ttagaaattc caatctgctt    960

gtaatttatc aataaacaaa atattaaata acaagctaaa gtaacaaata atatcaaact   1020

aatagaaaca gtaatctaat gtaacaaaac ataatctaat gctaatataa caaagcgcaa   1080

gatctatcat tttatatagt attattttca atcaacattc ttattaattt ctaaataata   1140

cttgtagttt tattaacttc taaatggatt gactattaat taaatgaatt agtcgaacat   1200

gaataaacaa ggtaacatga tagatcatgt cattgtgtta tcattgatct tacatttgga   1260

ttgattacag ttgataagag ctgcaaagca agattctaca tctccgtgat ttacatgggg   1320

aaggcctggt agaggtgctt gacgaaactt atcccttgcc ataagtactt cgtgtggact   1380

taaagtttgt atatctctat ttagattaac cccaaagttt ttaagcctga ctgcatatgg   1440

acgtataaca tgaaacaggc gtttcgatac atcatctgca tcttgaccca agggaacctc   1500

gatgacttct aattttctgt cggggacata agggcaaaca tcatggtcac tctcatttcg   1560

atattcaagt gtggatatct gcaaattatc aatgataccc tggatggcct gtgtctttga   1620

tccaggagtt gcagtaagag ccagtattct cagctgtatc ggtaccgcca tcaactcacg   1680

aactacaaca caataagaat aattccctaa agctcgatgt gcctcgtcga tcaccaagca   1740

aaccaagtag ttagtaagac atgttcctga c                                 1771
```

<210> SEQ ID NO 100
<211> LENGTH: 1259
<212> TYPE: DNA
<213> ORGANISM: Artificial Sequence
<220> FEATURE:
<223> OTHER INFORMATION: Chimeric DNA encoding a ledRNA construct, targeting a FANCM gene of A. thaliana

<400> SEQUENCE: 100

```
gggacataag ggcaaacatc atggtcactc tcatttcgat attcaagtgt ggatatctgc     60

aaattatcaa tgataccctg gatggcctgt gtctttgatc caggagttgc agtaagagcc    120

agtattctca gctgtatcgg taccgccatc aactcacgaa ctacaacaca ataagaataa    180

ttccctaaag ctcgatgtgc ctcgtcgatc accaagcaaa ccaagtagtt agtaagacat    240

gttcctgact gtatatcctt ctctaacact tgtggagtga caaagaaaac ccgtttgctt    300

ttccacaaaa aagctctttt cgaaggacat gtctgacccg tcaagtcaat cgtccattct    360

tgtggtattc caacaatatg tcaggaacat gtcttactaa ctacttggtt tgcttggtga    420

tcgacgaggc acatcgagct ttagggaatt attcttattg tgttgtagtt cgtgagttga    480

tggcggtacc gatacagctg agaatactgg ctcttactgc aactcctgga tcaaagacac    540

aggccatcca gggtatcatt gataatttgc agatatccac acttgaatat cgaaatgaga    600

gtgaccatga tgtttgccct tatgtccccg acagaaaatt agaagtcatc gaggttccct    660

tgggtcaaga tgcagatgat gtatcgaaac gcctgtttca tgttatacgt ccatatgcag    720

tcaggcttaa aaactttggg gttaatctaa atagagatat acaaacttta agtccacacg    780

aagtacttat ggcaagggat aagtttcgtc aagcacctct accaggcctt ccccatgtaa    840

atcacggaga tgtagaatct tgctttgcag ctcttatcat tcgtcatcct aatatcttca    900

ttcttactca tcaacctagc aaatggccct tctttcaatt tctcttctag catctcatac    960
```

gctggtctta ttccatgact agaaaggagc ttacgaatat gataaagagt gataagagct 1020
gcaaagcaag attctacatc tccgtgattt acatggggaa ggcctggtag aggtgcttga 1080
cgaaacttat cccttgccat aagtacttcg tgtggactta aagtttgtat atctctattt 1140
agattaaccc caaagttttt aagcctgact gcatatggac gtataacatg aaacaggcgt 1200
ttcgatacat catctgcatc ttgacccaag ggaacctcga tgacttctaa ttttctgtc 1259

<210> SEQ ID NO 101
<211> LENGTH: 4228
<212> TYPE: DNA
<213> ORGANISM: Brassica napus

<400> SEQUENCE: 101
tccaaaattg gttttgcccg ccaatgtggc ttcggcgagg gtttcttcca caaaacccca 60
ctcaacctaa aatctgattc ggcgagaaac gctgtctact tatctcacgc gaaaagaaag 120
gcgtagatcc accctaaact aaaacagagc atcaagtgaa atgggacccg agtttccgat 180
cgaactcgtt gaagaagaag atggattcga ttgggaagca gcagtcagag aaatcgactt 240
ggcttgcctc aaatccttaa acccttcttc ttcttcttcg acccatttca ccaacggcaa 300
tggcactaaa cctgctaaaa gacaatctac tcttgatcga ttcatcgcaa gagccgacca 360
caagcctcct cctccgtatc ctcctgttgt ttccgacccg agtttcgagt gtggtactaa 420
cgacaacact cccagcgtcg ggattgatcc tgagacagct aaaacttgga tttatccaat 480
gaacgttcct ctaagagatt atcagtttgc tataacgaag actgctttgt tttcaaacac 540
attagttgct ttaccaacag gccttggtaa aacgctcata gctgcagttg taatgtataa 600
ttacttcaga tggtttccac aaggtaaaat tgtctttgcc gcaccttcta ggcctcttgt 660
gatgcagcag attgaggcct gccataatat cgtggggata ccacaagaat ggacgattga 720
cttgacgggt cagacttgcc cttccaaaag agcttccttg tggaaaacca aaagggtttt 780
cttcgtcact ccacaagttc ttgagaagga tatacagtca ggaacgtgtg ttaccaactg 840
cttggtttgc ttggtgatcg acgaggcaca tcgagcttta gggaattatt cttattgtgt 900
tgtagttcgt gagttgatgg cagtaccagt gcagttgaga atattggctc ttactgcaac 960
tcctggatca aagacacagg ccatacaggg tatccttgat aatttgcaga tatcaacact 1020
tgaatatcga aacgagagtg accatgatgt ctgcccttat gtccacgaca gaaaagtaga 1080
actaatcgag gttcccttgg gtaaagatgc agatgaggta tctaaacgcc tattagatgt 1140
tatacgtcca tatgctgtca ggcttaaaaa tttcggggtc attctaagca gggattatca 1200
aactttgagt ccacacgaat tacttatggc aagggataag tttcgtgaag cacctgtacc 1260
aggcattccc catataagtc acggagatgt agaatcttgc tttgcagctc ttatcacgct 1320
ttatcacatt cgcaagcttc tttctagtca tggaataagg ccagcgtatg agatgcttga 1380
agaaaaactt caggaagggc catttgctag gttgatgagt aagaatgaag atattaggat 1440
gacgaagctt ttgatgcagc aaaggttgtc gaacggagca ccaagcccga aattgtccaa 1500
gatgttggag attctagttg atcactacaa aataaaagat ccgaggacat cacgggtcat 1560
tattttctcg aatttcagag gaagcgtaag agacataatg gacgcattaa gtaatattga 1620
agatgttgtc aaagcaactg agtttattgg tcaaagttca ggtaagacac tgaagggaca 1680
gtcgcaaaaa gttcagcaag ctgttctgga gaaatttaga tctggtgggt ttaatgttat 1740
tgttgcaaca tctatcggcg aagaaggctt ggatatcatg gaagtcgact tagttatatg 1800
ttttgatgct aatgtatccc ctctgaggat gatccaacgc atgggaagaa ctggaaggaa 1860

```
aaataatggc cgagttgtag ttcttgcttg tgaaggatct gaaaagaata gctatatgcg   1920
aaagaaagca aatggccaag ccattaaaaa acacatgcgg aatggaggaa tgaatagttt   1980
taattttcat cctagtccaa ggatgattcc ccatgtttat aagccagaag ttcagcatgt   2040
taagttttcg atcgagcaat tcattccacg tggaaagaag ctacaagatg agcctgccac   2100
tgagactcca gctttcaaga aaaagcttac accggaagag atggatatgc tcgccaagta   2160
tttcaaaccc aacgaggaaa agtggagagt ttccttgatt gctttccctc acttccaaac   2220
attgccatcc aaagtgcaca aagtaatgca ttcacgccaa acaagcatat taattgatgc   2280
tatgcagcat ctgcaagaga caactttgac agagcaaagt aaaagtttct tcattaagta   2340
tggagctcct ttggctgaaa gagatgagct tgacgcaggt ctgagggttg gtgatgatcc   2400
gaaaggtaaa tttagtctca atgatttgga tggcaacaca tcacagagaa aggcaaaaca   2460
aattttagaa tctcccacaa gcacattaga gactacagag aaggatttcg aagcatcttc   2520
acccacacac tgttatcttt tcagttcaga atgtgcgtcc gttgatactc tggggaaggt   2580
ctttgtattg ccggttcctc tctcattctc ttctaatgta ccagggtcag actgcgtggg   2640
aagagaaaaa gaactttctt ccccgaataa gtcccacact gacgttgttc cgatagatag   2700
ttcctcaaaa catcggcaag ataatatttc atgcaagtta aagcaaggat tcttgccaga   2760
ttgtgccaac gagactttgg agtcccaaag ccttttgaaa aggcactcca ccgatgtagg   2820
taaaggagat atagagaatt gtgctggaga aattatgata tcatcggatg aagaagacga   2880
ctgtgaggat ttggagctta gtccaaggct cactaacttc atcaagagtg gcgttgttcc   2940
agattcacct gtctatgacc aaggagttgc atacgaagca aacagagaag aagaccttga   3000
tcttccaccc acgagtttaa ctaatgaatt ggcagaagag ccatcgacac ctgagaaaaa   3060
ggttcacatt gcttctacgg ccaatgaatt cagaactcct cagaaggaag aagatttagc   3120
caacgaaaca gaaagcttcg ctgtttctcc aatgcctgag gagtggagaa ctcccttggc   3180
gaatatcacc aacgcaagca gcagcgctag caaagattgg cgcgtgagtt cgggagaaaa   3240
gtcagaaact cttcgacagc ctcgcaagtt gaagagactt cgtagacttg gagattgctc   3300
gagtgctgtg aaggagaata atcctggtat tgcaaagaca gaccatatca gatctcgttc   3360
tcgcagtgta aagaacataa gaggcaagaa gaagatacgc gcggataata atgctagaat   3420
cttcattgaa gcggaagctg aggtgtcttc ggaatcagaa atgtcggttg atgagaacgt   3480
agatttgacc agcgattcat ttgaagatag cttcatagat gacggtacaa tgcctacagc   3540
aaatactcaa gccgagtgtg ctaaagttga catgatggcc gtttacagac gttctctact   3600
cagccaatca ccattaccgg caagatttcg tgatgtagct gcatcaagtc cgagtcctta   3660
ttcttctggt ctcttgaaga caataaatga gagcagaagc gactcagata aatcattgtc   3720
ttctcttaga accccacaaa caacgaacaa cgagtcaaac aaggatgcag tggccacagg   3780
agactttttg gtagcacaaa tctcaacaga cagccggaaa aggaaattca gcttatgcaa   3840
ctcagcgaat gtcccagtga ttaacttgga aaacaagttt gaagctcatg cacaagccac   3900
ggagaaggaa agccatgaag gtccgagaag caatgcaggt gcatcacagt acaaggatga   3960
ggatgaagat gatgatgcat tctacgcgac actggacttt gatgccatgg aagcgcatgc   4020
gacattgcta ttgtcgaaac aaaggtcaga aacgaaaaca aaagaagatg catcggtgaa   4080
acctcatttg ggcaatcaga ggaatgatgg tttgccgaag gatgggccat cttttgatct   4140
tggtttgtgg tgattattct cctattaagt taaagtgtat aaaggttgac atttggatgt   4200
```

atgttttgtg tatttagttt gtgtcata 4228

<210> SEQ ID NO 102
<211> LENGTH: 1769
<212> TYPE: DNA
<213> ORGANISM: Artificial Sequence
<220> FEATURE:
<223> OTHER INFORMATION: Chimeric DNA encoding a hairpin RNAi (hpRNA) construct targeting a FANCM gene of B. napus

<400> SEQUENCE: 102
gggagaaatt atgatatcat cggatgaaga agacgactgt gtggatttgg agcttagtcc 60
aaggctcact aacttcatca agagtggcgt tgttccagat tcacctgtct atgaccaagt 120
tgcatacgaa gcaaacagtg aagaagacct tgatcttcca cacacgagtt taactaatga 180
attggcagaa gagccatcga cacctgagaa aaaggttcac attgcttcta cggccaatga 240
attcagaacc ccaacgaagg aagaagattt agccaacgaa acagaaagct tcgctgtttc 300
tccaatgcct gaggagtgga gaactccctt ggcgaatatc accaacgcaa gcagcagcgc 360
tagcaaagat tggcgcgtga gttcgggaga aaagtcagaa actcttcgac agcctcgcaa 420
gttgaagaga cttcgtagac ttggagattg ctcgagtgct gtgaaggaga ataatcctgg 480
tattgcaaag acagaccata tcgtaaggaa ataattattt tctttttttcc ttttagtata 540 aaatagttaa gtgatgttaa ttagtatgat tataataata tagttgttat aattgtgaaa 600
aaataattta taaatatatt gtttacataa acaacatagt aatgtaaaaa aatatgacaa 660
gtgatgtgta agacgaagaa gataaaagtt gagagtaagt atattatttt taatgaattt 720
gatcgaacat gtaagatgat atactagcat taatatttgt tttaatcata atagtaattc 780
tagctggttt gatgaattaa atatcaatga taaaatacta tagtaaaaat aagaataaat 840
aaattaaaat aatatttttt tatgattaat agtttattat ataattaaat atctatacca 900
ttactaaata ttttagttta aaagttaata aatattttgt tagaaattcc aatctgcttg 960
taatttatca ataaacaaaa tattaaataa caagctaaag taacaaataa tatcaaacta 1020
atagaaacag taatctaatg taacaaaaca taatctaatg ctaatataac aaagcgcaag 1080
atctatcatt ttatatagta ttattttcaa tcaacattct tattaatttc taaataatac 1140
ttgtagtttt attaacttct aaatggattg actattaatt aaatgaatta gtcgaacatg 1200
aataaacaag gtaacatgat agatcatgtc attgtgttat cattgatctt acatttggat 1260
tgattacagg atatggtctg tctttgcaat accaggatta ttctccttca cagcactcga 1320
gcaatctcca agtctacgaa gtctcttcaa cttgcgaggc tgtcgaagag tttctgactt 1380
ttctcccgaa ctcacgcgcc aatctttgct agcgctgctg cttgcgttgg tgatattcgc 1440
caagggagtt ctccactcct caggcattgg agaaacagcg aagctttctg tttcgttggc 1500
taaatcttct tccttcgttg gggttctgaa ttcattggcc gtagaagcaa tgtgaacctt 1560
tttctcaggt gtcgatggct cttctgccaa ttcattagtt aaactcgtgt gtggaagatc 1620
aaggtcttct tctctgtttg cttcgtatgc aacttggtca tagacaggtg aatctggaac 1680
aacgccactc ttgatgaagt tagtgagcct tggactaagc tccaaatcct cacagtcgtc 1740
ttcttcatcc gatgatatca taatttctc 1769

<210> SEQ ID NO 103
<211> LENGTH: 1769
<212> TYPE: DNA
<213> ORGANISM: Artificial Sequence
<220> FEATURE:

<223> OTHER INFORMATION: Chimeric DNA encoding a hairpin RNAi (hpRNA)
construct with G:U basepairs, targeting a FANCM gene of B. napus

<400> SEQUENCE: 103
gggagaaatt atgatattat tggatgaaga agatgattgt gtggatttgg agtttagttt 60
aaggtttatt aattttatta agagtggtgt tgttttagat ttatttgttt atgattaagt 120
tgtatatgaa gtaaatagtg aagaagattt tgatttttta tatatgagtt taattaatga 180
attggtagaa gagttattga tatttgagaa aaaggtttat attgttttta tggttaatga 240
atttagaatt ttaatgaagg aagaagattt agttaatgaa atagaaagtt ttgttgtttt 300
tttaatgttt gaggagtgga gaattttttt ggtgaatatt attaatgtaa gtagtagtgt 360
tagtaaagat tggtgtgtga gtttgggaga aaagttagaa attttttgat agttttgtaa 420
gttgaagaga ttttgtagat ttggagattg tttgagtgtt gtgaaggaga ataattttgg 480
tattgtaaag atagattata ttgtaaggaa ataattattt tctttttttcc ttttagtata 540 aaatagttaa gtgatgttaa ttagtatgat tataataata tagttgttat aattgtgaaa 600
aaataattta taaatatatt gtttacataa acaacatagt aatgtaaaaa aatatgacaa 660
gtgatgtgta agacgaagaa gataaaagtt gagagtaagt atattatttt taatgaattt 720
gatcgaacat gtaagatgat atactagcat taatatttgt tttaatcata atagtaattc 780
tagctggttt gatgaattaa atatcaatga taaaatacta tagtaaaaat aagaataaat 840
aaattaaaat aatatttttt tatgattaat agtttattat ataattaaat atctatacca 900
ttactaaata ttttagttta aaagttaata aatattttgt tagaaattcc aatctgcttg 960
taatttatca ataaacaaaa tattaaataa caagctaaag taacaaataa tatcaaacta 1020
atagaaacag taatctaatg taacaaaaca taatctaatg ctaatataac aaagcgcaag 1080
atctatcatt ttatatagta ttattttcaa tcaacattct tattaatttc taaataatac 1140
ttgtagtttt attaacttct aaatggattg actattaatt aaatgaatta gtcgaacatg 1200
aataaacaag gtaacatgat agatcatgtc attgtgttat cattgatctt acatttggat 1260
tgattacagg atatggtctg tctttgcaat accaggatta ttctccttca cagcactcga 1320
gcaatctcca agtctacgaa gtctcttcaa cttgcgaggc tgtcgaagag tttctgactt 1380
ttctcccgaa ctcacgcgcc aatctttgct agcgctgctg cttgcgttgg tgatattcgc 1440
caagggagtt ctccactcct caggcattgg agaaacagcg aagctttctg tttcgttggc 1500
taaatcttct tccttcgttg gggttctgaa ttcattggcc gtagaagcaa tgtgaacctt 1560
tttctcaggt gtcgatggct cttctgccaa ttcattagtt aaactcgtgt gtggaagatc 1620
aaggtcttct tctctgtttg cttcgtatgc aacttggtca tagacaggtg aatctggaac 1680
aacgccactc ttgatgaagt tagtgagcct tggactaagc tccaaatcct cacagtcgtc 1740
ttcttcatcc gatgatatca taatttctc 1769

<210> SEQ ID NO 104
<211> LENGTH: 1259
<212> TYPE: DNA
<213> ORGANISM: Artificial Sequence
<220> FEATURE:
<223> OTHER INFORMATION: Chimeric DNA encoding a ledRNA construct,
targeting a FANCM gene of B. napus

<400> SEQUENCE: 104
gggttctgaa ttcattggcc gtagaagcaa tgtgaacctt tttctcaggt gtcgatggct 60
cttctgccaa ttcattagtt aaactcgtgt gtggaagatc aaggtcttct tctctgtttg 120
cttcgtatgc aacttggtca tagacaggtg aatctggaac aacgccactc ttgatgaagt 180
tagtgagcct tggactaagc tccaaatcct cacagtcgtc ttcttcatcc gatgatatca 240
taatttctcc agcacaattc tctatatctc ctttacctac atcggtggag tgccttttca 300
aaaggctttg ggactccaaa gtctcgttgg cacaatctgg caagaatcct tgctttaact 360
tgcatgaaat attatcttgg agaaattatg atatcatcgg atgaagaaga cgactgtgtg 420
gatttggagc ttagtccaag gctcactaac ttcatcaaga gtggcgttgt tccagattca 480
cctgtctatg accaagttgc atacgaagca aacagtgaag aagaccttga tcttccacac 540
acgagtttaa ctaatgaatt ggcagaagag ccatcgacac ctgagaaaaa ggttcacatt 600
gcttctacgg ccaatgaatt cagaacccca acgaaggaag aagatttagc caacgaaaca 660
gaaagcttcg ctgtttctcc aatgcctgag gagtggagaa ctcccttggc gaatatcacc 720
aacgcaagca gcagcgctag caaagattgg cgcgtgagtt cgggagaaaa gtcagaaact 780
cttcgacagc ctcgcaagtt gaagagactt cgtagacttg gagattgctc gagtgctgtg 840
aaggagaata atcctggtat tgcaaagaca gaccatatcc agcttccgct tcaatgaaga 900
ttctagcatt attatccgcg cgtatcttct tcttgccttg aacacagagc aaaaggaaat 960
acagaatcat tttacctctt atgttcttta cactgcgaga acgagatctg atatggtctg 1020
tctttgcaat accaggatta ttctccttca cagcactcga gcaatctcca agtctacgaa 1080
gtctcttcaa cttgcgaggc tgtcgaagag tttctgactt ttctcccgaa ctcacgcgcc 1140
aatctttgct agcgctgctg cttgcgttgg tgatattcgc caagggagtt ctccactcct 1200
caggcattgg agaaacagcg aagctttctg tttcgttggc taaatcttct tccttcgtt 1259

<210> SEQ ID NO 105
<211> LENGTH: 7074
<212> TYPE: DNA
<213> ORGANISM: Nicotiana benthamiana

<400> SEQUENCE: 105
atgcgagctg tttttgaaac aaagcgtgat cgtgaaatct tggtccttgc tagtaaagtt 60
ctgggtcacc tagctagatc tggcggtgca atgactgcag atgaagtgga acgtcagata 120
aaagttgcac taggatggct tcgtggtgaa agaattgagt atcgtttctt tgctgctgtc 180
ttaatattga aggaaatggc ggaaaatgct tcaactgttt tcaatgttca tgtgccggac 240
tttgtggagg ttgtttgggt tgctctgaag gatccaacat tggctgttcg agagaaggct 300
gttgaggcat tgcgtgcctg ccttcgcgtt attgaaaagc gcgagacacg atggcgtgtt 360
cagtggtatt ataagatgtt tgaggctacc caagatggat tgaccagaac tgcgcctgtt 420
catagtatac atggctccct tctcgcagtg ggagagctgc taaggaatac aggagagttc 480
atgatgtcaa gatacaggga ggttgcagaa attgttataa gatacttgga gcaccgagat 540
cgcctagttc ggctcagcat aacttctcta cttcctcgaa ttgctcattt cctgcgtgat 600
cgatttgtga ctaactactt aacgatatgc atgaatcata tacttcatgt ccttaaaata 660
cctgcagaac gtgccagtgg gttcattgct cttggggaga tggctggtgc tctggatggt 720
gaactcatta actatttgcc gacaataacc tctcacttgc gtgatgcgat tgctccccgt 780
agaggcaggc cctcatttga ggctctggca tgtgttggaa atattgctaa agcaatggga 840
cctgcaatgg agcctcatgt tcgtggtctc ttggatgcta tgttttctgc tgggctttcc 900
ctgacactag tggaagcctt ggagcaaata actgaaagca ttccatcttt gttgccgacc 960

-continued

```
attcaagatc ggcttcttga atgtatttca gcaattctct ccagatctaa tcatgcactc   1020
tcaagacaat caactgctat gagtcgagga catattgcaa cagttacccc ccaagtacca   1080
gaactgagtg gtcctgcact agttcaactt gctttgcaga ctcttgctcg ttttaatttc   1140
aagggccatg atcttcttga gtttgcaagg gagtctgttg ttgtgtattt agaagatgag   1200
gatggagcta cacgaaaaga tgctgcgcta tgttgctgca aactagtagc aaattctttc   1260
ttggcgatat cttctaccca gtttagtcct agtagaatca atcgtgccag tggaaagcga   1320
cgtcgacttg ttgaagagat tgtgcaaaaa cttctcatcg ctgctgttgc cgacgctgat   1380
gttactgttc ggcattcaat tttttcttct ctgtatgctg atggaggatt cgatgagttt   1440
ctagctcagg ctgatagttt gacagctata tttgccactt taaatgatga ggattttgaa   1500
gttcgtgact atgcaatttc actagctggt agactatctg aaaagaatcc agcatatgtt   1560
cttccagcac ttcgtcgcca tcttattcag ctgttaactt acctagagca aagtgcagat   1620
aataaatgta aagaagagag tgcaaagtta ttgggttgct tgattcgcaa ttgtgaacga   1680
ttagttcttc catacattgc tcccatacac aaggctcttg ttgcgaaact ctgtgaaggc   1740
acaggagtca atgcgaatag tggcattatt agtggagttc tagtgactgt tggagatctt   1800
gccagagtgg gtggctttgc catgcggcag tatatttcag aacttatgcc attaatcgtt   1860
gaagctctac tggatggggc agctgccacc aaacgtgaag tggccgtttc aacacttggt   1920
caagttgtac agagtacagg atatgtcata actccataca atgagtatcc tcagttgctt   1980
ggtttactct tgaaactgct caatggtgaa ctggcttggt caaccagaag agaggttttg   2040
aaggttctcg gcatcatggg tgcattagat ccccatgtgc acaagcgcaa tcagcaaagc   2100
ttacccggat cccatggtga agttacccgg gtgactggtg atcctggtca acatatcaga   2160
tcaatggatg aattgcctat ggatctttgg ccctcctttg caacatctga agattattat   2220
tccactgttg ctatcaactc actcatgcgg atactcaggg atccatctct gtcaagttac   2280
caccagaaag tggttggatc tcttatgttt attttcaagt ccatgggcct tggctgtgtc   2340
ccttatttgc ctaaggtttt gcctgatctc tttcacattg tacgaacatg tgaggatggt   2400
ctaaaagaat ttataacatg gaagcttgga accttggtat ctattgtccg ccagcacatc   2460
cgtaagtatc tgccagagtt actctctctg atatcagaaa tatggtcatc tttcagcttg   2520
cctgttgcta acagacctgt tcacattgct cctattttgc atctcgtgga gcaactttgc   2580
ttggctctca acgatgaatt tagaaagtac cttgctgata tacttccctg ctgtattcaa   2640
gttcttactg atgcagagag gtttagtgac tacacatacg ttattcctat tctccacaca   2700
cttgaagttt ttggtgggac attagatgag catatgcatc tgcttcttcc tgcacttatt   2760
cggttgttta aattggatgc ttcagtagaa gtaagacgcg gtgcaatcaa aactctcaca   2820
agattgatac ctcgtgtgca ggtcactgga cacatatctt ctcttgtgca tcacttgaag   2880
cttgtcttgg acgggaacaa agaagagctc aggaaggatg ctgttgatgc actttgttgt   2940
ctagctcatg ctcttggaga ggacttcacc atttttattc attctattca caagcttatg   3000
gttaaacata ggctgcagca caaggaattt gaagaaatcc gaggacgact ggaaaaacgt   3060
gagccactga ttttggggag caccgcagct cagagattaa atcggcggtt cccagttgag   3120
gtcatcagtg atcctttgag tgatggagag aatgagcact acgaggttgg gacggacatg   3180
cataagcagc ttaaaagcca tcaggttaat gatggtagat tgcgtaccgc tggtgaggct   3240
tctcaacgaa gcactaaaga ggattgggca gagtggatga ggcatttcag cattgaactt   3300
ctgaaagaat cacctagtcc agcattgcga acttgtgcaa gactcgctca actgcagcct   3360
```

```
tttgttgggc gagagttgtt tgctgcaggt tttgttagct gctggtcaca acttaatgag   3420
gctagtcaaa ggcagctagt acgtagtcta gaaatggcat tttcgtctcc aaatatccct   3480
cctgaaattc ttgctacact tctgaacttg gcggagttta tggaacacga tgagagaccc   3540
cttcctattg atatccgtct gcttggtgct cttgcggaga agtgtcgagc atttgcaaag   3600
gccctacact acaaggaaat ggaatttgaa ggcgcacttt caaataggag ggatgcaaat   3660
cctgttgctg tagttgaagc tctaatccat ataaataatc aattacatca acatgaggca   3720
gctgttggaa tattaacata tgctcagcag catttggggg ttcaattgaa ggagtcatgg   3780
tacgagaaat tgcaacgctg ggatgatgct cttaaagcat acactgctaa ggcgtcacaa   3840
gcttcgagtc cacatcttgc tttggatgct actttagggc gtatgcgatg ccttgctgct   3900
ctagctcggt gggaggagct taacaatctt tgtaaggaat actggacacc agctgagcca   3960
gcagctcgac tggaaatggc accaatggct gctagtgcgg cctggaacat gggtgagtgg   4020
gatcagatgg cagagtatgt ttctcggctt gatgatggtg atgaaaccaa actgcgagtc   4080
ttgggaaata ccgctgccag tggcgatgga agtagtaatg gcaccttttt cagggctgtt   4140
cttctagttc ggcgagggaa gtacgatgaa gcacgtgaat atgttgaaag agcaaggaaa   4200
tgtttggcga ccgagctcgc tgcactggtt cttgagagct atgaacgtgc ttacagcaac   4260
atggtccgtg ttcagcagct ttctgaatta gaagaggtga ttgaatactg tactcttcct   4320
atgggaaacc ctgttgctga aggaagaaga gctcttgttc gcaatatgtg gaatgagcgc   4380
ataaagggta caaaaagaaa tgttgaggtt tggcaagtac ttttagctgt gagggcactt   4440
gtattgcctc ctacagaaga cattgaaaca tggatcaaat ttgcatcact ttgccggaag   4500
aatggcagaa ttagccaagc tagatctaca ttggttaaac ttttacagtt cgatccagaa   4560
tcaactcctg caactgtgcg gtatcatggt ccccctcagg tgatgctagc atacttaaag   4620
taccaatggt cacttggcga ggatcataag cgaaaggaag cctttgctag gttgcaggac   4680
cttgccatgg acctctcaag aacagcagct cttcaaccag tattgcagaa tggattagtt   4740
gcttcttctg gtgtgccact tgttgctcgt gtatatctca gactcggcac ttggaagtgg   4800
gcactttctc ctggtttgga tgatgattct attcaagaaa ttcttagtgc atttacaaat   4860
gctactcact gtgcaacgaa gtggggaaag gcatggcata cctgggcact tttcaatacc   4920
gcagtgatgt ctcattacac tctgagaggt tttgcgaata ttgcttcaca gtttgttgtt   4980
gctgccgtaa ctggttattt tcactctata gcatgcggag cacatgctaa gggtgttgat   5040
gatagtttac aggatattct tcgtcttctt actttgtggt tcaaccatgg agctacttcg   5100
gatgtccaaa tggcattgca gaaaggattc actcatgtta acatcaacac atggttggtt   5160
gttttacctc agattattgc acggatacat tcaaataacc atgctgtcag agaactgata   5220
caatccttgc tagtgcgaat tggacagagt catccacagg ctcttatgta tccgcttctt   5280
gtggcatgta agtcaattag caatttgcgc agagctgcgg ctcaagaagt ggttgataaa   5340
gttagacagc acagcggcgt actcgttgat caggcccaac ttgtctcaaa ggagcttatc   5400
agggttgcaa tactgtggca tgaaatgtgg catgaggcac tggaagaggc cagccgttta   5460
tattttggcg aacacaacat tgagggcatg ctgaaggtgt tagagcctct gcatgaaatg   5520
cttgaggaag gagcgatgag gaacaatacc actataaagg agaaagcatt catccaggca   5580
taccgtcttg agttgttgga ggcgtatgaa tgttgtatga agtatcggag aactggtaaa   5640
gatgctgaat taacgcaggc ttgggatctc tattatcatg tattcaggcg gatagataag   5700
```

cagcttcaaa cactcacaac cctggatttg cagtctgttt cccccgagtt actggagtgt 5760
cgaaatttgg agctagctgt tcctggaact tatatagcag atgcaccagt ggtgacaatt 5820
gcatcatttg caccccaact tgttgtaatt acatccaaac aacggcctcg aaaattgaca 5880
atccatggga gtgatggaga agactatgct tttttgctca aagggcacga agatctacgc 5940
caagatgaac gtgtcatgca gttgtttggt ctggttaata ctttgctcga gaattcaaga 6000
aagactgcag agaaagattt atcaattcaa cgatatgctg tcattccatt gtcccctaat 6060
agtggactga taggatgggt tccaaattgc gacaccttgc accagcttat tcgagaatat 6120
agggatgccc ggaagatcac cctaaatcaa gagcataaat tgatgctgag ttttgcaccg 6180
gattatgata atttgccact tattgctaag gtggaggtgt ttgaatatgc tttgcaaaat 6240
acagaaggga atgacttatc aagggttctt tggttaaaga gtcgtacttc tgaagtctgg 6300
ctggacagaa gaacaaatta tacaagaagt ttggctgtca tgagtatggt tggataccta 6360
cttggtctgg gtgatcgaca tcctagtaac ctcatgcttc accgatacag tgggaagatt 6420
ctgcatattg actttggaga ttgctttgaa gcttcaatga atcgggagaa gtttccagag 6480
aaggttccct ttcgactcac tagaatgctt gtaaaagcaa tggaggttag tggtatagag 6540
ggaaatttcc ggtcaacatg tgagaatgta atgcaagttc tccgactgca taaagatagt 6600
gttatggcta tgatggaggc ctttgttcac gatccactta taaattggcg tcttttcaac 6660
ttcaatgaag ttccgcaaat gtccgcactt gccagtgcac atgtccctcc tgttgtgaac 6720
agtgaggaat cttcttcaaa tagagagctt cttcagccac aaaggggtgc aagggagaga 6780
gaactgcttc aggcggtcaa tcaattaggt gatgccaatg aggttctaaa tgaacgtgct 6840
gtggctgtta tggctcgaat gagtaataaa ctcacaggac gtgattttgc tgctacttct 6900
acatctgcga gctctctaca acatgcactg gaccacagta cgttaatttc tggagagacg 6960
cgtgaagctg atcatggttt atcagtgaaa ctacaagtcc aaaaacttat tcaacaagcg 7020
tcgtctcatg aaaatctttg ccaaaattat gttgggtggt gtccattttg gtag 7074

<210> SEQ ID NO 106
<211> LENGTH: 1513
<212> TYPE: DNA
<213> ORGANISM: Artificial Sequence
<220> FEATURE:
<223> OTHER INFORMATION: Chimeric DNA encoding a ledRNA construct targeting a TOR gene of N. benthamiana

<400> SEQUENCE: 106
tgaatttagg tgacactata gaacaaagaa gagctcagga aggatgctgt tgatgcactt 60
tgttgtctag ctcatgctct tggagaggac ttcaccattt ttattcattc tattcacaag 120
cttatggtta aacataggct gcagcacaag gaatttgaag aaatccgagg acgactggaa 180
aaacgtgagc cactgatttt ggggagcacc gcagctcaga gattaaatcg gcggttccca 240
gttgaggtca tcagtgatcc tttgagtgat ggagagaatg agcactacga ggttgggacg 300
gacatgcata agcagcttaa aagccatcag gttaatgatg gtagattgcg taccgctggt 360
gaggcttctc aacgaagcac taaagaggat tgggcagagt ggatgaggca tttcagcatt 420
gaacttctga aagaatcacc tagtccagca ttgcgaactt ttaagctgct tatgcatgtc 480
cgtcccaacc tcgtagtgct cattctctcc atcactcaaa ggatcactga tgacctcaac 540
tgggaaccgc cgatttaatc tctgagctgc ggtgctcccc aaaatcagtg gctcacgttt 600
ttccagtcgt cctcggattt cttcaaattc cttgtgctgc agcctatgtt taaccataag 660
cttgtgaata gaatgaataa aaatggtgaa gtcctctcca agagcatgag ctagacaaca 720
aagtgcatca acagcatcct tcctgagctc ttctttgttc ccgtccaaga caagcttcaa 780
gtgatgcaca agagaagata tgtgtccagt gacctgcaca cgaggtatca atcttgtgag 840
agttttgatt gcaccgcgtc ttacttctac tgaagcatcc aatttaaaca accgaataag 900
tgcaggaaga agcagatgca tatgctcatc taatgtccca ccaaaaactt caagtgtgtg 960
gagaatagga ataacgtatg tgtagtcact aaacctctct gcatcagtaa gaacttgaat 1020
acagcaggga agtatatcag caaggtactt tctaaattca cacatccgta agtatctgcc 1080
agagttactc tctctgatat cagaaatatg gtcatctttc agcttgcctg ttgctaacag 1140
acctgttcac attgctccta ttttgcatct cgtggagcaa ctttgcttgg ctctcaacga 1200
tgaatttaga aagtaccttg ctgatatact tccctgctgt attcaagttc ttactgatgc 1260
agagaggttt agtgactaca catacgttat tcctattctc cacacacttg aagtttttgg 1320
tgggacatta gatgagcata tgcatctgct tcttcctgca cttattcggt tgtttaaatt 1380
ggatgcttca gtagaagtaa gacgcggtgc aatcaaaact ctcacaagat tgatacctcg 1440
tgtgcaggtc actggacaca tatcttctct tgtgcatcac ttgaagcttg tcttggacgg 1500
cccgggactc gaa 1513

<210> SEQ ID NO 107
<211> LENGTH: 1941
<212> TYPE: DNA
<213> ORGANISM: Hordeum vulgare

<400> SEQUENCE: 107
atggccgcag ccacctccgc cgccgtcgca ttctcgggcg ccgccgccgc cgccgcggcc 60
ttacccaagc ccgccctcca tcctctcccg cgccaccagc ccgcctcgcg ccgcgcgctc 120
cccgcccgcg tcgtcaggtg ctgcgccgcg tcccccgccg ccaccacggc cgcgcctccc 180
cccacctctc tccggccgtg gggccctcc gagccccgca agggcgccga catcctcgtc 240
gaggcgctcg agcgctgcgg catcgtcgac gtcttcgcct accccggcgg cgcgtccatg 300
gagatccacc aggcgctcac gcgctcgccc gtcatcacca accacctctt ccgccacgag 360
cagggggagg cgttcgcagc gtccgggtac gcacgcgcgt ccggccgcgt cggcgtctgc 420
gtcgccacct ccggccccgg ggccaccaac ctcgtctccg cgctcgccga cgctctcctc 480
gactccatcc ccatggtcgc catcacgggc caggtcccac gccgcatgat cggcacggac 540
gcgttccagg agacgcccat agtggaggtc acgcgctcca tcaccaagca caactacctg 600
gtccttgacg tggaggacat cccccgcgtc atccaggaag ccttcttcct cgcgtcctct 660
ggccgcccgg ggcctgtgct ggttgatatc ccccaaggaca tccagcagca gatggccgtg 720
cctgtttggg acacgccgat gagtttgcca gggtacatcg cccgcctgcc caagccacca 780
tctactgaat cgcttgagca ggtcctgcgc ctggttggcg aggcacggcg cccgattctg 840
tatgttggtg gcggctgcgc tgcatctggc gaggagttgc gccgctttgt tgagctcact 900
ggaattccag ttacaactac tctgatgggc cttggcaact tccccagtga cgacccactg 960
tcactgcgca tgcttgggat gcatggtacc gtgtatgcaa attatgcagt agataaggct 1020
gacctgttgc ttgcatttgg tgtgcggttt gatgatcgcg tgactgggaa aattgaggct 1080
tttgcaagca ggtccaagat tgtgcacatt gacattgatc cagctgagat tggcaagaac 1140
aagcagccac atgtctccat ttgtgcagat gttaagcttg ctttacaggg gttgaatggt 1200
ctattaagtg gcagcaaagc acaacagggt ctagattttg gtccatggca caaggagttg 1260

```
gatcagcaga agagggagtt tcctctagga tacaagactt ttggtgaggc aatcccaccg   1320

cagtatgcta tccaggtact ggatgagctg acaaaagggg aggcgattat tgccacaggt   1380

gttgggcagc atcagatgtg ggcggctcag tattacactt acaagcggcc acgtcagtgg   1440

ctgtcttcgt ctggtttggg ggcaatggga tttgggttgc cagctgcagc tggcgcttct   1500

gtggccaacc caggtgtcac agttgttgac attgatgggg atggtagttt cctcatgaac   1560

attcaggagt tggcgttgat ccgtattgag aacctcccag tgaaggtgat gatattgaac   1620

aaccagcacc tgggaatggt ggtgcagtgg gaggataggt tttacaaggc caaccgggcg   1680

cacacatacc ttggcaaccc agaaaatgag agtgagatat atccagattt tgtgacgatt   1740

gctaaaggat tcaacgttcc ggcagttcgt gtgacaaaga agagtgaagt cagtgcagct   1800

atcaagaaga tgcttgagac cccagggccg tacctgctgg atatcattgt cccgcatcag   1860

gagcacgtgc tgcctatgat cccaagcggt ggtgctttca aggacatgat catggagggt   1920

gatggcagga cctcgtatta a                                              1941
```

```
<210> SEQ ID NO 108
<211> LENGTH: 1505
<212> TYPE: DNA
<213> ORGANISM: Artificial Sequence
<220> FEATURE:
<223> OTHER INFORMATION: Chimeric DNA encoding a ledRNA targeting the
      ALS gene of barley (H. vulgare)

<400> SEQUENCE: 108

agatttaggt gacactatag aatggtggtg cagtgggagg ataggtttta caaggccaac     60

cgggcgcaca catacttgg caacccagaa aatgagagtg agatatatcc agattttgtg    120

acgattgcta aaggattcaa cgttccggca gttcgtgtga caaagaagag tgaagtcagt    180

gcagctatca agaagatgct tgagacccca gggccgtacc tgctggatat cattgtcccg    240

catcaggagc acgtgctgcc tatgatccca aacggtggtg ctttcaagga catgatcatg    300

gagggtgatg gcaggacctc gtattaatct gaatttcgac ctacaagacc tacaagtgtg    360

acatgcgcaa tcagcatgat gcctgcgtgt tgtatcaact actaggggtt cgactgtgaa    420

ccatgcgttt ttctagttta cttgtttcat tcatataaga ggtcctgcca tcaccctcca    480

tgatcatgtc cttgaaagca ccaccgtttg ggatcatagg cagcacgtgc tcctgatgcg    540

ggacaatgat atccagcagg tacggccctg gggtctcaag catcttcttg atagctgcac    600

tgacttcact cttctttgtc acacgaactg ccggaacgtt gaatccttta gcaatcgtca    660

caaaatctgg atatatctca ctctcatttt ctgggttgcc aaggtatgtg tgcgcccggt    720

tggccttgta aaacctatcc tcccactgca ccaccattcc caggtgctgg ttgttcaata    780

tcatcacctt cactgggagg ttctcaatac ggatcaacgc caactcctga atgttcatga    840

ggaaactacc atccccatca atgtcaacaa ctgtgacacc tgggttggcc acagaagcgc    900

cagctgcagc tggcaaccca aatcccattg cccccaaacc agacgaagac agccactgac    960

gtggccgctt gtaagtgtaa tactgagccg cccacatctg atgctgccca acacctgtgg   1020

caataatcgc ctcccctttt gtcagctcat ccagtacctg aatggtctat taagtggcag   1080

caaagcacaa cagggtctag attttggtcc atggcacaag gagttggatc agcagaagag   1140

ggagtttcct ctaggataca agacttttgg tgaggcaatc ccaccgcagt atgctatcca   1200

ggtactggat gagctgacaa aaggggaggc gattattgcc acaggtgttg ggcagcatca   1260

gatgtgggcg gctcagtatt acacttacaa gcggccacgt cagtggctgt cttcgtctgg   1320
```

tttgggggca atgggatttg ggttgccagc tgcagctggc gcttctgtgg ccaacccagg 1380
tgtcacagtt gttgacattg atggggatgg tagtttcctc atgaacattc aggagttggc 1440
gttgatccgt attgagaacc tcccagtgaa ggtgatgata ttgaacaacc agcacctggc 1500
ccggg 1505

<210> SEQ ID NO 109
<211> LENGTH: 1824
<212> TYPE: DNA
<213> ORGANISM: Hordeum vulgare

<400> SEQUENCE: 109
atgcagactc tgtcggcgca gcccctcgcc tcctcctctt cgatacagcg ccaccatggg 60
cgccgacgcg gccccggctc cgtccggttc gctccccgcg cggccgccgc ggctgccgcc 120
acgtccacca gcacggcccg ctcgccggcg tacgtctcgt cgccgtccac gaggaaggtg 180
cccgggtacg agcagtcgtc gccgcctgcc attgcctcgc cgcagaagca ggggagcagc 240
ggcggcgagg gcgagcagag cctcaacttc ttccagcgcg cggcggccgc ggcgctcgac 300
gcgttcgagg aggggttcat caacaatgtc ctggagcggc cccacgcgct gccgcgcacg 360
gccgacccgg ccgtgcagat cgccggcaac ttcgcccccg tcggcgagca gccccccgtg 420
cgcgccctca cggtctccgg ccgcatcccg cccttcatca acggcgtcta cgcccgcaac 480
ggcgccaacc cctgcttcga gcccacggcc ggccaccacc tcttcgacgg cgacggcatg 540
gtccacgcca tccgcatccg aaacggcgcc gccgagtcct acgcctgccg cttcaccgag 600
accgcccgcc tctcccagga gcgcgccgcg gggaggcccg tcttccctaa gaccatcggc 660
gagctccacg gccactctgg catcgcgagg ctggccctct tctacgcgcg cggcgcctgc 720
ggcctcgtcg acccgtccca cggcactggt gttgccaacg ccggcctcgt ctacttcaac 780
ggccgcctcc tcgccatgtc cgaggacgac ctcccgtacc aggtccgcgt caccgccggt 840
ggcgacctcg agaccgtcgg ccgctacgac ttcgacggcc agctcgactg cgccatgatc 900
gcgcacccca agctcgaccc tgtctccggc gagctcttcg cgctcagcta cgatgtcatc 960
aagaagccgt acctcaagta cttctacttc cacgccgacg gcaccaagtc cgccgacgtc 1020
gagatcgagc tcgaccagcc caccatgatc cacgacttcg ccatcaccga gaacttcgtc 1080
gtcgtgcccg accaccagat ggtgttcaag ctcgccgaga tgttccgcgg cggctcgccg 1140
gtgatgctcg acaaggagaa gacctcccgc ttcggcgtcc tcccaaagta cgccaaggac 1200
tcgtcggaga tgatgtgggt ggacgtgccg gactgcttct gtttccacct ctggaactcg 1260
tgggaggagc cggagacgga cgaggtggtg gtgatcggct cctgcacgac cccgcagac 1320 tccatcttca acgacacgga cgaccacctc gagagcgtgc tcaccgagat ccggctcaac 1380
acgcgcaccg gcgagtccac gcggcgggcc atcctgccgc tggagagcca ggtgaacctc 1440
gaggtcggca tggtgaaccg caacatgctg ggccggaaga cgaggtacgc ctacctggcc 1500
gtggccgagc cgtggcccaa ggtgtccggg ttcgccaagg tggacctggt gaccggcgag 1560
ctgaccaagt tcgagtacgg cgagggccgg ttcggcggcg agccgtgctt cgtgcccatg 1620
gacggcgagc acgcgcgccc cggcgccgag gacgacggct acgtgctctc cttcgtgcgc 1680
gacgaggacg ccggcacatc cgagctcctg gtcgtcaacg ccgccgacat gcggctcgag 1740
gccaccgtgc agctgccgtc ccgggtcccc tatggcttcc acggcacatt catcggcgac 1800
gccgacctcg acgcccagca ctaa 1824

<210> SEQ ID NO 110
<211> LENGTH: 1779
<212> TYPE: DNA
<213> ORGANISM: Hordeum vulgare

<400> SEQUENCE: 110
atgcagacac tcacagcgtc cagctcggtc tcctccatac agcggcaccg gccgcacccc 60
gcgggccgcc ggtccagctc ggtcaccttc tccgcccgcg ccgtcagctc cgcgccgcgc 120
gcgccggcac cgtcccggtt cgtgcgcggc gccgacgcgg cgcccgccaa gcccctcatt 180
gccgtcccca agccgcccgc cgtggagagg caggagaaga agctcaactt cttccagcgc 240
gccgcggtca cggcgctcga cgcgttcgag gaaggatttg tggccaacgt gctcgagcgc 300
ccgcacggcc tctccaggac ggtcgacccc gcggtgcaga tcgccggcaa cttcgcgcct 360
gtcggggaga cacctcctgt gcaggcgctg cccgtgaccg accgcatccc cccgttcatc 420
aacggcgtgt acgcccgcaa cggcgccaac ccgcacttcg accccgtcgc cgggcaccac 480
ctgttcgacg gcgacggcat ggtgcacgct ctgcgcatcc gcaacggcgt cgccgagacc 540
tacgcctccc gcttcaccga gacggagcgc ctgcagcagg agcgcgcgct ggggcgcccg 600
atgttcccca aggccattgg tgagctccat ggccactctg ggatcgcgcg ccttgctctg 660
ttctacgcgc gcgcggcctg cggcctcatc gacccctcgc gcggcaccgg cgtggccaac 720
gccggcctgg tctacttcaa cggccacctc ctcgccatgt ccgaggacga catcccgtac 780
cacgtccgcg tcaccgacga cggcgacctc cagaccgtcg gccgctacga cttcgacggg 840
cagctcgagt gccccatgat cgcgcacccc aaactcgacc ccgccaccgg ggagctccac 900
gcgctcagct acgacgtcat caagaagcct tacctgaagt acttctactt cgcggccgac 960
ggcaccaagt cggccgacgt cgagatcccg ctggaccagc ccaccatgat ccacgacttc 1020
gccatcaccg agaattacgt ggtcgtgccc gaccaccagg tggtgttcaa gctgcaggag 1080
atgctgcgcg gcggctcgcc cgtggtgctc gacaaggaga agacgtcccg cttcggcgtg 1140
ctgcccaagt gcgccgccga cgcgtcggag atggtgtggg tggacgtgcc ggactgcttc 1200
tgcttccacc tctggaacgc gtgggaggag gaggagaccg acgaggtggt ggtgatcggc 1260
tcctgcatga cccccgccga ctccatcttc aacgagtcgg acgagtgcct cgagagcgtg 1320
ctcacggaga tccgcctcaa cacccgcacc ggcgagtcca cgcggcgccc catcctggcg 1380
ctgtcagagc aggtgaacct ggaggtcggc atggtgaact ccaacctgct gggccgcaag 1440
acgcggtacg cctacctggc cgtggccgag ccgtggccca aggtgtccgg cttcgccaag 1500
gtcgacctgg ccacgggcga gctcaccaaa ttcgagtacg gcgagggccg gttcggcggc 1560
gagccctgct tcgtgcccat ggacccggcc acgtcccgcg gcgaggacga cgggtacatt 1620
ctcaccttcg tgcacgacga ggccgccggc acgtcggagc tgctggtggt caatgccgcc 1680
gacatgcggc tggaggcgac catccagctg ccgtcccgcg tgccatacgg gttccacggc 1740
accttcatca ccggcaagga gctcgaatcc caggcctga 1779

<210> SEQ ID NO 111
<211> LENGTH: 1500
<212> TYPE: DNA
<213> ORGANISM: Artificial Sequence
<220> FEATURE:
<223> OTHER INFORMATION: Chimeric DNA encoding a ledRNA construct targeting the NCED1 genes of barley Hordeum vulgare and wheat Triticum aestivum

<400> SEQUENCE: 111

```
taatacgact cactataggg tcgacgaggc cgcaggcgcc gcgcgcgtag aagagggcca     60
gcctcgcgat gccagagtgg ccgtggagct cgccgatggt cttagggaag acgggcctcc    120
ccgcggcgcg ctcctgggag aggcgggcgg tctcggtgaa gcggcaggcg taggactcgg    180
cggcgccgtt tcggatgcgg atggcgtgga ccatgccgtc gccgtcgaag aggtggtggc    240
cggccgtggg ctcgaagcag gggttggcgc cgttgcgggc gtagacgccg ttgatgaagg    300
gcgggatgcg gccggagacc gtgagggcgc gcacgggggg ctgctcgccg acgggggcga    360
agttgccggc gatctgcacg gccgggtcgg ccgtgcgcgg cagcgcgtgg ggccgctcca    420
ggacattgtt gatgaacccc tcctcgaacg cgtcgagctc cggccgcatc ccgcccttca    480
tcaacggcgt ctacgcccgc aacggcgcca acccctgctt cgagcccacg gccggccacc    540
acctcttcga cggcgacggc atggtccacg ccatccgcat ccgaaacggc gccgccgagt    600
cctacgcctg ccgcttcacc gagaccgccc gcctctccca ggagcgcgcc gcggggaggc    660
ccgtcttccc taagaccatc ggcgagctcc acggccactc tggcatcgcg aggctggccc    720
tcttctacgc gcgcggcgcc tgcggcctcg tcgacccgta ccacggcact ggtgttgcca    780
acgccggcct cgtctacttc aacggccgcc tcctcgccat gtccgaggac gacctcccgt    840
accaggtccg cgtcaccgcc ggtggcgacc tcgagaccgt cggccgctac gacttcgacg    900
gccagctcga ctgcgccatg atcgcgcacc ccaagctcga ccctgtctcc ggcgagctct    960
tcgcgctcag ctacgatgtc atcaagaagc cgtacctcaa gtacttctac ttcacgcccg   1020
acggcaccaa gtccgccgac gtcgagatcg agctcgacga agcgggaggt cttctccttg   1080
tcgagcatca ccggcgagcc gccgcggaac atctcggcga gcttgaacac catctggtgg   1140
tcgggcacga cgacgaagtt ctcggtgatg gcgaagtcgt ggatcatggt gggctggtcg   1200
agctcgatct cgacgtcggc ggacttggtg ccgtcgggcg tgaagtagaa gtacttgagg   1260
tacggcttct tgatgacatc gtagctgagc gcgaagagct cgccggagac agggtcgagc   1320
ttggggtgcg cgatcatggc gcagtcgagc tggccgtcga agtcgtagcg gccgacggtc   1380
tcgaggtcgc caccggcggt gacgcggacc tggtacggga ggtcgtcctc ggacatggcg   1440
aggaggcggc cgttgaagta gacgaggccg gcgttggcaa caccagtgcc gtggtacgta   1500
```

<210> SEQ ID NO 112
<211> LENGTH: 1500
<212> TYPE: DNA
<213> ORGANISM: Artificial Sequence
<220> FEATURE:
<223> OTHER INFORMATION: Chimeric DNA encoding a ledRNA construct targeting the NCED2 genes of barley Hordeum vulgare and wheat Triticum aestivum

<400> SEQUENCE: 112

```
taatacgact cactataggg ttggcgccgt tgcgggcgta cacgccgttg atgaacgggg     60
ggatgcggtc ggtcacgggc agcgcctgca caggaggtgt ctccccgaca ggcgcgaagt    120
tgccggcgat ctgcaccgcg gggtcgaccg tcctggagag gccgtgcggg cgctcgagca    180
cgttggccac aaatccttcc tcgaacgcgt cgagcgccgt gaccgcggcg cgctggaaga    240
agttgagctt cttctcctgc ctctccacgg cgggcggctt ggggacggca atgaggggct    300
tggcgggcgc cgcgtcggcg ccgcgcacga accgggacgg tgccggcgcg cgcggcgcgg    360
agctgacggc gcgggcggag aaggtgaccg agctggaccg gcggcccgcg gggtgcggcc    420
ggtgccgctg tatggaggag accgagctgg acgctgtcga cgcggcgccc gccaagcccc    480
```

tcattgccgt ccccaagccg cccgccgtgg agaggcagga gaagaagctc aacttcttcc 540
agcgcgccgc ggtcacggcg ctcgacgcgt tcgaggaagg atttgtggcc aacgtgctcg 600
agcgcccgca cggcctctcc aggacggtcg accccgcggt gcagatcgcc ggcaacttcg 660
cgcctgtcgg ggagacacct cctgtgcagg cgctgcccgt gaccgaccgc atccccccgt 720
tcatcaacgg cgtgtacgcc cgcaacggcg ccaacccgta cttcgacccc gtcgccgggc 780
accacctgtt cgacggcgac ggcatggtgc acgctctgcg catccgcaac ggcgtcgccg 840
agacctacgc ctcccgcttc accgagacgg agcgcctgca gcaggagcgc gcgctggggc 900
gcccgatgtt ccccaaggcc attggtgagc tccatggcca ctctgggatc gcgcgccttg 960
ctctgttcta cgcgcgcgcg gcctgcggcc tcatcgaccc ctcgcgcggc accggcgtgg 1020
ccaacgccgg cctggtctac ttcaacggcc acctcctccc cggtggcggg gtcgagtttg 1080
gggtgcgcga tcatggggca ctcgagctgc ccgtcgaagt cgtagcggcc gacggtctgg 1140
aggtcgccgt cgtcggtgac gcggacgtgg tacgggatgt cgtcctcgga catggcgagg 1200
aggtggccgt tgaagtagac caggccggcg ttggccacgc cggtgccgcg cgaggggtcg 1260
atgaggccgc aggccgcgcg cgcgtagaac agagcaaggc gcgcgatccc agagtggcca 1320
tggagctcac caatggcctt ggggaacatc gggcgcccca gcgcgcgctc ctgctgcagg 1380
cgctccgtct cggtgaagcg ggaggcgtag gtctcggcga cgccgttgcg gatgcgcaga 1440
gcgtgcacca tgccgtcgcc gtcgaacagg tggtgcccgg cgacggggtc gaagtacgta 1500

<210> SEQ ID NO 113
<211> LENGTH: 1521
<212> TYPE: DNA
<213> ORGANISM: Hordeum vulgare

<400> SEQUENCE: 113
atggccttct tcctcctcct gtgcatcctc gtctctgtgg ccatcgtgtc ctacgcccac 60
cacgcaatcc ggcggaggcg ccagggctgc gctcatggcc gtcatgagca ggccgccctc 120
aagctgcccc ccggctccat gggcctgcct tacgtcggcg agaccctgca gctctactcc 180
caggacccca gcgtcttcct ctcctccaag cagaagcggt acggcgagat cttcaagacg 240
cacctcctgg ggtgcccgtg cgtgatgctg gcgagcccgg aggcggcgcg cttcgtgctg 300
gtgtcgcggg cccacctctt caagccgacg tacccgcgga gcaaggagcg cctcatcggc 360
ccgtcggcgc tcttcttcca ccagggcgac taccacctcc gcctccgccg gctcgtccag 420
ggcccgctcg gccccgaggc cctgcgcaag ctcgtgccgg acatcgaggc cgccgttcgc 480
tccacgctcg ccgcctgggc ggacggcgac gtcgccagca ctttccacgc catgaagagg 540
ctctcgttcg acgtcggcat cgtgacgatc ttcggcgggc ggctggacga gcggcggaag 600
gaggagctca ggcggaacta cgccgtcgtg gagaaaggct acaactcctt ccccaacagc 660
ttccccggga cgctatacta caaggcgatc caggcgaggc ggcggctgaa cggcgtgctg 720
agcgacgtcg tgcacgagcg tagggagcgg ggcgagcacg gcgacgacct cctcggctgc 780
ctcatgcggt cgcgggccgg cggcgacgac gccgacgacg agggcgcgct gctgacggac 840
gagcaggtcg ccgacaacgt catcggcgtg ctgttcgcgg cgcaggacac gacggccagc 900
gtgctcacct ggatcgtcaa gtacctccac gaccgcccga agctgctcga ggccgtcagg 960
gcggagcacg cggcgatcca cgaggccaac gacggcggga ggcggccgct gacatgggcg 1020
cagacgagga gcatgacgct gacgcacagg gtgattttgg agagcctaag gatggccagc 1080
atcatctcct tcacgttcag ggaggccgtg gccgacgtgg agtacaaagg gtttcttatc 1140
cccaaggggt ggaaggtgat gccgctcttc aggaacatcc atcacagccc ggactacttc 1200
caggatccac acaagttcga cccttcgcga ttcaaggtgg cgccgcggcc gaacaccttc 1260
acsccgttcg ggagcggggt gcacgcgtgc ccggggaacg agctggccaa gctcgagatg 1320
ctggtgctca tccaccacct ggtcaccggc tacaggtggg aggttgttgg atcgagcgac 1380
gacgtcgagt acagcccatt ccccgttccc cgccatggcc tgctcgccag ggtacggcga 1440
gatgacggcg tctgcgcggg taggaagggg tgcccgactg atgaagatga caactacgac 1500
gacgacgaag tgatagtgtg a 1521

<210> SEQ ID NO 114
<211> LENGTH: 1506
<212> TYPE: DNA
<213> ORGANISM: Artificial Sequence
<220> FEATURE:
<223> OTHER INFORMATION: Chimeric DNA encoding a ledRNA construct targeting the ABA-OH-2 genes of barley Hordeum vulgare and wheat Triticum aestivum

<400> SEQUENCE: 114
taatacgact cactataggg cggtcgtgga ggtacttgac gatccaggtg agcacgctgg 60
ccgtcgtgtc ctgcgccgcg aacagcacgc cgatgacgtt gtcggcgacc tgctcgtccg 120
tcagcagcgc gccctcgtcg tcggcgtcgt cgccgccggc ccgcgaccgc atgaggcagc 180
cgaggaggtc gtcgccgtgc tcgccccgct ccctacgctc gtgcacgacg tcgctcagca 240
cgccgttcag ccgccgcctc gcctggatcg ccttgtagta tagcgtcccg gggaagctgt 300
tggggaagga gttgtagcct ttctccacga cggcgtagtt ccgcctgagc tcctccttcc 360
gccgctcgtc cagccgcccg ccgaagatcg tcacgatgcc gacgtcgaac gagagcctct 420
tcatggcgtg gaaagtgctg gcgacgtcgc cgtccgccta caactccttc cccaacagct 480
tccccgggac gctatactac aaggcgatcc aggcgaggcg gcggctgaac ggcgtgctga 540
gcgacgtcgt gcacgagcgt agggagcggg gcgagcacgg cgacgacctc ctcggctgcc 600
tcatgcggtc gcgggccggc ggcgacgacg ccgacgacga gggcgcgctg ctgacggacg 660
agcaggtcgc cgacaacgtc atcggcgtgc tgttcgcggc gcaggacacg acggccagcg 720
tgctcacctg gatcgtcaag tacctccacg accgcccgta gctgctcgag gccgtcaggg 780
cggagcacgc ggcgatccac gaggccaacg acggcgggag gcggccgctg acatgggcgc 840
agacgaggag catgacgctg acgcacaggg tgattttgga gagcctaagg atggccagca 900
tcatctcctt cacgttcagg gaggccgtgg ccgacgtgga gtacaaaggg tttcttatcc 960
ccaaggggtg gaaggtgatg ccgctcttca ggaacatcca tcacagcccg gactacttcc 1020
aggatccaca caagttcgac ccttcgcgat tcaaggtcgc tcgatccaac aacctcccac 1080
ctgtagccgg tgaccaggtg gtggatgagc accagcatct cgagcttggc cagctcgttc 1140
cccgggcacg cgtgcacccc gctcccgaac ggagtgaagg tgttcggccg cggcgccacc 1200
ttgaatcgcg aagggtcgaa cttgtgtgga tcctggaagt agtccgggct gtgatggatg 1260
ttcctgaaga gcggcatcac cttccacccc ttggggataa gaaacccttt gtactccacg 1320
tcggccacgg cctccctgaa cgtgaaggag atgatgctgg ccatccttag gctctccaaa 1380
atcaccctgt gcgtcagcgt catgctcctc gtctgcgccc atgtcagcgg ccgcctcccg 1440
ccgtcgttgg cctcgtggat cgccgcgtgc tccgccctga cggcctcgag cagctacgta 1500
ggtacc 1506

<210> SEQ ID NO 115
<211> LENGTH: 3885
<212> TYPE: DNA
<213> ORGANISM: Arabidopsis thaliana

<400> SEQUENCE: 115
atggaagctg aaattgtgaa tgtgagacct cagctagggt ttatccagag aatggttcct 60
gctctacttc ctgtcctttt ggtttctgtc ggatatattg atcccgggaa atgggttgca 120
aatatcgaag gaggtgctcg tttcgggtat gacttggtgg caattactct gcttttcaat 180
tttgccgcca tcttatgcca atatgttgca gctcgcataa gcgttgtgac tggtaaacac 240
ttggctcaga tctgcaatga agaatatgac aagtggacgt gcatgttctt gggcattcag 300
gcggagttct cagcaattct gctcgacctt accatggttg tgggagttgc gcatgcactt 360
aaccttttgt ttggggtgga gttatccact ggagtgtttt tggccgccat ggatgcgttt 420
ttatttcctg ttttcgcctc tttccttgaa aatggtatgg caaatacagt atccatttac 480
tctgcaggcc tggtattact tctctatgta tctggcgtct tgctgagtca gtctgagatc 540
ccactctcta tgaatggagt gttaactcgg ttaaatggag agagcgcatt cgcactgatg 600
ggtcttcttg gcgcaagcat cgtccctcac aatttttata tccattctta ttttgctggg 660
gaaagtacat cttcgtctga tgtcgacaag agcagcttgt gtcaagacca tttgttcgcc 720
atctttggtg tcttcagcgg actgtcactt gtaaattatg tattgatgaa tgcagcagct 780
aatgtgtttc acagtactgg ccttgtggta ctgacttttc acgatgcctt gtcactaatg 840
gagcaggtat ttatgagtcc gctcattcca gtggtctttt tgatgctctt gttcttctct 900
agtcaaatta ccgcactagc ttgggctttc ggtggagagg tcgtcctgca tgacttcctg 960
aagatagaaa tacccgcttg gcttcatcgt gctacaatca gaattcttgc agttgctcct 1020
gcgctttatt gtgtatggac atctggtgca gacggaatat accagttact tatattcacc 1080
caggtcttgg tggcaatgat gcttccttgc tcggtaatac cgcttttccg cattgcttcg 1140
tcgagacaaa tcatgggtgt ccataaaatc cctcaggttg gcgagttcct cgcacttaca 1200
acgtttttgg gatttctggg gttgaatgtt gtttttgttg ttgagatggt atttgggagc 1260
agtgactggg ctggtggttt gagatggaat accgtgatgg gcacctcgat tcagtacacc 1320
actctgcttg tatcgtcatg tgcatcctta tgcctgatac tctggctggc agccacgccg 1380
ctgaaatctg cgagtaacag agcggaagct caaatatgga acatggatgc tcaaaatgct 1440
ttatcttatc catctgttca agaagaggaa attgaaagaa cagaaacaag gaggaacgaa 1500
gacgaatcaa tagtgcggtt ggaaagcagg gtaaaggatc agttggatac tacgtctgtt 1560
actagctcgg tctatgattt gccagagaac attctaatga cggatcaaga aatccgttcg 1620
agccctccag aggaaagaga gttggatgta aagtactcta cctctcaagt tagtagtctt 1680
aaggaagact ctgatgtaaa ggaacagtct gtattgcagt caacagtggt taatgaggtc 1740
agtgataagg atctgattgt tgaaacaaag atggcgaaaa ttgaaccaat gagtcctgtg 1800
gagaagattg ttagcatgga gaataacagc aagtttattg aaaaggatgt tgaaggggtt 1860
tcatgggaaa cagaagaagc taccaaagct gctcctacaa gcaactttac tgtcggatct 1920
gatggtcctc cttcattccg cagcttaagt ggggaagggg gaagtgggac tggaagcctt 1980
tcacggttgc aaggtttggg acgtgctgcc cggagacact tatctgcgat ccttgatgaa 2040
ttttggggac atttatatga ttttcatggg caattggttg ctgaagccag ggcaaagaaa 2100
ctagatcagc tgtttggcac tgatcaaaag tcagcctctt ctatgaaagc agattcgttt 2160
ggaaaagaca ttagcagtgg atattgcatg tcaccaactg cgaagggaat ggattcacag 2220
atgacttcaa gtttatatga ttcactgaag cagcagagga caccgggaag tatcgattcg 2280
ttgtatggat tacaaagagg ttcgtcaccg tcaccgttgg tcaaccgtat gcagatgttg 2340
ggtgcatatg gtaacaccac taataataat aatgcttacg aattgagtga gagaagatac 2400
tctagcctgc gtgctccatc atcttcagag ggttgggaac accaacaacc agctacagtt 2460
cacggatacc agatgaagtc atatgtagac aatttggcaa aagaaaggct tgaagcctta 2520
caatcccgtg gagagatccc gacatcgaga tctatggcgc ttggtacatt gagctataca 2580
cagcaacttg ctttagcctt gaaacagaag tcccagaatg gtctaacccc tggaccagct 2640
cctgggtttg agaattttgc tgggtctaga agcatatcgc gacaatctga aagatcttat 2700
tacggtgttc catcttctgg caatactgat actgttggcg cagcagtagc caatgagaaa 2760
aaatatagta gcatgccaga tatctcagga ttgtctatgt ccgcaaggaa catgcattta 2820
ccaaacaaca agagtggata ctgggatccg tcaagtggag gaggagggta tggtgcgtct 2880
tatggtcggt taagcaatga atcatcgtta tattctaatt tggggtcacg ggtgggagta 2940
ccctcgactt atgatgacat ttctcaatca agaggaggct acagagatgc ctacagtttg 3000
ccacagagtg caacaacagg gaccggatcg ctttggtcca gacagccctt tgagcagttt 3060
ggtgtagcgg agaggaatgg tgctgttggt gaggagctca ggaatagatc gaatccgatc 3120
aatatagaca acaacgcttc ttctaatgtt gatgcagagg ctaagcttct tcagtcgttc 3180
aggcactgta ttctaaagct tattaaactt gaaggatccg agtggttgtt tggacaaagc 3240
gatggagttg atgaagaact gattgaccgg gtagctgcac gagagaagtt tatctatgaa 3300
gctgaagctc gagaaataaa ccaggtgggt cacatggggg agccactaat ttcatcggtt 3360
cctaactgtg gagatggttg cgtttggaga gctgatttga ttgtgagctt tggagtttgg 3420
tgcattcacc gtgtccttga cttgtctctc atggagagtc ggcctgagct ttggggaaag 3480
tacacttacg ttctcaaccg cctacaggga gtgattgatc cggcgttctc aaagctgcgg 3540
acaccaatga caccgtgctt ttgccttcag attccagcga gccaccagag agcgagtccg 3600
acttcagcta acggaatgtt acctccggct gcaaaaccgg ctaaaggcaa atgcacaacc 3660
gcagtcacac ttcttgatct aatcaaagac gttgaaatgg caatctcttg tagaaaaggc 3720
cgaaccggta cagctgcagg tgatgtggct ttcccaaagg ggaaagagaa tttggcttcg 3780
gttttgaagc ggtataaacg tcggttatcg aataaaccag taggtatgaa tcaggatgga 3840
cccggttcaa gaaaaaacgt gactgcgtac ggatcattgg gttga 3885

<210> SEQ ID NO 116
<211> LENGTH: 1080
<212> TYPE: DNA
<213> ORGANISM: Artificial Sequence
<220> FEATURE:
<223> OTHER INFORMATION: Chimeric DNA encoding a ledRNA construct targeting the EIN2 gene of A. thaliana

<400> SEQUENCE: 116
taatacgact cactataggg agctgcaaca tattggcata agatggcggc aaaattgaaa 60
agcagagtaa ttgccaccaa gtcatacccg aaacgagcac ctccttcgat atttgcaacc 120
catttcccgg gatcaatata tccgacagaa accaaaagga caggaagtag agcaggaacc 180
attctctgga taaaccctag ctgaggtctc acattcacaa tttcagcttc catcctaaat 240
ctatctgata atataattac tcagagtagg attcaaggta aactctacag tcgtggttca 300

```
ctaaaagcct cagttgagta aaattcacag atttgatcta aaacacctga atgtgagacc    360

tcagctaggg tttatccaga gaatggttcc tgctctactt cctgtccttt tggtttctgt    420

cggatatatt gatcccggga aatgggttgc aaatatcgaa ggaggtgctc gtttcgggta    480

tgacttggtg gcaattactc tgcttttcaa ttttgccgcc atcttatgcc aatatgttgc    540

agctcccaac agcgttgtga ctggtaaaca cttggctcag atctgcaatg aagaatatga    600

caagtggacg tgcatgttct tgggcattca ggcggagttc tcagcaattc tgctcgacct    660

taccatggtt gtgggagttg cgcatgcact taaccttttg tttggggtgg agttatccac    720

tggagtgttt ttggccgcca tggatgcgag tgggatctca gactgactca gcaagacgcc    780

agatacatag agaagtaata ccaggcctgc agagtaaatg gatactgtat ttgccatacc    840

attttcaagg aaagaggcga aaacaggaaa taaaaacgca tccatggcgg ccaaaaacac    900

tccagtggat aactccaccc caaacaaaag gttaagtgca tgcgcaactc ccacaaccat    960

ggtaaggtcg agcagaattg ctgagaactc cgcctgaatg cccaagaaca tgcacgtcca   1020

cttgtcatat tcttcattgc agatctgagc caagtgttta ccagtcacaa cgctgttgac   1080
```

<210> SEQ ID NO 117
<211> LENGTH: 1188
<212> TYPE: DNA
<213> ORGANISM: Arabidopsis thaliana

<400> SEQUENCE: 117

```
atggtgatgg ctggtgcttc ttctttggat gagatcagac aggctcagag agctgatgga     60

cctgcaggca tcttggctat tggcactgct aaccctgaga accatgtgct tcaggcggag    120

tatcctgact actacttccg catcaccaac agtgaacaca tgaccgacct caaggagaag    180

ttcaagcgca tgtgcgacaa gtcgacaatt cggaaacgtc acatgcatct gacggaggaa    240

ttcctcaagg aaaacccaca catgtgtgct tacatggctc cttctctgga caccagacag    300

gacatcgtgg tggtcgaagt ccctaagcta ggcaaagaag cggcagtgaa ggccatcaag    360

gagtggggcc agcccaagtc aaagatcact catgtcgtct tctgcactac ctccggcgtc    420

gacatgcctg gtgctgacta ccagctcacc aagcttcttg gtctccgtcc ttccgtcaag    480

cgtctcatga tgtaccagca aggttgcttc gccggcggta ctgtcctccg tatcgctaag    540

gatctcgccg agaacaatcg tggagcacgt gtcctcgttg tctgctctga gatcacagcc    600

gttaccttcc gtggtccctc tgacacccac cttgactccc tcgtcggtca ggctcttttc    660

agtgatggcg ccgccgcact cattgtgggg tcggaccctg acacatctgt cggagagaaa    720

cccatctttg agatggtgtc tgccgctcag accatccttc cagactctga tggtgccata    780

gacggacatt tgagggaagt tggtctcacc ttccatctcc tcaaggatgt tcccggcctc    840

atctccaaga acattgtgaa gagtctagac gaagcgttta aacctttggg gataagtgac    900

tggaactccc tcttctggat agcccaccct ggaggtccag cgatcctaga ccaggtggag    960

ataaagctag gactaaagga agagaagatg agggcgacac gtcacgtgtt gagcgagtat   1020

ggaaacatgt cgagcgcgtg cgttctcttc atactagacg agatgaggag gaagtcagct   1080

aaggatggtg tggccacgac aggagaaggg ttggagtggg gtgtcttgtt tggtttcgga   1140

ccaggtctca ctgttgagac agtcgtcttg cacagcgttc ctctctaa                1188
```

<210> SEQ ID NO 118
<211> LENGTH: 1080
<212> TYPE: DNA

```
<213> ORGANISM: Artificial Sequence
<220> FEATURE:
<223> OTHER INFORMATION: Chimeric DNA encoding a ledRNA construct
      targeting the CHS gene of A. thaliana

<400> SEQUENCE: 118

taatacgact cactataggg gccacaccat ccttagctga cttcctcctc atctcgtcta     60

gtatgaagag aacgcacgcg ctcgacatgt ttccatactc gctcaacacg tgacgtgtcg    120

ccctcatctt ctcttccttt agtcctagct ttatctccac ctggtctagg atcgctggac    180

ctccagggtg ggctatccag aagagggagt tccagtcact tatccccaaa ggtttaaacg    240

cttcgtctag actcttcaca atgttcttgg agatgaggcc gggaacatcc ttgaggagat    300

ggaaggtgag accaacttcc ctcaaatgtc cgtctatggc accatcagac tggaactccc    360

tcttctggat agcccaccct ggaggtccag cgatcctaga ccaggtggag ataaagctag    420

gactaaagga agagaagatg agggcgacac gtcacgtgtt gagcgagtat ggaaacatgt    480

cgagcgcgtg cgttctcttc atactagacg agatgaggag gaagtcagct aaggatggtg    540

tggccccgac aggagaaggg ttggagtggg gtgtcttgtt tggtttcgga ccaggtctca    600

ctgttgagac agtcgtcttg cacagcgttc ctctctaaac agaacgcttg ccttctatct    660

gcctacctac ctacgcaaaa ctttaatcct gtcttatgtt ttatataata taatcattat    720

atgtttacgc aataattaag gaagaatgac atttccaaac aaagatttga tgtcattcaa    780

gacccataga tttaatattg taaaaagaca caaaaaagag agtacaaaaa cagtcgaata    840

gacctgtcca gcacatatca catatcacat caaatgcatt cttccttaat tattgcgtaa    900

acatataatg attatattat ataaaacata agacaggatt aaagttttgc gtaggtaggt    960

aggcagatag aaggcaagcg ttctgtttag agaggaacgc tgtgcaagac gactgtctca   1020

acagtgagac ctggtccgaa accaaacaag acaccccact ccaacccttc tcctgtcaac   1080


<210> SEQ ID NO 119
<211> LENGTH: 3456
<212> TYPE: DNA
<213> ORGANISM: Lupinus angustifolius

<400> SEQUENCE: 119

atgttgactc ttcaacccac acatgagtca agtagtcaat accctcctca tacacttata     60

gctgagacct gtcactttga ttatctgtac tatactaatc aaagttctct aattatgtca    120

cttggagaat catccctgca atggaaatac catgttttct tgagttttag gggaggtgac    180

acccgcttaa gcttcactaa tcacttatat gctgcgttgg tgcgaaaagg aatcattact    240

ttccgagatg acaaacaact tcacaaagga gatgccattt ctcaacatct gcatcaatca    300

atccaacagt ctctagctgc cattgttgtt atctcggaga actatgcttc ttccacttgg    360

tgtttggatg agctaaaact aattcttgaa tcgagaatag atgtttttcc agtcttttat    420

ggtgtcactc cttctgatgt tcgataccag aaaaatagtt ttgctgaggc tttcaataaa    480

catgttgtaa gatttgaaca agatgaagag aaagtgcaaa aatggagaga ttgcttgaaa    540

gaagttgctg atttttctgg atgggagtcc aaggacatgg ctgaagcaga actcattgaa    600

gatgttattg aaaaggtatg gataaaacta caaccaaaat tgccatccta caatgaagga    660

gtggttggat ttgattcaag ggtgaagaaa atgatttcac ttttaagcat aggatcacaa    720

gatattcggt ttatcgggat atggggtatg gctggaactg gaaaaacaat tcttgctaga    780

gtaatctacg aaacaataag tagccaattt gagattaaat gtttccttct taatgttaga    840
```

```
gaggtttctc aaacatctga tggattggtt tccttacaaa gaaaacttct ttctaccctt    900
aagataagca acctagaaat tgatgatttg tatgatggaa agaagaaaat tatgaacctt    960
ttgtgcaaca aaagtgttct tcttgtcctt gatgacatta gtcatttaag tcagctagag   1020
aatttggcta aaactaaagg ttggtttggt ccatgcagca gagtgataat aacaaccaaa   1080
gatatgcact tactagtatc acatggtgcg tgtgagaagt atgagatgag aatcttaaat   1140
gaaagttctt cctttcaact cttcagccag aaagcattca gaagagataa acctccagag   1200
ggttatttag aaataactaa aagtatggtc aaatatgctg gaggtcttcc tttggcactt   1260
aaagtgttgg gttcttttgt ttgtggaaga agtctcagtc agtggaagga tgctttggat   1320
aagataaaac aagttctgcc gaaagacatt ttgaacacac taataatagg ttatgatgga   1380
ctagaagatg cagaaaagac tttgttttta gatattgctt tcttctttac aggacggtcg   1440
aaaattgaag tgatacaggt attggcagat tgtggcctta atccaacaat tggaataagt   1500
cttcttattg aaagatctct agtaagttgt tgtggaggaa ttttggaaat gcatgattta   1560
cttcaagaaa tgggtagaaa tattgtatat caagaatctc cggatgatgc aagcagacgc   1620
agtaggttat gctctttaga agatattaac cgagtattca gaaaaaacaa gggaaccaat   1680
atcattcaag gaatagttct gaaatcaagt gacccatgtg aagcatattg gcatcctgaa   1740
gccttctcaa aaatggataa tcttagagta ctcatcattt tgtgtgattt gcaccttccc   1800
ctcggcctca aatgtctctc tagttcatta aaacttcttg aatggaaggg atatcctttg   1860
gaatatctac catttggcct gcaactgcta gaacttgttc acttgaaaat gcattgcagc   1920
aaacttaaac aactttggaa tggaactcaa attttcagag agctaaaatc aattgatctc   1980
agtgattcca gagatctaat tcaaactcca gatatttctg aggttccatg tcttgagagt   2040
ttagttttga aaggttgtaa aaaccttgtt gaggttcatc aatctgttgc aaagcacaag   2100
aatgttgcta tactagacct ggaaggttgc atcagtctta agaccctgcc aagaaaattg   2160
gagatgaatg ctttggaaaa gttcattctc tccggctgct cacaaattaa aaaccttccc   2220
gaatttgggg agagtatgga atgtctatct atgcttaatt taagagattg cacaagtctt   2280
gtttctcttc cacagagtgt tcgaaacatg aaatccttta gagatctcaa tatccatggt   2340
tgctcaaaat tgtttaagct gacaaacaat tcaaatgaaa ataatgtcgt ggaagaaatt   2400
gatgagactg aaacaggtag gagagaagtg cattcatcat ggagcttttc tctccttact   2460
gagaaagtgt ttgatttcgt aaagtatcca gttagcatgg actcgaagtt gccttctctc   2520
tcaagtttcc ctcggttgaa gaaattagat atgggcaact gtaatctcag tgatggacca   2580
attatagatc atattggaca tttaacatca ctggaagtgt tatatttagc tgggaacaac   2640
tttgttgacc ttacagcaag cattggtaac ctttctcggc tacaacgcct tggtttatat   2700
aaatgccgaa gacttaggac attgcctgag cttccaccca gtgtatgcca gttacttatg   2760
aacgactgca ctcaactgga acctatgtta tttgacacac aaataatttt gaaaatattt   2820
gaggcaaata gatggagcct gacacgcgaa ttgtggttcc tgattccagg gagtgaaatc   2880
ccagcatggt ttgagcatca agattatttt agcctgaaac caagtttagc gcctttcgat   2940
tatcacgagg agtatgcttt tattgtttca acaatagtaa acatccctga ctattgcctt   3000
tcaagtgatt ggataggaat tattgtatgc tttttactgg aaagtggttt aaaggcagac   3060
ctacacagac atattcgtag aagtccggtc acgatcggat ggtcttttaa agatcccgat   3120
gcagaaacgg tttacccctt acgcttcact aaacgtcgtt ggacacattt caaaggcaat   3180
cacctattga ttactacttt tggaagtgat catagaatat acaagcacta cttaacttgt   3240
```

ggcaaaagca aagtgcaatt gatattttgt ggtgagaata tttgcaagtg cgggaagcta 3300
aagctgaaaa actgtgggat ccgtgtgatt tgtaaggaag atggtgtatc gcgtagaggc 3360
gaggaaacga gtgaagttga ggtgccttcc acttcagttg aatctgatgt tcacaaacaa 3420
tcacgaataa ctgaaattac agatgaatat gaataa 3456

<210> SEQ ID NO 120
<211> LENGTH: 1280
<212> TYPE: DNA
<213> ORGANISM: Artificial Sequence
<220> FEATURE:
<223> OTHER INFORMATION: Chimeric DNA encoding a ledRNA construct targeting the L. angustifolius N-like gene

<400> SEQUENCE: 120
taatacgact cactataggg tatcgaacat cagaaggagt gacaccataa aagactggaa 60
aaacatctat tctcgattca agaattagtt ttagctcatc caaacaccaa gtggaagagt 120
atttccattg cagggatgat tctccaagtg acataattag agaactttga ttagtatagt 180
acagataatc aaagtgacag gtctcagcta taagtgtatg aggagggtat tgactacttg 240
actcatgtgt gggttgaaga gtcaacatat agcttcacgg atcccacagt ttttcagctt 300
tagcttcccg cacttgcaaa tattctcacc acaaaatatc aattgcactt tgcttttgcc 360
acaagttaag tagtgcttgt atattctatg atcaccctgt tgactcttca acccacacat 420
gagtcaagta gtcaataccc tcctcataca cttatagctg agacctgtca ctttgattat 480
ctgtactata ctaatcaaag ttctctaatt atgtcacttg gagaatcatc cctgcaatgg 540
aaatactctt ccacttggtg tttggatgag ctaaaactaa ttcttgaatc gagaatagat 600
gtttttccag tcttttatgg tgtcactcct tctgatgttc gatacccgta gttttgctga 660
ggctttcaat aaacatgttg taagatttga acaagatgaa gagaaagtgc agtttgagca 720
tcaagattat tttagcctga aaccaagttt agcgcctttc gattatcacg aggagtatgc 780
ttttattgtt tcaacaatag taaacatccc tgactattgc ctttcaagtg attggatagg 840
aattattgta tgctttttac tggaaagtgg tttaaaggca gacctacaca gacatattcc 900
aaaagtagta atcaataggt gattgccttt gaaatgtgtc caacgacgtt tagtgaagcg 960
taaggggtaa accgtttctg catcgggatc tttaaaagac catccgatcg tgaccggact 1020
tctacgaata tgtctgtgta ggtctgcctt taaaccactt tccagtaaaa agcatacaat 1080
aattcctatc caatcacttg aaaggcaata gtcagggatg tttactattg ttgaaacaat 1140
aaaagcatac tcctcgtgat aatcgaaagg cgctaaactt ggtttcaggc taaaataatc 1200
ttgatgctca aactgcactt tctcttcatc ttgttcaaat cttacaacat gtttattgaa 1260
agcctcagca aaactacgta 1280

<210> SEQ ID NO 121
<211> LENGTH: 1527
<212> TYPE: DNA
<213> ORGANISM: Vitis pseudoreticulata

<400> SEQUENCE: 121
atggctggcg acgaggagac gacgacgacg gcagcaacac ttgaaacaac gtccacttgg 60
gctgttgcct ctgtttgctt tattttgatt gcactctcca tacttattga gcatgccctc 120
catctcttag ccaagtactt caacaagaag cggaggaggt ctctcattca tgctcttaac 180
aacgtcaaat cggagttgat gctcttgggg ttcgtctctt tgttgctgac tgtgtgccaa 240

```
aagtatattg cgaagatttg tatcccaagg agcgtaggtg aaacttttct tccctgcaag    300
accttgacag aaagtgattc agaagaagaa accaaatgcg aagagcaggg aaagatgtct    360
ttgctgtcta gacaaggcgt ggaggaacta caatacttaa ttttcgtgct ggccttcttc    420
cattccctct actgcgtcct cacattcggt cttgggatgg ccaagatgaa gaaatgggag    480
tcctgggagg cagaaacaag aacactggaa tatcagttta caaatgatcc acggaggttc    540
aggctcatcc atcagacatc atttggaaag caacatctga gatattggag tgagcatcag    600
atacttcgtt ggccggcttg ttttattcgg cagttctatc catccgtctc caaagtggat    660
tacttgactc ttagacatgg gttcattatg gcccattttg cagaaggaag caactatgac    720
ttccaaaagt atataaaaag agctttggaa aaagactttg gagtggtggt gggaggaagt    780
ttctgggttt ggagtttctc catgcttttt gtgttcttca atgctcaagt attttacaac    840
tatttatggc taccctttat tccattggtg atgctgttgt tggttggaac aaagctacag    900
ggcattataa ctaagatgtg cttagatagc catgataaag ctctcgttgt tagaggaact    960
ttgcttgtca ggcccagtga tcacttcttc tggtttggaa aaccggaatt gctcctacat   1020
cttatgcact ttatattgtt tcagaactct tttcaactgg cgttctttac atggacttgg   1080
tacaaatttg gattcagatc atgcttccat gatacaactg aggatatcgt cataaggctt   1140
gtcatgggtg tgttagtaca actcctttgt ggctacgtga cactgcctct gtatgccctg   1200
gtcacgcaga tggggacatc aatgaggaca attgtcttta ctgagggagt cgttgaaggt   1260
ctgaacagat ggagaaggaa agccaagaaa aacatagcac gcaggaacaa ccactcagct   1320
cgtccctccc tggatgcttc actcgacaat tcaccttctt ttaacactct ggatacttct   1380
ttctctgtag acctcgatca gccatcatca gatgctggtt atttgactgt tgaaatatca   1440
gatgaagaga cggtcgctac taaacggcca gaaccgcgtc agaagttggg atcttttgag   1500
ggtttcgact cgtgcaaaac atcataa                                      1527
```

<210> SEQ ID NO 122
<211> LENGTH: 1480
<212> TYPE: DNA
<213> ORGANISM: Artificial Sequence
<220> FEATURE:
<223> OTHER INFORMATION: Chimeric DNA encoding a first ledRNA construct targeting a Vitis MLO gene

<400> SEQUENCE: 122

```
taatacgact cactataggg tagccataaa tagttgtaaa atacttgagc attgaagaac     60
acaaaaagca tggagaaact ccaaacccag aaacttcctc ccaccaccac tccaaagtct    120
ttttccaaag ctctttttat atacttttgg aagtcatagt tgcttccttc tgcaaaatgg    180
gccataatga acccatgtct aagagtcaag taatccactt tggagacgga tggatagaac    240
tgctgaataa aacaaaccgg ccaacgaagt atccgatgct cactccaata tctcagatgt    300
tgctttccaa atgatgtctg atggatgagc gtgaacctcc gtggatcatt tgtaaactga    360
tattccagtg ttcttgtttc tgcctcccag gactcccatt tcttcatctt ggccatccca    420
agaccgaatg tgaggacgca gtagagcaca tcatttggaa agcaacatct gagatattgg    480
agtgagcatc ggatacttcg ttggccggtt tgttttattc agcagttcta tccatccgtc    540
tccaaagtgg attacttgac tcttagacat gggttcatta tggcccattt tgcagaagga    600
agcaactatg acttccaaaa gtatataaaa agagctttgg aaaaagactt tggagtggtg    660
gtgggaggaa gtttctgggt ttggagtttc tccatgcttt ttgtgttctt caatgctcaa    720
```

gtattttaca actatttatg gctacccgta attccattgg tgatgctgtt gttggttgga 780
acaaagctac agggcattat aactaagatg tgcctagata gccatgataa agctctcgtt 840
gttagaggaa ctttgcttgt caggcccagt gatcacttct tctggtttgg aaaaccggaa 900
ttgctcctac atcttatgca ctttatattg tttcagaact cttttcaact ggcgttcttt 960
acatggactt ggtacaaatt tggattcaga tcatgcttcc atgatacaac tgaggatatc 1020
gtcataaggc ttgtcatggg tgtgttatgg ctttccttct ccatctgttc agaccttcaa 1080
cgactccctc agtaaagaca attgtcctca ttgatgtccc catctgcgtg accagggcat 1140
acagaggcag tgtcacgtag ccacaaagga gttgtactaa cacacccatg acaagcctta 1200
tgacgatatc ctcagttgta tcatggaagc atgatctgaa tccaaatttg taccaagtcc 1260
atgtaaagaa cgccagttga aaagagttct gaaacaatat aaagtgcata agatgtagga 1320
gcaattccgg ttttccaaac cagaagaagt gatcactggg cctgacaagc aaagttcctc 1380
taacaacgag agctttatca tggctatcta ggcacatctt agttataatg ccctgtagct 1440
ttgttccaac caacaacagc atcaccaatg gaattacgta 1480

<210> SEQ ID NO 123
<211> LENGTH: 894
<212> TYPE: DNA
<213> ORGANISM: Myzus persicae

<400> SEQUENCE: 123
atgttcaaac acttgtgcaa taccgtttca caaagtataa aacctagtag ttttttatca 60
aaagtttgtt caaacaaata tctcgtcgtg ccgtaccgga tagcgatttt taacaacatg 120
ggaagttaca aattgtacct ggccgtcatg gcaatagctg tcatagctgc agttcaggaa 180
attagttgca aggttcagac ttccgaacag gacgatgatc aggaaggata ttacgatgat 240
gagggaggag tgaacgataa tcagggagaa gagaacgata atcagggaga agagaacgat 300
aatcagggag aagagaacga taatcaggga gaagagaagg aagaagtttc cgaaccagag 360
atggagcacc atcagtgcga agaatacaaa tcgaagatct ggaacgatgc atttagcaac 420
ccgaaggcta tgaacctgat gaaactgacg tttaatacag ctaaggaatt gggctccaac 480
gaagtgtgct cggacacgac ccgggcctta tttaacttcg tcgatgtgat ggccaccagc 540
ccgtacgccc acttctcgct aggtatgttt aacaagatgg tggcgtttat tttgagggag 600
gtggacacga catcggacaa atttaaagag acgaagcagg tggtcgaccg tatctcgaaa 660
actccagaga tccgtgacta tatcaggaac tcggccgcca agaccgtcga cttgctcaag 720
gaacccaaga ttagagcacg actgttcaga gtgatgaaag ccttcgagag tctgataaaa 780
ccaaacgaaa acgaagcatt aatcaaacag aagattaagg ggttaaccaa tgctcccgtc 840
aagttagcca agggtgccat gaaaacggtt ggacgtttct ttagacattt ttaa 894

<210> SEQ ID NO 124
<211> LENGTH: 960
<212> TYPE: DNA
<213> ORGANISM: Myzus persicae

<400> SEQUENCE: 124
atgactgaga caatgcaact ccgtggtacc cttcgtgggc ataatggttg ggttacgcag 60
atcgccacca atccgatcca cactgacatg attctgtctt gttcacgaga caagaccttg 120
attgtttggg atctgacacg tgatgagctc aactatggta tccccaagaa acgtttgtac 180

```
ggacattcgc acttcgtcag cgacgtcgtt ctttcatcag atggtaacta cgctctttcc    240

ggttcttggg ataagactct tcgtctgtgg gatttggctg ctggacgtac cactcgtcgt    300

tttgaagacc acaccaagga tgtattgagc gttgccttct ctgctgacaa ccgtcaaatc    360

gtttctggaa gtcgggacaa gactatcaag ttgtggaata ctttggctga gtgcaaatac    420

actattcagg atgatggaca tagcgattgg gtatcatgtg tacggttctc tcctaatatc    480

cataacccaa tcattgtgag tgctggttgg gacaaggttg tcaaggtatg gaacttaact    540

aactgccgca tcaagaccaa ccattatgga cacactggat accttaacac cgttactgtt    600

tcacctgatg gttctttgtg tgcttcagga ggaaaagatt gcaaagctat gttatgggat    660

cttaatgacg gcaaacactt gcacacactg gaccataacg atatcattga agctttgtgc    720

tttagcccca accgttactg gttgtgcgct gcatttggac catcaatcaa aatttgggat    780

ttggaaagca aagaaatggt tgaggaactt cgcccagaag ttgtatctca atcacagaat    840

agcaataccg aaccacccag atgtctgtca cttgcatggt caactgatgg acaaacattg    900

tttgctggat actcagacaa taacattaga gtttggcaag tgtctgtcag tgctcgttaa    960


<210> SEQ ID NO 125
<211> LENGTH: 1401
<212> TYPE: DNA
<213> ORGANISM: Artificial Sequence
<220> FEATURE:
<223> OTHER INFORMATION: Chimeric construct encoding the ledRNA
      targeting M.persicae C002 gene

<400> SEQUENCE: 125

gaattctaat acgactcact atagggtgct ccatctctgg ttcggaaact tcttccttct     60

cttctccctg attatcgttc tcttctccct gattatcgtt ctcttctccc tgattatcgt    120

tctcttctcc ctgattatcg ttcactcctc cctcatcatc gtaatatcct tcctgatcat    180

cgtcctgttc ggaagtctga accttgcaac taatttcctg aactgcagct atgacagcta    240

ttgccatgac ggccaggtac aatttgtaac ttcccatgtt gttaaaaatc gctatccggt    300

acggcacgac gagatatttg tttgaacaaa cttttgataa aaaactacta ggttttatac    360

tttgtgaaac ggtattgcac aagtgtttga acataagaga gttggaagtt acaaattgta    420

cctggccgtc atggcaatag ctgtcatagc tgcagttcag gaaattagtt gcaaggttca    480

gacttccgaa caggacgatg atcaggaagg atattacgat gatgagggag gagtgaacga    540

taatcaggga gaagagaacg ataatcaggg agaagagaac gataatcagg gagaagagaa    600

cgataatcag ggagaagaga aggaagaagt ttccgaacca gagatggagc acccaacagt    660

gcgaagaata caaatcgaag atctggaacg atgcatttag caacccgaag gctatgaacc    720

tgatgaaact gacgtttaat acagctaagg aattgggctc caacgaagtg tgctcggaca    780

cgacccgggc cttatttaac ttcgtcgatg tgatggccac cagcccgtac gcccacttct    840

cgctaggtat gtttaacaag atggtggcgt ttattttgag ggaggtggac acgacatcgg    900

acaatctgaa cagtcgtgct ctaatcttgg gttccttgag caagtggacg gtcttggcgg    960

ccgagttcct gatatagtca cggatctctg gagttttcga gatacgggcg accacctgct   1020

tcgtctcttt aaatttgtcc gatgtcgtgt ccacctccct caaaataaac gccaccatct   1080

tgttaaacat acctagcgag aagtgggcgt acgggctggt ggccatcaca tcgacgaagt   1140

taaataaggc ccgggtcgtg tccgagcaca cttcgttgga gcccaattcc ttagctgtat   1200

taaacgtcag tttcatcagg ttcatagcct tcgggttgct aaatgcatcg ttccagatct   1260
```

tcgatttgta ttcttcgcac tgttaacaag cttagcatat ccatgatatc tgttagtttt 1320
tttcctgaaa gagcggccgc cctagcataa ccccgcgggg cctcttcggg ggtctcgcgg 1380
ggttttttgc tgaaaggatc c 1401

<210> SEQ ID NO 126
<211> LENGTH: 1401
<212> TYPE: DNA
<213> ORGANISM: Artificial Sequence
<220> FEATURE:
<223> OTHER INFORMATION: Chimeric construct encoding the ledRNA targeting M.persicae Rack-1 gene

<400> SEQUENCE: 126
gaattctaat acgactcact atagggttat ggatattagg agagaaccgt acacatgata 60
cccaatcgct atgtccatca tcctgaatag tgtatttgca ctcagccaaa gtattccaca 120
acttgatagt cttgtcccga cttccagaaa cgatttgacg gttgtcagca gagaaggcaa 180
cgctcaatac atccttggtg tggtcttcaa aacgacgagt ggtacgtcca gcagccaaat 240
cccacagacg aagagtctta tcccaagaac cggaaagagc gtagttacca tctgatgaaa 300
gaacgacgtc gctgacgaag tgcgaatgtc cgtacaaacg tttcttgggg ataccatagt 360
tgagctcatc acgtgtcaga tcccaaacaa tcaaggtctt gtcccggttc ttgggataag 420
actcttcgtc tgtgggattt ggctgctgga cgtaccactc gtcgttttga agaccacacc 480
aaggatgtat tgagcgttgc cttctctgct gacaaccgtc aaatcgtttc tggaagtcgg 540
gacaagacta tcaagttgtg gaatactttg gctgagtgca aatacactat tcaggatgat 600
ggacatagcg attgggtatc atgtgtacgg ttctctccta atatccataa cccaaccatt 660
gtgagtgctg gttgggacaa ggttgtcaag gtatggaact taactaactg ccgcatcaag 720
accaaccatt atggacacac tggatacctt aacaccgtta ctgtttcacc tgatggttct 780
ttgtgtgctt caggaggaaa agattgcaaa gctatgttat gggatcttaa tgacggcaaa 840
cacttgcaca cactggacca taacgatatc attgaagctt tgtgctttag ccccaaccgt 900
tacacagaca tctgggtggt tcggtattgc tattctgtga ttgagataca acttctgggc 960
gaagttcctc aaccatttct ttgctttcca aatcccaaat tttgattgat ggtccaaatg 1020
cagcgcacaa ccagtaacgg ttggggctaa agcacaaagc ttcaatgata tcgttatggt 1080
ccagtgtgtg caagtgtttg ccgtcattaa gatcccataa catagctttg caatcttttc 1140
ctcctgaagc acacaaagaa ccatcaggtg aaacagtaac ggtgttaagg tatccagtgt 1200
gtccataatg gttggtcttg atgcggcagt tagttaagtt ccataccttg acaaccttgt 1260
cccaaccagc actcacaatg gttaacccgg gtagcatatc catgatatct gttagttttt 1320
ttcctgaaag agcggccgcc ctagcataac cccgcggggc ctcttcgggg gtctcgcggg 1380 gtttttgct gaaaggatcc c 1401

<210> SEQ ID NO 127
<211> LENGTH: 2396
<212> TYPE: DNA
<213> ORGANISM: Helicoverpa armigera

<400> SEQUENCE: 127
agacattgat tagtgagctc caaactccgt acgtacgttc ttagtttagt ttgttcgttc 60
gtattgtcgc agtcacatcg ctccggtgcc cgcttcgaca tttcccgcca aaagtgacgt 120
aacatatccg tgatctgtgt gaatatgtca gtgacttttt taaattaatt ttttaatagc 180

```
aaaattgtga tcgaaggaat tttacaaga tgacggctgg gaatgaagag catgagcctc    240
taattacatc gtctgtcgac aatcagcgtg tggcctacag taattcacca ccggatgacc    300
gcacaccaga atcttcttcc ccacgcggca gtggcggaga agtaacgcta gccataccat    360
cacaccgcaa ctatggagcc atcggaggcg tggagaaggt cacatacacc tgggcagaca    420
tcaatgcctt tgctactgaa tccaggtcta ggtcccgaag gatttggaac ttctggaagc    480
cctccgccag tggcatgttc cagcaaagga aacagttgtt gaggaatgta aatggagccg    540
cctacccagg cgaactgctc gccatcatgg gatcctccgg tgccgggaag accacactcc    600
tcaacactct gaccttccgc actccaagcg gggtgctgtc cagtggcact cgagcactga    660
acggccagcc tgctacccct gaggcgttat cagcactgtc tgcgtatgtt cagcagcagg    720
atctgttcat tggcacgctg actgtgaagg agcatttagt attccaggct atggtgcgga    780
tggaccgaca tataccgtat gcgcagcgca tgaggagagt tcaagaggtt attactgagt    840
tggcgctaac aaaatgccag aacacagtga taggcatccc tgggcggctg aagggtatct    900
ccggcgggga gatgaagagg ctgtccttcg ccagcgaggt gctcacggat ccaccgctca    960
tgttctgcga tgaacccacc tctggactcg attcttttat ggcgcagaat gttatacagg   1020
tactgaaagg tctcgcacaa aaaggcaaga cagtcgtatg cacgatccac cagccgtctt   1080
cggagctgta cgcgatgttc gataagctgc tcatcatggc agacgggaag gtcgccttcc   1140
tcggctcccc tgatcaggct aatgatttct ttaaagacct aggagcagcg tgtcctccta   1200
actacaaccc agcggaccac ttcatccaac tcctggcggg agtgccgggc agggaggaga   1260
ccacgcgcac cactatcgat actgtctgca cggcattcgc gcgctctgag gtcggctgca   1320
agattgctgc agaagctgaa aatgcactct actttgagcg caagatatcg cagggctggg   1380
cggacccggc gtggtctgaa gccacggcta tccgcgcgcg ccgctcgccg tacaaggcgt   1440
cgtggtgcgc gcagttccgc gcggtgctgt ggcgctcgtg gctgtccgtc actaaggagc   1500
ccatgctcat caaagtgcgc ttcctacaga ctattatggt atcgatcctg atcggcgtga   1560
tctacttcgg gcagcacctg gaccaggacg gcgtgatgaa catcaacggc gccatcttca   1620
tgttcctcac caacatgacc ttccagaaca tcttcgctgt tattaacgta ttctgctcag   1680
aactgccaat attcatacga gaacaccact ccgggatgta tcgagctgac gtgtacttcc   1740
tatcgaagac gttagccgaa gcacctgtgt tcgccaccat accacttgtg ttcaccacca   1800
tagcatacta catgataggg ctgaaccctg aacctaagcg gttctttata gcgtccggtt   1860
tggctgccct gattactaac gttgctacgt cgtttggcta cctgatatcg tgtgccagca   1920
acagcgtgag catggcagcg tcagtgggac ctcccatcat catccccttc atgttgttcg   1980
gaggcttctt cctcaacact ggctccgtac caccatacct gggctggata tcgtacctgt   2040
cctggttcca ctacggcaac gaagcgctgc tggtcaacca gtggtctgga gtggaaacca   2100
tcgcctgcac ccgggagaac ttcacctgtc ccgcctctgg gcaggtcgtc ttggatactc   2160
ttagcttttc tgaggatgac ttcacaatgg acgtggtgaa catgatccta cttttcatcg   2220
gcttcagatt tttggcgtat ctcgctctct tgtaccgcgc tcgccgaggc aagtgagtct   2280
taggtacaaa atgctgcgag aatgggccat atgaaggaag aatgttgaat aaatagtgta   2340
attatttagg atgtaaggag tcaatggaga tttgataaat aaaacaattt ataccg       2396
```

<210> SEQ ID NO 128
<211> LENGTH: 1480
<212> TYPE: DNA
<213> ORGANISM: Artificial Sequence
<220> FEATURE:
<223> OTHER INFORMATION: Chimeric DNA encoding a ledRNA construct targeting a ABC transporter white gene of Helicoverpa armigera

<400> SEQUENCE: 128

```
taatacgact cactataggg tatatgtcgg tccatccgca ccatagcctg gaatactaaa     60
tgctccttca cagtcagcgt gccaatgaac agatcctgct gctgaacata cgcagacagt    120
gctgataacg cctcaggggt agcaggctgg ccgttcagtg ctcgagtgcc actggacagc    180
accccgcttg gagtgcggaa ggtcagagtg ttgaggagtg tggtcttccc ggcaccggag    240
gatcccatga tggcgagcag ttcgcctggg taggcggctc catttacatt cctcaacaac    300
tgtttccttt gctggaacat gccactggcg gagggcttcc agaagttcca aatccttcgg    360
gacctagacc tggattcagt agcaaaggca ttgatgtctg cccaggtgta tgtgaccttc    420
tccacgcctc cgatggctcc atagttgttc cagcaaagga aacagttgtt gaggaatgta    480
aatggagccg cctacccagg cgaactgctc gccatcatgg gatcctccgg tgccgggaag    540
accacactcc tcaacactct gaccttccgc actccaagcg gggtgctgtc cagtggcact    600
cgagcactga acggccagcc tgctacccct gaggcgttat cagcactgtc tgcgtatgtt    660
cagcagcagg atctgttcat tggcacgctg actgtgaagg agcatttagt attccaggct    720
atggtgcgga tggaccgaca tatacccgta tgcgcagcgc atgaggagag ttcaagaggt    780
tattactgag ttggcgctaa caaaatgcca gaacacagtg ataggcatcc ctgggcggct    840
gaagggtatc tccggcgggg agatgaagag gctgtccttc gccagcgagg tgctcacgga    900
tccaccgctc atgttctgcg atgaacccac ctctggactc gattctttta tggcgcagaa    960
tgttatacag gtactgaaag gtctcgcaca aaaaggcaag acagtcgtat gcacgatcca   1020
ccagccgtct tcggagctgt acgcgatgat gaagtggtcc gctgggttgt agttaggagg   1080
acacgctgct cctaggtctt taaagaaatc attagcctga tcaggggagc cgaggaaggc   1140
gaccttcccg tctgccatga tgagcagctt atcgaacatc gcgtacagct ccgaagacgg   1200
ctggtggatc gtgcatacga ctgtcttgcc tttttgtgcg agacctttca gtacctgtat   1260
aacattctgc gccataaaag aatcgagtcc agaggtgggt tcatcgcaga acatgagcgg   1320
tggatccgtg agcacctcgc tggcgaagga cagcctcttc atctccccgc cggagatacc   1380
cttcagccgc ccagggatgc ctatcactgt gttctggcat tttgttagcg ccaactcagt   1440
aataacctct tgaactctcc tcatgcgctg cgcatacgta                         1480
```

<210> SEQ ID NO 129
<211> LENGTH: 811
<212> TYPE: DNA
<213> ORGANISM: Linepithema humile

<400> SEQUENCE: 129

```
agagagaacg atgaggacaa tgagatggaa aaaacaacaa cgtcccaacg tcccttcgac     60
gacgccattc caccagccct ataaaacccc gaggatcatc ggcgtcccaa cattactcgg    120
tcagagtctc gaggaacgcc gtgtccgaga tgatcatcac caggaaccgc atcaaccgcg    180
caactctaat ctgcgttctg gcgtcgtggc tttgcttggc gtctcgcgct tccgccgaat    240
acgaatcgcg ggagatgtcg aacggcggac cgggcgtcga cgcctcgtgc atcgagggca    300
agtgcatgaa gcgcaccgcc acgcaggatg ctaccgccag catgtggttc ggcccgcgtt    360
tgggaagacg gcgcagatcg gacgagaagc aggaagtgaa ttccgagata caggctctgg    420
cggaagcctt ggatagcggg cgtttggccc tatttgccat tccagctaac gacaagagac    480
```

```
aaccgactca atttacaccg cgactggggc gaggatcaga cgaggaccta tcctcctacg    540

gagacgcgat tgagaggaac gagatcgacg atcgtatatt acccgcgtta ttcgcgccgc    600

gtttaggacg acgaattcct tggtcaccgt cgccgagact tggacgccaa ttacgcagca    660

ttttgcgaaa aatgtaggcg ccgtcgaaag attattatca aaagttacaa atgaagagtg    720

atctcgtaga cctgcgcgtg aagatgaaat aacaactaaa attatagcac tattaagaca    780

taaagaaata aagtactgat gtttatttgt a                                   811
```

<210> SEQ ID NO 130
<211> LENGTH: 1360
<212> TYPE: DNA
<213> ORGANISM: Artificial Sequence
<220> FEATURE:
<223> OTHER INFORMATION: Chimeric DNA encoding a ledRNA construct targeting a PBAN gene in Argentine ants

<400> SEQUENCE: 130

```
taatacgact cactataggg aattcacttc ctgcttctcg tccgatctgc gccgtcttcc     60

caaacgcggg ccgaaccaca tgctggcggt agcatcctgc gtggcggtgc gcttcatgca    120

cttgccctcg atgcacgagg cgtcgacgcc cggtccgccg ttcgacatct cccgcgattc    180

gtattcggcg gaagcgcgag acgccaagca aagccacgac gccagaacgc agattagagt    240

tgcgcggttg atgcggttcc tggtgatgat catctcggac acggcgttcc tcgagactct    300

gaccgagtaa tgttgggacg ccgatgatcc tcggggtttt atagggctgg tggaatggcg    360

tcgtcgaagg gacgttggga cgttgttgtt ttttccatct cattgtcctc atcgttcacg    420

ccgtgtccga gatgatcatc accaggaacc gcatcaaccg cgcaactcta atctgcgttc    480

tggcgtcgtg gctttgcttg gcgtctcgcg cttccgccga atacgaatcg cgggagatgt    540

cgaacggcgg accgggcgtc gacgcctcgt gcatcgaggg caagtgcatg aagcgcaccg    600

ccacgcagga tgctaccgcc agcatgtggt tcggcccgcg tttgggaaga cggcgcagat    660

cggacgagaa gcaggaagtg aattcccgta atacaggctc tggcggaagc cttggatagc    720

gggcgtttgg ccctatttgc cattccagct aacgacaaga gacaaccgac tcaatttaca    780

ccgcgactgg ggcgaggatc agacgaggac ctatcctcct acggagacgc gattgagagg    840

aacgagatcg acgatcgtat attacccgcg ttattcgcgc cgcgtttagg acgacgaatt    900

ccttggtcac cgtcgccgag acttggacgc caattacgca gcattttgcg aaaaatgaaa    960

catcagtact ttatttcttt atgtcttaat agtgctataa ttttagttgt tatttcatct   1020

tcacgcgcag gtctacgaga tcactcttca tttgtaactt ttgataataa tctttcgacg   1080

gcgcctacat ttttcgcaaa atgctgcgta attggcgtcc aagtctcggc gacggtgacc   1140

aaggaattcg tcgtcctaaa cgcggcgcga ataacgcggg taatatacga tcgtcgatct   1200

cgttcctctc aatcgcgtct ccgtaggagg ataggtcctc gtctgatcct cgccccagtc   1260

gcggtgtaaa ttgagtcggt tgtctcttgt cgttagctgg aatggcaaat agggccaaac   1320

gcccgctatc caaggcttcc gccagagcct gtattacgta                          1360
```

<210> SEQ ID NO 131
<211> LENGTH: 1480
<212> TYPE: DNA
<213> ORGANISM: Artificial Sequence
<220> FEATURE:
<223> OTHER INFORMATION: Chimeric DNA encoding a ledRNA construct targeting a gene encoding V-type proton ATPase catalytic subunit A of L. cuprina

<400> SEQUENCE: 131
taatacgact cactataggg aagttcttgt catagaaatc atccaaagca cgcatgtatt 60
tggagtagga aatcaaccaa ttgatggagg ggaaatgttt acgttgggcc aatttcttgt 120
ccaaacccca gaacacttgt acgataccca aagtggcaga agtaacggga tcagagaaat 180
caccaccagg aggagataca gcaccgacaa tggaaacgga accttcacgt tcagggttac 240
ccaaacactt gacacgacca gcacgttcgt agaaggaggc caaacgggca cccaagtagg 300
ctgggtaacc ggaatcggca ggcatttcag ccaaacgacc agaaatttca cgaagagctt 360
cggcccaacg ggaggtagaa tcagccatca tagatacgtt gtaacccata tcacggaagt 420
attcagacaa ggtaataccg gtataaacga ttccggttac ccagcctact tgggtgcccg 480
tttggcctcc ttctacgaac gtgctggtcg tgtcaagtgt ttgggtaacc ctgaacgtga 540
aggttccgtt tccattgtcg gtgctgtatc tcctcctggt ggtgatttct ctgatcccgt 600
tacttctgcc actttgggta tcgtacaagt gttctggggt ttggacaaga aattggccca 660
acgtaaacat ttcccctcca tcaattggtt gatttcctac tccaaataca tgcgtgcttt 720
ggatgatttc tatgacaaga acttcccgta attcgtacca ttgcgtacca aggtcaagga 780
aatcttgcaa gaagaagaag atttgtccga aattgtacaa ttggtcggta aggcttcatt 840
ggccgaaact gacaagatca ccttggaagt cgccaaattg cttaaggacg atttcttgca 900
acagaactcc tactcatcat acgacagatt ctgccccttc tacaagagtg tgggtatgtt 960
gaagaacatc attgccttct acgacttggc tcgtcactcc gtcgaatcca ccgctcaatc 1020
tgaaaacaaa atcacctgga atgtcattct gaaagcctgt tgtaaatctt cgtgtaattg 1080
ttcaaagtca gccttgatct tggcttcacc gtccttaacg ggatccttga atttcatgga 1140
agacaattgg tacataatgt tacccatagc ttcacggatg acattccagg tgattttgtt 1200
ttcagattga gcggtggatt cgacggagtg acgagccaag tcgtagaagg caatgatgtt 1260
cttcaacata cccacactct tgtagaaggg gcagaatctg tcgtatgatg agtaggagtt 1320
ctgttgcaag aaatcgtcct taagcaattt ggcgacttcc aaggtgatct tgtcagtttc 1380
ggccaatgaa gccttaccga ccaattgtac aatttcggac aaatcttctt cttcttgcaa 1440
gatttccttg accttggtac gcaatggtac gaattacgta 1480

<210> SEQ ID NO 132
<211> LENGTH: 1480
<212> TYPE: DNA
<213> ORGANISM: Artificial Sequence
<220> FEATURE:
<223> OTHER INFORMATION: Chimeric DNA encoding a ledRNA construct targeting a gene encoding RNAse 1/2 of L. cuprina

<400> SEQUENCE: 132
taatacgact cactataggg aataatttgt ggtagacata gcgggttact tcctcatgtt 60
cgttaaagca gacctggtat tgtctcatga aacgggaaga tgacaattca aaaccaacat 120
tgacgagagt agtgccacca ttgcagctgc tgcccgactt cttagctaca aaagcaggcc 180
aactggtgca aacaagactg ggcagggagt gctgaacacc attgacttta aaagtggtgc 240
cactaacaca ggtagcgata tgggtcttgc ctgataaagg atgagcaaag ccactggtac 300
aatggatctc aatattcttg ccagcagcca catcaattct tccagtatca gaaaaagggt 360
agagttcagt agtgccaggt ttgatataca agggttgttt agccttaaga ccaccgcgaa 420
tgggtatgga acaaccacca ctgcgtggaa tattgagatc cattgtacca gtggctttgc 480
tcatccttta tcaggcaaga cccatatcgc tacctgtgtt agtggcacca cttttaaagt 540
caatggtgtt cagcactccc tgcccagtct tgtttgcacc agttggcctg cttttgtagc 600
taagaagtcg ggcagcagct gcaatggtgg cactactctc gtcaatgttg gttttgaatt 660
gtcatcttcc cgtttcatga gacaatacca ggtctgcttt aacgaacatg aggaagtaac 720
ccgctatgtc taccacaaat tattcccgta cccaacagcg tgccactttc ctattcatta 780
atgcagctcc ccagtggcaa gttttcaatg ccggtaattg ggctcgtgta gaggatggtg 840
tacgcgcctg ggtgtccaaa aataaaatca atgttcgatg ctataccggt gtttatggtg 900
tcaccactct acccaacaaa gagggacgtg agactcctct atatttgtct cgtgatgcca 960
ataataatgg tttgattcct gttcccaaat tatacttccg tgtggttata caacctgcca 1020
ccaataaggg tattgttttc gttggtgtca caggcataag aataaccagc agtgatatca 1080
gttttcttcc aactaatata gttaacctta tcactgacat ctttgcaaat aatatagtcc 1140
tttttgattt gttccaaagt caaatgggga ttgttgacac caacgaaaac aataccctta 1200
ttggtggcag gttgtataac cacacggaag tataatttgg gaacaggaat caaaccatta 1260
ttattggcat cacgagacaa atatagagga gtctcacgtc cctctttgtt gggtagagtg 1320
gtgacaccat aaacaccggt atagcatcga acattgattt tatttttgga cacccaggcg 1380
cgtacaccat cctctacacg agcccaatta ccggcattga aaacttgcca ctggggagct 1440
gcattaatga ataggaaagt ggcacgctgt tgggtacgta 1480

<210> SEQ ID NO 133
<211> LENGTH: 1480
<212> TYPE: DNA
<213> ORGANISM: Artificial Sequence
<220> FEATURE:
<223> OTHER INFORMATION: Chimeric DNA encoding a ledRNA construct
      targeting a gene encoding chitin synthase of L. cuprina

<400> SEQUENCE: 133
taatacgact cactataggg tggcttgatt tttatattaa caccatacac ctcaaatgca 60
gctttttcaa tgctggtaat caatattttt acatattcat tgagaggagg atttttcgga 120
ttctccacat atttttcatc cagtataaag gcatcatcaa agaaaatatt agctaaaatg 180
taaaaaaaag aaaacttaat tgatagatac tcttcattcc aatccacaat tcgtctattt 240
aatgttatac attgttcaac caaaaaacca caataccacg gacaaatgaa cagtttttcg 300
gtgggtaaat ttttatcatt ttttggacgc catatatgat ttgttatcca caattgtgac 360
agccaccaca acaaccatat ccaaagataa tctttagcga ccacattaaa aaaactccat 420
gtatcgtgac cgaagcccag tgacgttgat aaaaatttac ccaccgaaaa actgttcatt 480
tgtccgtggt attgtggttt tttggttgaa caatgtataa cattaaatag acgaattgtg 540
gattggaatg aagagtatct atcaattaag ttttcttttt tttacatttt agctaatatt 600
ttctttgatg atgcctttat actggatgaa aaatatgtgg agaatccgaa aaatcctcct 660
ctcaatgaat atgtaaaaat attgattacc agcattgaaa aagctgcatt tgaggtgtat 720
ggtgttaata taaaaatcaa gccacccgta aaaattgaaa caccttatgg cggtcgtttg 780
gtgtggacac tgcctggtcg ctcaaagatg attgcccatt taaaaaacaa agataaaata 840
cgacataaga aacgctggtc acaggttatg tacatgtact atttgttggg ttttcgtata 900
atggaattgg aatcagtatc ggccaagcgt aaggcagtga tagcagaaaa tacatttttg 960
ctggctcttg atggtgatat tgactttcaa ccgcaggcag tgcaactgtt aatagaccgt 1020
atgaaggcca tagatgaatt aggtgctagc caggactaca taaaacacaa ccaataacat 1080
gctctgttgc tttttgcaac caatgaccta tagcgtattc gaagatttga taccaaacca 1140
tagggcctct accaactgga tgaatacgac cacaggcagc acctaattca tctatggcct 1200
tcatacggtc tattaacagt tgcactgcct gcggttgaaa gtcaatatca ccatcaagag 1260
ccagcaaaaa tgtattttct gctatcactg ccttacgctt ggccgatact gattccaatt 1320
ccattatacg aaaacccaac aaatagtaca tgtacataac ctgtgaccag cgtttcttat 1380
gtcgtatttt atctttgttt tttaaatggg caatcatctt tgagcgacca ggcagtgtcc 1440
acaccaaacg accgccataa ggtgtttcaa tttttacgta 1480

<210> SEQ ID NO 134
<211> LENGTH: 1481
<212> TYPE: DNA
<213> ORGANISM: Artificial Sequence
<220> FEATURE:
<223> OTHER INFORMATION: Chimeric DNA encoding a ledRNA construct targeting a gene encoding ecdysone receptor (EcR) of L. cuprina

<400> SEQUENCE: 134
taatacgact cactataggg tgaaagatca tcacgacctg atgatatgga attagctgat 60
tcagatctgg gtgtatgatg catcatacta ctgttattca tatgatgatg gtgatgatga 120
tttaatccat tactgatgat actgtgaatg ccaatattgg catgaataac ttggccattt 180
tgtgaggcct gtaacgagtt taactgttgg gcattgctaa cgatattggg accattaata 240
ttgaccgata agccaccacc accgccgcca atacccatgt ggccatttgt gtggtgggaa 300
ctgctattac tgtgattact gttgctgttg tggtgtaaat gattgtggct gtgattgtga 360
ttattcactt gactgccacc accaccaccc agaccattga gtgaagtcat accgggtaca 420
ccaccaccac ctccacctcc tccaacaaat cacagtaata gcagttccca ccacacaaat 480
ggccacatgg gtattggcgg cggtggtggt ggcttatcgg tcaatattaa tggtcccaat 540
atcgttagca atgcccaaca gttaaactcg ttacaggcct cacaaaatgg ccaagttatt 600
catgccaata ttggcattca cagtatcatc agtaatggat taaatcatca tcaccatcat 660
catatgaata acagtagtat gatgcatcat acacccagat ctgaatcagc taattccata 720
tcatcaggtc gtgatgatct ttcacccgta tccaccaaat caccccctta gtggttcgaa 780
acacttgtgt tccatttgtg gagaccgcgc cagtggaaaa cattatgggg tctacagttg 840
tgagggttgt aaagggttct tcaaacgtac cgtacgcaag gacttgacat atgcttgtcg 900
tgaggacaga aattgcatta tagataaacg acaaagaaat cgttgccagt attgtcgtta 960
tcaaaagtgt ttagcttgtg gcatgaaacg cgaagcggtc caagaggaac gacaacgtgg 1020
tactcgtgct gctaacgcta gagctgcctt ttgctcggct tcaatgatgc gttctatagt 1080
gagatcacgt aatgaactgc tgggtttaaa gtcttctccg ccagcaccaa ccacattgct 1140
taccccacca ccacctcctc caccaccgcc agcaccagca gctctagcgt tagcagcacg 1200
agtaccacgt tgtcgttcct cttggaccgc ttcgcgtttc atgccacaag ctaaacactt 1260
ttgataacga caatactggc aacgatttct ttgtcgttta tctataatgc aatttctgtc 1320
ctcacgacaa gcatatgtca agtccttgcg tacggtacgt ttgaagaacc ctttacaacc 1380
ctcacaactg tagaccccat aatgttttcc actggcgcgg tctccacaaa tggaacacaa 1440
gtgtttcgaa ccactaaggg ggtgatttgg tggatacgta g 1481

<210> SEQ ID NO 135
<211> LENGTH: 1481
<212> TYPE: DNA
<213> ORGANISM: Artificial Sequence
<220> FEATURE:
<223> OTHER INFORMATION: Chimeric DNA encoding a ledRNA construct
targeting a gene encoding gamma-tubulin 1/1-like of L. cuprina

<400> SEQUENCE: 135
taatacgact cactataggg aaaacgctgt aggtttgtat aagtttctta ggaaaacgat 60
cagacaaacg ttccataata taagagccca tgccggaacc agtaccaccg gctatagaat 120
ggcatagaac aaatccctcc aaggaatcac tgccatctgc ctcacgatca ataatgtcaa 180
aaatttcctc ttgtaatttt tcaccttgac tatagccgga agcccaattg ttgccggcac 240
caccaccatg tttagacaag taaacatttt cgggattata taacttggca tagggtgaac 300
tcataatggt gtgtataact cgcggctcca aatccaaaag tacggcacgt ggtatatagt 360
gatcatcgtc agcctgataa aagaatacat ccttgcgatc tactccatct gtagcaaaat 420
cctctaacac tccactaggt gaaatgctat acacaccatt atgagttcac cctatgccaa 480
gttatataat cccgaaaatg tttacttgtc taaacatggt ggtggtgccg gcaacaattg 540
ggcttccggc tatagtcaag gtgaaaaatt acaagaggaa atttttgaca ttattgatcg 600
tgaggcagat ggcagtgatt ccttggaggg atttgttcta tgccattcta tagccggtgg 660
tactggttcc ggcatgggct cttatattat ggaacgtttg tctgatcgtt ttcctaagaa 720
acttatacaa acctacagcg ttttcccgta ccacaaccct acgttatcct tcatatatga 780
ataataattt gataggattg acggcacctt tgatacctac cccccaatta cattttctaa 840
tgaccggtta tactcctcta actacagata gtgatcccaa tttgaatata cgcaaaacta 900
cggtactaga tgttatgaga cgtttattgc aacccaaaaa tatgatggtt tcatcgggtc 960
cggataaagc aaatattcat tgttatattt ccatattaaa tattatacag ggtgaagtag 1020
atcccactca agtccacaaa tctctactga ttggccatca ttaggcccga aactttatga 1080
ttactttgta tatatggaga acttctggac aaggctactt gtatactggc cggaccccag 1140
ggtatgaatt gagctaattt gcgttcacgt atacgttgta gagatttgtg gacttgagtg 1200
ggatctactt caccctgtat aatatttaat atggaaatat aacaatgaat atttgcttta 1260
tccggacccg atgaaaccat catatttttg ggttgcaata aacgtctcat aacatctagt 1320
accgtagttt tgcgtatatt caaattggga tcactatctg tagttagagg agtataaccg 1380
gtcattagaa aatgtaattg gggggtaggt atcaaaggtg ccgtcaatcc tatcaaatta 1440
ttattcatat atgaaggata acgtagggtt gtggtacgta g 1481

<210> SEQ ID NO 136
<211> LENGTH: 1605
<212> TYPE: DNA
<213> ORGANISM: Triticum aestivum

<400> SEQUENCE: 136
atggcaaagg acgacgggta ccccccggcg cggacgctgc cggagacgcc gtcctgggcg 60
gtggcgctgg tcttcgccgt catgatcatc gtctccgtcc tcctggagca cgcgctccac 120
aagctcggcc attggttcca caagcggcac aagaacgcgc tggcggaggc gctggagaag 180
atgaaggcgg agctgatgct ggtgggattc atctcgctgc tgctcgccgt cacgcaggac 240
ccaatctccg ggatatgcat ctcccagaag gccgccagca tcatgcgccc ctgcaaggtg 300
gaacccggtt ccgtcaagag caagtacaag gactactact gcgccaaaga gggcaaggtg 360
gcgctcatgt ccacgggcag cctgcaccag ctccacatat tcatcttcgt gctagccgtc 420
ttccatgtca cctacagcgt catcatcatg gctctaagcc gtctcaagat gagaacatgg 480
aagaaatggg agacagagac cgcctccttg gaataccagt tcgcaaatga tcctgcgcgg 540
ttccgcttca cgcaccagac gtcgttcgtg aagcggcacc tgggcctgtc cagcaccccc 600
ggcgtcagat gggtggtggc cttcttcagg cagttcttca ggtcggtcac caaggtggac 660
tacctcatct tgagggcagg cttcatcaac gcgcacttgt cgcagaacag caagttcgac 720
ttccacaagt acatcaagag gtccatggag gacgacttca aagtcgtcgt tggcatcagc 780
ctcccgctgt gggctgtggc gatcctcacc ctcttccttg atatcgacgg gatcggcaca 840
ctcacctggg tttctttcat ccctctcatc atcctcttgt gtgttggaac caagctagag 900
atgatcatca tggagatggc cctggagatc caggaccggt cgagcgtcat caagggggca 960
cccgtggtcg agcccagcaa caagttcttc tggttccacc gccccgactg ggtcctcttc 1020
ttcatacacc tgacgctgtt ccagaacgcg tttcagatgg cacatttcgt gtggacagtg 1080
gccacgcccg gcttgaagga ctgcttccat atgaacatcg ggctgagcat catgaaggtc 1140
gtgctggggc tggctctcca gttcctgtgc agctacatca ccttccccct ctacgcgcta 1200
gtcacacaga tgggatcaaa catgaagagg tccatctttg acgagcagac agccaaggcg 1260
ctgaccaact ggcggaacac ggccaaggag aagaagaagg tccgagacac ggacatgctg 1320
atggcgcaga tgatcggcga cgcaacaccc agccgaggca cgtccccgat gcctagccgg 1380
ggctcatcgc cggtgcacct gcttcagaag ggcatgggac ggtctgacga tccccagagc 1440
gcaccgacct cgccaaggac catggaggag gctagggaca tgtacccggt tgtggtggcg 1500
catcctgtac acagactaaa tcctgctgac aggcggaggt cggtctcttc atcagccctc 1560
gatgccgaca tccccagcgc agatttttcc ttcagccagg gatga 1605

<210> SEQ ID NO 137
<211> LENGTH: 1277
<212> TYPE: DNA
<213> ORGANISM: Artificial Sequence
<220> FEATURE:
<223> OTHER INFORMATION: Chimeric DNA encoding a ledRNA construct, targeting Mlo from Triticum aestivum

<400> SEQUENCE: 137
taatacgact cactataggg tgcccccttg atgacgctcg accggtcctg gatctccagg 60
gccatctcca tgatgatcat ctctagcttg gttccaacac acaagaggat gatgagaggg 120
atgaaagaaa cccaggtgag tgtgccgatc ccgtcgatat caaggaagag ggtgaggatc 180
gccacagccc acagcgggag gctgatgcca acgacgactt tgaagtcgtc ctccatggac 240
ctcttgatgt acttgtggaa gtcgaacttg ctgttatgcg acaaatgcgc gttgatgaag 300
cctgccctca aggtgaggta gtccaccttg gtgaccgacc tgaagaactg cctgaagaag 360
gccaccaccc atctgacgcc gggggtgctg gagaggggtt cgacttccac aagtacatca 420
agaggtccat ggaggacgac ttcaaagtcg tcgttggcat cagcctcccg ctgtgggctg 480
tggcgatcct caccctcttc cttgatatcg acgggatcgg cacactcacc tgggtttctt 540
tcatccctct catcatcctc ttgtgtgttg gaaccaagct agagatgatc atcatggaga 600
tggccctgga gatccaggac cggtcgagcg tcatcaaggg ggcacccgac gtcgagccca 660
gcaacaagtt cttctggttc caccgccccg actgggtcct cttcttcata cacctgacgc 720
tgttccagaa gtcacacaga tgggatcaaa catgaagagg tccatcttcg acgagcagac 780
agccaaggcg ctgaccaact ggcggaacac ggccaaggag aagaagaagg tccgagacac 840
ggacatgctg atggcgcaga tgatcggcga cgcgacgccc agccgaggca cgtcccccac 900
cacaaccggg tacatgtccc tagcctcctc catggtcctt ggcgaggtcg gtgcgctctg 960
gggatcgtca gaccgtccca tgcccttctg aagcaggtgc accggcgatg agccccggct 1020
aggcatcggg gacgtgcctc ggctgggcgt cgcgtcgccg atcatctgcg ccatcagcat 1080
gtccgtgtct cggaccttct tcttctcctt ggccgtgttc cgccagttgg tcagcgcctt 1140
ggctgtctgc tcgtcgaaga tggacctctt catgtttgat cccatctgtg tgacttctgg 1200
aacagcgtca ggtgtatgaa gaagaggacc cagtcggggc ggtggaacca gaagaacttg 1260
ttgctgggct cgacgtc 1277

<210> SEQ ID NO 138
<211> LENGTH: 1527
<212> TYPE: DNA
<213> ORGANISM: Vitis pseudoreticulata

<400> SEQUENCE: 138
atggctggcg acgaggagac gacgacgacg gcagcaacac ttgaaacaac gtccacttgg 60
gctgttgcct ctgtttgctt tattttgatt gcactctcca tacttattga gcatgccctc 120
catctcttag ccaagtactt caacaagaag cggaggaggt ctctcattca tgctcttaac 180
aacgtcaaat cggagttgat gctcttgggg ttcgtctctt tgttgctgac tgtgtgccaa 240
aagtatattg cgaagatttg tatcccaagg agcgtaggtg aaacttttct tccctgcaag 300
accttgacag aaagtgattc agaagaagaa accaaatgcg aagagcaggg aaagatgtct 360
ttgctgtcta gacaaggcgt ggaggaacta caatacttaa ttttcgtgct ggccttcttc 420
cattccctct actgcgtcct cacattcggt cttgggatgg ccaagatgaa gaaatgggag 480
tcctgggagg cagaaacaag aacactggaa tatcagttta caaatgatcc acggaggttc 540
aggctcatcc atcagacatc atttggaaag caacatctga gatattggag tgagcatcag 600
atacttcgtt ggccggcttg ttttattcgg cagttctatc catccgtctc caaagtggat 660
tacttgactc ttagacatgg gttcattatg gcccattttg cagaaggaag caactatgac 720
ttccaaaagt atataaaaag agctttggaa aaagactttg gagtggtggt gggaggaagt 780
ttctgggttt ggagtttctc catgcttttt gtgttcttca atgctcaagt attttacaac 840
tatttatggc taccctttat tccattggtg atgctgttgt tggttggaac aaagctacag 900
ggcattataa ctaagatgtg cttagatagc catgataaag ctctcgttgt tagaggaact 960
ttgcttgtca ggcccagtga tcacttcttc tggtttggaa aaccggaatt gctcctacat 1020
cttatgcact ttatattgtt tcagaactct tttcaactgg cgttctttac atggacttgg 1080
tacaaatttg gattcagatc atgcttccat gatacaactg aggatatcgt cataaggctt 1140
gtcatgggtg tgttagtaca actcctttgt ggctacgtga cactgcctct gtatgccctg 1200
gtcacgcaga tggggacatc aatgaggaca attgtcttta ctgagggagt cgttgaaggt 1260
ctgaacagat ggagaaggaa agccaagaaa aacatagcac gcaggaacaa ccactcagct 1320
cgtccctccc tggatgcttc actcgacaat tcaccttctt ttaacactct ggatacttct 1380
ttctctgtag acctcgatca gccatcatca gatgctggtt atttgactgt tgaaatatca 1440
gatgaagaga cggtcgctac taaacggcca gaaccgcgtc agaagttggg atcttttgag 1500
ggtttcgact cgtgcaaaac atcataa 1527

<210> SEQ ID NO 139
<211> LENGTH: 1480
<212> TYPE: DNA
<213> ORGANISM: Artificial Sequence
<220> FEATURE:
<223> OTHER INFORMATION: Chimeric DNA encoding a ledRNA construct targeting a Vitis MLO gene

<400> SEQUENCE: 139
taatacgact cactataggg tagccataaa tagttgtaaa atacttgagc attgaagaac 60
acaaaaagca tggagaaact ccaaacccag aaacttcctc ccaccaccac tccaaagtct 120
ttttccaaag ctctttttat atacttttgg aagtcatagt tgcttccttc tgcaaaatgg 180
gccataatga acccatgtct aagagtcaag taatccactt tggagacgga tggatagaac 240
tgctgaataa aacaaaccgg ccaacgaagt atccgatgct cactccaata tctcagatgt 300
tgctttccaa atgatgtctg atggatgagc gtgaacctcc gtggatcatt tgtaaactga 360
tattccagtg ttcttgtttc tgcctcccag gactcccatt tcttcatctt ggccatccca 420
agaccgaatg tgaggacgca gtagagcaca tcatttggaa agcaacatct gagatattgg 480
agtgagcatc ggatacttcg ttggccggtt tgttttattc agcagttcta tccatccgtc 540
tccaaagtgg attacttgac tcttagacat gggttcatta tggcccattt tgcagaagga 600
agcaactatg acttccaaaa gtatataaaa agagctttgg aaaaagactt tggagtggtg 660
gtgggaggaa gtttctgggt ttggagtttc tccatgcttt ttgtgttctt caatgctcaa 720
gtattttaca actatttatg gctacccgta attccattgg tgatgctgtt gttggttgga 780
acaaagctac agggcattat aactaagatg tgcctagata gccatgataa agctctcgtt 840
gttagaggaa ctttgcttgt caggcccagt gatcacttct tctggtttgg aaaaccggaa 900
ttgctcctac atcttatgca ctttatattg tttcagaact cttttcaact ggcgttcttt 960
acatggactt ggtacaaatt tggattcaga tcatgcttcc atgatacaac tgaggatatc 1020
gtcataaggc ttgtcatggg tgtgttatgg ctttccttct ccatctgttc agaccttcaa 1080
cgactccctc agtaaagaca attgtcctca ttgatgtccc catctgcgtg accagggcat 1140
acagaggcag tgtcacgtag ccacaaagga gttgtactaa cacacccatg acaagcctta 1200
tgacgatatc ctcagttgta tcatggaagc atgatctgaa tccaaatttg taccaagtcc 1260
atgtaaagaa cgccagttga aaagagttct gaaacaatat aaagtgcata agatgtagga 1320
gcaattccgg ttttccaaac cagaagaagt gatcactggg cctgacaagc aaagttcctc 1380
taacaacgag agctttatca tggctatcta ggcacatctt agttataatg ccctgtagct 1440
ttgttccaac caacaacagc atcaccaatg gaattacgta 1480

<210> SEQ ID NO 140
<211> LENGTH: 1531
<212> TYPE: DNA
<213> ORGANISM: Rhizoctonia solani

<400> SEQUENCE: 140
cattccatcg ctgctacagt tgataccccg cgacgcgtcc ttaccgcctc ttgtgttcca 60
ctgggttcca attattggct ccgctatcgc gtacggtgat gaccctcttg catttctctt 120
ttcgtgccgc gaaaagtacg gcgacctgtt caccttcgtt cttctcggcc gcaaaatgac 180
cgtcgcgttg ggcccaaagg gtagtaattt tatcctggga ggaaaacttt cccaagtctc 240
agccgaggaa gcctacaccc accttaccac tccagtcttt ggcaaggatg ttgtctatga 300
cgtcccgaac catgtactca tggagcaaaa gaagtttgtc aagttcggac ttaccaccga 360
gaacttccga gcctacgtcg atatgatcgt agacgagacc gtgaacaacc tcattcgtaa 420
ggagctctcc cctgaaaact gcccacgcga ctcccagggc tgggggtgct tccatgcatt 480
caaaaagctg gccgagctca cgattctcac cgcctcgcgc acgctgcaag gcaacgaagt 540
tcgctccaac cttgacaaaa gcttcgcaga attgtatcag gacctcgatg gcggcttcac 600
ccctatcaac ttcctcttcc ccaaccttcc gctccctagt tactggcgtc gagaccgtgc 660
tcaaaagaag atgagcgact tttacgtgaa cattattgag aaacgtaagg cacagagtca 720
aggggatgag catgatatga ttgctgcttt gttgaatcag acctacaaag atggccgcgc 780
gctcagcgac cgtgaggtag ctcatatcat gattgcactc ctcatggccg gtcagcacac 840
tagttctgca acttcttcct ggacgcttct tcacctcgcc gatcgccctg atattgccga 900
gaaattgtac gaggaacaag tcaaagtctt tggtaatgcc gatggttcga tgcgcccctt 960
gaactacgag gagttgaagg atttgccagt actgagcgca gttatccgtg agaccttgcg 1020
catgcatccg cctatccaca gtatcatgcg caaatgcatt aacgatatgg ttgttccggc 1080
gtccctggct gcccccaccg gcaaggctaa cgagggccga acctacgttg ttcccaaggg 1140
ccactatctt ctggcatctc ccgccgttgc acaagtcgac cctcgtgtat ggcgtgacgc 1200
cgacaagtgg gatcctctgc gctggttgga cccaacggga gctgctgctc aggccggttc 1260
tttgtacaac gacgagcacg gtgaaacggt tgactatggt tggggtgccg ttagtaaggg 1320
taccgagagc ccttatcagc catttggtgc tggtaggcat aggtgcattg gtgaacaatt 1380
cgcaaatata caactcggcg ccattttgtc tactataatc cggaacatgg agatgcgtat 1440
cgaaaagcac gttcctgacc acaattacca tactatgatc gtcctgccta aagatccctg 1500
tggtatcagg ttcaagctcc gcaccaaggc g 1531

<210> SEQ ID NO 141
<211> LENGTH: 1617
<212> TYPE: DNA
<213> ORGANISM: Rhizoctonia solani

<400> SEQUENCE: 141
atgaaccagt tcgcatcttg cccatggctc gaatctgcca ccttcattcc tttactgggc 60
gcttcatgcg tgatcttgat ggccacctgt gcgtgcatcc ttttgaatgt catcgcccaa 120
ttggttatac cccctgatcc gtcattgcca cctcaggttt tctacgttct accgtatatt 180
ggctcggcca ttgaatacgg taaggatcca ataggtttct tatcatctgg caggagaaag 240
tatggggacg tttttacctt cgttctcttg ggacgccgag tgaccgtcgc gcttggtccc 300
aagggaagta atttcgtcct tgggggaaag ttgtcacagg tctcggccga agaagcgtac 360
acacacttga ctacacctgt cttcggcaag ggcgtgattt tcgatgttcc aaatcatgtc 420
tttatggaac agaagaagtt catcaaatcc ggcctcacaa ctgaaaatct acgcgcctac 480
gtgaacatga tatccgagga gactaccaca ttcctgaata aagacttggc tgatacctgt 540
cgtggaaagg aatgggggag gtttcatgta cttgacactc tggctgggct tacgatcctg 600
accgcctcga ggacgctcca aggcagagaa gtgcggtcgt ctctggataa gaccttttct 660
caggtttata aggatttgga tgggggattc acacccttga accttatgtt cgccaatctc 720
cctctgccca gttactggag gagggaccgt gctcaacgga aaatgagcga tttttatgtg 780
gacattatca ggaatcgcca agaggaacat cgggattctg aacatgacat gatctctgca 840
ttagcatcga gagagtacaa ggacggttct cctctaggcg accgcgagat cgctcacttg 900
atgatagcct tactcatggc tggcagcac accagctctt cgaccggttc ttgggcattg 960
ctacacttag ccgatcgccc agatgttgta aaacaactac ttgcagagca agaagaagtg 1020
cttggtaacg aagatggaaa cttacgacct ctaaccttcg agggcctcca aaaactcccc 1080
gttctcaact cggttattcg cgaaacttta cgtattcatc cgcccattca tagtatcatg 1140
cgcaaatgca tagacgatat tgttgtcccg gctactctcg cctccccaag ttcggactcg 1200
acttacatcg taccaaaagg acattttctc ctcgcctctc cggctcactc gcaagtcgac 1260
ccagacgttt ggttcagcgc gagcgaatgg gaccactcac gatggctaga tccaaacgga 1320
gtggccgctc aagccgagtc actctacctg ggtgaccaag gtgaaaaagt cgactatggg 1380
tggggtgtgg taagcaaagg gaccgagagc ccataccagc cattcggtgc tggaaggcat 1440
cgatgtatcg gtgagaagtt cgcttatgta caacttggga cgattctgtc gactgttgtg 1500
agaacaattg agatggggtt ggactcgggt gttccggcgc acaactatca taccatgatt 1560
gttcagccga aggagccctg catgattcag ttcaggttcc gggataggca aagggag 1617

<210> SEQ ID NO 142
<211> LENGTH: 1823
<212> TYPE: DNA
<213> ORGANISM: Artificial Sequence
<220> FEATURE:
<223> OTHER INFORMATION: Nucleotide sequence of a chimeric DNA encoding a ledRNA construct targeting a gene encoding Cyp51

<400> SEQUENCE: 142
aagaattcta atacgactca ctatagggtc caaccagcgc agaggatccc acttgtcggc 60
gtcacgccat acacgagggt cgacttgtgc aacggcggga gatgccagaa gatagtggcc 120
cttgggaaca acgtaggttc ggccctcgtt agccttgccg gtgggggcag ccagggacgc 180
cggaacaacc atatcgttaa tgcatttgcg catgatactg tggataggcg gatgcatgcg 240
caaggtctca cggataactg cgctcagtac tggcaaatcc ttcaactcct cgtagttcaa 300
ggggcgcatc gaaccatcgg cattaccaaa gactttgact tgttcctcgt acaatttctc 360
ggcaatatca gggcgatcgg cgaggtgaag aagcgtccag gaagaagttg cagaactagt 420
gtgctgaccg gccatgagga gtgcaatcat gatatgagct acctcacggt cgctgagcgc 480
gcggccatct ttgtaggtct gattcaacaa agcagcgccc tgatattgcc gagaaattgt 540
acgaggaaca agtcaaagtc tttggtaatg ccgatggttc gatgcgcccc ttgaactacg 600
aggagttgaa ggatttgcca gtactgagcg cagttatccg tgagaccttg cgcatgcatc 660
cgcctatcca cagtatcatg cgcaaatgca ttaacgatat ggttgttccg gcgtccctgg 720
ctgcccccac cggcaaggct aacgagggcc gaacctacgt tgttcccaag ggccactatc 780
ttctggcatc tcccgccgtt gcacaagtcg accctcgtgt atggcgtgac gccgacaagt 840
gggatcctct gcgctggttg gacccgtata ttggctcggc cattgaatac ggtaaggatc 900
caataggttt cttatcatct ggcaggagaa agtatgggga cgtttttacc ttcgttctct 960
tgggacgccg agtgaccgtc gcgcttggtc ccaagggaag taatttcgtc cttgggggaa 1020
agttgtcaca ggtctcggcc gaagaagcgt acacacactt gactacacct gtcttcggca 1080
agggcgtgat tttcgatgtt ccaaatcatg tctttatgga acagaagaag ttcatcaaat 1140
ccggcctcac aactgaaaat ctacgcgcct acgtgaacat gatatccgag gagactacca 1200
cattcctgaa taaagctgag aaaaggtctt atccagagac gaccgcactt ctctgccttg 1260
gagcgtcctc gaggcggtca ggatcgtaag cccagccaga gtgtcaagta catgaaacct 1320

```
cccccattcc tttccacgac aggtatcagc caagtcttta ttcaggaatg tggtagtctc   1380

ctcggatatc atgttcacgt aggcgcgtag attttcagtt gtgaggccgg atttgatgaa   1440

cttcttctgt tccataaaga catgatttgg aacatcgaaa atcacgccct tgccgaagac   1500

aggtgtagtc aagtgtgtgt acgcttcttc ggccgagacc tgtgacaact ttcccccaag   1560

gacgaaatta cttcccttgg gaccaagcgc gacggtcact cggcgtccca agagaacgaa   1620

ggtaaaaacg tccccatact ttctcctgcc agatgataag aaacctattg gatccttacc   1680

gtattcaatg gccgagccaa tatacgtagg tacccgggta gcatatccat gatatctgtt   1740

agttttttc ctgaaagagc ggccgcccta gcataacccc gcggggcctc ttcgggggtc   1800

tcgcggggtt ttttgctgaa aga                                           1823
```

<210> SEQ ID NO 143
<211> LENGTH: 3554
<212> TYPE: DNA
<213> ORGANISM: Phytophthora cinnamomi

<400> SEQUENCE: 143

```
atggggctca ccggcgcggg catcatcgcc tccgtcgtgg gcatcctggg cggcgtgtcg     60

ctgtcctgcg gcggctggtc gtcgctgtcc ctcggcgctc gctcgctctt cgtgacgacg    120

cagttcctct cggccttcgc catgtacgtg ccgcactgac catcactcct gctccaattc    180

tgaaacgagg gcgcactatt gggtgtcgtt tcggttctaa ttttggaacg ttccagacac    240

taatttgatt ttccgctgtt gtgatattcc acctcagggg attcgtggtc gccttcaccg    300

ccatctcgtc gctgacaagc accaacgagt ggatcgccgt ggcggccggc ggcggcgcgg    360

gcttcgtgat cgccctcatc gtgggcttca tgacggtctt cggcccgtac atcctgatcc    420

tcgtcacagg cggcatcatc gcctgctacc tgctgctcgt ggacgcgtac gacggcgtga    480

aactcttccc gtcagacaay cagctggcgc gccaggagtt cgtcatcgcc ttcatgatca    540

tcttcgagct cgtgtgctgc tcgtcgtcca agacgtcgga gctggagaac caccgcttca    600

agtacatcat cttctcggcc atcacgggcg gctggatggc ctcggacggc gtgtcccgcc    660

tcatcgactc gacggctgtt ctgtcggacg tggcctacac ctccatccag gacggcggct    720

cggccgcgct caagggcatc gacagcagcg cgcagacgct catgttcctc atctggggcg    780

ccgtcttcgt ggtcggcggc ctcaaccagc tctccatgcg ctggggactc atgtgctaca    840

accgcgttgg tgcgcacgcc cagctcggcc ccgtcgagga gcagatgccg gagctgccca    900

cgggcgccac gctgcctgcc cagaccatga acgagcgcgt gcgcctcgtg tgcgagaact    960

gtttcgccac ggtgcccagc ggcacggcct tctgtaccga gtgtggtgag gcaatgccct   1020

cggacgacgc cgacccgaac gtcagcatct cgcaggcgca gatgccgtcg gtcacgatga   1080

acaacaagtc tcaagtgccc gaccgctggc agcaggtgcc gcaccgcacg tacctcagca   1140

cgacgtcgtt tgtcgacccc aagcacgcca aggagggcgg cgtgagcatg aaggacaaca   1200

gccgcagcat ccgcttcatg gactcgggtg tgcagggccc cgacggcaag atgagccagt   1260

acaacgactc gatcgccggc gtgcgcaact attacgagcc ttcattccgg tcgttcgcca   1320

tgtcgaccta ctcgatcgcc aaccgcgccg ctgagcccgt tgacacgccc aacatccgca   1380

agtacaagat gtctggtagt ggcatgttcc acgtcttcta cttcggtacg gctgccaccg   1440

gtatcttctg gctgtactac ttgactacga tgtacccgca gcagtacttc tgcgaccacg   1500

cccgccccac gcttccctgc agtgagctgc ccagcagcga gatttcgggc tgctacagtt   1560
```

-continued

```
caacggtcaa cttcgactcc tcttccggcg agggttactg catcaagaac gtgccgttca   1620

tgtcgtggct catgtacgcg atgatgatct ttagcgagtt cctcaactac ttcctaggtc   1680

tgctgttcaa cttcagtatg tggcgtccga ttcgtcgtgg cgcccgttac atgaacgact   1740

tcaaaccgcc tatcccgaaa gagcagtggc cgaccgtcga catcttcctg tgtcactaca   1800

tggaacctgt gacggactcc atggctacgc tgaagaactg tcttgcgatg cagtaccctc   1860

cggagctgct gcacattttc atccttgatg atggttacgc caagtctgtg tgggacgcca   1920

acaaccactt caaggttacg gtcaacacca aggtgattga gatttgtggt gacctgcgtg   1980

gcgacgtcgc tcgcatcatg cacgagcgcg tggtcggccc tgtgcaggac gatcagtccc   2040

tgaagacgtg gcgtcgccag cacagctctg tgcgtgagct ccgcaaagag ggaagcaagg   2100

gcgtgcagcg tcgcgactgt gctgttggtt cactgtcgga cgactacgac taccgtgacc   2160

gcggtatccc gcgtgtgact ttcatcggtc gcatgaagcc cgaaacgcac cactccaagg   2220

ctggtaacat caacaacgcc ctcttcaacg aaggtgccga tggcaagtac ttgctgattc   2280

tggataatga tatgaagccg cacccgaagt tcttgcttgc cgtgctgccg ttcttcttct   2340

cggagggcga ggctgtggac ggcggaggcc gccagtacag tgacgacatt tcctggaacc   2400

aggtgtcgta cgtgcagact cctcagtact tcgaggacac gccccagctg accatcatgg   2460

gagacccgtg tggacacaag aacaccattt tcttcgacgc tgtacagtgt ggtcgtgatg   2520

gtttcgactc ggcagctttc gccggtacca acgccgtttt ccgtcgccag gctttcgact   2580

ccatcggtgg cattcagtac ggtacccaga cggaagatgc ctacacgggt aacgtgctgc   2640

acacttctgg ctgggactcg gtgtacttcc gcaaggattt cgagggtgat gccaaggacc   2700

gcattcgtct gtgcgaaggt gccgtgcccg aaacggtcgc tgctgccatg ggtcagaaga   2760

agcgttgggc caagggtgcc gtgcagattc tgctcatgaa gaatgagagc gaggtcgacc   2820

cggactggcg tccgccgcgt gtgcctgccc cggacccgaa gccggcgctt gcgttcccgc   2880

gcaagatgtt cttctacgac tcggtgctct acccgttcgg ttccattccc gctctgtgtt   2940

acgtggcgat cgctatttac tacctgtgta cgggtgacgc tcccatctac gctcgtggta   3000

ccaagttcct gtactctttc ttgcccgtga cgttctgccg ttgggtactc aacctgctgg   3060

ccaaccgcgc cgtcgacaac aacgatgtgt ggcgtgccca gcagacctgg ttctccttct   3120

ccttcatcac gatgatggct attgtggagg ctattcaggc gcgtgtgacg ggcaaagaca   3180

agtcgtgggc caacacgggt gccggtcaga agacgtcgtg gacagagatc cccaacgtgc   3240

tcttcttctt cacgctgctc tttagtcaac tggtggcgct gattcggttc tttgagtacg   3300

agaacgccac gaacccgtgg aactacgtgt ctgctatgtt cttcggcttc ttcgtgatga   3360

gtcagttcta ccccatggtc aagatgagta tcacggagta ctgtggttgg gaccacacgg   3420

ccgcgacctt tacggccaac gtgttcggct cgctgctggt ggtgtacatc gtggtgttcg   3480

tgcagctgtg gcaggtctac tacgagggca acctgcagac ggcccagggt acatcaggtt   3540

ccacttcgtc ttag                                                     3554
```

<210> SEQ ID NO 144
<211> LENGTH: 1409
<212> TYPE: DNA
<213> ORGANISM: Artificial Sequence
<220> FEATURE:
<223> OTHER INFORMATION: Nucleotide sequence of a chimeric DNA encoding a ledRNA construct targeting a gene encoding CesA3

<400> SEQUENCE: 144

-continued

```
aagaattcta atacgactca ctatagggtc ggcgtcgtcc gagggcattg cctcaccaca     60
ctcggtacag aaggccgtgc cgctgggcac cgtggcgaaa cagttctcgc acacgaggcg    120
cacgcgctcg ttcatggtct gggcaggcag cgtggcgccc gtgggcagct ccggcatctg    180
ctcctcgacg gggccgagct gggcgtgcgc accaacgcgg ttgtagcaca tgagtcccca    240
gcgcatggag agctggttga ggccgccgac cacgaagacg gcgccccaga tgaggaacat    300
gagcgtctgc gcgctgctgt cgatgccctt gagcgcggcc gagccgccgt cctggatgga    360
ggtgtaggcc acgtccgaca gaacagccgt cgagtcgatg aggcgtcgtg gtcggcggcc    420
tcaaccagct ctccatgcgc tggggactca tgtgctacaa ccgcgttggt gcgcacgccc    480
agctcggccc cgtcgaggag cagatgccgg agctgcccac gggcgccacg ctgcctgccc    540
agaccatgaa cgagcgcgtg cgcctcgtgt gcgagaactg tttcgccacg gtgcccagcg    600
gcacggcctt ctgtaccgag tgtggtgagg caatgccctc ggacgacgcc gacccgtacg    660
tcagcatctc gcaggcgcag atgccgtcgg tcacgatgaa caacaagtct caagtgcccg    720
accgctggca gcaggtgccg caccgcacgt acctcagcac gacgtcgttt gtcgacccca    780
agcacgccaa ggagggcggc gtgagcatga aggacaacag ccgcagcatc cgcttcatgg    840
actcgggtgt gcagggcccc gacggcaaga tgagccagta caacgactcg atcgccggcg    900
tgcgcagacg tggaacatgc cactaccaga catcttgtac ttgcggatgt tgggcgtgtc    960
aacgggctca gcggcgcggt tggcgatcga gtaggtcgac atggcgaacg accggaatga   1020
aggctcgtaa tagttgcgca cgccggcgat cgagtcgttg tactggctca tcttgccgtc   1080
ggggccctgc acacccgagt ccatgaagcg gatgctgcgg ctgttgtcct tcatgctcac   1140
gccgccctcc ttggcgtgct tggggtcgac aaacgacgtc gtgctgaggt acgtgcggtg   1200
cggcacctgc tgccagcggt cgggcacttg agacttgttg ttcatcgtga ccgacggcat   1260
ctgcgcctgc gagatgctga cgtacgtagg tacccgggta gcatatccat gatatctgtt   1320
agtttttttc ctgaaagagc ggccgcccta gcataacccc gcggggcctc ttcgggggtc   1380
tcgcggggtt ttttgctgaa agaagctta                                      1409
```